(12) United States Patent
Chinnaiyan et al.

(10) Patent No.: US 12,270,080 B2
(45) Date of Patent: *Apr. 8, 2025

(54) NcRNA AND USES THEREOF

(71) Applicant: THE REGENTS OF THE UNIVERSITY OF MICHIGAN, Ann Arbor, MI (US)

(72) Inventors: Arul Chinnaiyan, Plymouth, MI (US); John Prensner, Ann Arbor, MI (US); Matthew Iyer, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1092 days.

This patent is subject to a terminal disclaimer.

(21) Appl. No.: 16/523,008

(22) Filed: Jul. 26, 2019

(65) Prior Publication Data

US 2020/0224276 A1 Jul. 16, 2020

Related U.S. Application Data

(63) Continuation of application No. 15/156,936, filed on May 17, 2016, now Pat. No. 10,407,735, which is a continuation of application No. 13/797,106, filed on Mar. 12, 2013, now abandoned, which is a continuation-in-part of application No. 13/299,000, filed on Nov. 17, 2011, now abandoned.

(60) Provisional application No. 61/415,490, filed on Nov. 19, 2010.

(51) Int. Cl.
*C12Q 1/68* (2018.01)
*A61K 31/4184* (2006.01)
*C12Q 1/6886* (2018.01)

(52) U.S. Cl.
CPC ........ *C12Q 1/6886* (2013.01); *A61K 31/4184* (2013.01); *C12Q 2600/106* (2013.01); *C12Q 2600/112* (2013.01); *C12Q 2600/118* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,645,691 A | 2/1972 | Guenter et al. |
| 3,687,808 A | 8/1972 | Thomas, Jr. et al. |
| 4,323,546 A | 4/1982 | Crockfor et al. |
| 4,683,195 A | 7/1987 | Mullis et al. |
| 4,683,202 A | 7/1987 | Mullis et al. |
| 4,800,159 A | 1/1989 | Mullis et al. |
| 4,965,188 A | 10/1990 | Mullis et al. |
| 5,130,238 A | 7/1992 | Malek et al. |
| 5,143,854 A | 9/1992 | Pinung et al. |
| 5,225,326 A | 7/1993 | Bresser et al. |
| 5,270,184 A | 12/1993 | Walker et al. |
| 5,283,174 A | 2/1994 | Arnold et al. |
| 5,288,514 A | 2/1994 | Ellman |
| 5,384,261 A | 1/1995 | Winkle et al. |
| 5,399,491 A | 3/1995 | Kacian et al. |
| 5,455,166 A | 10/1995 | Walker |
| 5,480,784 A | 1/1996 | Kacian et al. |
| 5,494,810 A | 2/1996 | Barany et al. |
| 5,538,848 A | 7/1996 | Livak et al. |
| 5,545,524 A | 8/1996 | Trent et al. |
| 5,677,195 A | 10/1997 | Winkler et al. |
| 5,705,365 A | 1/1998 | Ryder et al. |
| 5,710,029 A | 1/1998 | Ryder et al. |
| 5,711,029 A | 1/1998 | Ryder et al. |
| 5,744,305 A | 4/1998 | Fodor et al. |
| 5,814,447 A | 9/1998 | Ishiguro et al. |
| 5,824,518 A | 10/1998 | Kacian et al. |
| 5,830,711 A | 11/1998 | Barany et al. |
| 5,846,717 A | 12/1998 | Brow et al. |
| 5,854,033 A | 12/1998 | Lizardi |
| 5,854,206 A | 12/1998 | Twardzik et al. |
| 5,888,779 A | 3/1999 | Kacian et al. |
| 5,925,517 A | 7/1999 | Tyagi et al. |
| 5,928,862 A | 7/1999 | Morrison |
| 5,965,360 A | 10/1999 | Zain et al. |
| 5,985,557 A | 11/1999 | Prudent et al. |
| 5,989,815 A | 11/1999 | Skolnick et al. |
| 5,994,069 A | 11/1999 | Hall et al. |
| 6,001,567 A | 12/1999 | Brow et al. |
| 6,022,692 A | 2/2000 | Coulie et al. |
| 6,027,887 A | 2/2000 | Zavada et al. |
| 6,034,218 A | 3/2000 | Reed et al. |
| 6,090,543 A | 7/2000 | Prudent et al. |

(Continued)

FOREIGN PATENT DOCUMENTS

| | | |
|---|---|---|
| CN | 101835902 A | 9/2010 |
| EP | 0 684 315 | 11/1995 |

(Continued)

OTHER PUBLICATIONS

US 5,962,233 A, 10/1999, Livak et al. (withdrawn)
Bannert et al., "Retroelements and the human genome: new perspectives on an old relation." Proc Natl Acad Sci U S A. Oct. 5, 2004; 101 Suppl 2:14572-9.
Birney et al., "Identification and analysis of functional elements in 1% of the human genome by the ENCODE pilot project." Nature. Jun. 14, 2007; 447(7146):799-816.

(Continued)

*Primary Examiner* — Jehanne S Sitton
(74) *Attorney, Agent, or Firm* — Tanya A. Arenson; Casimir Jones, S.C.

(57) ABSTRACT

The present invention relates to compositions and methods for cancer diagnosis, research and therapy, including but not limited to, cancer markers. In particular, the present invention relates to ncRNAs as diagnostic markers and clinical targets for prostate, lung, breast and pancreatic cancer.

7 Claims, 70 Drawing Sheets

Specification includes a Sequence Listing.

(56) References Cited

U.S. PATENT DOCUMENTS

| | | |
|---|---|---|
| 6,121,489 A | 9/2000 | Dorner et al. |
| 6,136,182 A | 10/2000 | Dolan et al. |
| 6,150,097 A | 11/2000 | Tyagi et al. |
| 6,198,107 B1 | 3/2001 | Seville |
| 6,218,523 B1 | 4/2001 | French |
| 6,225,051 B1 | 5/2001 | Sugiyama et al. |
| 6,251,639 B1 | 6/2001 | Kurn |
| 6,262,245 B1 | 7/2001 | Xu et al. |
| 6,268,142 B1 | 7/2001 | Duff et al. |
| 6,303,305 B1 | 10/2001 | Wittwer et al. |
| 6,410,278 B1 | 6/2002 | Notomi et al. |
| 6,436,642 B1 | 8/2002 | Gould-Rothberg et al. |
| 6,541,205 B1 | 4/2003 | Yokoyama et al. |
| 6,573,043 B1 | 6/2003 | Cohen et al. |
| 6,630,358 B1 | 10/2003 | Wagner et al. |
| 6,723,506 B2 | 4/2004 | Fletcher et al. |
| 6,828,429 B1 | 12/2004 | Srivastava et al. |
| 7,008,765 B1 | 3/2006 | Bussemakers et al. |
| 7,186,514 B2 | 3/2007 | Zavada et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordano et al. |
| 7,662,553 B2 | 2/2010 | Lenz et al. |
| 7,767,391 B2 | 8/2010 | Scott et al. |
| 7,901,881 B2 | 3/2011 | Libutti et al. |
| 7,901,888 B2 | 3/2011 | Kebebew |
| 7,914,988 B1 | 3/2011 | Chudin et al. |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,273,539 B2 | 9/2012 | Klee et al. |
| 8,293,880 B2 | 10/2012 | Cote et al. |
| 8,299,233 B2 | 10/2012 | Andre et al. |
| 8,338,109 B2 | 12/2012 | Vasmatzis et al. |
| 8,354,228 B2 | 1/2013 | Ron |
| 8,465,914 B2 | 6/2013 | Brown et al. |
| 8,541,170 B2 | 9/2013 | Kennedy et al. |
| 8,568,971 B2 | 10/2013 | Brown et al. |
| 8,669,057 B2 | 3/2014 | Kennedy et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,074,258 B2 | 7/2015 | Davicion et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,206,481 B2 | 12/2015 | Srivastava et al. |
| 9,206,482 B2 | 12/2015 | Davicioni et al. |
| 9,234,244 B2 | 1/2016 | Zeiger et al. |
| 9,435,812 B2 | 9/2016 | Pestano et al. |
| 9,495,515 B1 | 11/2016 | Giulia et al. |
| 9,534,249 B2 | 1/2017 | Vasmatzis et al. |
| 9,587,279 B2 | 3/2017 | Fahey, III et al. |
| 9,617,604 B2 | 4/2017 | Davicion et al. |
| 9,708,667 B2 | 7/2017 | Yanai et al. |
| 9,714,452 B2 | 7/2017 | Davicioni et al. |
| 9,856,537 B2 | 1/2018 | Kennedy et al. |
| 9,994,907 B2 | 6/2018 | Davicioni et al. |
| 10,114,924 B2 | 10/2018 | Kennedy et al. |
| 10,407,731 B2 | 9/2019 | Klee et al. |
| 10,407,735 B2 | 9/2019 | Chinnaiyan et al. |
| 10,422,009 B2 | 9/2019 | Davicioni et al. |
| 10,494,677 B2 | 12/2019 | Vasmatzis et al. |
| 10,513,737 B2 | 12/2019 | Davicioni et al. |
| 2001/0051344 A1 | 12/2001 | Shalon et al. |
| 2002/0076735 A1 | 6/2002 | Williams et al. |
| 2002/0090633 A1 | 7/2002 | Becker et al. |
| 2002/0119463 A1 | 8/2002 | Fads |
| 2002/0168638 A1 | 11/2002 | Schlegel et al. |
| 2002/0169137 A1 | 11/2002 | Reiner et al. |
| 2002/0182586 A1 | 12/2002 | Morris et al. |
| 2003/0119168 A1 | 6/2003 | Madison et al. |
| 2003/0152980 A1 | 8/2003 | Golub et al. |
| 2003/0175736 A1 | 9/2003 | Chinnaiyan et al. |
| 2003/0185830 A1 | 10/2003 | Xu et al. |
| 2003/0186248 A1 | 10/2003 | Erlander et al. |
| 2003/0190602 A1 | 10/2003 | Pressman et al. |
| 2003/0194734 A1 | 10/2003 | Jatkoe |
| 2003/0224399 A1 | 12/2003 | Reed et al. |
| 2003/0235820 A1 | 12/2003 | Mack et al. |
| 2004/0009481 A1 | 1/2004 | Schlegel et al. |
| 2004/0018493 A1 | 1/2004 | Anastasio et al. |
| 2004/0019466 A1 | 1/2004 | Minor et al. |
| 2004/0029114 A1 | 2/2004 | Mack et al. |
| 2004/0058378 A1 | 3/2004 | Kong et al. |
| 2004/0259086 A1 | 12/2004 | Schlegel et al. |
| 2005/0042222 A1 | 2/2005 | Yamamoto et al. |
| 2005/0042638 A1 | 2/2005 | Arnold et al. |
| 2005/0048533 A1 | 3/2005 | Sidransky et al. |
| 2005/0064455 A1 | 3/2005 | Baker et al. |
| 2005/0118625 A1 | 6/2005 | Mounts |
| 2005/0137805 A1 | 6/2005 | Lewin et al. |
| 2005/0202442 A1 | 9/2005 | Morris et al. |
| 2005/0227917 A1 | 10/2005 | Williams et al. |
| 2005/0240357 A1 | 10/2005 | Minor |
| 2005/0250125 A1 | 11/2005 | Novakoff |
| 2005/0260646 A1 | 11/2005 | Baker et al. |
| 2005/0266443 A1 | 12/2005 | Croce et al. |
| 2005/0266459 A1 | 12/2005 | Poulsen |
| 2006/0019256 A1 | 1/2006 | Clarke et al. |
| 2006/0019615 A1 | 1/2006 | Ditmer |
| 2006/0035244 A1 | 2/2006 | Riggins et al. |
| 2006/0046253 A1 | 3/2006 | Nakao |
| 2006/0046265 A1 | 3/2006 | Becker et al. |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2006/0134663 A1 | 6/2006 | Harkin et al. |
| 2006/0204989 A1 | 9/2006 | Kopreski |
| 2006/0211017 A1 | 9/2006 | Chinnaiyan et al. |
| 2007/0010469 A1 | 1/2007 | Chan |
| 2007/0020657 A1 | 1/2007 | Grebe et al. |
| 2007/0031873 A1 | 2/2007 | Wang et al. |
| 2007/0037165 A1 | 2/2007 | Venter et al. |
| 2007/0037186 A1 | 2/2007 | Jiang et al. |
| 2007/0048738 A1 | 3/2007 | Donkena et al. |
| 2007/0065827 A1 | 3/2007 | Pauloski et al. |
| 2007/0065833 A1 | 3/2007 | Gupta |
| 2007/0083334 A1 | 4/2007 | Mintz et al. |
| 2007/0099197 A1 | 5/2007 | Afar et al. |
| 2007/0099209 A1 | 5/2007 | Clarke et al. |
| 2007/0105133 A1 | 5/2007 | Clarke et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172841 A1 | 7/2007 | Wang |
| 2007/0172844 A1 | 7/2007 | Lancaster et al. |
| 2007/0212702 A1 | 9/2007 | Tomlins et al. |
| 2007/0220621 A1 | 9/2007 | Clarke et al. |
| 2007/0238119 A1 | 10/2007 | Yu et al. |
| 2007/0259352 A1 | 11/2007 | Bentwich et al. |
| 2007/0275915 A1 | 11/2007 | Hallenbeck et al. |
| 2008/0009001 A1 | 1/2008 | Bettuzzi et al. |
| 2008/0028302 A1 | 1/2008 | Meschkat |
| 2008/0044824 A1 | 2/2008 | Giordano et al. |
| 2008/0076674 A1 | 3/2008 | Litman et al. |
| 2008/0124344 A1 | 5/2008 | Combs et al. |
| 2008/0131892 A1 | 6/2008 | Becker et al. |
| 2008/0145841 A1 | 6/2008 | Libutti et al. |

(56) References Cited

U.S. PATENT DOCUMENTS

| | | |
|---|---|---|
| 2008/0254470 A1 | 10/2008 | Berlkin |
| 2008/0269157 A1 | 10/2008 | Srivastava et al. |
| 2008/0274457 A1 | 11/2008 | Eng et al. |
| 2008/0281568 A1 | 11/2008 | Kao et al. |
| 2009/0020433 A1 | 1/2009 | Cohen et al. |
| 2009/0036415 A1 | 2/2009 | Rubin et al. |
| 2009/0062144 A1 | 3/2009 | Guo |
| 2009/0075921 A1 | 3/2009 | Ikegawa |
| 2009/0149333 A1 | 6/2009 | Knudsen et al. |
| 2009/0239221 A1 | 6/2009 | Chinnaiyan |
| 2009/0191535 A1 | 7/2009 | Connelly et al. |
| 2009/0204333 A1 | 8/2009 | Friend et al. |
| 2009/0280490 A1 | 11/2009 | Baker et al. |
| 2009/0298082 A1 | 12/2009 | Klee et al. |
| 2010/0055704 A1 | 3/2010 | Giordano et al. |
| 2010/0075384 A1 | 3/2010 | Kong et al. |
| 2010/0099093 A1 | 4/2010 | Weaver et al. |
| 2010/0131286 A1 | 5/2010 | Houlgate et al. |
| 2010/0131432 A1 | 5/2010 | Kennedy et al. |
| 2010/0178653 A1 | 7/2010 | Aharonov et al. |
| 2010/0021538 A1 | 8/2010 | Iljin et al. |
| 2010/0257617 A1 | 10/2010 | Ami et al. |
| 2010/0279327 A1 | 11/2010 | Ossovskaya |
| 2010/0285979 A1 | 11/2010 | Zeiger et al. |
| 2011/0009286 A1 | 1/2011 | Andre et al. |
| 2011/0045462 A1 | 2/2011 | Fu et al. |
| 2011/0092375 A1 | 4/2011 | Zamore et al. |
| 2011/0136683 A1 | 6/2011 | Davicioni |
| 2011/0152110 A1 | 6/2011 | Vierlinger et al. |
| 2011/0178163 A1 | 7/2011 | Chowdhury |
| 2011/0212855 A1 | 9/2011 | Rafnar et al. |
| 2011/0229894 A1 | 9/2011 | Levy et al. |
| 2011/0230372 A1 | 9/2011 | Willman et al. |
| 2011/0236903 A1 | 9/2011 | McClelland |
| 2011/0287946 A1 | 11/2011 | Gudmundsson et al. |
| 2011/0294123 A1 | 12/2011 | Nakamura et al. |
| 2011/0312520 A1 | 12/2011 | Kennedy et al. |
| 2012/0015839 A1 | 1/2012 | Chinnaiyan |
| 2012/0015843 A1 | 1/2012 | Von et al. |
| 2012/0041274 A1 | 2/2012 | Stone et al. |
| 2012/0108453 A1 | 5/2012 | Smit et al. |
| 2012/0115743 A1 | 5/2012 | Davicioni et al. |
| 2012/0122698 A1 | 5/2012 | Stacey et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0214165 A1 | 8/2012 | Walfish et al. |
| 2012/0220474 A1 | 8/2012 | Kennedy et al. |
| 2012/0304318 A1 | 11/2012 | Ohnuma et al. |
| 2013/0004974 A1 | 1/2013 | Klee et al. |
| 2013/0023434 A1 | 1/2013 | Van |
| 2013/0142728 A1 | 6/2013 | Beaudenon-Huibregtse et al. |
| 2013/0150257 A1 | 6/2013 | Abdueva et al. |
| 2013/0172203 A1 | 7/2013 | Yeatman et al. |
| 2013/0184999 A1 | 7/2013 | Ding |
| 2013/0196866 A1 | 8/2013 | Pestano et al. |
| 2013/0225662 A1 | 8/2013 | Kennedy et al. |
| 2013/0231258 A1 | 9/2013 | Wilde et al. |
| 2013/0267443 A1 | 10/2013 | Chinnaiyan |
| 2013/0273543 A1 | 10/2013 | Gudmundsson et al. |
| 2013/0302808 A1 | 11/2013 | Vasmatzis |
| 2013/0302810 A1 | 11/2013 | Latham et al. |
| 2013/0303826 A1 | 11/2013 | Jurisica et al. |
| 2014/0030714 A1 | 1/2014 | Paschke et al. |
| 2014/0066323 A1 | 3/2014 | Buerki et al. |
| 2014/0080731 A1 | 3/2014 | Davicioni et al. |
| 2014/0087961 A1 | 3/2014 | Sulem et al. |
| 2014/0099261 A1 | 4/2014 | Keutgen et al. |
| 2014/0121126 A1 | 5/2014 | Bivona et al. |
| 2014/0143188 A1 | 5/2014 | Mackey et al. |
| 2014/0228237 A1 | 8/2014 | Kennedy et al. |
| 2014/0243240 A1 | 8/2014 | Soldin et al. |
| 2014/0302042 A1 | 10/2014 | Chin et al. |
| 2014/0315199 A1 | 10/2014 | Rhodes et al. |
| 2014/0315739 A1 | 10/2014 | Aharonov et al. |
| 2014/0349856 A1 | 11/2014 | Schnabel et al. |
| 2014/0349864 A1 | 11/2014 | Kennedy et al. |
| 2014/0371096 A1 | 12/2014 | Umbright et al. |
| 2015/0038376 A1 | 2/2015 | Tian et al. |
| 2015/0099665 A1 | 4/2015 | Rosenfeld et al. |
| 2015/0141470 A1 | 5/2015 | Garraway et al. |
| 2015/0275306 A1 | 10/2015 | Bernards et al. |
| 2015/0284802 A1 | 10/2015 | Chinnaiyan |
| 2015/0292030 A1 | 10/2015 | McConkey |
| 2015/0299808 A1 | 10/2015 | Gonzalez et al. |
| 2015/0307947 A1 | 10/2015 | Basu et al. |
| 2015/0329915 A1 | 11/2015 | Davicioni et al. |
| 2015/0368724 A1 | 12/2015 | Aharonov et al. |
| 2016/0024586 A1 | 1/2016 | Delfour et al. |
| 2016/0032395 A1 | 2/2016 | Davicioni et al. |
| 2016/0032400 A1 | 2/2016 | Gomis et al. |
| 2016/0068915 A1 | 3/2016 | Kennedy et al. |
| 2016/0076108 A1 | 3/2016 | Davicioni et al. |
| 2016/0115546 A1 | 4/2016 | Rosenfeld et al. |
| 2016/0120832 A1 | 5/2016 | Rabinowitz et al. |
| 2016/0251729 A1 | 9/2016 | Chinnaiyan |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |
| 2016/0348184 A1 | 12/2016 | Chinnaiyan |
| 2017/0016076 A1 | 1/2017 | Barnett-Itzhaki et al. |
| 2017/0145513 A1 | 5/2017 | Kennedy et al. |
| 2017/0166980 A1 | 6/2017 | Fahey, III et al. |
| 2017/0329894 A1 | 11/2017 | Kennedy et al. |
| 2018/0016642 A1 | 1/2018 | Kennedy et al. |
| 2018/0216197 A1 | 1/2018 | Davicioni et al. |
| 2018/0030540 A1 | 2/2018 | Davicioni et al. |
| 2018/0068058 A1 | 3/2018 | Abdueva et al. |
| 2018/0112275 A1 | 4/2018 | Davicioni et al. |
| 2018/0122508 A1 | 5/2018 | Wilde et al. |
| 2018/0127832 A1 | 5/2018 | Kennedy et al. |
| 2018/0291459 A1 | 10/2018 | Al-Deen Ashab et al. |
| 2019/0017123 A1 | 1/2019 | Davicioni et al. |
| 2019/0191133 A1 | 6/2019 | Ostrow |
| 2019/0204322 A1 | 7/2019 | Alshalalfa et al. |
| 2019/0218621 A1 | 7/2019 | Davicioni |
| 2020/0165682 A1 | 5/2020 | Chinnaiyan et al. |

FOREIGN PATENT DOCUMENTS

| | | |
|---|---|---|
| EP | 1 409 727 | 11/2005 |
| EP | 2 366 800 | 9/2011 |
| WO | WO 90/015070 | 12/1990 |
| WO | WO 92/010092 | 6/1992 |
| WO | WO 93/009668 | 5/1993 |
| WO | WO 93/022684 | 11/1993 |
| WO | WO 98/045420 | 10/1998 |
| WO | WO 199845420 A1 | 10/1998 |
| WO | WO 01/060860 | 8/2001 |
| WO | WO 01/066753 | 9/2001 |
| WO | WO 200166753 A1 | 9/2001 |
| WO | WO 02/000929 | 1/2002 |
| WO | WO 02/083921 | 10/2002 |
| WO | WO 03/012067 | 2/2003 |
| WO | WO 04/037972 | 5/2004 |
| WO | WO 2004037972 A2 | 5/2004 |
| WO | WO 05/040396 | 5/2005 |
| WO | WO 05/085471 | 9/2005 |
| WO | WO 05/100608 | 10/2005 |
| WO | WO 06/047484 | 5/2006 |
| WO | WO 06/091776 | 8/2006 |
| WO | WO 06/110264 | 10/2006 |
| WO | WO 06/127537 | 11/2006 |
| WO | WO 06/135596 | 12/2006 |
| WO | WO 07/056049 | 5/2007 |
| WO | WO 07/070621 | 6/2007 |
| WO | WO 07/081720 | 7/2007 |
| WO | WO 07/081740 | 7/2007 |
| WO | WO 08/023087 | 2/2008 |
| WO | WO 08/046911 | 4/2008 |
| WO | WO 08/086478 | 7/2008 |
| WO | WO 2008086478 A2 | 7/2008 |
| WO | WO 08/112283 | 9/2008 |

(56) References Cited

FOREIGN PATENT DOCUMENTS

| | | |
|---|---|---|
| WO | WO 09/009432 | 1/2009 |
| WO | WO 09/020521 | 2/2009 |
| WO | WO 09/020905 | 2/2009 |
| WO | WO 2009020905 A2 | 2/2009 |
| WO | WO 09/029266 | 3/2009 |
| WO | WO 09/045115 | 4/2009 |
| WO | WO 09/074968 | 6/2009 |
| WO | WO 09/143603 | 12/2009 |
| WO | WO 10/018601 | 2/2010 |
| WO | WO 10/056374 | 5/2010 |
| WO | WO 10/073248 | 7/2010 |
| WO | WO 10/099598 | 9/2010 |
| WO | WO 10/123626 | 10/2010 |
| WO | WO 10/124372 | 11/2010 |
| WO | WO 11/150453 | 12/2011 |
| WO | WO 12/031008 | 3/2012 |
| WO | WO 12/068383 | 5/2012 |
| WO | WO 2012068383 A2 | 5/2012 |
| WO | WO 12/135008 | 10/2012 |
| WO | WO 13/006495 | 1/2013 |
| WO | WO 13/088457 | 6/2013 |
| WO | WO 13/116742 | 8/2013 |
| WO | WO 14/028884 | 2/2014 |
| WO | WO 14/043803 | 3/2014 |
| WO | WO 14/085666 | 5/2014 |
| WO | WO 14/151764 | 9/2014 |
| WO | WO 15/071876 | 5/2015 |
| WO | WO 15/073949 | 5/2015 |
| WO | WO 16/141127 | 9/2016 |
| WO | WO 17/059549 | 4/2017 |
| WO | WO 17/062505 | 4/2017 |
| WO | WO 18/165600 | 9/2018 |
| WO | WO 19/023517 | 1/2019 |

OTHER PUBLICATIONS

Boorjian et al., "Long-term risk of clinical progression after biochemical recurrence following radical prostatectomy: the impact of time from surgery to recurrence." Eur Urol. Jun. 2011; 59(6):893-9.

Brouha et al., "Hot L1s account for the bulk of retrotransposition in the human population." Proc Natl Acad Sci U S A. Apr. 29, 2003;100(9):5280-5.

Bussemakers et al., "DD3: a new prostate-specific gene, highly overexpressed in prostate cancer." Cancer Res. Dec. 1, 1999; 59(23):5975-9.

Carninci et al., "The transcriptional landscape of the mammalian genome." Science. Sep. 2, 2005; 309(5740):1559-63.

Chalitchagorn et al., "Distinctive pattern of LINE-1 methylation level in normal tissues and the association with carcinogenesis." Oncogene. Nov. 18, 2004; 23(54):8841-6.

Cho et al., "Hypermethylation of CpG island loci and hypomethylation of LINE-1 and Alu repeats in prostate adenocarcinoma and their relationship to clinicopathological features." J Pathol. Feb. 2007; 211(3):269-77.

Chow et al., "LINE-1 activity in facultative heterochromatin formation during X chromosome inactivation." Cell. Jun. 11, 2010; 141(6):956-69.

Cordaux et al., "The impact of retrotransposons on human genome evolution." Nat Rev Genet. Oct. 2009; 10(10):691-703.

Day et al., "Estimating enrichment of repetitive elements from high-throughput sequence data." Genome Biol. 2010; 11(6):R69.

De Klein et al., "A cellular oncogene is translocated to the Philadelphia chromosome in chronic myelocytic leukaemia." Nature. Dec. 23, 1982; 300(5894):765-7.

Dechassa et al. "Architecture of the SWI/SNF-nucleosome complex." Mol Cell Biol. Oct. 2008;28(19):6010-21.

Dhanasekaran et al., "Delineation of prognostic biomarkers in prostate cancer." Nature. Aug. 23, 2001; 412(6849):822-6.

Fu et al., "Regulation of apoptosis by a prostate-specific and prostate cancer-associated noncoding gene, PCGEM1." DNA Cell Biol. Mar. 2006; 25(3):135-41.

Gupta et al., "Long non-coding RNA HOTAIR reprograms chromatin state to promote cancer metastasis." Nature. Apr. 15, 2010; 464(7291):1071-6.

Guttman et al., "Ab initio reconstruction of cell type-specific transcriptomes in mouse reveals the conserved multi-exonic structure of lincRNAs." Nat Biotechnol. May 2010; 28(5):503-10.

Guttman et al., "Chromatin signature reveals over a thousand highly conserved large non-coding RNAs in mammals." Nature. Mar. 12, 2009; 458(7235):223-7.

He et al., "The antisense transcriptomes of human cells." Science. Dec. 19, 2008; 322(5909):1855-7.

Huarte & Rinn, "Large non-coding RNAs: missing links in cancer?" Human Molecular Genetics 2010, 19(2): R152-R161.

Jones et al., "Frequent mutations of chromatin remodeling gene ARID1A in ovarian clear cell carcinoma." Science. Oct. 8, 2010; 330(6001):228-31.

Kunarso et al., "Transposable elements have rewired the core regulatory network of human embryonic stem cells." Nat Genet. Jul. 2010; 42(7):631-4.

Lin et al., "Nuclear receptor-induced chromosomal proximity and DNA breaks underlie specific translocations in cancer." Cell. Dec. 11, 2009; 139(6):1069-83.

Mitelman, "Recurrent chromosome aberrations in cancer", Mutation Research 2000, 462: 247-253.

Oosumi et al., "Mariner transposons in humans." Nature. Dec. 14, 1995; 378(6558):672.

Prensner et al., "Transcriptome sequencing across a prostate cancer cohort identifies PCAT-1, an unannotated lincRNA implicated in disease progression." 29(8): 742-749.

Rabbitts, "Chromosomal translocations in human cancer", Nature Nov. 10, 1994, 372: 143-149.

Reis et al., "Antisense intronic non-coding RNA levels correlate to the degree of tumor differentiation in prostate cancer." Oncogene. Aug. 26, 2004;23(39):6684-92.

Rinn et al., "Functional demarcation of active and silent chromatin domains in human HOX loci by noncoding RNAs." Cell. Jun. 29, 2007; 129(7):1311-23.

Roberts et al., "The SWI/SNF complex—chromatin and cancer." Nat Rev Cancer. Feb. 2004; 4(2):133-42.

Robertson et al., "Reconstructing the ancient mariners of humans." Nat Genet. Apr. 1996; 12(4):360-1.

Rowley, "A new Consistent Chromosomal Abnormality in Chronic Myelogenous Leukaemia Identified by Quinacrine Fluorescence and Giemsa Staining", Nature Jun. 1, 1973, 243:290-293.

Rowley, "Chromosome translocations: dangerous liaisons revisited", Nature Reviews: Cancer Dec. 2001, (1):245-250.

Shen et al., "The SWI/SNF ATPase Brm is a gatekeeper of proliferative control in prostate cancer." Cancer Res. Dec. 15, 2008; 68(24):10154-62.

Simmons et al., "Natural history of biochemical recurrence after radical prostatectomy: risk assessment for secondary therapy." Eur Urol. May 2007; 51(5):1175-84.

Slotkin et al., "Transposable elements and the epigenetic regulation of the genome." Nat Rev Genet. Apr. 2007; 8(4):272-85.

Srikantan et al., "PCGEM1, a prostate-specific gene, is overexpressed in prostate cancer." Proc Natl Acad Sci U S A. Oct. 24, 2000;97(22):12216-21.

Stavenhagen et al., "An ancient provirus has imposed androgen regulation on the adjacent mouse sex-limited protein gene." Cell. Oct. 21, 1988; 55(2):247-54.

Sun et al., "Aberrant expression of SWI/SNF catalytic subunits BRG1/BRM is associated with tumor development and increased invasiveness in prostate cancers." Prostate. Feb. 1, 2007; 67(2):203-13.

Taft et al., "Non-coding RNAs: regulators of disease." J Pathol. Jan. 2010; 220(2):126-39.

Tomlins et al., "Distinct classes of chromosomal rearrangements create oncogenic ETS gene fusions in prostate cancer." Nature. Aug. 2, 2007; 448(7153):595-9.

Varela et al., "Exome sequencing identifies frequent mutation of the SWI/SNF complex gene PBRM1 in renal carcinoma." Nature. Jan. 27, 2011; 469(7331):539-42.

(56) References Cited

OTHER PUBLICATIONS

Versteege et al., "Truncating mutations of hSNF5/INI1 in aggressive paediatric cancer." Nature. Jul. 9, 1998; 394(6689):203-6.
Wiegand et al., "ARID1A mutations in endometriosis-associated ovarian carcinomas." N Engl J Med. Oct. 14, 2010; 363(16):1532-43.
Yap et al., "Molecular interplay of the noncoding RNA ANRIL and methylated histone H3 lysine 27 by polycomb CBX7 in transcriptional silencing of INK4a." Mol Cell. Jun. 11, 2010; 38(5):662-74.
Yegnasubramanian et al., "DNA hypomethylation arises later in prostate cancer progression than CpG island hypermethylation and contributes to metastatic tumor heterogeneity." Cancer Res. Nov. 1, 2008;68(21):8954-67.
Yelin et al., "Widespread occurrence of antisense transcription in the human genome." Nat Biotechnol. Apr. 2003; 21(4):379-86.
Yu et al., "An integrated network of androgen receptor, polycomb, and TMPRSS2-ERG gene fusions in prostate cancer progression." Cancer Cell. May 18, 2010; 17(5):443-54.
International Search Report of PCT application No. PCT/US2011/061204, mailed Jun. 19, 2012, 11 pages.
Office Action of related AU Appl. No. 2015242941, dated May 18, 2017, 4 pages.
EP Search Report, EP Patent Application No. 18155318.1, mailed Apr. 24, 2018.
Bannert et al., "Retroelements and the human genome: new perspectives on an old relation." PNAS (Oct. 5, 2004) vol. 101, Suppl. 2, pp. 14572-14579.
Birney et al., "Identification and analysis of functional elements in 1% of the human genome by the ENCODE pilot project." Nature (2007) Jun. 14; 447(7146):799-816.
Brouha et al., "Hot L1s account for the bulk of retrotransposition in the human population." PNAS USA (Apr. 29, 2003) 100(9):5280-5.
Carninci et al., "The transcriptional landscape of the mammalian genome," Science (Sep. 2, 2005) 09(5740):1559-63.
Cho et al., "Hypermethylation of CpG island loci and hypomethylation of LINE-1 and Alu repeats in prostate denocarcinoma and their relationship to clinicopathological features", J Pathol (Feb. 2007) 211(3):269-77.
Dechassa et al., "Architecture of the SWI/SNF-nucleosome complex," Mol Cell Biol. (Oct. 2008) vol. 28, No. 19, pp. 6010-6021.
Dhanasekaran et al., "Delineation of prognostic biomarkers in prostate cancer," Nature (2001) 412: 822-826.
Guttman et al., "Ab initio reconstruction of transcriptomes of pluripotent and lineage committed cells reveals gene structures of thousands of lincRNAs," Nat Biotechnol. (May 2010) 28(5):503-10.
Huarte et al., "Large non-coding RNAs: missing links in cancer?" Human Molecular Genetics (Oct. 15, 2010) 19(2): R152-R161.
Prensner et al., "Transcriptome Sequencing Identifies PCAT-1, a Novel lincRNA Implicated in Prostate Cancer Progression," (2012) 29 (8): 742-749.
Rabbits, "Chromosomal translocations in human cancer", Nature (Nov. 10, 1994) 372: 143-149.
Reis et al., "Antisense intronic non-coding RNA levels correlate to the degree of tumor differentiation in prostate cancer," Oncogene (2004) 23(39):6684-6692.
Srikantan et al., "PCGEM1, a prostate-specific gene, is overexpressed in prostate cancer," PNAS (Oct. 24, 2000) 97(22): 12216-12221.
Stavenhagen et al., "An ancient provirus has imposed androgen regulation on the adjacent mouse sex-limited protein Jene." Cell (Oct. 21, 1988) 55(2):247-54.
Yap et al., "Molecular interplay of the noncoding RNA ANRIL and methylated histone H3 lysine 27 by polycomb CBX7 n transcriptional silencing of INK4a," Mol Cell. (Jun. 11, 2010) 38(5):662-74.
Yegnasubramanian et al., "DNA hypomethylation arises later in prostate cancer progression than CpG island hypermethylation and contributes to metastatic tumor heterogeneity," Cancer Res. (Nov. 1, 2008) 68(21): pp. 8954-8967.
Yeliin et al., "Widespread occurrence of antisense transcription in the human genome," Nat Biotechnol. (2003) 21(4):379-86.

Abdueva et al., "Quantitative Expression Profiting in Formalin-Fixed Paraffin-Embedded Samples by Affymetrix Microarrays," Journal of Molecular Diagnostics (Jul. 2010) vol. 12, No. 4, pp. 409-417.
Adamo and Ladomery, "The Oncogene ERG: A Key Factor in Prostate Cancer," *Oncogene* (2016), 35:403-414.
Affymetrix GeneChip Human Genome U133 Array Set HG-U133A, Geo, Mar. 11, 2002, retrieved on Mar. 11, 2002.
Affymetrix: Data Sheet, "GeneChip® Exon Array System for Human, Mouse, and Rat," Internet Citation, [Online] Jan. 25, 2012 [Retrieved from the Internet] lntp://www.biainformatics.atickland.aciaz/workshops/1O_March_2011 1Exon_EOST_Datash eet.pdf, 8 pages.
Agell et al., "A 12-Gene Expression Signature Is Associated with Aggressive Histological in Prostate Cancer: SEC14L1 and TCEB1 Genes Are Potential Markers of Progression," Am J Pathol (2012) vol. 181 (5), pp. 1585-1594.
Alberts et al., "Vesicular traffic in the secretory and endocytic pathways," Molecular Biology of the Cell (1994) 3rd Ed., p. 465.
Aldred et al., "Papillary and follicular thyroid carcinomas show distinctly different microarray expression profiles and can be distinguished by a minimum of five genes," J Clin Oncol. (2004) 22(17):3531-9.
Amling et al.: "Long-term hazard of progression after radical prostatectomy for clinically EB localized prostate cancer continued risk of biochemical failure after 5 years," J Urol. (2000) 164:101-105.
Amundadottir et al., "A common variant associated with prostate cancer in European and African populations," Nat Genet. (2006) 38:652-658.
Amundson et al., "Integrating global gene expression and radiation survival parameters across the 60 cell lines of the National Cancer Institute Anticancer Drug Screen," Cancer Research (2008) 68(2):415-424.
Ausubel, et al. Current Protocols in Molecular Biology. Wiley & Sons, New York (1995) Table of Contents.
Baetke et al., "Molecular Pathways Involved in Prostate Carcinogenesis: Insights from Public Microarray Datasets," PLoS ONE (2012) 7(11):e49831, 1-11.
Baggerly et al., "Deriving Chemosensitivity from Cell Lines: Forensic Bioinformatics and Reproducible Research in High-Throughput Biology," The Annals of Applied Sciences (2009) vol. 3, No. 4, pp. 1309-1334.
Ballman et al., "Faster cyclic loess: normalizing RNA arrays via linear models," Bioinformatics, 2004, 20 :2778-2786.
Barlow et al., "Analysis of Case-Cohort Designs," J Clin Epidemiol (1999) vol. 52 (12), 1165-1172.
Bauer et al., "Identification of Markers of Taxane Sensitivity Using Proteomic and Genomic Analyses of Breast Tumor from Patients Receiving Neoadjuvant Paclitaxel and Radiation," Clin. Cancer Res. (2010) 16(2):681-690, American Association for Cancer Research.
Benner et al., "Evolution, language and analogy in functional genomics," Trends in Genetics, (Jul. 2001) vol. 17, pp. 414-418.
Bergstralh et al., "Software for optimal matching in observation al studies," Epidemiology (1996) 7(3):331-332.
Best et al., "Molecular differentiation of high- and moderate-grade human prostate cancer by cDNA microarray analysis", Diagn Mol Pathol. (2003) 12(2):63-70.
Bibikova et al., "Expression signatures that correlated with Gleason score and relapse in prostate cancer," Genomics (2007) 89(6):666-672.
Bibikova et al., "Gene expression profiles in formalin-fixed, paraffin-embedded tissues obtained with a novel assay for microarray analysis," Clin Chem., 2004, 50:2384-2386.
Bibikova et al., "Quantitative gene expression profiling in formalin-fixed, paraffin-embedded tissues using universal bead arrays," Am J Pathol. (2004) 165:1799-1807.
Bismar et al., "ERG Protein Expression Reflects Hormonal Treatment Response and is Associated with Gleason Score and Prostate Cancer Specific Mortality," *Eur. J. Cancer* (2012), 48:538-546, Elsevier Ltd.

(56) References Cited

OTHER PUBLICATIONS

Biton et al., Nov. 20, 2014, Independent component analysis uncovers the landscape of the bladder tumor transcriptome and reveals insights into luminal and basal subtypes, Cell Reports, 9(4):1235-1245.
Blute et al., "Use of Gleason score, prostate specific antigen, seminal vesicle and margin status to predict biochemical failure after radical prostatectomy," J Urol (2001) 165: 119-125.
Boormans et al., "Identification of TDRD1 as a Direct Target Gene of ERG in Primary Prostate Cancer," Int. J. Cancer (2013), 133(2):335-346, UICC.
Bostwick et al., "Prognostic factors in prostate cancer: College of American Pathologists consensus statement," Arch Pathol Lab Med (2000) 124(7):995-1000.
Bott et al., "Prostate cancer management: (2) an update on locally advanced and metastatic disease", Postgrad Med J, Dec. 3, 2003, 79(937), 643-645.
Brase et al., "TMPRSS2-ERG—specific transcriptional modulation is associated with prostate cancer biomarkers and TGF-β signaling," BMC Cancer (2011) 11(507):1-8.
Breiman, "Random Forests," Machine Learning (2001) 45:5-32.
Bueno et al., "A diagnostic test for prostate cancer from gene expression profiling data," J Urol, Feb. 2004; 171(2 Pt 1):903-6.
Bull et al., "Identification of potential diagnostic markers of prostate cancer and prostatic intraepithelial neoplasia using cDNA microarray," British J Cancer (Jun. 1, 2001) 84(11):1512-1519.
Cerutti et al. "Diagnosis of suspicious thyroid nodules using four protein biomarkers," Clin Cancer Res. (2006) 12(11 Pt 1):3311-8.
Che et al.: "Prognostic Value of Abnormal p53 Expression in Locally Advanced Prostate Cancer Treated With Androgen Deprivation and Radiotherapy: A Study Based on RTOG 9202"; International Journal of Radiation: Oncology Biology Physics (Nov. 15, 2007) vol. 69, No. 4, pp. 1117-1123.
Chen et al., "Deregulation of a Hox Protein Regulatory Network Spanning Prostate Cancer Initiation and Progression," Clin Cancer Res (Jun. 2012) 18(16):4291-4302.
Chen et al., "Hepsin and maspin are inversely expressed in laser capture microdissectioned prostate cancer," J Urol. (Apr. 2003) 169(4):1316-1319.
Chen et al., "Significance of noninvasive diagnosis of prostate cancer with cytologic examination of prostatic fluid," J Nippon Med Sch. (Jun. 2006) 73(3):129-135.
Chen et al.: "Molecular determinants of resistance to antiandrogen therapy"; Nature Medicine, Nature Publishing Group, New York, NY (Jan. 1, 2004) vol. 10, No. 1, pp. 33-39.
Cheng et al. "Cell Proliferation in Prostate Cancer Patients with Lymph Node Metastasis", Clin Cancer Res (Oct. 1999) 5(10): 2820-2823.
Cheung et al., "Natural variation in human gene expression assessed in lymphoblastoid cells," Nature Genetics (2003) vol. 33, pp. 422-425.
Cheville et at., "Gene Panel Model Predictive of Outcome in Men at High-Risk of Systemic Progression and Death From Prostate Cancer After Radical Retropubic Prostatectomy," Journal Of Clinical Oncology (Aug. 20, 2008) vol. 26 , No. 24.
Chifman et al., "Conservation of immune gene signatures in solid tumors and prognostic implications," BMC Cancer (2016) 16:911, pp. 1-17. DOI 10.1186/S12885-016-2948-Z.
Choi et al., Feb. 2014, Identification of distinct basal and luminal subtypes of muscle-invasive bladder cancer with different sensitivities to frontline chemotherapy, Cancer Cell, 25(2):152-165.
Cibas, et al. "The Bethesda System for Reporting Thyroid Cytopathology," Am J Clin Pathol. (Nov. 2009) 132(5):658-65. doi: 10.1309/AJCPPHLWMI3JV4LA.
Clancy et al., "Profiling networks of distinct immune-cells in tumors," BMC Bioinformatics (2016) 17:263, pp. 1-15. DOI 10.1186/s12859-016-1141-3.
Clark-Langone et al. "Riornarker discovery for colon cancer using a 761 gene RT-PCR assay 2007," BMC Genomics (2007) 8:279 pp. 1-18.
Cologne et al., "Optimal Case-Control Matching in Practice," Epidemiology Resources Inc. (1995) 6(3):271-275.
Cooper et al., "Mechanisms of Disease: biomarkers and molecular targets from microarray gene expression studies in prostate cancer ," Nat Clin Pract Urol. (2007) Dee:4(12):677-87.
Cooperberg et al., "The CAPRA-S score: A straightforward tool for improved prediction of outcomes after radical prostatectomy," Cancer (2011) vol. 117 (22), pp. 5039-5046.
Cordon-Cardo et al., "Improved prediction of prostate cancer recurrence through systems pathology," The Journal of Clinical Investigation (Jul. 2007) vol. 117, No. 7, pp. 1876-1883.
Couzin-Frankel, Jennifer, "As Questions Grow, Duke Halts Trials, Launches Investigation," Science (Aug. 6, 2010) vol. 329, pp. 614-615.
Cuzik et al., "Prognostic value of an RNA expression signature derived from cell cycle proliferation genes in patients with prostate cancer: a retrospective study," thelancet.com/oncology (Mar. 2011) vol. 12, pp. 245-255.
Dahlman et al., "Effect of androgen deprivation therapy on the expression of prostate cancer biomarkers MSMB and MSMB-binding protein CRISP3," Prostate Cancer and Prostatic Diseases (2010) 13:369-375.
Dalela et al., "Contemporary Role of the Decipher Test in Prostate Cancer Management: Current Practice and Future Perspectives," Rev. Urol. (2016), 18(1):1-9, MedReviews®, LLC.
Dalsgaard Sorensen et al.: "Discovery of prostate cancer biomarkers by microarray gene expression profiling"; Expert Review of Molecular Diagnostics, vol. 10, No. 1, Jan. 1, 2010, pp. 49-64.
D'Amico et al., "Cancer-specific mortality after surgery or radiation for patients with clinically localized prostate cancer managed during the prostate-specific antigen era," J Clin Oncol. (2003) 21:2163-2172.
D'Amico et al., "Determinants of prostate cancer-specific survival after radiation therapy for patients with clinically localized prostate cancer," J Clin Oncol. (2002) 20:4567-4573.
Dawood, Shaheenah, "Novel Biomarkers of Metastatic Cancer," Expert Rev. Mo/. Diagn. (2010) 10(5):581-590, Expert Reviews Ltd.
De Marzo et al., "Pathological and molecular mechanisms of prostate carcinogenesis: implications for diagnosis, detection, prevention, and treatment," J Cell Biochem. (Feb. 15, 2004) 91(3):459-477.
Demichelis et al., "TMPRSS2:ERG gene fusion associated with lethal prostate cancer in a watchful waiting cohort," Oncogene (2007) 26:4596-4599.
Den et al., Mar. 10, 2015, Genomic classifier indentifies men with adverse pathology after racial prostatectomy who benefit from adjuvant radiation therapy, Journal of Clinical Oncology, 33(8):944-951.
Dougherty, "The fundamental role of pattern recognition for gene-expression/microarray data in bioinformatics," Pattern recognition (2005) 38:2226-2228.
Eder et al., "Genes differentially expressed in prostate cancer," BJU Int. (May 2004) 93(8): 1151-1155.
Edwards et al., "Expression analysis onto microarrays of randomly selected cDNA clones highlights HOXB13 as a marker of human prostate cancer," Br J Cancer. (Jan. 31, 2005) 92(2):376-381.
Edwards et al.: "MicroRNAs and Ultraconserved Genes as Diagnostic Markers and Therapeutic Targets in Cancer and Cardiovascular Diseases", Journal of Cardiovascular Translational Research (May 5, 2010) vol. 3, No. 3, pp. 271-279.
Englisch, et al., "Chemically Modified Oligonucleotides as Probes and Inhibitors," Angew. Chem. Int. Ed. Eng. (1991) 30:613-629.
Epstein et al., "Prognostic factors and reporting of prostate carcinoma in radical AU prostatectomy and pelvic lymphadenectomy specimens," Scand. J. Urol. Nephrol. Suppl. (2005) 216:34-63.
Erho et al., "Discovery and Validation of a Prostate Cancer Genomic Classifier that Predicts Early Metastasis Following Radical Prostatectomy," PLoS ONE (2013) 8(6):e66855, 1-12.
Ernst et al., "Decrease and gain of gene expression are equally discriminatory markers for prostate carcinoma: a gene expression analysis on total and microdissected prostate tissue," Am J Pathol. (Jun. 2002) 160(6):2169-2180.

(56) References Cited

OTHER PUBLICATIONS

Etzioni et al. "The case for early detection", Nature Reviews | Cancer (Apr. 2003) vol. 3, pp. 1-10.
Fan et al., "Concordance among gene- expression-based predictors for breast cancer," N Engl J Med. (2006) 355:560-569.
Feng et al., "Luminal and basal subtyping of prostate cancer," *J Clin Oncol* (Feb. 20, 2017) vol. 35, No. 6, p. 3, Abstract.
Feroze-Merzoug et al., "Molecular profiling in prostate cancer," Cancer Metastasis Rev. 1 (2001) 20(3-4):165-71.
Fine et al., "A Proportional Hazards Model for the Subdistribution of a Competing Risk," Journal of the American Statistical Association (1999) vol. 94 (446), pp. 496-509.
Finley et al., "Advancing the molecular diagnosis of thyroid nodules: defining benign lesions by molecular profiling," Thyroid (2005) 15(6):562-8.
Finley et al., "Discrimination of benign and malignant thyroid nodules by molecular profiling," Ann Surg. (2004) 240(3):425-36; discussion 436-7.
Fodor et al., "Light-directed, spatially addressable parallel chemical synthesis," Science (Feb. 15, 1991) 251(4995):767-773.
Foley et al., "Molecular pathology of prostate cancer: the key to identifying new biomarkers of disease," Endocrine-Related Cancer (2004) 11:477-488.
Fontaine, et al., "Increasing the number of thyroid lesions classes in microarray analysis improves the relevance of diagnostic markers," PLoS One (Oct. 29, 2009) 4(10):e7632. doi: 10.1371/journal.pone.0007632.
Fryknas et al., "Molecular markers for discrimination of benign and malignant follicular thyroid tumors," Tumour Biol. (2006) 27(4):211-20.
Fujarewicz et al., "A multi-gene approach to differentiate papillary thyroid carcinoma from benign lesions: gene selection using support vector machines with bootstrapping," Endocr Relat Cancer (Sep. 2007) 14(3):809-26.
Gait. Chapter 16: Oligoribonucleotides. Antisense Research and Applications, Crooke and Lebleu Eds., CRC Press (1993) pp. 289-302.
Galamb et al., "Diagnostic mRNA Expression Patterns of Inflamed, Benign, and Malignant Colorectal Biopsy Specimen and their Correlation with Peripheral Blood Results," Cancer Epidemiology, Biomarkers & Prevention (Oct. 2008) 17(10):2835-2845.
Galavotti et al., Apr. 2012, The autophagy-associated factors DRAM1 and p62 regulate cell migration and invasion in glioblastoma stem cells, Oncogene, 32:699-712.
Gao et al., "VISTA is an inhibitory immune checkpoint that is increased after ipilimumab therapy in patients with prostate cancer," Nat Med. (May 2017) 23(5):551-555.
Garber et al., "Diversity of gene expression in adenocarcinoma of the lung," PNAS (Nov. 20, 2001) vol. 98, No. 24, pp. 13784-13789.
Genevieve de Saint Basile et al., "Severe Combined Immunodeficiency Caused By Deficiency In Either The Ii Or the E Subunit Of CD3," Journal of Clinical Investigation (2004) vol. 114, No. 10. p. 1512-1517.
Gibb et al., "The functional role of long non-coding RNA in human carcinomas", Molecular Cancer, Biomed Central, London, GB (Apr. 13, 2011) vol. 10, No. 1, p. 38.
Giordano et al., "Organ-Specific Molecular Classification of Primary Lung, Colon, and Ovarian Adenocarcinomas Using Gene Expression Profiles," Am J Pathol (2001) 159(4): 1231-1238.
Gleason: "Histologic grading and clinical staging of prostatic carcinoma", Urologic pathology: the prostate, (Tannenbaum, ed.) (1977) Lea & Febiger, Philadelphia, PA, pp. 171-197.
Gleason: "Histologic grading of prostate cancer: a perspective"; Hum. Pathol. (1992) 23(3):273-279.
Gleave et al., "Randomized comparative study of 3 versus 8-month neoadjuvant hormonal therapy before radical prostatectomy: biochemical and pathological effects," J Urol. (2001) 166:500-507.
Glinsky et al., "Gene expression profiling predicts clinical outcome of prostate cancer," J Clin Investigation (2004) 113(6):913-923.
Glinsky et al., "Microarray analysis identifies a death-from-cancer signature predicting therapy i failure in patients with multiple types of cancer," J Clin Invest. (2005) 115: 1503-1521.
Gonzalgo et al: "Molecular pathways to prostate cancer"; J Urol. (2003) 170(6 Pt 1):2444-2452.
Grambsch et al., "Proportional Hazards Tests and Diagnostics Based on Weighted Residuals," Biometrika (2013) vol. 81 (3), pp. 515-526.
Greenbaum et al.: "Comparing protein abundance and mRNA expression levels on a genomic scale"; Genome Biology (2003) 4(9):117.1-117.8.
Griffith et al., "Meta-analysis and meta-review of thyroid cancer gene expression profiling studies identifies important diagnostic biomarkers," J Clin Oncol. (2006) 24(31):5043-51.
Griffith, et al. Biomarker panel diagnosis of thyroid cancer: a critical review. Expert Rev Anticancer Ther. (Sep. 2008) 8(9):1399-413. doi: 10.1586/14737140.8.9.1399.
Haiman et al.: "Multiple regions within 8q24 independently affect risk for prostate cancer"; Nat Genet. (2007) 39:638-644.
Hamada et al., "Diagnostic usefulness of PCR profiling of the differentially expressed marker genes in thyroid papillary carcinomas," Cancer Lett. (Jun. 28, 2005) 224(2):289-301. Epub Nov. 18, 2004.
Heagerty et al., "Time-Dependent ROC Curves for Censored Survival Data and a Diagnostic Marker," Biometrics (2000) vol. 56 (2), pp. 337-344.
Heemers, H. V. et al.: "Identification of a Clinically Relevant Androgen-Dependent Gene Signature in Prostate Cancer"; Cancer Research, vol. 71, No. 5 (2011) pp. 1978-1988.
Heidenreich et al., "EAU Guidelines on Prostate Cancer. Part 1: Screening, Diagnosis, and Treatment of Clinically Localised Disease," European Urology (2011) vol. 59, pp. 61-71.
Henrotin et al.: "Type II collagen peptides for measuring cartilage degradation," Biotheology (2004) 41 (3 -4): Abstract.
Henshall et al., "Survival Analysis of Genome-Wide Gene Expression Profiles of Prostate ancers Identifies New Prognostic Targets of Disease Relapse," Cancer Research (Jul. 15, 2003) 63, 14196-4203.
Holzbeierlein et al., "Gene expression analysis of human prostate carcinoma during hormonal therapy identifies androgen-responsive genes and mechanisms of therapy resistance," Am. J . Pathol. (Jan. 2004) 164(1):217-227.
Hornberger et al., "A Multigene Prognostic Assay for Selection of Adjuvant Chemotherapy in Patients with T3, Stage II Colon Cancer: Impact on Quality-Adjusted Life Expectancy and Costs," Value In Health 15 (2012) pp. 1014-1021.
Hughes et al., "Molecular pathology of prostate cancer," J Clin Pathol. (Jul. 2005) 58(7):673-684.
Hughes et al., "Topoisomerase II—a expression increases with increasing Gleason score and with hormone insensitivity in prostate carcinoma," J Clin Pathol. (Jul. 2006) 59(7): 721-724.
Humphrey et al: "Histologic grade, DNA ploidy, and intraglandular tumor extent as indicators of tumor progression of clinical Stage B prostatic carcinoma"; Am J Surg Pathol (1991) 15(12):1165-1170.
Ida et al., "Topoisomerase II alpha protein expression Is predictive of outcome in Gleason score 7 prostate cancer patients treated surgically and is dependent on ERG status." Mod Pathol. (Feb. 2010) Abstract 1895, 23 : 424A-425A.
Ito et al., "Linkage of elevated ets-2 expression to hepatocarcinogenesis," Anticancer Research (2002) 22(4):2385-2389.
Jemal et al.: "Cancer statistics," CA Cancer J Clin. (2005) 55:10-30.
Jenkins et al., "Prognostic significance of ailetic imbalance of chromosome arms 71, 8p, 16q, and 18q in stage T3NOMO prostate cancer," Genes, Chromosomes & Cancer (1998) 21:131-143.
Jhavar et al., "Integration of ERG gene mapping and gene-expression profiling identifies distinct categories of human prostate cancer," BJUI (2008) vol. 103 (9), pp. 1256-1269.
Jhavar et al., "Technical Advance: Detection of TMPRSS2-ERG Translocations in Human Prostate Cancer by Expression Profiling Using GeneChip Human Exon 1.0 ST Arrays," J Mol. Diag (Jan. 2008) vol. 10, No. 1, pp. 50-57.
Kanehisa, "Use of statistical criteria for screening potential homologies in nucleic acid sequences," Nucleic Acids Res. (Jan. 11, 1984) 12(1 Pt 1):203-13.

(56) References Cited

OTHER PUBLICATIONS

Karan et al., "Current status of the molecular genetics of human prostatic adenocarcinomas," Int J Cancer, 2003, 103(3):285-293.
Karayi et al., "Molecular biology of prostate cancer," Prostate Cancer Prostatic Dis. (2004) 7(1):6-20.
Karnes et al., "Radical prostatectomy for high-risk prostate cancer," Jpn. J. Clin. Oneal. (Oct. 19, 2009) 40 (1): 3-9, Epub.
Karnes et al., "The ability of biomarkers to predict systemic progression in men with high-risk prostate cancer treated surgically is dependent on ERG status," Cancer Res. (Nov. 9, 2010) 70(22):8994-9002, Epub.
Kasraeian, et al. , "A comparison of fine-needle aspiration, core biopsy, and surgical biopsy in the diagnosis of extremity soft tissue masses," Clin Orthop Relat Res. (Nov. 2010) 468(11):2992-3002.
Kawamorita et al., "Radical prostatectomy for high-risk prostate cancer: Biochemical outcome," International Journal of Urology (2009) 16:733-738.
Kebebew et al., "Diagnostic and extent of disease multigene assay for malignant thyroid neoplasms," Cancer (2006) 106(12):2592-7.
Kestin, "Potential survival advantage with early androgen deprivation for biochemical failure after external beam radiotherapy: the importance of accurately defining biochemical disease status," Int J Rad Oncol Biol Phys. (2004) 60:453-62.
Khor et al.: "Bcl-2 and Bax Expression Predict Prostate Cancer Outcome in Men Treated with Androgen Deprivation and Radiotherapy on Radiation Therapy Oncology Group Protocol 92-02"; Clinical Cancer Research (Jun. 15, 2007) vol. 13, No. 12, pp. 3585-3590.
Kiessling, et al., "D-TMPP: A novel androgen-regulated gene preferentially expressed in prostate and prostate cancer that is the first characterized member of an eukaryotic gene family," The Prostate (2005) 64:387-400.
Kikuchi et al., "Expression profiles of non-small cell lung cancers on cDNA microarrays: identification of genes for prediction of lymph-node metastasis and sensitivity to anti-cancer drugs," Oncogene (2003) 22, pp. 2192-2205.
Kishi et al., "Expression of the surviving gene in prostate cancer: correlation with clinicopathological characteristics, proliferative activity and apoptosis," J Urol. (May 2004) 171(5): 1855-1860.
Klee et al., "Candidate Serum Biomarkers for Prostate Adenocarcinoma identified by mRNA Differences in Prostate Tissue and Verified with Protein Measurements in Tissue and Blood," Clinical Chemistry (2012) 58(3):599-609.
Kosari et al., "Identification of biomarkers for prostate cancer," Clin. Cancer Res. (2008) 1734-1743.
Koshkin et al., "LNA (locked nucleic acids): An RNA mimic forming exceedingly stable LNA," LNA duplexes. J Am Chem Soc (1998) 120:13252-13253.
Koshkin et al., "LNA (locked nucleic acids): synthesis of the adenine, cytosine, guanine 5-methylcytosine, thymine and uracil bicyclonucleoside monomers, oligomerisation, and unprecedented nucleic acid recognition," Tetrahedron (1998) 54(14):3607-3630.
Kroschwitz The Concise Encyclopedia Of Polymer Science And Engineering (1990) (pp. 858-859).
Kube et al., "Optimization of laser capture microdissection and RNA amplification for gene expression profiling of prostate cancer," BMC Mol. Biol. (2007) 8:25.
Kumar, et al., "The first analogues of LNA (locked nucleic acids): phosphorothioate-LNA and 2'-thio-LNA," Bioorg Med Chem Lett. (Aug. 18, 1998) 8(16):2219-22.
Kumar-Sinha et al., "Molecular markers to identify patients al risk for recurrence after primary treatment for prostate cancer," Urology, 62 Suppl 1:19-35, Dec. 29, 2003.
Landers et al.: "Use of multiple biomarkers for a molecular diagnosis of prostate cancer"; Int. J. Cancer (May 10, 2005) 114 pp. 950-956.
Lapointe et al., "Gene expression profiling identifies clinically relevant subtypes of prostate cancer," PNAS USA (2004) 101:811-816.
Latulippe et al., "Comprehensive Gene Expression Analysis of Prostate Cancer Reveals Distinct Transcriptional Programs Associated with Metastatic Disease," Cancer Res. (2002) 62:4499-4506.
Lawton et al., "Updated results of the phase III Radiation Therapy Oncology Group (RTOG) trial 85-31 evaluating the potential benefit of androgen suppression following standard radiation therapy for unfavorable prognosis carcinoma of the prostate," Int J Rad Oncol Biol Phys. (2001) 49:937-946.
Leyten et al., "Identification of a Candidate Gene Panel for the Early Diagnosis of Prostate Cancer," Clinical Cancer Research (2015) 21(13):3061-3070.
Lin et al., "Cox Regression with Incomplete Covariate Measurements," Journal of the American Statistical Association (1993) vol. 88 (424), pp. 1341-1349.
Liong et al., "Blood-Based Biomarkers of Aggressive Prostate Cancer," PLoS ONE (Sep. 2012) vol. 7, Issue 7, e45802, pp. 1-7.
Liu et al., 2014, Synergistic killing of lung cancer cells by cisplatin and radiation via autophagy and apoptosis, Oncology Letters, 7:1903-1910.
Livingston et al., "*Homo sapiens* CDC20 Cell Division Cycle 20 Homolog (CDC20)," Gene (Apr. 24, 2006).
Lockstone, "Exon array data analysis using Affymetrix power tools and R statistical software," Briefings in bioinformatics (2011) vol. 12 (6), pp. 634-644.
Lunardi et al., "A co-clinical approach identified mechanisms and potential therapies for androgen deprivation resistance in prostate cancer," Nature Genetics (Jul. 2013) vol. 45, No. 7, pp. 747-757.
Luo et al., "Gene expression analysis of prostate cancers," Molecular Carcinogenesis (Jan. 2002) 33(1):25-35.
Luo et al., "Human Prostate Cancer and Benign Prostatic Hyperplasia : Molecular Dissection by Gene Expression Profiling," Cancer Res. (2001) 61:4683-4688.
Magee et al., "Expression Profiling Reveals Hepsin Overexpression in Prostate Cancer," Cancer Res. (2001) 61:5692-5696.
Martens-Uzunova, E. S. et al.: "Diagnostic and prognostic signatures from the small non-coding RNA transcriptome in prostate cancer", Oncogene (Jul. 18, 2011) vol. 31, No. 8, pp. 978-991.
Martin, "A New Access to 2'-O-Alkylated Ribonucleosides and Properties of 2'-O-Alkylated Oligoribonucleotides," Helv. Chim. Acta. (1995) 78:486-504. (in German with English abstract).
Mazzanti, et al., "Using gene expression profiling to differentiate benign versus malignant thyroid tumors," Cancer Res. (Apr. 15, 2004) 64(8):2898-903.
McCall et al., "Frozen robust multiarray analysis (fRMA)", Biostatistics (2010) vol. 11 (2), 242-253.
McConkey et al., Apr. 2015, Therapeutic opportunities in the intrinsic subtypes of muscle-invasive bladder cancer, Hematology/Oncology Clinics of North America, 29(2):377-394.
McConkey et al., May 2016, A prognostic gene expression signature in the molecular classification of chemotherapy-naïve urothelical cancer is predictive of clinical outcomes from neoadjuvant chemotherapy: a phase 2 trial of dose-dense methotrexate, vinblastine, doxorubicin, and cisplatin with bevacizumab in urothelial cancer, European Urology, 69(5):855-862.
Mendiratta et al., "Genomic signatures associated with the development, progression, rand outcome of prostate cancer," Molecular diagnosis & therapy (2007) 11(6):345-54.
Mercer, DW, "Use of multiple markers to enhance clinical utility", Immunol Ser. (1990) 53: 39-54.
Mineva et al., "Differential expression of alphaB-crystallin and Hsp27-1 in anaplastic thyroid carcinomas because of tumor-specific alphaB-crystallin gene (CRYAB) silencing." Cell Stress Chaperones (Autumn 2005) 10(3):171-84.
Montironi et al., "Carcinoma of the prostate: inherited susceptibility, somatic gene defects and androgen receptors," Virchows Arch. (Jun. 2004) 444(6):503-508.
Moul et al., "Early versus delayed hormonal therapy for prostate specific antigen only recurrence of prostate cancer after radical prostatectomy," J Urol. (2004) 171:1141-1147.
Moul, "Prostate specific antigen only progression of prostate cancer," J Urol. (2000) 163:1632-42.

(56) References Cited

OTHER PUBLICATIONS

Mühlenbruch et al., "Multiple imputation was a valid approach to estimate absolute risk from a prediction model based on case-cohort data," Journal of Clinical Epidemiology (2017) 84:130-141.
Nakagawa et al., "A Tissue Biomarker Panel Predicting Systemic Progression after PSA Recurrence Post-Definitive Prostate Cancer Therapy," PLos ONE (2008) 3(5):e2318, 14 pages.
Nelson, "Predicting prostate cancer behavior using transcript profiles," J Urol. (Nov. 2004) 172(5 Pt 2):S28-32; discussion S33.
Newson, Roger, "Confidence intervals for rank statistics: Somers' D and extensions," The Stata Journal (Sep. 2006) 6(3):309-334.
Nielsen et al., "Sequence-selective recognition of DNA by strand displacement with a thymine-substituted polyamide," Science (1991) 254: 1497-1500.
Noordzij et al. "The prognostic value of CD44 isoforms in prostate cancer patients treated by radical prostatectomy", Clin Cancer Res (May 1997) 3(5): 805-815.
Norman, James, "Thyroid Nodule Ultrasound", Endocrine website (Updated Oct. 13, 2010) http://www.endocrineweb.com/noduleus.html.
Ohl et al., "Gene expression studies in prostate cancer tissue: which reference gene should be selected for normalization?," J. Mol. Med . (2005) 83(12):1014-1024.
Ong et al., "Expression Profiling Identifies a Novel-Methylacyl-CoA Racemase Exon with Fumarate Hydratase Homology," Cancer Research (Jun. 15, 2003) 63:3296-3301.
Ozen et al., Sep. 24, 2007, Widespread deregulation of microRNA expression in human prostate cancer, Oncogene, 27:1788-1793.
Parker et al., "High expression levels of surviving protein independently predict a poor outcome for patients who undergo surgery for clear cell renal cell carcinoma," Cancer (2006) 107:37-45.
Pascal et al., "Correlation of mRNA and protein levels: Cell type-specific gene expression of cluster designation antigens in the prostate," BMC Genomics (2008) 9:246 (13 pages).
Patel et al., "Preoperative PSA velocity is an independent prognostic factor for relapse after radical prostatectomy," J Clin Oncol. (2005) 23:6157-6162.
Paulo et al., "Molecular Subtyping of Primary Prostate Cancer Reveals Specific and Shared Target Genes of Different ETS Rearrangements," Neoplasia (Jul. 2012) 14(7):600-611.
Penney et al., "mRNA Expression Signature of Gleason Grade Predicts Lethal Prostate Cancer," J Clin Oncol (Jun. 10, 2011) vol. 29, No. 17, pp. 2391-2396 and Appendix.
Pereira et al., "Coagulation factor V and VIIN ratio as predictors of outcome in paracetamol induced fulminant hepatic failure: relation to other prognostic indicators," Gut (1992) 33:98-102.
Perez et al., "Long, abundantly expressed non-coding transcripts are altered in cancer," Human Molecular Genetics (2008) vol. 17, No. 5, pp. 642-655. Published online Nov. 15, 2007.
Pienta et al. "The current state of preclinical prostate cancer animal models"; Prostate (2008) 69: 629-639.
Pilepich et al., "Phase III radiation therapy oncology group (RTOG) trial 86-10 of androgen deprivation adjuvant to definitive radiotherapy in locally advanced carcinoma of the prostate," Int. J. Radiation Oncology Biol. Phys. (2001) vol. 50, No. 5, pp. 1243-1252.
Pinover et al., "Validation of a treatment policy for patients with prostate specific antigen failure after three-dimensional conformal prostate radiation therapy," Cancer (Feb. 15, 2003) vol. 97, No. 4, pp. 1127-1133.
Pittoni et al., "The Dark Side of Mast Cell-Targeted Therapy in Prostate Cancer," Cancer Res. (2012) 72(4):831-835.
Porkka et al., "RAD21 and KIAA0196 at 8q24 are amplified and overexpressed in prostate cancer," Genes Chromosomes Cancer (2007) 39:1-10.
Porkka et al: Molecular mechanisms of prostate cancer; Eur Urol. (2004) 45(6):683-691.
Pound et al., "Natural history of progression after PSA elevation following radical prostatectomy," JAMA (1999) 281:1591-1597.
Prasad et al., "Identification of genes differentially expressed in benign versus malignant thyroid tumors," Clin Cancer Res. (2008) 14(11):3327-37.
Probe Set Listing for the Affymetrix Human Genome U133 Plus 2.0 array (Accessed from https://www.affymetrix.com/analysis/index.affx on Jul. 1, 2015) (Year: 2015).
Puskas, et al., "Gene profiling identifies genes specific for well-differentiated epithelial thyroid tumors," Cell Mol Biol (Noisy-le-grand) (Sep. 5, 2005) 51(2):177-86.
Reddy et al., "Clinical utility of microarray-derived genetic signatures in predicting outcomes in prostate cancer," Clinical Genitourinary Cancer (2006) 5(3):187-189.
Rhodes et al., "Large-scale meta-analysis of cancer microarray data identifies common transcriptional profiles of neoplastic transformation and progression," Proc Nat Acad Sci USA (2004) 101:9309-9314.
Rhodes et al., "Multiplex biomarker approach for determining risk of prostatespecific antigen-defined recurrence of prostate cancer," J Nat Cancer Inst. (May 7, 2003) vol. 95, No. 9, pp. 661-668.
Rhodes et al., "Oncomine: A Cancer Microarray Database and Integrated Data-Mining Platform," Neoplasia (2004) 6:1-6.
Robertson et al., "DNA in radical prostatectomy specimens. Prognostic value of tumor ploidy," Acta Oncologica (1991) 30(2):205-207.
Robinson et al., "A dynamic programming approach for the alignment of signal peaks in multiple gas chromatography-mass spectrometry experiments," BMC Bioinformatics (2007) 8.1:419.
Robinson, et al., "A comparison of Affymetrix gene expression arrays," BMC Bioinformatics (Nov. 15, 2007) 8:449.
Romanuik et al., "LNCaP Atlas: Gene expression associated with in vivo progression to castration-recurrent prostate cancer," GMB Medical Genomics (2010) 3:43, pp. 1-19.
Ross et al., "Tissue-based Genomics Augments Post-prostatectomy Risk Stratification in a Natural History Cohort of Intermediate- and High-Risk Men," European Urology 69 (2016) pp. 157-165.
Rotblat et al., "A Possible Role for Long Non-Coding RNA in Modulating Signaling Pathways," Med. Hvpotheses (2011) 77:962-965, Elsevier.
Rotunno et al., "A Gene Expression Signature from Peripheral Whole Blood for Stage I Lung Adenocarcinoma," Cancer Prevention Research (Jul. 8, 2011) 4(10) 1599-1607.
Rubin et al., "Molecular genetics of human prostate cancer," Modern Pathol. (2004) 17(3):380-388.
Saito-Hisaminato et al., "Genome-Wide Profiling of Gene Expression in 29 Normal Human Tissues with a cDNA Microarray," DNA Research (2002) vol. 9, pp. 35-45.
Saligan et al., "Supervised Classification by Filter Methods and Recursive Feature Elimination Predicts Rick of Radiotherapy-Related Fatigue in Patients with Prostate Cancer," Cancer Informatics (2014) 13: 141-152.
Sandler et al., "Overall survival after prostate-specific-antigen-detected recurrence following conformal radiation therapy," Int J Rad Oncol Biol Phvs. (2000) 48:629-633.
Sanghvi, "Heterocyclic base modifications in nucleic acids and their applications in antisense oligonucleotides in Antisense Research and Applications," Crooke, S. T. and Lebleu, B., ed., CRC Press. (1993) Ch 15 274-285.
Saramaki et al., "Amplification of EIF3S3 gene is associated with advanced stage in prostate cancer," Am J Pathol. (2001) 159:2089-2094.
Sato et al., "Clinical significance of alterations of chromosome 8 in high-grade, advanced, nonmetastatic prostate carcinoma," J Natl Cancer Inst. (1999) 91:1574-1580.
Savinainen et al., "Expression and copy number analysis of TRPS 1, EIF3S3 and MYC genes in breast and prostate cancer," Br J Cancer (2004) 90: 1041-1046.
Savinainen et al., "Over expression of EIF3S3 promotes cancer cell growth," The Prostate (2006) 66: 1144-1150.
Schlomm et al., "Molecular staging of prostate cancer in the year 2007," World .J. Urol. (Mar. 2007) 25(1):19-30.
Schmidt et al., "Lack of interferon consensus sequence binding protein (ICSBP) transcripts in human myeloid leukemias," Blood (1998) 91:22-29.

(56) References Cited

OTHER PUBLICATIONS

Schumacher et al., "A Common 8q24 Variant in Prostate and Breast Cancer from a Large Nested Case-Control Study," Cancer Res. (2007) 67:2951-2956.
Seiler et al., Oct. 2017, Impact of molecular subtypes in muscle-invasive bladder cancer on predicting response and survival after neoadjuvant chemotherapy, European Urology, 72(4):544-554.
Severi et al., "The Common Variant rs1447295 on Chromosome 8q24 and Prostate Cancer Risk: Results from an Australian Population-based Case-Control Study", Cancer Epidemiology, Biomarkers & Prevention (2007) 16:610-611.
Shariat et al., "An updated catalog of prostate cancer predictive tools," Cancer (2008) 113(11):3062-6.
Shariat et al., "Surviving expression is associated with features of biologically aggressive prostate carcinoma," Cancer (2004) 100(4): 751-757.
Shibru et al., "Does the 3-gene diagnostic assay accurately distinguish benign from malignant thyroid neoplasms?" Cancer (Sep. 1, 2008) 113(5):930-5. doi: 10.1002/cncr.23703.
Shipley et al., "Radiation therapy for clinically localized prostate cancer: a multi-institutional pooled analysis," JAMA (1999) 281:1598-1604.
Singh et al., "Gene expression correlates of clinical prostate cancer behavior," Cancer Cell (Mar. 2002) vol. 1, pp. 1203-1209.
Singh et al., "LNA (locked nucleic acids): synthesis and high-affinity nucleic acid recognition," Chem Commun (1998) 4:455-456.
Singh et al., "Synthesis of 2'-amino-LNA: A novel conformationally restricted high-affinity oligonucleotide analogues with a handle," J Org Chem (1998) 63:10035-10039.
Smit et al., "High-Resolution ERG-Expression Profiling on GeneChip Exon 1.0 ST Arrays in Primary and Castration-Resistant Prostate Cancer," *BJU International* (2013), 111(5):836-842, BJU International.
Solo et al., "Prevalence of prostate cancer (PC) clinical states (CS) in the United States: Estimates using a dynamic progression model," ASCO Annual Meeting, Journal of Clinical Oncology (May 20, 2011) vol. 29, No. 15, Abstract 4637.
Stamey et al., "Molecular genetic profiling of Gleason grade 415 prostate cancers compared to benign prostatichyperplasia," J Urol. (2001) 166(6):2171-2177.
Stanbrough et al., "Increased Expression of Genes Converting Adrenal Androgens to Testosterone in Androgen-Independent Prostate Cancer," Cancer Res (Mar. 1, 2006) 66(5):2815-2825.
Stephenson et al., "Integration of gene expression profiling and clinical variables to predict prostate carcinoma recurrence after radical prostatectomy," Cancer (Jul. 15, 2005) 104(2):290-298.
Stephenson et al., "Postoperative Nomogram Predicting the 10-Year Probability of Prostate Cancer Recurrence After Radical Prostatectomy," J Clin Oncol (2008) vol. 23 (28), pp. 7005-7012.
Subramanian et al., "Gene set enrichment analysis: A knowledge-based approach for interpreting genome-wide expression profiles," PNAS USA (2005) 102:15545-15550.
Takayama et al., "TACC2 Is an Androgen-Responsive Cell Cycle Regulator Promoting Androgen-Mediated and Castration-Resistant Growth of Prostate Cancer," Mol Endocrinol (May 2012) 26(5):748-761.
Talantov et al., "Gene Based Prediction of Clinically Localized Prostate Cancer Progression After Radical Prostatectomy," The Journal Of Urology (Oct. 2010) vol. 184, 1521-1528.
Taylor et al., "Integrative genomic profiling of human prostate cancer," Cancer Cell (Jul. 13, 2010) vol. 18 (1), pp. 11-22.
Thompson et al., "Adjuvant and Salvage Radiotherapy After Prostatectomy: AUA/ASTRO Guideline," J Urol. (2013) 190(2):441-449.
Thompson et al., "Is the GPSM scoring algorithm for patients with prostate cancer valid in the contemporary era?" J Urol. (Aug. 2007) vol. 178 (2), 459-463.

Thorsen et al., "Alternative Splicing in Colon, Bladder, and Prostate Cancer Identified by Exon Array Analysis," Molecular & Cellular Proteomics (Mar. 18, 2008) vol. 7, No. 7, pp. 1214-1224.
Tockman et al., "Considerations in bringing a cancer biomarker to clinical application," Cancer Research (1992) 52:2711-2718.
Tollefson et al., "Stratification of Patient Risk Based on Prostate-Specific Antigen Doubling Time After Radical Retropubic Prostatectomy," Mayo Clin Proc. (2007) 82:422-427.
Tomlins et al., "Integrative molecular concept modeling of prostate cancer progression," Nat Genet. (2007) 39:41-51.
Tomlins et al., "Recurrent Fusion of TMPRSS2 and ETS Transcription Factor Genes in Prostate Cancer," Science (2005) 310(5748):644-648.
Tomlins et al., "TMPRSS2:ETV4 Gene Fusions Define a Third Molecular Subtype of Prostate Cancer," Cancer Res. (2006) 66:3396-3400.
Tricoli et al., "Detection of prostate cancer and predicting progression: current and future diagnostic markers," Clinical Cancer Research (Jun. 15, 2004) 10:3943-3953.
True et al., "A molecular correlate to the Gleason grading system for prostate adenocarcinoma," PNAS (Jul. 18, 2006) vol. 103, No. 29, pp. 10991-10996.
Tsuchiya et al., "Clinical significance in situ hybridization analysis in pathologic of alterations of chromosome 8 detected by fluorescence organ-confined prostate cancer," Genes Chromosomes Cancer (2002) 34:363-371.
Tsuchiya et al., "Mapping and gene expression profile of the minimally overrepresented 8q24 region in prostate cancer," Am J Pathol. (May 2002) 160(5):1799-1806.
Vanaja et al., "PDLIM4 Repression by Hypermethylation as a Potential Biomarker for Prostate Cancer," Clin. Cancer Res. (2006) 12(4):1128-1136.
Vanaja et al., "Transcriptional Silencing of Zinc Finger Protein 185 Identified Profiling Is Associated with Prostate Cancer Progression," Cancer Research (Jul. 15, 2003) 63:3877-3882.
Varambally et al., "Integrative Genomic and Proteomic Analysis of Prostate Cancer Reveals Signatures of Metastatic Progression," Cancer Cell (Nov. 2005) 8(5):393-406.
Varricchi et al., "Are Mast Cells MASTers in Cancer?" Front Immunol. ePub (Apr. 12, 2017) 8:424.
Vickers et al., "Extensions to decision curve analysis, a novel method for evaluating diagnostic tests, prediction models and molecular markers, BMC Medical Informatics and Decision Making," (2008) 8(53):1-17.
Visakorpi, "The molecular genetics of prostate cancer," Urology (2003) 62(5 Suppl 1):3-10.
Wang et al., "RNA-Seq: a revolutionary tool for transcriptomics," Nature Reviews/Genetics (Jan. 2009) vol. 10, pp. 57-63.
Wang et al., "Two common chromosome 8q24 variants are associated with increased risk for prostate cancer," Cancer Res. (2007) 67:2944-2950.
Watson et al., "Future opportunities for the diagnosis and treatment of prostate cancer," Prostate Cancer Prostatic Dis. (2004) 7:S8-S13.
Weber et al., "The prognostic value of expression of HIF1[alpha], EGFR and VEGF-A, in localized prostate cancer for intermediate- and high-risk patients treated with radiation therapy with or without androgen deprivation therapy," Radiation Oncology (Apr. 30, 2012) vol. 7, No. 66, 8 pages.
Welsh et al., "Analysis of Gene Expression Identifies Candidate Markers and Pharmacological Targets in Prostate Cancer," Cancer Res. (Aug. 15, 2001) 61:5974-5978.
Willman et al., "Immunohistochemical staining for DNA topoisomerase II-alpha in benign, premalignant, and malignant lesions of the prostate," Prostate (Mar. 1, 2000) 42(4):280-286.
Winkler et al.: "Stage D1 prostatic adenocarcinoma: significance of nuclear DNA ploidy patterns studied by flow cytometry," Mayo Clin Proc. (1988) 63(2): 103-112.
Wyatt et al., "Heterogeneity in the inter-tumor transcriptome of high risk prostate cancer," *Genome Biology* (Aug. 26, 2014) vol. 15, No. 8, pp. 2-14.
Yates et al., "X:Map: annotation and visualization of genome structure for Affymetrix exon array analysis," Nucleic Acids Res. (2008) vol. 36:D780-D786.

(56) References Cited

OTHER PUBLICATIONS

Yeager et al., "Genome-wide association study of prostate cancer identifies a second risk locus at 8q24," Nat Genet (2007) 39:645-649.
Yu et al., "Gene expression alterations in prostate cancer predicting tumor aggression and preceding development of malignancy," J Clin Oncol. (Jul. 15, 2004) 22(14):2790-2799.
Yukinawa et al., "A multi-class predictor based on a probabilistic model: application to gene expression profiling-based diagnosis of thyroid tumors," BMC Genomics (Jul. 27, 2006) 7:190.
Zanetta et al., "Flow-cytometric analysis of deoxyribonucleic acid content in advanced ovarian carcinoma: its importance in long-term survival," Am J Obstet Gynecol (1996) 175(5): 1217-1225.
Zelefsky et al., "High dose radiation delivered by intensity modulated conformal radiotherapy improves the outcome of localized prostate cancer," The Journal of Urology (Sep. 2001) 166(3):876-881.
Zelefsky et al., "Neoadjuvant hormonal therapy improves the therapeutic ratio in patients with bulky prostatic cancer treated with three-dimensional conformal radiation therapy," Int J Radiat Oncol Biol Phvs. (1994) 29:755-761.
Zhao et al., "Development and validation of a 24-gene predictor of response to postoperative radiotherapy in prostate cancer: a matched, retrospective analysis," Lancet Oncol (2016) 17, pp. 1612-1620.
GenBank Accession No. AA462934 dated Jun. 10, 1997, 2 pages.
GenBank Accession No. AA920095 dated Apr. 20, 1998, 2 pages.
GenBank Accession No. AB028840 dated Jan. 12, 2000, 2 pages.
GenBank Accession No. AB030836 dated Oct. 23, 1999, 2 pages.
GenBank Accession No. AB036741 dated Dec. 22, 2000, 3 pages.
GenBank Accession No. AF077349 dated Dec. 14, 2000, 2 pages.
GenBank Accession No. AF077351 dated Dec. 20, 2000, 3 pages.
GenBank Accession No. AF115517 dated Nov. 23, 2005, 4 pages.
GenBank Accession No. AI413910 dated Feb. 9, 1999, 2 pages.
GenBank Accession No. AI414999 dated Feb. 9, 1999, 2 pages.
GenBank Accession No. AI425960 dated Mar. 9, 1999, 2 pages.
GenBank Accession No. AI851940 dated Jul. 15, 1999, 2 pages.
GenBank Accession No. AK018022 dated Sep. 19, 2008, 4 pages.
GenBank Accession No. AK019341 dated Sep. 19, 2008, 3 pages.
GenBank Accession No. AK019342 dated Sep. 19, 2008, 3 pages.
GenBank Accession No. AK034387 dated Sep. 19, 2008, 4 pages.
GenBank Accession No. AK038229 dated Sep. 19, 2008, 4 pages.
GenBank Accession No. AK038434 dated Sep. 19, 2008, 4 pages.
GenBank Accession No. AK041534 dated Sep. 19, 2008, 4 pages.
GenBank Accession No. AK042683 dated Sep. 19, 2008, 4 pages.
GenBank Accession No. AK136096 dated Sep. 19, 2008, 4 pages.
GenBank Accession No. AK136101 dated Sep. 19, 2008, 4 pages.
GenBank Accession No. AK142768 dated Sep. 19, 2008, 3 pages.
GenBank Accession No. AL591433 dated Jan. 15, 2009, 56 pages.
GenBank Accession No. BC004702 dated Jul. 15, 2006, 3 pages.
GenBank Accession No. BC055737 dated Jul. 15, 2006, 2 pages.
GenBank Accession No. BC086799 dated Sep. 21, 2006, 3 pages.
GenBank Accession No. BF449664 dated Dec. 1, 2000, 1 page.
GenBank Accession No. BG063957 dated Jan. 26, 2001, 2 pages.
GenBank Accession No. BG077309 dated Dec. 17, 2003, 2 pages.
GenBank Accession No. BM114282 dated Jan. 30, 2002, 2 pages.
GenBank Accession No. BY023910 dated Dec. 6, 2002, 2 pages.
GenBank Accession No. CN724527 dated May 18, 2004, 2 pages.
GenBank Accession No. NM_000130 dated Oct. 18, 2009, 6 pages.
GenBank Accession No. NM_000493 dated Mar. 15, 2009, 4 pages.
GenBank Accession No. NM_000598, GI No. 62243067 , dated Jun. 6, 2010, 5 pages.
GenBank Accession No. NM_000688, GI No. 40316942, dated Apr. 11, 2010, 5 pages.
GenBank Accession No. NM_001013398; GI No. 62243247, dated Jun. 6, 2010, 5 pages.
GenBank Accession No. NM_001034 dated Oct. 5, 2009, 5 pages.
GenBank Accession No. NM_001039573, GI No. 221316683, dated Mar. 4, 2010, 5 pages.
GenBank Accession No. NM_001049 dated Jun. 21, 2009, 4 pages.
GenBank Accession No. NM_001067 dated Oct. 18, 2009, 5 pages.
GenBank Accession No. NM_001098533, GI No. 237858579, dated May 7, 2010, 5 pages.
GenBank Accession No. NM_001130851; GI No. 195927024, dated Mar. 5, 2010, 4 pages.
GenBank Accession No. NM_001136154 dated Jan. 8, 2012, 6 pages.
GenBank Accession No. NM_001136155 dated Jan. 8, 2012, 6 pages.
GenBank Accession No. NM_001143998, GI No. 221316675, dated Mar. 4, 2010, 5 pages.
GenBank Accession No. NM_001143999, GI No. 221316679, dated Mar. 5, 2010, 5 pages.
GenBank Accession No. NM_001144001, GI No. 221316686, dated Mar. 4, 2010, 5 pages.
GenBank Accession No. NM_001160367, GI No. 237858581, dated May 7, 2010, 5 pages.
GenBank Accession No. NM_001786 dated Nov. 1, 2009, 4 pages.
GenBank Accession No. NM_001844 dated Sep. 28, 2009, 7 pages.
GenBank Accession No. NM_003003, GI No. 221316681, dated Mar. 4, 2010, 5 pages.
GenBank Accession No. NM_003014; GI No. 170784837, dated Mar. 13, 2010, 5 pages.
GenBank Accession No. NM_003184; GI No. 115527086, dated Mar. 4, 2010, 7 pages.
GenBank Accession No. NM_003873.3 dated Oct. 18, 2009, 4 pages.
GenBank Accession No. NM_004336; GI No. 211938448, dated Mar. 14, 2010, 6 pages.
GenBank Accession No. NM_004449 dated Jan. 8, 2012, 6 pages.
GenBank Accession No. NM_005025.2 dated Jul. 12, 2009, 4 pages.
GenBank Accession No. NM_005192, GI No. 195927023, dated Mar. 4, 2010, 4 pages.
GenBank Accession No. NM_005651.1 dated Oct. 27, 2009, 3 pages.
GenBank Accession No. NM_006265, GI No. 208879448, dated Apr. 11, 2010, 6 pages.
GenBank Accession No. NM_006558 dated 812109, 3 pages.
GenBank Accession No. NM_006727 dated Oct. 18, 2009, 3 pages.
GenBank Accession No. NM_006819; GI No. 110225356, dated May 17, 2010, 5 pages.
GenBank Accession No. NM_012152; GI No. 183396778, dated Apr. 5, 2010, 5 pages.
GenBank Accession No. NM_014846; GI No. 120952850, dated Mar. 4, 2010, 6 pages.
GenBank Accession No. NM_016623; GI No. 42734437, dated Mar. 29, 2009, 4 pages.
GenBank Accession No. NM_018930 dated Feb. 10, 2008, _ pages.
GenBank Accession No. NM_031966 GI No. 34304372, dated Jun. 6, 2010, 5 pages.
GenBank Accession No. NM_032334; GI No. 223468686, dated Mar. 5, 2010, 3 pages.
GenBank Accession No. NM_052987, GI No. 237858574, dated May 17, 2010, 5 pages.
GenBank Accession No. NM_052988, GI No. 237858573, dated May 17, 2010, 5 pages.
GenBank Accession No. NM_080546; GI No. 112363101, dated May 17, 2010, 6 pages.
GenBank Accession No. NM_080607 dated Sep. 3, 2009, 2 pages.
GenBank Accession No. NM_133445 dated Sep. 20, 2009, 5 pages.
GenBank Accession No. NM_138455; GI No. 34147546, dated May 7, 2010, 3 pages.
GenBank Accession No. NM_182918 dated Jan. 8, 2012, 6 pages.
GenBank Accession No. NM_199166, GI No. 40316938, dated Apr. 11, 2010, 5 pages.
GenBank Accession No. NP_001058 dated Dec. 25, 2011, 9 pages.
GenBank Accession No. W34764 dated May 13, 1996, 2 pages.
Supplemental Table 1 of U.S. Appl. No. 61/057,698, filed May 30, 2008, 13 pages.
Supplemental Table 2 of U.S. Appl. No. 61/057,698, filed May 30, 2008, 15 pages.

(56) References Cited

OTHER PUBLICATIONS

Supplemental Table 3 of U.S. Appl. No. 61/057,698, filed May 30, 2008, 21 pages.
Supplemental Table 4 of U.S. Appl. No. 61/057,698, filed May 30, 12008, 1 page.
Supplemental Table 5 of U.S. Appl. No. 61/057,698, filed May 30, 12008, 2 pages.
Supplemental Table 6 of U.S. Appl. No. 61/057,698, filed May 30, 2008, 1 page.
Deininger, et al., The development of imatinib as a therapeutic agent for chronic myeloid leukemia. Blood. Apr. 1, 2005;105(7):2640-53.
UCSC Genome Browser on Human Mar. 2006 (NCBI36/hg18) Assembly, Mar. 1, 2006, Retrieved from the Internet: URL:https://genome-euro.ucsc.edu/cgi-bin/hgTracks?db=hg18&lastVirtModeType=default&lastVirtModeExtraState=&virtModeType=default&virtMode=0&nonVirtPosition=&position=chr5%3A14025126%2D14062770&hgsid=232148223_IYly9VS0Lh0jhLdEBQ3nViBrQuB5.

Figure 1
Fig. 1a
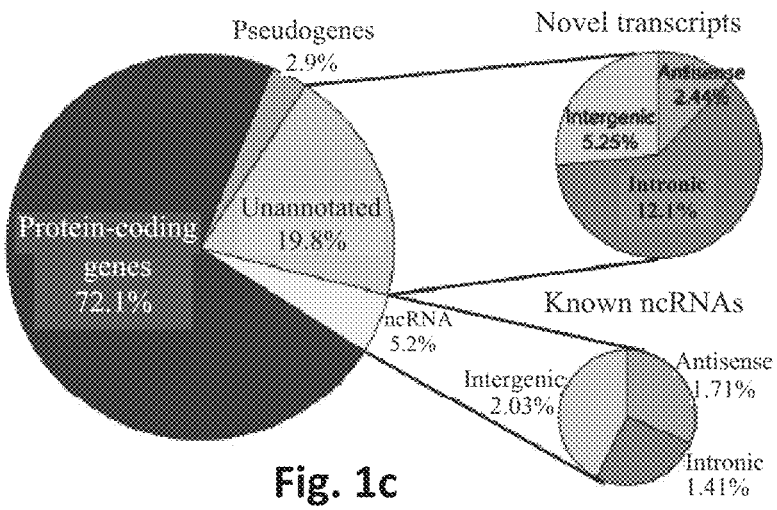
Fig. 1b
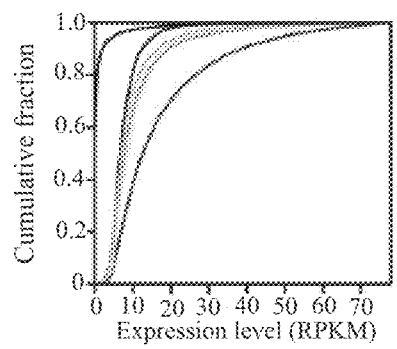
Fig. 1c
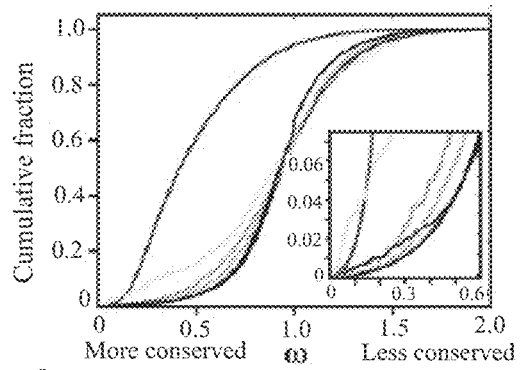
Fig. 1d
H3K4me2
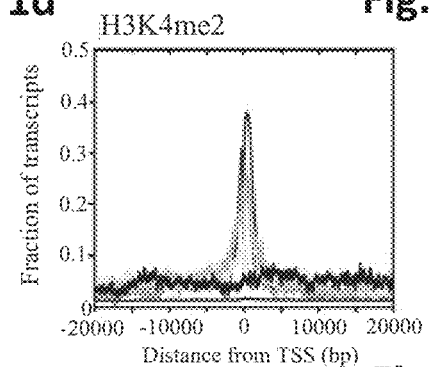
Fig. 1e
H3K4me3
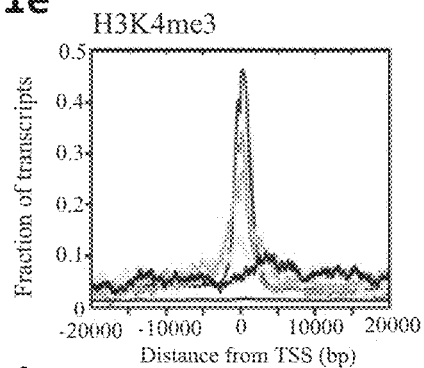
Fig. 1f
Acetyl-H3
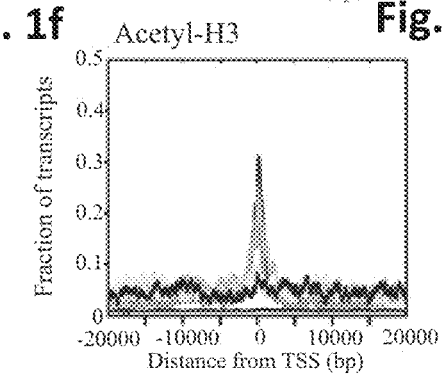
Fig. 1g
RNA Polymerase II
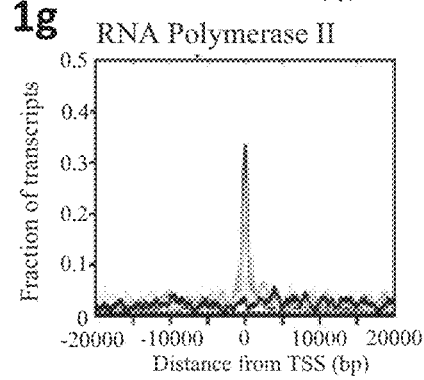
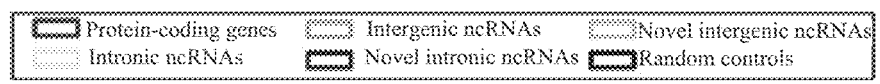

Figure 2
Fig. 2a
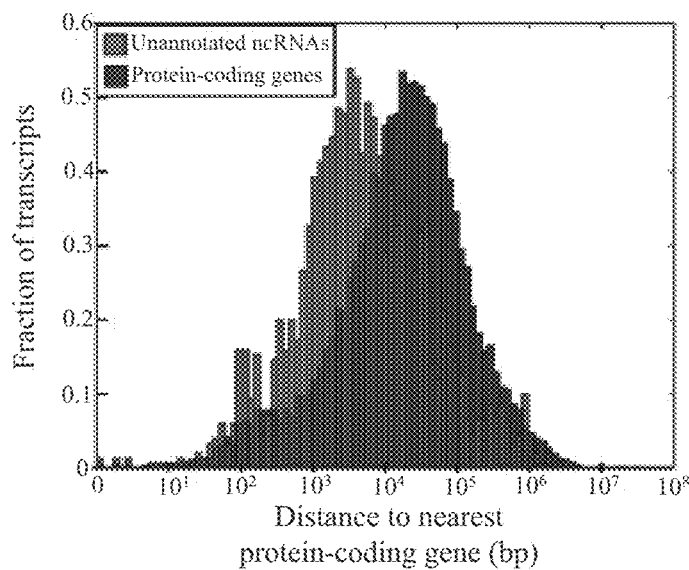
Fig. 2b
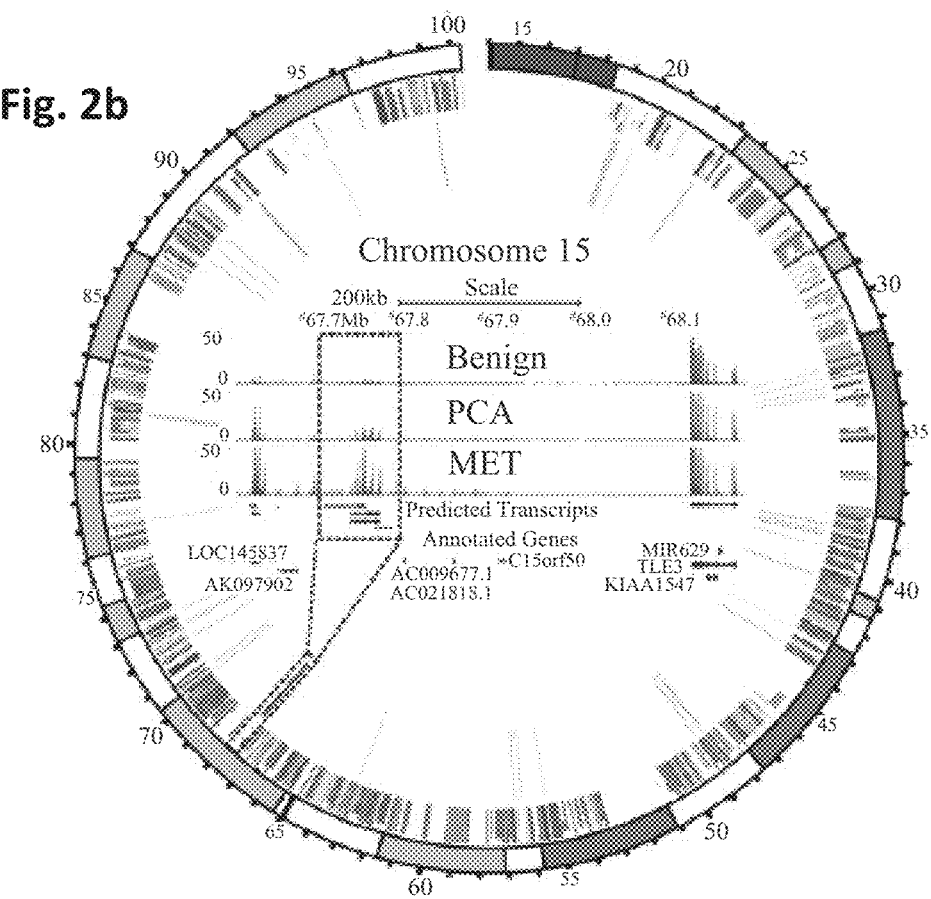

| Rank | Gene | Chromosomal Location | Outlier Score |
|---|---|---|---|
| 1 | CRISP3 | chr6:49803053-49813070 | 294.5644568 |
| 2 | SPINK1 | chr5:147184335-147191453 | 177.1951756 |
| 3 | PCAT-107 | chrX:66691350-66692032 | 130.7349145 |
| 4 | PCAT-108 | chr16:79420131-79423590 | 127.0430957 |
| 5 | PCAT-109 | chr2:180689090-180696402 | 123.5416436 |
| 6 | ERG | chr21:38673821-38792298 | 119.4460029 |
| 7 | C7orf68 | chr7:127883119-127885708 | 105.1850442 |
| 8 | CSRP3 | chr11:19160153-19180106 | 101.129471 |
| 9 | COL2A1 | chr12:46653014-46684552 | 99.16632908 |
| 10 | C1orf64 | chr1:16203317-16205771 | 98.0859221 |
| 11 | COL9A2 | chr1:40538749-40555526 | 74.40844283 |
| 12 | PLA2G7 | chr6:46780012-46811389 | 69.5211751 |
| 13 | AGT | chr1:228904891-228916959 | 69.31988642 |
| 14 | PCAT-113 | chr1:20685471-20686432 | 68.3572507 |
| 15 | ETV1 | chr7:13897382-13992664 | 68.21856853 |
| 16 | MUC6 | chr11:1002823-1026706 | 64.73280043 |
| 17 | PCAT-114 | chr10:42652247-42653596 | 60.91841567 |
| 18 | PCAT-115 | chr4:102257900-102306678 | 59.24997694 |
| 19 | RGL3 | chr19:11365731-11391018 | 57.5286889 |
| 20 | TMEM45B | chr11:129190950-129235108 | 55.88784464 |

Figure 3
Fig. 3a
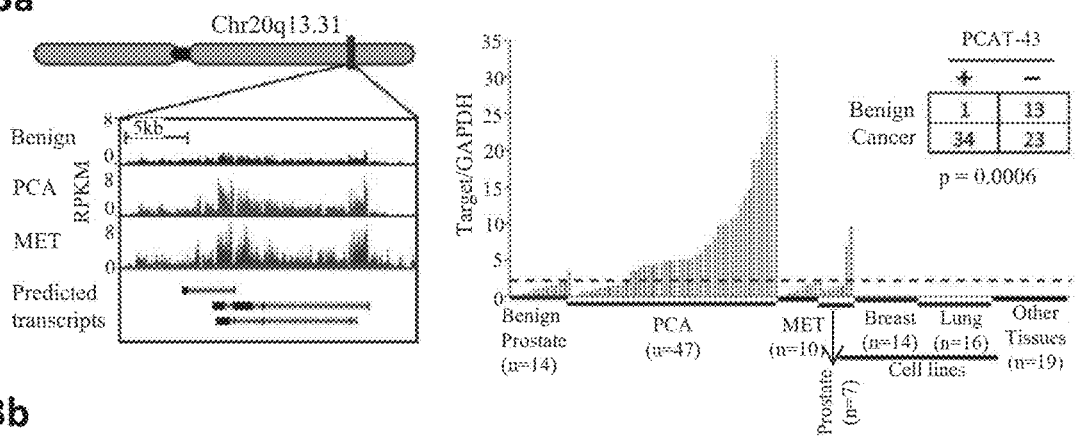
Fig. 3b
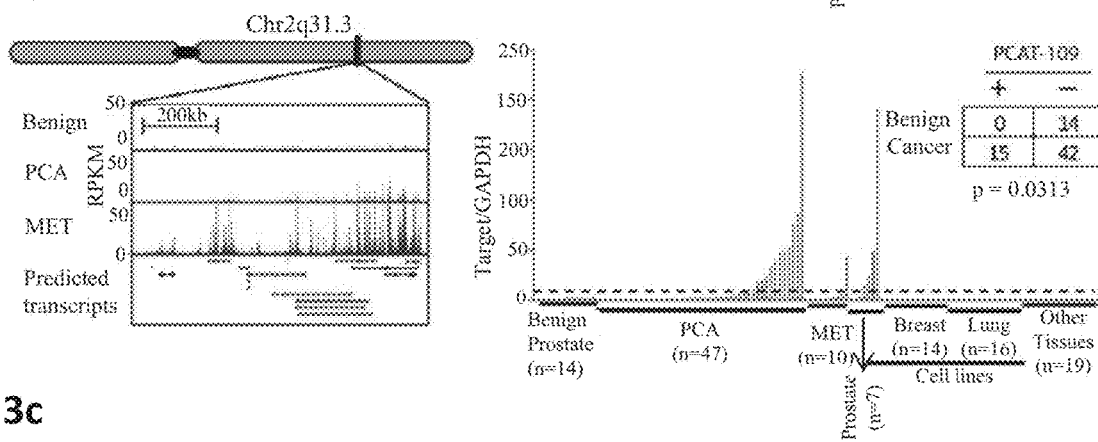
Fig. 3c
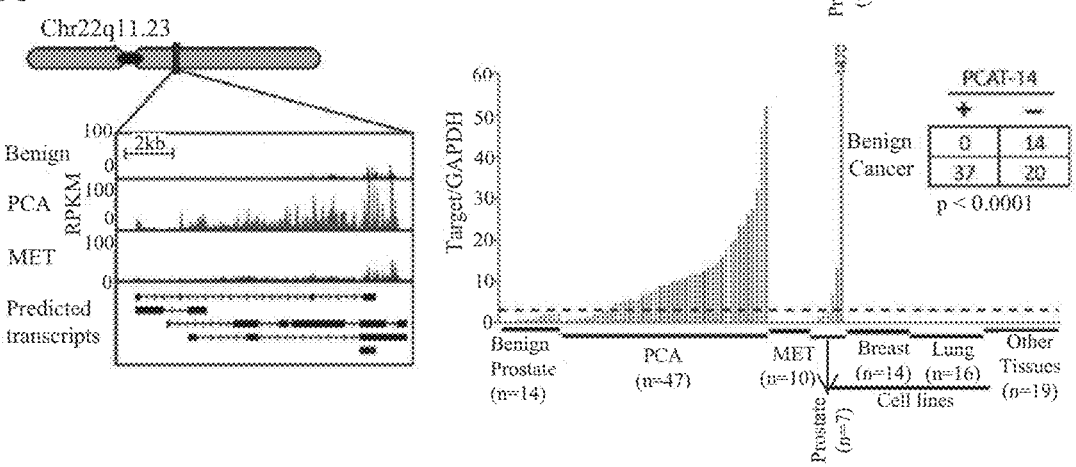

Figure 4
Fig. 4a
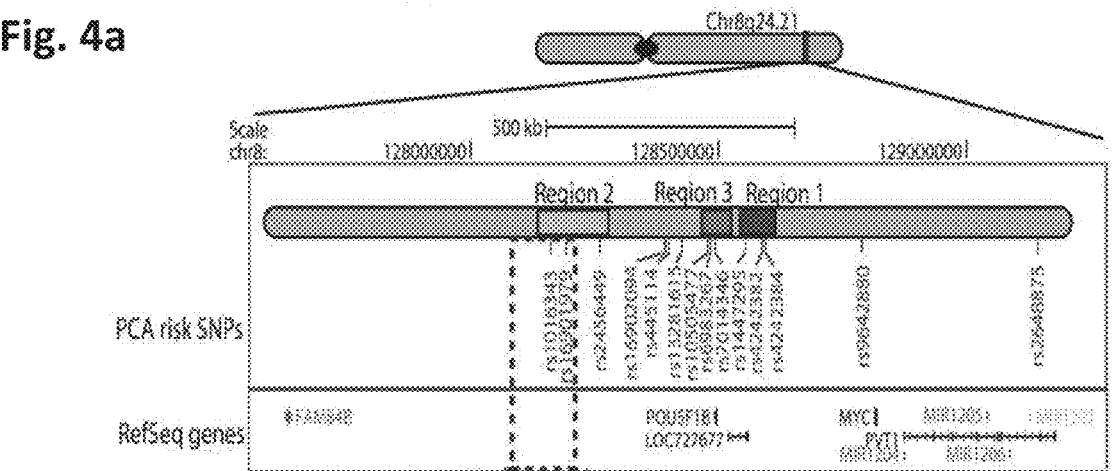
Fig. 4b
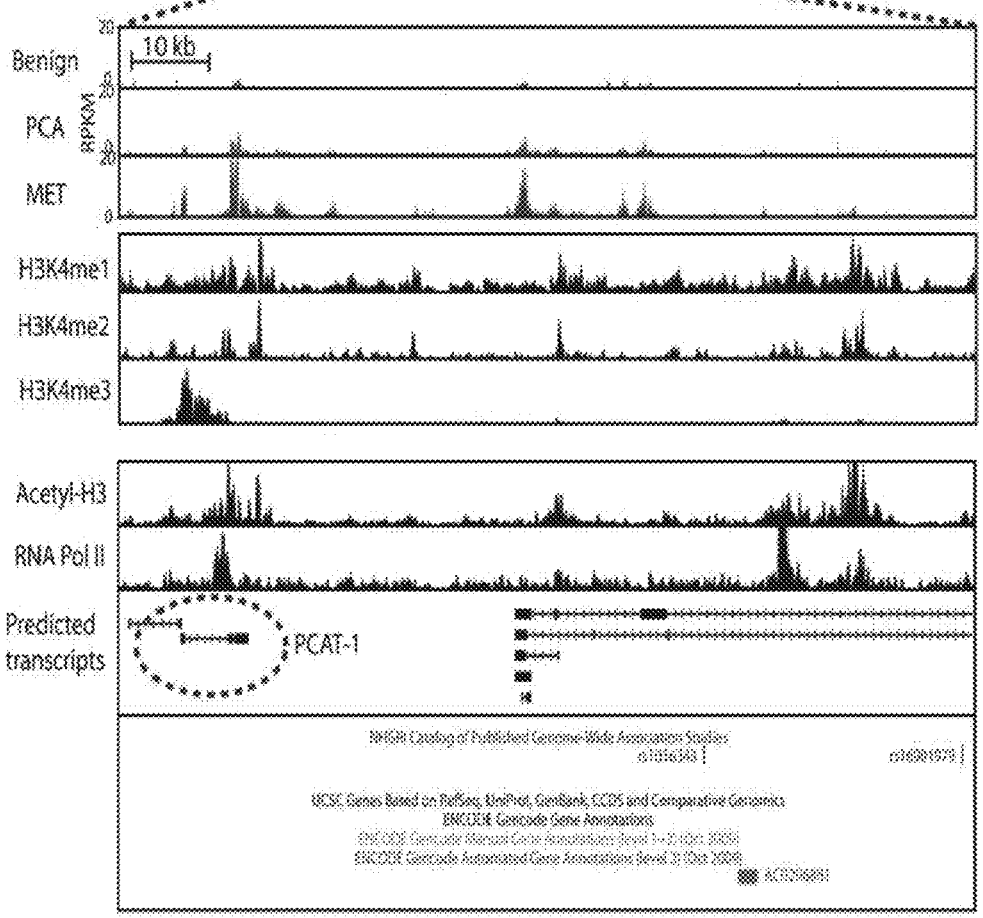
Fig. 4c
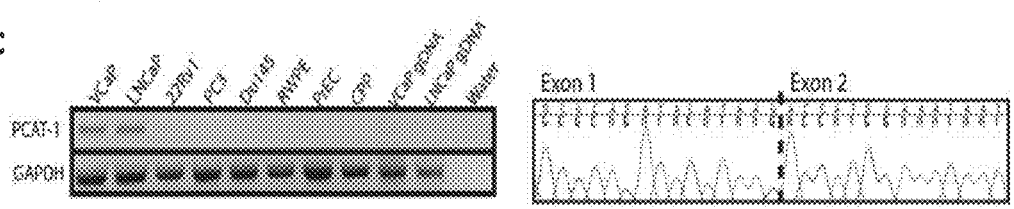

Figure 4 (cont.)
Fig. 4d
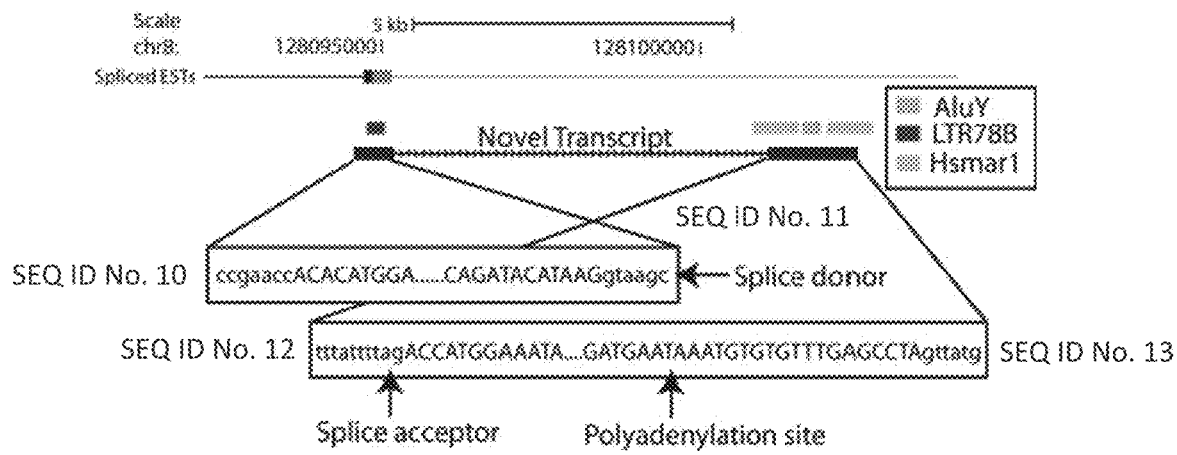
Fig. 4e
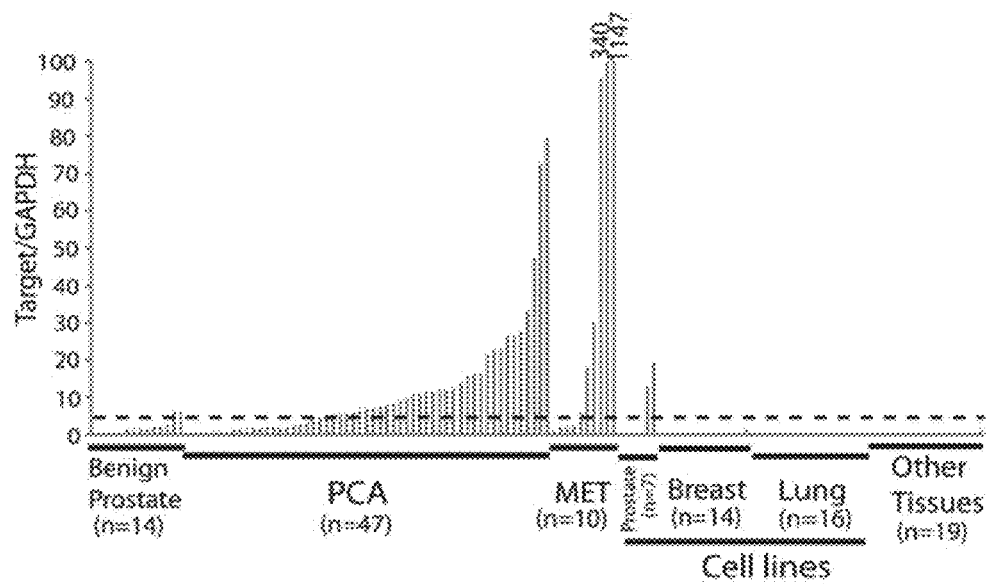
Fig. 4f
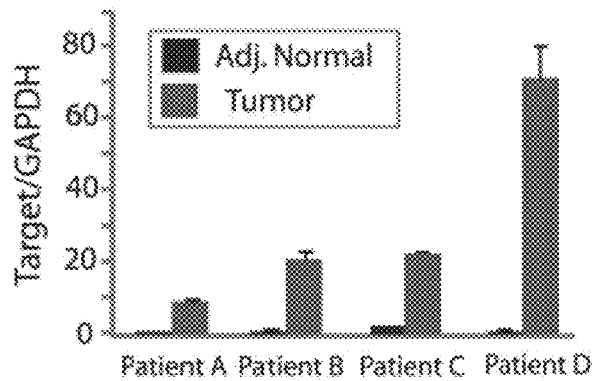

Figure 5
Fig. 5a
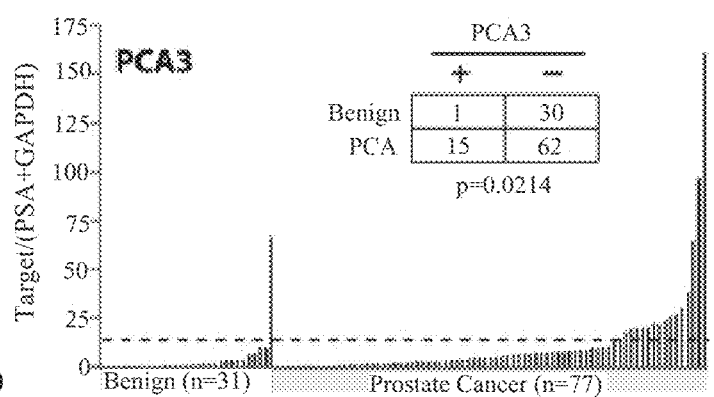
Fig. 5b
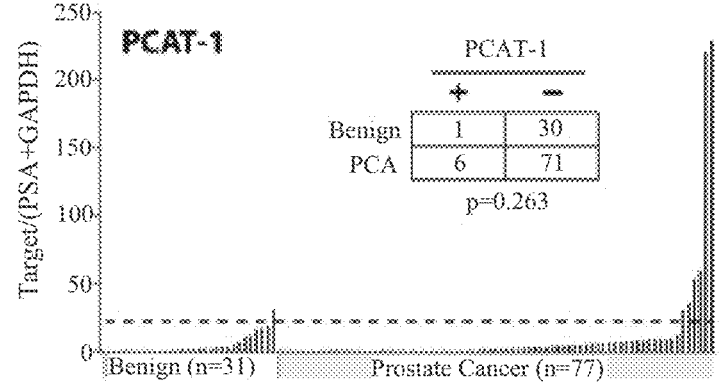
Fig. 5c
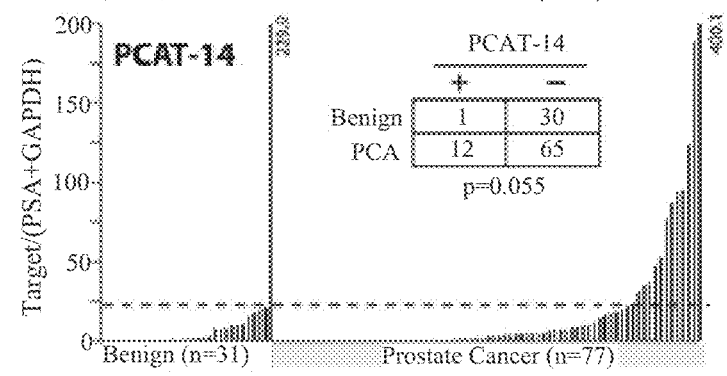

Figure 5 (cont)
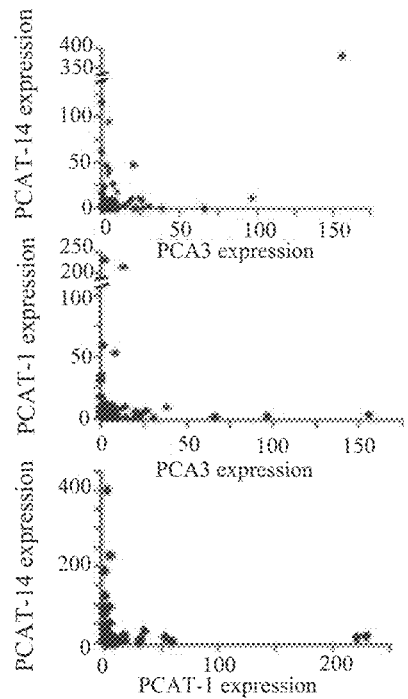
Fig. 5d
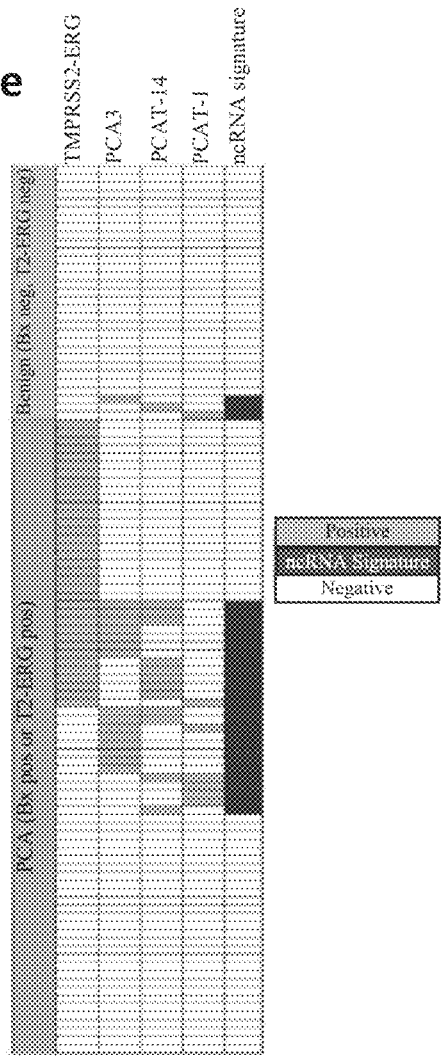
Fig. 5e
Fig. 5f
| | ncRNA signature | |
|---|---|---|
| | + | − |
| Benign | 3 | 28 |
| PCA | 26 | 51 |
p = 0.0062
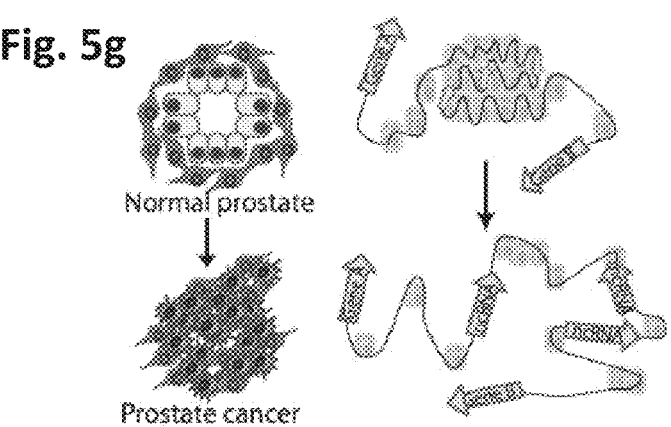
Fig. 5g

Figure 6
Fig. 6a
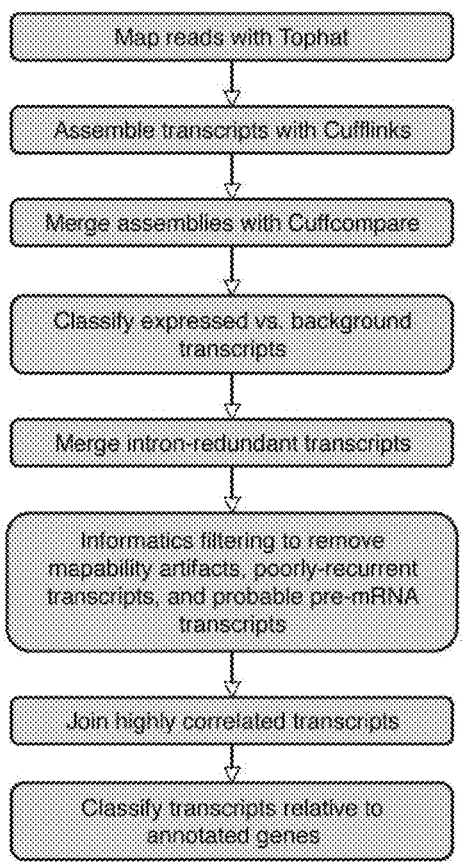
Fig. 6b
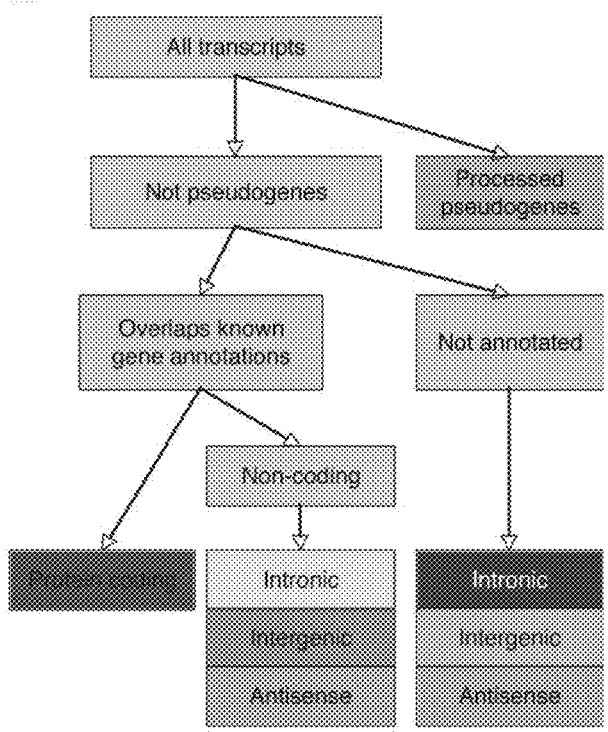

Figure 8
Fig. 8a
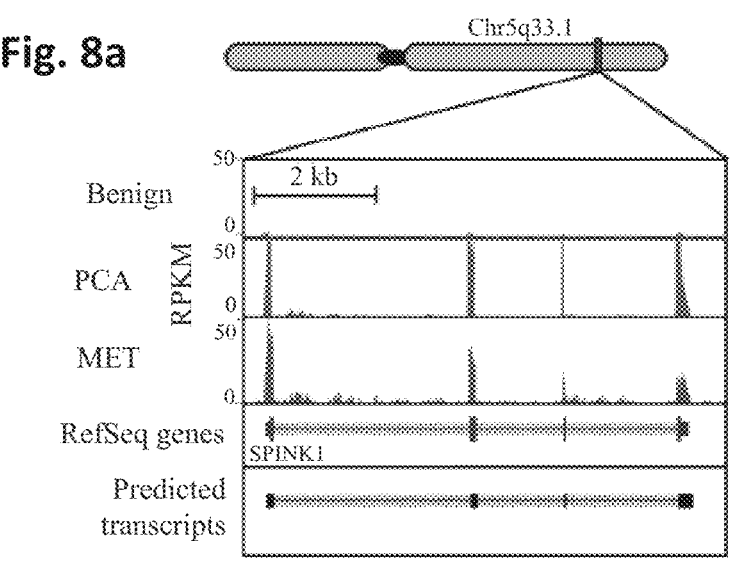
Fig. 8b
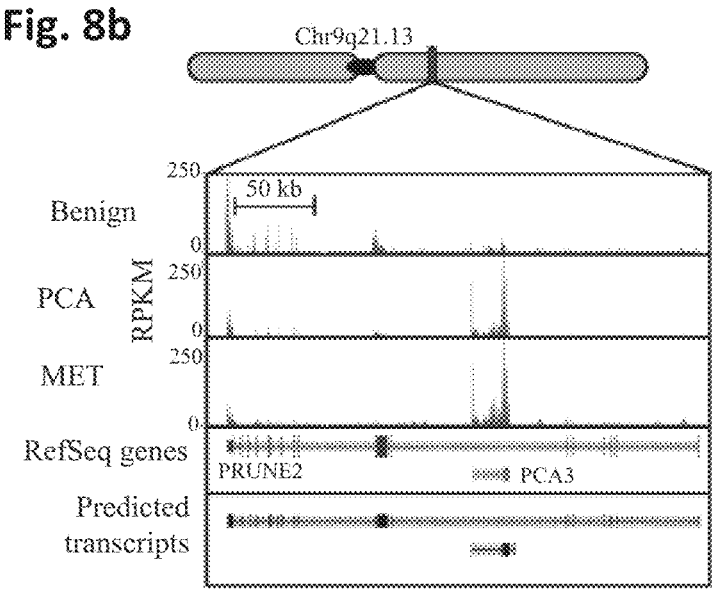

Figure 8 (cont.)
Fig. 8c
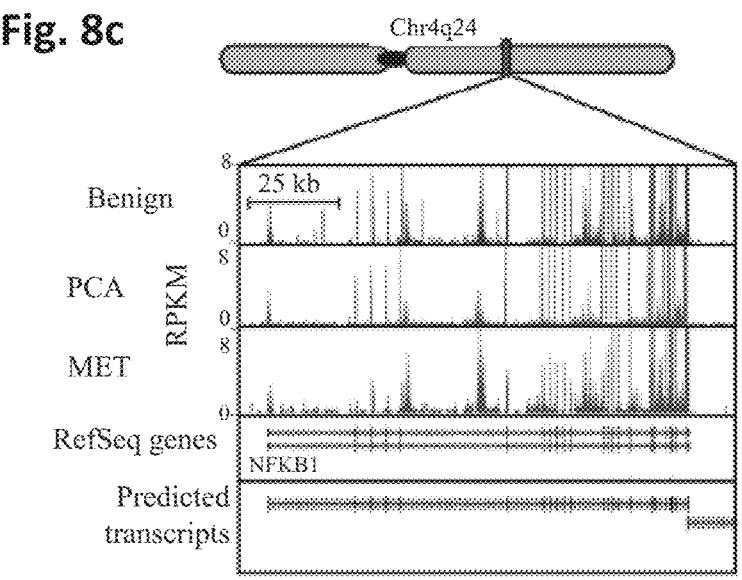
Fig. 8d
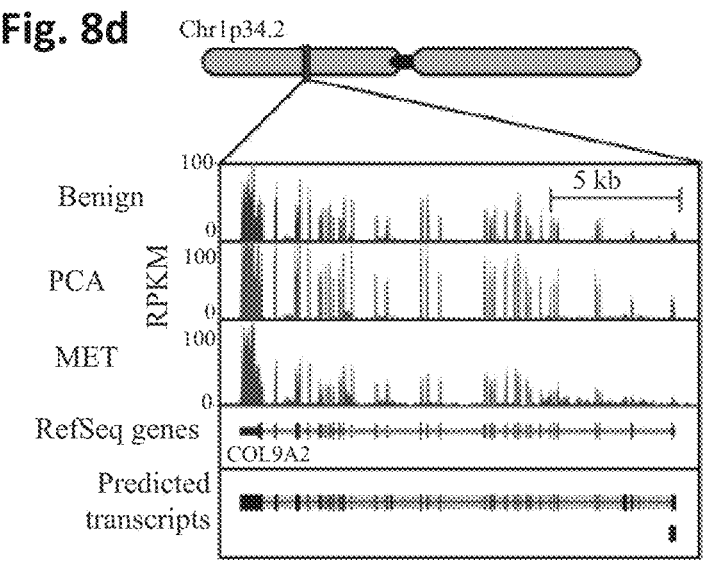

| Category | Transcripts | EST hits | Percent of all ESTs | ESTs per Transcript |
|---|---|---|---|---|
| Annotated proteins | 25550 | 4564852 | 56.43% | 178.6634834 |
| Intergenic ncRNA | 720 | 32891 | 0.41% | 45.68194444 |
| Intronic ncRNA | 500 | 57015 | 0.70% | 114.03 |
| Unannotated intergenic ncRNA | 1859 | 17478 | 0.22% | 9.40182894 |
| Unannotated intronic ncRNA | 4285 | 197142 | 2.44% | 46.00746791 |
| Total | 35415 | 4869378 | | |

Figure 13
Fig. 13a
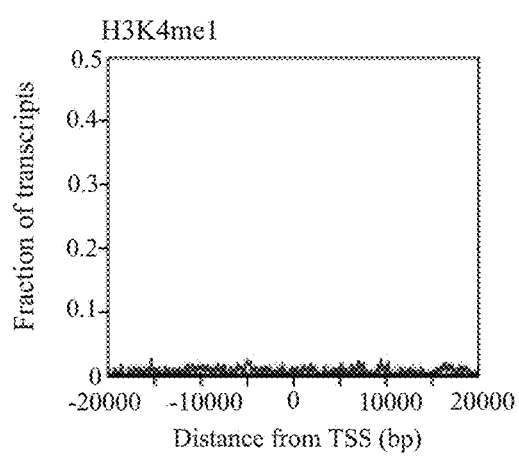
Fig. 13b
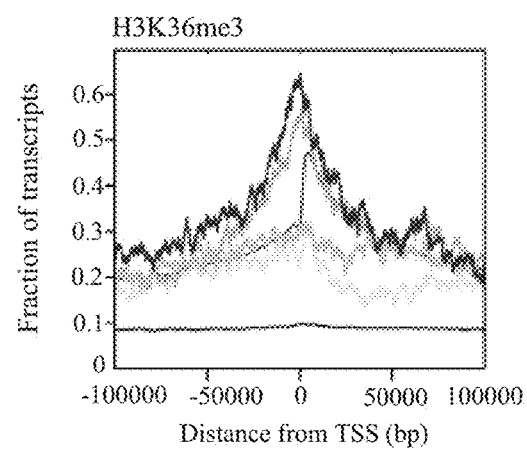
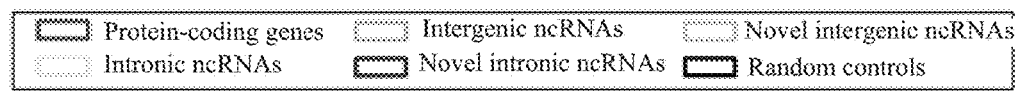

Figure 14
Fig. 14a
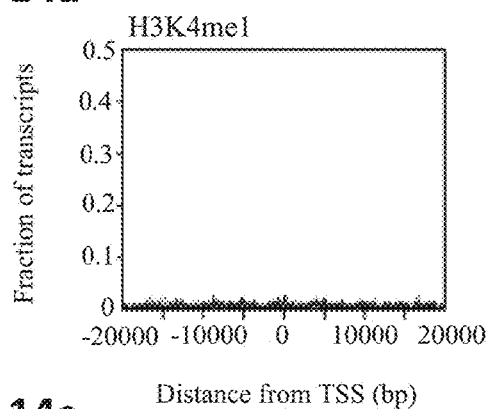
Fig. 14b
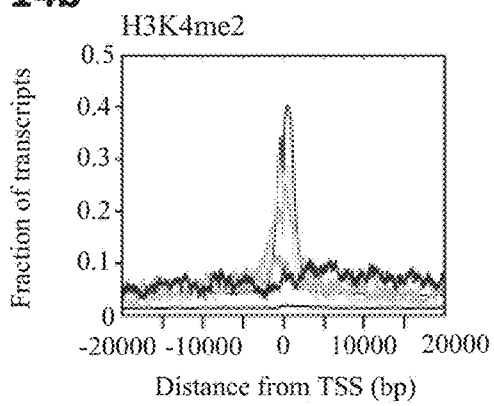
Fig. 14c
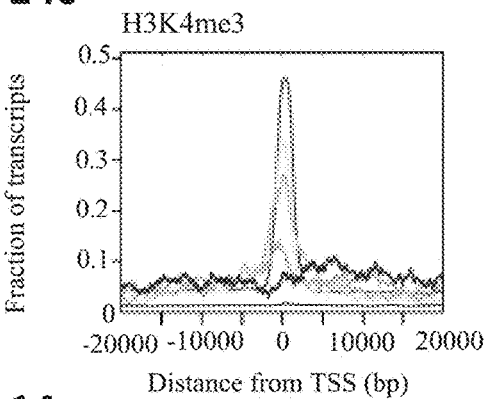
Fig. 14d
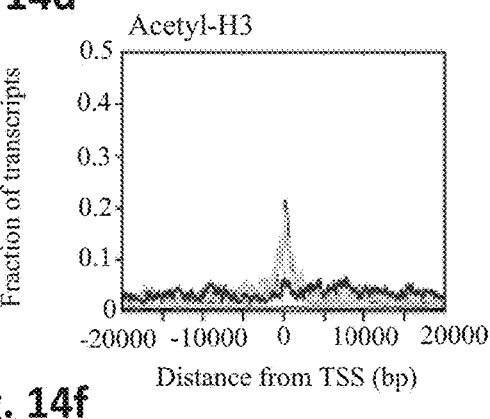
Fig. 14e
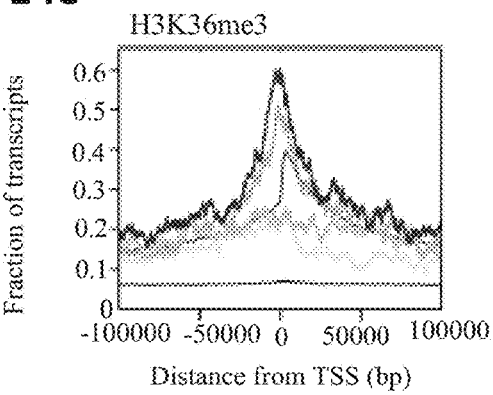
Fig. 14f
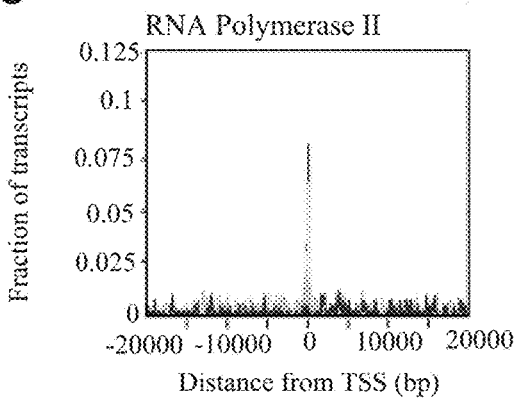
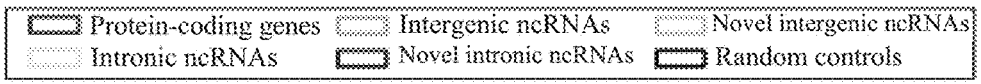

Fig. 15a Chromosome 15

Figure 20
Fig. 20a
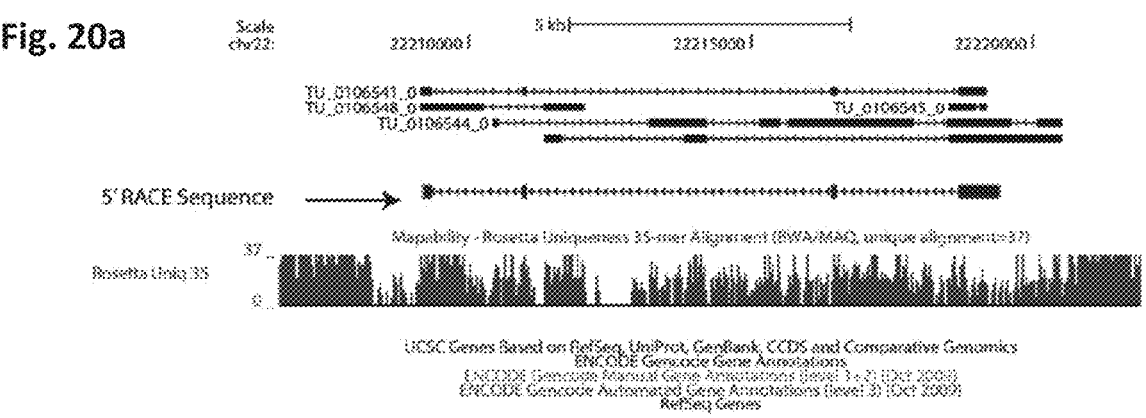
Fig. 20b
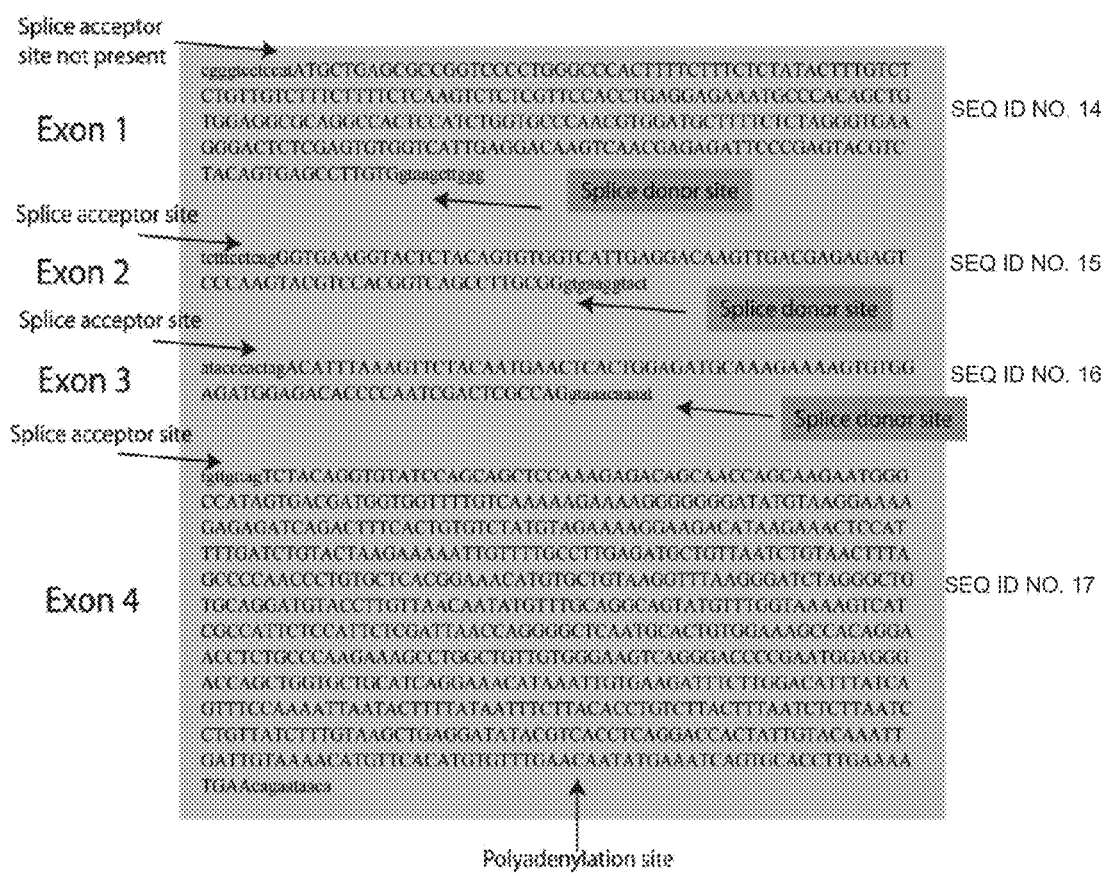

Figure 22
Fig. 22a
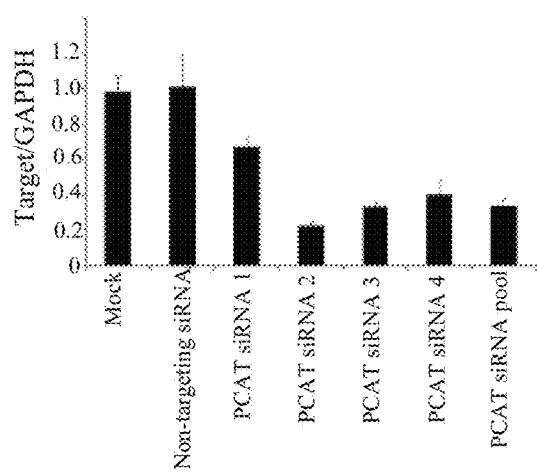
Fig. 22b
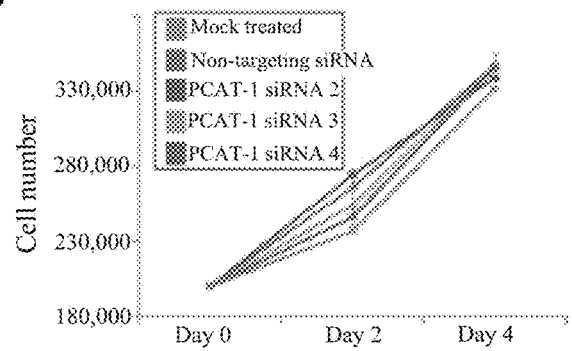
Fig. 22c
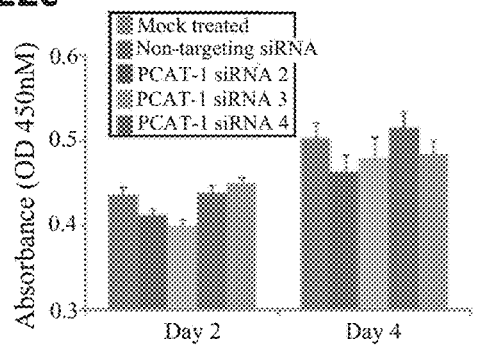
Fig. 22d
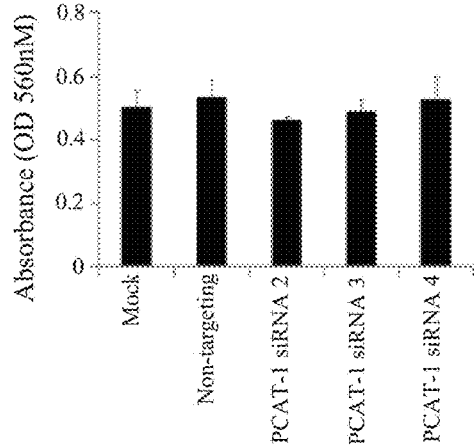

Figure 23
Fig. 23a
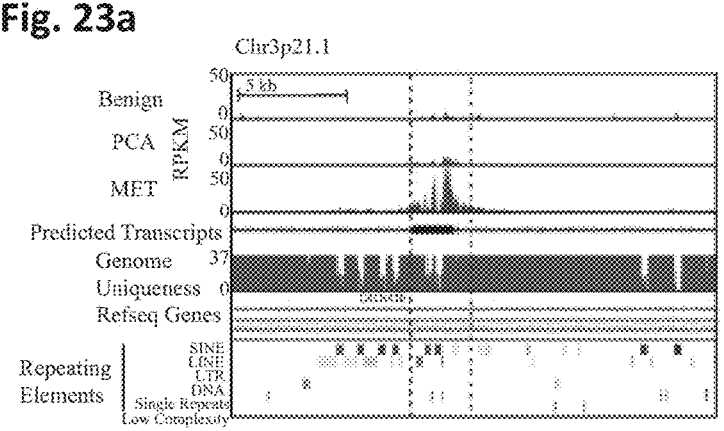
Fig. 23c
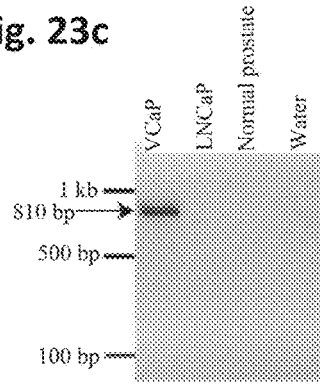
Fig. 23b
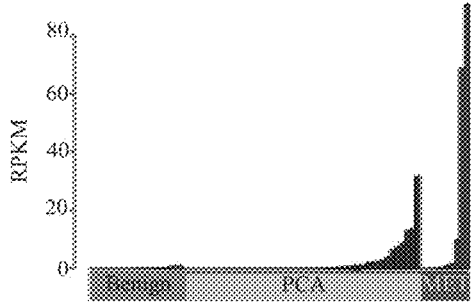
Fig. 23d
SEQ ID NO. 20
Fig. 23e
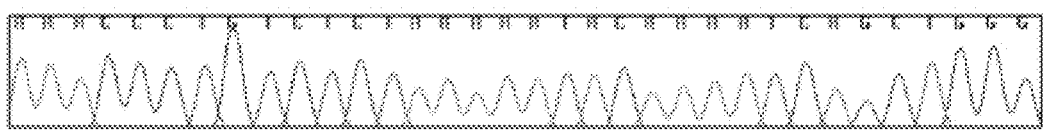

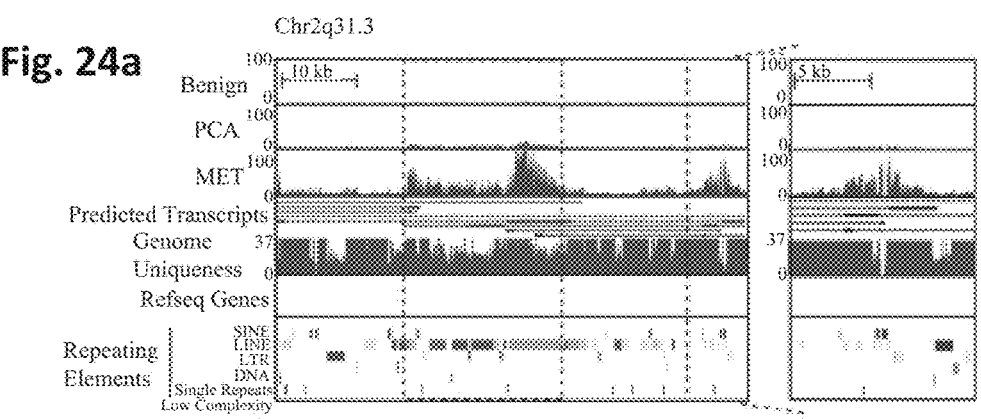

Fig. 24b

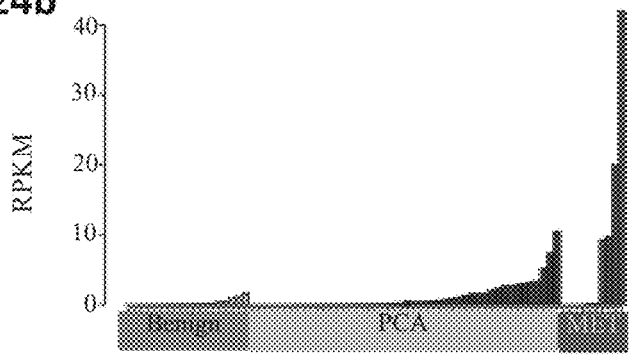

Fig. 24c

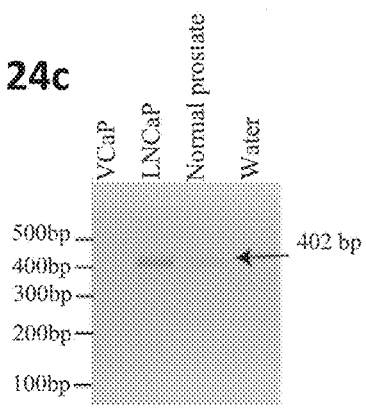

Fig. 24d

TCCTTGGTGGCTTAGGGGTACAGTTATTAATGCTGGCTGTGATGAAGTTTTGCTGGGG
ACCAGGATAACAGATGGTCCAGTCATGGGGGCCTCAGTGGTGGCAGTGATTAGCTGA
TCATGGCTGGCCTTTGGCCCCAGGTTGGCTTATGCTGGCACTTGTGTTGTTAGGGCCCA
AGCAGTCTGATTTGGGGGGCCTCCACATGGTTTGCTGGGATGTTGGTAGTTTCTGCTTC
CTGGCCTGATGTGGTACATCTGGGTGAGTGCAGCTCTGGTGGTATTAGCATGTAT
GTCAGCCTGTCCTTAGACCCTGGGAGAAGTGTTCATGTGCCAATGGTGGTAGACTGT
GCTGAGTGATTTCCAGGCCCCTGGACAGCATACTGAATTACTGAGAGGATGGGACT
GAGCA SEQ ID NO. 21

Figure 27
Fig. 27a
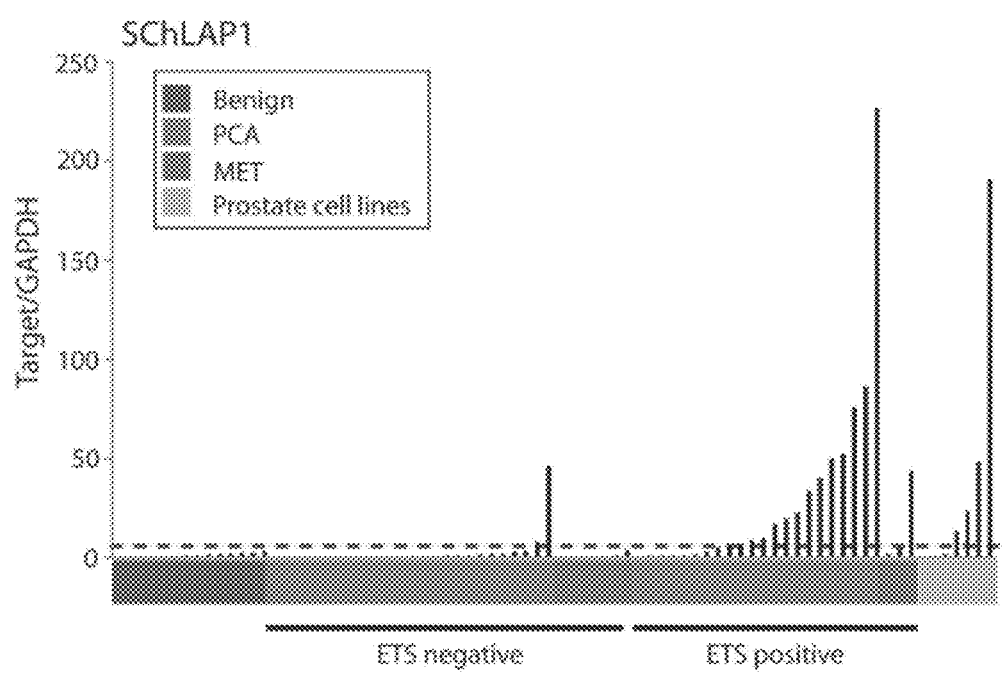
Fig. 27b
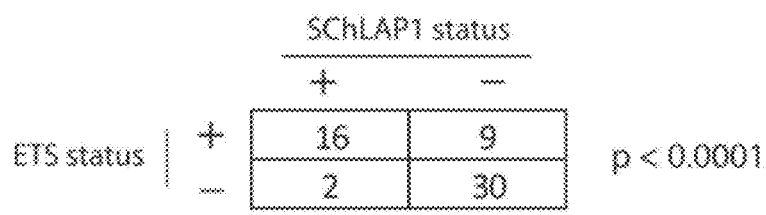

Figure 28

PCAT-1

Exon 1: chr8:128,094,581-128,095,201 (SEQ ID NO:1)

ACACATGGATATTGGATATCTGCATAGGCAGCTTGCTCCACGCCAGTGCCTACCTGTGCAGATGGGAAGGAAAGG
AAAGTGGCAAGGAGGCAGAGAAAGCATCTGTACCCTTACAATTTGGTGAGACAAGAATGTATGAATTCCCACAGG
TCAAATTATAATGAAGAAAGGAACCTCTCTTGAGTACAAAGAGCTACCTATGGTGGTCTGGAGCCGGAGGACCAC
AGCATCAAAGGATATAAGATGCATAGCCAACTGAGGAACCTGAGCAATTAAAGAGATCCACAGTTAAGTCACACT
TAACTGGCACTTGTGGAAGCCCCGCAAGGCCTGAAGGAGAGCTGACATAGGCACCCCGGAGAGCCAGAATCTGG
ATCCCATCTTAATAAGGCCATGAACACCAGTGGAGAAGAGGCAGAAACACCAATGGATAAGGAACATTCACATCT
TTCTTCCCATGTGCCTCTAAGTGCCAGTGCAGGCCCCACAGGCCAAGCTACAGGGAGAAAGGAGATGACGCAAAG
GAACCTAACTGGACTTTAATCACTAGAAGTGAGAAGAGAAATCTATTGGAACCTCCCAAGATAATGCCAAGGGTC
AAAGGGTGCGCAGATACATAAG

Exon 2: chr8:128,101,071-128,102,441 (SEQ ID NO:2)

ACCATGGAAATAATATCAGACAAAAAGCAGATTAGAGCAATTTTCTTTTTCGAGTTCAAAATGGGTTATAAAGCAG
CGGAGACAAACCGCAACATCACCAACGCCTTTGGCCCAGGAACTGCTAATGAAGGTACAGTGCAGTCACTGTTCA
GGAAGTTTTGCAAAGGAGACTAGAGCCTTGAAGATGAGGAGCATAGTGACCAGCCATTGGAAGTCGACAAAGAC
CAATTGAGAGGAATCATTGAAGCTGATCATCTTACAACTACACGAGAAGTTGTCAAAGAACGCAATGTTGACCATT
GTGTGGTCTTTTCGCATTTGAAGCAAATTGGAAAGGTGAAAAACTTGATAAGTGGGTGCCTTGTGAGCTCAGCAA
AAATCCAAAAAAATAATCATTTTTAAGTGTTGTCTTCTCTTATTCTACGCAACAACAATAACCATTTTGCAATCGGAT
TGTGATGTGCAATGAAAAGTGGATTTGGGGCCGGGCGCGGTGGCTCACGCCTGTAATCTCAGCACTTTGGAAGGC
CAAGGCGGGCAGATCACGAGGTCAGGAGATCAAGACCGTCCTGGCTAACACGGTGAAACCCCGTCTCTACTGAAA
ATACAAAAAATTAGCCGGGTGTGGTGGCTGGCGCCTGTAGTCCCAGCTACAGGCTGAGGCAGGAGAATGGCATG
AACCTGGGAGGCGGAGCTTGCAGTGAGCCGAGACCGTGCCACTGCACTCCAGCCTGGGCGACAGAGCGATACTC
CGTCAAAAAAAAAAAAAAAAAAAAAAAGACAAGTGGATTTTATATATGGCAACCAGCAATGACCAGCTCAGTG
GCTGGACTGAGAAGAAGCTCCAAAGCACTTCCCAAAGCCAAACTTGCACCAAAAAAAGGTCAGGGTCACTGTTT
GGTGGTCTGCTGCTGGTCTGATCCACCGCTGCTCTCTGAATCCTGGCAAAACCATTACATCTGAGAAGTATGCTCA
ACAAATCAATGAGCTACGCCAAAAACTGCAGCATCTGCAGCTGGCATTGGTCAACATAACGGGTCCAATTCTTCTC
CACGACAACGCTCAACTGCACCTTGCGCAAGCAGCGCTTCAAAAGTTGAACAAATTGGGCTACATAGTTTTTCCTC
ATCCGCCATATTCACCTGACGTCTTGCCAACTAACTACCACTTCTTCAAGTATCTCAACAACTTTTTGCAGGGAAAAC
ACTTCCACAACCAGCAGGATGCAGAACACGCTTTCCAAGAGTTTGTCGAATCCTGACGCACAGATTTTTATGCTAC
AGGAATAAACTAACTTATTTCTCATTGGCAAAAATGTGTTGATTGTAATGGTTCCTATTTTGATGAATAAATGTGTG
TTTGAGCCTA

Figure 28 (cont)

PCAT-14, isoform 1

Exon 1: chr22:22,209,086-22,209,323 (SEQ ID NO:3)

ATGCTGAGCGCCGGTCCCCTGGGCCCACTTTTCTTTCTCTATACTTTGTCTCTGTTGTCTTTCTTTTCTCAAGTCTCTC
GTTCCACCTGAGGAGAAATGCCCACAGCTGTGGAGGCGCAGGCCACTCCATCGGTGCCCAACGTGGATGCTTTT
CTCTAGGGTGAAGGGACTCTCGAGTGTGGTCATTGAGGACAAGTCAACGAGAGATTCCCGAGTACGTCTACAGTG
AGCCTTGTG

Exon 2: chr22:22,210,948-22,211,026 (SEQ ID NO:4)

GGTGAAGGTACTCTACAGTGTGGTCATTGAGGACAAGTTGACGAGAGAGTCCCAAGTACGTCCACGGTCAGCCTT
GCGG

Exon 3: chr22:22,216,415-22,216,493 (SEQ ID NO:5)

ACATTTAAAGTTCTACAATGAACTCACTGGAGATGCAAAGAAAAGTGTGGAGATGGAGACACCCCAATCGACTCG
CCAG

Exon 4: chr22:22,218,673-22,219,354 (SEQ ID NO:6)

TCTACAGGTGTATCCAGCAGCTCCAAAGAGACAGCAACCAGCAAGAATGGGCCATAGTGACGATGGTGGTTTTGT
CAAAAAGAAAAGGGGGGGATATGTAAGGAAAAGAGAGATCAGACTTTCACTGTGTCTATGTAGAAAAGGAAGAC
ATAAGAAACTCCATTTTGATCTGTACTAAGAAAAATTGTTTTGCCTTGAGATGCTGTTAATCTGTAACTTTAGCCCC
AACCCTGTGCTCACGGAAACATGTGCTGTAAGGTTTAAGGGATCTAGGGCTGTGCAGGATGTACCTTGTTAACAAT
ATGTTTGCAGGCAGTATGTTTGGTAAAAGTCATCGCCATTCTCCATTCTCGATTAACCAGGGGCTCAATGCACTGTG
GAAAGCCACAGGAACCTCTGCCCAAGAAAGCCTGGCTGTTGGGAAGTCAGGGACCCCGAATGGAGGGACCAG
CTGGTGCTGCATCAGGAAACATAAATTGTGAAGATTTCTTGGACATTTATCAGTTTCCAAAATTAATACTTTTATAA
TTTCTTACACCTGTCTTACTTTAATCTCTTAATCCTGTTATCTTTGTAAGCTGAGGATATACGTCACCTCAGGACCACT
ATTGTACAAATTGATTGTAAAACATGTTCACATGTGTTTGAACAATATGAAATCAGTGCACCTTGAAAATGAA

PCAT-14, isoform 2

Exon 1: chr22:22,209,086-22,209,323 (SEQ ID NO:7)

Figure 28 (cont)

ATGCTGAGCGCCGGTCCCCTGGGCCCACTTTTCTTTCTCTATACTTTGTCTCTGTTGTCTTTCTTTTCTCAAGTCTCTC
GTTCCACCTGAGGAGAAATGCCCACAGCTGTGGAGGCGCAGGCCACTCCATCTGGTGCCCAACGTGGATGCTTTT
CTCTAGGGTGAAGGGACTCTCGAGTGTGGTCATTGAGGACAAGTCAACGAGAGATTCCCGAGTACGTCTACAGTG
AGCCTTGTG

Exon 2: chr22:22,210,860-22,216,414 (SEQ ID NO:8)

TCTCTCATCCCTCCTGACGAGAAATACCCACAGGTGTGGAGGGGCTGGCCCCCTTCATCTGATGCCCAATGTGGGT
GCCTTTCTCTAGGGTGAAGGTACTCTACAGTGTGGTCATTGAGGACAAGTTGACGAGAGAGTCCCAAGTACGTCC
ACGGTCAGCCTTGCGGTAAGCTTGTGTGCTTAGAGGAACCCAGGGTAACGATGGGGCAAACTGAAAGTAAATAT
GCCTCTTATCTCAGCTTTATTAAAATTCTTTTAAGAAGAGGGGGAGTTAGAGCTTCTACAGAAAATCTAATTACGCT
ATTTCAAACAATAGAACAATTCTGCCCATGGTTTCCAGAACAGGGAACTTTAGATCTAAAAGATTGGGAAAAAATT
GGCAAAGAATTAAAACAAGCAAATAGGGAAGGTAAAATCATCCCACTTACAGTATGGAATGATTGGGCCATTATT
AAAGCAACTTTAGAACCATTTCAAACAGGAGAAGATATTGTTTCAGTTTCTGATGCCCCTAAAAGCTGTGTAACAG
ATTGTGAAGAAGAGGCAGGGACAGAATCCCAGCAAGGAACGGAAAGTTCACATTGTAAATATGTAGCAGAGTCT
GTAATGGCTCAGTCAACGCAAAATGTTGACTACAGTCAATTACAGGAGATAATATACCCTGAATCATCAAAATTGG
GGGAAGGAGGTCCAGAATCATTGGGGCCATCAGAGCCTAAACCACGATCGCCATCAACTCCTCCTCCCGTGGTTC
AGATGCCTGTAACATTACAACCTCAAACGCAGGTTAGACAAGCACAAACCCCAAGAGAAAATCAAGTAGAAAGGG
ACAGAGTCTCTATCCCGGCAATGCCAACTCAGATACAGTATCCACAATATCAGCCGGTAGAAAATAAGACCCAACC
GCTGGTAGTTTATCAATACCGGCTGCCAACCGAGCTTCAGTATCGGCCTCCTTCAGAGGTTCAATACAGACCTCAA
GCGGTGTGTCCTGTGCCAAATAGCACGGCACCATACCAGCAACCCACAGCGATGGCGTCTAATTCACCAGCAACA
CAGGACGCGGCGCTGTATCCTCAGCCGCCCACTGTGAGACTTAATCCTACAGCATCACGTAGTGGACAGGGTGGT
GCACTGCATGCAGTCATTGATGAAGCCAGAAAACAGGGCGATCTTGAGGCATGGCGGTTCCTGGTAATTTTACAA
CTGGTACAGGCCGGGGAAGAGACTCAAGTAGGAGCGCCTGCCCGAGCTGAGACTAGATGTGAACCTTTCACCAT
GAAAATGTTAAAAGATATAAAGGAAGGAGTTAAACAATATGGATCCAACTCCCCTTATATAAGAACATTATTAGAT
TCCATTGCTCATGGAAATAGACTTACTCCTTATGACTGGGAAATTTTGGCCAAATCTTCCCTTTCATCCTCTCAGTAT
CTACAGTTTAAAACCTGGTGGATTGATGGAGTACAAGAACAGGTACGAAAAAATCAGGCTACTAAGCCCACTGTT
AATATAGACGCAGACCAATTGTTAGGAACAGGTCCAAATTGGAGCACCATTAACCAACAATCAGTGATGCAGAAT
GAGGCTATTGAACAAGTAAGGGCTATTTGCCTCAGGGCCTGGGGAAAAATTCAGGACCCAGGAACAGCTTTCCCT
ATTAATTCAATTAGACAAGGCTCTAAAGAGCCATATCCTGACTTTGTGGCAAGATTACAAGATGCTGCTCAAAAGT
CTATTACAGATGACAATGCCCGAAAAGTTATTGTAGAATTAATGGCCTATGAAAATGCAAATCCAGAATGTCAGTC
GGCCATAAAGCCATTAAAAGGAAAAGTTCCAGCAGGAGTTGATGTAATTACAGAATATGTGAAGGCTTGTGATGG
GATTGGAGGAGCTATGCATAAGGCAATGCTAATGGCTCAAGCAATGAGGGGGCTCACTCTAGGAGGACAAGTTA
GAACATTTGGGAAAAAATGTTATAATTGTGGTCAAATCGGTCATCTGAAAAGGAGTTGCCCAGGCTTAAATAAAC
AGAATATAATAAATCAAGCTATTAACAGCAAAAAATAAAAAGCCATCTGGCCTGTGTCCAAAATGTGGAAAAGCA
AAACATTGGGCCAATCAATGTCATTCTAAATTTGATAAAGATGGGCAACCATTGTCTGGAAACAGGAAGAGGGGC

Figure 28 (cont)

CAGCCTCAGGCCCCCCAACAAACTGGGGCATTCCCAGTTAAACTGTTTGTTCCTCAGGGTTTTCAAGGACAACAAC
CCCTACAGAAAATACCACCACTTCAGGGAGTCAGCCAATTACAACAATCCAACAGCTGTCCCGCGCCACAGCAGGC
AGCACCGCAGTAGATTTATGTTCCACCCAAATGGTCTTTTTACTCCCTGGAAAGCCCCCACAAAAGATTCCTAGAG
GGGTATATGGCCCGCTGCCAGAAGGGAGGGTAGGCCTTTGAGGGAGATCGTCTAAATTTGAAGGGAGTCCAAAT
TCATACTGGGGTAATTTATTCAGATTATAAAGGGGGAATTCAGTTAGTGATCAGCTCCACTGTTCCCCGGAGTGCC
AATCCAGGTGATAGAATTGCTCAATTACTGCTTTTGCCTTATGTTAAAATTGGGGAAAACAAAAAGGAAAGAACAG
GAGGGTTTGGAAGTACCAACCCTGCAGGAAAAGCTGCTTATTGGGCTAATCAGGTCTCAGAGGATAGACCCGTGT
GTACAGTCACTATTCAGGGAAAGAGTTTGAAGGATTAGTGGATACCCAGGCTGATGTTTCTGTCATCGGCATAGG
TACTGCCTCAGAAGTGTATCAAAGTGCCATGATTTTACATTGTCCAGGATCTGATAATCAAGAAAGTACGGTTCAG
CCTGTGATCACTTCATTCCAATCAATTTATGGGGCCGAGACTTGTTACAACAATGGCATGCAGAGATTACTATCCCA
GCCTCCCTATACAGCCCCAGGAATAAAAAAATCATGACTAAAATGGGATAGCTCCCTAAAAAGGGACTAGGAAAG
AAGTCCCAATTGAGGCTGAAAAAAATCAAAAAAGAAAAGGAATAGGGCATCCTTTTAGGAGCGGTCACTGTAGA
GCCTCCAAAACCCATTCCATTAACTTGGGGGAAAAAAAAACAACTGTATGGTAAATCAGCAGCGCTTCCAAAACAA
AAACTGGAGGCTTTACATTTATTAGCAAAGAAACAATTAGAAAAAGGACATTGAGCCTTCATTTTCGCCTTGGAAT
TCTGTTTGTAATTCAGAAAAAATCCGGCAGATGGCGTATAATGCCGTAATTCAACCCATGGGGGCTCTCCCACCCC
GGTTGCCCTCTCCAGCCATGGTCCCCTTTAATTATAATTGATCTGAAGGATTGCTTTTTACCATTCCTCTGGCAAAA
CAGGATTTTGAAAAATTTGCTTTTACCACACCAGCCTAAATAATAAAGAACCAGCCACCAGGTTTCAGTGGAAAGT
ATTGCCTCAGGGAATGCTTAATAGTTCAACTATTTGTCAGCTCAAGCTCTGCAACCAGTTAGAGACAAGTTTTCAGA
CTGTTACATCGTTCACTATGTTGATATTTTGTGTGCTGCAGAAACGAGAGACAAATTAATTGACCGTTACACATTTC
TGCAGACAGAGGTTGCCAACGCGGGACTGACAATAACATCTGATAAGATTCAAACCTCTACTCCTTTCCGTTACTT
GGGAATGCAGGTAGAGGAAAGGAAAATTAAACCACAAAAAATAGAAATAAGAAAAGACACATTAAAGCATTAA
ATGAGTTTCAAAAGTTGCTAGGAGATACTAATTGGATTTGGAGATATTAATTGGATTTGGCCAACTCTAGGCATTC
CTACTTATGCCATGTCAAATTTGTTCTCTTTCTTAAGAGGGGACTCGGAATTAAATAGTGAAAGAACGTTAACTCCA
GAGGCAACTAAAGAAATTAAATTAATTGAAGAAAAAATTCGGTCAGCACAAGTAAATAGAATAGATCACTTGGCC
CCACTCCAAATTTTGATTTTTGCTACTGCACATTCCCTAACAGGCATCATTGTTCAAAATACAGATCTTGTGGAGTG
GTCCTTCCTTCCTCACAGTACAATTAAGACTTTTACATTGTACTTGGATCAAATGGCTACATTAATTGGTCAGGGAA
GATTATGAATAATAACATTGTGTGGAAATGACCCAGATAAAATCACTGTTCCTTTCAACAAGCAACAGGTTAGACA
AGCCTTTATCAATTCTGGTGCATGGCAGATTGGTCTTGCCGATTTTGTGGGAATTATTGACAATCGTTACCCCAAAA
CAAAAATCTTCCAGTTTTTAAAATTGACTACTTGGATTTTACCTAAAGTTACCAAACATAAGCCTTTAAAAAATGCTC
TGGCAGTGTTTACTGATGGTTCCAGCAATGGAAAAGTGGCTTACACCGGGCCAAAAGAATGAGTCATCAAAACTC
AGTATCACTTGACTCAAAGAGCAGAGTTGGTTGCCGTCATTACAGTGTTAACAAGATTTTAATCAGTCTATTAACAT
TGTATCAGATTCTGCATATGTAGTACAGGCTACAAAGGATATTGAGAGAGCCCTAATCAAATACATTATGGATGAT
CAGTTAAACCCGCTGTTTAATTTGTTACAACAAAATGTAAGAAAAGAAATTTCCCATTTTATATTACTCATATTCGA
GCACACACTAATTTACCAGGGCCTTTAACTAAAGCAAATGAACAAGCTGACTTGCTAGTATCATCTGCATTCATGG
AAGCACAAGAACTTCATGCCTTGACTCATGTAAATGCAATAGGATTAAAAAATAAATTTGATATCACATGGAAACA
GACAAAAAATATTGTACAACATTGCACCCAGTGTCAGATTCTACACCTGGCCACTCAGGAGGCAAGAGTTAATCCC
AGAGGTCTATGTCCTAATGTGTTATGGCAAATGGATGTCATGCACGTACCTTCATTTGGAAAATTGTCATTTGTCCA
TGTGACAGTTGATACTTATTCACATTTCATATGGGCAACCTGCCAGACAGGAGAAAGTACTTCCCATGTTAAAGA
CATTTATTATCTTGTTTTCCTGTCATGGGAGTTCCAGAAAAAGTTAAAACAGACAATGGGCCAGGTTACTGTAGTA

Figure 28 (cont)

AAGCAGTTCAAAAATTCTTAAATCAGTGGAAAATTACACATACAATAGGAATTCTCTATAATTCCCAAGGACAGGC
CATAATTGAAAGAACTAATAGAACACTCAAAGCTCAATTGGTTAAACAAAAAAAAGGAAAAGACAGGAGTATAAC
ACTCCCCAGATGCAACTTAATCTAGCACTCTATACTTTAAATGTTTTAAACATTTATAGAAATCAGACCACTACCTCT
GCAGAACAACATCTTACTGGTAAAAGGAACAGCCCACATGAAGGAAAACTGATTTGGTGGAAAGATAATAAAAAT
AAAACATGGGAAATGGGGAAGGTGATAACGTGGGGGAGAGGTTTTGCTTGTGTTTCACCAGGAGAAAATCAGCT
TCCTGTTTGGATACCCACTAG

PCAT-14, isoform 3

Exon 1: chr22:22,216,494-22,218,672 (SEQ ID NO:9)

GTAAACAAAATGGTGATATCAGAAGAACAGAAAAAGTTGCCTTCCATCAAGGAAGCAGAGTTGCCAATATAGGCA
CAATTAAAGAAGCTGACACAGTTAGCTAAAAAAAAAGCCTAGAGAATACAAAGGTGACACCAACTCCAGAGAAT
ATGCTGCTTGCAGCTCTGATGATTGTATCAACGGTGGTAAGTCTTCCCAAGTCTGCAGGAGCAGCTGCAGCTAATT
ATACTTACTGGGCCTATGTGCCTTTCCCACCCTTAATTCGGGCAGTTACATAGATGGATAATCCTATTGAAGTAGAT
GTTAATAATAGTGCATGGGTGCCTGGCCCCACAGATGACTGTTGCCCTGCCCAACCTGAAGAAGGAATGATGATG
AATATTTCCATTGGGTATCCTTATCCTCCTGTTTGCCTAGGGAAGGCACCAGGATGCTTAATGCCTACAACCCAAAA
TTGGTTGGTAGAAGTACCTACAGTCAGTGCTACCAGTAGATTTACTTATCACATGGTAAGTGGAATGTCACAGATA
AATAATTTACAGGACCCTTCTTATCAAAGATCATTACAATGTAGGCCTAAGGGGAAGGCTTGCCCCAAGGAAATTC
CCAAAGAATCAAAAAGCCCAGAAGTCTTAGTCTGCGGAGAATGTGTGGCTGATACTGCAGTGTAGTACAAAACAA
TGAATTTTGAACTATGATAGACTGGGTCCCTTGAGGCCAATTATATCATAACTGTACAGGCCAGACTCATTCATGTT
CACAGGCCCCATCCATCTGGCCCATTAATCCAGCCTATGACGGTGATGTAACTGAAAGGCTGGACCAGGTTTATAG
AAGGTTAGAATCACTCTGTCCAAGGAAATGGGGTGAAAAGGGAATTTCATCACCTTGACCAAAGTTAGTCCTGTTA
CTGGTCCTGAACATCCAGAATTAGGAAGCTTACTGTGGCCTCACACCACATTAGAATTTGTTCTGGAAATCAAGCT
ATAGGAACAAGAGATCGTAAGTCATATTATACTATCAACCTAAATTCCAGTCTGACAATTCCTTTGCAAAATTGTGT
AAAACTCCCTTATATTGCTAGTTGTAGGAAAAACATAGTTATTAAACCTGATTCCCAAACCATAATCTGTGAAAATT
GTGGAATGTTTACTTGCATTGATTTGACTTTTAATTGGCAGCACCGTATTCTACTAGGAAGAGCAAGAGAGGGTGT
GTGGATCCTTGTGTCCATGGACCGACCATGGGAGGCTTCGCTATCCATCCATATTTTAACGGAAGTATTAAAAGGA
ATTCTAACTAGATCCAAAAGATTCATTTTTACTTTGATGGCAGTGATTATGGGCCTCATTGCAGTCACAGCTACTGC
TGCGGCTGCTGGAATTGCTTTACACTCCTCTGTTCAAACTGCAGAATACGTAAATGATTGGCAAAAGAATTCCTCA
AAATTGTGGAATTCTCAGATCCAAATAGATCAAAAATTGGCAAACCAAATTAATGATCTTAGACAAACTGTCATTT
GGATGGGAGAGGCTCATGAGCTTGGAATATCTTTTTCAGTTACGATGTGACTGGAATACATCAGATTTTTGTGTTA
CACCACAAGCCTATAATGAGTCTGAGCATCACTGGGACATGGTTAGATGCCATCTGCAAGGAGGAGAAGATAATC
TTACTTTAGACATTTCAAAATTAAAAGAATTTTTTTTTTCTTTGAGACAGAGTCTCGCTCTGTCGCCCAGGCTGGAGT
GCAGTGGCGTGATCTCAGCTCACTGCAAGTTCCGCCTCCTGGGTTTACACCATTCTCCTGCCTCAGCCTCCCAAGTA
GTTGGGACTACAGGAGCCCACCACCATGCCTGGCTAATTTTTTTGGGTTTTTAATAGAGATGGAGTTTCACCGTGT
TAGCCAGGATGGTCTCGATCTCCTGACCTTGTGATCTGCCCACCTTGGCCTCCCAAAGTGCTGGGATTACAGTCGT

Figure 28 (cont)

GAGCCACCGTGCCCAGCCAAGAAAAAATTTTTGAGGCATCAAAAGCCCATTTAAATTTGGTGCCAGGAACGGAGA
CAATCGTGAAAGCTGCTGATAGCCTCACAAATCTTAAGCCAGTCACTTGGGTTAAAAGCATCAGAAGTTTCACTAT
TGTAAATTTCATATTAATCCTTGTATGCCTGTTCTGTCTGTTGTTAG

Figure 30
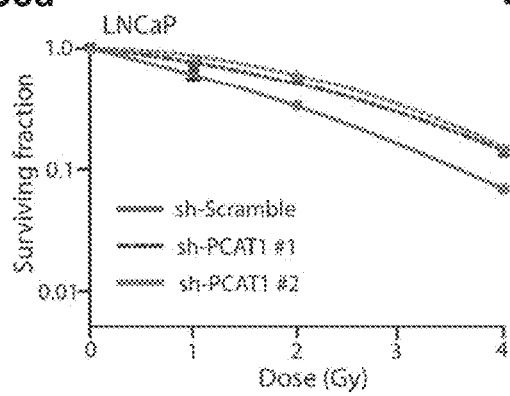
Fig. 30a
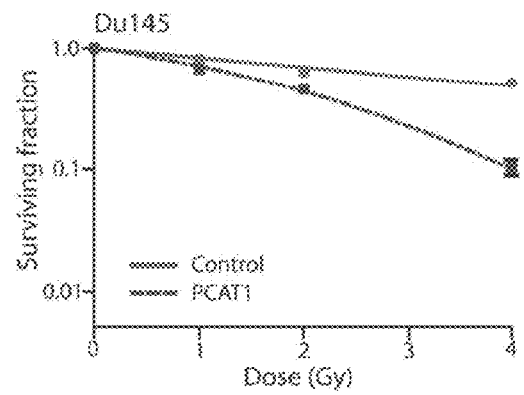
Fig. 30b
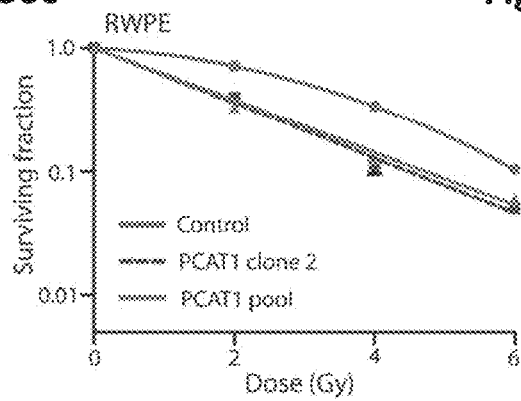
Fig. 30c
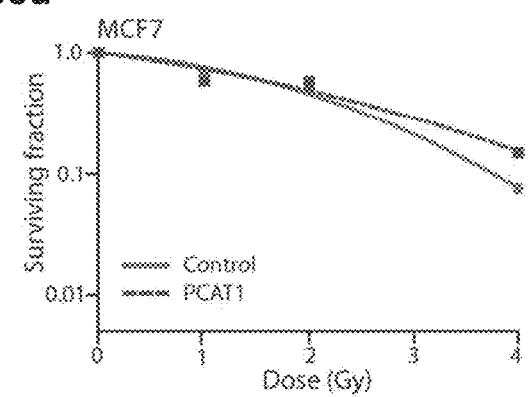
Fig. 30d

Figure 31
Fig. 31a
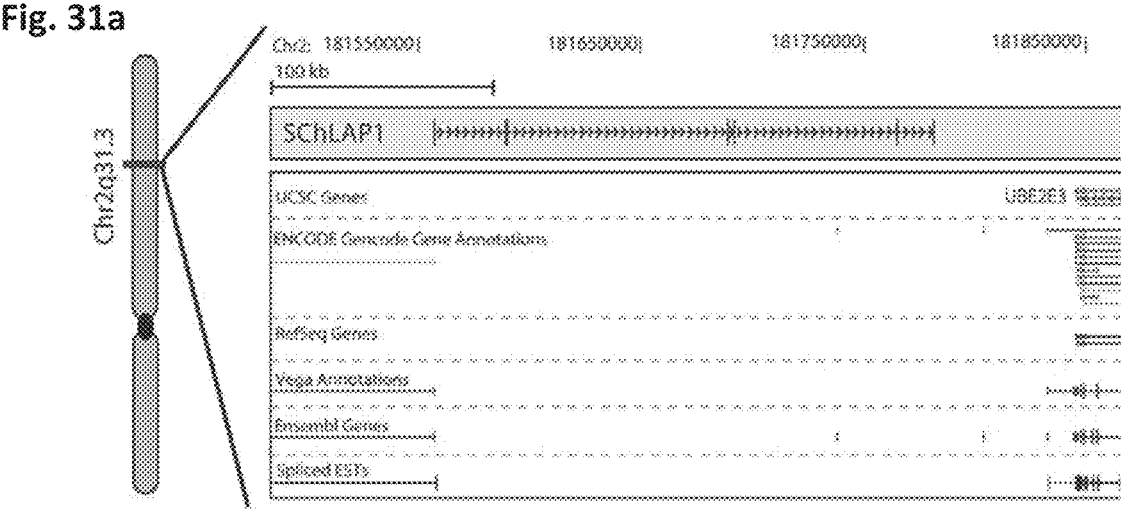
Fig. 31b
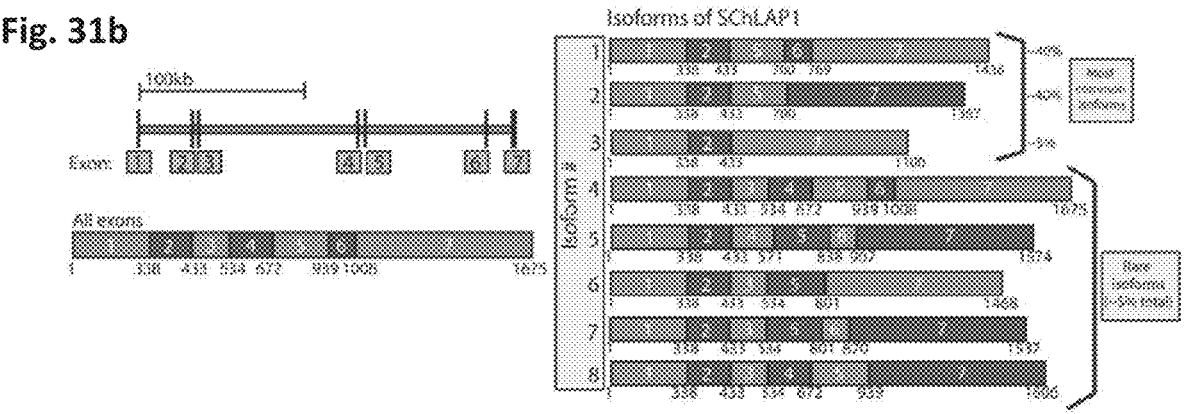

Figure 31 (cont.)
Fig. 31c
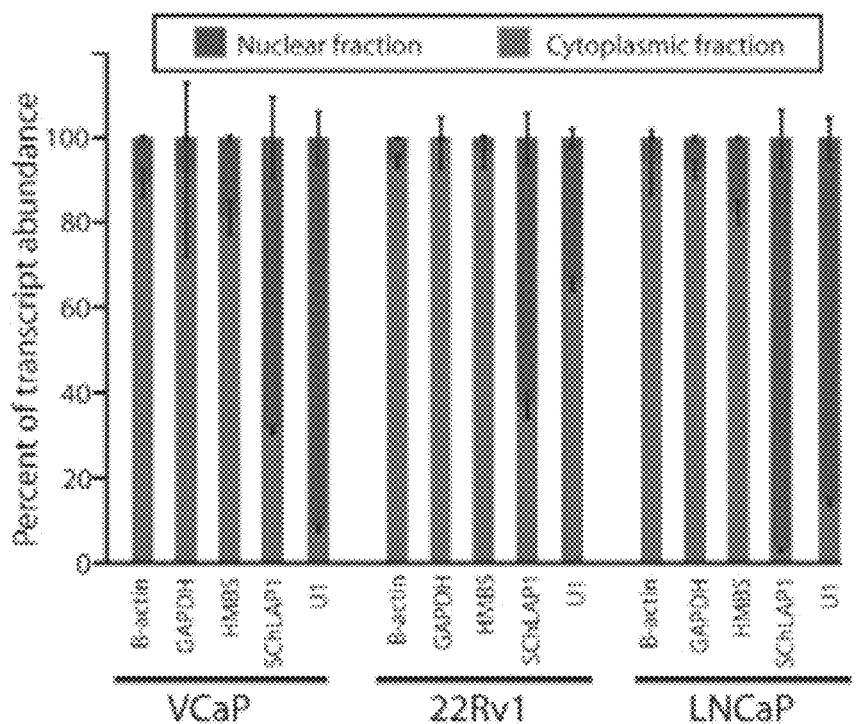
Fig. 31d
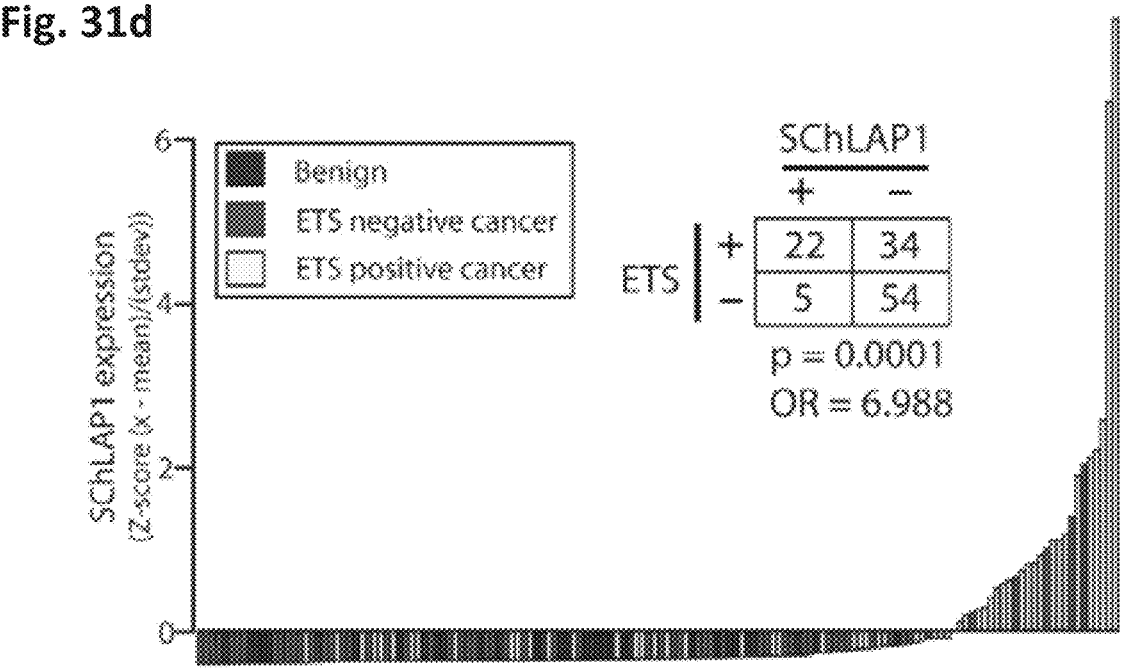

Figure 32
Fig. 32a
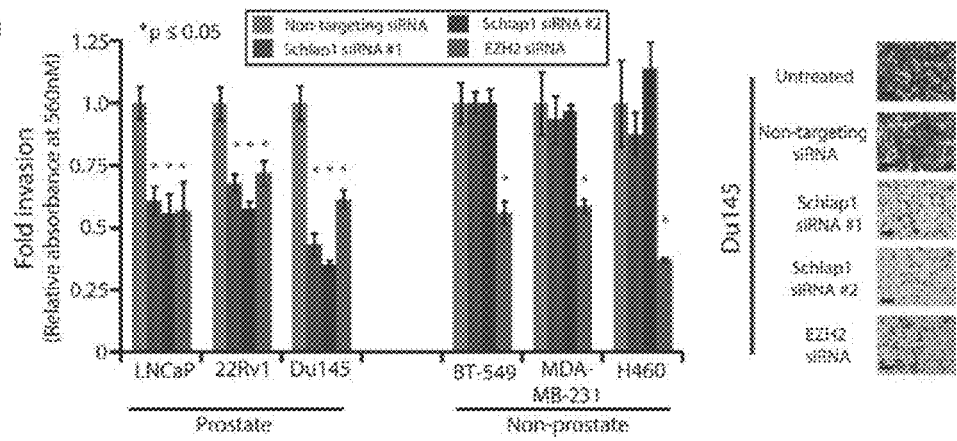
Fig. 32b
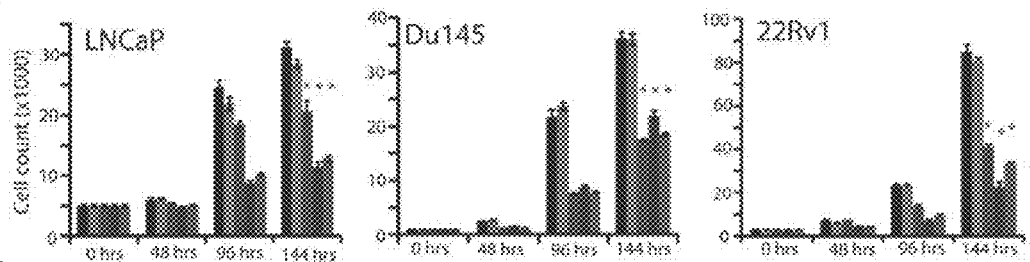
Fig. 32c
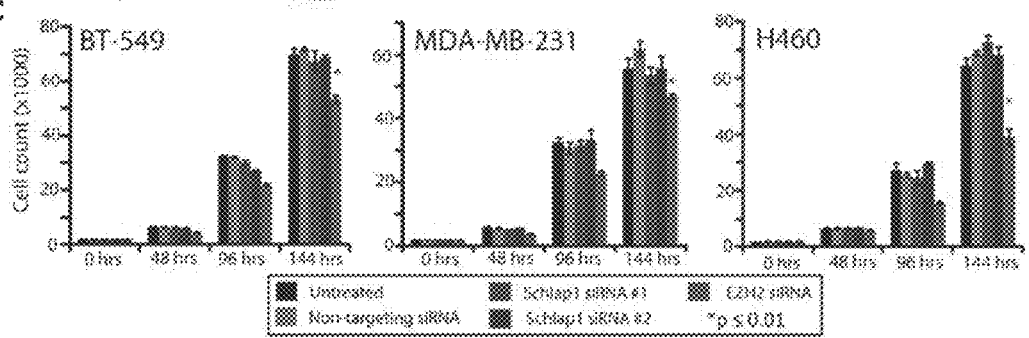
Fig. 32d
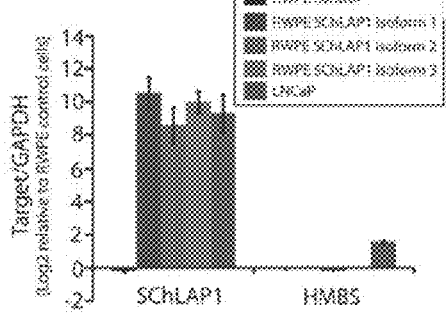
Fig. 32e
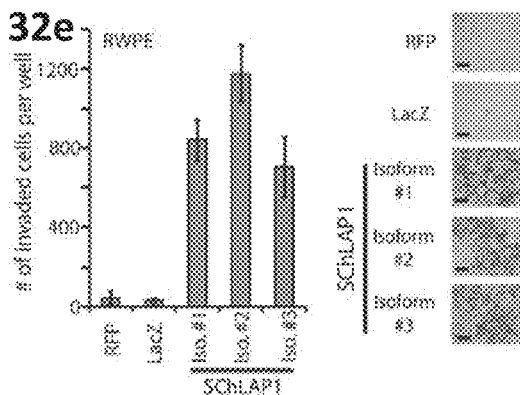

Figure 33
Fig. 33a          Fig. 33b
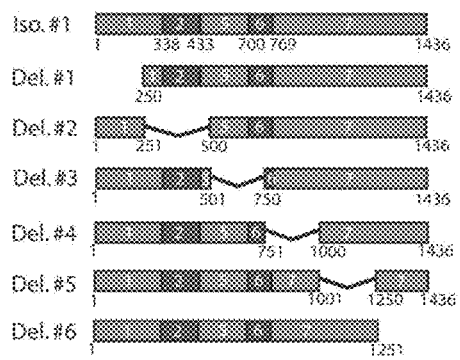
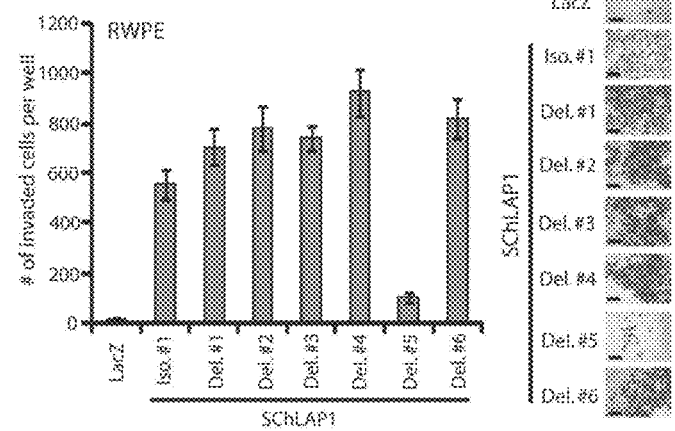

Figure 34
Fig. 34a
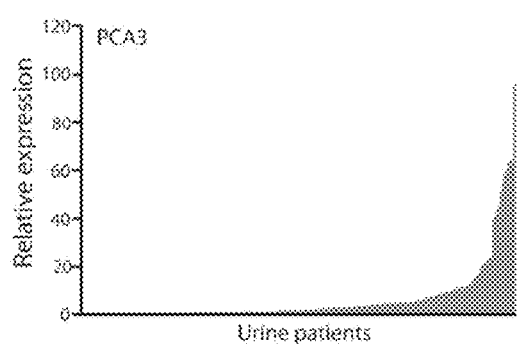
Fig. 34b
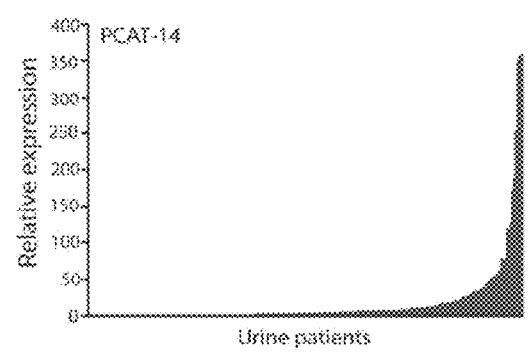
Fig. 34c
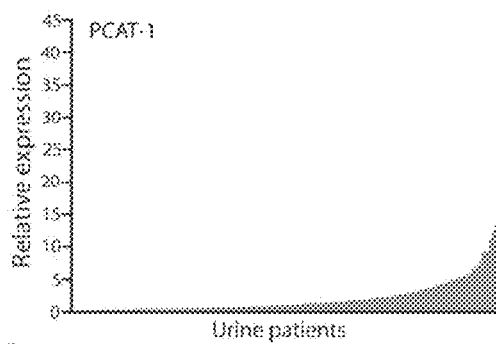
Fig. 34d
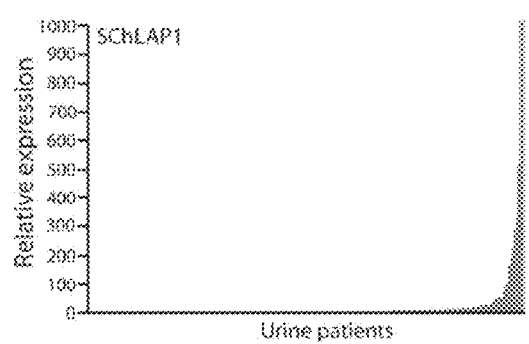
Fig. 34e
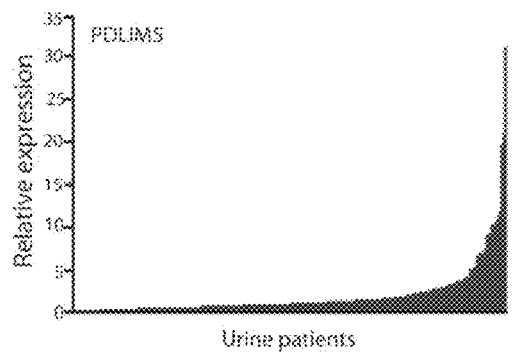

Figure 36
Fig. 36a
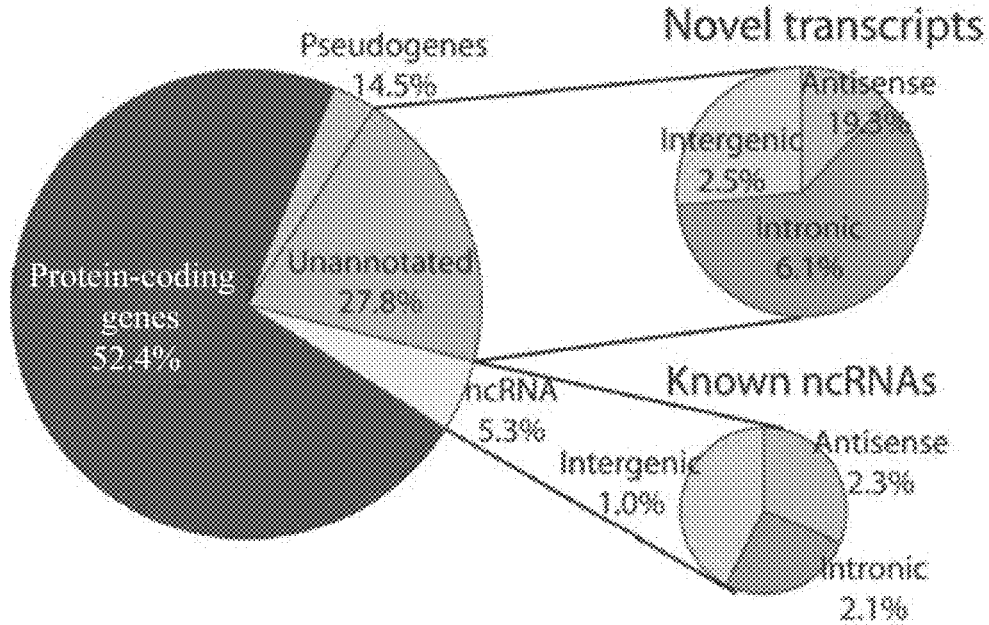
Fig. 36b
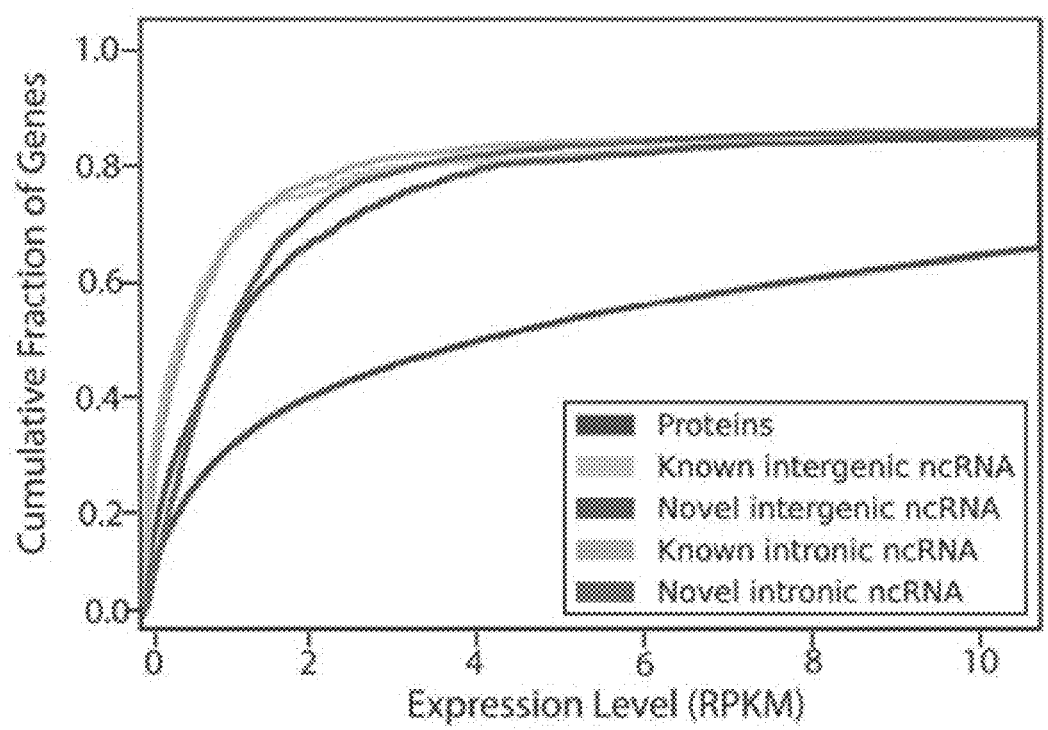

Figure 37
Fig. 37a
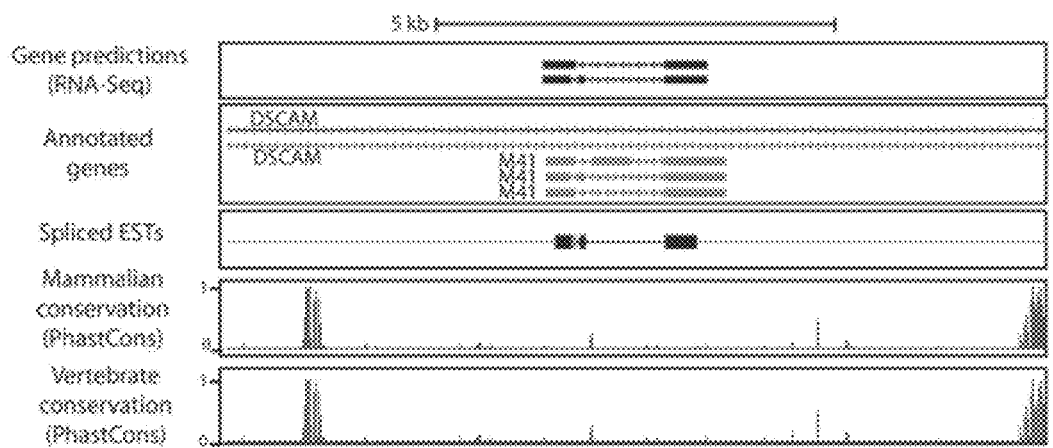
Fig. 37b
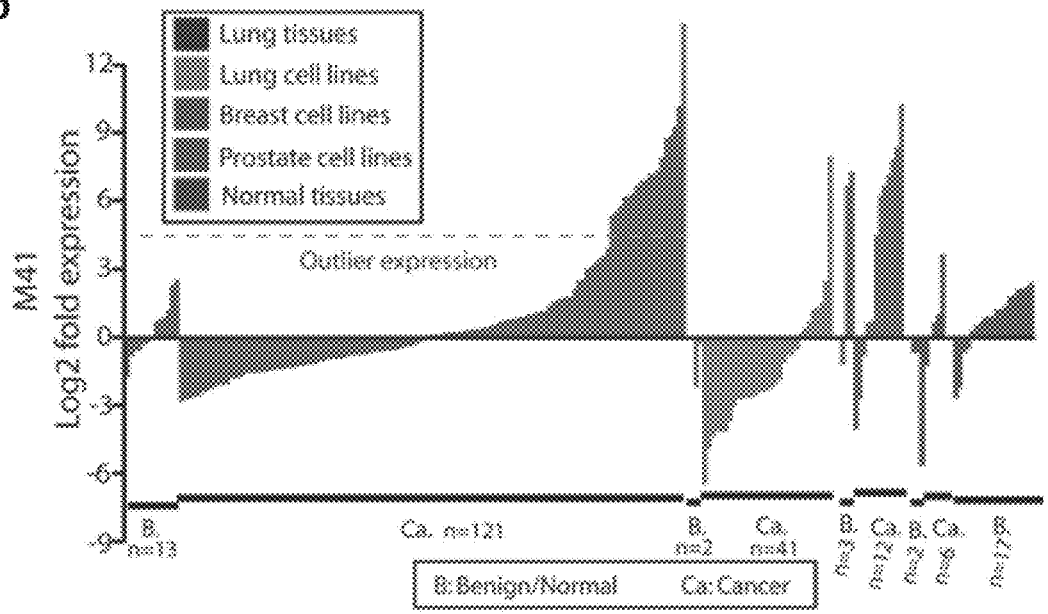

Figure 37 (cont.)
Fig. 37c
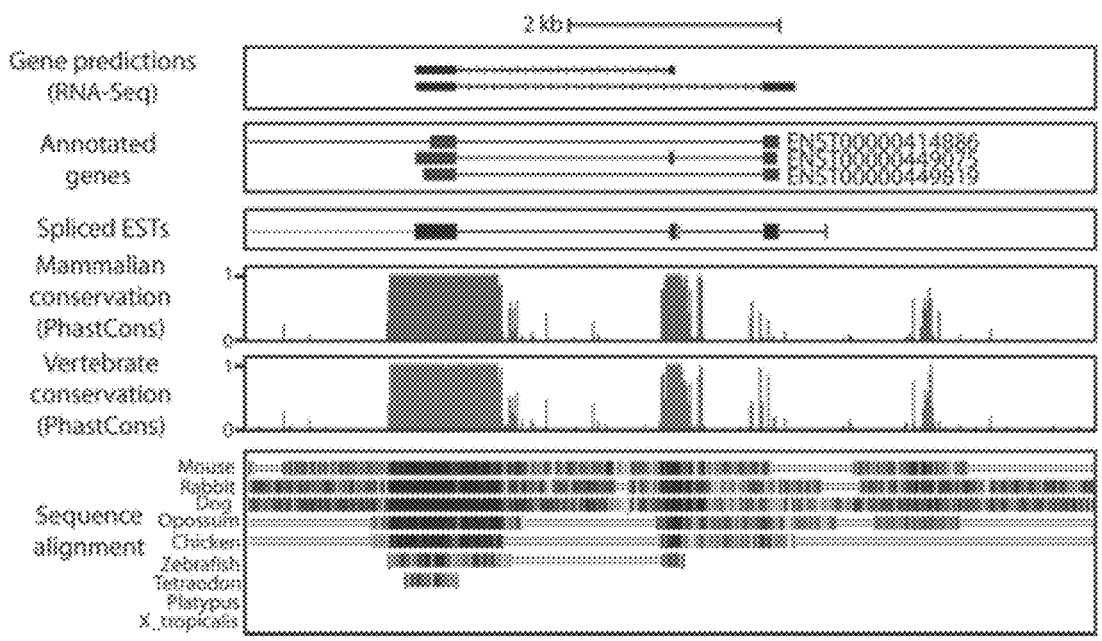
Fig. 37d
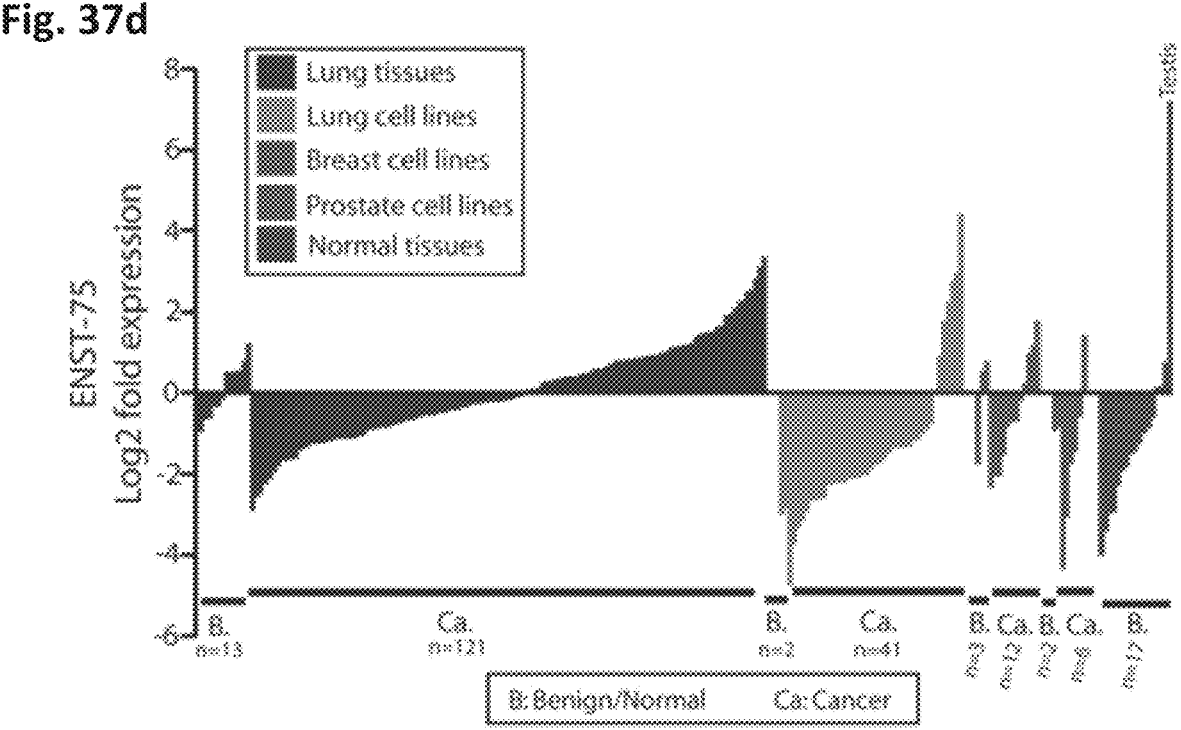

Figure 38
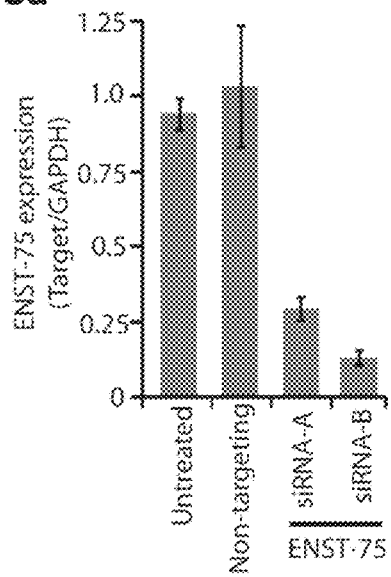
Fig. 38a
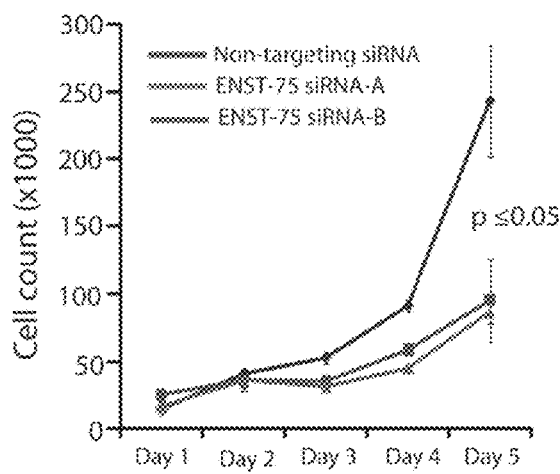
Fig. 38b
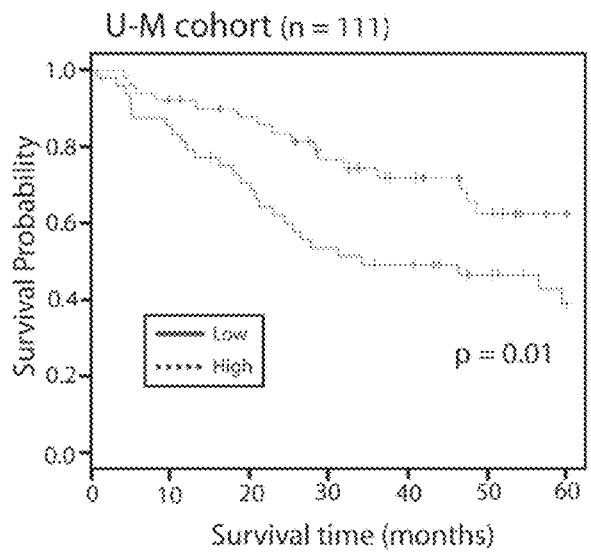
Fig. 38c
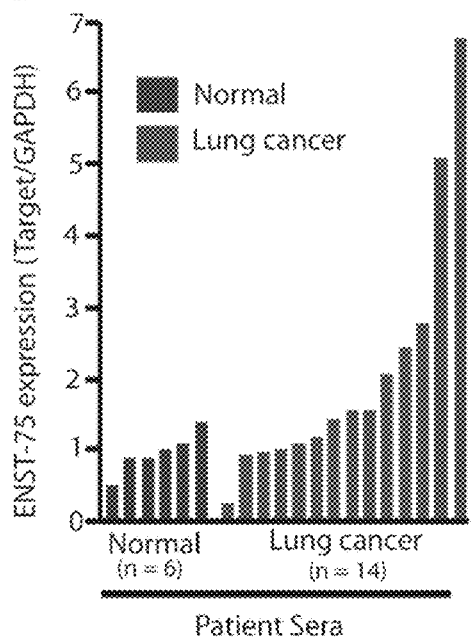
Fig. 38d FIGURE 39
Fig. 39a
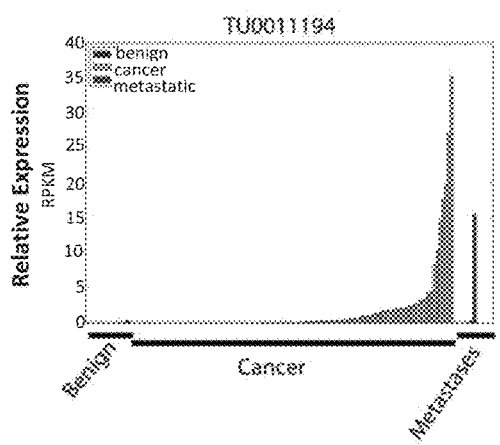
Fig. 39d
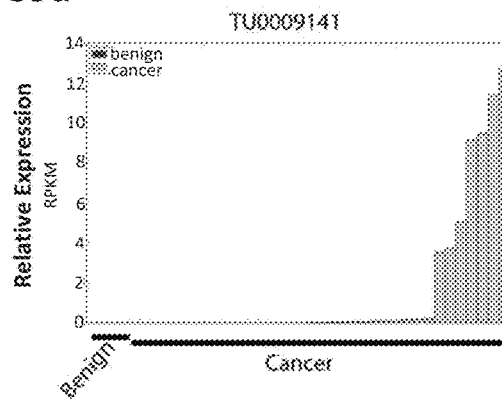
Fig. 39b
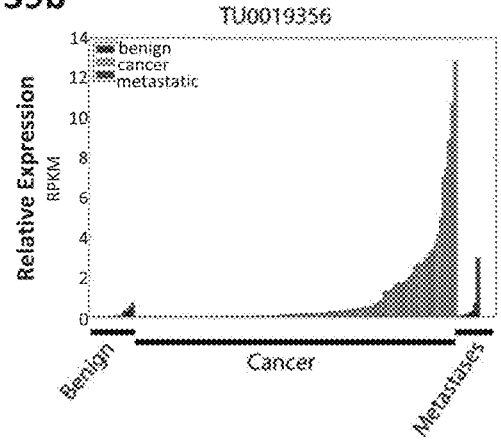
Fig. 39e
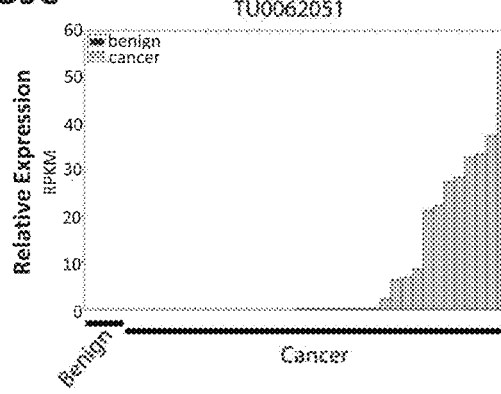
Fig. 39c
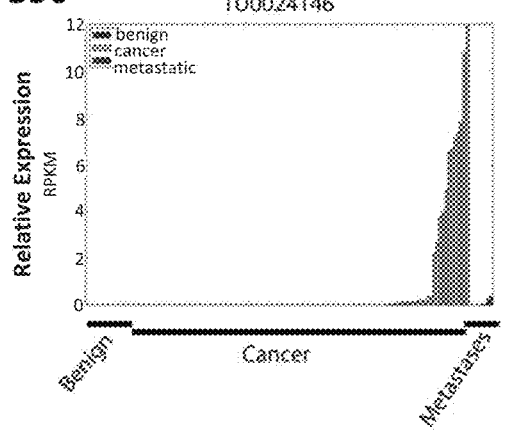
Fig. 39f
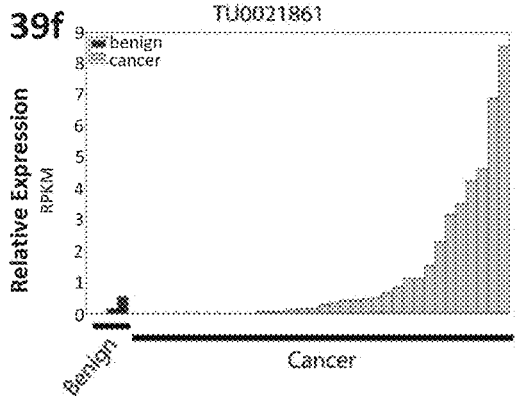

Figure 40 (cont.)
Fig. 40c
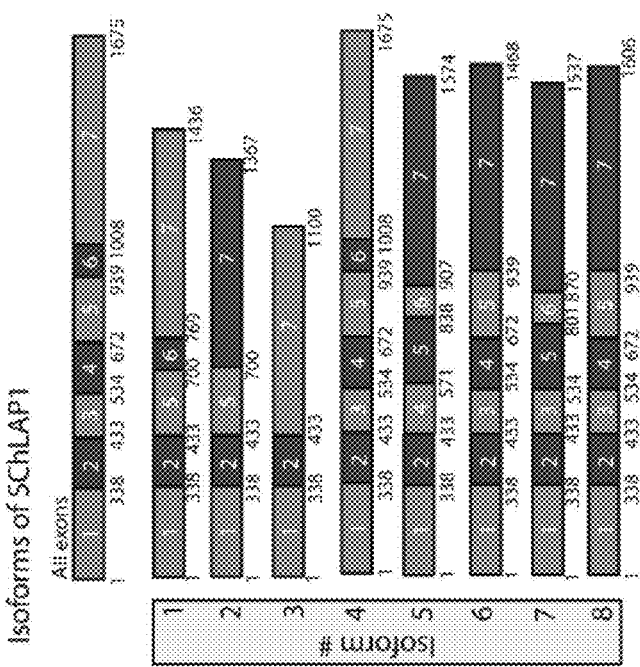
Fig. 40d
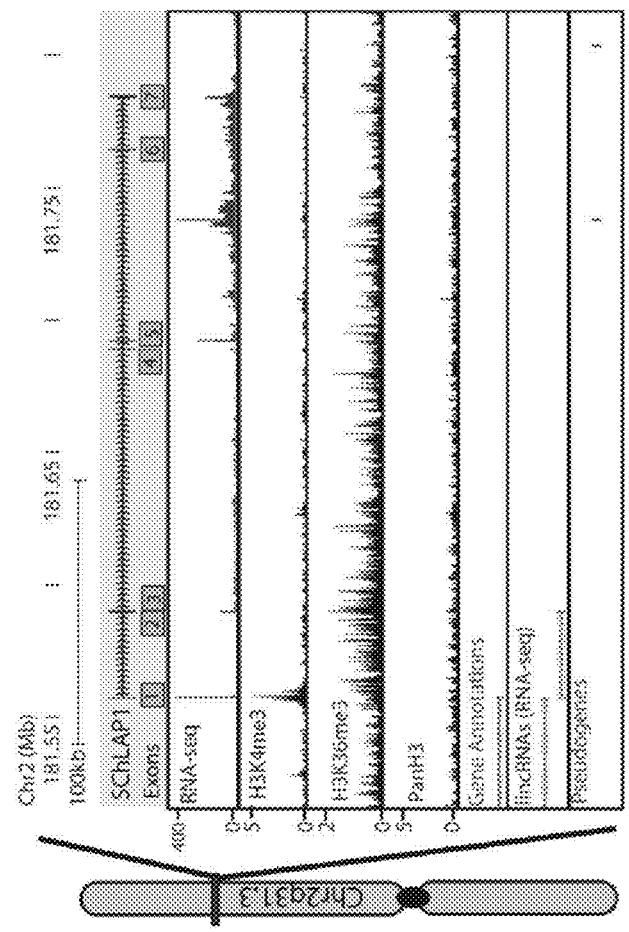

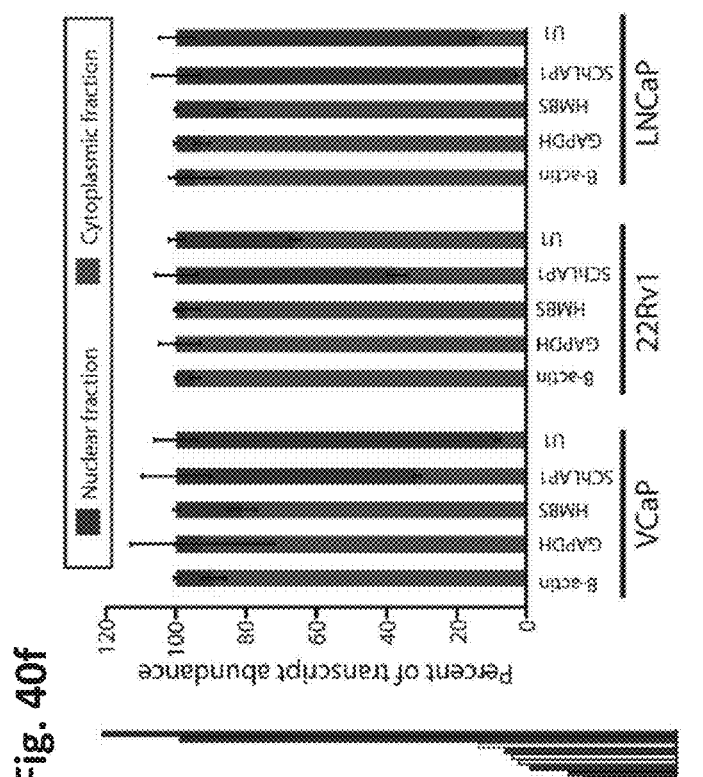
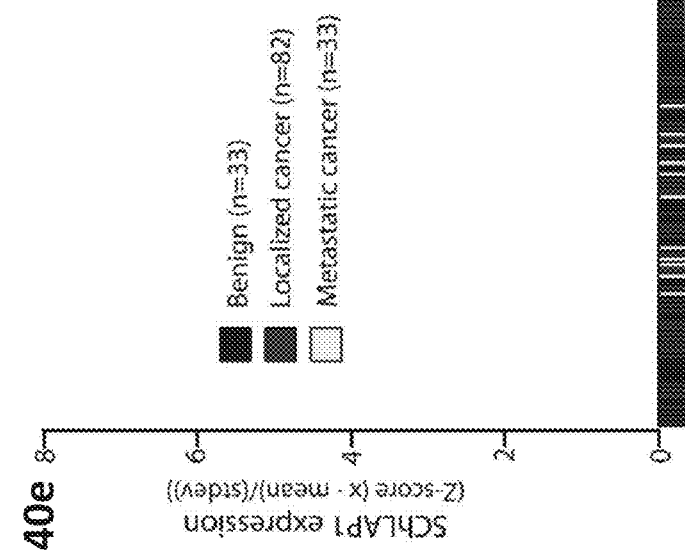
Figure 40 (cont.)

Figure 41 (cont.)
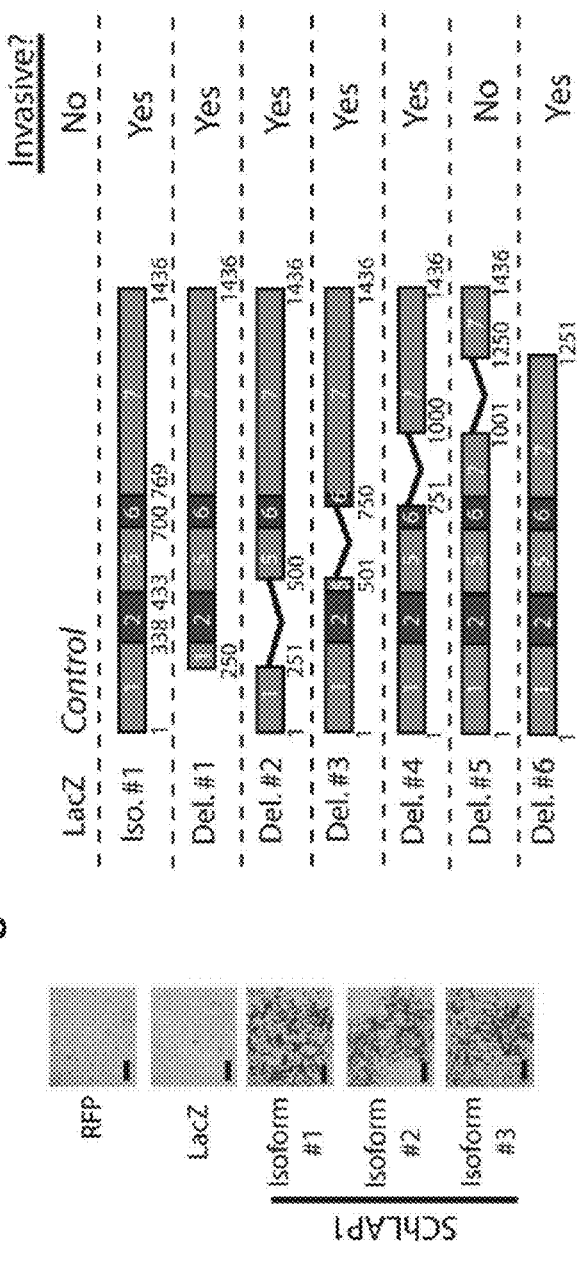
Fig. 41b
Fig. 41c
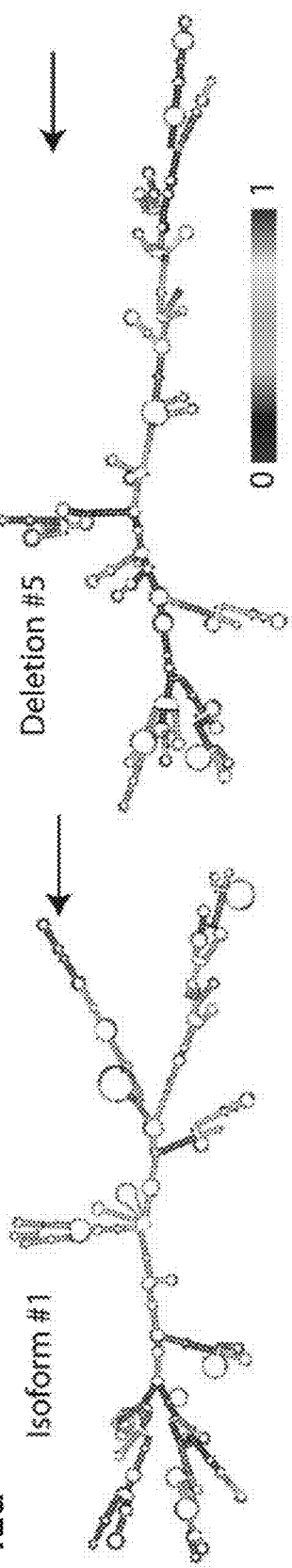
Fig. 41d

Figure 41 (cont.)

Figure 42
Fig. 42a
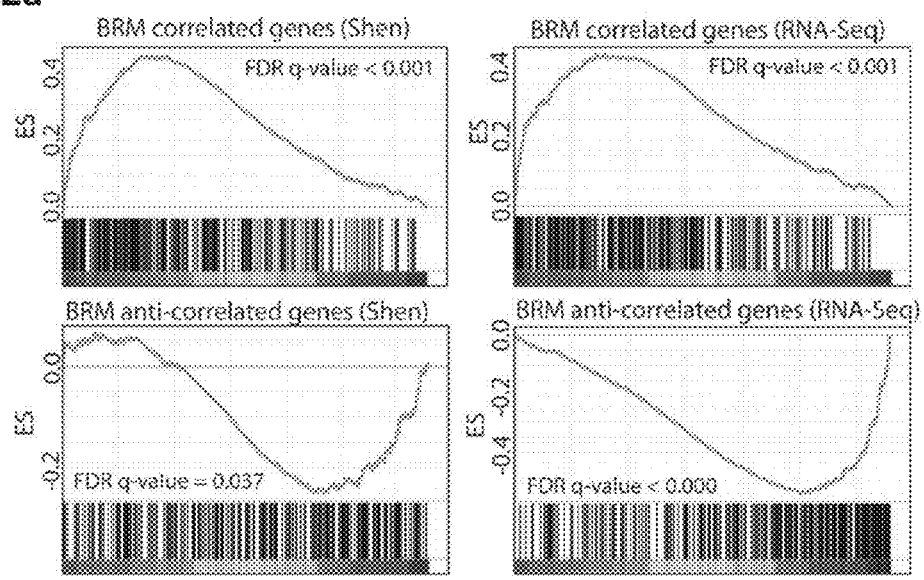
Fig. 42b
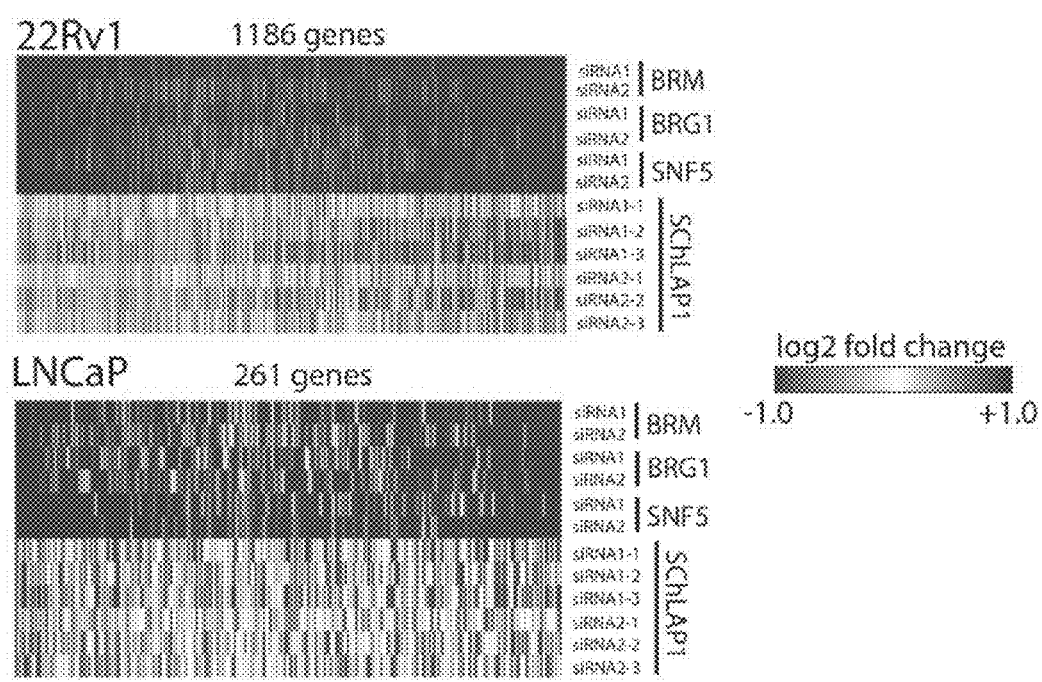

Figure 42 (cont.)
Fig. 42c
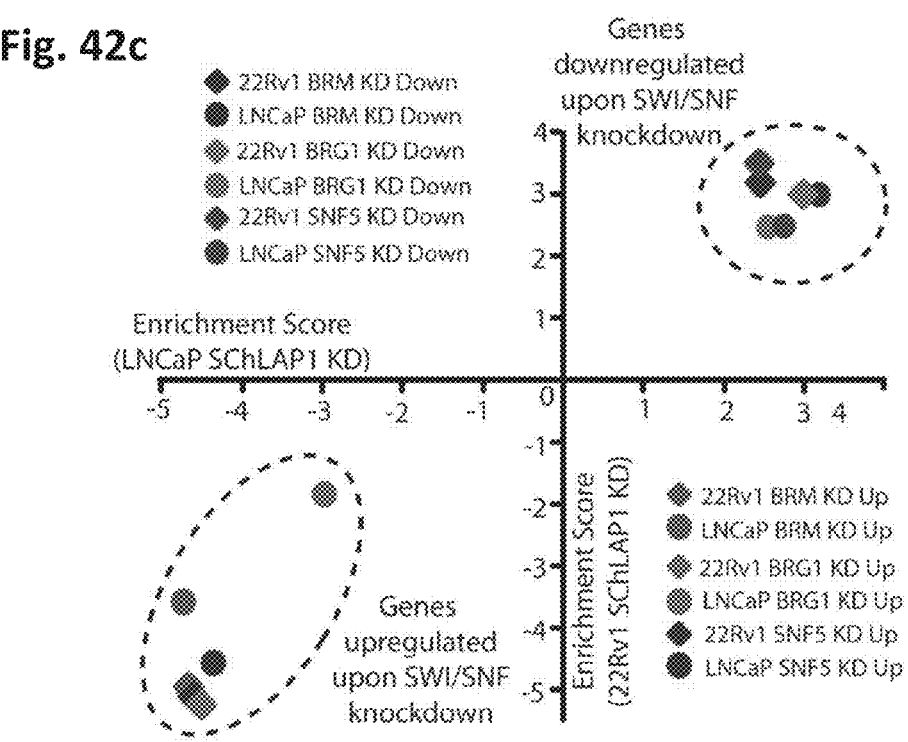
Fig. 42d
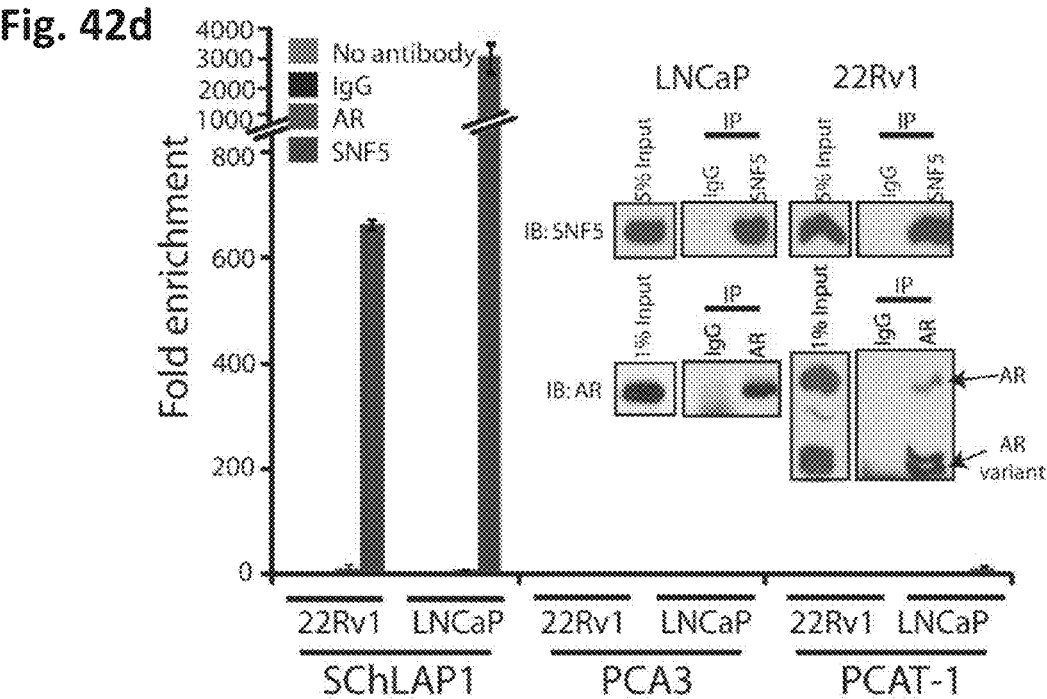

Figure 43 (cont.)
Fig. 43c
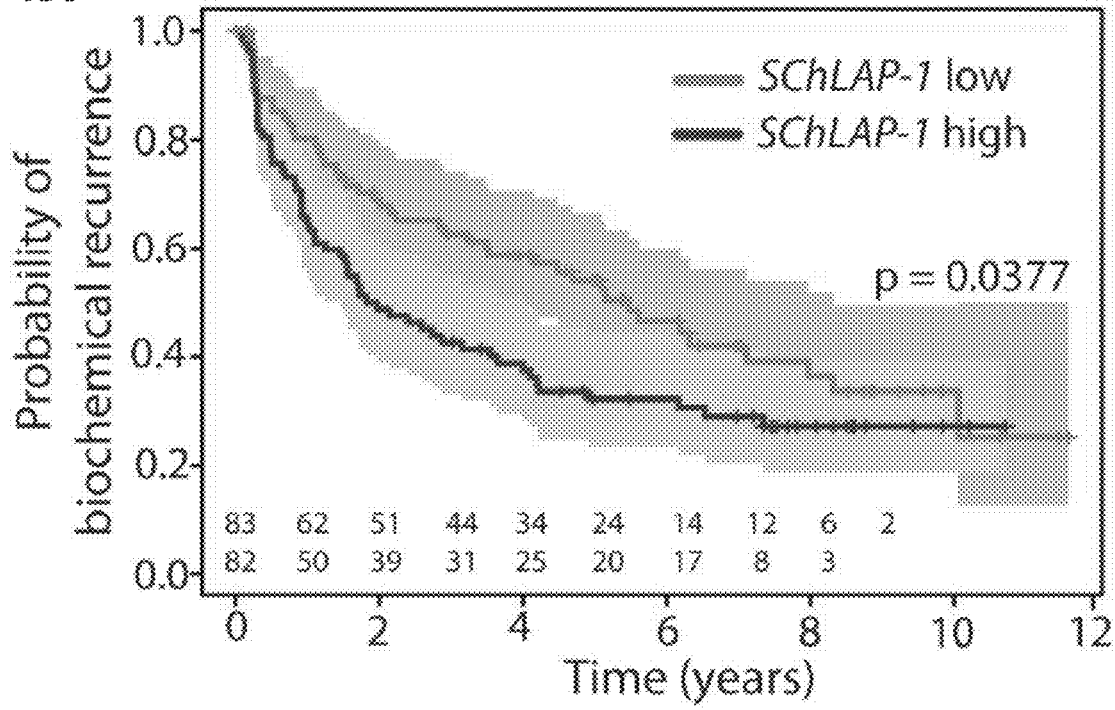
Fig. 43d
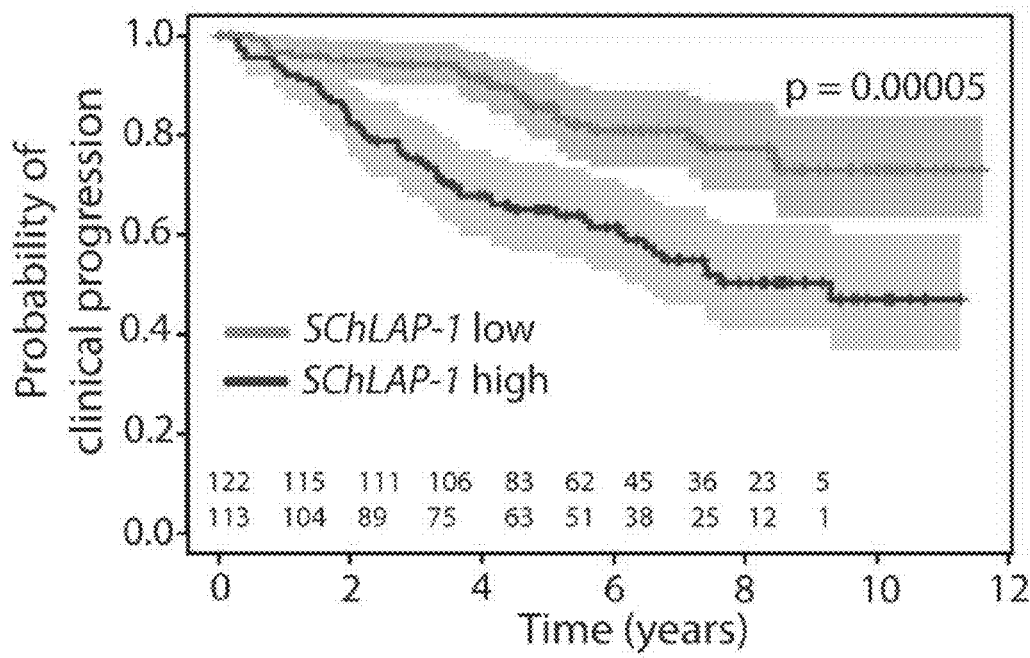

Figure 43 (cont.)
Fig. 43e
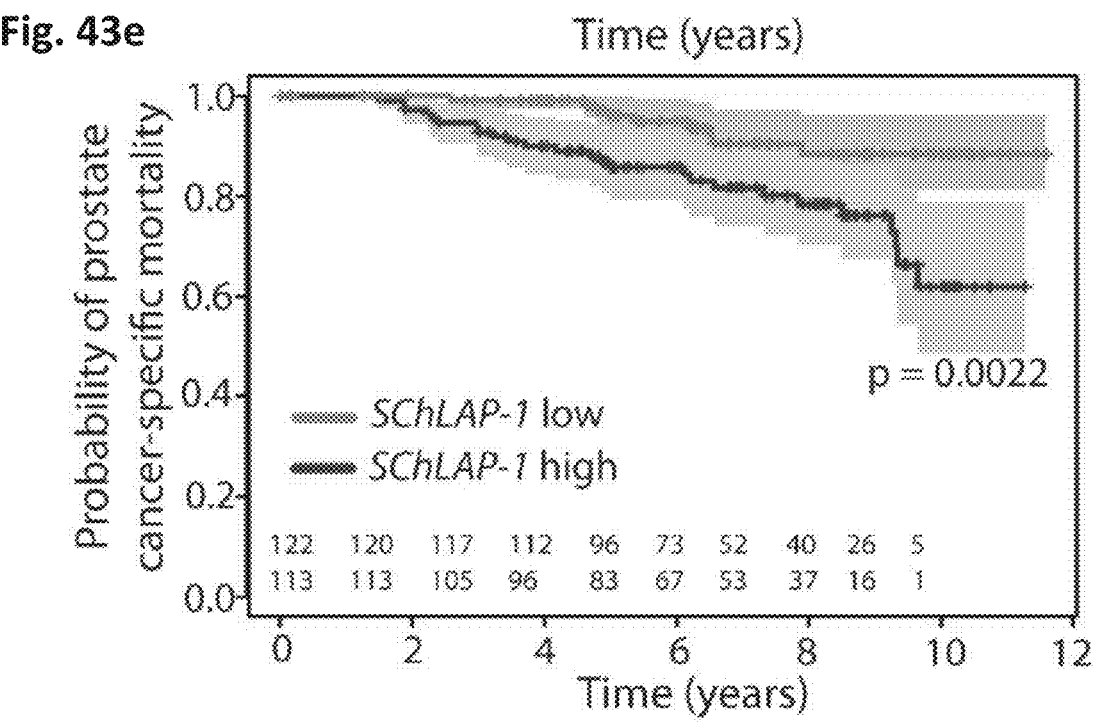
Fig. 43f
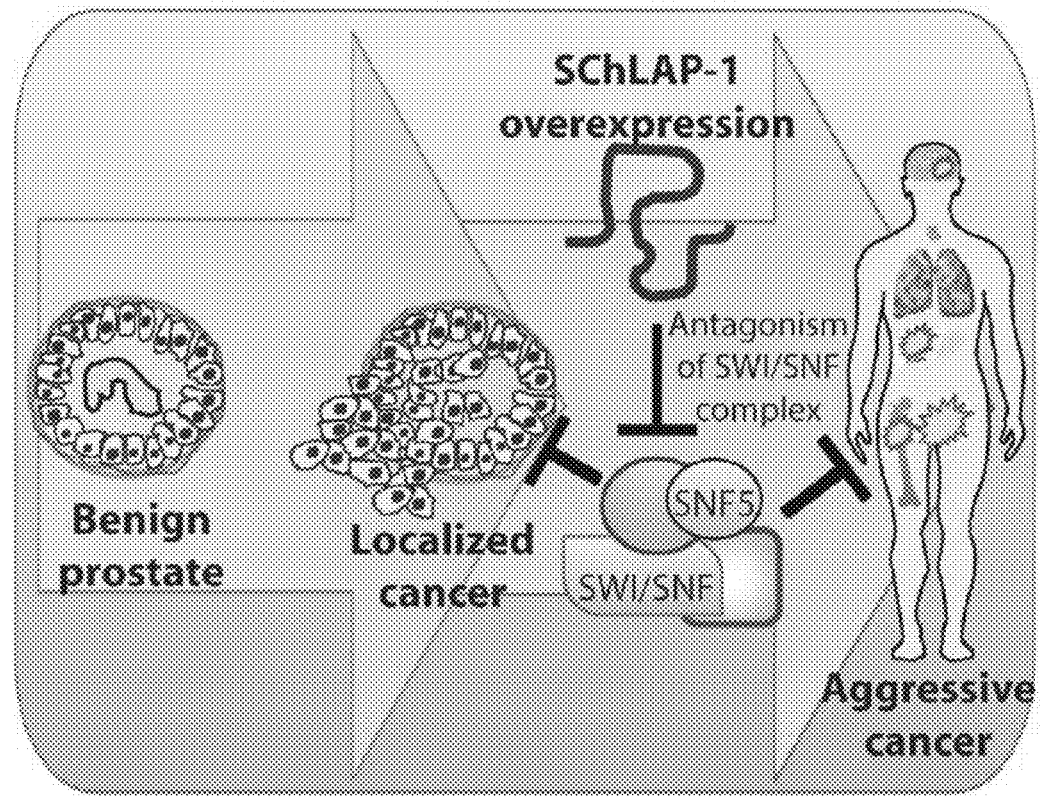

Figure 45

```
                Splice acceptor not present
                gggtcacaagCTTTTATGAGCTGTAACACTCACCGCGAAGGTCCGCAGCTTCACTCCTGAAGCCAGCGAG
                ACCACGAGCCTACTGGGAGGAACGAACAACTCCCGACGCGCCGGCCTTAAGAGCTGTAACACTCACCG
                CGAAGGTCTGCAGCTTCACTCCTGAGCCAGCGAGACCACGAACCCACCAGAAGGAAAAAACTCCGAA
 Exon 1         CACATCTGAACATCAGAAGCAACAAACTCCGGACACGCCGCCTTTAAGAACTGTAACACTCACTGCGA
                GGGTCCGCGGCTTCATTCTTGAAGTGAGTGAGACCAAGAACCCACCAGTTCTGGACACAATTTCAAGT
                CCTCAGgtaagtcac  Splice donor Splice acceptor
                ttgttctcacagTGCCATCAATATTCTGAAAATGGCAGTGATTTTTATTCAACCTGTATAAGGCACTTTCAC
 Exon 2         CATGTACCTGGAAGCAACATCTACATCTTTTTCAGgtaagtcc  Splice donor Splice acceptor
                tcaccacttcagTTTTCCTCTGTCCACTATGAAGGACTTTGTGACCACATTCTGACTCTGATGAGATCCTGC
 Exon 3         CCAGAATTGACCTGAACCCCAATAATTCACCTTTCTCTCACgtaagtcc  Splice donor Splice acceptor
                gttctcttcttcagTTTCTTCTACGCCAGGTGTGTGCTTAGCTCCATGACAAAAGGTGACAGCTTATTCTGCAG
 Exon 4         CACACACACATCATCAAAGTGGGAGCTGGTGAGACTGGCACACTGACAGTCTGTCCTAGCAGATTTCA
                GCTCACACTGgtgagtccacag  Splice donor Splice acceptor
                cctcacatgtcagCAATCTAGATGCTGGGGACACAAGGTCCACCTTCCAGGAATATGGCCATGACACCAGA
                AATCACAAACATGATGAGAATGGAATGACTGGGGAAGAAGTGCCAGATGCTTCACTTGTAAATGAAG
 Exon 5         ACCCAGCCTCTGGGGATGCAGATACCACCTCCCTGAAGAAGCTGAATATCTGCAGATAAGTGGAGTTC
                ACCAATGATGAGGAGCGGGATGGAGAAAGGAGGTAGGGAGAGTCATCCAAGGAACATGAGCAACAT
                GTTAAAAGgtaagtcc  Splice donor Splice acceptor
                ctctatccactcagCCAAGTGGTTTAATTTCTGGAGATGGTGAACCCAAGAGGCTCTGCTGGGAGACAACAA
 Exon 6         AAATAATGAAGgtaagtgaatcc  Splice donor Splice acceptor
                tcattcgctccagAATTGAACCAGAGTCCGGTGAATATCAGCACTGGGACCAGTTAGCAGAGGAAAAGGAA
                AGAATAAAAGCGAAAAGAATGAAGAGTCATATGATTACCAACTTTTCCTTTTTCATATAAATTGAGTG
                TATATGGGTCTGGAACAACCTGAATTTCCATCAAGTCCTGGCTAACCTCATTATGTCCTATGAATATTT
                TTGACTAATCCCACTTTACATTAATCTGTATTGTGAATGTGGATATTGAATTATATTTCTTTGTAATCCC
                ATTATCCAAAATCCAGTTCAGAGACTATTAGTTACCAATGTTCACTGTGAAGGAAAAAAAAAAAAAA
 Exon 7         AAGCTCAGGAGGATAAACATGTGATATGGTTTGGCTCTGTCTCCCCACCCAAATATCATCTTGAATTGTAG
                CTCCCATAATTCCCACGTGTTGTGGGAGGGACCCGGTGGGACATAATTGTATCATGGGGGTGGTTCCC
                CCATACTATTCTCATAGTAGTGAATAAGTCTCACAAAATCTGATGGTTTTATGAGGGAAAACCCCTTTC
                ACCTGGTTCTCATTCTCTTCTCTGGTCTGTCGTCATGTAAGACATGCCTTTCACCTTCTCCACCATGACT
                GTGAGGCCTCCCCAGCCACGTGGAACTGTGAGCCCATTAAACCTCTTTCACTTATAAATtcacaatcc
                                                 Polyadenylation              Splice donor
                                                   signal                    not present
```

NcRNA AND USES THEREOF

CROSS REFERENCE TO RELATED APPLICATIONS

This application is a continuation of U.S. application Ser. No. 15/156,936, filed May 17, 2016, now U.S. Pat. No. 10,407,735, Issued Sep. 10, 2019, which is a continuation of Abandoned U.S. application Ser. No. 13/797,106, filed Mar. 12, 2013, which is a continuation-in-part of Abandoned U.S. application Ser. No. 13/299,000, filed Nov. 17, 2011, which claims priority to U.S. Provisional Application No. 61/415,490, filed Nov. 19, 2010, each of which are herein incorporated by referenced in its entirety.

STATEMENT REGARDING FEDERALLY SPONSORED RESEARCH OR DEVELOPMENT

This invention was made with government support under CA111275 and CA069568 awarded by the National Institutes of Health and W81XWH-08-1-0031 and W81XWH-11-1-0520 awarded by the U. S. Army Medical Research and Materiel Command. The government has certain rights in the invention.

FIELD OF THE INVENTION

The present invention relates to compositions and methods for cancer diagnosis, research and therapy, including but not limited to, cancer markers. In particular, the present invention relates to ncRNAs as diagnostic markers and clinical targets for prostate, lung, breast and pancreatic cancer.

BACKGROUND OF THE INVENTION

A central aim in cancer research is to identify altered genes that are causally implicated in oncogenesis. Several types of somatic mutations have been identified including base substitutions, insertions, deletions, translocations, and chromosomal gains and losses, all of which result in altered activity of an oncogene or tumor suppressor gene. First hypothesized in the early 1900's, there is now compelling evidence for a causal role for chromosomal rearrangements in cancer (Rowley, Nat Rev Cancer 1: 245 (2001)). Recurrent chromosomal aberrations were thought to be primarily characteristic of leukemias, lymphomas, and sarcomas. Epithelial tumors (carcinomas), which are much more common and contribute to a relatively large fraction of the morbidity and mortality associated with human cancer, comprise less than 1% of the known, disease-specific chromosomal rearrangements (Mitelman, Mutat Res 462: 247 (2000)). While hematological malignancies are often characterized by balanced, disease-specific chromosomal rearrangements, most solid tumors have a plethora of non-specific chromosomal aberrations. It is thought that the karyotypic complexity of solid tumors is due to secondary alterations acquired through cancer evolution or progression.

Two primary mechanisms of chromosomal rearrangements have been described. In one mechanism, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to MYC leading to activation of this oncogene in B- and T-cell malignancies, respectively (Rabbitts, Nature 372: 143 (1994)). In the second mechanism, rearrangement results in the fusion of two genes, which produces a fusion protein that may have a new function or altered activity. The prototypic example of this translocation is the BCR-ABL gene fusion in chronic myelogenous leukemia (CML) (Rowley, Nature 243: 290 (1973); de Klein et al., Nature 300: 765 (1982)). Importantly, this finding led to the rational development of imatinib mesylate (Gleevec), which successfully targets the BCR-ABL kinase (Deininger et al., Blood 105: 2640 (2005)). Thus, diagnostic methods that specifically identify epithelial tumors are needed.

SUMMARY OF THE INVENTION

The present invention relates to compositions and methods for cancer diagnosis, research and therapy, including but not limited to, cancer markers. In particular, the present invention relates to ncRNAs as diagnostic markers and clinical targets for cancer (e.g., prostate, lung, breast and pancreatic cancer).

Embodiments of the present invention provide compositions, kits, and methods useful in the detection and screening of a cancer. Experiments conducted during the course of development of embodiments of the present invention identified upregration of one or more non-coding RNAs in cancer. Some embodiments of the present invention provide compositons and methods for detecting expression levels of such ncRNAs. Identification of ncRNAs finds use in screening, diagnostic and research uses.

For example, in some embodiments, the present invention provides a method of screening for the presence of a cancer in a subject, comprising contacting a biological sample from a subject with a reagent for detecting the level of expression of one or more non-coding RNAs (ncRNA); and detecting the level of expression of the ncRNA in the sample, wherein an increased level of expression of the ncRNA in the sample is indicative of a cancer in the subject. In some embodiments, the cancer is a prostate cancer. In some instances, the increased level of expression of the ncRNA in the sample is relative to the level of ncRNA in a control sample. The control sample may comprise one or more normal cells. In some instances, the normal cells are normal prostate cells. In other instances, the increased level of expression of the ncRNA in the sample is relative to the level of expression of the ncRNA in a sample from a prior time point. Alternatively, the increased level of expression of the ncRNA in the sample is relative to a pre-established threshold level. In some embodiments, the ncRNAs are described by SEQ ID NOs: 1-9. In some embodiments, the non-coding RNAs comprise one or more PCAT transcripts. In some embodiments, the non-coding RNAs are selected from the group comprising PCAT1, PCAT14, PCAT43 and PCAT 109. In some embodiments, the sample is tissue, blood, plasma, serum, urine, urine supernatant, urine cell pellet, semen, prostatic secretions or prostate cells. In some instances, detecting the level of expression of the ncRNA comprises one or more in vitro assays. In some embodiments, the detection is carried out utilizing a sequencing technique, a nucleic acid hybridization technique, a nucleic acid amplification technique, or an immunoassay. However, the invention is not limited to the technique employed. In some embodiments, the nucleic acid amplification technique is polymerase chain reaction, reverse transcription polymerase chain reaction, transcription-mediated amplification, ligase chain reaction, strand displacement amplification or nucleic acid sequence based amplification. In some embodiments, the prostate cancer is localized prostate cancer or metastatic prostate cancer. In some embodiments, the reagent is a pair of amplification oligonucleotides or an oligonucleotide probe.

Additional embodiments provide a method of screening for the presence of acancer in a subject, comprising contacting a biological sample from a subject with a reagent for detecting the level of expression of two or more (e.g., 10 or more, 25 or more, 50 or more, 100 or more or all 121) non-coding RNAs (ncRNA); and detecting the level of expression of the ncRNA in the sample, wherein an increased level of expression of the ncRNA in the sample is indicative of cancer in the subject. In some embodiments, the cancer is a prostate cancer. In some instances, the increased level of expression of the ncRNA in the sample is relative to the level of ncRNA in a control sample. The control sample may comprise one or more normal cells. In some instances, the normal cells are normal prostate cells. In other instances, the increased level of expression of the ncRNA in the sample is relative to the level of expression of the ncRNA in a sample from a prior time point. Alternatively, the increased level of expression of the ncRNA in the sample is relative to a pre-established threshold level. In some embodiments, at least one of the two or more ncRNAs are selected from a group comprising PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, and PCAT121. In some embodiments, the two or more ncRNAs are selected from the group comprising PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, and PCAT121. In some instances, detecting the level of expression of the ncRNA comprises one or more in vitro assays.

Further embodiments of the present invention provide an array, comprising reagents for detecting the level of expression of two or more (e.g., 10 or more, 25 or more, 50 or more, 100 or more or all 121) non-coding RNAs (ncRNA) selected from, for example, PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, or PCAT121. In some embodiments, the reagent is a pair of amplification oligonucleotides or an oligonucleotide probe.

In some embodiments, the present invention provides a method for screening for the presence of a cancer in a subject, comprising contacting a biological sample from a subject with a reagent for detecting the level of expression of one or more non-coding RNAs; and detecting the level of expression of the ncRNA in the sample, wherein an increased level of expression of the ncRNA in the sample is indicative of cancer in the subject. In some instances, the cancer is a lung cancer. In some instances, the increased level of expression of the ncRNA in the sample is relative to the level of ncRNA in a control sample. The control sample may comprise one or more normal cells. In some instances, the normal cells are normal lung cells. In other instances, the increased level of expression of the ncRNA in the sample is relative to the level of expression of the ncRNA in a sample from a prior time point. Alternatively, the increased level of expression of the ncRNA in the sample is relative to a pre-established threshold level. In some instances, the one or more non-coding RNAs are selected from the group comprising M41 and ENST-75. In some instances, detecting the level of expression of the ncRNA comprises one or more in vitro assays.

In some embodiments, the present invention provides a method for screening for the presence of a cancer in a subject, comprising contacting a biological sample from a subject with a reagent for detecting the level of expression of one or more non-coding RNAs; and detecting the level of expression of the ncRNA in the sample, wherein an increased level of expression of the ncRNA in the sample is indicative of cancer in the subject. In some instances, the cancer is a breast cancer. In some instances, the increased level of expression of the ncRNA in the sample is relative to the level of ncRNA in a control sample. The control sample may comprise one or more normal cells. In some instances, the normal cells are normal breast cells. In other instances, the increased level of expression of the ncRNA in the sample is relative to the level of expression of the ncRNA in a sample from a prior time point. Alternatively, the increased level of expression of the ncRNA in the sample is relative to a pre-established threshold level. In some instances, the one or more ncRNAs are selected from the group comprising TU0011194, TU0019356 and TU0024146. In some instances, detecting the level of expression of the ncRNA comprises one or more in vitro assays.

In some embodiments, the present invention provides a method for screening for the presence of cancer in a subject, comprising contacting a biological sample from a subject with a reagent for detecting the level of expression of one or more non-coding RNAs; and detecting the level of expression of the ncRNA in the sample, wherein an increased level of expression of the ncRNA in the sample is indicative of cancer in the subject. In some instances, the cancer is a pancreatic cancer. In some instances, the increased level of expression of the ncRNA in the sample is relative to the level of ncRNA in a control sample. The control sample may comprise one or more normal cells. In some instances, the normal cells are normal pancreatic cells. In other instances, the increased level of expression of the ncRNA in the sample is relative to the level of expression of the ncRNA in a sample from a prior time point. Alternatively, the increased level of expression of the ncRNA in the sample is relative to a pre-established threshold level. In some instances, the one or more ncRNAs are selected from the group comprising TU0011194, TU0019356 and TU0024146. In some instances, detecting the level of expression of the ncRNA comprises one or more in vitro assays.

In still further embodiments, the present invention provides a method of screening for the presence of acancer in a subject, comprising (a) contacting a biological sample from a subject with a gene expression detection assay, wherein the gene expression detection assay comprises a gene expression informative reagent for identification of the level of expression of SChLAP-1; (b) detecting the level of expression of SChLAP-1 in the sample; and (c) diagnosing cancer in the subject when an increased level of expression of SChLAP-1 in the sample is detected. In some instances, the cancer is a prostate cancer. In some instances, the increased level of expression of SChLAP-1 in the sample is relative to the level of SChLAP-1 in a control sample. The control sample may comprise one or more normal cells. In some instances, the normal cells are normal prostate cells. In other instances, the increased level of expression of SChLAP-1 in the sample is relative to the level of expression of SChLAP-1 in a sample from a prior time point. Alternatively, the increased level of expression of SChLAP-1 in the sample is relative to a pre-established threshold level. In some instances, detecting the level of expression of SChLAP-1 comprises one or more in vitro assays. In some instances, the gene expression detection assay further comprises a gene expression informative reagent for identification of the level of expression of one or more ncRNAs.

In additional embodiments, the present invention provides a method of identifying subjects at risk of cancer metastatis, comprising (a) contacting a biological sample from a subject with a gene expression detection assay, wherein the gene expression detection assay comprises a gene expression informative reagent for identification of the level of expression of SChLAP-1; (b) detecting the level of expression of SChLAP-1 in the sample using an in vitro assay; and (c) identifying subjects at risk of cancer metastasis when an increased level of expression of SChLAP-1 in the sample is detected. In some embodiments, the subject is at increased risk of lethal prostate cancer when an increased level of expression of SChLAP-1 in the sample is detected. In some instances, the cancer is a prostate cancer. In some instances, the increased level of expression of SChLAP-1 in the sample is relative to the level of SChLAP-1 in a control sample. The control sample may comprise one or more normal cells. In some instances, the normal cells are normal prostate cells. In other instances, the increased level of expression of SChLAP-1 in the sample is relative to the level of expression of SChLAP-1 in a sample from a prior time point. Alternatively, the increased level of expression of SChLAP-1 in the sample is relative to a pre-established threshold level. In some instances, detecting the level of expression of SChLAP-1 comprises one or more in vitro assays. In some instances, the gene expression detection assay further comprises a gene expression informative reagent for identification of the level of expression of one or more ncRNAs.

Disclosed herein may be methods, systems, compositions and kits for analyzing, diagnosing, prognosing, monitoring, and/or treating a cancer. Such systems may comprise (a) a probe set may comprise a plurality of probes, wherein the plurality of probes may comprise a sequence that hybridizes to at least a portion of one or more target molecules selected from the group may comprise PCAT, SChLAP-1, TU0011194, TU0019356, TU0024146, TU0009141, TU0062051, TU0021861, M41, ENST-75, and SEQ ID NOs: 1-9; and (b) a computer model or algorithm for analyzing an expression level and/or expression profile of a target molecule hybridized to the probe in a sample from a subject suffering from a cancer. The PCAT may be selected from the group may comprise PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, and PCAT121.

The system may further comprise an electronic memory for capturing and storing an expression profile.

The system may further comprise a computer-processing device, optionally connected to a computer network.

The system may further comprise a software module executed by the computer-processing device to analyze an expression profile.

The system may further comprise a software module executed by the computer-processing device to compare the expression profile to a standard or control.

The system may further comprise a software module executed by the computer-processing device to determine the expression level of the target.

The system may further comprise a machine to isolate the target molecule or the probe from the sample.

The system may further comprise a machine to sequence the target molecule or the probe.

The system may further comprise a machine to amplify the target molecule or the probe.

The system may further comprise a label that specifically binds to the target molecule the probe, or a combination thereof.

The system may further comprise a software module executed by the computer-processing device to transmit an analysis of the expression profile to the subject or a medical professional treating the subject.

The system may further comprise a software module executed by the computer-processing device to transmit a diagnosis or prognosis to the subject or a medical professional treating the subject.

Further disclosed herein are kits comprising (a) a probe set may comprise a plurality of probes, wherein the plurality of probes may comprise a sequence that hybridizes to at least a portion of one or more target molecules selected from the group may comprise PCAT, SChLAP-1, TU0011194, TU0019356, TU0024146, TU0009141, TU0062051, TU0021861, M41, ENST-75, and SEQ ID NOs: 1-9; and (b) a computer model or algorithm for analyzing an expression level and/or expression profile of the target molecules in a sample.

The kit may further comprise a computer model or algorithm for correlating the expression level or expression profile with disease state or outcome.

The kit may further comprise a computer model or algorithm for designating a treatment modality for the subject.

The kit may further comprise a computer model or algorithm for normalizing expression level or expression profile of the target molecules.

The kit may further comprise a computer model or algorithm may comprise a robust multichip average (RMA), probe logarithmic intensity error estimation (PLIER), non-linear fit (NLFIT) quantile-based, nonlinear normalization, or a combination thereof.

Methods for analyzing a cancer in a subject in need thereof may comprise (a) obtaining an expression profile from a sample obtained from the subject, wherein the expression profile comprises one or more target molecules selected from PCAT, SChLAP-1, TU0011194, TU0019356, TU0024146, TU0009141, TU0062051, TU0021861, M41, ENST-75, and SEQ ID NOs: 1-9; and (b) comparing the expression profile from the sample to an expression profile of a control or standard.

Disclosed herein may be methods, systems, compositions and kits for diagnosing a cancer. Such methods for diagnosing cancer in a subject in need thereof may comprise (a) obtaining an expression profile from a sample obtained from the subject, wherein the expression profile may comprise one or more target molecules selected from PCAT, SChLAP-1, TU0011194, TU0019356, TU0024146, TU0009141, TU0062051, TU0021861, M41, ENST-75, and SEQ ID NOs: 1-9; (b) comparing the expression profile from the sample to an expression profile of a control or standard; and (c) diagnosing a cancer in the subject if the expression profile of the sample (i) deviates from the control or standard from a healthy subject or population of healthy subjects, or (ii) matches the control or standard from a subject or population of subjects who have or have had the cancer.

Disclosed herein may be methods, systems, compositions and kits for predicting susceptibility to developing cancer. Such methods for predicting whether a subject may be susceptible to developing a cancer may comprise (a) obtaining an expression profile from a sample obtained from the subject, wherein the expression profile may comprise one or more target molecules selected from PCAT, SChLAP-1, TU0011194, TU0019356, TU0024146, TU0009141, TU0062051, TU0021861, M41, ENST-75, and SEQ ID NOs: 1-9; (b) comparing the expression profile from the sample to an expression profile of a control or standard; and (c) predicting the susceptibility of the subject for developing a cancer based on (i) the deviation of the expression profile of the sample from a control or standard derived from a healthy subject or population of healthy subjects, or (ii) the similarity of the expression profiles of the sample and a control or standard derived from a subject or population of subjects who have or have had the cancer.

Disclosed herein may be methods, systems, compositions and kits for predicting response to a treatment regimen for cancer. Such methods for predicting a subject's response to a treatment regimen for a cancer may comprise: (a) obtaining an expression profile from a sample obtained from the subject, wherein the expression profile may comprise one or more target molecules selected from PCAT, SChLAP-1, TU0011194, TU0019356, TU0024146, TU0009141, TU0062051, TU0021861, M41, ENST-75, and SEQ ID NOs: 1-9; (b) comparing the expression profile from the sample to an expression profile of a control or standard; and (c) predicting the subject's response to a treatment regimen based on (i) the deviation of the expression profile of the sample from a control or standard derived from a healthy subject or population of healthy subjects, or (ii) the similarity of the expression profiles of the sample and a control or standard derived from a subject or population of subjects who have or have had the cancer.

Disclosed herein may be methods, systems, compositions and kits for treating or determining a treatment regimen for cancer. Such methods treating or determining a treatment regimen for cancer may comprise: (a) obtaining an expression profile from a sample obtained from the subject, wherein the expression profile may comprise one or more target molecules selected from PCAT, SChLAP-1, TU0011194, TU0019356, TU0024146, TU0009141, TU0062051, TU0021861, M41, ENST-75, and SEQ ID NOs: 1-9; (b) comparing the expression profile from the sample to an expression profile of a control or standard; and (c) treating or determining a treatment regimen for cancer based on (i) the deviation of the expression profile of the sample from a control or standard derived from a healthy subject or population of healthy subjects, or (ii) the similarity of the expression profiles of the sample and a control or standard derived from a subject or population of subjects who have or have had the cancer.

The method may further comprise a software module executed by a computer-processing device to compare the expression profiles.

The method may further comprise providing diagnostic or prognostic information to the subject about the cancer based on the comparison.

The method may further comprise diagnosing the subject with a cancer if the expression profile of the sample (a) deviates from the control or standard from a healthy subject or population of healthy subjects, or (b) matches the control or standard from a subject or population of subjects who have or have had the cancer.

The method may further comprise predicting the susceptibility of the subject for developing a cancer based on (a) the deviation of the expression profile of the sample from a control or standard derived from a healthy subject or population of healthy subjects, or (b) the similarity of the expression profiles of the sample and a control or standard derived from a subject or population of subjects who have or have had the cancer.

The method may further comprise prescribing a treatment regimen based on (a) the deviation of the expression profile of the sample from a control or standard derived from a healthy subject or population of healthy subjects, or (b) the similarity of the expression profiles of the sample and a control or standard derived from a subject or population of subjects who have or have had the cancer.

The method may further comprise altering a treatment regimen prescribed or administered to the subject based on (a) the deviation of the expression profile of the sample from a control or standard derived from a healthy subject or population of healthy subjects, or (b) the similarity of the expression profiles of the sample and a control or standard derived from a subject or population of subjects who have or have had the cancer.

The method may further comprise predicting the subject's response to a treatment regimen based on (a) the deviation of the expression profile of the sample from a control or standard derived from a healthy subject or population of healthy subjects, or (b) the similarity of the expression profiles of the sample and a control or standard derived from a subject or population of subjects who have or have had the cancer.

The method may further comprise using a machine to isolate the one or more target molecules, one or more probes, or one or more probe hybridized target molecules from the sample.

The method may further comprise contacting the sample with a label that specifically binds to the target molecule, the probe, or a combination thereof.

The method may further comprise contacting the sample with a label that specifically binds to one or more target molecules.

The method may further comprise amplifying at least a portion of the target molecule, the probe, or any combination thereof.

The method may further comprise sequencing at least a portion of the target molecule, the probe, or any combination thereof.

Further disclosed herein is a probe set for assessing a cancer status of a subject may comprise a plurality of probes, wherein the probes in the probe set may be capable of detecting an expression level of one or more target molecules selected from the group may comprise PCAT, SChLAP-1, TU0011194, TU0019356, TU0024146, TU0009141, TU0062051, TU0021861, M41, ENST-75, and SEQ ID NOs: 1-9, wherein The expression level of the one or more target molecules may determine the cancer status of the subject with at least 40% accuracy.

The methods, systems, compositions and kits may comprise a plurality of probes. The plurality of probes may comprise a sequence that hybridizes to at least a portion of two or more target molecules selected from the group may comprise PCAT, SChLAP-1, TU0011194, TU0019356, TU0024146, TU0009141, TU0062051, TU0021861, M41, ENST-75, and SEQ ID NOs: 1-9. The plurality of probes may comprise a sequence that hybridizes to at least a portion of three or more target molecules selected from the group may comprise PCAT, SChLAP-1, TU0011194, TU0019356, TU0024146, TU0009141, TU0062051, TU0021861, M41, ENST-75, and SEQ ID NOs: 1-9. The plurality of probes may comprise a sequence that hybridizes to at least a portion of four or more target molecules selected from the group may comprise PCAT, SChLAP-1, TU0011194, TU0019356, TU0024146, TU0009141, TU0062051, TU0021861, M41, ENST-75, and SEQ ID NOs: 1-9. The plurality of probes may comprise a sequence that hybridizes to at least a portion of five or more target molecules selected from the group may comprise PCAT, SChLAP-1, TU0011194, TU0019356, TU0024146, TU0009141, TU0062051, TU0021861, M41, ENST-75, and SEQ ID NOs: 1-9. The plurality of probes may comprise a sequence that hybridizes to at least a portion of ten or more target molecules selected from the group may comprise PCAT, SChLAP-1, TU0011194, TU0019356, TU0024146, TU0009141, TU0062051, TU0021861, M41, ENST-75, and SEQ ID NOs: 1-9.

The plurality of probes may comprise a sequence that hybridizes to at least a portion of one or more target molecules selected from the group may comprise and SEQ ID NOs: 1-9. The plurality of probes may comprise a sequence that hybridizes to at least a portion of one or more target molecules selected from the group may comprise PCAT1, PCAT14, PCAT43 and PCAT 109. The plurality of probes may comprise a sequence that hybridizes to at least a portion of one or more target molecules may comprise SChLAP-1. The plurality of probes may comprise a sequence that hybridizes to at least a portion of one or more target molecules selected from the group may comprise PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, and PCAT121. The cancer may be a prostate cancer.

The plurality of probes may comprise a sequence that hybridizes to at least a portion of one or more target molecules selected from the group may comprise M41 and ENST-75. The cancer may be a lung cancer.

The plurality of probes may comprise a sequence that hybridizes to at least a portion of one or more target molecules selected from the group may comprise TU0011194, TU0019356 and TU0024146. The cancer may be a breast cancer.

The plurality of probes may comprise a sequence that hybridizes to at least a portion of one or more target molecules selected from the group may comprise TU0011194, TU0019356 and TU0024146. The cancer may be a pancreatic cancer.

The probes may be between about 15 nucleotides and about 500 nucleotides in length. The probes may be between about 15 nucleotides and about 450 nucleotides in length. The probes may be between about 15 nucleotides and about 400 nucleotides in length. The probes may be between about 15 nucleotides and about 350 nucleotides in length. The probes may be between about 15 nucleotides and about 300 nucleotides in length. The probes may be between about 15 nucleotides and about 250 nucleotides in length. The probes may be between about 15 nucleotides and about 200 nucleotides in length. The probes may be at least 15 nucleotides in length. The probes may be at least 25 nucleotides in length.

The cancer may be selected from the group may comprise prostate, lung, breast, and pancreatic cancer.

Assessing the cancer status may comprise assessing cancer recurrence risk. Assessing the cancer status may comprise determining a treatment modality. Assessing the cancer status may comprise determining the efficacy of treatment.

Obtaining an expression profile may comprise hybridizing one or more probes to the one or more target molecules to produce one or more probe hybridized target molecules.

The deviation may be the expression level of one or more targets from the sample may be greater than the expression level of one or more targets from a control or standard derived from a healthy subject or population of healthy subjects. The deviation may be the expression level of one or more targets from the sample may be at least about 30% greater than the expression level of one or more targets from a control or standard derived from a healthy subject or population of healthy subjects. The deviation may be the expression level of one or more targets from the sample may be less than the expression level of one or more targets from a control or standard derived from a healthy subject or population of healthy subjects. The deviation may be the expression level of one or more targets from the sample may be at least about 30% less than the expression level of one or more targets from a control or standard derived from a healthy subject or population of healthy subjects.

The expression level of the one or more target molecules may determine the cancer status of the subject with at least 50% accuracy. The expression level of the one or more target molecules may determine the cancer status of the subject with at least 60% accuracy. The expression level of the one or more target molecules may determine the cancer status of the subject with at least 65% accuracy. The expression level of the one or more target molecules may determine the cancer status of the subject with at least 70% accuracy. The expression level of the one or more target molecules may determine the cancer status of the subject with at least 75% accuracy. The expression level of the one or more target molecules may determine the cancer status of the subject with at least 80% accuracy.

The plurality of probes may determine the expression level of the one or more target molecules with at least about 50% specificity. The plurality of probes may determine the expression level of the one or more target molecules with at least about 60% specificity. The plurality of probes may determine the expression level of the one or more target molecules with at least about 65% specificity. The plurality of probes may determine the expression level of the one or more target molecules with at least about 70% specificity. The plurality of probes may determine the expression level of the one or more target molecules with at least about 75% specificity. The plurality of probes may determine the expression level of the one or more target molecules with at least about 80% specificity. The plurality of probes may determine the expression level of the one or more target molecules with at least about 85% specificity.

The plurality of probes may determine the expression level of the one or more target molecules with at least about 50% sensitivity. The plurality of probes may determine the expression level of the one or more target molecules with at least about 60% sensitivity. The plurality of probes may determine the expression level of the one or more target molecules with at least about 65% sensitivity. The plurality of probes may determine the expression level of the one or more target molecules with at least about 70% sensitivity. The plurality of probes may determine the expression level of the one or more target molecules with at least about 75% sensitivity. The plurality of probes may determine the expression level of the one or more target molecules with at least about 80% sensitivity. The plurality of probes may determine the expression level of the one or more target molecules with at least about 85% sensitivity.

Additional embodiments are described herein.

DESCRIPTION OF THE FIGURES

FIG. 1a. A global overview of transcription in prostate cancer. FIG. 1b. A line graph showing the cumulative fraction of genes that are expressed at a given RPKM level. FIG. 1c. Conservation analysis comparing unannotated transcripts to known genes and intronic controls shows a low but detectable degree of purifying selection among intergenic and intronic unannotated transcripts. FIG. 1d-g. Intersection plots displaying the fraction of unannotated transcripts enriched for H3K4me2 (FIG. 1d), H3K4me3 (FIG. 1e), Acetyl-H3 (FIG. 1f) or RNA polymerase II (FIG. 1g) at their transcriptional start site (TSS) using ChIP-Seq and RNA-Seq data for the VCaP prostate cancer cancer cell line. FIG. 1h. A heatmap representing differentially expressed transcripts, including novel unannotated transcripts, in prostate cancer.

FIG. 2a. A histogram plotting the genomic distance between an unannotated ncRNA and the nearest protein-coding gene. FIG. 2b. A Circos plot displaying the location of annotated transcripts and unannotated transcripts on Chr15q.

FIG. 3 shows validation of tissue-specific prostate cancer-associated non-coding RNAs. FIG. 3a-c. Quantitative real-time PCR was performed on a panel of prostate and non-prostate samples to measure expression levels of three nominated non-coding RNAs (ncRNAs), PCAT-43, PCAT-109, and PCAT-14, upregulated in prostate cancer compared to normal prostate tissues. FIG. 3a. PCAT-43 is a 20 kb ncRNA located 40 kb upstream of PMEPA1 on chr20q13.31. FIG. 3b. PCAT-109, located in a large, 0.5 Mb gene desert region on chr2q31.3 displays widespread transcription in prostate tissues, particularly metastases. FIG. 3c. PCAT-14, a genomic region on chr22q11.23 encompassing a human endogenous retrovirus exhibits marked upregulation in prostate tumors but not metastases.

FIG. 4 shows that prostate cancer ncRNAs populate the Chr8q24 gene desert. FIG. 4a. A schematic of the chr8q24 region. FIG. 4b. Comprehensive analysis of the chr8q24 region by RNA-Seq and ChIP-Seq reveals numerous transcripts supported by histone modifications, such as Acetyl-H3 and H3K4me3, demarcating active chromatin. FIG. 4c. RT-PCR and Sanger sequencing validation of the PCAT-1 exon-exon junction. FIG. 4d. The genomic location of PCAT-1 determined by 5' and 3' RACE. Sequence analysis of PCAT-1 shows that it is a viral long terminal repeat (LTR) promoter splicing to a marniner family transposase that has been bisected by an Alu repeat. FIG. 4e. qPCR on a panel of prostate and non-prostate samples shows prostate-specific expression and upregulation in prostate cancers and metastases compared to benign prostate samples. FIG. 4f. Four matched tumor/normal pairs included in the analysis in e. demonstrate somatic upregulation of PCAT-1 in matched cancer samples.

FIG. 5 shows that ncRNAs serve as urine biomarkers for prostate cancer. FIG. 5a-c. Three ncRNAs displaying biomarker status in prostate cancer tissues were evaluated on a cohort of urine samples from 77 patients with prostate cancer and 31 controls with negative prostate biopsy results and absence of the TMPRSS2-ERG fusion transcript. PCA3 (FIG. 5a); PCAT-1 (FIG. 5b); and PCAT-14 (FIG. 5c). FIG. 5d. Scatter plots demonstrating distinct patient subsets scoring positively for PCA3, PCAT-1, or PCAT-14 expression. FIG. 5e. A heatmap displaying patients positive and negative for several different prostate cancer biomarkers in urine sediment samples. FIG. 5f. A table displaying the statistical significance of the ncRNA signature. FIG. 5g. A model for non-coding RNA (ncRNA) activation in prostate cancer.

FIG. 6 shows Ab initio assembly of the prostate cancer transcriptome. (FIG. 6a) Reads were mapped with TopHat and assembled into library-specific transcriptomes by Cufflinks. (FIG. 6b) Transcripts corresponding to processed pseudogenes were isolated, and the remaining transcripts were categorized based on overlap with an aggregated set of known gene annotations.

FIG. 8 shows transcript assembly of known genes. ab initio transcript assembly on prostate transcriptome sequencing data was used to reconstruct the known prostate transcriptome.

FIG. 8a. SPINK1, a biomarker for prostate cancer. FIG. 8b. PRUNE2 with the PCA3 non-coding RNA within its intronic regions. FIG. 8c. NFKB1. FIG. 8d. COL9A2.

FIG. 13 shows overlap of unannotated transcripts with ChIP-Seq data in VCaP cells. Perviously published ChIP-Seq data for VCaP prostate cancer cells were intersected with unannotated prostate cancer transcripts and annotated control genes. FIG. 13a. H3K4me1 FIG. 13b. H3K36me3.

FIG. 14 shows overlap of unannotated transcripts with ChIP-Seq data in LNCaP cells. ChIP-Seq data for LNCaP prostate cancer cells were intersected with unannotated transcripts and annotated control genes. ncRNAs were divided into intergenic and intronic. FIG. 14a. H3K4me1 FIG. 14b. H3K4me2 FIG. 14c. H3K4me3 FIG. 14d. Acetyl-H3 FIG. 14e. H3K36me3 FIG. 14f. RNA polymerase II.

FIG. 15a. Coverage maps showing the average expression levels (RPKM) across the benign, localized tumor, and metastatic samples shows upregulation of a novel transcript downstream of TLE3.

FIG. 17b. Representative qPCR results using primers selected from a. The primers used in b are indicated by a red asterisk in a.

FIG. 20 shows analysis of PCAT-14 transcript structure. FIG. 20a. Representative 5'RACE results using a 3' primer confirms the presence of the sense transcript PCAT-14. Predicted novel transcripts are displayed above the RACE results. FIG. 20b. DNA sequence analysis of PCAT-14 indicates expected splice donor sites, splice acceptor sites, and a polyadenylation site.

FIG. 22 shows that knockdown of PCAT-1 does not affect invasion or proliferation of VCaP cells. VCaP cells were transfected with custom-made siRNAs targeting PCAT-1 or non-targeting controls. FIG. 22a. Knockdown efficiency for four siRNA oligos individually and pooled. FIG. 22b.-d. siRNAs 2-4 were tested for functional effect due to their higher efficiency of knockdown. FIG. 22b. A cell proliferation assay performed with a Coulter counter shows no significant difference in cell proliferation following knockdown of PCAT-1. FIG. 22c. A WST-1 assay indicates no change in VCaP cell viability following PCAT-1 knockdown. FIG. 22d. A transmembrane invasion assay shows no change in VCaP cell invasiveness following PCAT-1 knockdown.

FIG. 23 shows transcription of two Alu elements in a CACNA1D intron. FIG. 23a. Coverage maps representing average expression in RPKM in benign samples, localized tumors, and prostate metastases. FIG. 23b. RPKM expression values for the CACNA1D Alu transcript across the prostate transcriptome sequencing cohort. FIG. 23c. RT-PCR validation of the Alu transcript in cell line models. FIG. 23d. Sanger sequencing confirmation of RT-PCR fragments verifies the presence of AluSp transcript sequence. FIG. 23e. Raw sequencing data of a portion of the AluSp sequence.

FIG. 24 shows transcription of numerous repeat elements at the SChLAP1 locus. FIG. 24a. Coverage maps representing repeat elements transcribed at the chr2q31.3 locus. FIG. 24b. RPKM expression expression values for the LINE-1 repeat region on chr2q31.3 across the prostate transcriptome sequencing cohort. FIG. 24c. RTPCR validation of the LINE-1 repetitive element in cell line models. A 402 bp fragment was amplified. FIG. 24d. Sanger sequencing of the PCR fragment confirms identity of the LINE-1 amplicon.

FIG. 27 shows that the SChLAP1 locus is associated with ETS positive tumors. FIG. 27a. Expression of the SChLAP1 locus was assayed by qPCR as display in FIG. 3b on a cohort of 14 benign prostate tissues, 47 localized prostate tumors and 10 metastatic prostate cancers. FIG. 27b. Quantification of the SChLAP1 association with ETS status using the threshold indicated by the blue dotted line in a.

FIG. 28 shows the sequence of PCAT-1 and PCAT-14.

(FIG. 29a-d) treatment with the PARP1 inhibitor olaparib, (FIG. 29e-h) treatment with the PARP1 inhibitor ABT-888. Stable PCAT-1 knockdown in LNCAP prostate cells reduces sensitivity to olaparib (FIG. 29a) and ABT-888 (FIG. 29e). Stable overexpression in Du145 prostate cancer and RWPE benign prostate cells increases sensitivity to olaparib (FIG. 29b, FIG. 29c) and ABT-888 (FIG. 29f, FIG. 29g). Overexpression of PCAT-1 in MCF7 breast cancer cells does not recapitulate this effect (FIG. 29d, FIG. 29h).

FIG. 30 shows that PCAT-1 expression sensitizes prostate cancer cells to radiation treatment. (FIG. 30a) Stable PCAT-1 knockdown in LNCAP prostate cells reduces sensitivity to radiation. (FIG. 30b, FIG. 30c) Stable overexpression in Du145 prostate cancer and RWPE benign prostate cells increases sensitivity to radiation. (FIG. 30d). Overexpression of PCAT-1 in MCF7 breast cancer cells does not recapitulate this effect.

FIG. 31 shows that unannotated intergenic transcripts differentiate prostate cancer and benign samples. (FIG. 31a) The genomic location and exon structure of SChLAP-1. SChLAP-1 is located on chromosome 2 in a previously unannotated region. (FIG. 31b) The isoform structure of SChLAP-1. (FIG. 31c) Cell fractionation into nuclear and cytoplasmic fractions demonstrates that SChLAP-1 is predominantly nuclear in its localization. (FIG. 31d) Expression of SChLAP-1 in a cohort of prostate cancer and benign tissues indicates that SChLAP-1 is a prostate cancer outlier associated with cancers.

FIG. 32 shows that SChLAP-1 is required for prostate cancer cell invasion and proliferation. (FIG. 32a) Prostate and non-prostate cancer cell lines were treated with SChLAP-1 siRNAs. (FIG. 32b and FIG. 32c) As in (FIG. 32a), prostate and non-prostate cell lines were assayed for cell proliferation following SChLAP-1 knockdown. (FIG. 32d) The three most abundant isoforms of SChLAP-1 were cloned and overexpressed in RWPE benign immortalized prostate cells at levels similar to LNCaP cancer cells. (FIG. 32e) RWPE cells overexpressing SChLAP-1 isoforms show an increased ability to invade through Matrigel in Boyden chamber assays.

FIG. 33 shows that deletion analysis of SChLAP-1 identifies a region essential for its function. (FIG. 33a) RWPE cells overexpressing SChLAP-1 deletion constructs or full-length isoform #1 were generated as shown in the schematic of the constructs. (FIG. 33b) RWPE cells overexpressing SChLAP-1 deletion construct5 demonstrated an impaired ability to invade through Matrigel, while the other deletion constructs showed no reduction in their ability to induce RWPE cell invasion compared to the wild type SChLAP-1.

FIG. 34 shows detection of prostate cancer RNAs in patient urine samples. (FIG. 34a-e). (FIG. 34a) PCA3 (FIG. 34b) PCAT-14 (FIG. 34c) PCAT-1 (FIG. 34d) SChLAP-1 (FIG. 34e) PDLIM5

(FIG. 36a) 38 lung cell lines were analyzed by RNA-Seq and then lncRNA transcripts were reconstructed. (FIG. 36b) Expression levels of transcripts observed in lung cell lines.

FIG. 37 shows discovery of M41 and ENST-75 in lung cancer. (FIG. 37a) The genomic location of M41, which resides in an intron of DSCAM. M41 is poorly conserved across species. (FIG. 37b) qPCR of M41 demonstrates outlier expression in 15-20% of lung adenocarcinomas as well as high expression in breast cells. (FIG. 37c) The genomic location of ENST-75, which demonstrates high conservation across species. (FIG. 37d) qPCR of ENST-75 shows up-regulation in lung cancer but not breast or prostate cancers. High expression is observed in normal testis.

(FIG. 38a) Knockdown of ENST-75 in H1299 cells with independent siRNAs achieving>70% knockdown. (FIG. 38b) Knockdown of ENST-75 in H1299 cells impairs cell proliferation. Error bars represent s.e.m. (FIG. 38c) ENST-75 expression in lung adenocarcinomas stratifies patient overall survival. (FIG. 38d) Serum detection levels of ENST-75 in normal and lung cancer patients.

FIG. 39 shows nomination of cancer-associated lncRNAs in breast and pancreatic cancer. (FIG. 39a-c) (FIG. 39a) TU0011194 (FIG. 39b) TU0019356 (FIG. 39c) TU0024146 (FIG. 39d-f) Three novel pancreatic cancer lncRNAs nominated from RNA-Seq data. All show outlier expression patterns in pancreatic cancer samples but not benign samples. (FIG. 39d) TU0009141 (FIG. 39e) TU0062051 (FIG. 39f) TU0021861.

40c) A representation of the SChLAP-1 gene and its annotations in current databases. SChLAP-1 may consist of up to seven exons on Chr2q31.3. (FIG. 40d) A schematic summarizing the observed SChLAP-1 isoforms. (FIG. 40e) qPCR for SChLAP-1 on a panel of benign prostate (n=33), localized prostate cancer (n=82), and metastatic prostate cancer (n=33) samples. (FIG. 40f) SChLAP-1 expression is predominantly nuclear.

(FIG. 41b) Overexpression of SChLAP-1 in RWPE cells. (FIG. 41c) Deletion analysis of SChLAP-1. (FIG. 41d) RNA structural analysis of SChLAP-1.

(FIG. 42a) Gene set enrichment analysis (GSEA) of LNCaP and 22Rv1 cells treated with SChLAP-1 siRNAs. (FIG. 42b) Heatmap results for SChLAP-1 or SWI/SNF knockdown in LNCaP and 22Rv1 cells. (FIG. 42c) GSEA analysis of SChLAP-1 and SWI/SNF knockdowns. (FIG. 42d) RNA immunoprecipitation (RIP) of SNF5 and AR demonstrates SChLAP-1 binding to SNF5 in 22Rv1 and LNCaP cells.

(FIG. 43a) Network representation of Oncomine concepts analysis of genes positively and negatively correlated with SChLAP-1 expression levels in localized prostate cancers profiled by RNA-Seq. (FIG. 43c-e) Kaplan-Meier analyses of prostate cancer outcomes in the Mayo Clinic cohort. (FIG. 43c), clinical progression to systemic disease (FIG. 43d), and prostate cancer-specific mortality (FIG. 43e). (FIG. 43f) A model of SChLAP-1 activity in prostate cancer.

FIG. 45 shows the structure and sequence of SChLAP1.

DEFINITIONS

Figure 1:
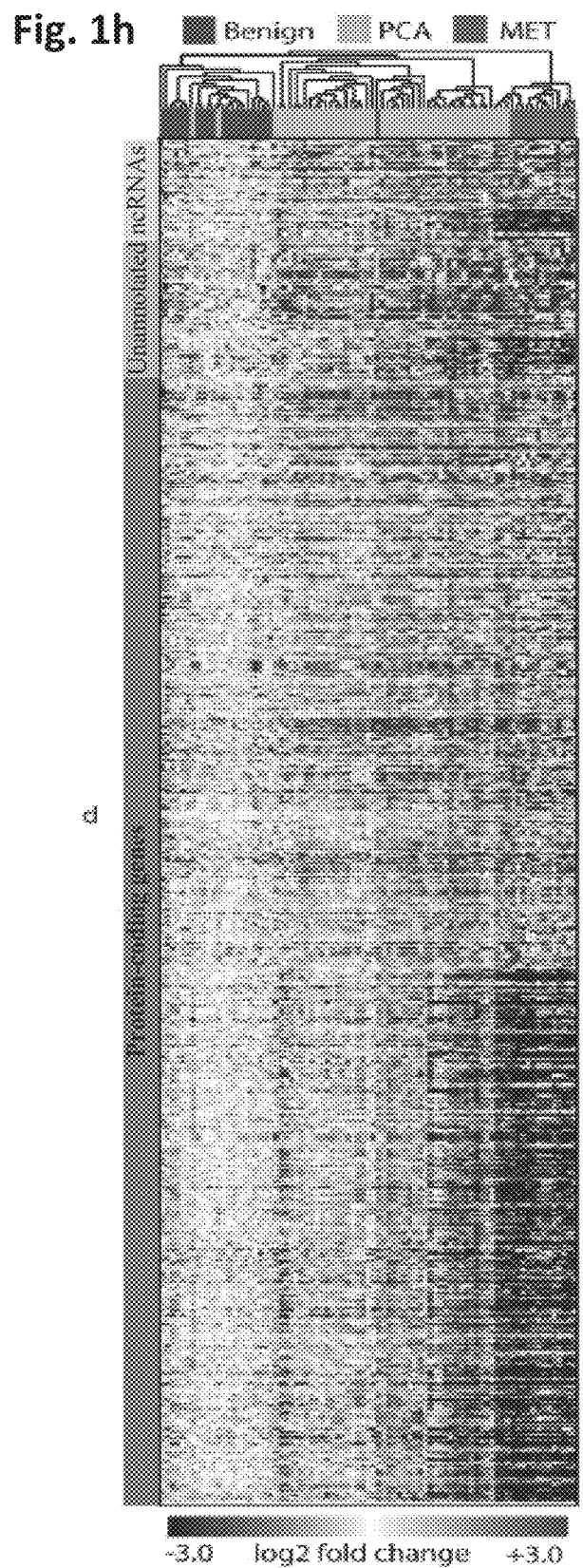
FIG. 1 shows that prostate cancer transcriptome sequencing reveals dysregulation of exemplary transcripts identified herein.

To facilitate an understanding of the present invention, a number of terms and phrases are defined below:

As used herein, the terms "detect", "detecting" or "detection" may describe either the general act of discovering or discerning or the specific observation of a composition. Detecting a composition may comprise determining the presence or absence of a composition. Detecting may comprise quantifying a composition. For example, detecting comprises determining the expression level of a composition. The composition may comprise a nucleic acid molecule. For example, the composition may comprise at least a portion of the ncRNAs disclosed herein. Alternatively, or additionally, the composition may be a detectably labeled composition.

As used herein, the term "subject" refers to any organisms that are screened using the diagnostic methods described herein. Such organisms preferably include, but are not limited to, mammals (e.g., murines, simians, equines, bovines, porcines, canines, felines, and the like), and most preferably includes humans. Alternatively, the organism is an avian, amphibian, reptile or fish.

The term "diagnosed," as used herein, refers to the recognition of a disease by its signs and symptoms, or genetic analysis, pathological analysis, histological analysis, and the like.

A "subject suspected of having cancer" encompasses an individual who has received an initial diagnosis (e.g., a CT scan showing a mass or increased PSA level) but for whom the stage of cancer or presence or absence of ncRNAs indicative of cancer is not known. The term further includes people who once had cancer (e.g., an individual in remission). In some embodiments, "subjects" are control subjects that are suspected of having cancer or diagnosed with cancer.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the ncRNAs disclosed herein.

As used herein, the term "characterizing prostate tissue in a subject" refers to the identification of one or more properties of a prostate tissue sample (e.g., including but not limited to, the presence of cancerous tissue, the presence or absence of ncRNAs, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The nucleic acid molecule may comprise one or more nucleotides. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF THE INVENTION

The present invention relates to compositions and methods for cancer diagnosis, research and therapy, including but not limited to, cancer markers. In particular, the present invention relates to ncRNAs as diagnostic markers and clinical targets for cancer. ncRNAs may be used as diagnostic markers and clinical targets for prostate, lung, breast and pancreatic cancer.

Experiments conducted during the development of embodiments of the present invention utilized RNA-Seq analyses of tissue samples and ab initio transcriptome assembly to predict the complete polyA+ transcriptome of prostate cancer. 6,144 novel ncRNAs found in prostate cancer were identified, including 121 ncRNAs that associated with disease progression (FIGS. 1, 2, 16 and 25). These data demonstrate the global utility of RNA-Seq in defining functionally-important elements of the genome.

The present invention is not limited to a particular mechanism. Indeed, an understanding of the mechanism is not necessary to practice the present invention. Nonetheless, although the biological role of these RNAs, especially the differentially-expressed ones, is not yet known, these results indicate a model in which specific intergenic loci are activated in prostate cancer, enabling the transcription of numerous disease-specific and tissue-specific ncRNAs (FIG. 5g). Clinically, these ncRNA signatures are suitable for urine-based assays to detect and diagnose prostate cancer in a non-invasive manner (See e.g., Example 1). It is further contemplated that specific ncRNA signatures occur universally in all disease states and applying these methodologies to other diseases reveals clinically important biomarkers, particularly for diseases that currently lack good protein biomarkers.

While traditional approaches have focused on the annotated reference genome, data generated during the course of development of embodiments of the present invention implicate large swaths of unannotated genomic loci in prostate cancer progression and prostate-specific expression. One example of this is the SChLAP1 locus, which represents a >500 kb stretch of coordinately regulated expression, and the chr8q24 locus, which contains a prostate specific region with the prostate cancer biomarker PCAT-1. The fact that the SChLAP1 locus is almost exclusively expressed in prostate cancers harboring an ETS gene fusion further confirms the capacity of ncRNAs to identify patient disease subtypes. In addition, these analyses reveal novel cancer-specific drivers of tumorigenesis. For example, the long ncRNA HOTAIR is known to direct cancer-promoting roles for EZH2 in breast cancer (Gupta et al., Nature 464 (7291), 1071 (2010)), while in the PC3 prostate cancer cell line a similar role has been proposed for the ANRIL ncRNA (Yap et al., Mol Cell 38 (5), 662 (2010)).

I. Diagnostic and Screening Methods

As described herein, embodiments of the present invention provide diagnostic and screening methods that utilize the detection of one or more ncRNAs. Exemplary ncRNAs include, but are not limited to, PCAT-1, PCAT-14, PCAT-43 and PCAT-109; SChLAP-1; and SEQ ID NOs: 1-9. Exemplary, non-limiting methods are described herein.

Any patient sample suspected of containing the ncRNAs may be tested according to methods of embodiments of the present invention. By way of non-limiting examples, the sample may be tissue (e.g., a biopsy sample, a prostate biopsy sample or a tissue sample obtained by prostatectomy), blood, urine, semen, prostatic secretions or a fraction thereof (e.g., plasma, serum, urine supernatant, urine cell pellet, cells or prostate cells). A urine sample may be collected immediately following an attentive digital rectal examination (DRE), which causes prostate cells from the prostate gland to shed into the urinary tract.

In some embodiments, the patient sample is subjected to preliminary processing designed to isolate or enrich the sample for the ncRNAs or cells that contain the ncRNAs. A variety of techniques known to those of ordinary skill in the art may be used for this purpose, including but not limited to: centrifugation; immunocapture; cell lysis; nucleic acid amplification; and, nucleic acid target capture (See, e.g., EP Pat. No. 1 409 727, herein incorporated by reference in its entirety).

The ncRNAs may be detected along with other markers in a multiplex or panel format. Markers may be selected for their predictive value alone or in combination with the gene fusions. Exemplary prostate cancer markers include, but are not limited to: AMACR/P504S (U.S. Pat. No. 6,262,245); PCA3 (U.S. Pat. No. 7,008,765); PCGEM1 (U.S. Pat. No. 6,828,429); prostein/P501S, P503S, P504S, P509S, P510S, prostase/P703P, P710P (U.S. Publication No. 20030185830); RAS/KRAS (Bos, Cancer Res. 49:4682-89 (1989); Kranenburg, Biochimica et Biophysica Acta 1756: 81-82 (2005)); and, those disclosed in U.S. Pat. Nos. 5,854, 206 and 6,034,218, 7,229,774, each of which is herein incorporated by reference in its entirety. Markers for other cancers, diseases, infections, and metabolic conditions are also contemplated for inclusion in a multiplex or panel format.

In some embodiments, multiplex or array formats are utilized to detect multiple markers in combination. For example, in some embodiments, the level of expression of one or more, 2 or more, 3 or more, 4 or more, 5 or more, 10 or more, 15 or more, 20 or more, 25 or more, 30 or more, 35 or more, 40 or more 45 or more, 50 or more, 60 or more, 70 or more, 80 or more, 90 or more, 100 or more or all 121) non-coding RNAs (ncRNAs) is utilized in the research, screening, diagnostic and prognositic compositions and methods described herein. The one or more ncRNAs may be selected from the group comprising SChLAP-1, PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, and PCAT121.

i. DNA and RNA Detection

The ncRNAs of the present invention are detected using a variety of nucleic acid techniques known to those of ordinary skill in the art, including but not limited to: nucleic acid sequencing; nucleic acid hybridization; and, nucleic acid amplification.

The methods, compositions and kits may comprise one or more ncRNAs. The methods, compositions and kits may comprise 2 or more, 3 or more, 4 or more, 5 or more, 6 or more, 7 or more, 8 or more, 9 or more, 10 or more, 15 or more, 20 or more, 25 or more, 30 or more, 40 or more, 45 or more, 50 or more, 55 or more, 60 or more, 70 or more, 80 or more, 90 or more, 100 or more, 110 or more, 120 or more, 130 or more, 140 or more, 150 or more ncRNAs.

The one or more ncRNAs may be selected from the group comprising PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, PCAT121, SChLAP-1, TU0011194, TU0019356, TU0024146, TU0009141, TU0062051, TU0021861, M41, ENST-75, and SEQ ID NOs: 1-9.

The one or more ncRNAs of the present invention may comprise one or more prostate cancer-associated ncRNA transcripts (PCATs). The one or more PCATs may be selected from the group comprising PCAT1, PCAT2, PCAT3, PCAT4, PCAT5, PCAT6, PCAT7, PCAT8, PCAT9, PCAT10, PCAT11, PCAT12, PCAT13, PCAT14, PCAT15, PCAT16, PCAT17, PCAT18, PCAT19, PCAT20, PCAT21, PCAT22, PCAT23, PCAT24, PCAT25, PCAT26, PCAT27, PCAT28, PCAT29, PCAT30, PCAT31, PCAT32, PCAT33, PCAT34, PCAT35, PCAT36, PCAT37, PCAT38, PCAT39, PCAT40, PCAT41, PCAT42, PCAT43, PCAT44, PCAT45, PCAT46, PCAT47, PCAT48, PCAT49, PCAT50, PCAT51, PCAT52, PCAT53, PCAT54, PCAT55, PCAT56, PCAT57, PCAT58, PCAT59, PCAT60, PCAT61, PCAT62, PCAT63, PCAT64, PCAT65, PCAT66, PCAT67, PCAT68, PCAT69, PCAT70, PCAT71, PCAT72, PCAT73, PCAT74, PCAT75, PCAT76, PCAT77, PCAT78, PCAT79, PCAT80, PCAT81, PCAT82, PCAT83, PCAT84, PCAT85, PCAT86, PCAT87, PCAT88, PCAT89, PCAT90, PCAT91, PCAT92, PCAT93, PCAT94, PCAT95, PCAT96, PCAT97, PCAT98, PCAT99, PCAT100, PCAT101, PCAT102, PCAT103, PCAT104, PCAT105, PCAT106, PCAT107, PCAT108, PCAT109, PCAT110, PCAT111, PCAT112, PCAT113, PCAT114, PCAT115, PCAT116, PCAT117, PCAT118, PCAT119, PCAT120, and PCAT121. The one or more ncRNAs may comprise PCAT1, PCAT14, PCAT43, PCAT 109, or a combination thereof.

Alternatively, or additionally, the ncRNAs of the present invention may comprise SChLAP-1. The ncRNAs may comprise M41, ENST-75, or a combination thereof. The ncRNAs may comprise TU0011194, TU0019356, TU0024146, or a combination thereof. The ncRNAs may comprise TU0009141, TU0062051, TU0021861 or a combination thereof. The ncRNAs may comprise any one of SEQ ID NOs: 1-9 or a combination thereof.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

The methods disclosed herein can comprise transcriptome sequencing (e.g., RNA-Seq). Sequencing can comprise platforms such as the Illumina GenomeAnalyzer platform, ABI Solid Sequencing or Life Science's 454 Sequencing. Alternatively, sequencing comprises Helicos' Direct RNA Sequencing (DRSTM) technology. The sequencing reactions may comprise capillary sequencing, next generation sequencing, Sanger sequencing, sequencing by synthesis, single molecule nanopore sequencing, sequencing by ligation, sequencing by hybridization, sequencing by nanopore current restriction, or a combination thereof. Sequencing by synthesis may comprise reversible terminator sequencing, processive single molecule sequencing, sequential nucleotide flow sequencing, or a combination thereof. Sequential nucleotide flow sequencing may comprise pyrosequencing, pH-mediated sequencing, semiconductor sequencing or a combination thereof. Conducting one or more sequencing reactions comprises whole genome sequencing or exome sequencing.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts (e.g., ncRNAs) within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, ncRNAs are detected using fluorescence in situ hybridization (FISH). In some embodiments, FISH assays utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on the patient sample. The methods disclosed herein may comprise performing a FISH assay on one or more cells, tissues, organs, or fluids surrounding such cells, tissues and organs. In some instances, the methods disclosed herein further comprise performing a FISH assy on human prostate cells, human prostate tissue or on the fluid surrounding said human prostate cells or human prostate tissue. Alternatively, or additionally, the methods disclosed herien comprise performing a FISH assay on breast cells, lung cells, pancreatic cells, liver cells, breast tissue, lung tissue, pancreatic tissue, liver tissue, or on the fluid surrounding the cells or tissues. Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, MD). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

The one or more ncRNAs may be detected by conducting one or more hybridization reactions. The one or more hybridization reactions may comprise one or more hybridization arrays, hybridization reactions, hybridization chain reactions, isothermal hybridization reactions, nucleic acid hybridization reactions, or a combination thereof. The one or more hybridization arrays may comprise hybridization array genotyping, hybridization array proportional sensing, DNA hybridization arrays, macroarrays, microarrays, high-density oligonucleotide arrays, genomic hybridization arrays, comparative hybridization arrays, or a combination thereof.

3. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., ncRNAs) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

3. Amplification

The methods disclosed herein may comprise conducting one or more amplification reactions. Nucleic acids (e.g., ncRNAs) may be amplified prior to or simultaneous with detection. Conducting one or more amplification reactions may comprise one or more PCR-based amplifications, non-PCR based amplifications, or a combination thereof. Illustrative non-limiting examples of nucleic acid amplification techniques include, but are not limited to, polymerase chain reaction (PCR), reverse transcription polymerase chain reaction (RT-PCR), nested PCR, linear amplification, multiple displacement amplification (MDA), real-time SDA, rolling circle amplification, circle-to-circle amplification transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, DC (1993)).

4. Detection Methods

Non-amplified or amplified nucleic acids can be detected by any conventional means. For example, the ncRNAs can be detected by hybridization with a detectably labeled probe and measurement of the resulting hybrids. In another example, the ncRNAs can be detected by sequencing. Illustrative non-limiting examples of detection methods are described herein.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541, 205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety). Additional detection methods may include microarrays and electrophoresis (e.g., gel electrophoresis). Detection methods can be quantitative or semi-quantitative. Detection methods may also comprise the use of one or more labels (e.g., radioisotopes, fluorophores, chemiluminophores, enzymes, colloidal particles, and fluorescent microparticles, as well as antigens, antibodies, haptens, avidin/streptavidin, biotin, haptens, or enzyme cofactors/substrates, enzymes).

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

ii. In Vivo Imaging ncRNAs may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of embodiments of the present invention are useful in the identification of cancers that express ncRNAs (e.g., prostate cancer). In vivo imaging is used to visualize the presence or level of expression of a ncRNA. Such techniques allow for diagnosis without the use of an unpleasant biopsy. The in vivo imaging methods of embodiments of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the ncRNA, to insure that the antigen binding site on the antibody will be protected. The antigen is separated after labeling.

In still further embodiments, in vivo biophotonic imaging (Xenogen, Almeda, CA) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

iii. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personnel, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by one or more medical personnel (e.g., a treating clinician, physician assistant, nurse, or pharmacist). For example, rather than providing raw expression data, the prepared format may represent a diagnosis or risk assessment (e.g., presence or absence of a ncRNA) for the subject, along with recommendations for particular treatment options. The data may be displayed to the medical personnel by any suitable method. For example, in some embodiments, the profiling service generates a report that can be printed for the medical personnel (e.g., at the point of care) or displayed to the medical personnel on a computer monitor.

In some embodiments, the information is first analyzed at the point of care or at a regional facility. The raw data is then sent to a central processing facility for further analysis and/or to convert the raw data to information useful for medical personnel or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the medical personnel, the subject, or researchers.

In some embodiments, the subject is able to directly access the data using the electronic communication system. The subject may chose further intervention or counseling based on the results.

In some embodiments, the data is used for research use. For example, the data may be used to further optimize the inclusion or elimination of markers as useful indicators of a particular condition or stage of disease or as a companion diagnostic to determine a treatment course of action.

iv. Compositions & Kits

Compositions for use in the diagnostic methods described herein include, but are not limited to, probes, amplification oligonucleotides, and the like.

The probe and antibody compositions of the present invention may also be provided in the form of an array.

The compositions and kits may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, 80 or more, 90 or more, 100 or more, 110 or more, 120 or more probes.

The probes may hybridize to 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, 80 or more, 90 or more, 100 or more, 110 or more, 120 or more target molecules. The target molecules may be a ncRNA, RNA, DNA, cDNA, mRNA, a portion or fragment thereof or a combination thereof. In some instances, at least a portion of the target molecules are ncRNAs. The probes may hybridize to 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, 80 or more, 90 or more, 100 or more, 110 or more, 120 or more ncRNAs disclosed herein.

Typically, the probes comprise a target specific sequence. The target specific sequence may be complementary to at least a portion of the target molecule. The target specific sequence may be at least about 50% or more, 55% or more, 60% or more, 65% or more, 70% or more, 75% or more, 80% or more, 85% or more, 90% or more, 95% or more, 97% or more, 98% or more, or 100% complementary to at leat a portion of the target molecule.

The target specific sequence may be at least about 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more nucleotides in length. In some instances, the target specific sequence is between about 8 to about 20 nucleotides, 10 to about 18 nucleotides, or 12 to about 16 nucleotides in length.

The compositions and kits may comprise a plurality of probes, wherein the two or more probes of the plurality of probes comprise identical target specific sequences. The compositions and kits may comprise a plurality of probes, wherein the two or more probes of the plurality of probes comprise different target specific sequences.

The probes may further comprise a unique sequence. The unique sequence is noncomplementary to the ncRNA. The unique sequence may comprise a label, barcode, or unique identifier. The unique sequence may comprise a random sequence, nonrandom sequence, or a combination thereof. The unique sequence may be at least about 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 22 or more, 24 or more, 26 or more, 28 or more, 30 or more nucleotides in length. In some instances, the unique sequence is between about 8 to about 20 nucleotides, 10 to about 18 nucleotides, or 12 to about 16 nucleotides in length.

The unique sequence may allow differentiation of two or more target molecules. The two or more target molecules may have identical sequences. Thus, the unique sequence may allow quantification of a target molecule. Alternatively, the two or more target molecules may have different sequences. Thus, the unique sequence may allow detection of the target molecules. The compositions and kits may comprise a plurality of probes for quantifying one or more target molecules. The compositions and kits may comprise a plurality of probes for detecting one or more target molecules.

The unique sequence may allow differentiation of two or more samples. The compositions and kits may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more probe sets for differentiating two or more samples from one or more subjects. The two or more samples may be from two or more different subjects. For example, the compositions and kits comprise a first set of probes comprising a first unique sequence that is specific for a first subject and a second set of probes comprsing a second unique sequence that is specific for a second subject. The compositions and kits may further comprise one or more sets of probes with one or more unique sequences to differentiate one or more additional subjects.

The compositions and kits may comprise 2 or more probe sets for differentiating from 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more samples from 1 or more subjects.

The compositions and kits may comprise 2 or more probe sets for differentiating 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more samples from one or more cells, tissues, organs, bodily fluid, or a combination thereof.

The compositions and kits may comprise 2 or more probe sets for differentiating samples from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more subjects.

Alternatively, or additionally, the two or more samples may be from two or more different timepoints from the same subject or different subjects. For example, the compositions and kits comprise a first set of probes comprising a first unique sequence that is specific for a first subject and a second set of probes comprosing a second unique sequence that is specific for a second subject. The compositions and kits may comprise 2 or more probe sets for differentiating samples from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more timepoints. The timepoints may be every 1, 2, 3, 4, 5, 6, 7, 8, 9, 10, 11, 12, 13, 14, 15, 16, 17, 18, 19, 20, 21, 22, 23, 24 or more hours. The timepoints may be every 1, 2, 3, 4, 5, 6, 7, 8, 9, 10, 11, 12, 13, 14, 15, 16, 17, 18, 19, 20, 21, 22, 23, 24 or more days. The timepoints may be every 1, 2, 3, 4, 5, 6, 7, 8, 9, 10, 11, 12, 13, 14, 15, 16, 17, 18, 19, 20, 21, 22, 23, 24 or more weeks. The timepoints may be every 1, 2, 3, 4, 5, 6, 7, 8, 9, 10, 11, 12, 13, 14, 15, 16, 17, 18, 19, 20, 21, 22, 23, 24 or more months. The timepoints may be every 1, 2, 3, 4, 5, 6, 7, 8, 9, 10, 11, 12, 13, 14, 15, 16, 17, 18, 19, 20, 21, 22, 23, 24 or more years. The timepoints may be before diagnosis, after diagnosis, before treatment, during treatment, after treatment, before metastasis, after metastatis, before remission, during remission, or a combination thereof.

The compositions and kits may comprise a first probe comprising a first target-specific sequence and a first unique sequence and a second probe comprising a second target-specific sequence and a second unique sequence, wherein the first target specific sequence and the second target specific sequence are identical and the first unique sequence and the second unique sequence are different. The compositions and kits may comprise a first probe comprising a first target-specific sequence and a first unique sequence and a second probe comprising a second target-specific sequence and a second unique sequence, wherein the first target specific sequence and the second target specific sequence are different and the first unique sequence and the second unique sequence are different. The compositions and kits may comprise a first probe comprising a first target-specific sequence and a first unique sequence and a second probe comprising a second target-specific sequence and a second unique sequence, wherein the first target specific sequence and the second target specific sequence are identical and the first unique sequence and the second unique sequence are identical. The compositions and kits may comprise a first probe comprising a first target-specific sequence and a first unique sequence and a second probe comprising a second target-specific sequence and a second unique sequence, wherein the first target specific sequence and the second target specific sequence are different and the first unique sequence and the second unique sequence are identical.

The probes may further comprise a universal sequence. The universal sequence may comprise a primer binding site. The universal sequence may enable detection of the target sequence. The universal sequence may enable amplification of the target sequence. The universal sequence may enable transcription or reverse transcription of the target sequence. The universal sequence may enable sequencing of the target sequence.

The probe and antibody compositions of the present invention may also be provided on a solid support. The solid support may comprise one or more beads, plates, solid surfaces, wells, chips, or a combination thereof. The beads may be magnetic, antibody coated, protein A crosslinked, protein G crosslinked, streptavidin coated, oligonucleotide conjugated, silica coated, or a combination thereof. Examples of beads include, but are not limited to, Ampure beads, AMPure XP beads, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbead, anti-fluorochrome microbead, and BcMagTM Carboxy-Terminated Magnetic Beads.

The compositions and kits may comprise primers and primer pairs capable of amplifying target molecules, or fragments or subsequences or complements thereof. The nucleotide sequences of the target molecules may be provided in computer-readable media for in silico applications and as a basis for the design of appropriate primers for amplification of one or more target molecules.

Primers based on the nucleotide sequences of target molecules can be designed for use in amplification of the target molecules. For use in amplification reactions such as PCR, a pair of primers can be used. The exact composition of the primer sequences is not critical to the invention, but for most applications the primers may hybridize to specific sequences of the target molecules or the universal sequence of the probe under stringent conditions, particularly under conditions of high stringency, as known in the art. The pairs of primers are usually chosen so as to generate an amplification product of at least about 15 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 450 or more, 500 or more, 600 or more, 700 or more, 800 or more, 900 or more, or 1000 or more nucleotides. Algorithms for the selection of primer sequences are generally known, and are available in commercial software packages. These primers may be used in standard quantitative or qualitative PCR-based assays to assess transcript expression levels of target molecules. Alternatively, these primers may be used in combination with probes, such as molecular beacons in amplifications using real-time PCR.

One skilled in the art also appreciates that the nucleotide sequence of the entire length of the primer does not need to be derived from the target sequence. Thus, for example, the primer may comprise nucleotide sequences at the 5' and/or 3' termini that are not derived from the target molecule. Nucleotide sequences which are not derived from the nucleotide sequence of the target molecule may provide additional functionality to the primer. For example, they may provide a restriction enzyme recognition sequence or a "tag" that facilitates detection, isolation, purification or immobilization onto a solid support. Alternatively, the additional nucleotides may provide a self-complementary sequence that allows the primer to adopt a hairpin configuration. Such configurations may be necessary for certain primers, for example, molecular beacon and Scorpion primers, which can be used in solution hybridization techniques.

The probes or primers can incorporate moieties useful in detection, isolation, purification, or immobilization, if desired. Such moieties are well-known in the art (see, for example, Ausubel et al., (1997 & updates) *Current Protocols in Molecular Biology*, Wiley & Sons, New York) and are chosen such that the ability of the probe to hybridize with its target molecule is not affected.

Examples of suitable moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like.

A label can optionally be attached to or incorporated into a probe or primer to allow detection and/or quantitation of a target polynucleotide representing the target molecule of interest. The target polynucleotide may be the expressed target molecule RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different target molecules may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the target molecule. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a target polynucleotide may comprise a biotin-binding species, and an optically detectable label may be conjugated to biotin and then bound to the labeled target polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

Coding schemes may optionally be used, comprising encoded particles and/or encoded tags associated with different polynucleotides of the invention. A variety of different coding schemes are known in the art, including fluorophores, including SCNCs, deposited metals, and RF tags.

Polynucleotides from the described target molecules may be employed as probes for detecting target molecules expression, for ligation amplification schemes, or may be used as primers for amplification schemes of all or a portion of a target molecules. When amplified, either strand produced by amplification may be provided in purified and/or isolated form.

In some instances, the compositions and kits comprise a biomarker library. The biomarker library may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, 80 or more, 90 or more, 100 or more, 110 or more, 120 or more target molecules. The target molecules may be a ncRNA, RNA, DNA, cDNA, mRNA, a portion or fragment thereof or a combination thereof. In some instances, at least a portion of the target molecules are ncRNAs. The biomarker library may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, 80 or more, 90 or more, 100 or more, 110 or more, 120 or more ncRNAs disclosed herein. The biomarker library may comprise one or more PCATs, SChLAP-1, M41, ENST-75, TU0011194, TU0019356, TU0024146, TU0009141, TU0062051, TU0021861, M41, ENST-75, any one of SEQ ID NOs 1-9, or a combination thereof.

In some embodiments, is a kit for analyzing a cancer comprising (a) a probe set comprising a plurality of probes comprising target specific sequences complementary to one or more target molecules, wherein the one or more target molecules comprise one or more ncRNAs; and (b) a computer model or algorithm for analyzing an expression level and/or expression profile of the one or more target molecules in a sample. The target molecules may comprose one or more PCATs, SChLAP-1, M41, ENST-75, TU0011194, TU0019356, TU0024146, TU0009141, TU0062051, TU0021861, any one of SEQ ID NOs 1-9, or a combination thereof.

In some embodiments, is a kit for analyzing a cancer comprising (a) a probe set comprising a plurality of probes comprising target specific sequences complementary to one or more target molecules of a biomarker library; and (b) a computer model or algorithm for analyzing an expression level and/or expression profile of the one or more target molecules in a sample. Control samples and/or nucleic acids may optionally be provided in the kit. Control samples may include tissue and/or nucleic acids obtained from or representative of tumor samples from a healthy subject, as well as tissue and/or nucleic acids obtained from or representative of tumor samples from subjects diagnosed with a cancer.

Instructions for using the kit to perform one or more methods of the invention can be provided, and can be provided in any fixed medium. The instructions may be located inside or outside a container or housing, and/or may be printed on the interior or exterior of any surface thereof. A kit may be in multiplex form for concurrently detecting and/or quantitating one or more different target polynucleotides representing the expressed target molecules.

v. Devices

Devices useful for performing methods of the invention are also provided. The devices can comprise means for characterizing the expression level of a target molecule of the invention, for example components for performing one or more methods of nucleic acid extraction, amplification, and/or detection. Such components may include one or more of an amplification chamber (for example a thermal cycler), a plate reader, a spectrophotometer, capillary electrophoresis apparatus, a chip reader, and or robotic sample handling components. These components ultimately can obtain data that reflects the expression level of the target molecules used in the assay being employed.

The devices may include an excitation and/or a detection means. Any instrument that provides a wavelength that can excite a species of interest and is shorter than the emission wavelength(s) to be detected can be used for excitation. Commercially available devices can provide suitable excitation wavelengths as well as suitable detection component.

Exemplary excitation sources include a broadband UV light source such as a deuterium lamp with an appropriate filter, the output of a white light source such as a xenon lamp or a deuterium lamp after passing through a monochromator to extract out the desired wavelength(s), a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of a label used in an assay.

The devices typically comprise a means for identifying a given sample, and of linking the results obtained to that sample. Such means can include manual labels, barcodes, and other indicators which can be linked to a sample vessel, and/or may optionally be included in the sample itself, for example where an encoded particle is added to the sample. The results may be linked to the sample, for example in a computer memory that contains a sample designation and a record of expression levels obtained from the sample. Linkage of the results to the sample can also include a linkage to a particular sample receptacle in the device, which is also linked to the sample identity.

The devices also comprise a means for correlating the expression levels of the target molecules being studied with a prognosis of disease outcome. Such means may comprise one or more of a variety of correlative techniques, including lookup tables, algorithms, multivariate models, and linear or nonlinear combinations of expression models or algorithms. The expression levels may be converted to one or more likelihood scores, reflecting a likelihood that the patient providing the sample may exhibit a particular disease outcome. The models and/or algorithms can be provided in machine readable format and can optionally further designate a treatment modality for a patient or class of patients.

The device also comprises output means for outputting the disease status, prognosis and/or a treatment modality. Such output means can take any form which transmits the results to a patient and/or a healthcare provider, and may include a monitor, a printed format, or both. The device may use a computer system for performing one or more of the steps provided.

The methods disclosed herein may also comprise the transmission of data/information. For example, data/information derived from the detection and/or quantification of the target may be transmitted to another device and/or instrument. In some instances, the information obtained from an algorithm may also be transmitted to another device and/or instrument. Transmission of the data/information may comprise the transfer of data/information from a first source to a second source. The first and second sources may be in the same approximate location (e.g., within the same room, building, block, campus). Alternatively, first and second sources may be in multiple locations (e.g., multiple cities, states, countries, continents, etc).

Transmission of the data/information may comprise digital transmission or analog transmission. Digital transmission may comprise the physical transfer of data (a digital bit stream) over a point-to-point or point-to-multipoint communication channel. Examples of such channels are copper wires, optical fibres, wireless communication channels, and storage media. The data may be represented as an electromagnetic signal, such as an electrical voltage, radiowave, microwave, or infrared signal.

Analog transmission may comprise the transfer of a continuously varying analog signal. The messages can either be represented by a sequence of pulses by means of a line code (baseband transmission), or by a limited set of continuously varying wave forms (passband transmission), using a digital modulation method. The passband modulation and corresponding demodulation (also known as detection) can be carried out by modem equipment. According to the most common definition of digital signal, both baseband and passband signals representing bit-streams are considered as digital transmission, while an alternative definition only considers the baseband signal as digital, and passband transmission of digital data as a form of digital-to-analog conversion.

vii. Samples

Samples for use with the compositions and kits and in the methods of the present invention comprise nucleic acids suitable for providing RNA expression information. In principle, the biological sample from which the expressed RNA is obtained and analyzed for target molecule expression can be any material suspected of comprising cancer tissue or cells. The sample can be a biological sample used directly in a method of the invention. Alternatively, the sample can be a sample prepared from a biological sample.

In one embodiment, the sample or portion of the sample comprising or suspected of comprising cancer tissue or cells can be any source of biological material, including cells, tissue, secretions, or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs. Alternatively, or additionally, the source of the sample can be urine, bile, excrement, sweat, tears, vaginal fluids, spinal fluid, and stool. In some instances, the sources of the sample are secretions. In some instances, the secretions are exosomes.

The samples may be archival samples, having a known and documented medical outcome, or may be samples from current patients whose ultimate medical outcome is not yet known.

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Hely solution, osmic acid solution and Carnoy solution.

Crosslinking fixatives can comprise any agent suitable for forming two or more covalent bonds, for example, an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion.

One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFMFM, Cryo-Gef™, and OCT Compound (Electron Microscopy Sciences, Hatfield, PA). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

II. Drug Screening Applications

In some embodiments, the present invention provides drug screening assays (e.g., to screen for anticancer drugs). The screening methods of the present invention utilize ncRNAs. For example, in some embodiments, the present invention provides methods of screening for compounds that alter the expression or activity of ncRNAs. The compounds may increase the expression or activity of the ncRNAs. The compounds may decrease the expression or activity of the ncRNAs. The compounds or agents may interfere with transcription, by interacting, for example, with the promoter region. The compounds or agents may interfere with mRNA (e.g., by RNA interference, antisense technologies, etc.). The compounds or agents may interfere with pathways that are upstream or downstream of the biological activity of ncRNAs. In some embodiments, candidate compounds are antisense or interfering RNA agents (e.g., oligonucleotides) directed against ncRNAs. In other embodiments, candidate compounds are antibodies or small molecules that specifically bind to a ncRNA regulator. Alternatively, or additionally, the candidate compounds are expression products that inhibit thebiological function of the ncRNAs.

In one screening method, candidate compounds are evaluated for their ability to alter ncRNAs expression by contacting a compound with a cell expressing a ncRNA and then assaying for the effect of the candidate compounds on expression. In some embodiments, the effect of candidate compounds on expression of ncRNAs is assayed for by detecting the level ncRNA expressed by the cell. mRNA expression can be detected by any suitable method.

III. Diagnosis, Prognosis, and Monitoring

The methods, compositions, and kits disclosed herein may be used for the diagnosis, prognosis, and/or monitoring the status or outcome of a cancer in a subject. In some embodiments, the diagnosing, predicting, and/or monitoring the status or outcome of a cancer comprises determining the malignancy or malignant potential of the cancer or tumor. Alternatively, the diagnosing, predicting, and/or monitoring the status or outcome of a cancer comprises determining the stage of the cancer. The diagnosing, predicting, and/or monitoring the status or outcome of a cancer can comprise determining the tumor grade. Alternatively, the diagnosing, predicting, and/or monitoring the status or outcome of a cancer comprises assessing the risk of developing a cancer. In some embodiments, the diagnosing, predicting, and/or monitoring the status or outcome of a cancer includes assessing the risk of cancer recurrence. In some embodiments, diagnosing, predicting, and/or monitoring the status or outcome of a cancer may comprise determining the efficacy of treatment.

In some embodiments, diagnosing, predicting, and/or monitoring the status or outcome of a cancer may comprise determining a therapeutic regimen. Determining a therapeutic regimen may comprise administering an anti-cancer therapeutic. Alternatively, determining the treatment for the cancer may comprise modifying a therapeutic regimen. Modifying a therapeutic regimen may comprise increasing, decreasing, or terminating a therapeutic regimen.

In some instances, the methods disclosed herein can diagnose, prognose, and/or monitor the status or outcome of a cancer in a subject with an accuracy of at least about 50%. In other instances, the methods disclosed herein can diagnose, prognose, and/or monitor the status or outcome of a cancer in a subject with an accuracy of at least about 60%. The methods disclosed herein can diagnose, prognose, and/or monitor the status or outcome of a cancer in a subject with an accuracy of at least about 65%. Alternatively, the methods disclosed herein can diagnose, prognose, and/or monitor the status or outcome of a cancer in a subject with an accuracy of at least about 70%. In some instances, the methods disclosed herein can diagnose, prognose, and/or monitor the status or outcome of a cancer in a subject with an accuracy of at least about 75%. In other instances, the methods disclosed herein can diagnose, prognose, and/or monitor the status or outcome of a cancer in a subject with an accuracy of at least about 80%. The methods disclosed herein can diagnose, prognose, and/or monitor the status or outcome of a cancer in a subject with an accuracy of at least about 85%. Alternatively, the methods disclosed herein can diagnose, prognose, and/or monitor the status or outcome of a cancer in a subject with an accuracy of at least about 90%. The methods disclosed herein can diagnose, prognose, and/or monitor the status or outcome of a cancer in a subject with an accuracy of at least about 95%.

The invention also encompasses any of the methods disclosed herein where the sensitivity is at least about 45%. In some embodiments, the sensitivity is at least about 50%. In some embodiments, the sensitivity is at least about 55%. In some embodiments, the sensitivity is at least about 60%. In some embodiments, the sensitivity is at least about 65%. In some embodiments, the sensitivity is at least about 70%. In some embodiments, the sensitivity is at least about 75%. In some embodiments, the sensitivity is at least about 80%. In some embodiments, the sensitivity is at least about 85%. In some embodiments, the sensitivity is at least about 90%. In some embodiments, the sensitivity is at least about 95%.

The invention also encompasses any of the methods disclosed herein where the expression level determines the status or outcome of a cancer in the subject with at least about 45% specificity. In some embodiments, the expression level determines the status or outcome of a cancer in the subject with at least about 50% specificity. In some embodiments, the expression level determines the status or outcome of a cancer in the subject with at least about 55% specificity. In some embodiments, the expression level determines the status or outcome of a cancer in the subject with at least about 60% specificity. In some embodiments, the expression level determines the status or outcome of a cancer in the subject with at least about 65% specificity. In some embodiments, the expression level determines the status or outcome of a cancer in the subject with at least about 70% specificity. In some embodiments, the expression level determines the status or outcome of a cancer in the subject with at least about 75% specificity. In some embodiments, the expression level determines the status or outcome of a cancer in the subject with at least about 80% specificity. In some embodiments, the expression level determines the status or outcome of a cancer in the subject with at least about 85% specificity. In some embodiments, the expression level determines the status or outcome of a cancer in the subject with at least about 90% specificity. In some embodiments, the expression level determines the status or outcome of a cancer in the subject with at least about 95% specificity.

Cancer

The systems, compositions and methods disclosed herein may be used to diagnosis, monitor and/or predict the status or outcome of a cancer. Generally, a cancer is characterized by the uncontrolled growth of abnormal cells anywhere in a body. The abnormal cells may be termed cancer cells, malignant cells, or tumor cells. Many cancers and the abnormal cells that compose the cancer tissue are further identified by the name of the tissue that the abnormal cells originated from (for example, breast cancer, lung cancer, colon cancer, prostate cancer, pancreatic cancer, thyroid cancer). Cancer is not confined to humans; animals and other living organisms can get cancer.

In some instances, the cancer may be malignant. Alternatively, the cancer may be benign. The cancer may be a recurrent and/or refractory cancer. Most cancers can be classified as a carcinoma, sarcoma, leukemia, lymphoma, myeloma, or a central nervous system cancer.

The cancer may be a sarcoma. Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Alternatively, the cancer may be a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penic cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. Preferably, the cancer is a prostate cancer. Alternatively, the cancer may be a thyroid cancer. The cancer can be a pancreatic cancer. In some instances, the cancer is a bladder cancer.

In some instances, the cancer is a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The cancer may be leukemia. The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic-leukemia.

In some instances, the cancer is a lymphoma. Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenstrom macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Cancer Staging

Diagnosing, predicting, or monitoring a status or outcome of a cancer may comprise determining the stage of the cancer. Generally, the stage of a cancer is a description (usually numbers I to IV with IV having more progression) of the extent the cancer has spread. The stage often takes into account the size of a tumor, how deeply it has penetrated, whether it has invaded adjacent organs, how many lymph nodes it has metastasized to (if any), and whether it has spread to distant organs. Staging of cancer can be used as a predictor of survival, and cancer treatment may be determined by staging. Determining the stage of the cancer may occur before, during, or after treatment. The stage of the cancer may also be determined at the time of diagnosis.

Cancer staging can be divided into a clinical stage and a pathologic stage. Cancer staging may comprise the TNM classification. Generally, the TNM Classification of Malignant Tumours (TNM) is a cancer staging system that describes the extent of cancer in a patient's body. T may describe the size of the tumor and whether it has invaded nearby tissue, N may describe regional lymph nodes that are involved, and M may describe distant metastasis (spread of cancer from one body part to another). In the TNM (Tumor, Node, Metastasis) system, clinical stage and pathologic stage are denoted by a small "c" or "p" before the stage (e.g., cT3N1M0 or pT2N0).

Often, clinical stage and pathologic stage may differ. Clinical stage may be based on all of the available information obtained before a surgery to remove the tumor. Thus, it may include information about the tumor obtained by physical examination, radiologic examination, and endoscopy. Pathologic stage can add additional information gained by examination of the tumor microscopically by a pathologist. Pathologic staging can allow direct examination of the tumor and its spread, contrasted with clinical staging which may be limited by the fact that the information is obtained by making indirect observations at a tumor which is still in the body. The TNM staging system can be used for most forms of cancer.

Alternatively, staging may comprise Ann Arbor staging. Generally, Ann Arbor staging is the staging system for lymphomas, both in Hodgkin's lymphoma (previously called Hodgkin's disease) and Non-Hodgkin lymphoma (abbreviated NHL). The stage may depend on both the place where the malignant tissue is located (as located with biopsy, CT scanning and increasingly positron emission tomography) and on systemic symptoms due to the lymphoma ("B symptoms": night sweats, weight loss of >10% or fevers). The principal stage may be determined by location of the tumor. Stage I may indicate that the cancer is located in a single region, usually one lymph node and the surrounding area. Stage I often may not have outward symptoms. Stage II can indicate that the cancer is located in two separate regions, an affected lymph node or organ and a second affected area, and that both affected areas are confined to one side of the diaphragm—that is, both are above the diaphragm, or both are below the diaphragm. Stage III often indicates that the cancer has spread to both sides of the diaphragm, including one organ or area near the lymph nodes or the spleen. Stage IV may indicate diffuse or disseminated involvement of one or more extralymphatic organs, including any involvement of the liver, bone marrow, or nodular involvement of the lungs.

Modifiers may also be appended to some stages. For example, the letters A, B, E, X, or S can be appended to some stages. Generally, A or B may indicate the absence of constitutional (B-type) symptoms is denoted by adding an "A" to the stage; the presence is denoted by adding a "B" to the stage. E can be used if the disease is "extranodal" (not in the lymph nodes) or has spread from lymph nodes to adjacent tissue. X is often used if the largest deposit is >10 cm large ("bulky disease"), or whether the mediastinum is wider than ⅓ of the chest on a chest X-ray. S may be used if the disease has spread to the spleen.

The nature of the staging may be expressed with CS or PS. CS may denote that the clinical stage as obtained by doctor's examinations and tests. PS may denote that the pathological stage as obtained by exploratory laparotomy (surgery performed through an abdominal incision) with splenectomy (surgical removal of the spleen).

Therapeutic Regimens

Diagnosing, predicting, or monitoring a status or outcome of a cancer may comprise treating a cancer or preventing a cancer progression. In addition, diagnosing, predicting, or monitoring a status or outcome of a cancer may comprise identifying or predicting responders to an anti-cancer therapy. In some instances, diagnosing, predicting, or monitoring may comprise determining a therapeutic regimen. Determining a therapeutic regimen may comprise administering an anti-cancer therapy. Alternatively, determining a therapeutic regimen may comprise modifying, recommending, continuing or discontinuing an anti-cancer regimen. In some instances, if the sample expression patterns are consistent with the expression pattern for a known disease or disease outcome, the expression patterns can be used to designate one or more treatment modalities (e.g., therapeutic regimens, anti-cancer regimen). An anti-cancer regimen may comprise one or more anti-cancer therapies. Examples of anti-cancer therapies include surgery, chemotherapy, radiation therapy, immunotherapy/biological therapy, photodynamic therapy.

Surgical oncology uses surgical methods to diagnose, stage, and treat cancer, and to relieve certain cancer-related symptoms. Surgery may be used to remove the tumor (e.g., excisions, resections, debulking surgery), reconstruct a part of the body (e.g., restorative surgery), and/or to relieve symptoms such as pain (e.g., palliative surgery). Surgery may also include cryosurgery. Cryosurgery (also called cryotherapy) may use extreme cold produced by liquid nitrogen (or argon gas) to destroy abnormal tissue. Cryosurgery can be used to treat external tumors, such as those on the skin. For external tumors, liquid nitrogen can be applied directly to the cancer cells with a cotton swab or spraying device. Cryosurgery may also be used to treat tumors inside the body (internal tumors and tumors in the bone). For internal tumors, liquid nitrogen or argon gas may be circulated through a hollow instrument called a cryoprobe, which is placed in contact with the tumor. An ultrasound or MRI may be used to guide the cryoprobe and monitor the freezing of the cells, thus limiting damage to nearby healthy tissue. A ball of ice crystals may form around the probe, freezing nearby cells. Sometimes more than one probe is used to deliver the liquid nitrogen to various parts of the tumor. The probes may be put into the tumor during surgery or through the skin (percutaneously). After cryosurgery, the frozen tissue thaws and may be naturally absorbed by the body (for internal tumors), or may dissolve and form a scab (for external tumors).

Chemotherapeutic agents may also be used for the treatment of cancer. Examples of chemotherapeutic agents include alkylating agents, anti-metabolites, plant alkaloids and terpenoids, vinca alkaloids, podophyllotoxin, taxanes, topoisomerase inhibitors, and cytotoxic antibiotics. Cisplatin, carboplatin, and oxaliplatin are examples of alkylating agents. Other alkylating agents include mechlorethamine, cyclophosphamide, chlorambucil, ifosfamide. Alkylating agens may impair cell function by forming covalent bonds with the amino, carboxyl, sulfhydryl, and phosphate groups in biologically important molecules. Alternatively, alkylating agents may chemically modify a cell's DNA.

Anti-metabolites are another example of chemotherapeutic agents. Anti-metabolites may masquerade as purines or pyrimidines and may prevent purines and pyrimidines from becoming incorporated in to DNA during the "S" phase (of the cell cycle), thereby stopping normal development and division. Antimetabolites may also affect RNA synthesis. Examples of metabolites include azathioprine and mercaptopurine.

Alkaloids may be derived from plants and block cell division may also be used for the treatment of cancer. Alkyloids may prevent microtubule function. Examples of alkaloids are vinca alkaloids and taxanes. Vinca alkaloids may bind to specific sites on tubulin and inhibit the assembly of tubulin into microtubules (M phase of the cell cycle). The vinca alkaloids may be derived from the Madagascar periwinkle, *Catharanthus roseus* (formerly known as *Vinca rosea*). Examples of vinca alkaloids include, but are not limited to, vincristine, vinblastine, vinorelbine, or vindesine. Taxanes are diterpenes produced by the plants of the genus *Taxus* (yews). Taxanes may be derived from natural sources or synthesized artificially. Taxanes include paclitaxel (Taxol) and docetaxel (Taxotere). Taxanes may disrupt microtubule function. Microtubules are essential to cell division, and taxanes may stabilize GDP-bound tubulin in the microtubule, thereby inhibiting the process of cell division. Thus, in essence, taxanes may be mitotic inhibitors. Taxanes may also be radiosensitizing and often contain numerous chiral centers.

Alternative chemotherapeutic agents include podophyllotoxin. Podophyllotoxin is a plant-derived compound that may help with digestion and may be used to produce cytostatic drugs such as etoposide and teniposide. They may prevent the cell from entering the G1 phase (the start of DNA replication) and the replication of DNA (the S phase).

Topoisomerases are essential enzymes that maintain the topology of DNA. Inhibition of type I or type II topoisomerases may interfere with both transcription and replication of DNA by upsetting proper DNA supercoiling. Some chemotherapeutic agents may inhibit topoisomerases. For example, some type I topoisomerase inhibitors include camptothecins: irinotecan and topotecan. Examples of type II inhibitors include amsacrine, etoposide, etoposide phosphate, and teniposide.

Another example of chemotherapeutic agents is cytotoxic antibiotics. Cytotoxic antibiotics are a group of antibiotics that are used for the treatment of cancer because they may interfere with DNA replication and/or protein synthesis. Cytotoxic antiobiotics include, but are not limited to, actinomycin, anthracyclines, doxorubicin, daunorubicin, valrubicin, idarubicin, epirubicin, bleomycin, plicamycin, and mitomycin.

In some instances, the anti-cancer treatment may comprise radiation therapy. Radiation can come from a machine outside the body (external-beam radiation therapy) or from radioactive material placed in the body near cancer cells (internal radiation therapy, more commonly called brachytherapy). Systemic radiation therapy uses a radioactive substance, given by mouth or into a vein that travels in the blood to tissues throughout the body.

External-beam radiation therapy may be delivered in the form of photon beams (either x-rays or gamma rays). A photon is the basic unit of light and other forms of electromagnetic radiation. An example of external-beam radiation therapy is called 3-dimensional conformal radiation therapy (3D-CRT). 3D-CRT may use computer software and advanced treatment machines to deliver radiation to very precisely shaped target areas. Many other methods of external-beam radiation therapy are currently being tested and used in cancer treatment. These methods include, but are not limited to, intensity-modulated radiation therapy (IMRT), image-guided radiation therapy (IGRT), Stereotactic radiosurgery (SRS), Stereotactic body radiation therapy (SBRT), and proton therapy.

Intensity-modulated radiation therapy (IMRT) is an example of external-beam radiation and may use hundreds of tiny radiation beam-shaping devices, called collimators, to deliver a single dose of radiation. The collimators can be stationary or can move during treatment, allowing the intensity of the radiation beams to change during treatment sessions. This kind of dose modulation allows different areas of a tumor or nearby tissues to receive different doses of radiation. IMRT is planned in reverse (called inverse treatment planning). In inverse treatment planning, the radiation doses to different areas of the tumor and surrounding tissue are planned in advance, and then a high-powered computer program calculates the required number of beams and angles of the radiation treatment. In contrast, during traditional (forward) treatment planning, the number and angles of the radiation beams are chosen in advance and computers calculate how much dose may be delivered from each of the planned beams. The goal of IMRT is to increase the radiation dose to the areas that need it and reduce radiation exposure to specific sensitive areas of surrounding normal tissue.

Another example of external-beam radiation is image-guided radiation therapy (IGRT). In IGRT, repeated imaging scans (CT, MRI, or PET) may be performed during treatment. These imaging scans may be processed by computers to identify changes in a tumor's size and location due to treatment and to allow the position of the patient or the planned radiation dose to be adjusted during treatment as needed. Repeated imaging can increase the accuracy of radiation treatment and may allow reductions in the planned volume of tissue to be treated, thereby decreasing the total radiation dose to normal tissue.

Tomotherapy is a type of image-guided IMRT. A tomotherapy machine is a hybrid between a CT imaging scanner and an external-beam radiation therapy machine. The part of the tomotherapy machine that delivers radiation for both imaging and treatment can rotate completely around the patient in the same manner as a normal CT scanner. Tomotherapy machines can capture CT images of the patient's tumor immediately before treatment sessions, to allow for very precise tumor targeting and sparing of normal tissue.

Stereotactic radiosurgery (SRS) can deliver one or more high doses of radiation to a small tumor. SRS uses extremely accurate image-guided tumor targeting and patient positioning. Therefore, a high dose of radiation can be given without excess damage to normal tissue. SRS can be used to treat small tumors with well-defined edges. It is most commonly used in the treatment of brain or spinal tumors and brain metastases from other cancer types. For the treatment of some brain metastases, patients may receive radiation therapy to the entire brain (called whole-brain radiation therapy) in addition to SRS. SRS requires the use of a head frame or other device to immobilize the patient during treatment to ensure that the high dose of radiation is delivered accurately.

Stereotactic body radiation therapy (SBRT) delivers radiation therapy in fewer sessions, using smaller radiation fields and higher doses than 3D-CRT in most cases. SBRT may treat tumors that lie outside the brain and spinal cord. Because these tumors are more likely to move with the normal motion of the body, and therefore cannot be targeted as accurately as tumors within the brain or spine, SBRT is usually given in more than one dose. SBRT can be used to treat small, isolated tumors, including cancers in the lung and liver. SBRT systems may be known by their brand names, such as the CyberKnife®.

In proton therapy, external-beam radiation therapy may be delivered by proton. Protons are a type of charged particle. Proton beams differ from photon beams mainly in the way they deposit energy in living tissue. Whereas photons deposit energy in small packets all along their path through tissue, protons deposit much of their energy at the end of their path (called the Bragg peak) and deposit less energy along the way. Use of protons may reduce the exposure of normal tissue to radiation, possibly allowing the delivery of higher doses of radiation to a tumor.

Other charged particle beams such as electron beams may be used to irradiate superficial tumors, such as skin cancer or tumors near the surface of the body, but they cannot travel very far through tissue.

Internal radiation therapy (brachytherapy) is radiation delivered from radiation sources (radioactive materials) placed inside or on the body. Several brachytherapy techniques are used in cancer treatment. Interstitial brachytherapy may use a radiation source placed within tumor tissue, such as within a prostate tumor. Intracavitary brachytherapy may use a source placed within a surgical cavity or a body cavity, such as the chest cavity, near a tumor. Episcleral brachytherapy, which may be used to treat melanoma inside the eye, may use a source that is attached to the eye. In brachytherapy, radioactive isotopes can be sealed in tiny pellets or "seeds." These seeds may be placed in patients using delivery devices, such as needles, catheters, or some other type of carrier. As the isotopes decay naturally, they give off radiation that may damage nearby cancer cells. Brachytherapy may be able to deliver higher doses of radiation to some cancers than external-beam radiation therapy while causing less damage to normal tissue.

Brachytherapy can be given as a low-dose-rate or a high-dose-rate treatment. In low-dose-rate treatment, cancer cells receive continuous low-dose radiation from the source over a period of several days. In high-dose-rate treatment, a robotic machine attached to delivery tubes placed inside the body may guide one or more radioactive sources into or near a tumor, and then removes the sources at the end of each treatment session. High-dose-rate treatment can be given in one or more treatment sessions. An example of a high-dose-rate treatment is the MammoSite® system. Bracytherapy may be used to treat patients with breast cancer who have undergone breast-conserving surgery.

The placement of brachytherapy sources can be temporary or permanent. For permament brachytherapy, the sources may be surgically sealed within the body and left there, even after all of the radiation has been given off. In some instances, the remaining material (in which the radioactive isotopes were sealed) does not cause any discomfort or harm to the patient. Permanent brachytherapy is a type of low-dose-rate brachytherapy. For temporary brachytherapy, tubes (catheters) or other carriers are used to deliver the radiation sources, and both the carriers and the radiation sources are removed after treatment. Temporary brachytherapy can be either low-dose-rate or high-dose-rate treatment. Brachytherapy may be used alone or in addition to external-beam radiation therapy to provide a "boost" of radiation to a tumor while sparing surrounding normal tissue.

In systemic radiation therapy, a patient may swallow or receive an injection of a radioactive substance, such as radioactive iodine or a radioactive substance bound to a monoclonal antibody. Radioactive iodine (1311) is a type of systemic radiation therapy commonly used to help treat cancer, such as thyroid cancer. Thyroid cells naturally take up radioactive iodine. For systemic radiation therapy for some other types of cancer, a monoclonal antibody may help target the radioactive substance to the right place. The antibody joined to the radioactive substance travels through the blood, locating and killing tumor cells. For example, the drug ibritumomab tiuxetan (Zevalin®) may be used for the treatment of certain types of B-cell non-Hodgkin lymphoma (NHL). The antibody part of this drug recognizes and binds to a protein found on the surface of B lymphocytes. The combination drug regimen of tositumomab and iodine I 131 tositumomab (Bexxar®) may be used for the treatment of certain types of cancer, such as NHL. In this regimen, nonradioactive tositumomab antibodies may be given to patients first, followed by treatment with tositumomab antibodies that have 1311 attached. Tositumomab may recognize and bind to the same protein on B lymphocytes as ibritumomab. The nonradioactive form of the antibody may help protect normal B lymphocytes from being damaged by radiation from 1311.

Some systemic radiation therapy drugs relieve pain from cancer that has spread to the bone (bone metastases). This is a type of palliative radiation therapy. The radioactive drugs samarium-153-lexidronam (Quadramet®) and strontium-89 chloride (Metastron®) are examples of radiopharmaceuticals may be used to treat pain from bone metastases.

Biological therapy (sometimes called immunotherapy, biotherapy, or biological response modifier (BRM) therapy) uses the body's immune system, either directly or indirectly, to fight cancer or to lessen the side effects that may be caused by some cancer treatments. Biological therapies include interferons, interleukins, colony-stimulating factors, monoclonal antibodies, vaccines, gene therapy, and nonspecific immunomodulating agents.

Interferons (IFNs) are types of cytokines that occur naturally in the body. Interferon alpha, interferon beta, and interferon gamma are examples of interferons that may be used in cancer treatment.

Like interferons, interleukins (ILs) are cytokines that occur naturally in the body and can be made in the laboratory. Many interleukins have been identified for the treatment of cancer. For example, interleukin-2 (IL-2 or aldesleukin), interleukin 7, and interleukin 12 have may be used as an anti-cancer treatment. IL-2 may stimulate the growth and activity of many immune cells, such as lymphocytes, that can destroy cancer cells. Interleukins may be used to treat a number of cancers, including leukemia, lymphoma, and brain, colorectal, ovarian, breast, kidney and prostate cancers.

Colony-stimulating factors (CSFs) (sometimes called hematopoietic growth factors) may also be used for the treatment of cancer. Some examples of CSFs include, but are not limited to, G-CSF (filgrastim) and GM-CSF (sargramostim). CSFs may promote the division of bone marrow stem cells and their development into white blood cells, platelets, and red blood cells. Bone marrow is critical to the body's immune system because it is the source of all blood cells.

Because anticancer drugs can damage the body's ability to make white blood cells, red blood cells, and platelets, stimulation of the immune system by CSFs may benefit patients undergoing other anti-cancer treatment, thus CSFs may be combined with other anti-cancer therapies, such as chemotherapy. CSFs may be used to treat a large variety of cancers, including lymphoma, leukemia, multiple myeloma, melanoma, and cancers of the brain, lung, esophagus, breast, uterus, ovary, prostate, kidney, colon, and rectum.

Another type of biological therapy includes monoclonal antibodies (MOABs or MoABs). These antibodies may be produced by a single type of cell and may be specific for a particular antigen. To create MOABs, human cancer cells may be injected into mice. In response, the mouse immune system can make antibodies against these cancer cells. The mouse plasma cells that produce antibodies may be isolated and fused with laboratory-grown cells to create "hybrid" cells called hybridomas. Hybridomas can indefinitely produce large quantities of these pure antibodies, or MOABs. MOABs may be used in cancer treatment in a number of ways. For instance, MOABs that react with specific types of cancer may enhance a patient's immune response to the cancer. MOABs can be programmed to act against cell growth factors, thus interfering with the growth of cancer cells.

MOABs may be linked to other anti-cancer therapies such as chemotherapeutics, radioisotopes (radioactive substances), other biological therapies, or other toxins. When the antibodies latch onto cancer cells, they deliver these anti-cancer therapies directly to the tumor, helping to destroy it. MOABs carrying radioisotopes may also prove useful in diagnosing certain cancers, such as colorectal, ovarian, and prostate.

Rituxan® (rituximab) and Herceptin® (trastuzumab) are examples of MOABs that may be used as a biological therapy. Rituxan may be used for the treatment of non-Hodgkin lymphoma. Herceptin can be used to treat metastatic breast cancer in patients with tumors that produce excess amounts of a protein called HER2. Alternatively, MOABs may be used to treat lymphoma, leukemia, melanoma, and cancers of the brain, breast, lung, kidney, colon, rectum, ovary, prostate, and other areas.

Cancer vaccines are another form of biological therapy. Cancer vaccines may be designed to encourage the patient's immune system to recognize cancer cells. Cancer vaccines may be designed to treat existing cancers (therapeutic vaccines) or to prevent the development of cancer (prophylactic vaccines). Therapeutic vaccines may be injected in a person after cancer is diagnosed. These vaccines may stop the growth of existing tumors, prevent cancer from recurring, or eliminate cancer cells not killed by prior treatments. Cancer vaccines given when the tumor is small may be able to eradicate the cancer. On the other hand, prophylactic vaccines are given to healthy individuals before cancer develops. These vaccines are designed to stimulate the immune system to attack viruses that can cause cancer. By targeting these cancer-causing viruses, development of certain cancers may be prevented. For example, cervarix and gardasil are vaccines to treat human papilloma virus and may prevent cervical cancer. Therapeutic vaccines may be used to treat melanoma, lymphoma, leukemia, and cancers of the brain, breast, lung, kidney, ovary, prostate, pancreas, colon, and rectum. Cancer vaccines can be used in combination with other anti-cancer therapies.

Gene therapy is another example of a biological therapy. Gene therapy may involve introducing genetic material into a person's cells to fight disease. Gene therapy methods may improve a patient's immune response to cancer. For example, a gene may be inserted into an immune cell to enhance its ability to recognize and attack cancer cells. In another approach, cancer cells may be injected with genes that cause the cancer cells to produce cytokines and stimulate the immune system.

In some instances, biological therapy includes nonspecific immunomodulating agents. Nonspecific immunomodulating agents are substances that stimulate or indirectly augment the immune system. Often, these agents target key immune system cells and may cause secondary responses such as increased production of cytokines and immunoglobulins. Two nonspecific immunomodulating agents used in cancer treatment are bacillus Calmette-Guerin (BCG) and levamisole. BCG may be used in the treatment of superficial bladder cancer following surgery. BCG may work by stimulating an inflammatory, and possibly an immune, response. A solution of BCG may be instilled in the bladder. Levamisole is sometimes used along with fluorouracil (5-FU) chemotherapy in the treatment of stage III (Dukes' C) colon cancer following surgery. Levamisole may act to restore depressed immune function.

Photodynamic therapy (PDT) is an anti-cancer treatment that may use a drug, called a photosensitizer or photosensitizing agent, and a particular type of light. When photosensitizers are exposed to a specific wavelength of light, they may produce a form of oxygen that kills nearby cells. A photosensitizer may be activated by light of a specific wavelength. This wavelength determines how far the light can travel into the body. Thus, photosensitizers and wavelengths of light may be used to treat different areas of the body with PDT.

In the first step of PDT for cancer treatment, a photosensitizing agent may be injected into the bloodstream. The agent may be absorbed by cells all over the body but may stay in cancer cells longer than it does in normal cells. Approximately 24 to 72 hours after injection, when most of the agent has left normal cells but remains in cancer cells, the tumor can be exposed to light. The photosensitizer in the tumor can absorb the light and produces an active form of oxygen that destroys nearby cancer cells. In addition to directly killing cancer cells, PDT may shrink or destroy tumors in two other ways. The photosensitizer can damage blood vessels in the tumor, thereby preventing the cancer from receiving necessary nutrients. PDT may also activate the immune system to attack the tumor cells.

The light used for PDT can come from a laser or other sources. Laser light can be directed through fiber optic cables (thin fibers that transmit light) to deliver light to areas inside the body. For example, a fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumors, such as skin cancer. PDT is usually performed as an outpatient procedure. PDT may also be repeated and may be used with other therapies, such as surgery, radiation, or chemotherapy.

Extracorporeal photopheresis (ECP) is a type of PDT in which a machine may be used to collect the patient's blood cells. The patient's blood cells may be treated outside the body with a photosensitizing agent, exposed to light, and then returned to the patient. ECP may be used to help lessen the severity of skin symptoms of cutaneous T-cell lymphoma that has not responded to other therapies. ECP may be used to treat other blood cancers, and may also help reduce rejection after transplants.

Additionally, photosensitizing agent, such as porfimer sodium or Photofrin®, may be used in PDT to treat or relieve the symptoms of esophageal cancer and non-small cell lung cancer. Porfimer sodium may relieve symptoms of esophageal cancer when the cancer obstructs the esophagus or when the cancer cannot be satisfactorily treated with laser therapy alone. Porfimer sodium may be used to treat non-small cell lung cancer in patients for whom the usual treatments are not appropriate, and to relieve symptoms in patients with non-small cell lung cancer that obstructs the airways. Porfimer sodium may also be used for the treatment of precancerous lesions in patients with Barrett esophagus, a condition that can lead to esophageal cancer.

Laser therapy may use high-intensity light to treat cancer and other illnesses. Lasers can be used to shrink or destroy tumors or precancerous growths. Lasers are most commonly used to treat superficial cancers (cancers on the surface of the body or the lining of internal organs) such as basal cell skin cancer and the very early stages of some cancers, such as cervical, penile, vaginal, vulvar, and non-small cell lung cancer.

Lasers may also be used to relieve certain symptoms of cancer, such as bleeding or obstruction. For example, lasers can be used to shrink or destroy a tumor that is blocking a patient's trachea (windpipe) or esophagus. Lasers also can be used to remove colon polyps or tumors that are blocking the colon or stomach.

Laser therapy is often given through a flexible endoscope (a thin, lighted tube used to look at tissues inside the body).

The endoscope is fitted with optical fibers (thin fibers that transmit light). It is inserted through an opening in the body, such as the mouth, nose, anus, or vagina. Laser light is then precisely aimed to cut or destroy a tumor.

Laser-induced interstitial thermotherapy (LITT), or interstitial laser photocoagulation, also uses lasers to treat some cancers. LITT is similar to a cancer treatment called hyperthermia, which uses heat to shrink tumors by damaging or killing cancer cells. During LITT, an optical fiber is inserted into a tumor. Laser light at the tip of the fiber raises the temperature of the tumor cells and damages or destroys them. LITT is sometimes used to shrink tumors in the liver.

Laser therapy can be used alone, but most often it is combined with other treatments, such as surgery, chemotherapy, or radiation therapy. In addition, lasers can seal nerve endings to reduce pain after surgery and seal lymph vessels to reduce swelling and limit the spread of tumor cells.

Lasers used to treat cancer may include carbon dioxide ($CO_2$) lasers, argon lasers, and neodymium:yttrium-aluminum-garnet (Nd:YAG) lasers. Each of these can shrink or destroy tumors and can be used with endoscopes. CO2 and argon lasers can cut the skin's surface without going into deeper layers. Thus, they can be used to remove superficial cancers, such as skin cancer. In contrast, the Nd:YAG laser is more commonly applied through an endoscope to treat internal organs, such as the uterus, esophagus, and colon. Nd:YAG laser light can also travel through optical fibers into specific areas of the body during LITT. Argon lasers are often used to activate the drugs used in PDT.

EXPERIMENTAL

The following examples are provided in order to demonstrate and further illustrate certain preferred embodiments and aspects of the present invention and are not to be construed as limiting the scope thereof.

Example 1

A. Methods
Methods Summary

All prostate tissue samples were obtained from the University of Michigan Specialized Program Of Research Excellence (S.P.O.R.E.) using an IRB-approved informed consent protocol. Next generation sequencing and library preparation was performed as previously described (Maher et al., *Proc Natl Acad Sci USA* 106 (30), 12353 (2009)). Uniquely mapping sequencing reads were aligned with TopHat and sequencing data for all samples was merged. Ab initio transcriptome assembly was performed by aligning sequences with TopHat and using uniquely mapped read positions to build transcripts with Cufflinks. Informatics approaches were used to refine the assembly and predict expressed transcriptional units. Unannotated transcripts were nominated based upon their absence in the UCSC, RefSeq, ENSEMBL, ENCODE, and Vega databases. Differential expression was determined using the Significance Analysis of Microarrays (SAM) algorithm (Tusher et al., *Proc Natl Acad Sci USA* 98 (9), 5116 (2001)) on log 2 mean expression in benign, cancer, and metastatic samples. Cancer outlier profile analysis (COPA) was performed as previously described (Tomlins et al., *Science* 310 (5748), 644 (2005)) with slight modifications. PCR experiments were performed according to standard protocols, and RACE was performed with the GeneRacer Kit (Invitrogen) according to manufacturer's instructions. ChIP-seq data was obtained from previously published data (Yu et al., *Cancer Cell* 17 (5), 443). siRNA knockdown was performed with custom siRNA oligos (Dharmacon) with Oligofectamine (Invitrogen). Transmembrane invasion assays were performed with Matrigel (BD Biosciences) and cell proliferation assays were performed by cell count with a Coulter counter. Urine analyses were performed as previously described (Laxman et al., *Cancer Res* 68 (3), 645 (2008)) with minor modifications.

Cell Lines and Tissues

The benign immortalized prostate cell line RWPE as well as PC3, Du145, LNCaP, VCaP, 22Rv1, CWR22, C4-2B, NCI-660, MDA PCa 2b, WPMY-1, and LAPC-4 prostate cell lines were obtained from the American Type Culture Collection (Manassas, VA). Benign non-immortalized prostate epithelial cells (PrEC) and prostate smooth muscle cells (PrSMC) were obtained from Lonza (Basel, Switzerland). Cell lines were maintained using standard media and conditions. For androgen treatment experiments, LNCaP and VCaP cells were grown in androgen depleted media lacking phenol red and supplemented with 10% charcoal-stripped serum and 1% penicillin-streptomycin. After 48 hours, cells were treated with 5 nM methyltrienolone (R1881, NEN Life Science Products) or an equivalent volume of ethanol. Cells were harvested for RNA at 6, 24, and 48 hours post-treatment. Prostate tissues were obtained from the radical prostatectomy series and Rapid Autopsy Program at the University of Michigan tissue core. These programs are part of the University of Michigan Prostate Cancer Specialized Program Of Research Excellence (S.P.O.R.E.). All tissue samples were collected with informed consent under an Institutional Review Board (IRB) approved protocol at the University of Michigan.

PC3, Du145, LNCaP, 22Rv1, and CRW22 cells were grown in RPMI 1640 (Invitrogen) and supplemented with 10% fetal bovine serum (FBS) and 1% penicillin-streptomycin. LNCaP CDS parent cells were grown in RPMI 1640 lacking phenol red (Invitrogen) supplemented with 10% charcoal-dextran stripped FBS (Invitrogen) and 1% penicillin-streptomycin. LNCaP CDS 1, 2, and 3 are androgen-independent subclones derived from extended cell culture in androgendepleted media. VCaP and WPMY-1 cells were grown in DMEM (Invitrogen) and supplemented with 10% fetal bovine serum (FBS) with 1% penicillin-streptomycin. NCI-H660 cells were grown in RPMI 1640 supplemented with 0.005 mg/ml insulin, 0.01 mg/ml transferring, 30 nM sodium selenite, 10 nM hydrocortisone, 10 nM beta-estradiol, 5% FBS and an extra 2 mM of L-glutamine (for a final concentration of 4 mM). MDA PCa 2b cells were grown in F-12K medium (Invitrogen) supplemented with 20% FBS, 25 ng/ml cholera toxin, 10 ng/ml EGF, 0.005 mM phosphoethanolamine, 100 pg/ml hydrocortisone, 45 nM selenious acid, and 0.005 mg/ml insulin. LAPC-4 cells were grown in Iscove's media (Invitrogen) supplemented with 10% FBS and 1 nM R1881. C4-2B cells were grown in 80% DMEM supplemented with 20% F12, 5% FBS, 3 g/L $NaCo_3$, 5 µg/ml insulin, 13.6 pg/ml triiodothyonine, 5 µg/ml transferrin, 0.25 µg/ml biotin, and 25 µg/ml adenine. PrEC cells were grown in PrEGM supplemented with 2 ml BPE, 0.5 ml hydrocortisone, 0.5 ml EGF, 0.5 ml epinephrine, 0.5 ml transferring, 0.5 ml insulin, 0.5 ml retinoic acid, and 0.5 ml triiodothyronine, as part of the PrEGM BulletKit (Lonza). PrSMC cells were grown in SmGM-2 media supplemented with 2 ml BPE, 0.5 ml hydrocortisone, 0.5 ml EGF, 0.5 ml epinephrine, 0.5 ml transferring, 0.5 ml insulin, 0.5 ml retinoic acid, and 0.5 ml triiodothyronine, as part of the SmGM-2 BulletKit (Lonza).

RNA-Seq Library Preparation.

Next generation sequencing of RNA was performed on 21 prostate cell lines, 20 benign adjacent prostates, 47 localized tumors, and 14 metastatic tumors according to Illumina's protocol using 2 µg of RNA. RNA integrity was measured using an Agilent 2100 Bioanalyzer, and only samples with a RIN score>7.0 were advanced for library generation. RNA was poly-A+ selected using the OligodT beads provided by Ilumina and fragmented with the Ambion Fragmentation Reagents kit (Ambion, Austin, TX). cDNA synthesis, end-repair, A-base addition, and ligation of the Illumina PCR adaptors (single read or paired-end where appropriate) were performed according to Illumina's protocol. Libraries were then size-selected for 250-300 bp cDNA fragments on a 3.5% agarose gel and PCR-amplified using Phusion DNA polymerase (Finnzymes) for 15-18 PCR cycles. PCR products were then purified on a 2% agarose gel and gel-extracted. Library quality was credentialed by assaying each library on an Agilent 2100 Bioanalyzer of product size and concentration. Libraries were sequenced as 36-45 mers on an Illumina Genome Analyzer I or Genome Analyzer II flowcell according to Illumina's protocol. All single read samples were sequenced on a Genome Analyzer I, and all paired-end samples were sequenced on a Genome Analyzer II.

RNA Isolation and cDNA Synthesis

Total RNA was isolated using Trizol and an RNeasy Kit (Invitrogen) with DNase I digestion according to the manufacturer's instructions. RNA integrity was verified on an Agilent Bioanalyzer 2100 (Agilent Technologies, Palo Alto, CA). cDNA was synthesized from total RNA using Superscript III (Invitrogen) and random primers (Invitrogen).

Quantitative Real-Time PCR

Quantitative Real-time PCR (qPCR) was performed using Power SYBR Green Mastermix (Applied Biosystems, Foster City, CA) on an Applied Biosystems 7900HT Real-Time PCR System. All oligonucleotide primers were obtained from Integrated DNA Technologies (Coralville, Iowa). The housekeeping gene, GAPDH, was used as a loading control. Fold changes were calculated relative to GAPDH and normalized to the median value of the benign samples.

Reverse-Transcription PCR

Reverse-transcription PCR (RT-PCR) was performed for primer pairs using Platinum Taq High Fidelity polymerase (Invitrogen). PCR products were resolved on a 2% agarose gel. PCR products were either sequenced directly (if only a single product was observed) or appropriate gel products were extracted using a Gel Extraction kit (Qiagen) and cloned into per4-TOPO vectors (Invitrogen). PCR products were bidirectionally sequenced at the University of Michigan Sequencing Core using either gene-specific primers or M13 forward and reverse primers for cloned PCR products. All oligonucleotide primers were obtained from Integrated DNA Technologies (Coralville, Iowa).

RNA-Ligase-Mediated Rapid Amplification of cDNA Ends (RACE)

5' and 3' RACE was performed using the GeneRacer RLM-RACE kit (Invitrogen) according to the manufacturer's instructions. RACE PCR products were obtained using Platinum Taq High Fidelity polymerase (Invitrogen), the supplied GeneRacer primers, and appropriate gene-specific primers. RACEPCR products were separated on a 2% agarose gels. Gel products were extracted with a Gel Extraction kit (Qiagen), cloned into per4-TOPO vectors (Invitrogen), and sequenced bidirectionally using M13 forward and reverse primers at the University of Michigan Sequencing Core. At least three colonies were sequenced for every gel product that was purified.

Paired-End Next-Generation Sequencing of RNA

2 µg total RNA was selected for polyA+ RNA using Sera-Mag oligo(dT) beads (Thermo Scientific), and paired-end next-generation sequencing libraries were prepared as previously described (Maher et al., supra) using Illumina-supplied universal adaptor oligos and PCR primers (Illumina). Samples were sequenced in a single lane on an Illumina Genome Analyzer II flowcell using previously described protocols (Maher et al., supra). 36-45 mer paired-end reads were according to the protocol provided by Illumina.

siRNA Knockdown Studies

Cells were plated in 100 mM plates at a desired concentration and transfected with 20 µM experimental siRNA oligos or non-targeting controls twice, at 12 hours and 36 hours post-plating. Knockdowns were performed with Oligofectamine and Optimem. Knockdown efficiency was determined by qPCR. 72 hours post-transfection, cells were trypsinized, counted with a Coulter counter, and diluted to 1 million cells/mL. For proliferation assays, 200,000 cells were plated in 24-well plates and grown in regular media. 48 and 96 hours post-plating, cells were harvested and counted using a Coulter counter. For invasion assays, Matrigel was diluted 1:4 in serum-free media and 100 µL of the diluted Matrigel was applied to a Boyden chamber transmembrane insert and allowed to settle overnight at 37° C. 200,000 cells suspended in serum-free media were applied per insert and 500 µL of serum-containing media was placed in the bottom of the Boyden (fetal bovine serum functioning as a chemoattractant). Cells were allowed to invade for 48 hours, at which time inserts were removed and noninvading cells and Matrigel were gently removed with a cotton swab. Invading cells were stained with crystal violet for 15 minutes and air-dried. For colorimetric assays, the inserts were treated with 200 µl of 10% acetic acid and the absorbance at 560 nm was measured using a spectrophotometer. For WST-1 assays, 20,000 cells were plated into 96-well plates and grown in 100 µL of serum-containing media. 48 and 96 hours post-plating, cells were measured for viability by adding 10 µL of WST-1 reagent to the cell media, incubating for 2 hours at 37° C. and measuring the absorbance at 450 nM using a spectrophotomer.

Urine qPCR

Urine samples were collected from 120 patients with informed consent following a digital rectal exam before either needle biopsy or radical prostatectomy at the University of Michigan with Institutional Review Board approval as described previously (Laxman et al., Cancer Res 68 (3), 645 (2008)). Isolation of RNA from urine and TransPlex whole transcriptome amplification were performed as described previously (Laxman et al., Neoplasia 8 (10), 885 (2006)). qPCR on urine samples was performed for KLK3 (PSA), TMPRSS2-ERG, GAPDH, PCA3, PCAT-1 and PCAT-14 using Power SYBR Mastermix (Applied Biosystems) as described above. Raw Ct values were extracted and normalized in the following manner. First, samples with GAPDH Ct values>25 or KLK3 Ct values>30 were removed from analysis to ensure sufficient prostate cell collection, leaving $10^8$ samples for analysis. The GAPDH and KLK3 raw Ct values were average for each sample. ΔCt analysis was performed by measuring each value against the average of CtGAPDH and CtKLK3, and ΔCt values were normalized to the median ΔCt of the benign samples. Fold change was then calculated at 2−ΔCt. Samples were considered to be prostate cancer if histopathological analysis observed cancer or if the TMPRSS2-ERG transcript achieved a Ct value<37. Benign samples were defined as samples with normal histology and TMPRSS2-ERG transcript Ct values>37.

Statistical Analyses for Experimental Studies

All data are presented as means±s.e.m. All experimental assays were performed in duplicate or triplicate.

Bioinformatics Analyses

To achieve an ab initio prediction of the prostate cancer transcriptome existing publicly tools for mapping, assembly, and quantification of transcripts were supplemented with additional informatics filtering steps to enrich the results for the most robust transcript predictions (FIG. 6a). Transcripts were then identified and classified by comparing them against gene annotation databases (FIG. 6b). Details of the bioinformatics analyses are provided below.

Mapping Reads with TopHat

Reads were aligned using TopHat v1.0.13 (Feb. 5, 2010) (Trapnell et al., *Bioinformatics* 25, 1105-11 (2009)), a gapped aligner capable of discovering splice junctions ab initio. Briefly, TopHat aligns reads to the human genome using Bowtie (Langmead et al., *Genome Biol* 10, R25 (2009)) to determine a set of "coverage islands" that may represent putative exons. TopHat uses these exons as well as the presence of GT-AG genomic splicing motifs to build a second set of reference sequences spanning exon-exon junctions. The unmapped reads from the initial genome alignment step are then remapped against this splice junction reference to discover all the junction-spanning reads in the sample. TopHat outputs the reads that successfully map to either the genome or the splice junction reference in SAM format for further analysis. For this study a maximum intron size of 500 kb, corresponding to over 99.98% of RefSeq (Wheeler et al. *Nucleic Acids Res* 28, 10-4 (2000)) introns was used. For sequencing libraries the insert size was determined using an Agilent 2100 Bioanalyzer prior to data analysis, and it was found that this insert size agreed closely with software predictions. An insert size standard deviation of 20 bases was chosen in order to match the most common band size cut from gels during library preparation. In total, 1.723 billion fragments were generated from 201 lanes of sequencing on the Illumina Genome Analyzer and Illumina Genome Analyzer II. Reads were mapped to the human genome (hg18) downloaded from the UCSC genome browser website (Karolchik et al., *Nucleic Acids Res* 31, 51-4 (2003); Kent et al., *Genome Res* 12, 996-1006 (2002)). 1.418 billion unique alignments were obtained, including 114.4 million splice junctions for use in transcriptome assembly. Reads with multiple alignments with less than two mismatches were discarded.

Ab Initio Assembly and Quantification with Cufflinks

Aligned reads from TopHat were assembled into sample-specific transcriptomes with Cufflinks version 0.8.2 (Mar. 26, 2010) (Trapnell et al., *Nat Biotechnol* 28, 511-5). Cufflinks assembles exonic and splice-junction reads into transcripts using their alignment coordinates. To limit false positive assemblies a maximum intronic length of 300 kb, corresponding to the 99.93% percentile of known introns was used. After assembling transcripts, Cufflinks computes isoform-level abundances by finding a parsimonious allocation of reads to the transcripts within a locus. Transcripts with abundance less than 15% of the major transcript in the locus, and minor isoforms with abundance less than 5% of the major isoform were filtered. Default settings were used for the remaining parameters.

The Cufflinks assembly stage yielded a set of transcript annotations for each of the sequenced libraries. The transcripts were partitioned by chromosome and the Cuffcompare utility provided by Cufflinks was used to merge the transcripts into a combined set of annotations. The Cuffcompare program performs a union of all transcripts by merging transcripts that share all introns and exons. The 5' and 3' exons of transcripts were allowed to vary by up to 100 nt during the comparison process.

Distinguishing Transcripts from Background Signal

Figure 7:
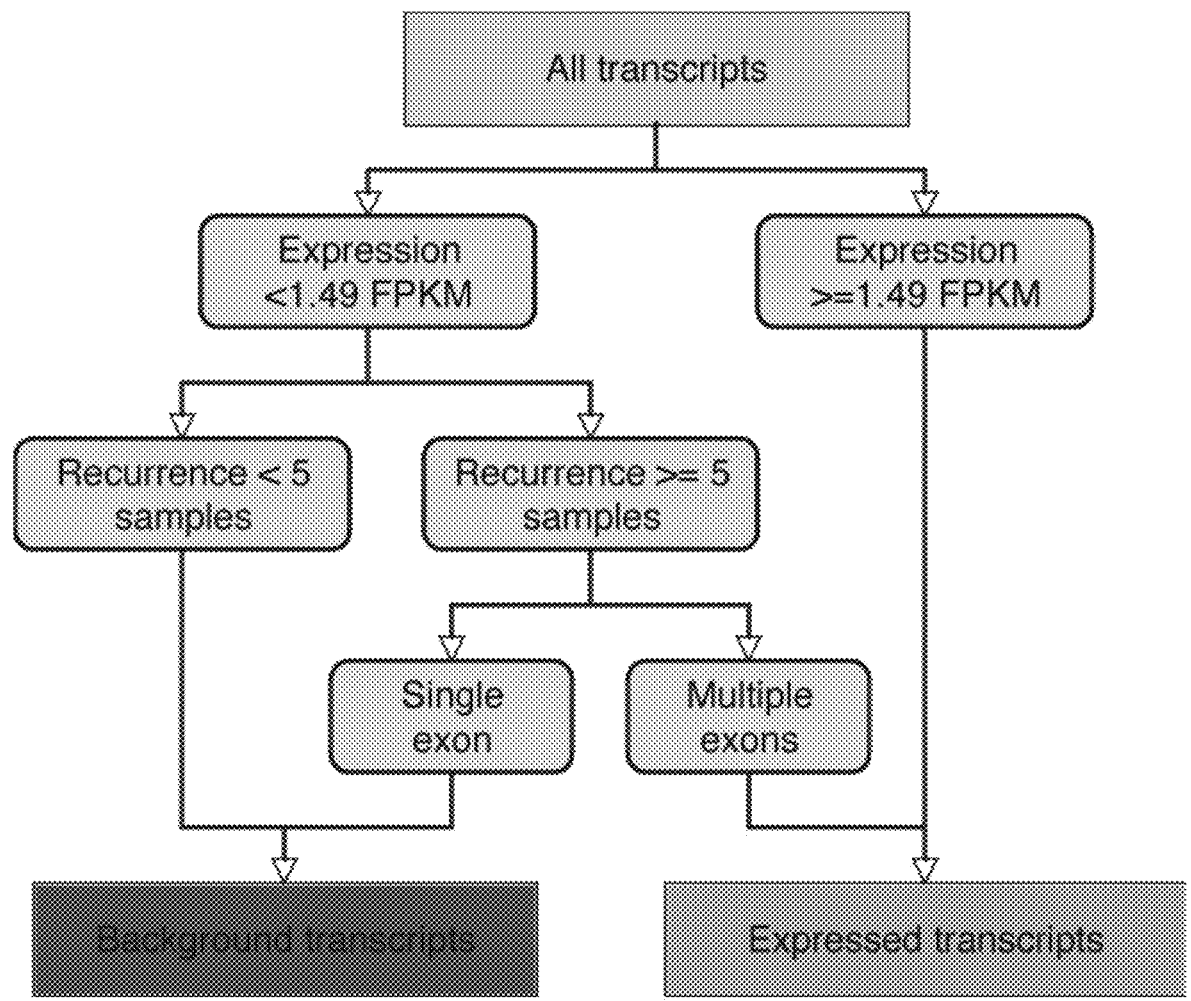
FIG. 7 shows classification tree results for Chromosome 1. The recursive regression and partitioning trees (mart) machine learning algorithm was used to predict expressed transcripts versus background signal.
Figures 9, 9A, 9B:
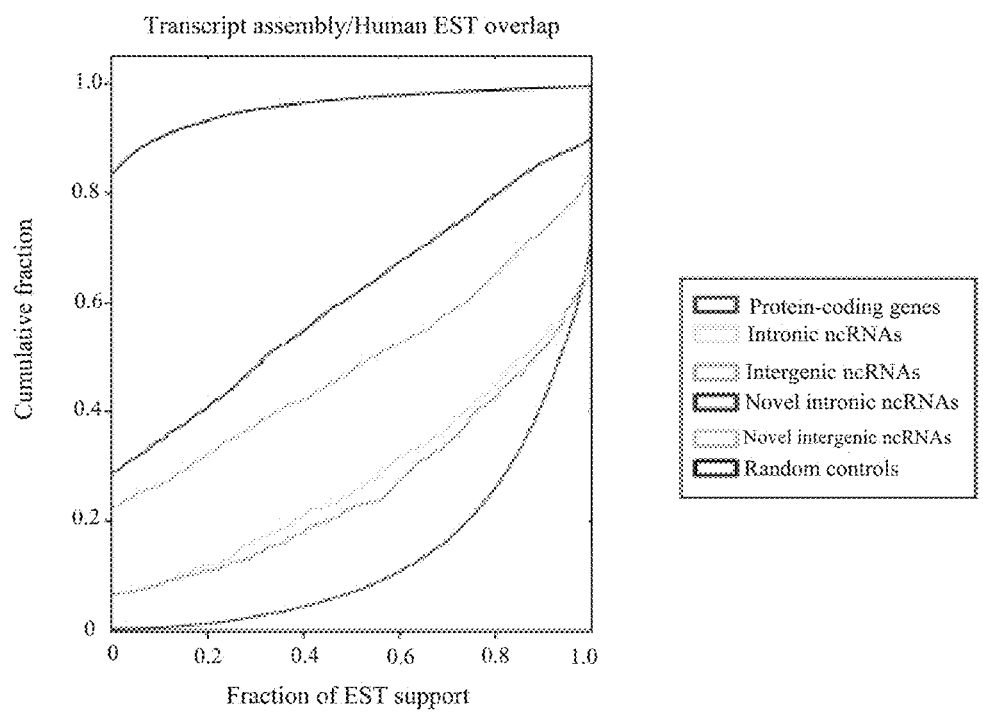
FIG. 9 shows analysis of EST support for exemplary transcripts. ESTs from the UCSC database table "Human ESTs" were used to evaluate the amount of overlap between ESTs and novel transcripts.
FIG. 9a. A line graph showing the fraction of genes whose transcripts are supported by a particular fraction of ESTs.
FIG. 9b. A table displaying the number of ESTs supporting each class of transcripts

Cuffcompare reported a total of 8.25 million distinct transcripts. Manual inspection of these transcripts in known protein coding gene regions indicated that most of the transcripts were likely to be poor quality reconstructions of overlapping larger transcripts. Also, many of the transcripts were unspliced and had a total length smaller than the size selected fragment length of approximately ~250 nt. Furthermore, many of these transcripts were only present in a single sample. A statistical classifier to predict transcripts over background signal was designed to identify highly recurrent transcripts that may be altered in prostate cancer. AceView (Thierry-Mieg et al. *Genome Biol* 7 Suppl 1, S12 1-14 (2006)) were used. For each transcript predicted by Cufflinks the following statistics were collected: length (bp), number of exons, recurrence (number of samples in which the transcript was predicted), 95th percentile of abundance (measured in Fragments per Kilobase per Million reads (FPKM)) across all samples, and uniqueness of genomic DNA harboring the transcript transcript (measured using the Rosetta uniqueness track from UCSC (Rhead et al. 2010. *Nucleic Acids Res* 38, D613-9). Using this information, recursive partitioning and regression trees in R (package rpart) were used to predict, for each transcript, whether its expression patterns and structural properties resembled those of annotated genes. Classification was performed independently for each chromosome in order to incorporate the effect of gene density variability on expression thresholds. Transcripts that were not classified as annotated genes were discarded, and the remainder were subjected to additional analysis and filtering steps. By examining the decision tree results it was observed that the 95th percentile of expression across all samples as well as the recurrence of each transcript were most frequently the best predictors of expressed versus background transcripts (FIG. 7).

Refinement of Transcript Fragments

The statistical classifier predicted a total 2.88 million (34.9%) transcript fragments as "expressed" transcripts. A program was developed to extend and merge intron-redundant transcripts to produce a minimum set of transcripts that describes the assemblies produced by Cufflinks. The merging step produced a total of 123,554 independent transcripts. Tanscript abundance levels were re-computed for these revised transcripts in Reads per Kilobase per Million (RPKM) units. These expression levels were used for the remainder of the study. Several additional filtering steps were used to isolate the most robust transcripts. First, transcripts with a total length less than 200 nt were discarded. Single exon transcripts with greater than 75% overlap to another longer transcript were also discarded. Transcripts that lacked a completely unambiguous genomic DNA stretch of at least 40 nt were also removed. Genomic uniqueness was measured using the Rosetta uniqueness track downloaded from the UCSC genome browser website. Transcripts that were not present in at least 5% of the cohort (>5 samples) at more than 5.0 RPKM were retained.

In certain instances transcripts were observed that were interrupted by poorly mappable genomic regions. Additionally, for low abundance genes fragmentation due to the lack of splice junction or paired-end read evidence needed to connect nearby fragments were observed. The difference in the Pearson correlation between expression of randomly chosen exons on the same transcript versus expression of spatially proximal exons on different transcripts was measured and it was found that in the cohort, a Pearson correlation>0.8 had a positive predictive value (PPV) of >95% for distinct exons to be part of the same transcript. Using this criteria, hierarchical agglomerative clustering to extend transcript fragments into larger transcriptional units was performed. Pairs of transcripts further than 100 kb apart, transcripts on opposite strands, and overlapping transcripts were not considered for clustering. Groups of correlated transcripts were merged, and introns<40 nt in length were removed.

Comparison with Gene Annotation Databases

The 44,534 transcripts produced by the bioinformatics pipeline were classified by comparison with a comprehensive list of "annotated" transcripts from UCSC, RefSeq, ENCODE, Vega, and Ensembl. First, transcripts corresponding to processed pseudogenes were separated. This was done to circumvent a known source of bias in the TopHat read aligner. TopHat maps reads to genomic DNA in its first step, predisposing exon-exon junction reads to align to their spliced retroposed pseudogene homologues. Next, transcripts with >1 bp of overlap with at least one annotated gene on the correct strand were designated "annotated", and the remainder were deemed "unannotated". Transcripts with no overlap with protein coding genes were subdivided into intronic, intergenic, or partially intronic antisense categories based on their relative genomic locations.

Informatics Filtering of Unspliced Pre-mRNA Isoforms

An increase in the percentage of intronic transcripts in the assembly relative to known intronic ncRNAs was observed. This led to the observation that in many cases unspliced pre mRNAs appear at sufficient levels to escape the filtering steps employed by Cufflinks during the assembly stage. Intronic and antisense transcripts that were correlated (Pearson correlation>0.5) to their overlapping protein coding genes were removed. This effectively removed transcripts within genes such as PCA3 and HPN that were obvious premRNA artifacts, while leaving truly novel intronic transcripts—such as those within FBXL7 and CDH13—intact. These steps produced a consensus set of 35,415 transcripts supporting long polyadenylated RNA molecules in human prostate tissues and cell lines. Per chromosome transcript counts closely mirrored known transcript databases (Table 2), indicating that the informatics procedures employed compensate well for gene density variability across chromosomes. Overall a similar number of transcripts as present in the either the RefSeq or UCSC databases (Wheeler et al. *Nucleic Acids Res* 28, 10-4 (2000)) were detected.

Coding Potential Analysis

Figure 10:
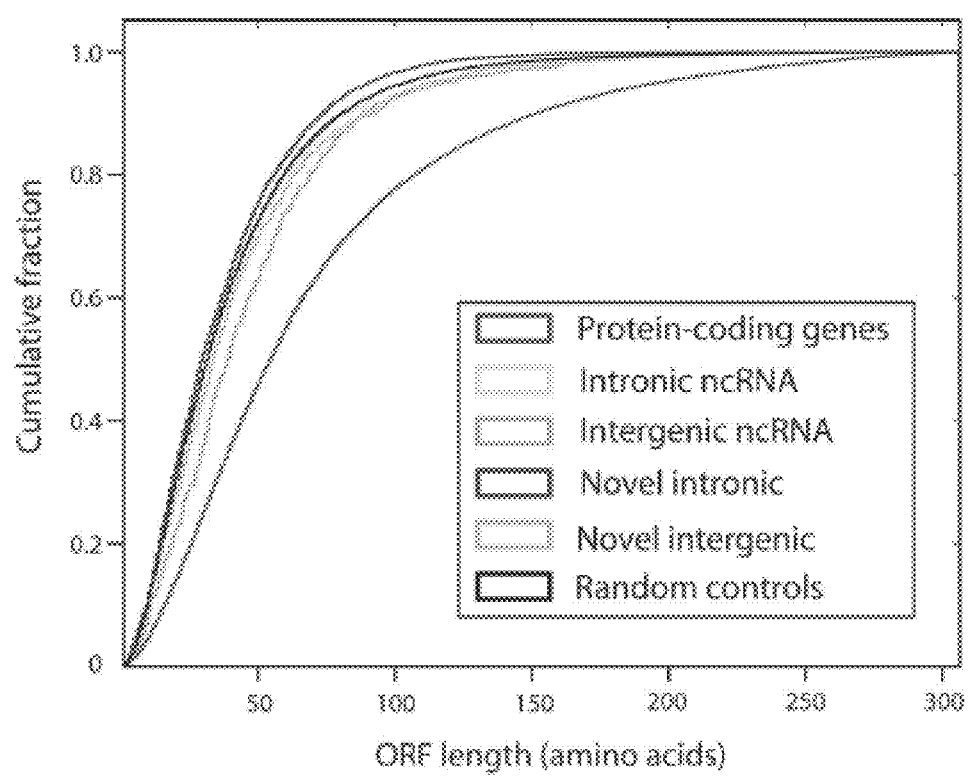
FIG. 10 shows analysis of coding potential of unannotated transcripts. DNA sequences for each transcript were extracted and searched for open reading frames (ORFs) using the txCdsPredict program from the UCSC source tool set.

To analyze coding potential, DNA sequences for each transcript were extracted and searched for open reading frames (ORFs) using the txCdsPredict program from the UCSC source tool set (Kent et al. *Genome Res* 12, 996-1006 (2002)). This program produces a score corresponding to the protein coding capacity of a given sequence, and scores>800 are ~90% predictive of protein coding genes. This threshold was used to count transcripts with coding potential, and found only 5 of 6,641 unannotated genes with scores>800, compared with 1,669 of 25,414 protein coding transcripts. Additionally, it was observed that protein coding genes possess consistently longer ORFs than either unannotated or annotated ncRNA transcripts, indicating that the vast majority of the unannotated transcripts represent ncRNAs (FIG. 10).

Separation of Transcripts into Repetitive and Non-Repetitive Categories

Figure 11:
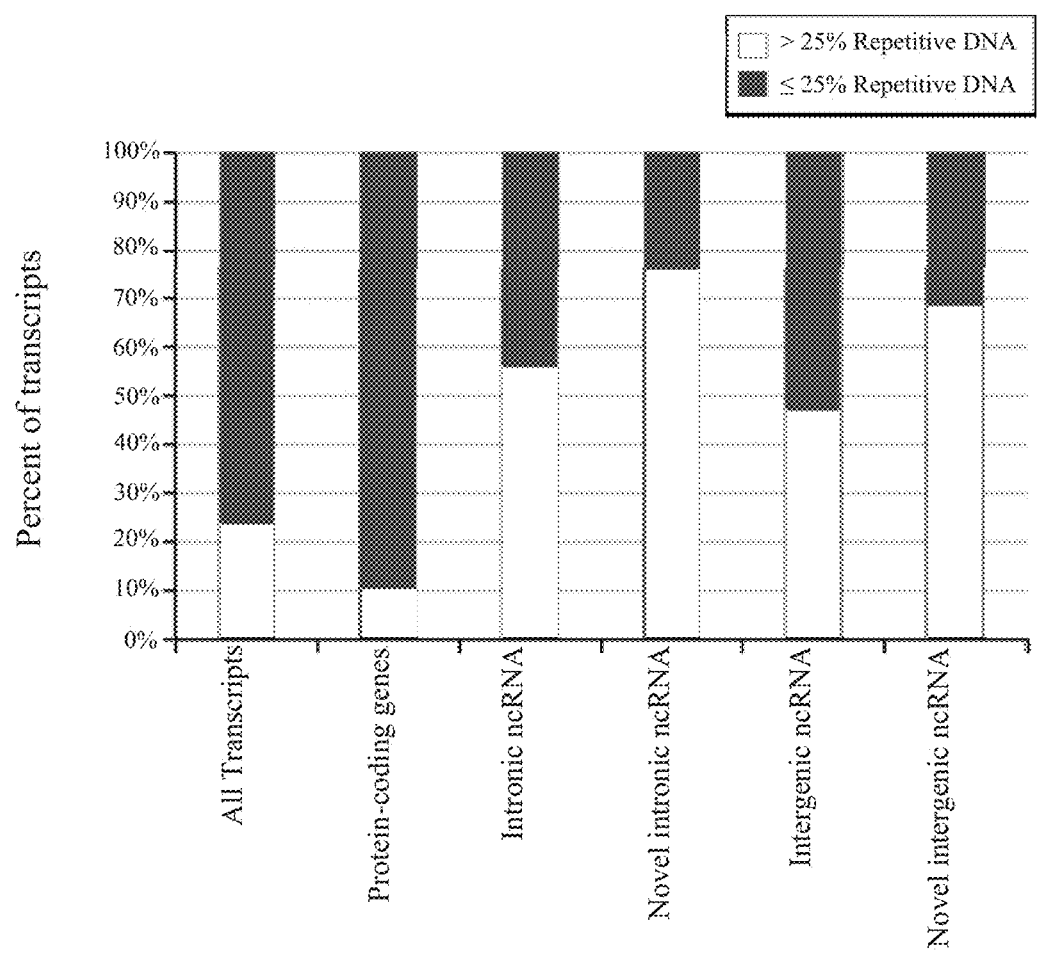
FIG. 11 shows repetitive content of novel transcripts. The percentage of repetitive sequences was assessed in all transcripts by calculating the percentage of repeatmasked nucleotides in each sequence.
Figure 12:
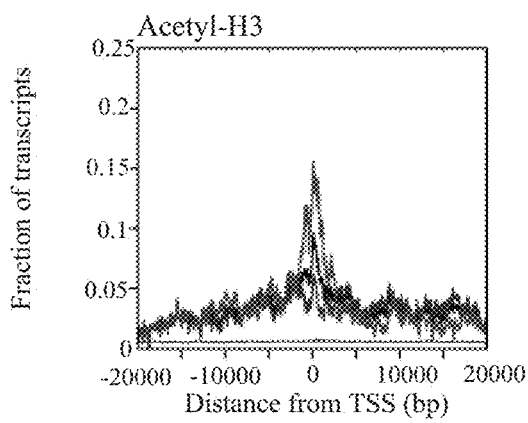
FIG. 12 shows distinct ChIP-Seq signatures for repeat-associated and nonrepeat novel ncRNAs. Unannotated transcripts were divided into two groups, repeat-associated and non-repeat, and intersected with ChIP-Seq data for Acetyl-H3 and H3K4me3, two histone modifications strongly associated with transcriptional start sites (TSS), in two prostate cancer cell lines.
Figure 12A:
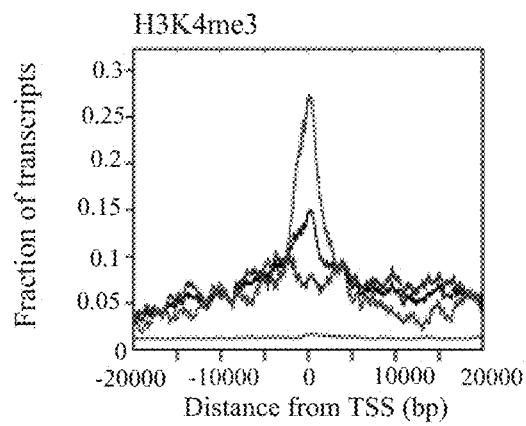
FIG. 12a. Acetyl-H3 in LNCaP cells.
Figure 12B:
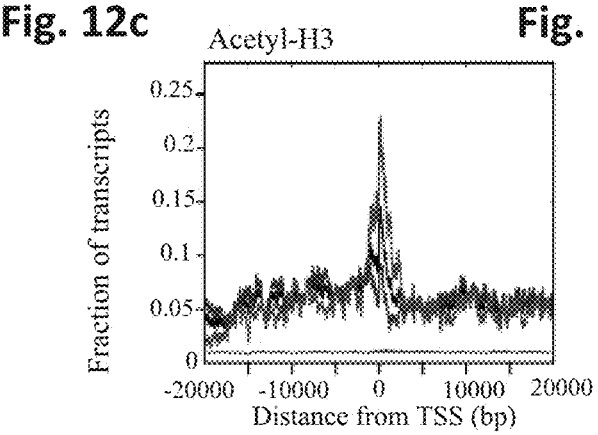
FIG. 12b. H3K4me3 in LNCaP cells.
Figure 12C:
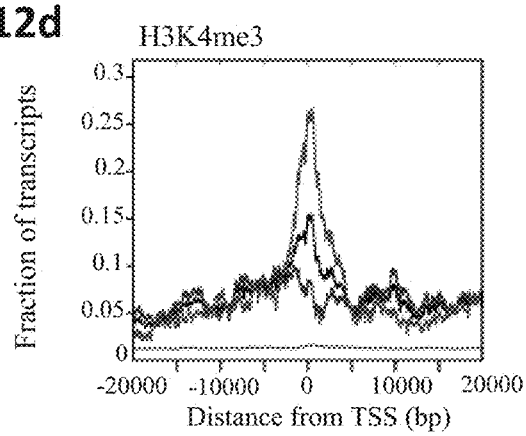
FIG. 12c. Acetyl-H3 in VCaP cells.
Figure 12D:
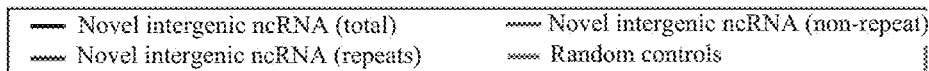
FIG. 12d. H3K4me3 in VCaP cells.

To separate transcripts into "repeat" and "non-repeat" transcripts, the genomic DNA corresponding to the transcript exons was extracted and the fraction of repeat-masked nucleotides in each sequence were calculated. For the designation of repeat classes, RepMask 3.2.7 UCSC Genome Browser track (Kent, supra) was used. It was observed that transcripts enriched with repetitive DNA tended to be poorly conserved and lacked ChIP-seq marks of active chromatin (FIG. 12). Transcripts containing >25% repetitive DNA (FIG. 11) were separated for the purposes of the ChIP-seq and conservation analyses discussed below.

Conservation Analysis

The SiPhy package (Garber et al. *Bioinformatics* 25, i54-62 (2009)) was used to estimate the locate rate of variation ($\omega$) of all non-repetitive transcript exons across 29 placental mammals. The program was run as described on the SiPhy website.

ChIP-Seq Datasets

Published ChIP-Seq datasets for H3K4me1, H3K4me2, H3K4me3, Acetylated H3, Pan-H3, and H3K36me3 were used (Yu et al. *Cancer Cell* 17, 443-54). These data are publically available through the NCBI Geo Omnibus (GEO GSM353632). The raw ChIP-Seq data was analyzed using MACS34 (H3K4me1, H3K4me2, H3K4me3, Acetylated H3, and Pan-H3) or SICER35 (H3K36me3) peak finder programs using default settings. These peak finders were used based upon their preferential suitability to detect different types of histone modifications (Pepke et al., *Nat Methods* 6, S22-32 (2009)). The H3K4me3-H3K36me3 chromatin signature used to identify lincRNAs was determined from the peak coordinates by associating each H3K4me3 peak with the closest H3K36me3-enriched region up to a maximum of 10 kb away. The enhancer signature (H3K4me1 but not H3K4me3) was determined by subtracting the set of overlapping H3K4me3 peaks from the entire set of H3K4me1 peaks. These analyses were performed with the bx-python libraries distributed as part of the Galaxy bioinformatics infrastructure.

Differential Expression Analysis

To predict differentially expressed transcripts a matrix of log-transformed, normalized RPKM expression values was prepared by using the base 2 logarithm after adding 0.1 to all RPKM values. The data were first centered by subtracting the median expression of the benign samples for each transcript. The Significance Analysis of Microarrays (SAM) method (Tusher et al., *Proc Natl Acad Sci USA* 98, 5116-21 (2001)) with 250 permutations of the Tusher et al. S0 selection method was used to predict differentially expressed genes. A delta value corresponding to the 90th percentile FDR desired for individual analyses was used. The Multi-Experiment Viewer application (Chu et al., *Genome Biol* 9, R118 (2008)) was used to run SAM and generate heatmaps. It was confirmed that the results matched expected results through comparison with microarrays and known prostate cancer biomarkers.

Outlier Analysis

A modified COPA analysis was performed on the 81 tissue samples in the cohort. RPKM expression values were used and shifted by 1.0 in order to avoid division by zero. The COPA analysis had the following steps (MacDonald & Ghosh, *Bioinformatics* 22, 2950-1 (2006); Tomlins et al. *Science* 310, 644-8 (2005)): 1) gene expression values were median centered, using the median expression value for the gene across the all samples in the cohort. This sets the gene's median to zero. 2) The median absolute deviation (MAD) was calculated for each gene, and then each gene expression value was scaled by its MAD. 3) The 80, 85, 90, 98 percentiles of the transformed expression values were calculated for each gene and the average of those four values was taken. Then, genes were rank ordered according to this "average percentile", which generated a list of outliers genes arranged by importance. 4) Finally, genes showing an outlier profile in the benign samples were discarded. Six novel transcripts ranked as both outliers and differentially-expressed genes in the analyses. These six were manually classified either as differentially-expressed or outlier status based on what each individual's distribution across samples indicated.

Repeat Enrichment Analysis

To assess the enrichment of repetitive elements in the assembly, 100 random permutations of the transcript positions on the same chromosome and strand were generated. To mirror the original constraints used to nominate transcripts it was ensured that permuted transcript positions contained a uniquely mappable stretch of genomic DNA at least 50 nt long. To account for the effects of mappability difficulties, each exon was padded by ±0 bp, 50 bp, 100 bp, or 500 bp of additional genomic sequence before intersecting the exons with repeat elements in the RepeatMasker 3.2.7 database. It was observed that padding by more than 50 bp did not improve enrichment results and padded exons by ±50 bp in subsequent analyses and tests. Finally, the Shapiro-Wilk test for normality was performed and it was verified that the number of matches to highly abundant repetitive element types was approximately normally distributed.

B. Results

Prostate Cancer Transcriptome Sequencing

Transcriptome sequencing (RNA-Seq) was performed on 21 prostate cell lines, 20 benign adjacent prostates (benign), 47 localized tumors (PCA), and 14 metastatic tumors (MET). A total of 201 RNA-Seq libraries from this cohort were sequenced yielding a total of 1.41 billion mapped reads, with a median 4.70 million mapped reads per sample (Table 1 for sample information).

To analyze these data a method for ab initio transcriptome assembly to reconstruct transcripts and transcript abundance levels was used (FIG. 6 and Table 2) (Trapnell et al., NatBiotechnol 28 (5), 511; Trapnell et al., Bioinformatics 25 (9), 1105 (2009)). Sample-specific transcriptomes were predicted and individual predication were merged into a consensus transcriptome and the most robust transcripts were retained (FIG. 7). The ab initio transcriptome assembly and subsequent refinement steps yielded 35,415 distinct transcriptional loci (see FIG. 8 for examples).

The assembled transcriptome was compared to the UCSC, Ensembl, Refseq, Vega, and ENCODE gene databases to identify and categorize transcripts. While the majority of the transcripts (77.3%) corresponded to annotated protein coding genes (72.1%) and noncoding RNAs (5.2%), a significant percentage (19.8%) lacked any overlap and were designated "unannotated" (FIG. 1a). These included partially intronic antisense (2.44%), totally intronic (12.1%), and intergenic transcripts (5.25%). These results agree with previous data indicating that large fractions of the transcriptome represent unannotated transcription (Birney et al., Nature 447 (7146), 799 (2007); Carninci et al., Science 309 (5740), 1559 (2005) and that significant percentages of genes may harbor related antisense transcripts (He et al., Science 322 (5909), 1855 (2008); Yelin et al., Nat Biotechnol 21(4), 379 (2003)). Due to the added complexity of characterizing antisense or partially intronic transcripts without strand-specific RNA-Seq libraries, studies focused on totally intronic and intergenic transcripts.

Characterization of Novel Transcripts

Global characterization of novel transcripts corroborated previous reports that they are relatively poorly conserved and more lowly expressed than protein coding genes (Guttman et al., Nat Biotechnol 28 (5), 503; Guttman et al., Nature 458 (7235), 223 (2009)). Expression levels of unannotated prostate cancer transcripts were consistently higher than randomly permuted controls, but lower than annotated ncRNAs or protein coding genes (FIG. 1b). Unannotated transcripts also showed less overlap with known expressed sequence tags (ESTs) than protein-coding genes but more than randomly permuted controls (FIG. 5). Unannotated transcripts showed a clear but subtle increase in conservation over control genomic intervals (novel intergenic transcripts $p=2.7\times10-4\pm0.0002$ for $0.4<\omega<0.8$; novel intronic transcripts $p=2.6\times10-5\pm0.0017$ for $0<\omega<0.4$, FIG. 1c). Only a small subset of novel intronic transcripts showed increased conservation (FIG. 1c insert), but this conservation was quite profound. By contrast, a larger number of novel intergenic transcripts showed more mild increases in conservation. Finally, analysis of coding potential revealed that only 5 of 6,144 transcripts harbored a high quality open reading frame (ORF), indicating that the overwhelming majority of these transcripts represent ncRNAs (FIG. 10).

Next, published prostate cancer ChIP-Seq data for two prostate cell lines (Yu et al., Cancer Cell 17 (5), 443; VCaP and LNCaP was used in order to interrogate the overlap of unannotated transcripts with histone modifications supporting active transcription (H3K4me1, H3K4me2, H3K4me3, H3K36me3, Acetyl-H3 and RNA polymerase II, see Table 3). Because unannotated ncRNAs showed two clear subtypes, repeat-associated and non-repeats (FIG. 11 and discussed below), it was contemplated that these two subtypes may display distinct histone modifications as noted in previous research (Day et al., Genome Biol 11 (6), R69). Whereas non-repeat transcripts showed strong enrichment for histone marks of active transcription at their putative transcriptional start sites (TSSs), repeat-associated transcripts showed virtually no enrichment (FIG. 12), and for the remaining ChIP-Seq analyses non-repeat transcripts only were considered. In this set of unannotated transcripts, strong enrichment for histone modifications characterizing TSSs and active transcription, including H3K4me2, H3K4me3, Acetyl-H3 and RNA Polymerase II (FIG. 1d-g) but not H3K4me1 was observed, which characterizes enhancer regions (FIGS. 13 and 14). Intergenic ncRNAs performed much better in these analyses than intronic ncRNAs (FIG. 1d-g). To elucidate global changes in transcript abundance between prostate cancer and benign tissues, differential expression was performed analysis for all transcripts. 836 genes differentially-expressed between benign and PCA samples (FDR<0.01) were found, with protein-coding genes constituting 82.8% of all differentially-expressed genes (FIG. 1h and Table 4). This category contained the most significant transcripts, including numerous known prostate cancer genes such as AMACR32 and Hepsin (Dhanasekaran et al., Nature 412 (6849), 822 (2001)). Annotated ncRNAs represented 7.4% of differentially-expressed genes, including the ncRNA PCA334, which resides within an intron of the PRUNE2 gene and ranked #4 overall (12.2 fold change; adj. $p<2\times10-4$, Wilcoxon rank sum test, Benjamini-Hochberg correction) (FIG. 8). Finally, 9.8% of differentially-expressed genes corresponded to unannotated ncRNAs, including 3.2% within gene introns and 6.6% in intergenic regions, indicating that these species contribute significantly to the complexity of the prostate cancer transcriptome.

Dysregulation of Unannotated Non-Coding RNAs

Figures 2, 2C, 2D:
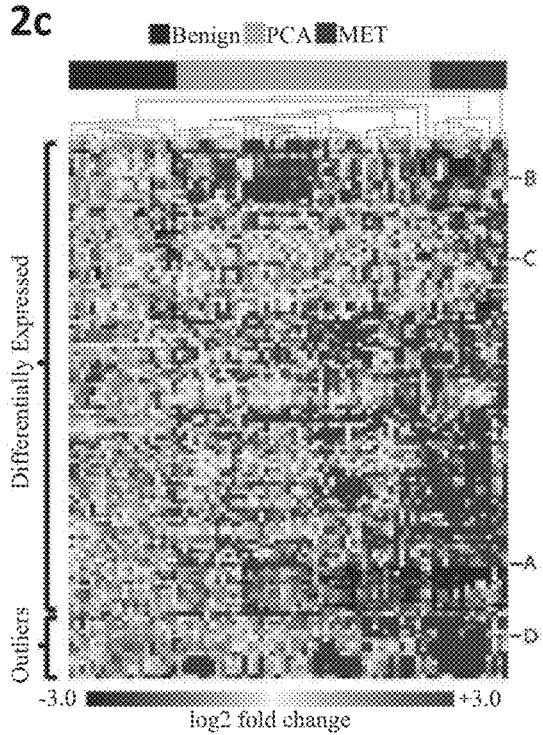
FIG. 2 shows that unannotated intergenic transcripts differentiate prostate cancer and benign prostate samples.
FIG. 2c. A heatmap of differentially expressed or outlier unannotated intergenic transcripts clusters benign samples, localized tumors, and metastatic cancers by unsupervised clustering analyses.
FIG. 2d. Cancer outlier profile analysis (COPA) outlier analysis for the prostate cancer transcriptome reveals known outliers (SPINK1, ERG, and ETV1), as well as numerous unannotated transcripts.
Figure 15:
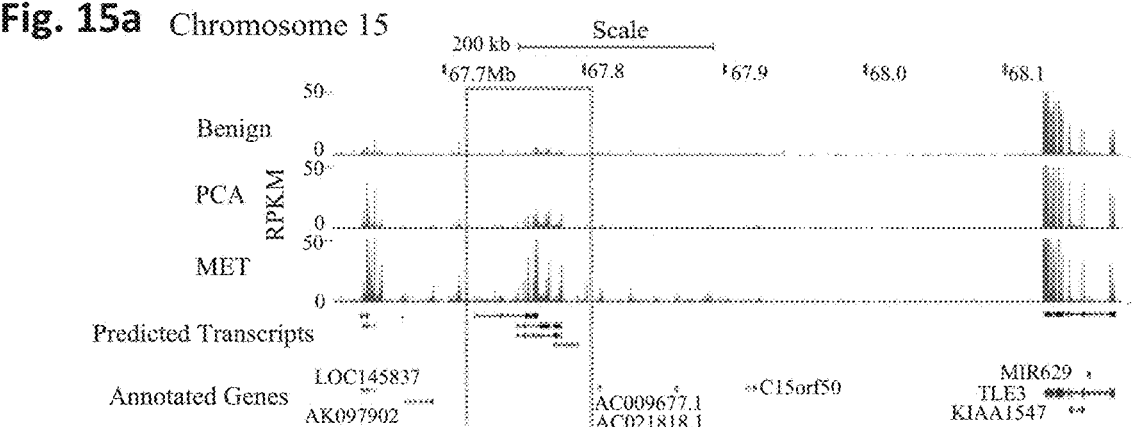
FIG. 15 shows validation of a novel transcript on chromosome 15.
Figure 15B:
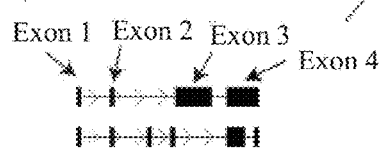
FIG. 15b. Several predicted isoforms of this transcript were nominated which retained common exons 1 and 2.
Figure 15C:
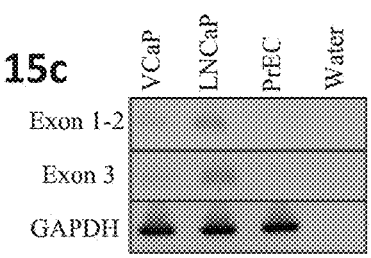
FIG. 15c. The exon-exon boundary between exons 1 and 2, as well as an internal portion of exon 3, was validated by RT-PCR in prostate cell line models.
Figure 15D:
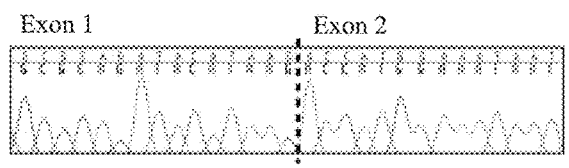
FIG. 15d. Sanger sequencing of the RT-PCR product confirmed the junction of exon 1 and exon 2.

Recent reports of functional long intervening non-coding RNAs (Dhanasekaran et al., Nature 412 (6849), 822 (2001); Gupta et al., Nature 464 (7291), 1071; Rinn et al., Cell 129 (7), 1311 (2007); Guttman et al., Nature 458 (7235), 223 (2009)) (lincRNAs) in intergenic regions led to an exploration of intergenic ncRNAs further. A total of 1859 unannotated intergenic RNAs were found throughout the human genome. The present invention is not limited to a particular mechanism. Indeed, an understanding of the mechanism is not necessary to practice the present invention. Nonetheless it is contemplated that this is an underestimate due to the inability to detect small RNAs eliminated by the ~250 bp size selection performed during RNA-Seq library generation (Methods). Overall, novel intergenic RNAs resided closer to protein-coding genes than protein-coding genes do to each other (the median distance to the nearest protein-coding gene is 4292 kb for novel genes and 8559 kb for protein-coding genes, FIG. 2a). For instance, if two protein-coding genes, Gene A and Gene B, are separated by the distance AB, then the furthest an unannotated ncRNA can be from both of them is 0.5*AB, which is exactly what was observed (4292/8559=0.501). Supporting this observation, 34.1% of unannotated transcripts are located ≥10 kb from the nearest protein-coding gene. As an example, the Chr15q arm was visualized using the Circos program. Eighty-nine novel intergenic transcripts were nominated across this chromosomal region, including several differentially-expressed loci centromeric to TLE3 (FIG. 2b) which were validated by PCR in prostate cancer cell lines (FIG. 15). A focused analysis of the 1859 novel intergenic RNAs yielded 106 that were differentially expressed in localized tumors (FDR<0.05; FIG. 2c). These Prostate Cancer Associated Transcripts (PCATs) were ranked according to their fold change in localized tumor versus benign tissue (Tables 5 and 6).

Figure 16:
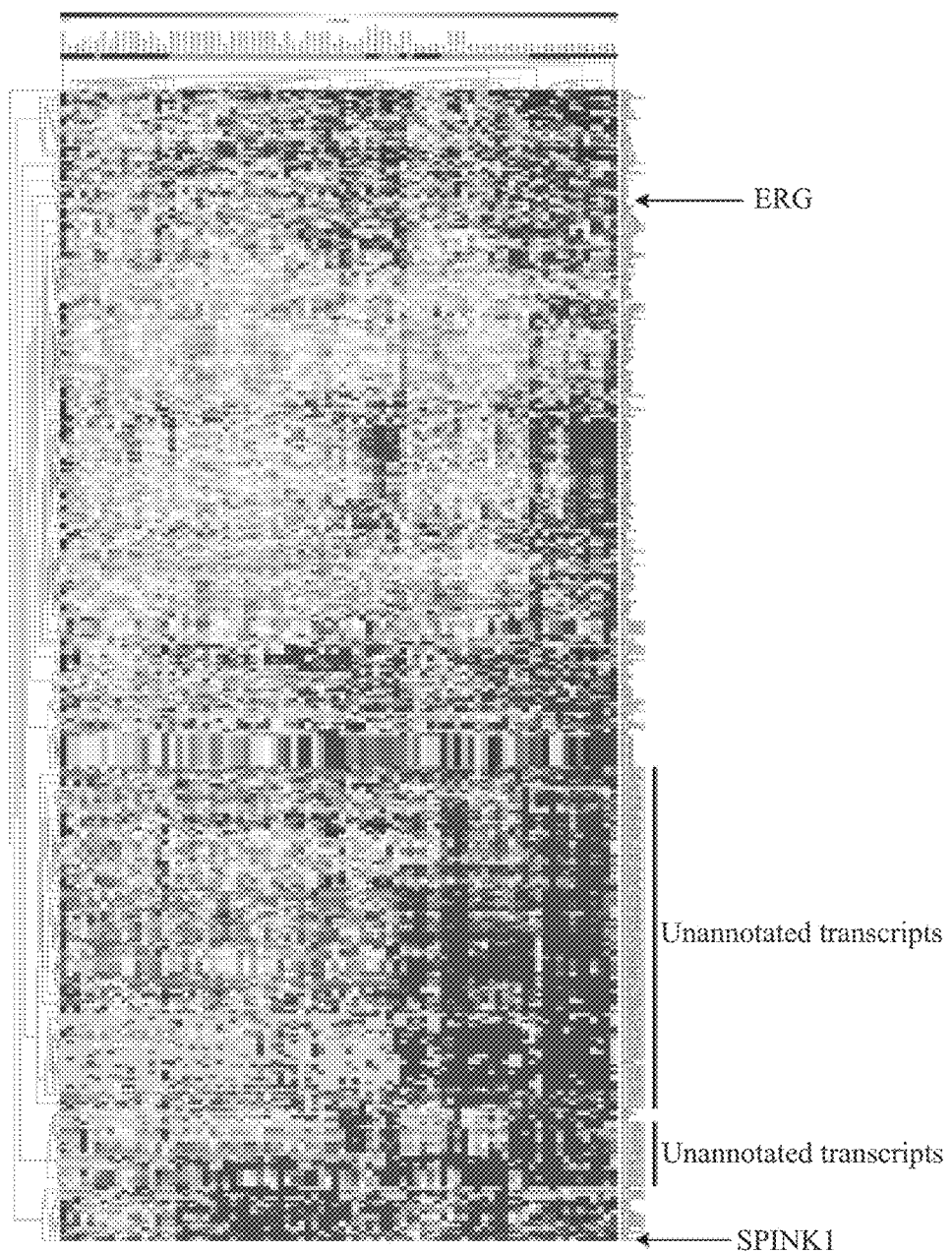
FIG. 16 shows clustering of prostate cancer with outliers. Transcripts with outlier profile scores in the top 10% were clustered using hierarchical trees.

Similarly, performing a modified cancer outlier profile analysis (COPA) on the RNA-Seq dataset re-discovered numerous known prostate cancer outliers, such as ERG7, ETV17, SPINK135, and CRISP336,37, and nominated numerous unannotated ncRNAs as outliers (FIG. 2d and Tables 6 and 7). Merging the results from the differential expression and COPA analyses resulted in a set of 121 unannotated transcripts that accurately discriminated benign, localized tumor, and metastatic prostate samples by unsupervised clustering (FIG. 2c). These data provide evidence that PCATs serve as biomarkers for prostate cancer and novel prostate cancer subtypes. Clustering analyses using novel ncRNA outliers also provide disease subtypes (FIG. 16).

Confirmation and Tissue-Specificity of ncRNAs

Figures 17, 17A:
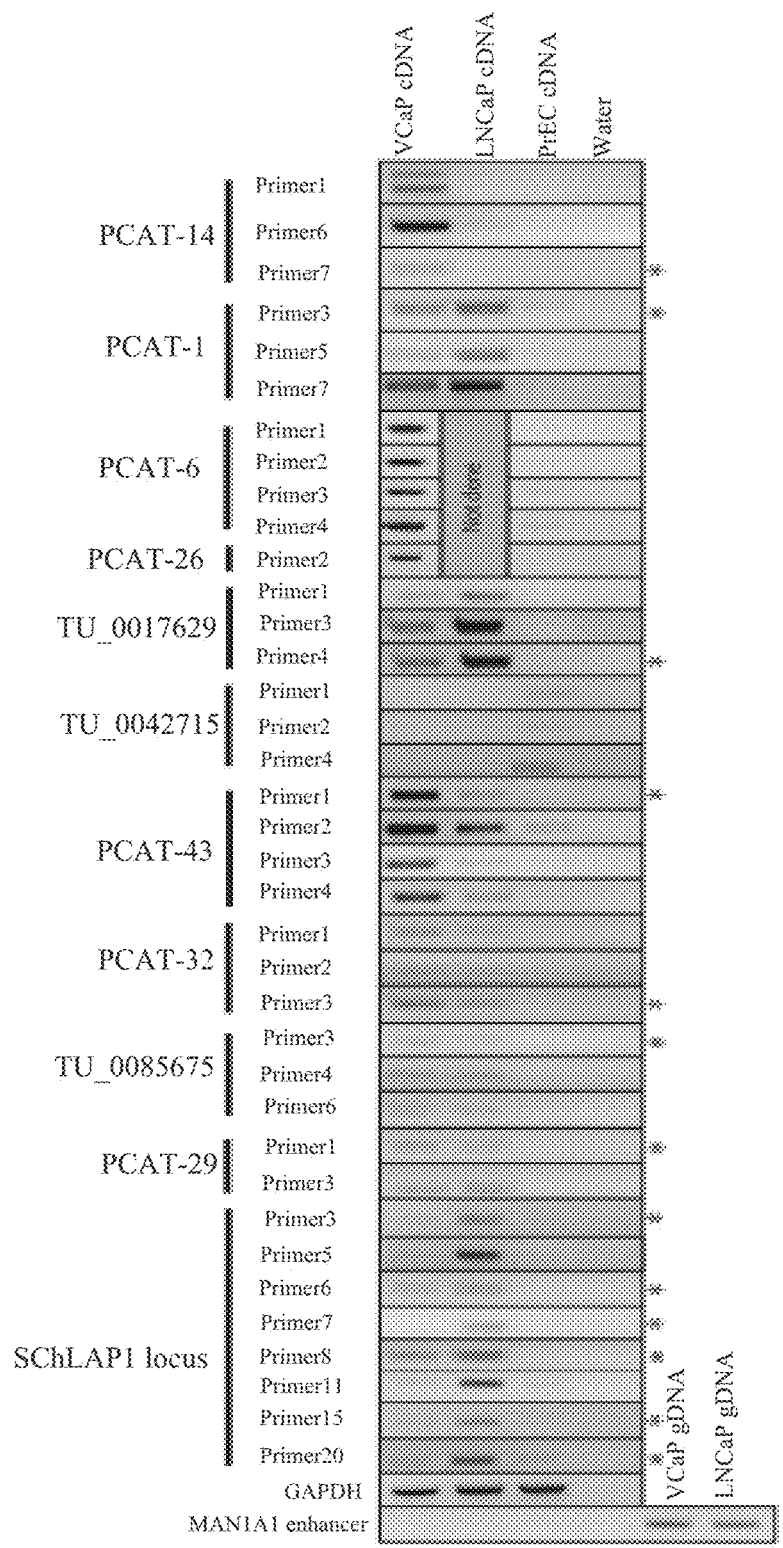
FIG. 17 shows validation of novel transcripts in prostate cell lines. 11/14 unannotated transcripts selected for validation by RT-PCR and qPCR were confirmed in cell line models.
FIG. 17a. RT-PCR gels showing expected bands for the 11 transcripts that validated.
Figures 17, 17B:
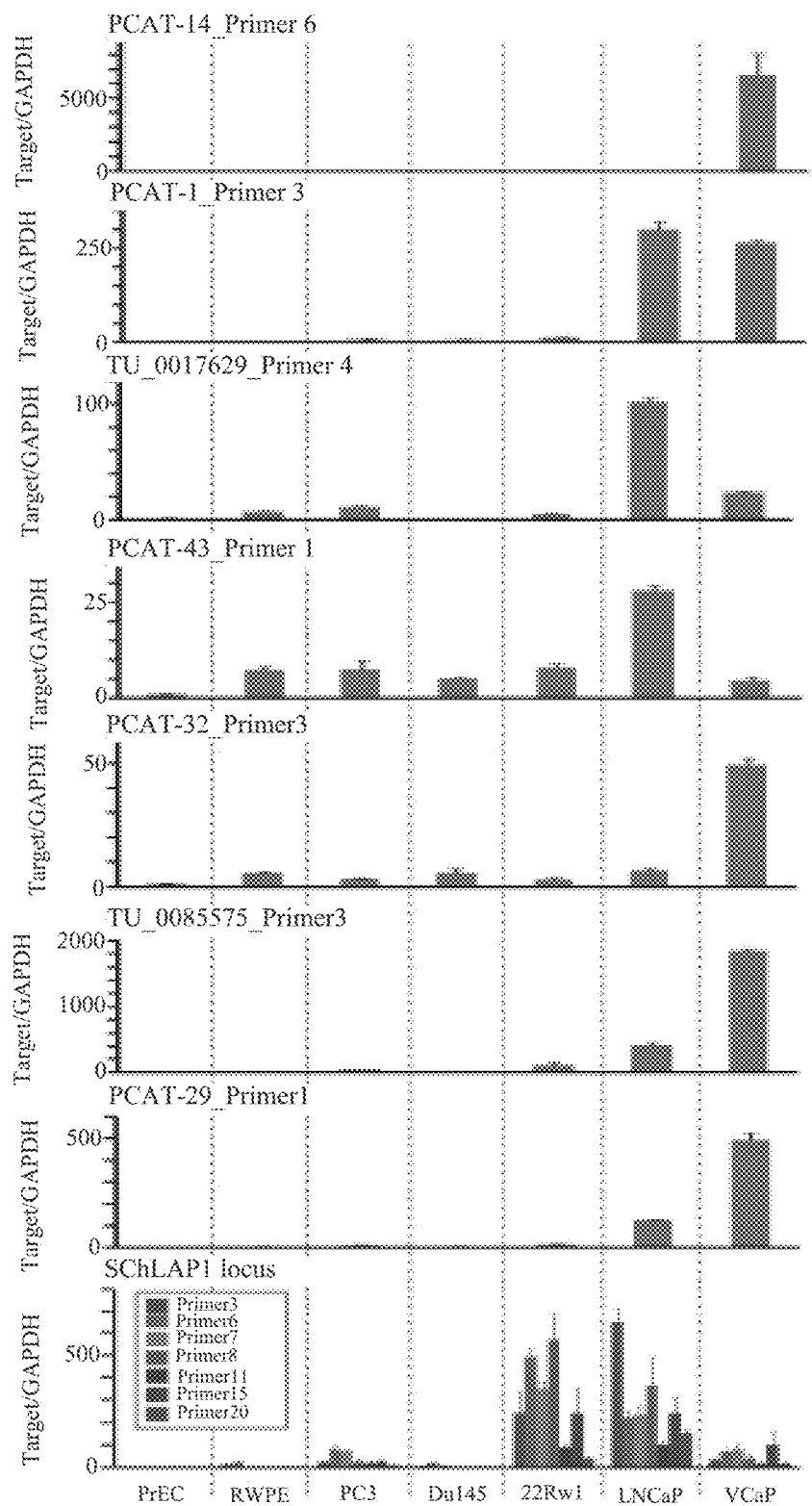
Figure 18:
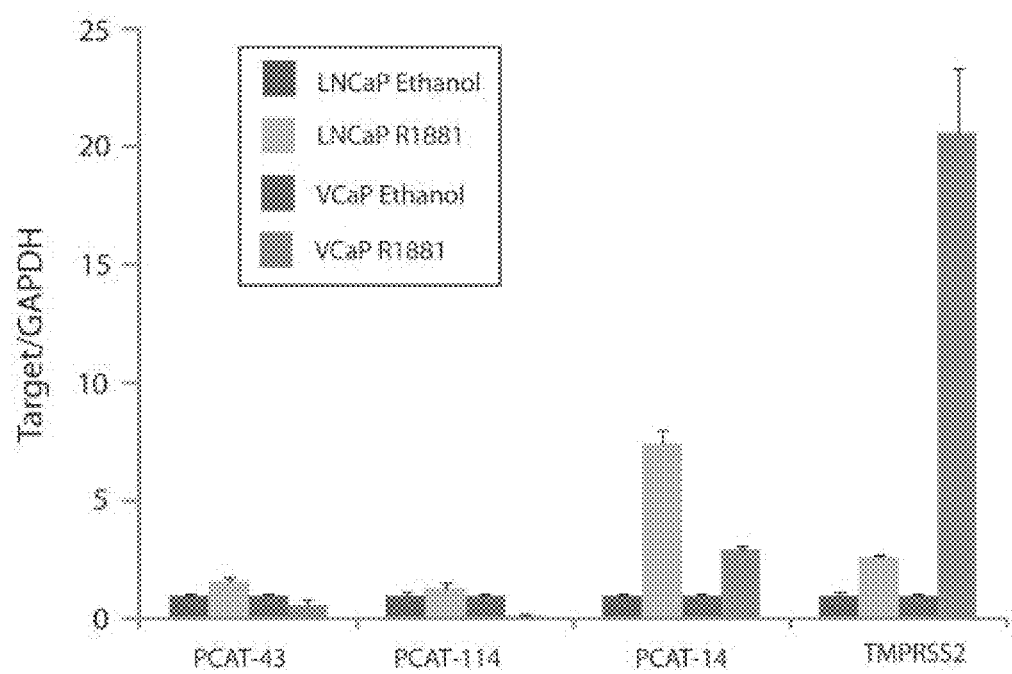
FIG. 18 shows that PCAT-14 is upregulated by androgen signaling. VCaP and LNCaP cells were treated 5 nM R1881 or vehicle (ethanol) control.
Figure 19:
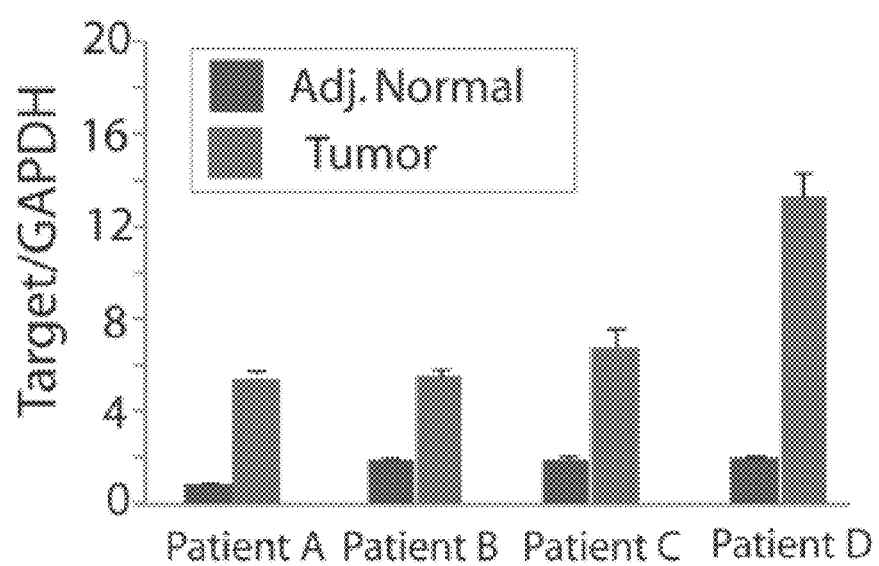
FIG. 19 shows that PCAT-14 is upregulated in matched tumor tissues. Four matched tumor-normal patient tissue samples were assayed for PCAT-14 expression by qPCR.
Figure 21:
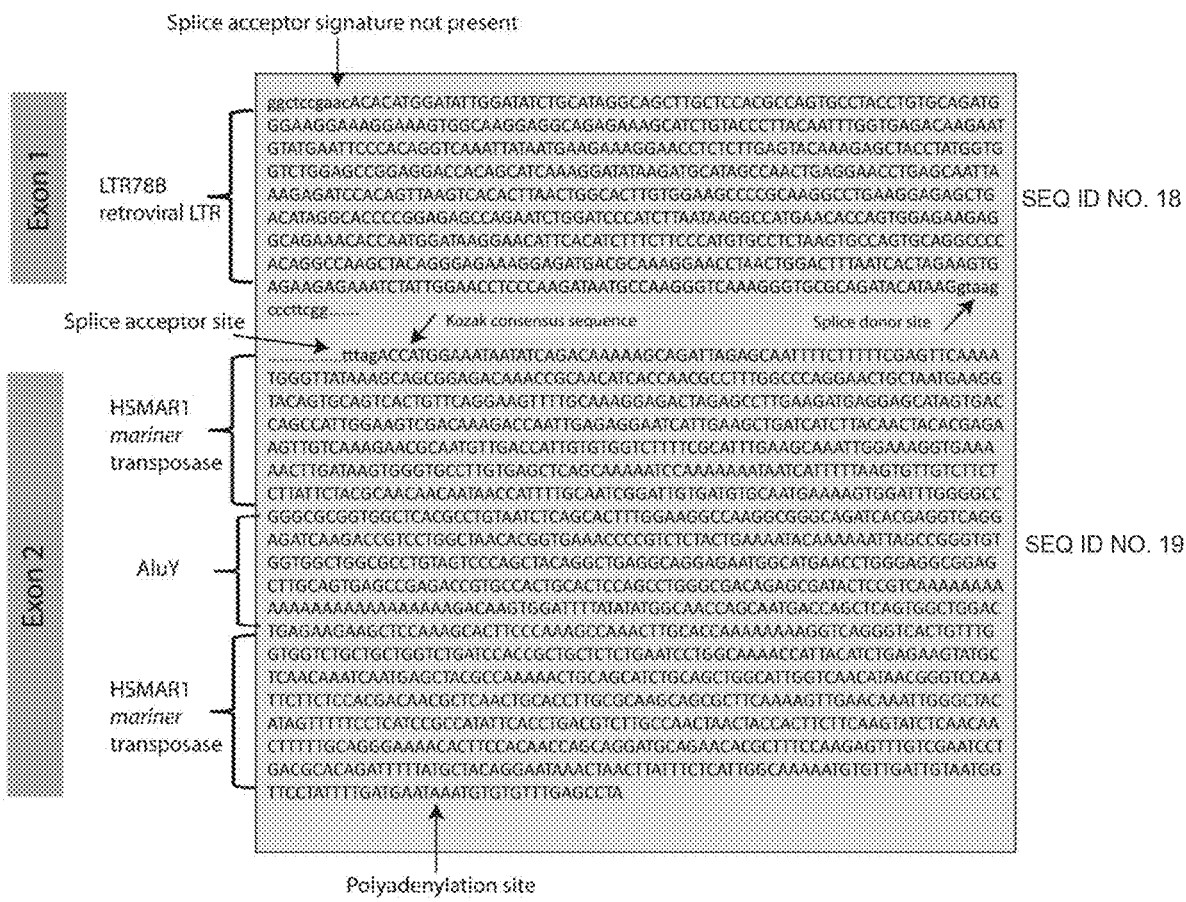
FIG. 21 shows analysis of PCAT-1 transcript structure. 5' and 3' RACE experiments showed a ncRNA transcript containing two exons.

Validation studies were performed on 14 unannotated expressed regions, including ones both included and not present in the list of differentially expressed transcripts. Reverse transcription PCR (RT-PCR) and quantitative real-time PCR (qPCR) experiments demonstrated a ~78% (11/14) validation rate in predicted cell line models for both transcript identity and expression level (FIG. 17). Next, three transcripts (PCAT-109, PCAT-14, and PCAT-43) selectively upregulated in prostate cancer compared to normal prostate were examined. From the sequencing data, each genomic loci shows significantly increased expression in prostate cancer and metastases, except for PCAT-14, which appears absent in metastases (FIG. 3a-c). PCAT-109 also ranks as the #5 best outlier in prostate cancer, just ahead of ERG (FIG. 2d and Table 6). qPCR on a cohort of 14 benign prostates, 47 tumors, and 10 metastases confirmed expression of these transcripts (FIG. 3a-c). All three appear to be prostate-specific, with no expression seen in breast or lung cancer cell lines or in 19 normal tissue types (Table 8). This tissue specificity was not necessarily due to regulation by androgen signaling, as only PCAT-14 expression was induced by treatment of androgen responsive VCaP and LNCaP cells with the synthetic androgen R1881, consistent with previous data from this genomic locus (FIG. 18) (Tomlins et al., Nature 448 (7153), 595 (2007); Stavenhagen et al., Cell 55 (2), 247 (1988)). PCAT-14, but not PCAT-109 or PCAT-43, also showed differential expression when tested on a panel of matched tumor-normal samples, indicating that this transcript, which is comprised of an endogenous retrovirus in the HERV-K family (Bannert and Kurth, Proc Natl Acad Sci USA 101 Suppl 2, 14572 (2004)), can be used as a somatic marker for prostate cancer (FIG. 19). 5' and 3' rapid amplification of cDNA ends (RACE) at this locus revealed the presence of individual viral protein open reading frames (ORFs) and a transcript splicing together individual ORF 5' untranslated region (UTR) sequences (FIG. 20). It was observed that the top-ranked intergenic ncRNA resided in the chromosome 8q24 gene desert nearby to the c-Myc oncogene. This ncRNA, termed PCAT-1, is located on the edge of the prostate cancer susceptibility region 240-43 (FIG. 4a) and is about 0.5 Mb away from c-Myc. This transcript is supported by clear peaks in H3K4me3, Acetyl-H3, and RNA polymerase II ChIP-Seq data (FIG. 4b). The exon-exon junction in cell lines was validated by RT-PCR and Sanger sequencing of the junction (FIG. 4c), and 5' and 3' RACE was performed to elucidate transcript structure (FIG. 4d). By this analysis, PCAT-1 is a mariner family transposase (Oosumi et al., Nature 378 (6558), 672 (1995); Robertson et al., Nat Genet 12 (4), 360 (1996)) interrupted by an Alu retrotransposon and regulated by a viral long terminal repeat (LTR) promoter region (FIG. 4d and FIG. 21). By qPCR, PCAT-1 expression is specific to prostate tissue, with striking upregulation in prostate cancers and metastases compared to benign prostate tissue (FIG. 4e). PCAT-1 ranks as the second best overall prostate cancer biomarker, just behind AMACR (Table 3), indicating that this transcript is a powerful discriminator of this disease. Matched tumor normal pairs similarly showed marked upregulation in the matched tumor samples (FIG. 4f). RNA interference (RNAi) was performed in VCaP cells using custom siRNAs targeting PCAT-1 sequences and no change in the cell proliferation or invasion upon PCAT-1 knock-down was observed (FIG. 22)

Selective Re-Expression of Repetitive Elements in Cancer

Figure 25:
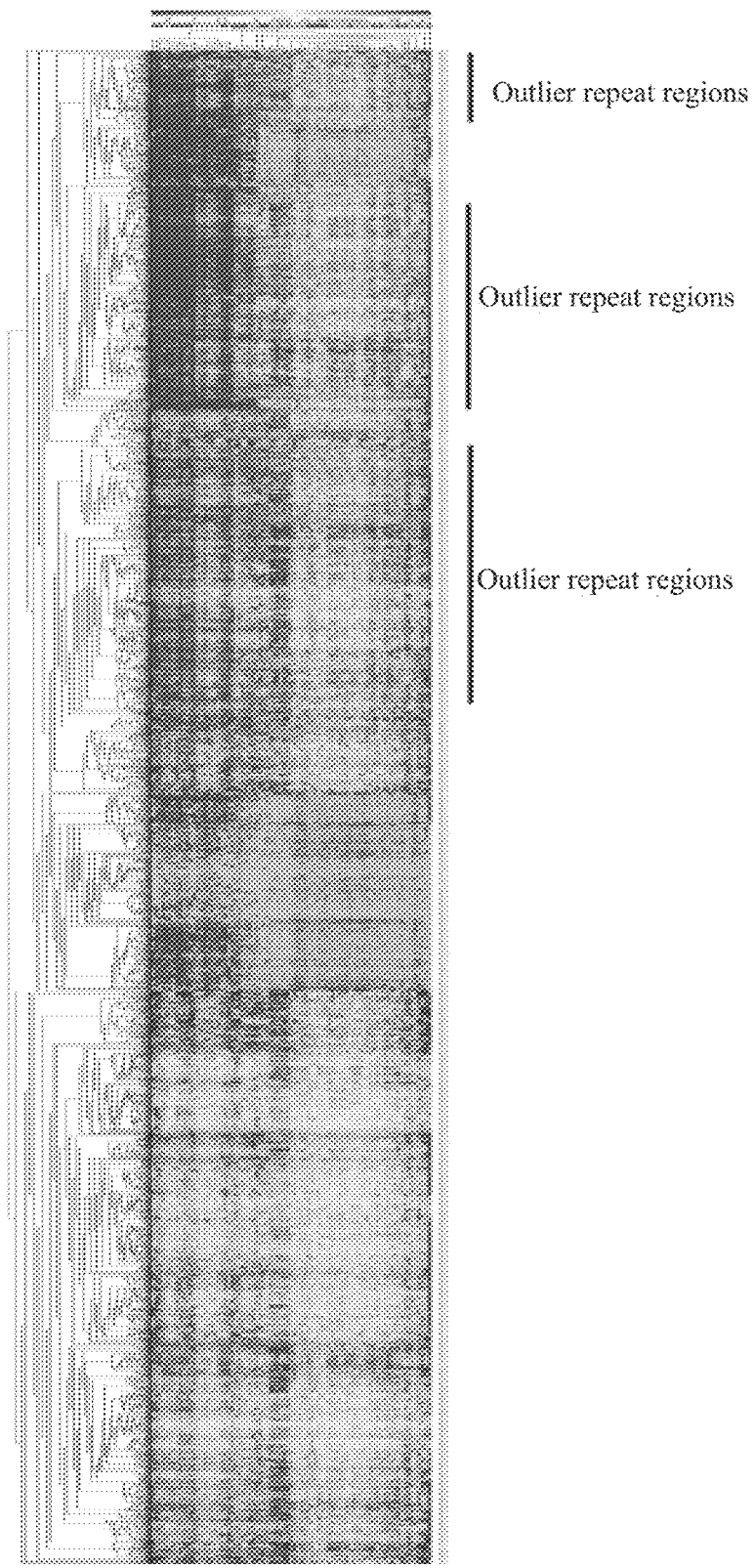
FIG. 25 shows a heatmap of repeats clusters prostate cancer samples. Unannotated transcripts that contained repeat elements were used to cluster prostate cancer samples in an unsupervised manner.
Figure 26:
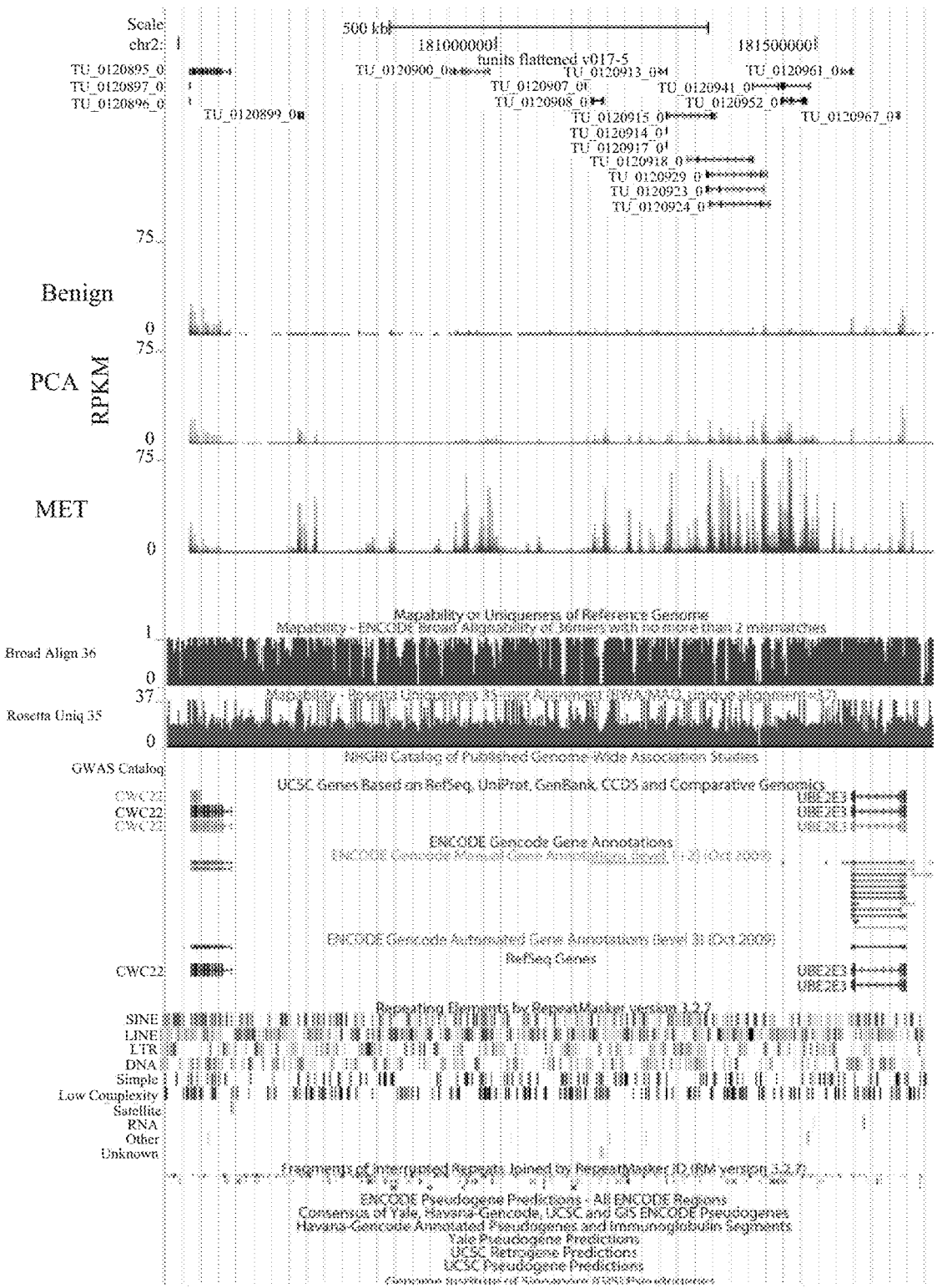
FIG. 26 shows that the SChLAP1 locus spans>500 kb. Visualization of transcriptome sequencing data in the UCSC genome browser indicates that a large, almost 1 Mb section of chromosome 2 is highly activated in cancer, contributing to many individual transcripts regulated in a coordinated fashion.

The presence of repetitive elements in PCAT-1 led to an exploration of repetitive elements. Repetitive elements, such as Alu and LINE-1 retrotransposons, are broadly known to be degenerate in humans (Oosumi et al, supra; Robertson et al., supra; Cordaux et al., Nat Rev Genet 10 (10), 691 (2009), with only ~100 LINE-1 elements (out of 12~500,000) showing possible retrotransposon activity (Brouha et al., Proc Natl Acad Sci USA 100 (9), 5280 (2003)). While transcription of these elements is frequently repressed through DNA methylation and repressive chromatin modifications (Slotkin and Martienssen, Nat Rev Genet 8 (4), 272 (2007)), in cancer widespread hypomethylation has been reported (Cho et al., J Pathol 211 (3), 269 (2007); Chalitchagorn et al., Oncogene 23 (54), 8841 (2004); Yegnasubramanian et al., *Cancer Res* 68 (21), 8954 (2008)). Moreover, recent evidence indicates that these elements have functional roles in both normal biology (Kunarso et al., *Nat Genet.*) and cancer (Lin et al., *Cell* 139 (6), 1069 (2009)), even if their sequences have mutated away from their evolutionary ancestral sequence (Chow et al., *Cell* 141 (6), 956). To date, only RNA-Seq platforms enable discovery and quantification of specific transposable elements expressed in cancer. As described above, it was observed that >50% of unannotated exons in the assembly overlap with at least one repetitive element (FIG. 11). Since these elements pose mappability challenges when performing transcriptome assembly with unique reads, these loci typically appear as "mountain ranges" of expression, with uniquely mappable regions forming peaks of expression separated by unmappable "ravines" (FIGS. 23 and 24). PCR and Sanger sequencing experiments were performed to confirm that these transposable elements of low mappability are expressed as part of these loci (FIGS. 23 and 24). To probe this observation further, the exons from unannotated transcripts in the assembly, with the addition of the flanking 50, 100, or 500 bp of additional genomic sequence to the 5' and 3' end of the exons were generated, the overlap of these intervals with repetitive elements to randomly permuted genomic intervals of similar sizes was performed. A highly significant enrichment for repetitive elements in the dataset was observed (OR 2.82 (95% CI 2.68-2.97), p<10-100). Examination of the individual repetitive element classes revealed a specific enrichment for SINE elements, particularly Alus (p≤2×10-16, Tables 10 and 11). A subset of LINE-1 and Alu transposable elements demonstrate marked differential expression in a subset of prostate cancer tumors (FIG. 25). One locus on chromosome 2 (also highlighted in FIG. 3b) is a 500+ kb region with numerous expressed transposable elements (FIG. 26). This locus, termed Second Chromosome Locus Associated with Prostate-1 (SChLAP1), harbors transcripts that perform extremely well in outlier analyses for prostate cancer (Tables 6 and 7). PCAT-109, discussed above, is one outlier transcript in this region. Moreover, the SChLAP1 locus is highly associated with patients positive for ETS gene fusions (p<0.0001, Fisher's exact test, FIG. 27), whereas this association was not observed with other expressed repeats. A direct regulatory role for ERG on this region was not identified using siRNA-mediated knockdown of ERG in the VCaP cell line. These data indicate that the dysregulation of repeats in cancer is highly specific, and that this phenomenon associates with only a subset of tumors and metastases. Thus, the broad hypomethylation of repeat elements observed in cancer (Cho et al., *J Pathol* 211 (3), 269 (2007); Chalitchagorn et al., *Oncogene* 23 (54), 8841 (2004); Yegnasubramanian et al., *Cancer Res* 68 (21), 8954 (2008)) does not account for the high specificity of repeat expression.

Non-Invasive Detection of ncRNAs in Urine

Taken together, these data show an abundance of novel ncRNA biomarkers for prostate cancer, many of which appear to have tissue specificity. 77 urine sediments obtained from patients with prostate cancer and 31 control patients without known disease were analyzed (Laxman et al., *Cancer Res* 68 (3), 645 (2008)). The control patients are defined as those lacking cancer histology upon prostate biopsy and lacking the TMPRSS2-ERG fusion transcript in urine sediment RNA (Laxman et al., supra). PCAT-1 and PCAT-14, as well as the known ncRNA biomarker PCA3, were selected for evaluation on this urine panel due to their biomarker status in patient tissue samples. qPCR analysis led to an observation of specificity in their ability to detect prostate cancer patients and not patients with normal prostates (FIG. 5a-c). In several cases, patients with ETS-negative prostate cancer that were misclassified as "benign" are clearly evident (FIGS. 5a and 5c). Moreover, PCAT-14 appears to perform almost as well as PCA3 as a urine biomarker, nearly achieving statistical significance (p=0.055, Fisher's exact test) despite the small number of patients used for this panel. It was next evaluated whether these unannotated ncRNAs identified a redundant set of patients that would also be identified by other urine tests, such as PCA3 or TMPRSS2-ERG transcripts. Comparing PCAT-1 and PCAT-14 expression in urine samples to PCA3 or to each other revealed that these ncRNAs identified distinct patient sets, indicating that a patient's urine typically harbors PCAT-1 or PCAT-14 transcripts but not both (FIG. 5d). Using the cut-offs displayed in FIG. 5a-c, a binary heatmap comparing these three ncRNAs with patients' TMPRSS2-ERG status was generated (FIG. 5e). The ncRNAs were able to detect additional ETS-negative patients with prostate cancer through this urine test, indicating that they have clinical utility as highly specific markers for prostate cancer using a multiplexed urine test. Combining PCAT-1, PCAT-14 and PCA3 into a single "non-coding RNA signature" generated a highly specific urine signature (p=0.0062, Fisher's exact test, FIG. 5f) that identifies a number of prostate cancer patients that is broadly comparable to the TMPRSS2-ERG fusion (33% vs. 45%).

Figure 35:
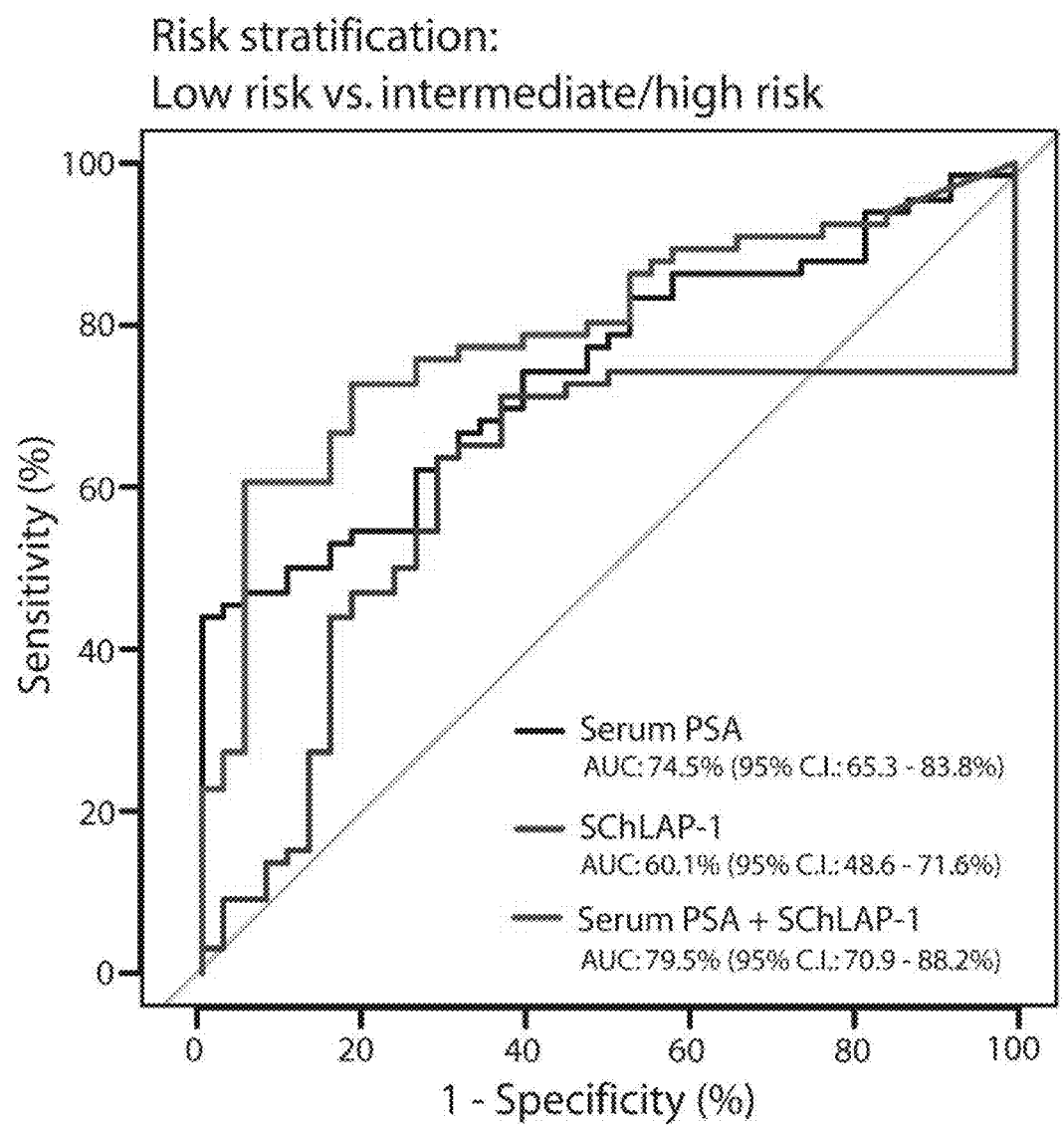
FIG. 35 shows multiplexing urine SChLAP-1 measurements with serum PSA improves prostate cancer risk stratification.

FIG. 34 shows detection of prostate cancer RNAs in patient urine samples using qPCR. All RNA species were detectable in urine. FIG. 35 shows that multiplexing urine SChLAP-1 measurements with serum PSA improves prostate cancer risk stratification. Individually, SChLAP-1 is a predictor for prostate cancers with intermediate or high clinical risk of aggressiveness. Multiplexing this measurement with serum PSA improves upon serum PSA's ability to predict for more aggressive disease.

Additional Characterization

Figure 29:
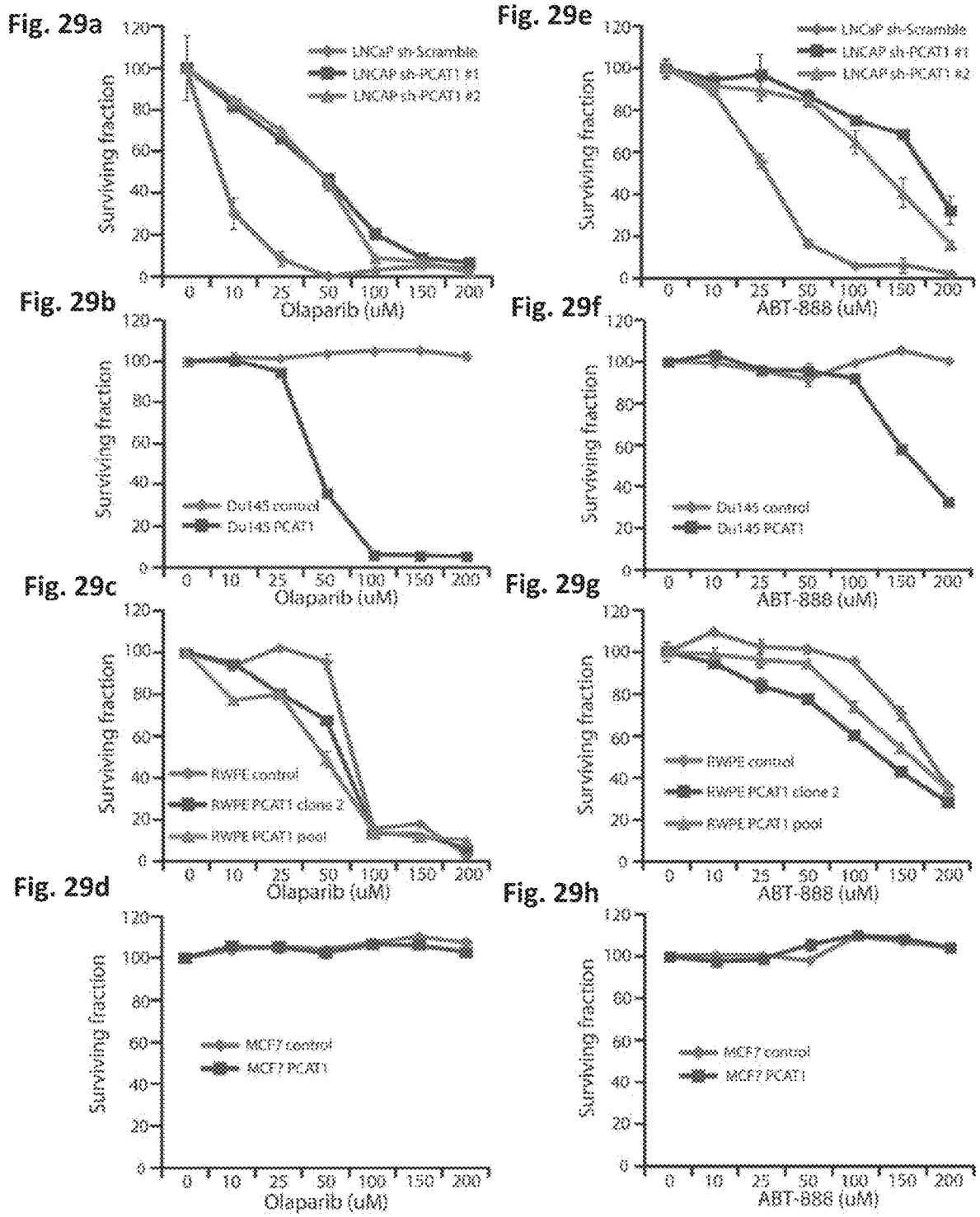
FIG. 29 shows that PCAT-1 expression sensitizes prostate cancer cells to treatment with PARP-1 inhibitors.

Additional experiments were conducted related to PCAT-1 and SChLAP-1 region in prostate cancer. FIG. 29 demonstrates that PCAT-1 expression sensitizes prostate cancer cells to treatment with PARP-1 inhbitors. FIG. 30 demonstrates that PCAT-1 expression sensitizes prostate cells to radiation treatment.

FIG. 31 demonstrates that unannotated intergeic transcripts in SChLAP-1 differentiate prostate cancer and benign samples. FIG. 32 demonstrates that SChLAP-1 is required for prostate cancer cell invasion and proliferation. Prostate cell lines, but not non-prostate cells, showed a reduction in invasion by Boyden chamber assays. EZH2 and non-targeting siRNAs served as positive and negative controls, respectively. Deletion analysis of SChLAP-1 was performed. FIG. 33 shows that a regionessential for its function was identified.

ncRNAs in Lung, Breast, and Pancreatic Cancers

Figures 36, 36C:
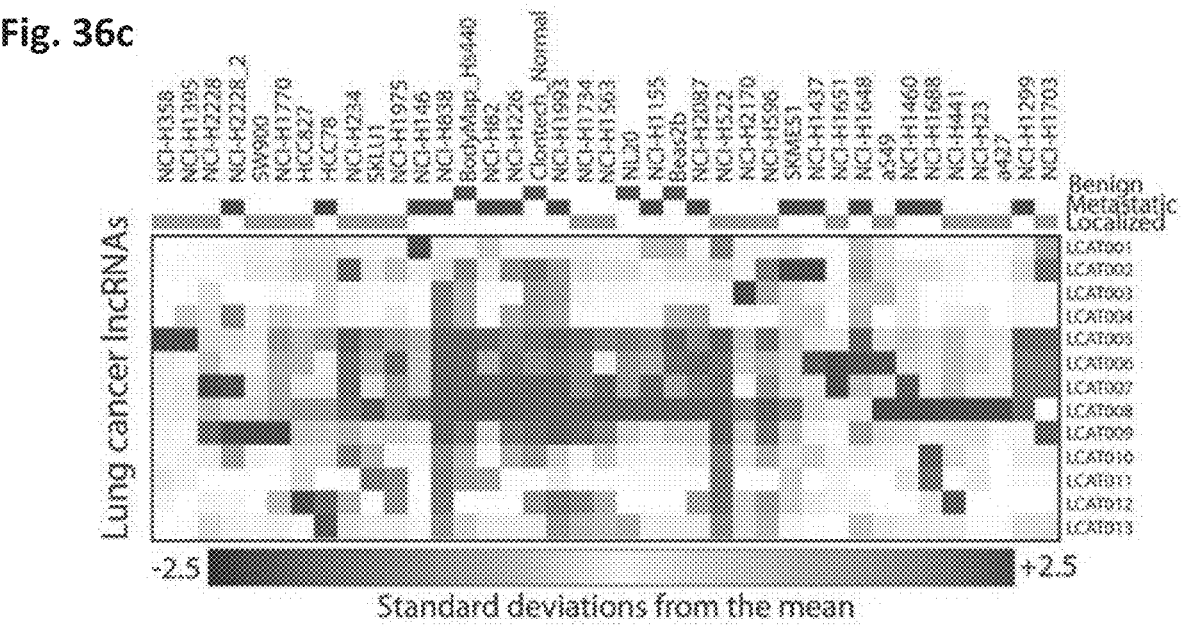
FIG. 36 shows analysis of the lung cancer transcriptome.
(FIG. 36c) An outlier analyses of 13 unannotated transcripts shows the presence of novel lncRNAs in subtypes of lung cancer cell lines.
Figures 38, 38E:
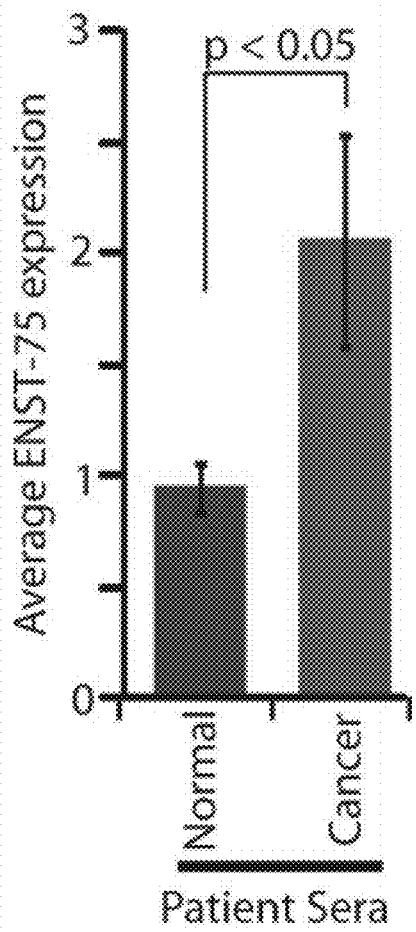
FIG. 38 shows lncRNAs are drivers and biomarkers in lung cancer.
(FIG. 38e) Average ENST-75 expression in lung cancer patient sera compared to normal patient sera. Error bars represent s.e.m.

Analysis of the lung cancer transcriptome (FIG. 36) was performed. 38 lung cell lines were analyzed by RNA-Seq and then lncRNA transcripts were reconstructed. Unannotated transcripts accounted for 27% of all transcripts. Novel transcripts well more highly expressed than annotated ncRNAs but not protein-coding transcripts. An outlier analyses of 13 unannotated transcripts shows novel lncRNAs in subtypes of lung cancer cell lines. FIG. 37 shows discovery of M41 and ENST-75 ncRNAs in lung cancer. FIG. 38 shows that lncRNAs are drivers and biomarkers in lung cancer. FIG. 39 shows identification of cancer-associated lncRNAs in breast and pancreatic cancer. Three novel breast cancer lncRNAs were nominated from RNA-Seq data (TU0011194, TU0019356, and TU0024146. All show outlier expression patterns in breast cancer samples but not benign samples. Three novel pancreatic cancer lncRNAs were nominated from RNA-Seq data (TU0009141, TU0062051, and TU0021861). All show outlier expression patterns in pancreatic cancer samples but not benign samples.

TABLE 1

| Library ID | Sample Name | Type | Sample Type | Read Type | Read Length | Total Reads (x2 for PE) | TopHat Mapped Reads |
|---|---|---|---|---|---|---|---|
| ctp_42B08AAXX_2 | PWR-1E | RNA-Seq | Cell Line | paired_end | 40 | 7363048 | 8367825 |
| mctp_30CYNAAXX_5 | PrEC | RNA-Seq | Cell Line | single_read | 40 | 3078462 | 955130 |
| mctp_209ENAAXX_8 | PrEC | RNA-Seq | Cell Line | single_read | 30 | 3319066 | 871560 |
| mctp_314T1AAXX_1 | PrEC | RNA-Seq | Cell Line | paired_end | 40 | 7748627 | 7443379 |
| mctp_30351AAXX_7 | PrEC | RNA-Seq | Cell Line | paired_end | 40 | 8883459 | 9562343 |
| mctp_314T1AAXX_2 | PrSMC | RNA-Seq | Cell Line | paired_end | 40 | 8464529 | 8626281 |
| mctp_20E6CAAXX_6 | RWPE | RNA-Seq | Cell Line | single_read | 36 | 5300188 | 1693464 |
| mctp_20E6CAAXX_7 | RWPE | RNA-Seq | Cell Line | single_read | 36 | 5347764 | 1710762 |
| mctp_20E6CAAXX_8 | RWPE | RNA-Seq | Cell Line | single_read | 36 | 4778245 | 1539225 |
| mctp_20F0BAAXX_6 | RWPE | RNA-Seq | Cell Line | single_read | 36 | 4833610 | 1565250 |
| mctp_20F0BAAXX_7 | RWPE | RNA-Seq | Cell Line | single_read | 36 | 5005497 | 1622033 |
| mctp_20F0BAAXX_8 | RWPE | RNA-Seq | Cell Line | single_read | 36 | 4955663 | 1607124 |
| mctp_20F0GAAXX_7 | RWPE | RNA-Seq | Cell Line | single_read | 36 | 4866438 | 1568635 |
| mctp_20F0GAAXX_8 | RWPE | RNA-Seq | Cell Line | single_read | 36 | 4809235 | 1550957 |
| mctp_20F0GAAXX_6 | RWPE | RNA-Seq | Cell Line | single_read | 36 | 4904467 | 1580424 |
| mctp_42B08AAXX_3 | WPMY-1 | RNA-Seq | Cell Line | paired_end | 40 | 7593911 | 8103303 |
| mctp_20F69AAXX_1 | 22Rv1 | RNA-Seq | Cell Line | single_read | 36 | 5301735 | 2345205 |
| mctp_314NNAAXX_6 | 22Rv1 | RNA-Seq | Cell Line | paired_end | 40 | 9214420 | 9600616 |
| mctp_429T4AAXX_5 | CA-HPV.10 | RNA-Seq | Cell Line | paired_end | 40 | 13654861 | 14731620 |
| mctp_429T4AAXX_7 | CWR22 | RNA-Seq | Cell Line | paired_end | 40 | 13882984 | 14791235 |
| mctp_30DJDAAXX_2 | VCaP | RNA-Seq | Cell Line | single_read | 45 | 8175900 | 1400656 |
| mctp_20CCAAAXX_7 | VCaP | RNA-Seq | Cell Line | single_read | 36 | 5372814 | 981204 |
| mctp_20CCAAAXX_6 | VCaP | RNA-Seq | Cell Line | single_read | 36 | 5210292 | 957549 |
| mctp_20CCAAAXX_4 | VCaP | RNA-Seq | Cell Line | single_read | 36 | 5220542 | 956622 |
| mctp_20CCAAAXX_3 | VCaP | RNA-Seq | Cell Line | single_read | 36 | 5405126 | 988972 |
| mctp_20CCAAAXX_2 | VCaP | RNA-Seq | Cell Line | single_read | 36 | 5091526 | 938272 |
| mctp_20CCAAAXX_1 | VCaP | RNA-Seq | Cell Line | single_read | 36 | 4273325 | 804030 |
| mctp_20E6CAAXX_1 | VCaP | RNA-Seq | Cell Line | single_read | 36 | 4717324 | 861856 |
| mctp_20CCAAAXX_8 | VCaP | RNA-Seq | Cell Line | single_read | 36 | 5024204 | 926214 |
| mctp_207D6AAXX_2 | VCaP | RNA-Seq | Cell Line | single_read | 36 | 4491727 | 807997 |
| mctp_429T4AAXX_4 | NCI-H660 | RNA-Seq | Cell Line | paired_end | 40 | 12322606 | 15104197 |
| mctp_20F0GAAXX_4 | LNCaP | RNA-Seq | Cell Line | single_read | 36 | 5109403 | 1430548 |
| mctp_20F0GAAXX_1 | LNCaP | RNA-Seq | Cell Line | single_read | 36 | 5018345 | 1402514 |
| mctp_20F0GAAXX_3 | LNCaP | RNA-Seq | Cell Line | single_read | 36 | 5106724 | 1426834 |
| mctp_20F0GAAXX_2 | LNCaP | RNA-Seq | Cell Line | single_read | 36 | 4990256 | 1398161 |
| mctp_20E6CAAXX_2 | LNCaP | RNA-Seq | Cell Line | single_read | 36 | 4893789 | 1370920 |
| mctp_20E6CAAXX_3 | LNCaP | RNA-Seq | Cell Line | single_read | 36 | 5402666 | 1510040 |
| mctp_20E6CAAXX_4 | LNCaP | RNA-Seq | Cell Line | single_read | 36 | 4831947 | 1304247 |
| mctp_42PMUAAXX_6 | LNCaP CDS2 | RNA-Seq | Cell Line | paired_end | 38 | 10714939 | 10272130 |
| mctp_42PMUAAXX_7 | LNCaP CDS3 | RNA-Seq | Cell Line | paired_end | 38 | 9643473 | 9586206 |
| mctp_42TA8AAXX_7 | DU-145 | RNA-Seq | Cell Line | paired_end | 38 | 12804352 | 13651384 |
| mctp_42TA8AAXX_6 | DU-145 | RNA-Seq | Cell Line | paired_end | 38 | 15765949 | 15918891 |
| mctp_42TA8AAXX_5 | DU-145 | RNA-Seq | Cell Line | paired_end | 38 | 14187743 | 14960879 |
| mctp_42TA8AAXX_3 | DU-145 | RNA-Seq | Cell Line | paired_end | 38 | 12150298 | 13047948 |
| mctp_42TA8AAXX_2 | DU-145 | RNA-Seq | Cell Line | paired_end | 38 | 12863744 | 13718578 |
| mctp_42TA8AAXX_1 | DU-145 | RNA-Seq | Cell Line | paired_end | 38 | 10904533 | 6437287 |
| mctp_42TBDAAXX_8 | DU-145 | RNA-Seq | Cell Line | paired_end | 38 | 9229144 | 10026773 |
| mctp_42PFAAAXX_6 | LNCaP CDS parent | RNA-Seq | Cell Line | paired_end | 38 | 12368674 | 9518829 |
| mctp_42PFAAAXX_5 | LNCaP CDS1 | RNA-Seq | Cell Line | paired_end | 38 | 14469668 | 13998752 |
| mctp_20BC5AAXX_8 | DU-145 | RNA-Seq | Cell Line | single_read | 36 | 5351406 | 2568642 |
| mctp_20F69AAXX_2 | DU-145 | RNA-Seq | Cell Line | single_read | 36 | 5069249 | 2437193 |
| mctp_30DJDAAXX_3 | DU-145 | RNA-Seq | Cell Line | single_read | 45 | 8586532 | 4162580 |
| mctp_429T4AAXX_3 | LAPC-4 | RNA-Seq | Cell Line | paired_end | 40 | 14785826 | 16711055 |
| mctp_3064YAAXX_1 | PC3 | RNA-Seq | Cell Line | paired_end | 40 | 10267396 | 10291560 |
| mctp_20F69AAXX_3 | PC3 | RNA-Seq | Cell Line | single_read | 36 | 5364050 | 2547308 |
| mctp_429T4AAXX_2 | C4-2B | RNA-Seq | Cell Line | paired_end | 40 | 12759909 | 12823209 |
| mctp_429T4AAXX_6 | MDA PCa2b | RNA-Seq | Cell Line | paired_end | 40 | 13341323 | 14909946 |
| mctp_42B08AAXX_4 | WPE1-NB26 | RNA-Seq | Cell Line | paired_end | 40 | 10593920 | 9930621 |
| mctp_42B48AAXX_4 | PrBe10013 | RNA-Seq | Tissue | paired_end | 40 | 15313395 | 18040527 |
| mctp_30WU2AAXX_5 | PrBe10013 | RNA-Seq | Tissue | paired_end | 38 | 9822744 | 12263152 |
| mctp_42B48AAXX_8 | PrBe10014 | RNA-Seq | Tissue | paired_end | 40 | 11242142 | 9036878 |
| mctp_42PFAAAXX_2 | PrBe10014 | RNA-Seq | Tissue | paired_end | 38 | 6646551 | 6389875 |
| mctp_30WU2AAXX_6 | PrBe10014 | RNA-Seq | Tissue | paired_end | 38 | 3977109 | 4253690 |
| mctp_42CJJAAXX_7 | PrBe10015 | RNA-Seq | Tissue | paired_end | 40 | 7584480 | 7927754 |
| mctp_42NY4AAXX_2 | PrBe10015 | RNA-Seq | Tissue | paired_end | 38 | 14331227 | 12877894 |
| mctp_42B48AAXX_1 | PrBe10016 | RNA-Seq | Tissue | paired_end | 40 | 12122294 | 11750631 |
| mctp_42NY4AAXX_3 | PrBe10016 | RNA-Seq | Tissue | paired_end | 38 | 11809596 | 11367863 |
| mctp_30WU2AAXX_7 | PrBe10017 | RNA-Seq | Tissue | paired_end | 38 | 1859890 | 2156367 |
| mctp_42CJFAAXX_5 | PrBe10017 | RNA-Seq | Tissue | paired_end | 40 | 14245213 | 14383797 |

TABLE 1-continued

| | | | | | | |
|---|---|---|---|---|---|---|
| mctp_42B20AAXX_5 | PrBe10018 | RNA-Seq | Tissue | paired_end | 38 | 16616393 | 17002418 |
| mctp_42NY4AAXX_6 | PrBe10018 | RNA-Seq | Tissue | paired_end | 38 | 15877894 | 16489882 |
| mctp_42D3NAAXX_5 | aN10_6 | RNA-Seq | Tissue | paired_end | 40 | 10102958 | 11948284 |
| mctp_3064YAAXX_2 | aN11_1 | RNA-Seq | Tissue | paired_end | 40 | 9792955 | 10708088 |
| mctp_42P6UAAXX_1 | aN11_1 | RNA-Seq | Tissue | paired_end | 40 | 14658825 | 10917481 |
| mctp_301YWAAXX_1 | aN13_2 | RNA-Seq | Tissue | paired_end | 40 | 14755517 | 15347535 |
| mctp_42P6UAAXX_4 | aN13_2 | RNA-Seq | Tissue | paired_end | 40 | 16107801 | 16070565 |
| mctp_3064YAAXX_3 | aN14_4 | RNA-Seq | Tissue | paired_end | 40 | 9282092 | 9526550 |
| mctp_42P6UAAXX_2 | aN14_4 | RNA-Seq | Tissue | paired_end | 40 | 12317092 | 11968962 |
| mctp_30653AAXX_5 | PrBe10002 | RNA-Seq | Tissue | paired_end | 40 | 10282216 | 3480927 |
| mctp_30CYNAAXX_6 | PrBe10002 | RNA-Seq | Tissue | single_read | 40 | 4389340 | 877146 |
| mctp_30CYNAAXX_7 | PrBe10003 | RNA-Seq | Tissue | single_read | 40 | 4724195 | 382030 |
| mctp_42P6UAAXX_3 | aN15_3 | RNA-Seq | Tissue | paired_end | 40 | 14035929 | 10890695 |
| mctp_3064YAAXX_7 | aN15_3 | RNA-Seq | Tissue | paired_end | 40 | 8772663 | 8101379 |
| mctp_30DM2AAXX_6 | aN23 | RNA-Seq | Tissue | single_read | 35 | 6359089 | 2998000 |
| mctp_30DM2AAXX_4 | aN25 | RNA-Seq | Tissue | single_read | 35 | 5162304 | 2181784 |
| mctp_30DM2AAXX_3 | aN25 | RNA-Seq | Tissue | single_read | 35 | 5667482 | 2632682 |
| mctp_30DM2AAXX_1 | aN27 | RNA-Seq | Tissue | single_read | 35 | 4771661 | 1856628 |
| mctp_30DM2AAXX_2 | aN27 | RNA-Seq | Tissue | single_read | 35 | 5843509 | 2090978 |
| mctp_30DM2AAXX_7 | aN29 | RNA-Seq | Tissue | single_read | 35 | 5661652 | 1555510 |
| mctp_30DM2AAXX_8 | aN29 | RNA-Seq | Tissue | single_read | 35 | 5201944 | 1472975 |
| mctp_20FCKAAXX_1 | aN31 | RNA-Seq | Tissue | single_read | 36 | 4206556 | 1642681 |
| mctp_20FCKAAXX_2 | aN31 | RNA-Seq | Tissue | single_read | 35 | 3624043 | 1504320 |
| mctp_20FCKAAXX_4 | aN32 | RNA-Seq | Tissue | single_read | 36 | 4445596 | 1866001 |
| mctp_20FCKAAXX_3 | aN32 | RNA-Seq | Tissue | single_read | 36 | 4352455 | 1835242 |
| mctp_20FCKAAXX_7 | aN33 | RNA-Seq | Tissue | single_read | 35 | 5375947 | 2024782 |
| mctp_20FCKAAXX_8 | aN33 | RNA-Seq | Tissue | single_read | 35 | 3974268 | 1587869 |
| mctp_42D3NAAXX_6 | aT12_4 | RNA-Seq | Tissue | paired_end | 40 | 10323732 | 10700318 |
| mctp_42P6UAAXX_6 | aT12_4 | RNA-Seq | Tissue | paired_end | 40 | 12591851 | 12687329 |
| mctp_20A0MAAXX_7 | aT54 | RNA-Seq | Tissue | single_read | 35 | 4951150 | 2395362 |
| mctp_301YWAAXX_3 | aT5_5 | RNA-Seq | Tissue | paired_end | 40 | 14290078 | 15157510 |
| mctp_20A0MAAXX_8 | aT62 | RNA-Seq | Tissue | single_read | 35 | 5144018 | 2594526 |
| mctp_20093AAXX_3 | aT76 | RNA-Seq | Tissue | single_read | 30 | 4482645 | 2095392 |
| mctp_42D3NAAXX_7 | aT8_2 | RNA-Seq | Tissue | paired_end | 40 | 9949944 | 10269470 |
| mctp_42P6UAAXX_7 | aT8_2 | RNA-Seq | Tissue | paired_end | 40 | 13165443 | 12758016 |
| mctp_20A0MAAXX_6 | aT20 | RNA-Seq | Tissue | single_read | 35 | 4905934 | 2380289 |
| mctp_30Y5NAAXX_6 | aT52 | RNA-Seq | Tissue | paired_end | 34 | 9555248 | 11236237 |
| mctp_20093AAXX_4 | PrCa10001 | RNA-Seq | Tissue | single_read | 30 | 5073375 | 2003723 |
| mctp_30CYNAAXX_2 | PrCa10002 | RNA-Seq | Tissue | single_read | 40 | 3979846 | 1573898 |
| mctp_20093AAXX_7 | PrCa10002 | RNA-Seq | Tissue | single_read | 30 | 5337734 | 2185509 |
| mctp_30CW7AAXX_4 | PrCa10003 | RNA-Seq | Tissue | single_read | 40 | 7245088 | 3325480 |
| mctp_30CYNAAXX_1 | PrCa10003 | RNA-Seq | Tissue | single_read | 40 | 2232676 | 996717 |
| mctp_20093AAXX_6 | PrCa10003 | RNA-Seq | Tissue | single_read | 30 | 4209584 | 1868531 |
| mctp_20093AAXX_2 | PrCa10004 | RNA-Seq | Tissue | single_read | 30 | 4877618 | 2429172 |
| mctp_30CW7AAXX_3 | PrCa10004 | RNA-Seq | Tissue | single_read | 40 | 8502651 | 4337931 |
| mctp_20093AAXX_1 | PrCa10006 | RNA-Seq | Tissue | single_read | 30 | 4697349 | 2219408 |
| mctp_30CW7AAXX_5 | PrCa10006 | RNA-Seq | Tissue | single_read | 40 | 7780464 | 3825883 |
| mctp_30WU2AAXX_8 | PrCa10013 | RNA-Seq | Tissue | paired_end | 38 | 7094073 | 8465055 |
| mctp_42PFAAAXX_3 | PrCa10013 | RNA-Seq | Tissue | paired_end | 38 | 13129950 | 14850397 |
| mctp_42CJFAAXX_4 | PrCa10013 | RNA-Seq | Tissue | paired_end | 40 | 11855634 | 13593367 |
| mctp_42B08AAXX_5 | PrCa10014 | RNA-Seq | Tissue | paired_end | 40 | 11559996 | 11278990 |
| mctp_42B08AAXX_1 | PrCa10014 | RNA-Seq | Tissue | paired_end | 40 | 9629325 | 7576252 |
| mctp_42CJJAAXX_5 | PrCa10014 | RNA-Seq | Tissue | paired_end | 40 | 15188424 | 17200396 |
| mctp_30WU2AAXX_1 | PrCa10014 | RNA-Seq | Tissue | paired_end | 38 | 13833345 | 15792364 |
| mctp_42B48AAXX_3 | PrCa10015 | RNA-Seq | Tissue | paired_end | 40 | 14322439 | 14744516 |
| mctp_30WU2AAXX_4 | PrCa10015 | RNA-Seq | Tissue | paired_end | 38 | 9081533 | 10010115 |
| mctp_42NY4AAXX_4 | PrCa10016 | RNA-Seq | Tissue | paired_end | 38 | 11879138 | 13526717 |
| mctp_42B48AAXX_6 | PrCa10016 | RNA-Seq | Tissue | paired_end | 40 | 11883818 | 13459171 |
| mctp_42B48AAXX_2 | PrCa10017 | RNA-Seq | Tissue | paired_end | 40 | 7583235 | 7555611 |
| mctp_42PFAAAXX_1 | PrCa10017 | RNA-Seq | Tissue | paired_end | 38 | 13554764 | 11318051 |
| mctp_42NY4AAXX_5 | PrCa10018 | RNA-Seq | Tissue | paired_end | 38 | 16107721 | 18636010 |
| mctp_42CJFAAXX_2 | PrCa10018 | RNA-Seq | Tissue | paired_end | 40 | 12506692 | 14935573 |
| mctp_30Y5NAAXX_4 | PrCa10018 | RNA-Seq | Tissue | paired_end | 34 | 8565125 | 10521603 |
| mctp_42CJJAAXX_8 | PrCa10019 | RNA-Seq | Tissue | paired_end | 40 | 14204491 | 12235106 |
| mctp_42B48AAXX_5 | PrCa10021 | RNA-Seq | Tissue | paired_end | 40 | 14583654 | 15470222 |
| mctp_42CJFAAXX_1 | PrCa10023 | RNA-Seq | Tissue | paired_end | 40 | 9473417 | 11040935 |
| mctp_42CJJAAXX_6 | PrCa10024 | RNA-Seq | Tissue | paired_end | 40 | 5249645 | 5541745 |
| mctp_42PF0AAXX_3 | PrCa10024 | RNA-Seq | Tissue | paired_end | 38 | 8109134 | 7508966 |
| mctp_42CJFAAXX_3 | PrCa10028 | RNA-Seq | Tissue | paired_end | 40 | 5344366 | 6256991 |
| mctp_42TB9AAXX_3 | PrCa10030 | RNA-Seq | Tissue | paired_end | 38 | 17239720 | 18212019 |
| mctp_42TB9AAXX_1 | PrCa10031 | RNA-Seq | Tissue | paired_end | 38 | 17881940 | 19792732 |
| mctp_42TB9AAXX_6 | PrCa10032 | RNA-Seq | Tissue | paired_end | 38 | 16892184 | 18313947 |
| mctp_42TB9AAXX_2 | PrCa10033 | RNA-Seq | Tissue | paired_end | 38 | 10736010 | 7148288 |
| mctp_42TB9AAXX_7 | PrCa10034 | RNA-Seq | Tissue | paired_end | 38 | 16494766 | 18616451 |
| mctp_42P6UAAXX_5 | aT1_3 | RNA-Seq | Tissue | paired_end | 40 | 14031093 | 15128363 |
| mctp_301YWAAXX_2 | aT1_3 | RNA-Seq | Tissue | paired_end | 40 | 14017921 | 15424771 |
| mctp_42B48AAXX_7 | aT38 | RNA-Seq | Tissue | paired_end | 40 | 14028075 | 14206815 |
| mctp_30Y5NAAXX_3 | aT38 | RNA-Seq | Tissue | paired_end | 34 | 9148041 | 10857079 |
| mctp_42Y2TAAXX_2 | aT42 | RNA-Seq | Tissue | paired_end | 38 | 15907739 | 17336906 |
| mctp_30DJDAAXX_5 | aT42 | RNA-Seq | Tissue | single_read | 45 | 9446722 | 4597917 |

TABLE 1-continued

| | | | | | | | |
|---|---|---|---|---|---|---|---|
| mctp_42Y2TAAXX_3 | aT45 | RNA-Seq | Tissue | paired_end | 38 | 16395435 | 13748230 |
| mctp_30DJDAAXX_6 | aT45 | RNA-Seq | Tissue | single_read | 45 | 9154922 | 3918914 |
| mctp_42B08AAXX_7 | aT53 | RNA-Seq | Tissue | paired_end | 40 | 12164542 | 13040082 |
| mctp_20F66AAXX_6 | aT56 | RNA-Seq | Tissue | single_read | 36 | 4655382 | 2002111 |
| mctp_30CW7AAXX_2 | aT56 | RNA-Seq | Tissue | single_read | 40 | 7586627 | 3048288 |
| mctp_20F65AAXX_1 | aT56 | RNA-Seq | Tissue | single_read | 36 | 4894127 | 1968986 |
| mctp_30U00AAXX_4 | aT57 | RNA-Seq | Tissue | paired_end | 40 | 9490697 | 9403761 |
| mctp_42CJFAAXX_8 | aT58 | RNA-Seq | Tissue | paired_end | 40 | 4160283 | 4703591 |
| mctp_42B08AAXX_8 | aT61 | RNA-Seq | Tissue | paired_end | 40 | 10252280 | 10445106 |
| mctp_20F66AAXX_7 | aT66 | RNA-Seq | Tissue | single_read | 36 | 5016117 | 2455183 |
| mctp_30CW7AAXX_1 | aT66 | RNA-Seq | Tissue | single_read | 40 | 8055624 | 3791022 |
| mctp_20F65AAXX_2 | aT66 | RNA-Seq | Tissue | single_read | 36 | 5184870 | 2368556 |
| mctp_42P6UAAXX_8 | aT6_1 | RNA-Seq | Tissue | paired_end | 40 | 936249 | 998194 |
| mctp_42CJFAAXX_7 | aT6_1 | RNA-Seq | Tissue | paired_end | 40 | 9428987 | 7353536 |
| mctp_42PFAAAXX_4 | aT6_1 | RNA-Seq | Tissue | paired_end | 38 | 13242928 | 9178336 |
| mctp_30CW5AAXX_7 | PrCa10007 | RNA-Seq | Tissue | single_read | 42 | 7909935 | 3246264 |
| mctp_42D3NAAXX_2 | PrCa10025 | RNA-Seq | Tissue | paired_end | 40 | 8614808 | 9085984 |
| mctp_42D3NAAXX_1 | PrCa10026 | RNA-Seq | Tissue | paired_end | 40 | 7781206 | 8539677 |
| mctp_42D3NAAXX_3 | PrCa10027 | RNA-Seq | Tissue | paired_end | 40 | 10305382 | 11427244 |
| mctp_42TB9AAXX_4 | PrCa10029 | RNA-Seq | Tissue | paired_end | 38 | 8674521 | 9910831 |
| mctp_42Y6WAAXX_6 | PrCa10029 | RNA-Seq | Tissue | paired_end | 38 | 13229893 | 14068633 |
| mctp_3064YAAXX_4 | T-2927 | RNA-Seq | Tissue | paired_end | 40 | 9642506 | 8623117 |
| mctp_42B3YAAXX_4 | aT47 | RNA-Seq | Tissue | paired_end | 40 | 7806523 | 7010780 |
| mctp_20F66AAXX_3 | aM23 | RNA-Seq | Tissue | single_read | 36 | 4680303 | 2048538 |
| mctp_20F66AAXX_4 | aM23 | RNA-Seq | Tissue | single_read | 36 | 4913495 | 2187836 |
| mctp_20F69AAXX_4 | aM28 | RNA-Seq | Tissue | single_read | 36 | 5374558 | 2203543 |
| mctp_20LV8AAXX_6 | aM28 | RNA-Seq | Tissue | single_read | 30 | 5517555 | 2234529 |
| mctp_20LV8AAXX_7 | aM28 | RNA-Seq | Tissue | single_read | 30 | 5548780 | 2250821 |
| mctp_20A0MAAXX_4 | aM29 | RNA-Seq | Tissue | single_read | 35 | 4903432 | 1839767 |
| mctp_20PETAAXX_6 | aM29 | RNA-Seq | Tissue | single_read | 36 | 5092573 | 1777721 |
| mctp_2074VAAXX_1 | aM38 | RNA-Seq | Tissue | single_read | 36 | 5126432 | 2559949 |
| mctp_30CYNAAXX_4 | aM38 | RNA-Seq | Tissue | single_read | 40 | 4759734 | 2287003 |
| mctp_30TYGAAXX_3 | aM38 | RNA-Seq | Tissue | paired_end | 40 | 6778936 | 3689892 |
| mctp_42B20AAXX_6 | aM15 | RNA-Seq | Tissue | paired_end | 38 | 13826315 | 11684423 |
| mctp_2074VAAXX_3 | aM15 | RNA-Seq | Tissue | single_read | 36 | 4744456 | 2087670 |
| mctp_2074VAAXX_5 | aM37 | RNA-Seq | Tissue | single_read | 36 | 4509553 | 1941952 |
| mctp_205K4AAXX_2 | aM41 | RNA-Seq | Tissue | single_read | 36 | 4480735 | 1702019 |
| mctp_20FETAAXX_8 | aM41 | RNA-Seq | Tissue | single_read | 36 | 5372905 | 2051694 |
| mctp_2074VAAXX_2 | aM41 | RNA-Seq | Tissue | single_read | 36 | 5222746 | 2184030 |
| mctp_3064YAAXX_6 | B11239-97 | RNA-Seq | Tissue | paired_end | 40 | 9663726 | 10247077 |
| mctp_3064YAAXX_5 | B2440-97 | RNA-Seq | Tissue | paired_end | 40 | 9822270 | 10358661 |
| mctp_20EYPAAXX_7 | aM11 | RNA-Seq | Tissue | single_read | 36 | 5201588 | 2333757 |
| mctp_42CJFAAXX_6 | aM20 | RNA-Seq | Tissue | paired_end | 40 | 9038499 | 8821509 |
| mctp_20EYPAAXX_6 | aM36 | RNA-Seq | Tissue | single_read | 36 | 5587558 | 2277795 |
| mctp_30CW7AAXX_6 | aM36 | RNA-Seq | Tissue | single_read | 40 | 9198611 | 3833469 |
| mctp_30TYGAAXX_1 | aM36 | RNA-Seq | Tissue | paired_end | 40 | 7749518 | 2430300 |
| mctp_205K4AAXX_1 | aM36 | RNA-Seq | Tissue | single_read | 36 | 5097473 | 2217107 |
| mctp_20EYPAAXX_2 | aM39 | RNA-Seq | Tissue | single_read | 36 | 5516548 | 2339212 |
| mctp_30TYGAAXX_5 | aM39 | RNA-Seq | Tissue | paired_end | 40 | 6279578 | 3568922 |
| mctp_20FETAAXX_7 | aM39 | RNA-Seq | Tissue | single_read | 36 | 5354844 | 2117551 |
| mctp_20EYPAAXX_8 | aM43 | RNA-Seq | Tissue | single_read | 36 | 5497785 | 1680082 |
| mctp_30CW7AAXX_7 | aM43 | RNA-Seq | Tissue | single_read | 40 | 8489329 | 3952621 |
| | | | | TOTAL | | 1723713421 | 1417627939 |

| Library ID | TopHat Splice Junction Reads | % Splice | Diagnosis | ETS status |
|---|---|---|---|---|
| ctp_42B08AAXX_2 | 1091179 | 13.04% | Benign | Negative |
| mctp_30CYNAAXX_5 | 107311 | 11.24% | Benign | Negative |
| mctp_209ENAAXX_8 | 67610 | 7.76% | Benign | Negative |
| mctp_314T1AAXX_1 | 747751 | 10.05% | Benign | Negative |
| mctp_30351AAXX_7 | 892380 | 9.33% | Benign | Negative |
| mctp_314T1AAXX_2 | 935503 | 10.84% | Benign | Negative |
| mctp_20E6CAAXX_6 | 149383 | 8.82% | Benign | Negative |
| mctp_20E6CAAXX_7 | 150130 | 8.78% | Benign | Negative |
| mctp_20E6CAAXX_8 | 135996 | 8.84% | Benign | Negative |
| mctp_20F0BAAXX_6 | 137416 | 8.78% | Benign | Negative |
| mctp_20F0BAAXX_7 | 143185 | 8.83% | Benign | Negative |
| mctp_20F0BAAXX_8 | 141358 | 8.80% | Benign | Negative |
| mctp_20F0GAAXX_7 | 138224 | 8.81% | Benign | Negative |
| mctp_20F0GAAXX_8 | 136049 | 8.77% | Benign | Negative |
| mctp_20F0GAAXX_6 | 138674 | 8.77% | Benign | Negative |
| mctp_42B08AAXX_3 | 1011035 | 12.48% | Benign | Negative |
| mctp_20F69AAXX_1 | 169257 | 7.22% | Localized | Negative |
| mctp_314NNAAXX_6 | 1063132 | 11.07% | Localized | Negative |
| mctp_429T4AAXX_5 | 1750416 | 11.88% | Localized | Negative |
| mctp_429T4AAXX_7 | 1530790 | 10.35% | Localized | Negative |
| mctp_30DJDAAXX_2 | 167746 | 11.98% | Metastatic | ERG+ |
| mctp_20CCAAAXX_7 | 89660 | 9.14% | Metastatic | ERG+ |

TABLE 1-continued

| | | | | |
|---|---|---|---|---|
| mctp_20CCAAAXX_6 | 86199 | 9.00% | Metastatic | ERG+ |
| mctp_20CCAAAXX_4 | 88342 | 9.23% | Metastatic | ERG+ |
| mctp_20CCAAAXX_3 | 90075 | 9.11% | Metastatic | ERG+ |
| mctp_20CCAAAXX_2 | 85147 | 9.07% | Metastatic | ERG+ |
| mctp_20CCAAAXX_1 | 72804 | 9.05% | Metastatic | ERG+ |
| mctp_20E6CAAXX_1 | 78164 | 9.07% | Metastatic | ERG+ |
| mctp_20CCAAAXX_8 | 85535 | 9.23% | Metastatic | ERG+ |
| mctp_207D6AAXX_2 | 73610 | 9.11% | Metastatic | ERG+ |
| mctp_429T4AAXX_4 | 1377708 | 9.12% | Metastatic | ERG+ |
| mctp_20F0GAAXX_4 | 119470 | 8.35% | Metastatic | ETV1+ |
| mctp_20F0GAAXX_1 | 117293 | 8.36% | Metastatic | ETV1+ |
| mctp_20F0GAAXX_3 | 119462 | 8.37% | Metastatic | ETV1+ |
| mctp_20F0GAAXX_2 | 117850 | 8.43% | Metastatic | ETV1+ |
| mctp_20E6CAAXX_2 | 114874 | 8.38% | Metastatic | ETV1+ |
| mctp_20E6CAAXX_3 | 126177 | 8.36% | Metastatic | ETV1+ |
| mctp_20E6CAAXX_4 | 112489 | 8.62% | Metastatic | ETV1+ |
| mctp_42PMUAAXX_6 | 1057574 | 10.30% | Metastatic | Negative |
| mctp_42PMUAAXX_7 | 973617 | 10.16% | Metastatic | Negative |
| mctp_42TA8AAXX_7 | 1370507 | 10.04% | Metastatic | Negative |
| mctp_42TA8AAXX_6 | 1570336 | 9.86% | Metastatic | Negative |
| mctp_42TA8AAXX_5 | 1485534 | 9.93% | Metastatic | Negative |
| mctp_42TA8AAXX_3 | 1320224 | 10.12% | Metastatic | Negative |
| mctp_42TA8AAXX_2 | 1384118 | 10.09% | Metastatic | Negative |
| mctp_42TA8AAXX_1 | 653992 | 10.16% | Metastatic | Negative |
| mctp_42TBDAAXX_8 | 1013731 | 10.11% | Metastatic | Negative |
| mctp_42PFAAAXX_6 | 966543 | 10.15% | Metastatic | Negative |
| mctp_42PFAAAXX_5 | 1411356 | 10.08% | Metastatic | Negative |
| mctp_20BC5AAXX_8 | 235883 | 9.18% | Metastatic | Negative |
| mctp_20F69AAXX_2 | 225574 | 9.26% | Metastatic | Negative |
| mctp_30DJDAAXX_3 | 498466 | 11.97% | Metastatic | Negative |
| mctp_429T4AAXX_3 | 1790200 | 10.71% | Metastatic | Negative |
| mctp_3064YAAXX_1 | 1185473 | 11.52% | Metastatic | Negative |
| mctp_20F69AAXX_3 | 237597 | 9.33% | Metastatic | Negative |
| mctp_429T4AAXX_2 | 1591197 | 12.41% | Metastatic | Negative |
| mctp_429T4AAXX_6 | 1634544 | 10.96% | Metastatic | Negative |
| mctp_42B08AAXX_4 | 1240048 | 12.49% | Metastatic | Negative |
| mctp_42B48AAXX_4 | 1435670 | 7.96% | Benign | Negative |
| mctp_30WU2AAXX_5 | 927390 | 7.56% | Benign | Negative |
| mctp_42B48AAXX_8 | 715431 | 7.92% | Benign | Negative |
| mctp_42PFAAAXX_2 | 471883 | 7.38% | Benign | Negative |
| mctp_30WU2AAXX_6 | 321691 | 7.56% | Benign | Negative |
| mctp_42CJJAAXX_7 | 632270 | 7.98% | Benign | Negative |
| mctp_42NY4AAXX_2 | 936438 | 7.27% | Benign | Negative |
| mctp_42B48AAXX_1 | 820710 | 6.98% | Benign | Negative |
| mctp_42NY4AAXX_3 | 741989 | 6.53% | Benign | Negative |
| mctp_30WU2AAXX_7 | 152020 | 7.05% | Benign | Negative |
| mctp_42CJFAAXX_5 | 1025161 | 7.13% | Benign | Negative |
| mctp_42B20AAXX_5 | 1465145 | 8.62% | Benign | Negative |
| mctp_42NY4AAXX_6 | 1418434 | 8.60% | Benign | Negative |
| mctp_42D3NAAXX_5 | 938291 | 7.85% | Benign | Negative |
| mctp_3064YAAXX_2 | 844013 | 7.88% | Benign | Negative |
| mctp_42P6UAAXX_1 | 823116 | 7.54% | Benign | Negative |
| mctp_301YWAAXX_1 | 1174999 | 7.66% | Benign | Negative |
| mctp_42P6UAAXX_4 | 1231884 | 7.67% | Benign | Negative |
| mctp_3064YAAXX_3 | 733492 | 7.70% | Benign | Negative |
| mctp_42P6UAAXX_2 | 894313 | 7.47% | Benign | Negative |
| mctp_30653AAXX_5 | 190504 | 5.47% | Benign | Negative |
| mctp_30CYNAAXX_6 | 39125 | 4.46% | Benign | Negative |
| mctp_30CYNAAXX_7 | 17102 | 4.48% | Benign | Negative |
| mctp_42P6UAAXX_3 | 928850 | 8.53% | Benign | Negative |
| mctp_3064YAAXX_7 | 714429 | 8.82% | Benign | Negative |
| mctp_30DM2AAXX_6 | 171398 | 5.72% | Benign | Negative |
| mctp_30DM2AAXX_4 | 100935 | 4.63% | Benign | Negative |
| mctp_30DM2AAXX_3 | 123775 | 4.70% | Benign | Negative |
| mctp_30DM2AAXX_1 | 93266 | 5.02% | Benign | Negative |
| mctp_30DM2AAXX_2 | 103544 | 4.95% | Benign | Negative |
| mctp_30DM2AAXX_7 | 87547 | 5.63% | Benign | Negative |
| mctp_30DM2AAXX_8 | 83463 | 5.67% | Benign | Negative |
| mctp_20FCKAAXX_1 | 122140 | 7.44% | Benign | Negative |
| mctp_20FCKAAXX_2 | 107996 | 7.18% | Benign | Negative |
| mctp_20FCKAAXX_4 | 118140 | 6.33% | Benign | Negative |
| mctp_20FCKAAXX_3 | 115876 | 6.31% | Benign | Negative |
| mctp_20FCKAAXX_7 | 122564 | 6.05% | Benign | Negative |
| mctp_20FCKAAXX_8 | 96704 | 6.09% | Benign | Negative |
| mctp_42D3NAAXX_6 | 891873 | 8.34% | Localized | ERG+ |
| mctp_42P6UAAXX_6 | 1035642 | 8.16% | Localized | ERG+ |
| mctp_20A0MAAXX_7 | 153160 | 6.39% | Localized | ERG+ |
| mctp_301YWAAXX_3 | 1231918 | 8.13% | Localized | ERG+ |
| mctp_20A0MAAXX_8 | 146853 | 5.66% | Localized | ERG+ |
| mctp_20093AAXX_3 | 77035 | 3.68% | Localized | ERG+ |

TABLE 1-continued

| | | | | |
|---|---|---|---|---|
| mctp_42D3NAAXX_7 | 745408 | 7.26% | Localized | ERG+ |
| mctp_42P6UAAXX_7 | 925564 | 7.25% | Localized | ERG+ |
| mctp_20A0MAAXX_6 | 168032 | 7.06% | Localized | ETV1+ |
| mctp_30Y5NAAXX_6 | 579321 | 5.16% | Localized | ETV1+ |
| mctp_20093AAXX_4 | 81777 | 4.08% | Localized | Negative |
| mctp_30CYNAAXX_2 | 142307 | 9.04% | Localized | Negative |
| mctp_20093AAXX_7 | 134758 | 6.17% | Localized | Negative |
| mctp_30CW7AAXX_4 | 200975 | 6.04% | Localized | Negative |
| mctp_30CYNAAXX_1 | 47049 | 4.72% | Localized | Negative |
| mctp_20093AAXX_6 | 80219 | 4.29% | Localized | Negative |
| mctp_20093AAXX_2 | 101279 | 4.17% | Localized | Negative |
| mctp_30CW7AAXX_3 | 261531 | 6.03% | Localized | Negative |
| mctp_20093AAXX_1 | 86343 | 3.89% | Localized | Negative |
| mctp_30CW7AAXX_5 | 211003 | 5.52% | Localized | Negative |
| mctp_30WU2AAXX_8 | 698526 | 8.25% | Localized | Negative |
| mctp_42PFAAAXX_3 | 1205327 | 8.12% | Localized | Negative |
| mctp_42CJFAAXX_4 | 1193752 | 8.78% | Localized | Negative |
| mctp_42B08AAXX_5 | 923485 | 8.19% | Localized | Negative |
| mctp_42B08AAXX_1 | 705179 | 9.31% | Localized | Negative |
| mctp_42CJJAAXX_5 | 1326961 | 7.71% | Localized | Negative |
| mctp_30WU2AAXX_1 | 1122174 | 7.11% | Localized | Negative |
| mctp_42B48AAXX_3 | 1043965 | 7.08% | Localized | Negative |
| mctp_30WU2AAXX_4 | 675880 | 6.75% | Localized | Negative |
| mctp_42NY4AAXX_4 | 954576 | 7.06% | Localized | Negative |
| mctp_42B48AAXX_6 | 1027559 | 7.63% | Localized | Negative |
| mctp_42B48AAXX_2 | 622237 | 8.24% | Localized | Negative |
| mctp_42PFAAAXX_1 | 852274 | 7.53% | Localized | Negative |
| mctp_42NY4AAXX_5 | 1472850 | 7.90% | Localized | Negative |
| mctp_42CJFAAXX_2 | 1301243 | 8.71% | Localized | Negative |
| mctp_30Y5NAAXX_4 | 649435 | 6.17% | Localized | Negative |
| mctp_42CJJAAXX_8 | 884253 | 7.23% | Localized | Negative |
| mctp_42B48AAXX_5 | 1147556 | 7.42% | Localized | Negative |
| mctp_42CJFAAXX_1 | 939157 | 8.51% | Localized | Negative |
| mctp_42CJJAAXX_6 | 432904 | 7.81% | Localized | Negative |
| mctp_42PF0AAXX_3 | 541558 | 7.21% | Localized | Negative |
| mctp_42CJFAAXX_3 | 516414 | 8.25% | Localized | Negative |
| mctp_42TB9AAXX_3 | 1265021 | 6.95% | Localized | Negative |
| mctp_42TB9AAXX_1 | 1356072 | 6.85% | Localized | Negative |
| mctp_42TB9AAXX_6 | 1420206 | 7.75% | Localized | Negative |
| mctp_42TB9AAXX_2 | 460799 | 6.45% | Localized | Negative |
| mctp_42TB9AAXX_7 | 1416932 | 7.61% | Localized | Negative |
| mctp_42P6UAAXX_5 | 1089323 | 7.20% | Localized | Negative |
| mctp_30lYWAAXX_2 | 1120415 | 7.26% | Localized | Negative |
| mctp_42B48AAXX_7 | 1075647 | 7.57% | Localized | Negative |
| mctp_30Y5NAAXX_3 | 634116 | 5.84% | Localized | Negative |
| mctp_42Y2TAAXX_2 | 1111429 | 6.41% | Localized | Negative |
| mctp_30DJDAAXX_5 | 345881 | 7.52% | Localized | Negative |
| mctp_42Y2TAAXX_3 | 814457 | 5.92% | Localized | Negative |
| mctp_30DJDAAXX_6 | 273181 | 6.97% | Localized | Negative |
| mctp_42B08AAXX_7 | 1055172 | 8.09% | Localized | Negative |
| mctp_20F66AAXX_6 | 109234 | 5.46% | Localized | Negative |
| mctp_30CW7AAXX_2 | 189576 | 6.22% | Localized | Negative |
| mctp_20F65AAXX_1 | 108306 | 5.50% | Localized | Negative |
| mctp_30U00AAXX_4 | 688415 | 7.32% | Localized | Negative |
| mctp_42CJFAAXX_8 | 386748 | 8.22% | Localized | Negative |
| mctp_42B08AAXX_8 | 718210 | 6.88% | Localized | Negative |
| mctp_20F66AAXX_7 | 153987 | 6.27% | Localized | Negative |
| mctp_30CW7AAXX_1 | 268911 | 7.09% | Localized | Negative |
| mctp_20F65AAXX_2 | 149558 | 6.31% | Localized | Negative |
| mctp_42P6UAAXX_8 | 78698 | 7.88% | Localized | Negative |
| mctp_42CJFAAXX_7 | 524419 | 7.13% | Localized | Negative |
| mctp_42PFAAAXX_4 | 610189 | 6.65% | Localized | Negative |
| mctp_30CW5AAXX_7 | 303738 | 9.36% | Localized | Negative |
| mctp_42D3NAAXX_2 | 903098 | 9.94% | Localized | Negative |
| mctp_42D3NAAXX_1 | 801237 | 9.38% | Localized | Negative |
| mctp_42D3NAAXX_3 | 1110643 | 9.72% | Localized | Negative |
| mctp_42TB9AAXX_4 | 734269 | 7.41% | Localized | Negative |
| mctp_42Y6WAAXX_6 | 1060520 | 7.54% | Localized | Negative |
| mctp_3064YAAXX_4 | 638903 | 7.41% | Localized | Negative |
| mctp_42B3YAAXX_4 | 354081 | 5.05% | Localized | Negative |
| mctp_20F66AAXX_3 | 116179 | 5.67% | Metastatic | ERG+ |
| mctp_20F66AAXX_4 | 127972 | 5.85% | Metastatic | ERG+ |
| mctp_20F69AAXX_4 | 99339 | 4.51% | Metastatic | ERG+ |
| mctp_20LV8AAXX_6 | 79073 | 3.54% | Metastatic | ERG+ |
| mctp_20LV8AAXX_7 | 80013 | 3.55% | Metastatic | ERG+ |
| mctp_20A0MAAXX_4 | 73792 | 4.01% | Metastatic | ERG+ |
| mctp_20PETAAXX_6 | 73464 | 4.13% | Metastatic | ERG+ |
| mctp_2074VAAXX_1 | 150938 | 5.90% | Metastatic | ERG+ |
| mctp_30CYNAAXX_4 | 139731 | 6.11% | Metastatic | ERG+ |
| mctp_30TYGAAXX_3 | 280553 | 7.60% | Metastatic | ERG+ |

TABLE 1-continued

| | | | | |
|---|---|---|---|---|
| mctp_42B20AAXX_6 | 950874 | 8.14% | Metastatic | ERG+ |
| mctp_2074VAAXX_3 | 95102 | 4.56% | Metastatic | ERG+ |
| mctp_2074VAAXX_5 | 91631 | 4.72% | Metastatic | ETV1+ |
| mctp_205K4AAXX_2 | 74579 | 4.38% | Metastatic | ETV1+ |
| mctp_20FETAAXX_8 | 82686 | 4.03% | Metastatic | ETV1+ |
| mctp_2074VAAXX_2 | 88780 | 4.06% | Metastatic | ETV1+ |
| mctp_3064YAAXX_6 | 1004315 | 9.80% | Metastatic | Negative |
| mctp_3064YAAXX_5 | 951893 | 9.19% | Metastatic | Negative |
| mctp_20EYPAAXX_7 | 108578 | 4.65% | Metastatic | Negative |
| mctp_42CJFAAXX_6 | 572135 | 6.49% | Metastatic | Negative |
| mctp_20EYPAAXX_6 | 104747 | 4.60% | Metastatic | Negative |
| mctp_30CW7AAXX_6 | 193678 | 5.05% | Metastatic | Negative |
| mctp_30TYGAAXX_1 | 141723 | 5.83% | Metastatic | Negative |
| mctp_205K4AAXX_1 | 126224 | 5.69% | Metastatic | Negative |
| mctp_20EYPAAXX_2 | 113774 | 4.86% | Metastatic | Negative |
| mctp_30TYGAAXX_5 | 236294 | 6.62% | Metastatic | Negative |
| mctp_20FETAAXX_7 | 102001 | 4.82% | Metastatic | Negative |
| mctp_20EYPAAXX_8 | 72729 | 4.33% | Metastatic | Negative |
| mctp_30CW7AAXX_7 | 200213 | 5.07% | Metastatic | Negative |
| TOTAL | 114448745 | 8.07% | | |

TABLE 2

| Chromosome | Cuffcompare | Classification tree filter | Merge intron-redundant transcripts | Informatic filters | Join transcript fragments | Filter intronic pre-mRNA | UCSC Canonical | Refseq |
|---|---|---|---|---|---|---|---|---|
| chr1 | 759121 | 272072 | 12701 | 5030 | 4489 | 3652 | 2499 | 3334 |
| chr2 | 581574 | 206281 | 9353 | 3224 | 2856 | 2361 | 1579 | 2023 |
| chr3 | 518621 | 167071 | 5706 | 2917 | 2560 | 2053 | 1312 | 1816 |
| chr4 | 329950 | 103113 | 5160 | 2019 | 1731 | 1444 | 977 | 1238 |
| chr5 | 380613 | 126139 | 5833 | 2365 | 2067 | 1694 | 1104 | 1465 |
| chr6 | 396848 | 145607 | 7580 | 2590 | 2309 | 1874 | 1370 | 1667 |
| chr7 | 432152 | 134051 | 6432 | 2355 | 2132 | 1703 | 1326 | 1583 |
| chr8 | 308935 | 97724 | 4226 | 1729 | 1529 | 1243 | 848 | 1210 |
| chr9 | 359300 | 122626 | 4069 | 1937 | 1767 | 1402 | 1114 | 1272 |
| chr10 | 354625 | 103512 | 3509 | 1672 | 1508 | 1226 | 998 | 1382 |
| chr11 | 424606 | 165211 | 6909 | 2922 | 2640 | 2102 | 1566 | 2023 |
| chr12 | 425280 | 138650 | 6872 | 2653 | 2373 | 1858 | 1233 | 1668 |
| chr13 | 159649 | 68284 | 3616 | 1118 | 908 | 751 | 425 | 549 |
| chr14 | 261497 | 123741 | 4842 | 1806 | 1619 | 1308 | 885 | 1102 |
| chr15 | 291241 | 108058 | 5816 | 1884 | 1626 | 1321 | 1362 | 1127 |
| chr16 | 364747 | 124182 | 3968 | 2002 | 1835 | 1386 | 1093 | 1311 |
| chr17 | 473261 | 168469 | 5581 | 2780 | 2582 | 1950 | 1480 | 1907 |
| chr18 | 144300 | 49112 | 2504 | 785 | 682 | 539 | 377 | 459 |
| chr19 | 494738 | 189411 | 7209 | 3543 | 3239 | 2269 | 1668 | 2314 |
| chr20 | 217223 | 70308 | 3059 | 1243 | 1158 | 907 | 659 | 926 |
| chr21 | 113368 | 29728 | 939 | 495 | 436 | 354 | 306 | 427 |
| chr22 | 223385 | 73509 | 2401 | 1156 | 1068 | 798 | 633 | 771 |
| chrX | 222743 | 94591 | 4997 | 1516 | 1349 | 1161 | 959 | 1841 |
| chrY | 15190 | 4039 | 272 | 81 | 71 | 59 | 148 | 254 |
| Total | 8253710 | 2885489 | 123554 | 49822 | 44534 | 35415 | 25921 | 33669 |

TABLE 3

| GEO ID | File name | Pubme ID | Antibody used | Antibody vender | Peak Finder Used | # Uniquely mapped reads (in millions) | # Peaks Called |
|---|---|---|---|---|---|---|---|
| GSM353631 | VCaP_regular_medium_H3K4me1 | 20478527 | ab8895 | Abcam | MACS | 6.96 | 23116 |
| GSM353632 | VCaP_regular_medium_H3K4me2 | 20478527 | ab7766 | Abcam | MACS | 5.97 | 74153 |
| GSM353620 | VCaP_regular_medium_H3K4me3 | 20478527 | ab8580 | Abcam | MACS | 10.95 | 30043 |
| GSM353624 | VCaP_regular_medium_H3K35me3 | 20478527 | ab9050 | Abcam | SICER | 9.91 | 29860 |
| GSM353629 | VCaP_regular_medium_Ace_H3 | 20478527 | 06-599 | Millipore | MACS | 4.76 | 41971 |
| GSM353622 | VCaP_regular_medium_Pan_H3 | 20478527 | ab1791 | Abcam | MACS | 5.91 | control |
| GSM353623 | VCaP_regular_medium_PolII | 20478527 | ab817 | Abcam | MACS | 6.88 | 16041 |
| GSM353634 | LNCaP_regular_medium_H3K4me1 | 20478527 | ab8895 | Abcam | MACS | 6.19 | 31109 |

TABLE 3-continued

| GEO ID | File name | Pubme ID | Antibody used | Antibody vender | Peak Finder Used | # Uniquely mapped reads (in millions) | # Peaks Called |
|---|---|---|---|---|---|---|---|
| GSM353635 | LNCaP_regular_medium_H3K4me2 | 20478527 | ab7766 | Abcam | MACS | 6.14 | 62061 |
| GSM353626 | LNCaP_regular_medium_H3K4me3 | 20478527 | ab8580 | Abcam | MACS | 10.22 | 19638 |
| GSM353627 | LNCaP_regular_medium_H3K36me3 | 20478527 | ab9050 | Abcam | SICER | 9.15 | 24932 |
| GSM353628 | LNCaP_regular_medium_Ace_H3 | 20478527 | 06-599 | Millipore | MACS | 4.76 | 33211 |
| GSM353617 | LNCaP_Eth1_PolII | 20478527 | ab817 | Abcam | MACS | 1.36 | 8232 |
| GSM353653 | tissue_H3K4me3 | 20478527 | ab8580 | Abcam | MACS | 11.85 | 23750 |

TABLE 4

| Category | Type | Name | Interval | Fold change (Unlogged) | SAM score ((r)/(s + s0)) |
|---|---|---|---|---|---|
| PROTEIN | UPREG. | TU_0084471_0 | chr5:33980375-34087779 | 12.75 | 7.71 |
| NOVEL | UPREG. | TU_0099865_0 | chr8:128087842-128095202 | 7.07 | 7.41 |
| PROTEIN | UPREG. | TU_0123088_0 | chr2:238147710-2381697 | 3.01 | 7.01 |
| ncRNA | UPREG. | TU_0102832_0 | chr9:78569118-78593537 | 12.23 | 6.93 |
| PROTEIN | UPREG. | TU_0078322_0 | chr12:32260254-32260805 | 4.52 | 6.82 |
| ncRNA | UPREG. | TU_0101270_0 | chr21:41853044-41875166 | 9.82 | 6.79 |
| PROTEIN | UPREG. | TU_0027326_0 | chrX:16874726-17077384 | 3.31 | 6.79 |
| PROTEIN | UPREG. | TU_0092114_0 | chr11:60223535-60239968 | 7.40 | 6.65 |
| PROTEIN | UPREG. | TU_0044448_0 | chr13:51509122-51537693 | 4.77 | 6.59 |
| PROTEIN | UPREG. | TU_0023159_0 | chr19:40224450-40249316 | 3.69 | 6.56 |
| PROTEIN | UPREG. | TU_0092116_0 | chr11:60238519-60239968 | 7.50 | 6.44 |
| PROTEIN | UPREG. | TU_0123090_0 | chr2:238164428-238165452 | 3.57 | 6.24 |
| ncRNA | UPREG. | TU_0046239_0 | chr4:1185645-1201937 | 5.19 | 6.22 |
| PROTEIN | UPREG. | TU_0122750_0 | chr2:231610299-231625861 | 4.56 | 6.14 |
| PROTEIN | UPREG. | TU_0082723_0 | chr12:1201452512-120219979 | 3.26 | 6.13 |
| PROTEIN | UPREG. | TU_0123089_0 | chr2:238164428-238165452 | 4.22 | 6.12 |
| PROTEIN | UPREG. | TU_0101111_0 | chr21:36989329-37045253 | 4.04 | 6.04 |
| PROTEIN | UPREG. | TU_0090152_0 | chr11:4965639-4969515 | 6.38 | 5.99 |
| PROTEIN | UPREG. | TU_0101113_0 | chr21:36994126-37045258 | 3.76 | 5.98 |
| PROTEIN | UPREG. | TU_0045026_0 | chr13:94660907-94668260 | 3.68 | 5.97 |
| ncRNA | UPREG. | TU_0101274_0 | chr21:41869930-41870631 | 8.95 | 5.88 |
| PROTEIN | UPREG. | TU_0046235_0 | chr4:1181913-1189142 | 4.28 | 5.87 |
| NOVEL | UPREG. | TU_0054603_0 | chr16:82380935-82394836 | 7.25 | 5.84 |
| PROTEIN | UPREG. | TU_0101308_0 | chr21:42605257-42608791 | 4.97 | 5.83 |
| PROTEIN | UPREG. | TU_0084137_0 | chr5:13981150-13997615 | 3.91 | 5.80 |
| PROTEIN | UPREG. | TU_0084127_0 | chr5:13882635-13892514 | 4.95 | 5.79 |
| PROTEIN | UPREG. | TU_0101119_0 | chr21:37034016-37045253 | 3.56 | 5.78 |
| PROTEIN | UPREG. | TU_0054919_0 | chr16:68188842-88191143 | 3.46 | 5.75 |
| PROTEIN | UPREG. | TU_0120563_0 | chr2:172658361-172662549 | 27.56 | 5.66 |
| PROTEIN | UPREG. | TU_0044977_0 | chr13:94524392-94621526 | 3.64 | 5.64 |
| PROTEIN | UPREG. | TU_0052614_0 | chr16:20542057-20616514 | 6.65 | 5.63 |
| NOVEL | UPREG. | TU_0084303_0 | chr5:15899476-15955226 | 7.46 | 5.61 |
| PROTEIN | UPREG. | TU_0060406_0 | chr1:28134091-28158290 | 3.03 | 5.61 |
| PROTEIN | UPREG. | TU_0060407_0 | chr1:28155047-28170460 | 2.41 | 5.60 |
| ncRNA | UPREG. | TU_0103252_0 | chr9:96357168-96369978 | 5.00 | 5.58 |
| PROTEIN | UPREG. | TU_0034719_0 | chr14:73490756-73655773 | 2.51 | 5.67 |
| PROTEIN | UPREG. | TU_0070457_0 | chr20:2258975-2269890 | 6.49 | 5.56 |
| NOVEL | UPREG. | TU_0114240_0 | chr2:1534883-1538193 | 5.25 | 5.54 |
| PROTEIN | UPREG. | TU_0087676_0 | chr5:138643394-138648458 | 2.75 | 5.50 |
| PROTEIN | UPREG. | TU_0084138_0 | chr5:13976388-13981285 | 4.09 | 5.48 |
| ncRNA | UPREG. | TU_0046237_0 | chr4:1162036-1195088 | 4.29 | 5.47 |
| ncRNA | UPREG. | TU_0060421_0 | chr1:28157480-28158290 | 3.12 | 5.44 |
| PROTEIN | UPREG. | TU_0061436_0 | chr1:37954250-37957136 | 2.66 | 5.41 |
| PROTEIN | UPREG. | TU_0044894_0 | chr13:94470096-94752898 | 2.85 | 5.38 |
| PROTEIN | UPREG. | TU_0034720_0 | chr14:73486609-73503474 | 2.20 | 5.38 |
| PROTEIN | UPREG. | TU_0090153_0 | chr11:4969009-4970185 | 7.37 | 5.34 |
| PROTEIN | UPREG. | TU_0061432_0 | chr1:37954250-37958679 | 2.65 | 5.31 |
| PROTEIN | UPREG. | TU_0090268_0 | chr11:6659768-6661138 | 1.76 | 5.30 |
| PROTEIN | UPREG. | TU_0084120_0 | chr5:13743434-13864864 | 3.59 | 5.29 |
| PROTEIN | UPREG. | TU_0045059_0 | chr13:94638351-94639152 | 2.93 | 5.28 |
| ncRNA | UPREG. | TU_0075807_0 | chr10:101676895-101680049 | 2.61 | 5.27 |
| PROTEIN | UPREG. | TU_0078285_0 | chr12:32150992-32421799 | 3.02 | 5.26 |
| PROTEIN | UPREG. | TU_0103019_0 | chr9:878266542-87905011 | 2.77 | 5.22 |
| PROTEIN | UPREG. | TU_0046244_0 | chr4:1185645-1236291 | 3.81 | 5.21 |
| PROTEIN | UPREG. | TU_0075664_0 | chr10:98752046-98935267 | 4.15 | 5.20 |
| PROTEIN | UPREG. | TU_0090949_0 | chr11:24475021-25059245 | 3.50 | 6.19 |
| NOVEL | UPREG. | TU_0099864_0 | chr8:128094589-128103681 | 3.56 | 6.17 |
| PROTEIN | UPREG. | TU_0030273_0 | chrx:106690714-106735138 | 3.52 | 5.15 |

TABLE 4-continued

| Category | Type | Name | Interval | Fold change (Unlogged) | SAM score ((r)/(s + s0)) |
|---|---|---|---|---|---|
| PROTEIN | UPREG. | TU_0090128_0 | chr11:4656012-4675667 | 5.26 | 5.15 |
| PROTEIN | UPREG. | TU_0017700_0 | chr17:51183394-51209728 | 2.05 | 5.13 |
| ncRNA | UPREG. | TU_0018760_0 | chr17:71645643-71652049 | 6.41 | 5.08 |
| PROTEIN | UPREG. | TU_0018765_0 | chr17:71652262-71747927 | 5.18 | 5.06 |
| ncRNA | UPREG. | TU_0114235_0 | chr2:1521347-1608386 | 4.22 | 5.04 |
| PROTEIN | UPREG. | TU_0084132_0 | chr5:13964466-13969509 | 4.30 | 5.03 |
| NOVEL | UPREG. | TU_0049368_0 | chr4:106772318-106772770 | 3.40 | 5.03 |
| PROTEIN | UPREG. | TU_0115204_0 | chr2:27175274-27195587 | 2.37 | 4.99 |
| PROTEIN | UPREG. | TU_0115205_0 | chr2:27163593-27178264 | 2.49 | 4.98 |
| PROTEIN | UPREG. | TU_0062449_0 | chr1:46418568-46424753 | 1.95 | 4.96 |
| PROTEIN | UPREG. | TU_0072027_0 | chr20:35964872-36007156 | 3.91 | 4.95 |
| ncRNA | UPREG. | TU_0086706_0 | chr5:116818427-116835522 | 2.91 | 4.92 |
| PROTEIN | UPREG. | TU_0084136_0 | chr5:13972327-13976416 | 3.37 | 4.91 |
| PROTEIN | UPREG. | TU_0042761_0 | chr13:23200813-23363667 | 3.54 | 4.90 |
| PROTEIN | UPREG. | TU_0114168_0 | chr15:99658271-99847175 | 2.25 | 4.89 |
| ncRNA | UPREG. | TU_0018764_0 | chr17:71650143-71652049 | 6.28 | 4.86 |
| PROTEIN | UPREG. | TU_0085832_0 | chr5:76150818-76167055 | 3.84 | 4.86 |
| NOVEL | UPREG. | TU_0090142_0 | chr11:4748677-4760303 | 12.08 | 4.86 |
| PROTEIN | UPREG. | TU_0103018_0 | chr9:87745936-87851451 | 2.41 | 4.83 |
| NOVEL | UPREG. | TU_0096472_0 | chr11:133844590-133862924 | 6.85 | 4.82 |
| PROTEIN | UPREG. | TU_0029229_0 | chrx:70349443-70577695 | 2.34 | 4.81 |
| NOVEL | UPREG. | TU_0084306_0 | chr5:15896315-15947068 | 5.37 | 4.78 |
| PROTEIN | UPREG. | TU_0024934_0 | chr19:54352845-54407356 | 1.88 | 4.77 |
| NOVEL | UPREG. | TU_0096473_0 | chr11:133844596-133862995 | 6.96 | 4.76 |
| ncRNA | UPREG. | TU_0101131_0 | chr21:36994126-37041774 | 3.57 | 4.74 |
| PROTEIN | UPREG. | TU_0008239_0 | chr7:7362890-7537552 | 3.00 | 4.73 |
| PROTEIN | UPREG. | TU_0000022_0 | chr6:1567650-2190842 | 2.14 | 4.72 |
| PROTEIN | UPREG. | TU_0065193_0 | chr1:145122471-145163544 | 2.72 | 4.72 |
| PROTEIN | UPREG. | TU_0061439_0 | chr1:37954250-37971671 | 2.46 | 4.71 |
| ncRNA | UPREG. | TU_0096470_0 | chr11:133841573-133880753 | 6.44 | 4.70 |
| PROTEIN | UPREG. | TU_0046213_0 | chr4:993725-995193 | 3.90 | 4.69 |
| NOVEL | UPREG. | TU_0075288_0 | chr12:32393283-32405731 | 2.47 | 4.67 |
| PROTEIN | UPREG. | TU_0101115_0 | chr21:37000839-37005920 | 3.31 | 4.67 |
| NOVEL | UPREG. | TU_0099884_0 | chr8:128301493-128307576 | 2.65 | 4.66 |
| PROTEIN | UPREG. | TU_0008459_0 | chr7:23685581-23708958 | 1.70 | 4.64 |
| PROTEIN | UPREG. | TU_0042767_0 | chr13:23186666-23204319 | 4.82 | 4.64 |
| PROTEIN | UPREG. | TU_0061430_0 | chr1:37930752-37957012 | 2.30 | 4.64 |
| PROTEIN | UPREG. | TU_0079451_0 | chr12:52696814-52736068 | 3.77 | 4.64 |
| PROTEIN | UPREG. | TU_0069545_0 | chr1:226711356-226711534 | 2.36 | 4.63 |
| PROTEIN | UPREG. | TU_0045837_0 | chr13:113151239-113151448 | 3.73 | 4.61 |
| PROTEIN | UPREG. | TU_0101138_0 | chr21:36994126-37804810 | 3.54 | 4.61 |
| PROTEIN | UPREG. | TU_0049362_0 | chr4:106693102-106771686 | 3.06 | 4.58 |
| PROTEIN | UPREG. | TU_0065044_0 | chr16:85589437-88613428 | 2.23 | 4.55 |
| PROTEIN | UPREG. | TU_0065605_0 | chr3:52689830-52704651 | 1.54 | 4.55 |
| ncRNA | UPREG. | TU_0062653_0 | chr1:5176544-51799759 | 2.52 | 4.54 |
| PROTEIN | UPREG. | TU_0080359_0 | chr12:63512292-63558851 | 1.87 | 4.53 |
| PROTEIN | UPREG. | TU_0012481_0 | chr7:111155336-111217880 | 2.04 | 4.52 |
| PROTEIN | UPREG. | TU_0076353_0 | chr10:115970327-115995953 | 10.34 | 4.52 |
| PROTEIN | UPREG. | TU_0099892_0 | chr8:128817416-128822629 | 2.33 | 4.52 |
| ncRNA | UPREG. | TU_0060484_0 | chr1:28706931-28707187 | 2.53 | 4.51 |
| PROTEIN | UPREG. | TU_0046232_0 | chr4:1147069-1175181 | 2.75 | 4.50 |
| PROTEIN | UPREG. | TU_0107858_0 | chr22:40664589-40673116 | 2.27 | 4.50 |
| PROTEIN | UPREG. | TU_0042794_0 | chr13:23228589-23228839 | 3.47 | 4.49 |
| PROTEIN | UPREG. | TU_0057850_0 | chr1:1523259-1525375 | 2.80 | 4.48 |
| PROTEIN | UPREG. | TU_0023156_0 | chr19:40109515-40127909 | 2.56 | 4.48 |
| PROTEIN | UPREG. | TU_0102821_0 | chr9:78263916-78312152 | 2.98 | 4.48 |
| PROTEIN | UPREG. | TU_0081659_0 | chr12:108636297-108700791 | 2.90 | 4.47 |
| PROTEIN | UPREG. | TU_0049370_0 | chr4:106776991-106847697 | 2.15 | 4.47 |
| PROTEIN | UPREG. | TU_0047672_0 | chr4:41807710-41840313 | 2.51 | 4.47 |
| PROTEIN | UPREG. | TU_0114959_0 | chr2:24865860-24869912 | 1.68 | 4.46 |
| PROTEIN | UPREG. | TU_0037043_0 | chr3:13332730-13436812 | 1.77 | 4.46 |
| PROTEIN | UPREG. | TU_0087443_0 | chr5:135237637-135247034 | 4.09 | 4.46 |
| PROTEIN | UPREG. | TU_0086635_0 | chr5:114489075-114543908 | 2.02 | 4.43 |
| PROTEIN | UPREG. | TU_0107859_0 | chr22:40654589-40665721 | 2.38 | 4.42 |
| NOVEL | UPREG. | TU_0106548_0 | chr22:22209111-22212055 | 6.49 | 4.42 |
| PROTEIN | UPREG. | TU_0067165_0 | chr1:160787907-160835987 | 1.81 | 4.40 |
| PROTEIN | UPREG. | TU_0020146_0 | chr19:3728970-3737293 | 2.53 | 4.39 |
| PROTEIN | UPREG. | TU_0107642_0 | chr22:39046992-39047479 | 1.69 | 4.38 |
| PROTEIN | UPREG. | TU_0016185_0 | chr17:31415814-31422953 | 3.63 | 4.38 |
| NOVEL | UPREG. | TU_0104717_0 | chr9:130697835-130698832 | 2.79 | 4.36 |
| PROTEIN | UPREG. | TU_0052105_0 | chr16:4785874-4786488 | 2.99 | 4.36 |
| PROTEIN | UPREG. | TU_0059663_0 | chr1:21795295-21850886 | 1.99 | 4.35 |
| PROTEIN | UPREG. | TU_0108030_0 | chr22:43527117-43638770 | 1.74 | 4.34 |
| PROTEIN | UPREG. | TU_0093781_0 | chr11:67151993-67154057 | 2.48 | 4.33 |
| PROTEIN | UPREG. | TU_0086924_0 | chr5:126233852-126241807 | 2.89 | 4.32 |

TABLE 4-continued

| Category | Type | Name | Interval | Fold change (Unlogged) | SAM score ((r)/ (s + s0) |
|---|---|---|---|---|---|
| PROTEIN | UPREG. | TU_0048191_0 | chr4:72423780-72424347 | 2.93 | 4.32 |
| PROTEIN | UPREG. | TU_0034727_0 | chr14:73508223-73508442 | 2.29 | 4.32 |
| PROTEIN | UPREG. | TU_0096297_0 | chr11:128342286-128353900 | 1.84 | 4.31 |
| PROTEIN | UPREG. | TU_0007829_0 | chr7:3625233-4275129 | 4.39 | 4.30 |
| PROTEIN | UPREG. | TU_0116252_0 | chr2:47449510-47467636 | 1.93 | 4.30 |
| PROTEIN | UPREG. | TU_0115216_0 | chr2:27175274-27177793 | 2.92 | 4.27 |
| PROTEIN | UPREG. | TU_0018409_0 | chr17:65013419-65049811 | 2.02 | 4.26 |
| PROTEIN | UPREG. | TU_0090847_0 | chr8:126511614-126519830 | 2.75 | 4.25 |
| PROTEIN | UPREG. | TU_0035152_0 | chr14:81062791-81063412 | 2.22 | 4.25 |
| PROTEIN | UPREG. | TU_0040936_0 | chr8:155391785-155458293 | 2.10 | 4.25 |
| PROTEIN | UPREG. | TU_0027558_0 | chrx:23595491-23514436 | 1.66 | 4.25 |
| PROTEIN | UPREG. | TU_0076460_0 | chr10:121248954-121292235 | 1.56 | 4.24 |
| PROTEIN | UPREG. | TU_0067170_0 | chr1:160826739-160826994 | 2.10 | 4.23 |
| PROTEIN | UPREG. | TU_0103050_0 | chr9:89409681-89512477 | 2.30 | 4.23 |
| PROTEIN | UPREG. | TU_0112868_0 | chr15:77390455-77402242 | 1.55 | 4.23 |
| PROTEIN | UPREG. | TU_0090960_0 | chr11:25059388-25880757 | 3.35 | 4.23 |
| PROTEIN | UPREG. | TU_0072165_0 | chr20:40142077-40204030 | 4.69 | 4.22 |
| PROTEIN | UPREG. | TU_0044687_0 | chr13:74756644-74954891 | 2.04 | 4.21 |
| ncRNA | UPREG. | TU_0096477_0 | chr11:133879414-133880753 | 4.43 | 4.21 |
| PROTEIN | UPREG. | TU_0093947_0 | chr11:68205575-68215218 | 4.41 | 4.20 |
| PROTEIN | UPREG. | TU_0103253_0 | chr9:96405246-96442373 | 1.69 | 4.20 |
| PROTEIN | UPREG. | TU_0091863_0 | chr11:57008498-57039966 | 2.69 | 4.20 |
| PROTEIN | UPREG. | TU_0106199_0 | chr22:18308042-16314411 | 3.94 | 4.20 |
| NOVEL | UPREG. | TU_0090140_0 | chr11:4748163-4769145 | 6.33 | 4.20 |
| PROTEIN | UPREG. | TU_0103051_0 | chr9:89302442-89409890 | 2.37 | 4.19 |
| NOVEL | UPREG. | TU_0078290_0 | chr12:32394534-32410898 | 3.20 | 4.19 |
| PROTEIN | UPREG. | TU_0029336_0 | chrx:70669659-70712461 | 1.70 | 4.18 |
| PROTEIN | UPREG. | TU_0092155_0 | chr11:60871597-60886554 | 1.80 | 4.18 |
| PROTEIN | UPREG. | TU_0095597_0 | chr11:114549577-114880335 | 1.75 | 4.18 |
| PROTEIN | UPREG. | TU_0082724_0 | chr12:120230545-120274516 | 1.42 | 4.17 |
| PROTEIN | UPREG. | TU_0079770_0 | chr12:65040665-55042824 | 4.25 | 4.16 |
| PROTEIN | UPREG. | TU_0000263_0 | chr6:4060925-4080831 | 1.55 | 4.16 |
| NOVEL | UPREG. | TU_0040394_0 | chr3:133418632-133441282 | 3.46 | 4.15 |
| PROTEIN | UPREG. | TU_0066594_0 | chr1:15424543-154257363 | 1.40 | 4.15 |
| PROTEIN | UPREG. | TU_0099852_0 | chr8:126515081-126519830 | 2.81 | 4.15 |
| PROTEIN | UPREG. | TU_0100363_0 | chr8:144891741-144899598 | 2.24 | 4.14 |
| PROTEIN | UPREG. | TU_0095461_0 | chr11:133751095-133757235 | 2.10 | 4.13 |
| ncRNA | UPREG. | TU_0044488_0 | chr13:51641093-51641310 | 2.76 | 4.13 |
| PROTEIN | UPREG. | TU_0048990_0 | chr4:95592056-95804933 | 2.30 | 4.13 |
| NOVEL | UPREG. | TU_0078293_0 | chr12:32396393-32414822 | 2.90 | 4.13 |
| PROTEIN | UPREG. | TU_0046201_0 | chr4:991841-1010686 | 2.57 | 4.12 |
| PROTEIN | UPREG. | TU_0091866_0 | chr11:57008498-57010253 | 2.54 | 4.12 |
| PROTEIN | UPREG. | TU_0011133_0 | chr7:94378726-94759741 | 1.77 | 4.12 |
| PROTEIN | UPREG. | TU_0122941_0 | chr2:234410713-234427931 | 3.28 | 4.12 |
| PROTEIN | UPREG. | TU_0084131_0 | chr6:13929889-13953380 | 2.62 | 4.12 |
| NOVEL | UPREG. | TU_0084142_0 | chr6:14017046-14021379 | 3.59 | 4.11 |
| PROTEIN | UPREG. | TU_0087955_0 | chr6:140931645-140931865 | 2.00 | 4.10 |
| PROTEIN | UPREG. | TU_0085953_0 | chr6:79430592-73410909 | 3.35 | 4.10 |
| PROTEIN | UPREG. | TU_0022288_0 | chr19:18557979-18360121 | 2.75 | 4.09 |
| PROTEIN | UPREG. | TU_0085951_0 | chr5:79366959-79414885 | 3.01 | 4.09 |
| PROTEIN | UPREG. | TU_0060849_0 | chr1:3257201-32574435 | 1.81 | 4.09 |
| PROTEIN | UPREG. | TU_0087441_0 | chr3:134934290-134942617 | 2.74 | 4.09 |
| PROTEIN | UPREG. | TU_0042725_0 | chr13:32148723-23200531 | 4.96 | 4.09 |
| PROTEIN | UPREG. | TU_0039018_0 | chr3:56510506-66634168 | 1.63 | 4.08 |
| PROTEIN | UPREG. | TU_0095299_0 | chr11:128340164-128347506 | 1.70 | 4.07 |
| PROTEIN | UPREG. | TU_0022290_0 | chr19:18357973-18359195 | 2.64 | 4.07 |
| PROTEIN | UPREG. | TU_0100684_0 | chr8:146190487-146191030 | 1.89 | 4.06 |
| PROTEIN | UPREG. | TU_0042974_0 | chr13:26148671-26148967 | 2.51 | 4.06 |
| NOVEL | UPREG. | TU_0084308_0 | chr6:15938753-15949124 | 4.08 | 4.06 |
| NOVEL | UPREG. | TU_0082746_0 | chr12:120197102-120197416 | 4.97 | 4.06 |
| PROTEIN | UPREG. | TU_0014355_0 | chr17:2650561-2887730 | 1.92 | 4.06 |
| PROTEIN | UPREG. | TU_0114110_0 | chr15:99250637-99274351 | 2.01 | 4.06 |
| PROTEIN | UPREG. | TU_0095341_0 | chr11:129534843-129585465 | 1.54 | 4.04 |
| PROTEIN | UPREG. | TU_0052083_0 | chr16:4734094-4805339 | 2.71 | 4.04 |
| NOVEL | UPREG. | TU_0078296_0 | chr12:32394534-32405549 | 2.92 | 4.04 |
| PROTEIN | UPREG. | TU_0084126_0 | chr6:13892443-13903812 | 3.64 | 4.03 |
| NOVEL | UPREG. | TU_0047312_0 | chr4:39237669-39222163 | 3.83 | 4.02 |
| PROTEIN | UPREG. | TU_0008287_0 | chr7:8119340-8268973 | 1.65 | 4.02 |
| PROTEIN | UPREG. | TU_0018937_0 | chr17:73714011-73714967 | 1.61 | 4.01 |
| PROTEIN | UPREG. | TU_0048995_0 | chr4:95805027-95808417 | 2.47 | 4.00 |
| PROTEIN | UPREG. | TU_0038694_0 | chr3:53810226-53855769 | 2.03 | 3.99 |
| ncRNA | UPREG. | TU_0046233_0 | chr4:1202157-1232168 | 2.45 | 3.99 |
| PROTEIN | UPREG. | TU_0019018_0 | chr17:75372094-75381243 | 2.25 | 3.98 |
| PROTEIN | UPREG. | TU_0042326_0 | chr3:199123974-199126319 | 1.77 | 3.98 |
| PROTEIN | UPREG. | TU_0099893_0 | chr8:128817416-128819105 | 2.33 | 3.98 |

TABLE 4-continued

| Category | Type | Name | Interval | Fold change (Unlogged) | SAM score ((r)/ (s + s0)) |
|---|---|---|---|---|---|
| PROTEIN | UPREG. | TU_0012491_0 | chr7:111304238-111362856 | 1.91 | 3.98 |
| PROTEIN | UPREG. | TU_0112335_0 | chr15:70816880-70864494 | 1.71 | 3.97 |
| PROTEIN | UPREG. | TU_0047954_0 | chr4:57020861-57038533 | 1.74 | 3.97 |
| PROTEIN | UPREG. | TU_0052565_0 | chr16:19362784-19409995 | 1.98 | 3.96 |
| NOVEL | UPREG. | TU_0042717_0 | chr13:23149908-23200198 | 4.95 | 3.96 |
| PROTEIN | UPREG. | TU_0017374_0 | chr17:43360056-43404182 | 1.53 | 3.95 |
| PROTEIN | UPREG. | TU_0071058_0 | chr20:20318209-20549154 | 2.02 | 3.96 |
| PROTEIN | UPREG. | TU_0105741_0 | chrX:6971017-6998339 | 2.20 | 3.95 |
| PROTEIN | UPREG. | TU_0018995_0 | chr17:74491566-74517485 | 1.64 | 3.94 |
| PROTEIN | UPREG. | TU_0103055_0 | chr9:89512509-89513286 | 1.92 | 3.93 |
| PROTEIN | UPREG. | TU_0041139_0 | chr3:171237964-171285906 | 1.91 | 3.93 |
| PROTEIN | UPREG. | TU_0042325_0 | chr3:199124975-199143480 | 1.74 | 3.93 |
| PROTEIN | UPREG. | TU_0020688_0 | chr3:95180054-8237335 | 1.90 | 3.93 |
| PROTEIN | UPREG. | TU_0118314_0 | chr2:99086923-99100654 | 1.78 | 3.92 |
| PROTEIN | UPREG. | TU_0017875_0 | chr17:54652767-54706896 | 2.33 | 3.92 |
| PROTEIN | UPREG. | TU_0037277_0 | chr3:24134438-24511318 | 1.75 | 3.92 |
| PROTEIN | UPREG. | TU_0047593_0 | chr4:40446839-40457235 | 1.90 | 3.91 |
| PROTEIN | UPREG. | TU_0114108_0 | chr16:139235494-99274389 | 2.00 | 3.91 |
| ncRNA | UPREG. | TU_0024530_0 | chr19:50889160-50969766 | 1.72 | 3.91 |
| PROTEIN | UPREG. | TU_0008957_0 | chr7:38308886-38325838 | 2.62 | 3.91 |
| PROTEIN | UPREG. | TU_0043122_0 | chr13:28981556-28989371 | 1.73 | 3.90 |
| PROTEIN | UPREG. | TU_0076644_0 | chr10:127398227-127398696 | 2.06 | 3.90 |
| PROTEIN | UPREG. | TU_0045423_0 | chr13:100053877-100125073 | 2.02 | 3.89 |
| PROTEIN | UPREG. | TU_0045495_0 | chr13:107720446-107737194 | 2.06 | 3.88 |
| PROTEIN | UPREG. | TU_0076648_0 | chr10:127412714-127442685 | 1.64 | 3.88 |
| NOVEL | UPREG. | TU_0068857_0 | chr6:172259171-172275517 | 1.69 | 3.87 |
| NOVEL | UPREG. | TU_0044453_0 | chr13:51505777-61524622 | 2.98 | 3.86 |
| NOVEL | UPREG. | TU_0047330_0 | chr4:39217641-39222163 | 3.43 | 3.86 |
| PROTEIN | UPREG. | TU_0100838_0 | chr21:30508275-30630244 | 2.43 | 3.86 |
| NOVEL | UPREG. | TU_0106544_0 | chr22:22241421-22220506 | 4.27 | 3.85 |
| ncRNA | UPREG. | TU_0100275_0 | chr8:144520506-144537551 | 2.11 | 3.85 |
| PROTEIN | UPREG. | TU_0057466_0 | chr18:72853744-72866791 | 1.58 | 3.84 |
| PROTEIN | UPREG. | TU_0040010_0 | chr3:126311839-126412928 | 2.16 | 3.84 |
| PROTEIN | UPREG. | TU_0042800_0 | chr13:23360816-23370548 | 2.73 | 3.84 |
| PROTEIN | UPREG. | TU_0117501_0 | chr2:74065748-74174193 | 1.71 | 3.83 |
| PROTEIN | UPREG. | TU_0053389_0 | chr16:45673980-45701001 | 2.66 | 3.83 |
| PROTEIN | UPREG. | TU_0057944_0 | chr5:140674777-140978925 | 1.47 | 3.85 |
| PROTEIN | UPREG. | TU_0017393_0 | chr17:43389397-43390300 | 1.90 | 3.82 |
| PROTEIN | UPREG. | TU_0008910_0 | chr7:38257158-38271020 | 1.93 | 3.82 |
| PROTEIN | UPREG. | TU_0033383_0 | chr14:50259793-50367616 | 1.51 | 3.82 |
| PROTEIN | UPREG. | TU_0048911_0 | chr4:139304784-139382962 | 2.45 | 3.82 |
| PROTEIN | UPREG. | TU_0024366_0 | chr19:50100808-50104487 | 1.86 | 3.82 |
| PROTEIN | UPREG. | TU_0070109_0 | chr1:243979271-244159914 | 1.56 | 3.81 |
| PROTEIN | UPREG. | TU_0120975_0 | chr2:182104631-182103832 | 1.86 | 3.80 |
| NOVEL | UPREG. | TU_0044933_0 | chr13:94755992-94760688 | 2.52 | 3.80 |
| PROTEIN | UPREG. | TU_0103689_0 | chr9:111019219-111122750 | 1.75 | 3.80 |
| PROTEIN | UPREG. | TU_0096450_0 | chr11:133734857-133786962 | 2.09 | 3.79 |
| PROTEIN | UPREG. | TU_0071115_0 | chr20:24934888-24986948 | 1.48 | 3.79 |
| PROTEIN | UPREG. | TU_0093783_0 | chr11:67153661-67153870 | 2.48 | 3.79 |
| PROTEIN | UPREG. | TU_0047691_0 | chr4:40457999-40508655 | 1.79 | 3.79 |
| PROTEIN | UPREG. | TU_0112336_0 | chr16:70830765-70838346 | 1.63 | 3.78 |
| PROTEIN | UPREG. | TU_0066664_0 | chr1:154481433-154435049 | 2.29 | 3.78 |
| PROTEIN | UPREG. | TU_0018812_0 | chr17:72119376-72151549 | 3.38 | 3.78 |
| PROTEIN | UPREG. | TU_0130225_0 | chr15:43510091-43512722 | 3.69 | 3.78 |
| ncRNA | UPREG. | TU_0054545_0 | chr16:79431010-79431652 | 10.26 | 3.78 |
| PROTEIN | UPREG. | TU_0107643_0 | chr22:39072466-39093168 | 1.36 | 3.78 |
| PROTEIN | UPREG. | TU_0025230_0 | chr19:55992773-56000199 | 1.86 | 3.78 |
| PROTEIN | UPREG. | TU_0012480_0 | chr7:111153704-111155311 | 1.81 | 3.77 |
| PROTEIN | UPREG. | TU_0070621_0 | chr20:8997167-9409281 | 1.64 | 3.77 |
| PROTEIN | UPREG. | TU_0103873_0 | chr9:115151636-115178183 | 1.52 | 3.77 |
| PROTEIN | UPREG. | TU_0018813_0 | chr17:72128611-72133119 | 3.56 | 3.76 |
| NOVEL | UPREG. | TU_0112004_0 | chr15:67644390-67650387 | 3.56 | 3.76 |
| PROTEIN | UPREG. | TU_0043118_0 | chr13:25981555-29067879 | 1.76 | 3.76 |
| NOVEL | UPREG. | TU_0112005_0 | chr15:67645590-67775246 | 3.12 | 3.76 |
| NOVEL | UPREG. | TU_0060446_0 | chr1:28438629-28450158 | 3.23 | 3.75 |
| PROTEIN | UPREG. | TU_0122972_0 | chr2:236068012-236432693 | 1.69 | 3.75 |
| NOVEL | UPREG. | TU_0106545_0 | chr22:22218478-22219162 | 3.99 | 3.74 |
| PROTEIN | UPREG. | TU_0087283_0 | chr5:133753241-133766074 | 1.85 | 3.74 |
| ncRNA | UPREG. | TU_0025312_0 | chr19:57058519-57145170 | 1.89 | 3.74 |
| PROTEIN | UPREG. | TU_0079679_0 | chr12:54760142-54783545 | 1.58 | 3.73 |
| PROTEIN | UPREG. | TU_0074564_0 | chr10:64241765-6424612 | 2.62 | 3.73 |
| PROTEIN | UPREG. | TU_0106189_0 | chr22:18235213-18328816 | 1.82 | 3.73 |
| PROTEIN | UPREG. | TU_0078994_0 | chr12:49412412-49428706 | 1.41 | 3.72 |
| ncRNA | UPREG. | TU_0003229_0 | chr6:41598975-41621874 | 2.05 | 3.72 |
| PROTEIN | UPREG. | TU_0040937_0 | chr3:155439710-155458293 | 1.96 | 3.72 |

TABLE 4-continued

| Category | Type | Name | Interval | Fold change (Unlogged) | SAM score ((r)/(s + s0)) |
|---|---|---|---|---|---|
| PROTEIN | UPREG. | TU_0040095_0 | chr3:128530751-128574336 | 1.87 | 3.72 |
| NOVEL | UPREG. | TU_0106542_0 | chr22:22211315-22220506 | 3.77 | 3.71 |
| PROTEIN | UPREG. | TU_0019375_0 | chr17:77608812-77616980 | 1.63 | 3.71 |
| PROTEIN | UPREG. | TU_0042563_0 | chr13:20264762-20334966 | 1.85 | 3.71 |
| PROTEIN | UPREG. | TU_0103386_0 | chr9:99095734-99110148 | 1.89 | 3.71 |
| PROTEIN | UPREG. | TU_0030004_0 | chrX:100534013-100534540 | 1.84 | 3.71 |
| NOVEL | UPREG. | TU_0089906_0 | chr11:1042845-1045705 | 2.94 | 3.71 |
| NOVEL | UPREG. | TU_0089014_0 | chr5:176014905-176015351 | 2.01 | 3.71 |
| ncRNA | UPREG. | TU_0056173_0 | chr13:22523074-22537627 | 3.31 | 3.70 |
| PROTEIN | UPREG. | TU_0052880_0 | chr16:28393117-28411069 | 1.48 | 3.70 |
| PROTEIN | UPREG. | TU_0100355_0 | chr8:144884230-144910177 | 2.00 | 3.69 |
| PROTEIN | UPREG. | TU_0096216_0 | chr11:125271293-125271517 | 2.08 | 3.69 |
| PROTEIN | UPREG. | TU_0092161_0 | chr11:60884289-60892364 | 1.99 | 3.68 |
| PROTEIN | UPREG. | TU_0086926_0 | chr5:126241963-126394149 | 2.27 | 3.68 |
| NOVEL | UPREG. | TU_0088230_0 | chr5:148864170-148864752 | 1.94 | 3.68 |
| ncRNA | UPREG. | TU_0099940_0 | chr8:129065546-129182684 | 1.61 | 3.68 |
| PROTEIN | UPREG. | TU_0089017_0 | chr5:176222085-176240501 | 10.21 | 3.67 |
| PROTEIN | UPREG. | TU_0078586_0 | chr12:46643629-46648944 | 1.47 | 3.67 |
| PROTEIN | UPREG. | TU_0053467_0 | chr16:51028455-51138080 | 2.19 | 3.67 |
| PROTEIN | UPREG. | TU_0089452_0 | chr5:179258704-179258997 | 1.62 | 3.67 |
| PROTEIN | UPREG. | TU_0076329_0 | chr10:115501382-115531028 | 2.60 | 3.67 |
| PROTEIN | UPREG. | TU_0047688_0 | chr4:42105164-42354144 | 1.68 | 3.67 |
| PROTEIN | UPREG. | TU_0059142_0 | chr1:16203274-16206548 | 12.41 | 3.67 |
| PROTEIN | UPREG. | TU_0116906_0 | chr2:63135968-63138462 | 2.81 | 3.66 |
| PROTEIN | UPREG. | TU_0000154_0 | chr6:3063923-3099152 | 1.53 | 3.66 |
| PROTEIN | UPREG. | TU_0088782_0 | chr5:170625426-170659593 | 1.78 | 3.66 |
| NOVEL | UPREG. | TU_0089905_0 | chr11:1042845-1045705 | 2.77 | 3.66 |
| PROTEIN | UPREG. | TU_0101704_0 | chr9:8266495-3516005 | 2.33 | 3.64 |
| ncRNA | UPREG. | TU_0044897_0 | chr13:94746488-94760688 | 2.17 | 3.64 |
| PROTEIN | UPREG. | TU_0071059_0 | chr20:20549245-20641260 | 2.39 | 3.64 |
| ncRNA | UPREG. | TU_0046268_0 | chr4:1199598-1211108 | 1.93 | 3.63 |
| PROTEIN | UPREG. | TU_0071601_0 | chr20:32827590-32828002 | 1.75 | 3.62 |
| PROTEIN | UPREG. | TU_0100712_0 | chr21:15258179-15359100 | 2.14 | 3.62 |
| PROTEIN | UPREG. | TU_0092156_0 | chr11:60885030-60893249 | 1.45 | 3.62 |
| PROTEIN | UPREG. | TU_0091402_0 | chr11:46255779-46299542 | 1.71 | 3.62 |
| PROTEIN | UPREG. | TU_0039019_0 | chr3:6637322-66514060 | 1.50 | 3.62 |
| PROTEIN | UPREG. | TU_0100378_0 | chr8:144899799-144900640 | 2.00 | 3.62 |
| NOVEL | UPREG. | TU_0112025_0 | chr15:67780574-67782345 | 3.42 | 3.62 |
| PROTEIN | UPREG. | TU_0106031_0 | chr22:16336630-16412806 | 2.01 | 3.62 |
| PROTEIN | UPREG. | TU_0050785_0 | chr4:174395360-174453823 | 2.36 | 3.61 |
| PROTEIN | UPREG. | TU_0058834_0 | chr1:11768665-11783670 | 1.50 | 3.61 |
| PROTEIN | UPREG. | TU_0039496_0 | chr3:106755939-106754201 | 1.99 | 3.61 |
| ncRNA | UPREG. | TU_0098397_0 | chr8:69379259-69406175 | 2.73 | 3.61 |
| PROTEIN | UPREG. | TU_0017847_0 | chr17:54188675-54413808 | 2.82 | 3.61 |
| PROTEIN | UPREG. | TU_0108299_0 | chr22:49267227-49270226 | 2.03 | 3.60 |
| PROTEIN | UPREG. | TU_0076846_0 | chr10:135042714-135056670 | 2.27 | 3.59 |
| PROTEIN | UPREG. | TU_0096351_0 | chr11:129611827-129689996 | 1.61 | 3.59 |
| PROTEIN | UPREG. | TU_0019298_0 | chr17:77242472-77300154 | 1.51 | 3.59 |
| PROTEIN | UPREG. | TU_0057465_0 | chr18:72830973-72973769 | 1.56 | 3.59 |
| PROTEIN | UPREG. | TU_0013475_0 | chr7:148137800-148212367 | 1.74 | 3.59 |
| PROTEIN | UPREG. | TU_0001426_0 | chr6:28655044-28662198 | 2.59 | 3.59 |
| NOVEL | UPREG. | TU_0106541_0 | chr22:22209111-22219162 | 4.02 | 3.58 |
| PROTEIN | UPREG. | TU_0073805_0 | chr10:19005564-19007055 | 1.84 | 3.58 |
| PROTEIN | UPREG. | TU_0040100_0 | chr3:129253916-129289610 | 1.39 | 3.58 |
| PROTEIN | UPREG. | TU_0001431_0 | chr6:28978594-28999755 | 1.33 | 3.58 |
| PROTEIN | UPREG. | TU_0076643_0 | chr10:127398227-127407663 | 1.73 | 3.57 |
| PROTEIN | UPREG. | TU_0089137_0 | chr5:176814485-176815986 | 1.93 | 3.57 |
| PROTEIN | UPREG. | TU_0098700_0 | chr8:82805988-82833618 | 1.76 | 3.57 |
| PROTEIN | UPREG. | TU_0093785_0 | chr11:67186209-67198838 | 8.74 | 3.57 |
| NOVEL | UPREG. | TU_0056158_0 | chr18:22477042-22477666 | 5.05 | 3.57 |
| PROTEIN | UPREG. | TU_0067222_0 | chr1:164063363-164147501 | 1.63 | 3.57 |
| PROTEIN | UPREG. | TU_0052172_0 | chr16:8799176-8799379 | 1.61 | 3.57 |
| PROTEIN | UPREG. | TU_0008350_0 | chr7:16652301-16712672 | 1.46 | 3.57 |
| PROTEIN | UPREG. | TU_0035610_0 | chr14:93580687-93682188 | 2.05 | 3.56 |
| PROTEIN | UPREG. | TU_0000168_0 | chr6:3100128-3102765 | 2.10 | 3.56 |
| PROTEIN | UPREG. | TU_0039649_0 | chr3:115180992-115164502 | 1.72 | 3.56 |
| PROTEIN | UPREG. | TU_0052845_0 | chr16:27143818-27187607 | 1.42 | 3.56 |
| NOVEL | UPREG. | TU_0024959_0 | chr19:54450100-54452968 | 2.11 | 3.56 |
| PROTEIN | UPREG. | TU_0008504_0 | chr7:24656812-24693891 | 1.99 | 3.55 |
| PROTEIN | UPREG. | TU_0061102_0 | chr1:35671678-35795597 | 1.44 | 3.55 |
| PROTEIN | UPREG. | TU_0032890_0 | chr14:36736878-36788106 | 2.36 | 3.55 |
| ncRNA | UPREG. | TU_0046241_0 | chr4:1158292-1167160 | 2.53 | 3.55 |
| NOVEL | UPREG. | TU_0008499_0 | chr7:24236191-24236455 | 5.44 | 3.54 |
| PROTEIN | UPREG. | TU_0100172_0 | chr8:142471307-142511866 | 1.78 | 3.54 |
| NOVEL | UPREG. | TU_0086543_0 | chr3:110311813-110312092 | 1.53 | 3.53 |

TABLE 4-continued

| Category | Type | Name | Interval | Fold change (Unlogged) | SAM score ((r)/ (s + s0) |
|---|---|---|---|---|---|
| PROTEIN | UPREG. | TU_0072450_0 | chr20:44619899-44747359 | 1.83 | 3.53 |
| NOVEL | UPREG. | TU_0044931_0 | chr13:94755980-94759335 | 2.15 | 3.53 |
| PROTEIN | UPREG. | TU_0093950_0 | chr11:68214748-68215218 | 1.49 | 3.53 |
| PROTEIN | UPREG. | TU_0006239_0 | chr13:138649313-138671427 | 2.22 | 3.53 |
| PROTEIN | UPREG. | TU_0065894_0 | chr1:150044684-150070988 | 1.54 | 3.52 |
| PROTEIN | UPREG. | TU_0078675_0 | chr12:47602047-47602939 | 1.58 | 3.52 |
| PROTEIN | UPREG. | TU_0052150_0 | chr16:8799176-8854674 | 1.42 | 3.52 |
| NOVEL | UPREG. | TU_0112021_0 | chr15:67762926-67783593 | 2.66 | 3.52 |
| PROTEIN | UPREG. | TU_0041581_0 | chr3:18545013-185459240 | 1.77 | 3.52 |
| PROTEIN | UPREG. | TU_0017269_0 | chr17:42127174-42189979 | 1.59 | 3.52 |
| PROTEIN | UPREG. | TU_0103138_0 | chr9:94055563-940056563 | 1.61 | 3.52 |
| PROTEIN | UPREG. | TU_0078683_0 | chr12:47603989-47604485 | 1.69 | 3.52 |
| PROTEIN | UPREG. | TU_0090209_0 | chr11:6453771-6459210 | 1.44 | 3.51 |
| ncRNA | UPREG. | TU_0045193_0 | chr13:93851959-97852689 | 1.99 | 3.51 |
| PROTEIN | UPREG. | TU_0050499_0 | chr7:156862572-156862939 | 1.82 | 3.51 |
| PROTEIN | UPREG. | TU_0058025_0 | chr5:142130134-142254086 | 1.89 | 3.51 |
| PROTEIN | UPREG. | TU_0052554_0 | chr16:19329285-19424724 | 1.78 | 3.51 |
| PROTEIN | UPREG. | TU_0085663_0 | chr6:70918890-70990273 | 2.39 | 3.51 |
| PROTEIN | UPREG. | TU_0101238_0 | chr21:41610494-41641888 | 1.89 | 3.50 |
| PROTEIN | UPREG. | TU_0098639_0 | chr8:82355436-82355977 | 4.15 | 3.49 |
| PROTEIN | UPREG. | TU_0100271_0 | chr8:144522379-144537561 | 1.93 | 3.49 |
| PROTEIN | UPREG. | TU_0013258_0 | chr7:139750340-139773086 | 1.85 | 3.49 |
| PROTEIN | UPREG. | TU_0122559_0 | chr2:224338108-224338327 | 2.32 | 3.49 |
| PROTEIN | UPREG. | TU_0068947_0 | chr1:212567070-212567723 | 1.74 | 3.48 |
| PROTEIN | UPREG. | TU_0101300_0 | chr21:42512421-42593934 | 1.60 | 3.48 |
| PROTEIN | UPREG. | TU_0105268_0 | chr9:138238031-138277254 | 1.49 | 3.47 |
| PROTEIN | UPREG. | TU_0080269_0 | chr12:62524730-62664317 | 2.05 | 3.47 |
| PROTEIN | UPREG. | TU_0001992_0 | chr6:31939105-31955076 | 1.56 | 3.47 |
| PROTEIN | UPREG. | TU_0018485_0 | chr17:70458432-70480451 | 1.58 | 3.47 |
| ncRNA | UPREG. | TU_0050495_0 | chr1:28705947-28706605 | 1.60 | 3.45 |
| PROTEIN | UPREG. | TU_0085975_0 | chr5:79478814-79496113 | 1.91 | 3.46 |
| PROTEIN | UPREG. | TU_0018919_0 | chr17:73678343-73714970 | 1.48 | 3.46 |
| ncRNA | UPREG. | TU_0054534_0 | chr15:79404014-79431652 | 9.85 | 3.46 |
| PROTEIN | UPREG. | TU_0076107_0 | chr10:104464315-104486075 | 1.67 | 3.45 |
| ncRNA | UPREG. | TU_0069658_0 | chr1:229724782-229731269 | 1.75 | 3.45 |
| NOVEL | UPREG. | TU_0120387_0 | chr2:170267824-170281386 | 2.10 | 3.45 |
| PROTEIN | UPREG. | TU_0015665_0 | chr17:24073407-24077926 | 1.52 | 3.45 |
| ncRNA | UPREG. | TU_0070414_0 | chr20:325059-1303172 | 1.65 | 3.45 |
| NOVEL | UPREG. | TU_0072624_0 | chr20:47335522-47338977 | 1.65 | 3.45 |
| PROTEIN | UPREG. | TU_0012495_0 | chr7:111373031-111411626 | 2.29 | 3.45 |
| PROTEIN | UPREG. | TU_0076659_0 | chr10:127514501-127575128 | 1.31 | 3.45 |
| PROTEIN | UPREG. | TU_0088525_0 | chr5:156625701-156755178 | 1.53 | 3.45 |
| PROTEIN | UPREG. | TU_0046096_0 | chr4:759449-809939 | 2.01 | 3.44 |
| ncRNA | UPREG. | TU_0074332_0 | chr10:43420869-43421283 | 1.52 | 3.44 |
| PROTEIN | UPREG. | TU_0062983_0 | chr12:121778239-121779189 | 2.65 | 3.44 |
| PROTEIN | UPREG. | TU_0008361_0 | chr7:16759923-16790805 | 1.58 | 3.44 |
| PROTEIN | UPREG. | TU_0061443_0 | chr1:38032067-38039550 | 1.67 | 3.44 |
| PROTEIN | UPREG. | TU_0042715_0 | chr13:25148223-23264319 | 3.68 | 3.43 |
| ncRNA | UPREG. | TU_0119128_0 | chr2:118310197-118313068 | 1.62 | 3.43 |
| PROTEIN | UPREG. | TU_0112349_0 | chr15:70834440-70835126 | 1.67 | 3.43 |
| PROTEIN | UPREG. | TU_0027543_0 | chrX:21921233-21922374 | 2.45 | 3.43 |
| PROTEIN | UPREG. | TU_0062582_0 | chr1:47489058-47552320 | 1.83 | 3.43 |
| ncRNA | UPREG. | TU_0050791_0 | chr4:174322695-174323924 | 2.13 | 3.41 |
| PROTEIN | UPREG. | TU_0048346_0 | chr4:77175264-77176185 | 2.48 | 3.41 |
| ncRNA | UPREG. | TU_0093068_0 | chr13:64956616-64961189 | 2.13 | 3.41 |
| PROTEIN | UPREG. | TU_0033869_0 | chr14:60248258-60260801 | 1.71 | 3.41 |
| PROTEIN | UPREG. | TU_0000031_0 | chr6:2190031-2190908 | 2.44 | 3.41 |
| PROTEIN | UPREG. | TU_0082131_0 | chr12:113151572-11135227 | 1.85 | 3.40 |
| PROTEIN | UPREG. | TU_0038169_0 | chr3:49035494-49041923 | 1.35 | 3.40 |
| NOVEL | UPREG. | TU_0044898_0 | chr13:94753009-94760688 | 2.11 | 3.40 |
| PROTEIN | UPREG. | TU_0089144_0 | chr5:176814485-176815986 | 1.86 | 3.40 |
| PROTEIN | UPREG. | TU_0094504_0 | chr11:74812477-74817273 | 2.40 | 3.40 |
| PROTEIN | UPREG. | TU_0035633_0 | chr14:94304291-94305127 | 2.17 | 3.40 |
| PROTEIN | UPREG. | TU_0085819_0 | chr5:75734806-76039614 | 1.64 | 3.40 |
| PROTEIN | UPREG. | TU_0061431_0 | chr1:37961347-37973585 | 2.62 | 3.40 |
| NOVEL | UPREG. | TU_0078299_0 | chr12:32290896-53034598 | 3.67 | 3.39 |
| PROTEIN | UPREG. | TU_0004059_0 | chr6:52976378-53034598 | 1.65 | 3.39 |
| PROTEIN | UPREG. | TU_0098927_0 | chr8:95722432-95788870 | 1.48 | 3.39 |
| ncRNA | UPREG. | TU_0013886_0 | chr7:155957953-156090820 | 2.50 | 3.39 |
| PROTEIN | UPREG. | TU_0068377_0 | chr1:201452418-201458956 | 1.84 | 3.39 |
| NOVEL | UPREG. | TU_0101085_0 | chr21:36419563-36421930 | 1.84 | 3.39 |
| PROTEIN | UPREG. | TU_0062957_0 | chr1:54089897-54128073 | 1.43 | 3.39 |
| PROTEIN | UPREG. | TU_0099854_0 | chr8:127633901-127639897 | 1.63 | 3.38 |
| PROTEIN | UPREG. | TU_0048743_0 | chr4:87924751-87955166 | 1.47 | 3.38 |
| PROTEIN | UPREG. | TU_0086478_0 | chr5:102510255-102521832 | 1.95 | 3.38 |

TABLE 4-continued

| Category | Type | Name | Interval | Fold change (Unlogged) | SAM score ((r)/ (s + s0)) |
|---|---|---|---|---|---|
| PROTEIN | UPREG. | TU_0120565_0 | chr2:172672776-172675279 | 4.31 | 3.38 |
| PROTEIN | UPREG. | TU_0122360_0 | chr2:219554051-219557439 | 2.92 | 3.38 |
| PROTEIN | UPREG. | TU_0092154_0 | chr11:60857271-60874474 | 1.44 | 3.37 |
| PROTEIN | UPREG. | TU_0015718_0 | chr17:24095069-24100305 | 1.64 | 3.37 |
| PROTEIN | UPREG. | TU_0039284_0 | chr8:95208686-95249573 | 2.23 | 3.37 |
| PROTEIN | UPREG. | TU_0082089_0 | chr12:111082307-111187476 | 1.44 | 3.37 |
| PROTEIN | UPREG. | TU_0035148_0 | chr14:81009021-81069951 | 1.64 | 3.37 |
| PROTEIN | UPREG. | TU_0054849_0 | chr16:87403253-87406669 | 1.47 | 3.37 |
| PROTEIN | UPREG. | TU_0113375_0 | chr15:87432680-87545107 | 2.13 | 3.36 |
| PROTEIN | UPREG. | TU_0019481_0 | chr17:77998514-77999441 | 1.55 | 3.36 |
| PROTEIN | UPREG. | TU_0007004_0 | chr6:15896021-158440190 | 1.47 | 3.36 |
| PROTEIN | UPREG. | TU_0092190_0 | chr11:60876795-60877493 | 1.85 | 3.36 |
| ncRNA | UPREG. | TU_0001995_0 | chr6:31941546-31959679 | 1.43 | 3.36 |
| NOVEL | UPREG. | TU_0066689_0 | chr1:154569233-154510967 | 1.61 | 3.36 |
| PROTEIN | UPREG. | TU_0035151_0 | chr14:81015445-81021875 | 2.00 | 3.35 |
| PROTEIN | UPREG. | TU_0092865_0 | chr11:6395211-63975675 | 3.20 | 3.35 |
| PROTEIN | UPREG. | TU_0050482_0 | chr4:156807332-156877628 | 1.69 | 3.35 |
| PROTEIN | UPREG. | TU_0022391_0 | chr19:19076718-19094443 | 1.60 | 3.35 |
| PROTEIN | UPREG. | TU_0048729_0 | chr4:87734463-87924743 | 1.74 | 3.35 |
| PROTEIN | UPREG. | TU_0103472_0 | chr9:100564124-100570357 | 1.61 | 3.35 |
| PROTEIN | UPREG. | TU_0087465_0 | chr5:136431191-136433490 | 2.47 | 3.35 |
| PROTEIN | UPREG. | TU_0058833_0 | chr1:11768665-11788581 | 1.45 | 3.34 |
| PROTEIN | DOWNREG. | TU_0009047_0 | chr7:41967123-41970103 | 0.65 | −3.35 |
| PROTEIN | DOWNREG. | TU_0020039_0 | chr19:2748637-2980244 | 0.65 | −3.36 |
| PROTEIN | DOWNREG. | TU_0024046_0 | chr19:47194316-47201741 | 0.53 | −3.36 |
| PROTEIN | DOWNREG. | TU_0120035_0 | chr2:154042114-154043553 | 0.49 | −3.36 |
| PROTEIN | DOWNREG. | TU_0014542_0 | chr17:4790024-4790984 | 0.77 | −3.36 |
| PROTEIN | DOWNREG. | TU_0058703_0 | chr1:10457547-10613394 | 0.66 | −3.37 |
| NOVEL | DOWNREG. | TU_0084922_0 | chr5:44337239-44338127 | 0.55 | −3.37 |
| PROTEIN | DOWNREG. | TU_0067338_0 | chr1:167362572-167539064 | 0.68 | −3.37 |
| PROTEIN | DOWNREG. | TU_0030086_0 | chrX:101794939-101798995 | 0.64 | −3.37 |
| PROTEIN | DOWNREG. | TU_0031101_0 | chrX:134247418-134254372 | 0.69 | −3.37 |
| PROTEIN | DOWNREG. | TU_0063762_0 | chr1:87566944-87551813 | 0.66 | −3.38 |
| PROTEIN | DOWNREG. | TU_0107584_0 | chr22:38075931-38123806 | 0.66 | −3.38 |
| PROTEIN | DOWNREG. | TU_0102296_0 | chr9:34979701-34988409 | 0.57 | −3.38 |
| PROTEIN | DOWNREG. | TU_0038435_0 | chr3:51951347-51958668 | 0.65 | −3.38 |
| PROTEIN | DOWNREG. | TU_0062948_0 | chr1:53744574-53746867 | 0.46 | −3.38 |
| PROTEIN | DOWNREG. | TU_0092655_0 | chr11:63282470-63288729 | 0.73 | −3.38 |
| PROTEIN | DOWNREG. | TU_0035606_0 | chr14:95470258-93500717 | 0.58 | −3.38 |
| PROTEIN | DOWNREG. | TU_0055688_0 | chr18:10470831-10478699 | 0.58 | −3.38 |
| PROTEIN | DOWNREG. | TU_0056462_0 | chr18:41558112-41584622 | 0.49 | −3.39 |
| PROTEIN | DOWNREG. | TU_0002739_0 | chr6:35321958-35328561 | 0.55 | −3.39 |
| PROTEIN | DOWNREG. | TU_0030147_0 | chrX:102727067-102729284 | 0.65 | −3.39 |
| NOVEL | DOWNREG. | TU_0030209_0 | chrX:103250907-103253228 | 0.66 | −3.39 |
| ncRNA | DOWNREG. | TU_0068206_0 | chr1:200132176-200134973 | 0.60 | −3.39 |
| PROTEIN | DOWNREG. | TU_0081627_0 | chr12:105186419-103190411 | 0.63 | −3.40 |
| PROTEIN | DOWNREG. | TU_0068194_0 | chr1:200132176-200132322 | 0.59 | −3.40 |
| PROTEIN | DOWNREG. | TU_0049308_0 | chr4:104220026-104220361 | 0.45 | −3.40 |
| NOVEL | DOWNREG. | TU_0068431_0 | chr1:202350966-202363482 | 0.62 | −3.40 |
| PROTEIN | DOWNREG. | TU_0073506_0 | chr10:7630096-7723954 | 0.60 | −3.40 |
| PROTEIN | DOWNREG. | TU_0054695_0 | chr16:83411105-83499914 | 0.62 | −3.40 |
| PROTEIN | DOWNREG. | TU_0012556_0 | chr7:115934290-115935899 | 0.50 | −3.41 |
| PROTEIN | DOWNREG. | TU_0018647_0 | chr17:1259157-71294839 | 0.74 | −3.41 |
| NOVEL | DOWNREG. | TU_0030577_0 | chrX:118036531-118036860 | 0.43 | −3.41 |
| PROTEIN | DOWNREG. | TU_0089961_0 | chr11:22456339-2247566 | 0.52 | −3.41 |
| PROTEIN | DOWNREG. | TU_0000658_0 | chr6:19947236-19950403 | 0.56 | −3.41 |
| PROTEIN | DOWNREG. | TU_0002212_0 | chr6:32224073-32225328 | 0.56 | −3.41 |
| PROTEIN | DOWNREG. | TU_0024749_0 | chr19:52937559-52939100 | 0.58 | −3.41 |
| PROTEIN | DOWNREG. | TU_0101225_0 | chr21:40161189-40161418 | 0.52 | −3.41 |
| ncRNA | DOWNREG. | TU_0100030_0 | chr13:134653589-134655316 | 0.41 | −3.41 |
| PROTEIN | DOWNREG. | TU_0102256_0 | chr9:34356684-34366854 | 0.56 | −3.41 |
| PROTEIN | DOWNREG. | TU_0039040_0 | chr3:69107066-69108860 | 0.62 | −3.42 |
| ncRNA | DOWNREG. | TU_0115808_0 | chr2:37722515-37725828 | 0.61 | −3.42 |
| PROTEIN | DOWNREG. | TU_0115807_0 | chr2:37722515-37725828 | 0.61 | −3.42 |
| NOVEL | DOWNREG. | TU_0038811_0 | chr3:57890130-57890834 | 0.43 | −3.43 |
| PROTEIN | DOWNREG. | TU_0197000_0 | chr22:29790122-29830660 | 0.60 | −3.43 |
| PROTEIN | DOWNREG. | TU_0065126_0 | chr1:144274405-144279906 | 0.53 | −3.43 |
| PROTEIN | DOWNREG. | TU_0065093_0 | chr1:144167535-144181746 | 0.72 | −3.43 |
| PROTEIN | DOWNREG. | TU_0066887_0 | chr1:158352167-158379985 | 0.56 | −3.44 |
| PROTEIN | DOWNREG. | TU_0034681_0 | chr14:73248251-73250768 | 0.61 | −3.44 |
| PROTEIN | DOWNREG. | TU_0064872_0 | chr1:115373945-115394701 | 0.60 | −3.44 |
| PROTEIN | DOWNREG. | TU_0115146_0 | chr2:26806070-26809827 | 0.49 | −3.44 |
| PROTEIN | DOWNREG. | TU_0023552_0 | chr19:43433715-43439100 | 0.52 | −3.44 |
| PROTEIN | DOWNREG. | TU_0013056_0 | chr7:134269121-134269574 | 0.41 | −3.44 |
| PROTEIN | DOWNREG. | TU_0078015_0 | chr12:21809160-21817495 | 0.61 | −3.45 |

TABLE 4-continued

| Category | Type | Name | Interval | Fold change (Unlogged) | SAM score ($(r)/(s + s0)$) |
|---|---|---|---|---|---|
| PROTEIN | DOWNREG. | TU_0010849_0 | chr7:84462824-84454228 | 0.41 | −3.45 |
| PROTEIN | DOWNREG. | TU_0018278_0 | chr17:6223556-62237319 | 0.62 | −3.45 |
| PROTEIN | DOWNREG. | TU_0106896_0 | chr22:28206216-28217370 | 0.46 | −3.46 |
| PROTEIN | DOWNREG. | TU_0086308_0 | chr5:9558335-95184222 | 0.54 | −3.46 |
| PROTEIN | DOWNREG. | TU_0059500_0 | chr1:19842799-19857540 | 0.66 | −3.46 |
| PROTEIN | DOWNREG. | TU_0030156_0 | chrX:102749504-102752161 | 0.61 | −3.46 |
| PROTEIN | DOWNREG. | TU_0053209_0 | chr16:30815439-30839057 | 0.45 | −3.46 |
| PROTEIN | DOWNREG. | TU_0102372_0 | chr9:35672000-35681106 | 0.58 | −3.46 |
| PROTEIN | DOWNREG. | TU_0040491_0 | chr3:134947802-134980329 | 0.35 | −3.46 |
| PROTEIN | DOWNREG. | TU_0063025_0 | chr1:54832256-54849445 | 0.56 | −3.46 |
| PROTEIN | DOWNREG. | TU_0016741_0 | chr17:37808007-37816100 | 0.61 | −3.47 |
| PROTEIN | DOWNREG. | TU_0079672_0 | chr12:55272841-55276238 | 0.79 | −3.47 |
| NOVEL | DOWNREG. | TU_0072214_0 | chr20:42166331-42172501 | 0.45 | −3.47 |
| PROTEIN | DOWNREG. | TU_0069254_0 | chr1:223745854-223750945 | 0.54 | −3.48 |
| PROTEIN | DOWNREG. | TU_0014474_0 | chr17:4410320-4410614 | 0.34 | −3.48 |
| PROTEIN | DOWNREG. | TU_0002034_0 | chr6:31975375-31977685 | 0.61 | −3.48 |
| ncRNA | DOWNREG. | TU_0115605_0 | chr2:37722515-37727509 | 0.64 | −3.48 |
| PROTEIN | DOWNREG. | TU_0106487_0 | chr22:21742726-21797216 | 0.56 | −3.48 |
| PROTEIN | DOWNREG. | TU_0100880_0 | chr21:32808766-32809639 | 0.62 | −3.48 |
| PROTEIN | DOWNREG. | TU_0028960_0 | chrX:64873768-64873981 | 0.59 | −3.48 |
| PROTEIN | DOWNREG. | TU_0103717_0 | chr9:1126765334-112576369 | 0.59 | −3.48 |
| PROTEIN | DOWNREG. | TU_0016732_0 | chr17:37807991-37828819 | 0.65 | −3.48 |
| PROTEIN | DOWNREG. | TU_0075579_0 | chr10:96987317-97040810 | 0.65 | −3.48 |
| PROTEIN | DOWNREG. | TU_0108979_0 | chr15:34659121-34889737 | 0.68 | −3.48 |
| PROTEIN | DOWNREG. | TU_0039868_0 | chr3:123526763-123543198 | 0.51 | −3.48 |
| PROTEIN | DOWNREG. | TU_0032236_0 | chr14:2285061-22893832 | 0.61 | −3.48 |
| PROTEIN | DOWNREG. | TU_0103902_0 | chr9:115957988-116128421 | 0.59 | −3.49 |
| PROTEIN | DOWNREG. | TU_0004251_0 | chr6:71069214-71069482 | 0.36 | −3.49 |
| PROTEIN | DOWNREG. | TU_0115344_0 | chr2:27568254-27571692 | 0.64 | −3.49 |
| NOVEL | DOWNREG. | TU_0090307_0 | chr11:7977293-7979927 | 0.69 | −3.49 |
| PROTEIN | DOWNREG. | TU_0020914_0 | chr19:9718612-9723799 | 0.47 | −3.49 |
| PROTEIN | DOWNREG. | TU_0014009_0 | chr7:15813133-158531217 | 0.48 | −3.50 |
| PROTEIN | DOWNREG. | TU_0111467_0 | chr15:62817064-62854842 | 0.58 | −3.50 |
| NOVEL | DOWNREG. | TU_0058552_0 | chr5:157103352-157120455 | 0.64 | −3.50 |
| PROTEIN | DOWNREG. | TU_0016616_0 | chr17:36992058-37034423 | 0.44 | −3.50 |
| PROTEIN | DOWNREG. | TU_0109820_0 | chr15:41600571-41611159 | 0.56 | −3.51 |
| PROTEIN | DOWNREG. | TU_0083744_0 | chr5:23638-237985 | 0.50 | −3.51 |
| PROTEIN | DOWNREG. | TU_0038899_0 | chr3:58465926-58495821 | 0.58 | −3.51 |
| PROTEIN | DOWNREG. | TU_0018817_0 | chr17:72183287-72184800 | 0.61 | −3.51 |
| PROTEIN | DOWNREG. | TU_0096362_0 | chr11:129779777-129794214 | 0.56 | −3.51 |
| ncRNA | DOWNREG. | TU_0104765_0 | chr9:131134480-131144297 | 0.53 | −3.51 |
| PROTEIN | DOWNREG. | TU_0047809_0 | chr4:52581019-52582331 | 0.62 | −3.52 |
| PROTEIN | DOWNREG. | TU_0114638_0 | chr2:11804193-11854972 | 0.68 | −3.52 |
| PROTEIN | DOWNREG. | TU_0110215_0 | chr15:43246574-43254766 | 0.63 | −3.52 |
| PROTEIN | DOWNREG. | TU_0117024_0 | chr2:66515747-66653430 | 0.61 | −3.52 |
| PROTEIN | DOWNREG. | TU_0109004_0 | chr15:35178588-35180010 | 0.39 | −3.53 |
| PROTEIN | DOWNREG. | TU_0114005_0 | chr15:97462760-97493368 | 0.56 | −3.53 |
| PROTEIN | DOWNREG. | TU_0079534_0 | chr12:53260191-53268540 | 0.41 | −3.53 |
| PROTEIN | DOWNREG. | TU_0068435_0 | chr1:202366748-202385528 | 0.62 | −3.53 |
| PROTEIN | DOWNREG. | TU_0014730_0 | chr17:7034460-7061662 | 0.61 | −3.53 |
| PROTEIN | DOWNREG. | TU_0113099_0 | chr15:57738640-57756015 | 0.70 | −3.54 |
| PROTEIN | DOWNREG. | TU_0079355_0 | chr12:1906937-51912605 | 0.54 | −3.54 |
| PROTEIN | DOWNREG. | TU_0107389_0 | chr22:36670710-36671784 | 0.59 | −3.54 |
| PROTEIN | DOWNREG. | TU_0105434_0 | chr9:138991774-138996018 | 0.54 | −3.54 |
| PROTEIN | DOWNREG. | TU_0122441_0 | chr2:220000175-220002664 | 0.38 | −3.54 |
| ncRNA | DOWNREG. | TU_0074041_0 | chr10:29785041-30065975 | 0.64 | −3.55 |
| PROTEIN | DOWNREG. | TU_0114819_0 | chr2:23779564-23785016 | 0.65 | −3.55 |
| PROTEIN | DOWNREG. | TU_0013666_0 | chr7:150180552-150189309 | 0.34 | −3.55 |
| PROTEIN | DOWNREG. | TU_0036844_0 | chr3:9930678-9933062 | 0.54 | −3.56 |
| PROTEIN | DOWNREG. | TU_0014467_0 | chr17:4407802-4410614 | 0.49 | −3.56 |
| NOVEL | DOWNREG. | TU_0036397_0 | chr14:104617328-104624500 | 0.45 | −3.56 |
| PROTEIN | DOWNREG. | TU_0014721_0 | chr17:6882853-6884238 | 0.60 | −3.57 |
| PROTEIN | DOWNREG. | TU_0061867_0 | chr1:41618433-41621890 | 0.61 | −3.57 |
| PROTEIN | DOWNREG. | TU_0090901_0 | chr11:20061238-20099725 | 0.60 | −3.57 |
| PROTEIN | DOWNREG. | TU_0089503_0 | chr5:179949721-179951068 | 0.47 | −3.57 |
| NOVEL | DOWNREG. | TU_0112056_0 | chr15:6965838-69678468 | 0.46 | −3.57 |
| NOVEL | DOWNREG. | TU_0052454_0 | chr16:15702084-15702374 | 0.40 | −3.57 |
| PROTEIN | DOWNREG. | TU_0004248_0 | chr6:70983350-71069482 | 0.52 | −3.57 |
| PROTEIN | DOWNREG. | TU_0111118_0 | chr15:58426685-58428608 | 0.59 | −3.58 |
| PROTEIN | DOWNREG. | TU_0047256_0 | chr4:38781223-38804739 | 0.63 | −3.58 |
| PROTEIN | DOWNREG. | TU_0092308_0 | chr11:61305022-61326508 | 0.62 | −3.58 |
| PROTEIN | DOWNREG. | TU_0037381_0 | chr3:33159367-33165995 | 0.70 | −3.59 |
| PROTEIN | DOWNREG. | TU_0088765_0 | chr5:169767435-169749043 | 0.53 | −3.60 |
| PROTEIN | DOWNREG. | TU_0039072_0 | chr3:70098064-70100160 | 0.63 | −3.60 |
| NOVEL | DOWNREG. | TU_0112059_0 | chr15:69667695-69691724 | 0.41 | −3.60 |

TABLE 4-continued

| Category | Type | Name | Interval | Fold change (Unlogged) | SAM score ((r)/ (s + s0)) |
|---|---|---|---|---|---|
| PROTEIN | DOWNREG. | TU_0030975_0 | chrX:130235170-13023814 | 0.49 | −3.60 |
| PROTEIN | DOWNREG. | TU_0038532_0 | chr3:52258212-52287726 | 0.77 | −3.60 |
| PROTEIN | DOWNREG. | TU_0014418_0 | chr17:3748115-3749717 | 0.39 | −3.60 |
| PROTEIN | DOWNREG. | TU_0001986_0 | chr6:31791087-31793378 | 0.48 | −3.61 |
| PROTEIN | DOWNREG. | TU_0111109_0 | chr15:58426685-58477514 | 0.65 | −3.61 |
| PROTEIN | DOWNREG. | TU_0064151_0 | chr1:98933815-98937074 | 0.46 | −3.61 |
| PROTEIN | DOWNREG. | TU_0111253_0 | chr15:61121812-51151157 | 0.63 | −3.61 |
| PROTEIN | DOWNREG. | TU_0058947_0 | chr1:13782831-13817026 | 0.61 | −3.62 |
| PROTEIN | DOWNREG. | TU_0031484_0 | chrX:131890690-131892673 | 0.59 | −3.62 |
| PROTEIN | DOWNREG. | TU_0076212_0 | chr10:105781059-105835687 | 0.47 | −3.62 |
| PROTEIN | DOWNREG. | TU_0062567_0 | chr1:47050692-47056967 | 0.47 | −3.62 |
| NOVEL | DOWNREG. | TU_0020667_0 | chr19:7888598-7889980 | 0.41 | −3.62 |
| PROTEIN | DOWNREG. | TU_0029358_0 | chrX:71263703-71263507 | 0.66 | −3.63 |
| PROTEIN | DOWNREG. | TU_0065339_0 | chr1:148457403-148475104 | 0.56 | −3.63 |
| PROTEIN | DOWNREG. | TU_0063765_0 | chr1:87583867-875877269 | 0.58 | −3.63 |
| NOVEL | DOWNREG. | TU_0036395_0 | chr14:104617328-104623671 | 0.53 | −3.63 |
| PROTEIN | DOWNREG. | TU_0103872_0 | chr9:115178483-115203441 | 0.59 | −3.63 |
| PROTEIN | DOWNREG. | TU_0050244_0 | chr4:143565059-148586558 | 0.63 | −3.63 |
| PROTEIN | DOWNREG. | TU_0031913_0 | chr14:20554755-20563715 | 0.64 | −3.63 |
| PROTEIN | DOWNREG. | TU_0065343_0 | chr1:148501147-148501585 | 0.37 | −3.63 |
| PROTEIN | DOWNREG. | TU_0084945_0 | chr5:50715235-50726033 | 0.69 | −3.64 |
| PROTEIN | DOWNREG. | TU_0090342_0 | chr11:8671475-684962 | 0.64 | −3.64 |
| PROTEIN | DOWNREG. | TU_0120044_0 | chr2:155422693-155423038 | 0.26 | −3.64 |
| PROTEIN | DOWNREG. | TU_0023267_0 | chr19:40937250-40940189 | 0.52 | −3.64 |
| PROTEIN | DOWNREG. | TU_0023553_0 | chr19:43433715-43434071 | 0.51 | −3.65 |
| PROTEIN | DOWNREG. | TU_0115806_0 | chr2:37722515-37726663 | 0.60 | −3.65 |
| PROTEIN | DOWNREG. | TU_0085256_0 | chr5:59099679-59100724 | 0.53 | −3.65 |
| PROTEIN | DOWNREG. | TU_0038056_0 | chr3:48563574-48623119 | 0.68 | −3.65 |
| PROTEIN | DOWNREG. | TU_0022088_0 | chr19:16864768-16929718 | 0.55 | −3.65 |
| ncRNA | DOWNREG. | TU_0053408_0 | chr12:129197899-129212499 | 0.58 | −3.65 |
| PROTEIN | DOWNREG. | TU_0059155_0 | chr1:16397144-16405288 | 0.61 | −3.65 |
| PROTEIN | DOWNREG. | TU_0046595_0 | chr4:3264549-3411602 | 0.68 | −3.65 |
| PROTEIN | DOWNREG. | TU_0099476_0 | chr8:108331106-108578694 | 0.58 | −3.66 |
| PROTEIN | DOWNREG. | TU_0091498_0 | chr11:46834081-46849744 | 0.65 | −3.65 |
| PROTEIN | DOWNREG. | TU_0098359_0 | chr8:68586418-65693042 | 0.45 | −3.65 |
| PROTEIN | DOWNREG. | TU_0046627_0 | chr4:3735533-3740037 | 0.45 | −3.67 |
| NOVEL | DOWNREG. | TU_0103946_0 | chr9:116821701-11682181 | 0.48 | −3.67 |
| PROTEIN | DOWNREG. | TU_0098057_0 | chr7:5519816-5536775 | 0.62 | −3.67 |
| PROTEIN | DOWNREG. | TU_0100219_0 | chr8:143849604-143856276 | 0.59 | −3.67 |
| PROTEIN | DOWNREG. | TU_0087532_0 | chr5:137802634-137810548 | 0.53 | −3.68 |
| PROTEIN | DOWNREG. | TU_0066743_0 | chr1:154859563-134862200 | 0.43 | −3.68 |
| PROTEIN | DOWNREG. | TU_0052586_0 | chr16:19637116-19779369 | 0.64 | −3.68 |
| PROTEIN | DOWNREG. | TU_0075308_0 | chr10:83708340-88712998 | 0.51 | −3.68 |
| PROTEIN | DOWNREG. | TU_0032240_0 | chr14:22894053-22905637 | 0.57 | −3.68 |
| PROTEIN | DOWNREG. | TU_0046399_0 | chr4:4031053-2040569 | 0.44 | −3.70 |
| PROTEIN | DOWNREG. | TU_0081487_0 | chr12:104248577-104289423 | 0.56 | −3.70 |
| PROTEIN | DOWNREG. | TU_0096978_0 | chr8:22135174-22140356 | 0.47 | −3.70 |
| PROTEIN | DOWNREG. | TU_0054692_0 | chr16:83411105-83500516 | 0.62 | −3.70 |
| PROTEIN | DOWNREG. | TU_0067818_0 | chr1:180509414-180511335 | 0.72 | −3.71 |
| PROTEIN | DOWNREG. | TU_0098841_0 | chr8:92038228-92039575 | 0.39 | −3.71 |
| PROTEIN | DOWNREG. | TU_0121595_0 | chr2:202193170-202196672 | 0.62 | −3.71 |
| PROTEIN | DOWNREG. | TU_0023218_0 | chr19:40679964-40694184 | 0.55 | −3.71 |
| PROTEIN | DOWNREG. | TU_0112386_0 | chr15:71818130-71820041 | 0.55 | −3.71 |
| PROTEIN | DOWNREG. | TU_0024601_0 | chr19:51605296-51609005 | 0.56 | −3.71 |
| PROTEIN | DOWNREG. | TU_0055238_0 | chr18:2561572-2606627 | 0.59 | −3.71 |
| PROTEIN | DOWNREG. | TU_0085908_0 | chr5:73401241-7842780 | 0.52 | −3.72 |
| ncRNA | DOWNREG. | TU_0111315_0 | chr15:61676589-61681634 | 0.55 | −3.72 |
| PROTEIN | DOWNREG. | TU_0111311_0 | chr15:61676589-61681634 | 0.55 | −3.72 |
| PROTEIN | DOWNREG. | TU_0023241_0 | chr19:40856254-40861198 | 0.41 | −3.72 |
| PROTEIN | DOWNREG. | TU_0068139_0 | chr1:199127296-199147465 | 0.42 | −3.72 |
| ncRNA | DOWNREG. | TU_0102684_0 | chr9:70336502-70344481 | 0.56 | −3.73 |
| PROTEIN | DOWNREG. | TU_0068764_0 | chr1:207854842-207892483 | 0.49 | −3.73 |
| PROTEIN | DOWNREG. | TU_0053636_0 | chr16:55846971-558353340 | 0.58 | −3.74 |
| PROTEIN | DOWNREG. | TU_0054025_0 | chr5:6501949-6545706 | 0.54 | −3.74 |
| NOVEL | DOWNREG. | TU_0032151_0 | chr14:22508055-22508830 | 0.58 | −3.74 |
| PROTEIN | DOWNREG. | TU_0014680_0 | chr17:6295379-6305574 | 0.62 | −3.74 |
| PROTEIN | DOWNREG. | TU_0076124_0 | chr10:104619299-104651033 | 0.60 | −3.75 |
| PROTEIN | DOWNREG. | TU_0085198_0 | chr5:58300638-58305429 | 0.60 | −3.75 |
| PROTEIN | DOWNREG. | TU_0102686_0 | chr9:70337677-70344573 | 0.55 | −3.76 |
| PROTEIN | DOWNREG. | TU_0112385_0 | chr15:71818130-71831566 | 0.54 | −3.76 |
| PROTEIN | DOWNREG. | TU_0100675_0 | chr21:32795506-3289539 | 0.61 | −3.78 |
| PROTEIN | DOWNREG. | TU_0065928_0 | chr1:151800274-151855449 | 0.49 | −3.78 |
| PROTEIN | DOWNREG. | TU_0063298_0 | chr1:62474433-62474872 | 0.36 | −3.78 |
| PROTEIN | DOWNREG. | TU_0100861_0 | chr21:32604246-32608457 | 0.62 | −3.79 |
| PROTEIN | DOWNREG. | TU_0101015_0 | chr21:35010830-35012376 | 0.55 | −3.79 |

TABLE 4-continued

| Category | Type | Name | Interval | Fold change (Unlogged) | SAM score ((r)/(s + s0) |
|---|---|---|---|---|---|
| ncRNA | DOWNREG. | TU_0031086_0 | chrX:133993992-133995935 | 0.73 | -3.79 |
| PROTEIN | DOWNREG. | TU_0068759_0 | chr1:209669209-207672813 | 0.45 | -3.79 |
| NOVEL | DOWNREG. | TU_0069253_0 | chr1:223741202-223745600 | 0.62 | -3.79 |
| PROTEIN | DOWNREG. | TU_0020150_0 | chr19:3877291-3879097 | 0.52 | -3.79 |
| ncRNA | DOWNREG. | TU_0084069_0 | chr5:9599340-9503383 | 0.59 | -3.80 |
| PROTEIN | DOWNREG. | TU_0016922_0 | chr17:38430856-38435173 | 0.51 | -3.80 |
| PROTEIN | DOWNREG. | TU_0013053_0 | chr7:134114695-134805949 | 0.56 | -3.81 |
| PROTEIN | DOWNREG. | TU_0017406_0 | chr17:43458534-43470076 | 0.58 | -3.81 |
| PROTEIN | DOWNREG. | TU_0014681_0 | chr17:6295379-6305877 | 0.50 | -3.81 |
| PROTEIN | DOWNREG. | TU_0058447_0 | chr1:9040090-9052233 | 0.36 | -3.81 |
| PROTEIN | DOWNREG. | TU_0055624_0 | chr18:11872611-11875972 | 0.64 | -3.82 |
| PROTEIN | DOWNREG. | TU_0003717_0 | chr6:43381215-43381963 | 0.49 | -3.82 |
| NOVEL | DOWNREG. | TU_0016578_0 | chr17:35881203-35854855 | 0.52 | -3.82 |
| PROTEIN | DOWNREG. | TU_0191224_0 | chr21:40161189-40223184 | 0.50 | -3.82 |
| PROTEIN | DOWNREG. | TU_0064871_0 | chr1:115391459-115433611 | 0.59 | -3.83 |
| PROTEIN | DOWNREG. | TU_0097452_0 | chr8:37773618-37822041 | 0.55 | -3.83 |
| PROTEIN | DOWNREG. | TU_0066742_0 | chr1:154860755-154862200 | 0.42 | -3.83 |
| PROTEIN | DOWNREG. | TU_0090638_0 | chr11:14242208-14246823 | 0.55 | -3.83 |
| PROTEIN | DOWNREG. | TU_0046626_0 | chr4:3735533-3740037 | 0.46 | -3.83 |
| PROTEIN | DOWNREG. | TU_0024608_0 | chr19:51842682-51856041 | 0.53 | -3.83 |
| PROTEIN | DOWNREG. | TU_0071146_0 | chr20:25381375-25432639 | 0.58 | -3.84 |
| PROTEIN | DOWNREG. | TU_0080097_0 | chr12:56301840-56307003 | 0.56 | -3.85 |
| PROTEIN | DOWNREG. | TU_0062615_0 | chr1:48974664-48997227 | 0.51 | -3.85 |
| PROTEIN | DOWNREG. | TU_0013669_0 | chr7:150272983-150305963 | 0.52 | -3.86 |
| PROTEIN | DOWNREG. | TU_0102682_0 | chr9:70197177-70337519 | 0.56 | -3.86 |
| PROTEIN | DOWNREG. | TU_0104855_0 | chr9:131689267-131691419 | 0.64 | -3.86 |
| PROTEIN | DOWNREG. | TU_0116336_0 | chr2:48677181-48685259 | 0.65 | -3.86 |
| PROTEIN | DOWNREG. | TU_0116619_0 | chr2:60532830-60533546 | 0.47 | -3.87 |
| PROTEIN | DOWNREG. | TU_0034462_0 | chr14:69415893-69568826 | 0.48 | -3.87 |
| PROTEIN | DOWNREG. | TU_0067213_0 | chr1:163086189-163087634 | 0.59 | -3.87 |
| PROTEIN | DOWNREG. | TU_0065337_0 | chr1:148457403-148475119 | 0.56 | -3.87 |
| NOVEL | DOWNREG. | TU_0062461_0 | chr1:46461750-46463004 | 0.51 | -3.88 |
| PROTEIN | DOWNREG. | TU_0080098_0 | chr12:56302807-56307707 | 0.56 | -3.88 |
| PROTEIN | DOWNREG. | TU_0034421_0 | chr14:68410559-68412495 | 0.62 | -3.88 |
| PROTEIN | DOWNREG. | TU_0016601_0 | chr17:36911114-36928728 | 0.39 | -3.88 |
| PROTEIN | DOWNREG. | TU_0079221_0 | chr12:51194639-51200498 | 0.43 | -3.89 |
| PROTEIN | DOWNREG. | TU_0112752_0 | chr15:76184009-76210733 | 0.55 | -3.90 |
| PROTEIN | DOWNREG. | TU_0028410_0 | chrX:48910899-48929704 | 0.68 | -3.91 |
| PROTEIN | DOWNREG. | TU_0076498_0 | chr10:123227854-123347940 | 0.56 | -3.92 |
| NOVEL | DOWNREG. | TU_0093208_0 | chr11:6536931-65397655 | 0.45 | -3.92 |
| PROTEIN | DOWNREG. | TU_0078129_0 | chr12:27016771-27017190 | 0.47 | -3.92 |
| PROTEIN | DOWNREG. | TU_0064620_0 | chr1:111962071-112059304 | 0.61 | -3.92 |
| PROTEIN | DOWNREG. | TU_0005224_0 | chr6:107917248-108088034 | 0.60 | -3.93 |
| PROTEIN | DOWNREG. | TU_0023668_0 | chr19:44114820-44158190 | 0.56 | -3.93 |
| PROTEIN | DOWNREG. | TU_0041856_0 | chr3:190990156-191097717 | 0.44 | -3.93 |
| PROTEIN | DOWNREG. | TU_0107364_0 | chr22:36658502-36671784 | 0.62 | -3.93 |
| PROTEIN | DOWNREG. | TU_0079224_0 | chr12:511946-51199100 | 0.43 | -3.94 |
| PROTEIN | DOWNREG. | TU_0027357_0 | chrX:17728093-17737982 | 0.57 | -3.94 |
| PROTEIN | DOWNREG. | TU_0071013_0 | chr20:19141491-19652034 | 0.55 | -3.95 |
| PROTEIN | DOWNREG. | TU_0060281_0 | chr1:27204050-27211524 | 0.48 | -3.95 |
| PROTEIN | DOWNREG. | TU_0096007_0 | chr11:119487208-119514087 | 0.45 | -3.95 |
| PROTEIN | DOWNREG. | TU_0058810_0 | chr1:11631005-11637486 | 0.50 | -3.95 |
| ncRNA | DOWNREG. | TU_0102668_0 | chr9:67902293-67904671 | 0.52 | -3.96 |
| PROTEIN | DOWNREG. | TU_0103126_0 | chr9:93524079-93559558 | 0.56 | -3.96 |
| PROTEIN | DOWNREG. | TU_0098384_0 | chr8:68508843-68581618 | 0.43 | -3.96 |
| NOVEL | DOWNREG. | TU_0084068_0 | chr5:9602147-960338 | 0.49 | -3.96 |
| ncRNA | DOWNREG. | TU_0018887_0 | chr17:73068191-73068655 | 0.29 | -3.97 |
| PROTEIN | DOWNREG. | TU_0020916_0 | chr19:9720305-9727203 | 0.55 | -3.97 |
| PROTEIN | DOWNREG. | TU_0018819_0 | chr17:72184340-72195820 | 0.59 | -3.97 |
| NOVEL | DOWNREG. | TU_0042081_0 | chr3:197374550-197376798 | 0.46 | -3.97 |
| PROTEIN | DOWNREG. | TU_0065864_0 | chr1:149850009-149852238 | 0.46 | -3.98 |
| PROTEIN | DOWNREG. | TU_0111301_0 | chr15:61676589-61684028 | 0.54 | -3.98 |
| PROTEIN | DOWNREG. | TU_0073448_0 | chr10:5556713-5568609 | 0.43 | -3.99 |
| PROTEIN | DOWNREG. | TU_0030581_0 | chrX:118096546-118104692 | 0.38 | -3.99 |
| PROTEIN | DOWNREG. | TU_0039780_0 | chr3:120543608-12056813 | 0.55 | -4.00 |
| PROTEIN | DOWNREG. | TU_0081660_0 | chr12:108705678-108718771 | 0.50 | -4.00 |
| PROTEIN | DOWNREG. | TU_0046397_0 | chr4:2032569-2050090 | 0.46 | -4.00 |
| PROTEIN | DOWNREG. | TU_0122440_0 | chr2:219991398-219999705 | 0.53 | -4.01 |
| PROTEIN | DOWNREG. | TU_0011534_0 | chr7:99083477-99096154 | 0.36 | -4.01 |
| PROTEIN | DOWNREG. | TU_0047206_0 | chr4:37815997-37817190 | 0.59 | -4.02 |
| PROTEIN | DOWNREG. | TU_0017005_0 | chr17:39308253-39337366 | 0.52 | -4.02 |
| PROTEIN | DOWNREG. | TU_0052436_0 | chr16:15704459-15858435 | 0.54 | -4.03 |
| PROTEIN | DOWNREG. | TU_0014761_0 | chr17:7128572-7131411 | 0.46 | -4.03 |
| PROTEIN | DOWNREG. | TU_0080075_0 | chr12:56290183-56301803 | 0.53 | -4.03 |
| PROTEIN | DOWNREG. | TU_0089295_0 | chr5:177597111-177621358 | 0.48 | -4.03 |

TABLE 4-continued

| Category | Type | Name | Interval | Fold change (Unlogged) | SAM score ((r)/ (s + s0)) |
|---|---|---|---|---|---|
| PROTEIN | DOWNREG. | TU_0052594_0 | chr16:19775320--19780719 | 0.69 | −4.03 |
| PROTEIN | DOWNREG. | TU_0068168_0 | chr1:199700556-199742901 | 0.61 | −4.04 |
| ncRNA | DOWNREG. | TU_0102657_0 | chr9:67902293-67908869 | 0.54 | −4.04 |
| PROTEIN | DOWNREG. | TU_0083729_0 | chr6:43525496-43528789 | 0.55 | −4.04 |
| PROTEIN | DOWNREG. | TU_0071246_0 | chr20:29913077-29921837 | 0.42 | −4.05 |
| NOVEL | DOWNREG. | TU_0050224_0 | chr4:147115887-147190781 | 0.25 | −4.06 |
| PROTEIN | DOWNREG. | TU_0110166_0 | chr15:43172154-43198892 | 0.49 | −4.07 |
| PROTEIN | DOWNREG. | TU_0030085_0 | chrX:101782933-101800062 | 0.56 | −4.07 |
| PROTEIN | DOWNREG. | TU_0021042_0 | chr19:10435468-10441506 | 0.61 | −4.08 |
| PROTEIN | DOWNREG. | TU_0097463_0 | chr8:37812227-37826549 | 0.58 | −4.08 |
| PROTEIN | DOWNREG. | TU_0101681_0 | chr9:734412-736069 | 0.67 | −4.08 |
| PROTEIN | DOWNREG. | TU_0030157_0 | chrX:102750729-102751737 | 0.44 | −4.09 |
| NOVEL | DOWNREG. | TU_0098190_0 | chr8:61704765-61708199 | 0.49 | −4.09 |
| PROTEIN | DOWNREG. | TU_0062947_0 | chr1:53744955-53838542 | 0.42 | −4.09 |
| PROTEIN | DOWNREG. | TU_0078008_0 | chr12:21679541-21702042 | 0.57 | −4.09 |
| PROTEIN | DOWNREG. | TU_0017582_0 | chr17:45858594-45907395 | 0.54 | −4.09 |
| PROTEIN | DOWNREG. | TU_0090021_0 | chr6:1555144-1559122 | 0.53 | −4.09 |
| PROTEIN | DOWNREG. | TU_0031424_0 | chrX:149432223-149433104 | 0.47 | −4.10 |
| PROTEIN | DOWNREG. | TU_0065603_0 | chr1:149275738-149286201 | 0.42 | −4.10 |
| PROTEIN | DOWNREG. | TU_0037859_0 | chr3:45240966-45242817 | 0.49 | −4.11 |
| PROTEIN | DOWNREG. | TU_0102271_0 | chr9:34511045-34512853 | 0.50 | −4.11 |
| PROTEIN | DOWNREG. | TU_0035605_0 | chr14:93254401-93273368 | 0.49 | −4.11 |
| PROTEIN | DOWNREG. | TU_0054624_0 | chr1:112047953-112062396 | 0.54 | −4.11 |
| ncRNA | DOWNREG. | TU_0031098_0 | chrX:134057388-134058604 | 0.47 | −4.11 |
| PROTEIN | DOWNREG. | TU_0018799_0 | chr17:72061371-72080938 | 0.61 | −4.11 |
| PROTEIN | DOWNREG. | TU_0011129_0 | chr7:94135068-94136943 | 0.41 | −4.11 |
| NOVEL | DOWNREG. | TU_0036396_0 | chr14:104617328-104619095 | 0.41 | −4.12 |
| PROTEIN | DOWNREG. | TU_0056255_0 | chr5:32944250-92956054 | 0.57 | −4.12 |
| ncRNA | DOWNREG. | TU_0074501_0 | chr10:60429298-6041091 | 0.42 | −4.12 |
| PROTEIN | DOWNREG. | TU_0073757_0 | chr10:17672347-17699461 | 0.56 | −4.13 |
| PROTEIN | DOWNREG. | TU_0015457_0 | chr17:19581898-19587356 | 0.45 | −4.13 |
| PROTEIN | DOWNREG. | TU_0122402_0 | chr2:219821926-219824743 | 0.61 | −4.13 |
| PROTEIN | DOWNREG. | TU_0116618_0 | chr2:60532830-60633902 | 0.49 | −4.13 |
| PROTEIN | DOWNREG. | TU_0029963_0 | chrX:100220537-100238005 | 0.51 | −4.15 |
| PROTEIN | DOWNREG. | TU_0028949_0 | chrX:64504077-64878518 | 0.61 | −4.15 |
| PROTEIN | DOWNREG. | TU_0068443_0 | chr5:154178336-154210363 | 0.57 | −4.16 |
| PROTEIN | DOWNREG. | TU_0107371_0 | chr22:36668731-36671784 | 0.56 | −4.17 |
| PROTEIN | DOWNREG. | TU_0016830_0 | chr17:38070906-38071660 | 0.57 | −4.17 |
| PROTEIN | DOWNREG. | TU_0016599_0 | chr17:36923524-36946925 | 0.50 | −4.17 |
| PROTEIN | DOWNREG. | TU_0014764_0 | chr17:7131441-7134452 | 0.45 | −4.18 |
| PROTEIN | DOWNREG. | TU_0070473_0 | chr20:2621571-2702522 | 0.60 | −4.18 |
| PROTEIN | DOWNREG. | TU_0065602_0 | chr1:149282206-149288718 | 0.40 | −4.19 |
| PROTEIN | DOWNREG. | TU_0105435_0 | chr9:138997874-138999099 | 0.37 | −4.19 |
| PROTEIN | DOWNREG. | TU_0015445_0 | chr17:19415396-19422913 | 0.46 | −4.20 |
| PROTEIN | DOWNREG. | TU_0019012_0 | chr17:74597027-74990278 | 0.42 | −4.21 |
| PROTEIN | DOWNREG. | TU_0048538_0 | chr4:81336928-81344460 | 0.41 | −4.22 |
| PROTEIN | DOWNREG. | TU_0098385_0 | chr8:68508843-68509111 | 0.41 | −4.22 |
| PROTEIN | DOWNREG. | TU_0076499_0 | chr10:123227854-123248042 | 0.53 | −4.23 |
| PROTEIN | DOWNREG. | TU_0117582_0 | chr2:73973607-74000287 | 0.58 | −4.23 |
| PROTEIN | DOWNREG. | TU_0114778_0 | chr2:20264034-20288661 | 0.45 | −4.24 |
| PROTEIN | DOWNREG. | TU_0016316_0 | chr17:33917848-33935788 | 0.53 | −4.25 |
| PROTEIN | DOWNREG. | TU_0071893_0 | chr20:34603301-34611746 | 0.50 | −4.25 |
| PROTEIN | DOWNREG. | TU_0073523_0 | chr10:8136827-8157157 | 0.44 | −4.26 |
| PROTEIN | DOWNREG. | TU_0064500_0 | chr1:110061334-110079791 | 0.42 | −4.27 |
| PROTEIN | DOWNREG. | TU_0065862_0 | chr1:149850009-149552444 | 0.41 | −4.27 |
| PROTEIN | DOWNREG. | TU_0030054_0 | chrX:101268429-101269091 | 0.44 | −4.28 |
| PROTEIN | DOWNREG. | TU_0060278_0 | chr1:27192773-27200190 | 0.51 | −4.28 |
| PROTEIN | DOWNREG. | TU_0000013_0 | chr6:1257191-1259972 | 0.36 | −4.29 |
| PROTEIN | DOWNREG. | TU_0120707_0 | chr2:176665681-176669190 | 0.46 | −4.31 |
| PROTEIN | DOWNREG. | TU_0016744_0 | chr17:37790358-37809206 | 0.54 | −4.31 |
| PROTEIN | DOWNREG. | TU_0016827_0 | chr17:38065830-38071660 | 0.63 | −4.31 |
| PROTEIN | DOWNREG. | TU_0056190_0 | chr18:26824024-26842486 | 0.43 | −4.33 |
| PROTEIN | DOWNREG. | TU_0096954_0 | chr8:22027917-22043914 | 0.47 | −4.35 |
| PROTEIN | DOWNREG. | TU_0030062_0 | chrX:101267701-101269091 | 0.41 | −4.35 |
| ncRNA | DOWNREG. | TU_0120711_0 | chr2:176590351-176596560 | 0.49 | −4.36 |
| PROTEIN | DOWNREG. | TU_0011587_0 | chr7:99085728-99111736 | 0.39 | −4.39 |
| PROTEIN | DOWNREG. | TU_0107366_0 | chr22:35668731-36673469 | 0.54 | −4.39 |
| PROTEIN | DOWNREG. | TU_0065341_0 | chr1:148496851-148500610 | 0.35 | −4.39 |
| PROTEIN | DOWNREG. | TU_0015076_0 | chr17:12510065-12612990 | 0.50 | −4.40 |
| PROTEIN | DOWNREG. | TU_0087752_0 | chr5:139206352-139211438 | 0.44 | −4.40 |
| PROTEIN | DOWNREG. | TU_0108990_0 | chr15:34970176-35180015 | 0.51 | −4.41 |
| PROTEIN | DOWNREG. | TU_0062565_0 | chr1:47037330-47057598 | 0.43 | −4.42 |
| PROTEIN | DOWNREG. | TU_0018825_0 | chr17:72192513-72192794 | 0.47 | −4.43 |
| PROTEIN | DOWNREG. | TU_0002566_0 | chr6:33797424-3379978 | 0.37 | −4.44 |
| PROTEIN | DOWNREG. | TU_0074074_0 | chr10:29814868-29815135 | 0.26 | −4.44 |

TABLE 4-continued

| Category | Type | Name | Interval | Fold change (Unlogged) | SAM score ((r)/ (s + s0)) |
|---|---|---|---|---|---|
| PROTEIN | DOWNREG. | TU_0110179_0 | chr15:43196205-43235205 | 0.43 | −4.46 |
| PROTEIN | DOWNREG. | TU_0082372_0 | chr12:116130336-116130610 | 0.41 | −4.47 |
| ncRNA | DOWNREG. | TU_0102653_0 | chr9:67902293-67908683 | 0.46 | −4.48 |
| PROTEIN | DOWNREG. | TU_0024160_0 | chr19:48777171-48778386 | 0.51 | −4.49 |
| PROTEIN | DOWNREG. | TU_0031081_0 | chrX:133993992-134013925 | 0.64 | −4.49 |
| PROTEIN | DOWNREG. | TU_0015447_0 | chr17:19421649-19423000 | 0.46 | −4.50 |
| PROTEIN | DOWNREG. | TU_0016834_0 | chr17:38072130-38072515 | 0.54 | −4.50 |
| PROTEIN | DOWNREG. | TU_0120709_0 | chr2:176677352-176697902 | 0.49 | −4.50 |
| PROTEIN | DOWNREG. | TU_0041205_0 | chr3:171619688-171634575 | 0.48 | −4.53 |
| PROTEIN | DOWNREG. | TU_0110178_0 | chr15:43196270-43241274 | 0.43 | −4.54 |
| PROTEIN | DOWNREG. | TU_0064473_0 | chr1:110000292-110079791 | 0.51 | −4.58 |
| ncRNA | DOWNREG. | TU_0120715_0 | chr2:176692475-176697902 | 0.50 | −4.58 |
| PROTEIN | DOWNREG. | TU_0110180_0 | chr15:43196205-43243358 | 0.43 | −4.63 |
| PROTEIN | DOWNREG. | TU_0024922_0 | chr19:54253368-54259943 | 0.42 | −4.64 |
| ncRNA | DOWNREG. | TU_0115816_0 | chr2:38109039-38116939 | 0.32 | −4.64 |
| ncRNA | DOWNREG. | TU_0067289_0 | chr1:156307141-156318970 | 0.48 | −4.69 |
| NOVEL | DOWNREG. | TU_0095765_0 | chr11:117640504-117642734 | 0.36 | −4.69 |
| PROTEIN | DOWNREG. | TU_0058445_0 | chr1:9017797-9040122 | 0.33 | −4.70 |
| PROTEIN | DOWNREG. | TU_0047068_0 | chr4:23402764-23403824 | 0.41 | −4.72 |
| PROTEIN | DOWNREG. | TU_0016882_0 | chr17:38260060-38263683 | 0.51 | −4.82 |
| NOVEL | DOWNREG. | TU_0098382_0 | chr8:68494189-68495887 | 0.29 | −4.83 |
| PROTEIN | DOWNREG. | TU_0110177_0 | chr15:43196768-43245735 | 0.47 | −4.85 |
| PROTEIN | DOWNREG. | TU_0089598_0 | chr11:303980-310982 | 0.35 | −4.87 |
| PROTEIN | DOWNREG. | TU_0107527_0 | chr22:37740155-37746215 | 0.44 | −4.88 |
| PROTEIN | DOWNREG. | TU_0107528_0 | chr22:37741248-37746215 | 0.43 | −4.90 |
| PROTEIN | DOWNREG. | TU_0032311_0 | chr14:23612588-23617134 | 0.32 | −5.04 |

TABLE 5

| PCAT ID | Gene | Chromosomal Location | Expected score (dExp) | Observed score(d) | Fold change (PCA vs Benign | q-value (%) |
|---|---|---|---|---|---|---|
| PCAT-1 | TU_0099865_0 | chr8:128087842-128095202 | −2.2654014 | 5.444088 | 6.9071784 | 0 |
| PCAT-2 | TU_0090142_0 | chr11:4748677-4760303 | −2.4400573 | 4.6781354 | 11.39658 | 0 |
| PCAT-3 | TU_0054603_0 | chr16:82380933-82394836 | −2.1786723 | 4.4612455 | 5.8916535 | 0 |
| PCAT-4 | TU_0090140_0 | chr11:4748163-4759145 | −2.1153426 | 4.4345 | 7.1999164 | 0 |
| PCAT-5 | TU_0078288_0 | chr12:32393283-32405731 | −1.9164219 | 4.312603 | 3.5655262 | 0 |
| PCAT-6 | TU_0099864_0 | chr8:128094589-128103681 | −1.7214081 | 4.265536 | 3.8997242 | 0 |
| PCAT-7 | TU_0084308_0 | chr5:15938753-15949124 | −1.9636476 | 4.124071 | 4.747601 | 0 |
| PCAT-8 | TU_0084303_0 | chr5:15899476-15955226 | −2.0245786 | 4.0520086 | 7.1035967 | 0 |
| PCAT-9 | TU_0082746_0 | chr12:120197102-120197416 | −1.861408 | 3.7551165 | 5.1431665 | 0 |
| PCAT-10 | TU_0078296_0 | chr12:32394534-32405549 | −1.5944241 | 3.6902914 | 3.084959 | 0 |
| PCAT-11 | TU_0078290_0 | chr12:32394534-32410898 | −1.5337954 | 3.675318 | 3.1572607 | 0 |
| PCAT-12 | TU_0002597_0 | chr6:34335202-34338521 | −1.6263148 | 3.6469774 | 3.352418 | 0 |
| PCAT-13 | TU_0049368_0 | chr4:106772318-106772770 | −1.6894134 | 3.6079373 | 2.8299346 | 0 |
| PCAT-14 | TU_0106548_0 | chr22:22209111-22212055 | −1.939075 | 3.591358 | 5.962547 | 0 |
| PCAT-15 | TU_0078293_0 | chr12:32396393-32414822 | −1.5212961 | 3.5705945 | 2.9219174 | 0 |
| PCAT-16 | TU_0099884_0 | chr8:128301493-128307576 | −1.4445064 | 3.5658643 | 2.516981 | 0 |
| PCAT-17 | TU_0112014_0 | chr15:67722165-67739990 | −1.6326295 | 3.562463 | 3.6594224 | 0 |
| PCAT-18 | TU_0084306_0 | chr5:15896315-15947088 | −1.845 | 3.5603588 | 5.746707 | 0 |
| PCAT-19 | TU_0114240_0 | chr2:1534883-1538193 | −1.6970209 | 3.5233572 | 4.339947 | 0 |
| PCAT-20 | TU_0008499_0 | chr7:24236191-24236455 | −1.8302058 | 3.5071697 | 6.6821446 | 0 |

TABLE 5-continued

| PCAT ID | Gene | Chromosomal Location | Expected score (dExp) | Observed score(d) | Fold change (PCA vs Benign) | q-value (%) |
|---|---|---|---|---|---|---|
| PCAT-21 | TU_0078299_0 | chr12:32290896-32292169 | −1.7297353 | 3.506232 | 3.2923684 | 0 |
| PCAT-22 | TU_0000033_0 | chr6:1619606-1668581 | −1.7680657 | 3.494188 | 2.2470818 | 0 |
| PCAT-23 | TU_0096472_0 | chr11:133844590-133862924 | −1.8782617 | 3.410355 | 5.9854193 | 0 |
| PCAT-24 | TU_0114259_0 | chr2:1606782-1607314 | −1.6662377 | 3.3919659 | 5.060926 | 0 |
| PCAT-25 | TU_0096473_0 | chr11:133844590-133862995 | −1.8963361 | 3.3859823 | 6.1071715 | 0 |
| PCAT-26 | TU_0100361_0 | chr8:144914456-144930753 | −1.6521469 | 3.3805158 | 3.8420231 | 0 |
| PCAT-27 | TU_0040394_0 | chr3:133418632-133441282 | −1.6208398 | 3.3201025 | 2.9724674 | 0 |
| PCAT-28 | TU_0043432_0 | chr13:34032994-34050503 | −1.6739471 | 3.2037551 | 3.2093527 | 0 |
| PCAT-29 | TU_0112020_0 | chr15:67764259-67801825 | −1.5603316 | 3.1937351 | 3.593551 | 0 |
| PCAT-30 | TU_0042717_0 | chr13:23149908-23200198 | −2.0654948 | 3.1685438 | 4.9699407 | 0 |
| PCAT-31 | TU_0078292_0 | chr12:32290485-32406307 | −1.4503003 | 3.151379 | 2.8911364 | 0 |
| PCAT-32 | TU_0084146_0 | chr5:14025126-14062770 | −1.6452767 | 3.1257985 | 2.6190455 | 0 |
| PCAT-33 | TU_0056168_0 | chr18:22477042-22477666 | −1.5381516 | 3.0557241 | 3.1951044 | 0 |
| PCAT-34 | TU_0040383_0 | chr3:133360541-133429262 | −1.5558791 | 3.0416508 | 3.7478442 | 0 |
| PCAT-35 | TU_0112025_0 | chr15:67780574-67782345 | −1.6815377 | 3.0412362 | 3.433415 | 0 |
| PCAT-36 | TU_0041688_0 | chr3:186741299-186741933 | −1.4749297 | 3.0062308 | 2.543468 | 0 |
| PCAT-37 | TU_0103642_0 | chr9:109187089-109187455 | −1.7387192 | 2.998956 | 6.6124363 | 0 |
| PCAT-38 | TU_0040375_0 | chr3:133280694-133394609 | −1.5469999 | 2.9753568 | 3.9068055 | 0 |
| PCAT-39 | TU_0047312_0 | chr4:39217669-39222163 | −1.6388936 | 2.9124916 | 3.6121209 | 0 |
| PCAT-40 | TU_0106545_0 | chr22:22218478-22219162 | −1.7586497 | 2.889856 | 3.7357745 | 0 |
| PCAT-41 | TU_0054541_0 | chr16:79408800-79435066 | −1.7485934 | 2.8699164 | 6.647557 | 0 |
| PCAT-42 | TU_0060446_0 | chr1:28438629-28450156 | −1.4880521 | 2.857332 | 1.9824111 | 0 |
| PCAT-43 | TU_0072907_0 | chr20:55759486-55771563 | −1.5254781 | 2.7966201 | 2.812179 | 0 |
| PCAT-44 | TU_0043403_0 | chr13:33844637-33845921 | −1.5793877 | 2.7919009 | 3.6403422 | 0 |
| PCAT-45 | TU_0038678_0 | chr3:53515951-53517078 | −1.7047809 | 2.7858517 | 3.6908987 | 0 |
| PCAT-46 | TU_0101706_0 | chr9:3408690-3415374 | −1.4780945 | 2.7822099 | 3.3066912 | 0 |
| PCAT-47 | TU_0101709_0 | chr9:3411967-3415374 | −1.4652373 | 2.7622206 | 3.1886175 | 0 |
| PCAT-48 | TU_0106544_0 | chr22:22210421-22220506 | −1.6153399 | 2.7578135 | 3.7418716 | 0 |
| PCAT-49 | TU_0046121_0 | chr4:766363-766599 | −1.5697786 | 2.7573307 | 1.435532 | 0 |
| PCAT-50 | TU_0106542_0 | chr22:22211315-22220506 | −1.6098742 | 2.755721 | 3.3781004 | 0 |
| PCAT-51 | TU_0106541_0 | chr22:22209111-22219162 | −1.6593723 | 2.7341027 | 3.664146 | 0 |
| PCAT-52 | TU_0044453_0 | chr13:51505777-51524522 | −1.3416 | 2.732019 | 2.536953 | 0 |
| PCAT-53 | TU_0104717_0 | chr9:130697833-130698832 | −1.2938 | 2.7219732 | 2.3344588 | 0 |
| PCAT-54 | TU_0089014_0 | chr5:176014905-176015351 | −1.3967873 | 2.7047238 | 1.7803582 | 0 |
| PCAT-55 | TU_0108452_0 | chr15:19344745-19362916 | −1.5839852 | 2.6759455 | 1.8484153 | 0 |
| PCAT-56 | TU_0112003_0 | chr15:67645590-67775246 | −1.4386703 | 2.668052 | 3.045022 | 0 |
| PCAT-57 | TU_0078286_0 | chr12:32395588-32405731 | −1.3580605 | 2.6660874 | 2.6121044 | 0 |
| PCAT-58 | TU_0078303_0 | chr12:32274210-32274530 | −1.5020599 | 2.65866 | 3.3306372 | 0 |

TABLE 5-continued

| PCAT ID | Gene | Chromosomal Location | Expected score (dExp) | Observed score(d) | Fold change (PCA vs Benign | q-value (%) |
|---|---|---|---|---|---|---|
| PCAT-59 | TU_0112004_0 | chr15:67644390-67650387 | −1.5175762 | 2.6509888 | 2.9933636 | 0 |
| PCAT-60 | TU_0071087_0 | chr20:21428679-21429454 | −1.4916688 | 2.649109 | 4.6481714 | 0 |
| PCAT-61 | TU_0072906_0 | chr20:55759768-55770657 | −1.5059631 | 2.645004 | 2.95756 | 0 |
| PCAT-62 | TU_0054240_0 | chr16:70155175-70173873 | −1.4715649 | 2.6437716 | 3.5309577 | 0 |
| PCAT-63 | TU_0047330_0 | chr4:39217641-39222163 | −1.5139307 | 2.6277235 | 3.0695639 | 0 |
| PCAT-64 | TU_0055435_0 | chr18:6718938-6719172 | −1.6048826 | 2.6173768 | 2.9221427 | 0 |
| PCAT-65 | TU_0079791_0 | chr12:54971063-54971481 | −1.4415668 | 2.6010823 | 2.0141602 | 0 |
| PCAT-66 | TU_0043411_0 | chr13:33918267-33926769 | −1.495064 | 2.5991623 | 3.3860362 | 0 |
| PCAT-67 | TU_0056121_0 | chr18:20196762-20197522 | −1.2526748 | 2.5938754 | 1.7191441 | 0 |
| PCAT-68 | TU_0043412_0 | chr13:33918267-33935946 | −1.5891836 | 2.590199 | 4.2804046 | 0 |
| PCAT-69 | TU_0065837_0 | chr1:149791252-149795934 | −1.3852053 | 2.5882297 | 2.9343975 | 0 |
| PCAT-70 | TU_0043401_0 | chr13:33825711-33845275 | −1.5994886 | 2.5853698 | 4.3461533 | 0 |
| PCAT-71 | TU_0006463_0 | chr6:144659819-144660143 | −1.4985942 | 2.5744107 | 2.2007995 | 0 |
| PCAT-72 | TU_0048506_0 | chr4:80329017-80348259 | −1.5744382 | 2.5690413 | 2.8022916 | 0 |
| PCAT-73 | TU_0084140_0 | chr5:14003669-14054874 | −1.4040573 | 2.5472755 | 2.5979335 | 0 |
| PCAT-74 | TU_0082982_0 | chr12:121776584-121777370 | −1.5293782 | 2.5458217 | 2.6197503 | 0 |
| PCAT-75 | TU_0013212_0 | chr7:138990883-139001515 | −1.2296493 | 2.544434 | 1.6879753 | 0 |
| PCAT-76 | TU_0072912_0 | chr20:55779532-55780817 | −1.4302964 | 2.5406737 | 3.8653345 | 0 |
| PCAT-77 | TU_0112281_0 | chr15:70586704-70590792 | −1.4590155 | 2.5375097 | 2.4288568 | 0 |
| PCAT-78 | TU_0048767_0 | chr4:88120066-88124880 | −1.3735119 | 2.5323946 | 2.233308 | 0 |
| PCAT-79 | TU_0108455_0 | chr15:19358326-19365341 | −1.5651321 | 2.5261333 | 1.9462687 | 0 |
| PCAT-80 | TU_0091997_0 | chr11:58560356-58573012 | −1.3149309 | 2.5185204 | 2.1176686 | 0 |
| PCAT-81 | TU_0121655_0 | chr2:202985284-202998634 | −1.4014161 | 2.476237 | 2.2194188 | 0.859614 |
| PCAT-82 | TU_0071798_0 | chr20:33775260-33778511 | −1.3356665 | 2.4645917 | 1.6566333 | 0.850371 |
| PCAT-83 | TU_0049200_0 | chr4:102469973-102476087 | −1.3222212 | 2.456723 | 1.9456172 | 0.841324 |
| PCAT-84 | TU_0121714_0 | chr2:203295212-203314868 | −1.3457565 | 2.4496663 | 1.7624274 | 0.832468 |
| PCAT-85 | TU_0098937_0 | chr8:95748751-95751321 | −1.4532137 | 2.42248 | 2.2326834 | 0.823797 |
| PCAT-86 | TU_0108453_0 | chr15:19356996-19364013 | −1.8033699 | 2.4094539 | 3.839975 | 0.767811 |
| PCAT-87 | TU_0114170_0 | chr15:99659312-99669199 | −1.4358851 | 2.4062114 | 2.1252658 | 0.767811 |
| PCAT-88 | TU_0089906_0 | chr11:1042845-1045705 | −1.3899238 | 2.401665 | 2.6390955 | 0.767811 |
| PCAT-89 | TU_0001559_0 | chr6:30283700-30286011 | −1.3517065 | 2.3987799 | 1.5110766 | 0.767811 |
| PCAT-90 | TU_0050557_0 | chr4:159976338-160016453 | −1.17525 | 2.398688 | 2.0524442 | 0.767811 |
| PCAT-91 | TU_0078294_0 | chr12:32395632-32413064 | −1.4560982 | 2.3969867 | 2.1863208 | 0.767811 |
| PCAT-92 | TU_0044933_0 | chr13:94755992-94760688 | −1.2905197 | 2.3965187 | 2.189938 | 0.767811 |
| PCAT-93 | TU_0017730_0 | chr17:52346638-52346880 | −1.4169512 | 2.3874657 | 1.4708191 | 0.760428 |
| PCAT-94 | TU_0039020_0 | chr3:66578329-66607777 | −1.2662895 | 2.3720088 | 1.7112709 | 0.712473 |
| PCAT-95 | TU_0049213_0 | chr4:102461960-102476087 | −1.2725139 | 2.3671806 | 1.8876821 | 0.712473 |
| PCAT-96 | TU_0093070_0 | chr11:64945809-64961189 | −1.2954472 | 2.3645105 | 1.9128969 | 0.712473 |

TABLE 5-continued

| PCAT ID | Gene | Chromosomal Location | Expected score (dExp) | Observed score(d) | Fold change (PCA vs Benign | q-value (%) |
|---|---|---|---|---|---|---|
| PCAT-97 | TU_0051063_0 | chr4:187244297-187244767 | 1.8922831 | -2.8485844 | 0.50983155 | 0.732264 |
| PCAT-98 | TU_0098190_0 | chr8:61704765-61708199 | 1.9825526 | -2.8612607 | 0.4027831 | 0.732264 |
| PCAT-99 | TU_0038811_0 | chr3:57890130-57890834 | 1.9620296 | -2.8837616 | 0.44431657 | 0.732264 |
| PCAT-100 | TU_0020914_0 | chr19:9718612-9721799 | 1.6433232 | -2.9243097 | 0.50623006 | 0.732264 |
| PCAT-101 | TU_0112056_0 | chr15:69658838-69678469 | 1.837821 | -3.0355222 | 0.46161976 | 0 |
| PCAT-102 | TU_0036396_0 | chr14:104617328-104619095 | 1.849786 | -3.1192882 | 0.45514825 | 0 |
| PCAT-103 | TU_0095765_0 | chr11:117640504-117642734 | 2.1002219 | -3.2632742 | 0.38160667 | 0 |
| PCAT-104 | TU_0050224_0 | chr4:147115887-147190781 | 2.1981242 | -3.2975357 | 0.28569755 | 0 |
| PCAT-105 | TU_0112059_0 | chr15:69667695-69691724 | 1.8148681 | -3.3816626 | 0.43667468 | 0 |
| PCAT-106 | TU_0098382_0 | chr8:68494189-68495887 | 2.5413978 | -4.0586042 | 0.30793378 | 0 |

TABLE 6

| PCAT-ID | Gene | Chromosomal Location | Outlier Score | Median Expression (RPKM) | Maximum Expression (RPKM) |
|---|---|---|---|---|---|
| PCAT-107 | TU_0029004_0 | chrX:66691350-66692032 | 130.7349145 | 1 | 90.921 |
| PCAT-108 | TU_0054542_0 | chr16:79420131-79423590 | 127.0430957 | 5.60998 | 135.85 |
| PCAT-109 | TU_0120899_0 | chr2:180689090-180696402 | 123.5416436 | 1.0525222 | 94.6932 |
| PCAT-110 | TU_0054540_0 | chr16:79419351-79423673 | 119.090847 | 4.161985 | 94.4461 |
| PCAT-111 | TU_0120918_0 | chr2:181297540-181400892 | 112.710111 | 1.4533705 | 92.1795 |
| PCAT-112 | TU_0054538_0 | chr15:79408946-79450819 | 98.01851659 | 1.830343 | 93.1207 |
| PCAT-113 | TU_0059541_0 | chr1:20685471-20686432 | 63.3572507 | 1.783103 | 1375.15 |
| PCAT-114 | TU_0120924_0 | chr2:181331111-181427485 | 63.95455962 | 1.3891845 | 365.202 |
| PCAT-115 | TU_0074308_0 | chr10:42652247-42653596 | 60.91841567 | 1.393607 | 65.7712 |
| PCAT-116 | TU_0049192_0 | chr4:102257900-102306678 | 59.24997694 | 1.3854525 | 69.2423 |
| PCAT-117 | TU_0054537_0 | chr16:79406933-79430041 | 58.04481977 | 1.8534395 | 42.751 |
| PCAT-118 | TU_120900_0 | chr2:180926864-180985967 | 55.8438747 | 1 | 67.6582 |
| PCAT-119 | TU_0114527_0 | chr2:10858318-10858530 | 54.76455104 | 1.2969775 | 35.0059 |
| PCAT-120 | TU_0120923_0 | chr2:181328053-181419226 | 52.9793227 | 1.2821 | 232.556 |
| PCAT-121 | TU_0049231_0 | chr4:102257900-102259655 | 52.77001947 | 1.34042 | 67.6276 |

TABLE 7

| Rank | Gene | Chromosomal location | Outlier Score | Median Expression (RPKI) | Maximum Expression (RPKM) |
|---|---|---|---|---|---|
| 1 | CRISP3 | chr6:49803053-49813070 | 294.56446 | 1.5414775 | 478.812 |
| 2 | SPINK1 | chr5:147184335-147191453 | 177.19518 | 2.484455 | 624.733 |
| 3 | TU_0029004_0 | chrX:66691350-66692032 | 130.73491 | 1 | 90.921 |
| 4 | TU_0054542_0 | chr16:79420131-79423590 | 127.0431 | 5.60998 | 135.85 |
| 5 | TU_0120899_0 | chr2:180689090-180696402 | 123.54164 | 1.0525222 | 94.6932 |
| 6 | ERG | chr21:38673821-38792298 | 119.446 | 3.421615 | 178.826 |
| 7 | TU_0054540_0 | chr16:79419351-79423673 | 119.09085 | 4.161985 | 94.4461 |
| 8 | ERG | chr21:38673821-38792298 | 117.60294 | 3.470755 | 176.186 |
| 9 | ERG | chr21:38673821-38355574 | 117.26408 | 3.385695 | 170.663 |
| 10 | ERG | chr21:38673821-38955574 | 163.3448 | 3.40077 | 170.443 |
| 11 | TU_0120918_0 | chr2:181297540-181400892 | 112.71011 | 1.4533705 | 92.1795 |
| 12 | C7orf68 | chr7:127883119-127885708 | 105.18504 | 6.835525 | 336.148 |
| 13 | CSRP3 | chr11:19160153-19180106 | 101.12947 | 1 | 148.45 |
| 14 | C7orf68 | chr7:127883119-127885708 | 100.63202 | 7.08303 | 337.76 |
| 15 | COL2A1 | chr12:46653014-46684552 | 99.166329 | 1.2285615 | 96.0977 |
| 16 | C1orf64 | chr1:16203317-16205771 | 98.085922 | 3.62012 | 252.013 |
| 17 | TU_0054538_0 | chr16:79408946-79450819 | 98.018517 | 1.830343 | 93.1207 |
| 18 | COL2A1 | chr12:46653014-46684552 | 97.347905 | 1.2416035 | 94.6672 |
| 19 | CSRP3 | chr11:19160153-19180165 | 96.730187 | 1 | 141.963 |
| 20 | COL9A2 | chr1:40538749-40555526 | 74.408443 | 19.24815 | 570.961 |
| 21 | PLA2G7 | chr6:46780012-46811389 | 69.521175 | 10.83567 | 97.8331 |

TABLE 7-continued

| Rank | Gene | Chromosomal location | Outlier Score | Median Expression (RPKI) | Maximum Expression (RPKM) |
|---|---|---|---|---|---|
| 22 | AGT | chr1:228904891-228916959 | 69.319886 | 4.797365 | 189.281 |
| 23 | TU_0059541_0 | chr1:20685471-20686432 | 68.357251 | 1.783109 | 1375.15 |
| 24 | ETV1 | chr7:13897382-13992664 | 68.218569 | 1.932797 | 138.519 |
| 25 | ETV1 | chr7:13897382-13992664 | 67.723331 | 1.9899945 | 142.406 |
| 26 | ETV1 | chr7:13897382-13992664 | 67.680571 | 1.9915925 | 143.632 |
| 27 | PLA2G7 | chr6:46780011-46811110 | 67.089039 | 10.62 | 95.3551 |
| 28 | ETV1 | chr7:13897382-13997390 | 66.381191 | 2.097225 | 143.975 |
| 29 | ETV1 | chr7:13897382-13997575 | 65.563724 | 2.074935 | 141.069 |
| 30 | MUC6 | chr11:1002823-1026706 | 64.7328 | 1.466194 | 351.862 |
| 31 | TU_0120924_0 | chr2:181331111-181427485 | 63.95456 | 1.3891845 | 365.202 |
| 32 | ETV1 | chr7:13897382-13996167 | 63.929225 | 2.05648 | 135.131 |
| 33 | ETV1 | chr7:13897382-13996167 | 62.424072 | 2.03086 | 131.644 |
| 34 | TU_0074308_0 | chr10:42652247-42653596 | 60.918416 | 1.393607 | 65.7712 |
| 35 | TU_0049192_0 | chr4:102257900-102306678 | 59.249977 | 1.3854525 | 69.2423 |
| 36 | TU_0054537_0 | chr16:79406933-79430041 | 58.04482 | 1.8534395 | 42.751 |
| 37 | RGL3 | chr19:11365731-11391018 | 57.528689 | 7.660035 | 91.2238 |
| 38 | RGL3 | chr19:11365731-11391018 | 57.393056 | 7.6377 | 94.6437 |
| 39 | TMEM45B | chr11:129190950-129235108 | 55.887845 | 4.87695 | 60.0414 |
| 40 | TU_0120900_0 | chr2:180926864-160985967 | 55.843875 | 1 | 67.6582 |
| 41 | PTK6 | chr20:61630219-61639151 | 55.101291 | 3.420545 | 114.116 |
| 42 | TU_0114527_0 | chr2:10858318-10858530 | 54.764551 | 1.2969775 | 35.0059 |
| 43 | TU_0112020_0 | chr15:67764259-67801825 | 53.882759 | 2.0281615 | 88.99 |
| 44 | TU_01209230 | chr2:181328.093-181419226 | 57.979373 | 1.2871 | 232.556 |
| 45 | TU_0049231_0 | chr4:102257900-102259695 | 52.770019 | 1.34042 | 67.5276 |
| 46 | MON1B | chr16:75782336-75791044 | 51.717027 | 26.00355 | 187.807 |
| 47 | TU_0054541_0 | chr16:79408800-79435066 | 50.445246 | 1.7164375 | 32.5832 |
| 48 | TU_0087466_0 | chr5:136779809-136798173 | 50.285169 | 1.2738505 | 42.0309 |
| 49 | DLX1 | chr2:172658453-172662647 | 50.048039 | 2.088625 | 43.0035 |
| 50 | TU_0108209_0 | chr22:46493579-46531245 | 47.753833 | 1.0491419 | 26.6643 |
| 51 | DLX1 | chr2:172658453-172662647 | 47.159314 | 1.9682735 | 38.4705 |
| 52 | SMC4 | chr3:161600123-161635435 | 47.127047 | 4.581655 | 63.2353 |
| 53 | SMC4 | chr3:161601040-161635435 | 46.967013 | 4.442065 | 61.2756 |
| 54 | TU_0102399_0 | chr9:35759438-35761676 | 46.664973 | 6.44675 | 179.711 |
| 55 | TU_0029005_0 | chrX:66690414-66704178 | 46.155567 | 1.0870047 | 38.3022 |
| 56 | C15orf48 | chr15:43510054-43512939 | 45.732195 | 19.02125 | 223.42 |
| 57 | C15orf48 | chr15:43510054-43512939 | 45.549287 | 21.28355 | 248.097 |
| 58 | EFNA3 | chr1:153317971-153326638 | 44.993943 | 3.68358 | 70.5016 |
| 59 | TU_0043412_0 | chr13:33918267-33935946 | 44.506741 | 1.311142 | 15.1968 |
| 60 | TU_0069093_9 | chr1:220878648-220886461 | 42.645673 | 1.443496 | 160.898 |
| 61 | UGT1A6 | chr2:234265059-234346684 | 42.500058 | 1.937622 | 45.753 |
| 62 | TU_0057051_0 | chr18:54524352-54598419 | 42.108622 | 2.418785 | 56.0712 |
| 63 | AMH | chr19:2200112-2203072 | 41.744334 | 2.16026 | 91.244 |
| 64 | TU_0120908_0 | chr2:181147971-181168431 | 41.650097 | 1.0750564 | 48.7957 |
| 65 | TU_0099873_0 | chr8:128138926-128140075 | 41.420293 | 1.51101 | 38.7353 |
| 66 | HN1 | chr17:70642938-70662369 | 40.495209 | 16.35625 | 110.208 |
| 67 | TU_0022570_0 | chr19:20341299-20343938 | 39.964803 | 2.912835 | 98.5739 |
| 58 | TU_0098937_0 | chr8:95748751-95751321 | 39.740546 | 1.4422495 | 51.5935 |
| 69 | TU_0040375_9 | chr3:133280694-133394609 | 39.664781 | 2.149005 | 90.9787 |
| 70 | HN1 | chr17:70642938-70662370 | 39.655603 | 16.34725 | 109.587 |
| 71 | TU_0120929_0 | chr2:181328093-184423017 | 39.419483 | 1.2116475 | 189.765 |
| 72 | TU_0112004_0 | chr15:67644390-67650387 | 34.300973 | 6.10665 | 76.723 |
| 73 | TU_0108439_0 | chr15:19293567-19296333 | 39.131646 | 1 | 27.7534 |
| 74 | HN1 | chr17:70642936-70662369 | 39.00893 | 15.53595 | 103.782 |
| 75 | SULT1C2 | chr2:108271526-108292803 | 39.007062 | 1.2259165 | 91.5617 |
| 76 | STXI9 | chr3:95215904-95230144 | 38.954223 | 4.521255 | 46.0375 |
| 77 | TU_0030420_0 | chrX:112642982-112685485 | 38.715477 | 1.0890785 | 62.9419 |
| 78 | TU_0099875_0 | chr8:128138047-128140075 | 38.489447 | 1.393413 | 35.8984 |
| 79 | UBE2T | chr1:200567408-200577717 | 38.387515 | 3.070345 | 85.9738 |
| 80 | SULT1C | chr2:108271525-108292803 | 37.517555 | 1.215033 | 88.0858 |
| 81 | TU_0049429_0 | chr4:109263508-109272353 | 37.794245 | 1.09915225 | 29.1838 |
| 82 | STMN1 | chr1:26099193-26105955 | 37.319869 | 14.3784 | 187.062 |
| 83 | UGT1A1 | chr2:234333657-234346684 | 37.267194 | 1.660554 | 35.9475 |
| 84 | LRRN1 | chr3:3816120-3864387 | 37.229013 | 3.9912 | 37.117 |
| 85 | TU_008563_0 | chr5:113801649-113806936 | 36.896806 | 1.0501165 | 29.6561 |
| 86 | ORM2 | chr9:116131889-116135357 | 36.578698 | 3.614505 | 120.139 |

TABLE 7-continued

| Rank | Gene | Chromosomal location | Outlier Score | Median Expression (RPKI) | Maximum Expression (RPKM) |
|---|---|---|---|---|---|
| 87 | TU_0084060_0 | chr5:7932238-7932523 | 36.507599 | 1 | 23.1979 |
| 88 | TU_0099644_0 | chr8:81204784-81207034 | 36.779294 | 1.6013735 | 64.9663 |
| 89 | ACSM1 | chr16:20542059-20610079 | 36.280896 | 13.3707 | 317.077 |
| 90 | STMN1 | chr1:26099193-26105231 | 35.682914 | 12.73275 | 154.721 |
| 91 | STMN1 | chr1:26099193-26105580 | 35.823453 | 14.31935 | 185.329 |
| 92 | TU_0120914_0 | chr2:181265370-181265053 | 35.551458 | 1.053468 | 30.7074 |
| 93 | UGT1A7 | chr2:234255322-234346684 | 35.073999 | 1.667349 | 33.4378 |
| 94 | TU_0087462_0 | chr5:136386339-136403134 | 34.992335 | 1.4450115 | 27.1703 |
| 95 | UGT1A3 | chr2:234302511-234346684 | 34.952247 | 1.6889365 | 33.4202 |
| 96 | UGT1A5 | chr2:234286376-234346684 | 34.950003 | 1.6639345 | 33.1718 |
| 97 | FOXDI | chr5:72777840-72780108 | 34.875512 | 1.2373575 | 10.80944 |
| 98 | ADM | chr11:10283217-10285499 | 34.855767 | 11.83635 | 276.194 |
| 99 | PPFIA4 | chr1:201286933-201314487 | 34.769924 | 1.566044 | 43.9812 |
| 100 | UGT1A10 | chr2:234209861-234346690 | 34.738527 | 1.652799 | 32.7318 |
| 101 | UGT1A4 | chr2:234292176-234346684 | 34.663597 | 1.655924 | 32.9264 |
| 102 | UGT1A9 | chr2:234245282-234346690 | 34.648086 | 1.655272 | 32.852 |
| 103 | TU_0090142_0 | chr11:4748677-4760303 | 34.517072 | 1.5226305 | 51.3411 |
| 104 | TU_0082746_0 | chr12:120197102-120197416 | 34.499713 | 2.531095 | 59.9026 |
| 105 | UGT1A8 | chr2:234191029-234346684 | 34.433379 | 1.6498025 | 32.5849 |
| 106 | TU_0112207_0 | chr15:70278422-70285121 | 34.308752 | 1.040266 | 112.274 |
| 107 | LOC145837 | chr15:67641112-67650833 | 34.291574 | 7.59729 | 74.9194 |
| 108 | TU_0050712_0 | chr4:170217424-170228463 | 34.23107 | 1.504313 | 65.5606 |
| 109 | TU_0049410_0 | chr13:33929484-33944669 | 34.112491 | 1.393529 | 24.8401 |
| 110 | SNHG1 | chr11:62776035-62379936 | 33.971939 | 33.74365 | 270.512 |
| 111 | MUC1 | chr1:153424923-153429324 | 33.838428 | 16.3238 | 664.278 |
| 112 | MUC1 | chr1:153424923-153429324 | 33.823147 | 15.8436 | 644.44 |
| 113 | TU_0099871_0 | chr8:128138047-128143500 | 33.697295 | 1.412972 | 33.2958 |
| 114 | TU_0040383_0 | chr3:133360541-133429262 | 33.548813 | 2.553955 | 85.9384 |
| 115 | MUC1 | chr1:153424923-153429324 | 33.495501 | 15.91355 | 627.622 |
| 116 | TU_00451202_0 | chr4:102257900-102304755 | 33.391066 | 1.5555505 | 39.7522 |
| 117 | TU_0120913_0 | chr2:181254530-181266950 | 33.188328 | 1 | 43.8515 |
| 118 | B4GALNT4 | chr11:359794-372116 | 33.176248 | 6.3749 | 80.9639 |
| 119 | TU_0100059_0 | chr8:141258835-141260573 | 33.169029 | 1.3615565 | 44.9943 |
| 120 | TOP2A | chr17:35798321-35827695 | 33.132056 | 1.9725825 | 34.1032 |
| 121 | MUC1 | chr1:153424923-153429324 | 33.081326 | 15.9539 | 532.042 |
| 122 | TU_0001265_0 | chr6:27081719-27082291 | 33.045746 | 1.3391905 | 100.5401 |

TABLE 7

| | | | | | |
|---|---|---|---|---|---|
| 123 | C7orf 53 | chr7:11908143411918171 | 33.024251 | 2.820945 | 32.2465 |
| 124 | SLC45A2 | chr5:33980477-34020537 | 32.952911 | 2.012104 | 54.8589 |
| 125 | TU_0099869_0 | chr8:128138047428225937 | 32.928048 | 1.308804 | 30.4667 |
| 126 | UGT1A6 | chr2:234266250-234346690 | 32.918772 | 1.662221 | 31.4671 |
| 127 | TU_0120917_0 | chr2:181265370-181266950 | 32.796137 | 1.0771403 | 36.3557 |
| 128 | CACNA1D | chr3:53504070-53821532 | 32.608094 | 4.51306 | 44.9904 |
| 129 | UBE2C | chr20:43874661-43879003 | 32.456813 | 1.6391285 | 58.398 |
| 130 | ALDOC | chr17:23924259-23928078 | 32.455953 | 14.98415 | 228.812 |
| 131 | MUC1 | chr1:53424323453429324 | 32.44845 | 15.5895 | 599.062 |
| 132 | MMPII | chr22:22445035-22456503 | 32.411555 | 3.257735 | 73.9158 |
| 133 | TU_0084303_0 | chr5:158994764.5955226 | 32.39036 | 2.21168 | 14.4385 |
| 134 | CACNA1D | chr3:53504070-53821532 | 32.381439 | 4.484655 | 44.6867 |
| 135 | UBE2C | chr20:43874661-43879003 | 32.358151 | 1.705223 | 57.559 |
| 136 | CACNA1D | chr3:53504070-53821532 | 32.353332 | 4.463805 | 44.2455 |
| 137 | FGFRL1 | chr4:995609-1010686 | 32.275762 | 26.0133 | 450.449 |
| 138 | FGFRL1 | chr4:996251-1010686 | 32.075261 | 27.0148 | 468.809 |
| 139 | FGFRL1 | chr4:995759-1010686 | 32.069901 | 26.92945 | 467.246 |
| 140 | MUC1 | chr1:153424923-153429324 | 32.011017 | 15.3218 | 586.058 |
| 141 | TU_0099922_0 | chr8:128979617-128981414 | 31.333339 | 3.32544 | 32.6893 |
| 142 | TU_0001173_0 | chr6:26385234-26386052 | 31.823293 | 2.339595 | 71.3388 |
| 143 | MUC1 | chr1:153424923-153429324 | 31.781267 | 15.22945 | 587.582 |
| 144 | TMEM178 | chr2:39746141-39798605 | 31.614406 | 13.40605 | 182.03 |
| 145 | UBE2C | chr20:43874661-43879003 | 31.37539 | 1.7154185 | 58.1531 |
| 146 | KCNC2 | chr12:73720162-73889778 | 31.294059 | 1.8783795 | 104.225 |
| 147 | MAGEC2 | chrX:141117794-141120742 | 31.286618 | 1 | 34.1099 |
| 148 | SERHL2 | chr22:41279868-41300332 | 31.131788 | 3.670135 | 61.9969 |
| 149 | KCNC2 | chr12:73720162-73889778 | 31.126593 | 1.868714 | 108.199 |
| 150 | GRAMD4 | chr22:45401321-45454352 | 31.063732 | 5.977725 | 79.8338 |

Table 8 shows the number of cancer-associated lncRNAs nominated for four major cancer types. The number validated is indicated in the column on the right. This table reflects ongoing efforts.

TABLE 8

|  | # of cancer-specific lncRNAs nominated | # validated to date |
| --- | --- | --- |
| Prostate cancer | 121 | 11 |
| Breast cancer | 6 | 6 |
| Lung cancer | 36 | 32 |
| Pancreatic cancer | 34 | 0 |

Example 2

SchLAP-1 ncRNA
Methods
Cell lines

All cell lines were obtained from the American Type Culture Collection (Manassas, VA). Cell lines were maintained using standard media and conditions. SChLAP-1 or control expressing cell lines were generated by cloning SChLAP-1 or control into the pLenti6 vector (Invitrogen). Stably-transfected RWPE, HME and MCF7 cells were selected using blasticidin (Invitrogen). For LNCAP and 22Rv1 cells with stable knockdown of SChLAP-1, cells were transfected with SChLAP-1 or non-targeting shRNA lentiviral constructs for 48 hours. GFP+ cells were drug-selected using puromycin.

RNA Isolation; cDNA Synthesis; and PCR Experiments

RNA isolation and cDNA synthesis was performed according standard protocols. Quantitative PCR was performed using Power SYBR Green Mastermix (Applied Biosystems, Foster City, CA), using GAPDH and HMBS as housekeeping control genes. The relative quantity of the target gene was completed for each sample using the ΔΔCt method.

Murine Intracardiac and Subcutaneous In Vivo Models

Intracardiac injection model: $5 \times 10^5$ cells were introduced to CB-17 severe combine immunodefiecient mice (CB-17 SCID) at 6 weeks of age. Beginning one week post injection, bioluminescent imaging of mice was performed weekly using a CCD IVIS system with a 50-mm lens (Xenogen Corp.) and the results were analyzed using LivingImage software (Xenogen). Subcutaneous injection model: $1 \times 10^6$ cells were introduced to mice (CB-17 SCID), ages 5-7 weeks, with a matrigel scaffold (BD Matrigel Matrix, BD Biosciences) in the posterior dorsal flank region (n=10 per cell line). Tumors were measured weekly using a digital caliper, and endpoint was determined as a tumor volume of 1000 mm$^3$.

Immunoblot Analysis

Cells were lysed in RIPA lysis buffer (Sigma, St. Louis, MO) supplemented with HALT protease inhibitor (Fisher). Western blotting analysis was performed with standard protocols using Polyvinylidene Difluoride membrane (GE Healthcare, Piscataway, NJ) and the signals visualized by enhanced chemiluminescence system as described by the manufacturer (GE Healthcare).

siRNA Knockdown, Proliferation and Invasion Studies

Cells were plated in 100 mM plates at a desired concentration and transfected with 20 uM experimental siRNA oligos or non-targeting controls according to standard protocols. 72 hours post-transfection with siRNA, cells were trypsinized, counted with a Coulter counter, and diluted to 1 million cells/mL. Proliferation assays were performed with a Coulter counter, and invasion of cells through Matrigel (BD Biosciences) was performed according to standard protocols RNA Immunoprecipitation RIP assays were performed using a Millipore EZ-Magna RIP RNA-Binding Protein Immunoprecipitation kit (Millipore, #17-701) according to the manufacturer's instructions.

Mayo Clinic Cohort Analyses

Formalin-fixed paraffin embedded (FFPE) samples from 235 prostate cancer patients from the Mayo Clinic43 were processed for total RNA using the RNeasy FFPE nucleic acid extraction kit (Qiagen). RNA was subjected to whole-transcriptome amplification using the WT-Ovation FFPE system (NuGen, San Carlos, CA), biotin-labelled with the Encore Biotin Module (NuGen), and hybridized to Affymetrix Human Exon (HuEx) 1.0 ST GeneChips (Affymetrix, Santa Clara CA). Microarray data was analyzed as detailed previously (Vergara et al. Front Genet 3, 23, (2012), and SChLAP-1 expression was determined by Partition Around Medoids (PAM) unsupervised clustering using probe selection region 2518129.

Statistical Analyses for Experimental Studies

All data are presented as means±S.E.M. All experimental assays were performed in duplicate or triplicate. Statistical analyses shown in figures represent Fisher's exact tests or two-tailed Student t-tests, as indicated.

Results

Figures 40, 40A, 40B:
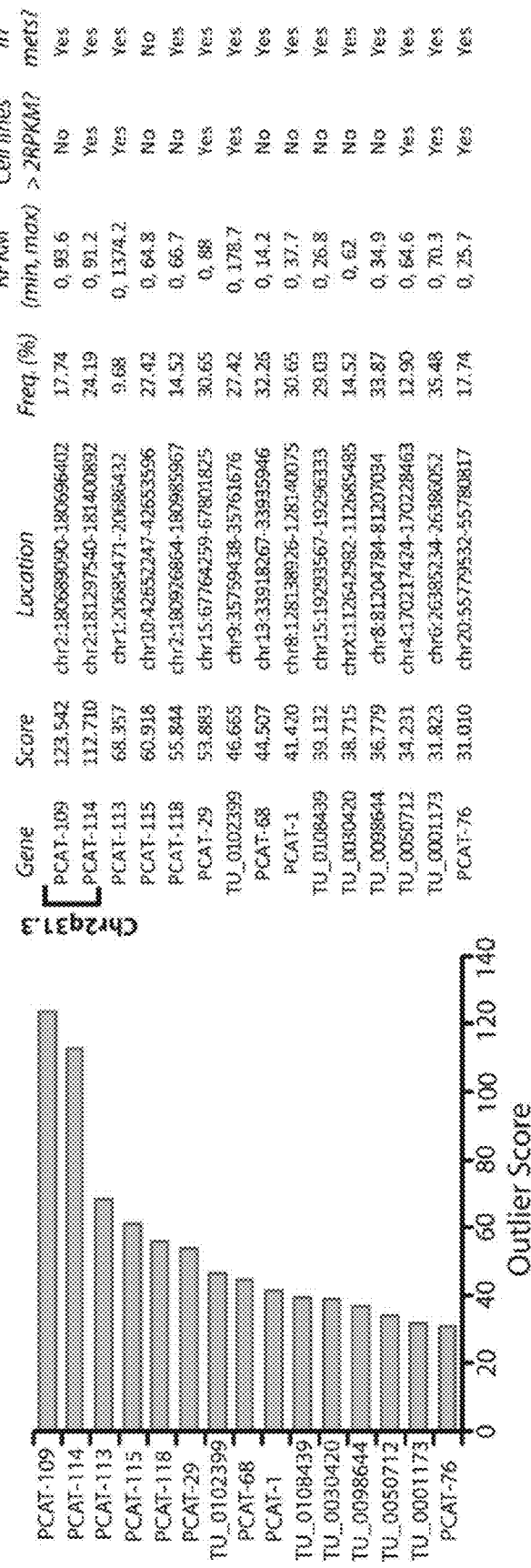
FIG. 40 shows discovery of SChLAP-1 as a prostate cancer lncRNA.
(FIG. 40a) Cancer outlier profile analysis (COPA) for intergenic lncRNAs in prostate cancer nominates two transcripts, PCAT-109 and PCAT-114, as prominent outliers.
(FIG. 40b) A comparison of lncRNA outliers nominated by COPA, including their location, frequency in clinical samples, their expression in tissues and cell lines, and whether they occur in metastatic prostate samples. (FIG.
Figure 43:
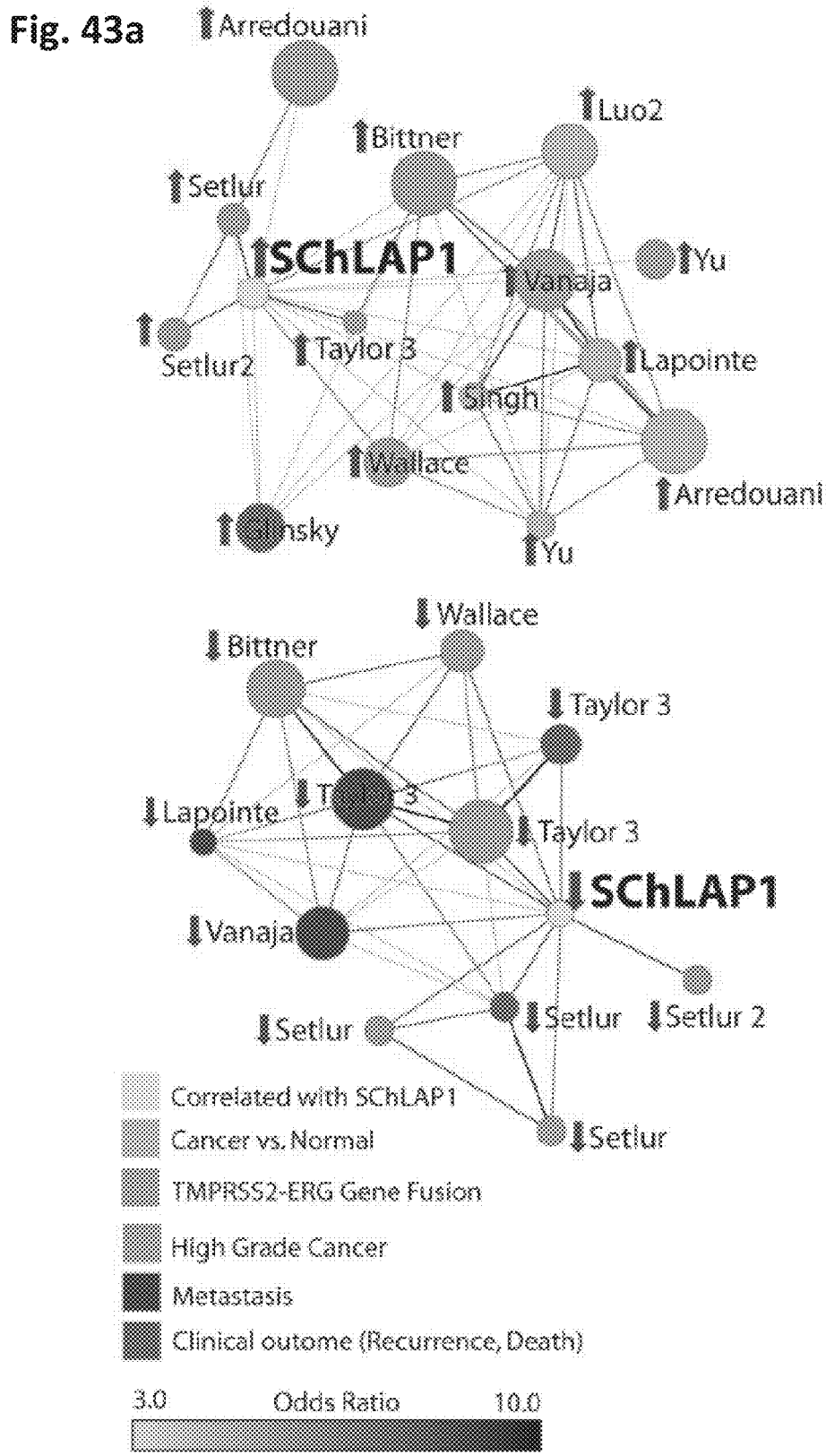
FIG. 43 shows that SChLAP-1 expression characterizes aggressive prostate cancer.

RNA-Seq has been used to profile >100 prostate cell lines and tissues, including both localized and metastatic prostate cancers (Prensner, et al. Nat Biotechnol 29, 742-749, (2011)). Given that only a fraction of prostate cancers present with aggressive clinical features (Cooperberg et al., J Clin Oncol 23, 8146-8151 (2005)), cancer outlier profile analysis (COPA; Tomlins et al., Tomlins, S. A. et al. Recurrent fusion of TMPRSS2 and ETS transcription factor Tomlins et al., Science 310, 644-648, science 310 644-648 (2005)) was performed to nominate intergenic lncRNAs selectively upregulated in a subset of cancers. PCAT-109 and PCAT-114 showed striking outlier profiles and ranked among the best outliers in prostate cancer when compared to protein-coding genes (FIG. 40a). Notably, both are located in a "gene desert" on Chromosome 2q31.3, a region with previously unknown ties to prostate cancer (FIG. 40b and FIG. 43).

Figure 44:
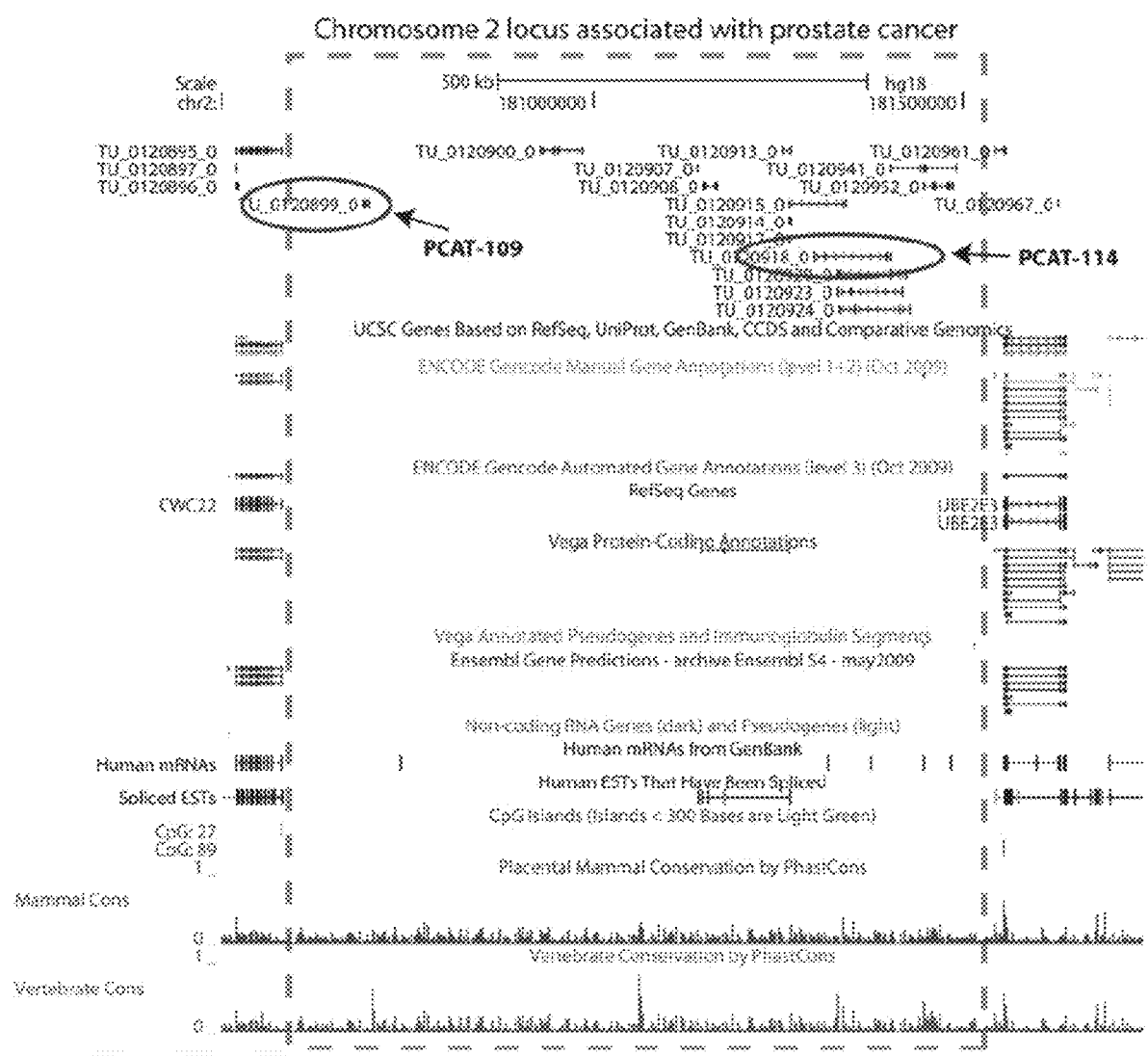
FIG. 44 shows that chromosome 2 region contains prostate cancer-associated transcripts.
Figure 46:
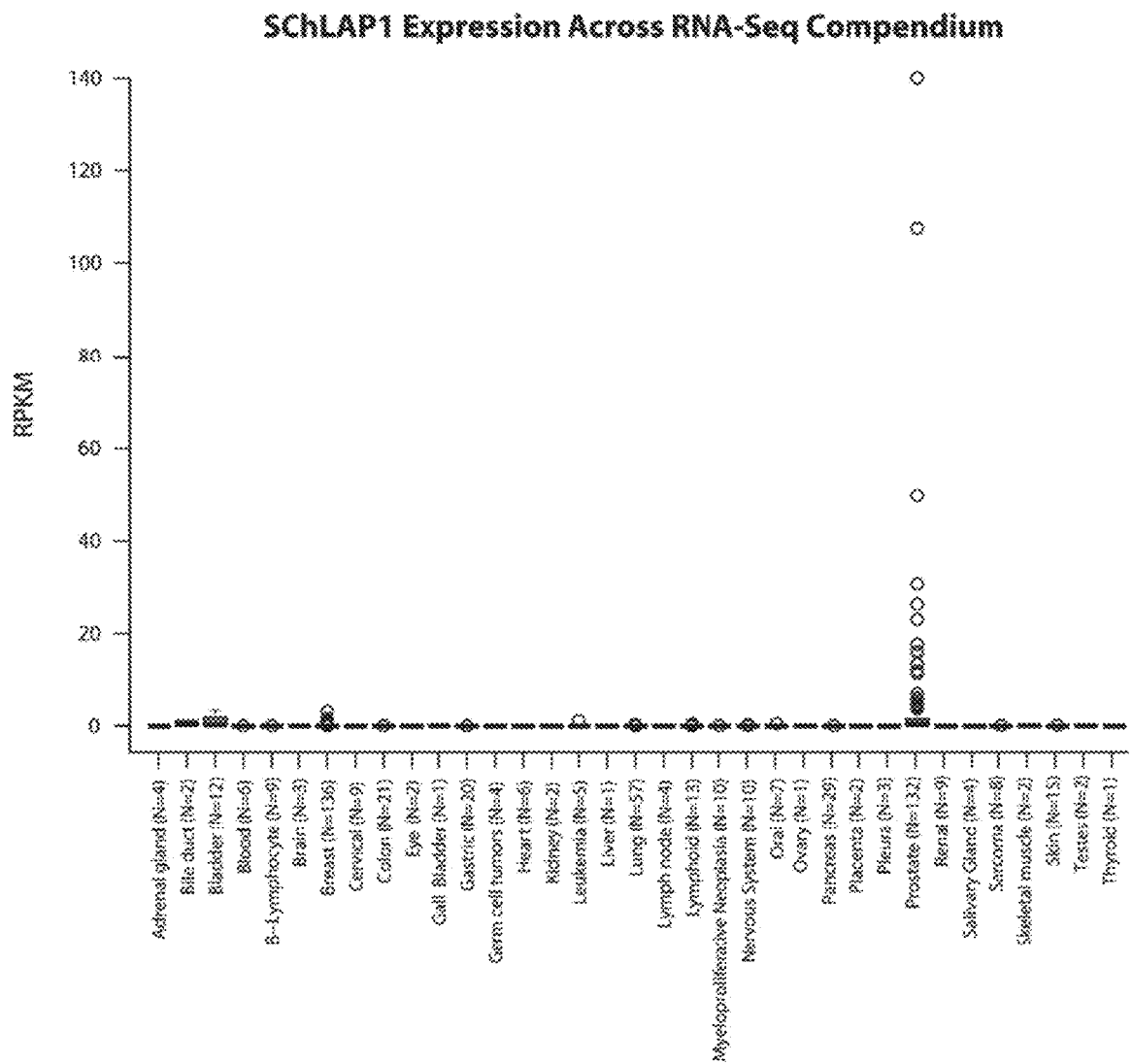
FIG. 46 shows expression of SChLAP-1 across cancers.

Efforts to validate PCAT-109 by PCR and rapid amplification of cDNA ends (RACE) failed, partly due to the fact that this gene is not robustly expressed in any prostate cell lines (FIG. 40b and data not shown). By contrast, in the PCAT-114 region, PCR experiments and 5' and 3' RACE defined a 1.4 kb, poly-adenylated gene composed of up to seven exons and spanning nearly 200 kb on Ch2q31.3 (FIG. 40c and FIG. 44). This gene was named Second Chromosome Locus Associated with Prostate-1 (SChLAP-1) after its genomic location. To further characterize this gene, a published ChIP-Seq dataset of prostate cancer (Yu et al. Cancer Cell 17, 443-454 (2010)) was used and it was found that the transcriptional start site (TSS) of SChLAP-1 was marked by tri-methylation of H3K4 (H3K4me3) and its gene body harbored tri-methylation of H3K36 (H3K36me3) (FIG. 40c), an epigenetic signature consistent with canonical protein-coding genes and lncRNAs (Guttman et al., Nature 458, 223-227 (2009)). PCR assays defined numerous splicing isoforms of this gene of which three (termed isoforms #1, #2, and #3, respectively) constituted the vast majority (>90%) of transcripts in the cell (FIG. 40d).

Using quantitative PCR (qPCR), it was validated that SChLAP-1 was highly expressed in ~20% of prostate cancers, including metastatic prostate cancer (FIG. 40e). Moreover, examination of SChLAP-1 expression in an RNA-seq compendium of >600 samples, representing >30 tissue types, demonstrated that SChLAP-1 expression was relatively absent in other tumor types (FIG. 4), demonstrating prostate caner specific activity. To establish SChLAP-1 as a non-coding gene, three isoforms (isoforms 1, 2 and 3) were cloned and in vitro translation assays were perfomed, which were negative. It was also found that SChLAP-1 expression in prostate cell lines was predominantly located in the nucleus (FIG. 40f), while most protein-coding mRNAs are located in the cytoplasm, where they engage the ribosomal translation machinery.

Figures 41, 41A:
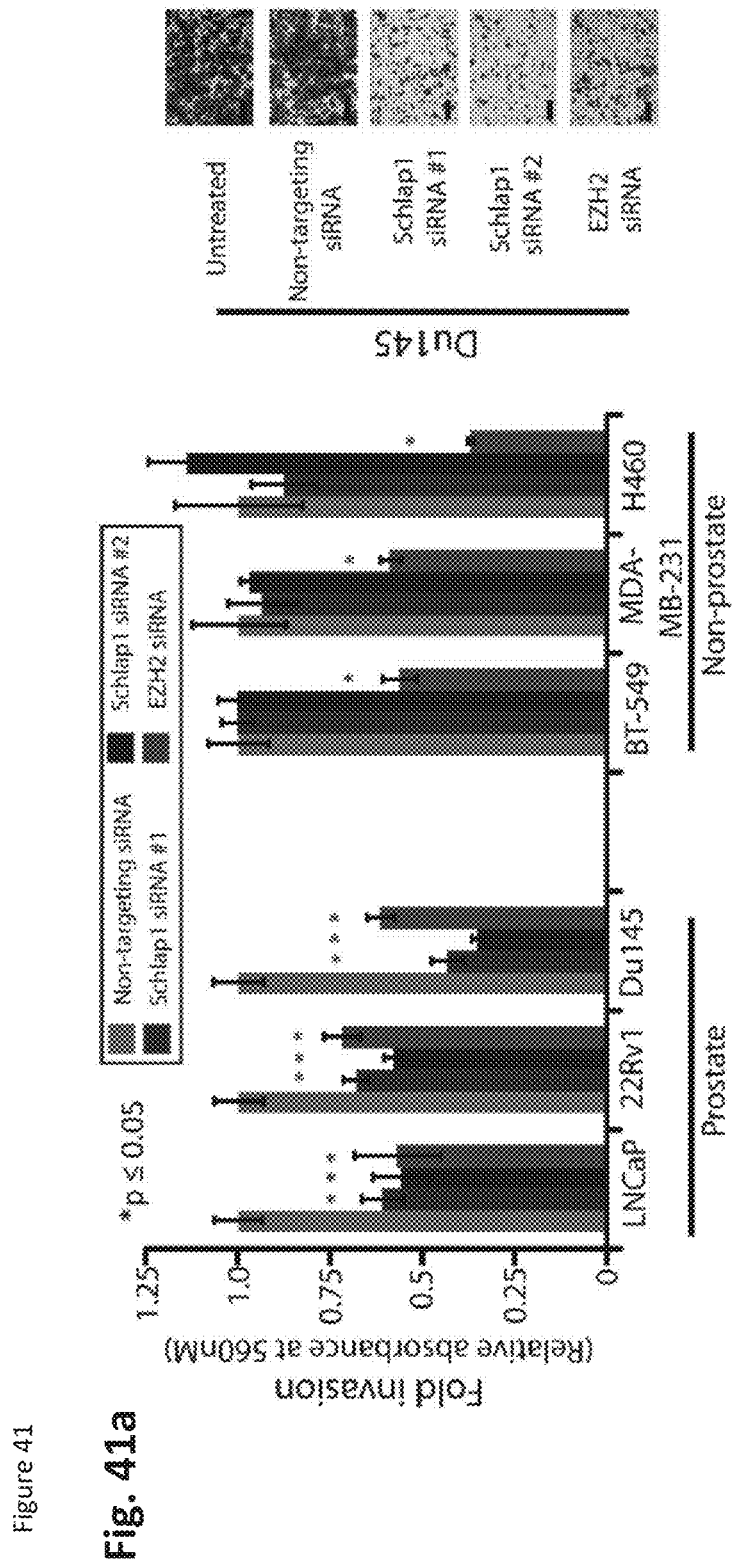
FIG. 41 shows that SChLAP-1 coordinates prostate cancer cell invasion.
(FIG. 41a) siRNA knockdown of SChLAP-1 in vitro.

To elucidate the functional role for SChLAP-1 in prostate cancer, siRNA knockdowns of this gene was performed using two independent siRNAs as well as siRNA to EZH2, which is essential for cancer cell invasion (Kleer, et al. Proc Natl Acad Sci USA 100, 11606-11611, (2003); Varambally, S. et al. Nature 419, 624-629, (2002)) as a positive control. In three prostate cancer cell lines but not breast and lung cancer cells, knockdown of SChLAP-1 dramatically impaired cell invasion in vitro at a level comparable to EZH2 (FIG. 41a). SChLAP-1 knockdown also impaired cell proliferation in prostate cells but not nonprostate cells. To confirm this phenotype, the three most abundant SChLAP-1 isoforms were overexpressed in RWPE benign immortalized prostate cells at physiologic levels similar to the LNCaP cell line. While SChLAP-1 overexpression did not impact cell proliferation, RWPE cells expressing all three SChLAP-1 isoforms, but not control cells, exhibited the ability to invade through Matrigel model basement membrane matrix in vitro (FIG. 41b). Overexpression of SChLAP-1 in HME benign breast or MCF7 breast cancer cells did not induce cell invasion, consistent with its prostate-specific expression pattern. These data support a lineage-specific role for SChLAP-1.

To characterize specific regions of SChLAP-1 essential for its function, deletion constructs tiling every 250 bp were overexpressed in RWPE cells. Deletion of a single 250 bp region (bp 1001-1250 for SChLAP-1 isoform #1) shared by all three major isoforms abrogated SChLAP-1 mediated invasion in RWPE (FIG. 41c). In silico modeling with RNAfold22 of the SChLAP-1 RNA structure indicated the presence of a RNA hairpin in this region that is lost specifically in deletion construct #5 (FIG. 41d), implicating this secondary structure in the function of the molecule.

Figure 41E:
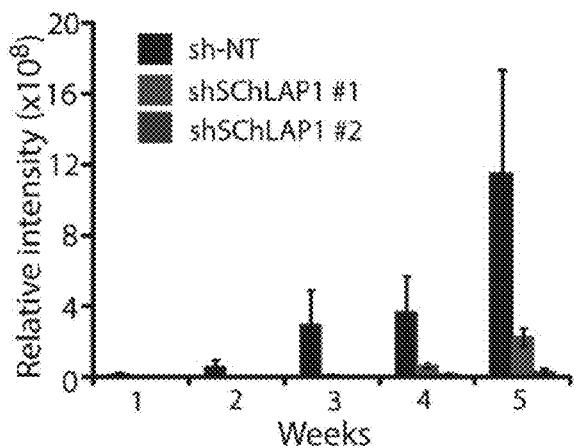
(FIG. 41e) Tumor seeding with SChLAP-1 knockdown in vivo.
Figure 41F:
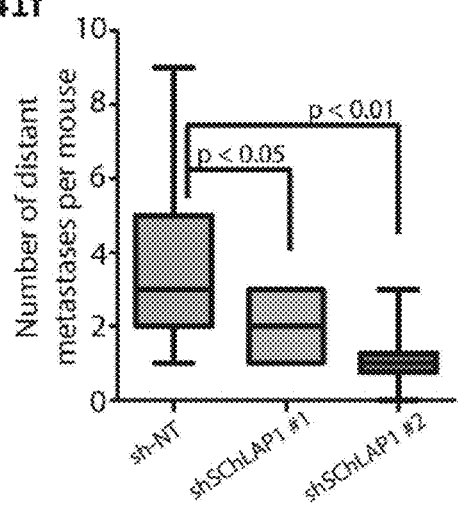
(FIG. 41f) The number of gross metastatic sites observed by luciferase signal in 22Rv1 shSChLAP-1 cells or shNT controls.
Figure 41G:
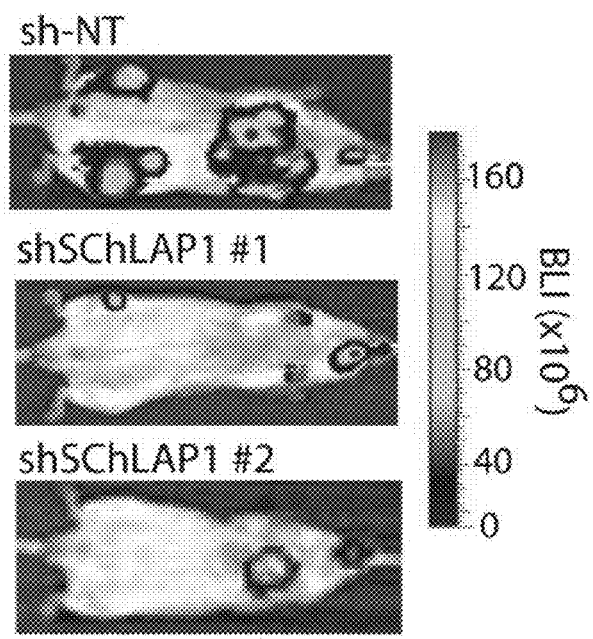
(FIG. 41g) Example luciferase bioluminescence images from 22Rv1 shNT, shSChLAP-1 #1, and shSChLAP-1 #2 mice five weeks following intracardiac injection.

Xenograft analysis of 22Rv1 cells stably knocking down SChLAP-1 further confirmed that this gene is necessary for appropriate cancer cell metastatic seeding in vivo. To test this, intracardiac injection of tumor cells was performed and luciferase signal from mouse lungs and distant metastases was monitored. These experiments showed that 22Rv1 shSChLAP-1 cells displayed impaired metastatic seeding at both proximal (lungs) and distal sites (FIG. 41e). 22Rv1 shSChLAP-1 cells displayed both fewer gross metastatic sites overall (an average 3.66 metastatic sites in shNT mice vs. 2.07 metastatic sites in shSChLAP-1 #1 and 1.07 sites in shSChLAP-1 #2 mice, p<0.05, Student's t-test) as well as smaller metastatic tumors when they did form (FIG. 41f). shSChLAP-1 subcutaneous xenografts displayed slower tumor progression in vivo, though this was due to delayed tumor engraftment rather than altered tumor growth kinetics. Together, these in vitro and in vivo data support a prostate-specific role for SChLAP-1 in cancer cell invasion, metastasis, and aggressiveness.

To interrogate SChLAP-1 function, microarray profiling of 22Rv1 and LNCaP prostate cancer cells treated with SChLAP-1 or control siRNAs was performed, which revealed 165 upregulated and 264 downregulated genes in a highly significant manner (q-value<0.001), indicating that SChLAP-1 contributes to the positive and negative regulation of numerous genes.

After ranking genes according to differential expression by Significance Analysis of Microarrays (SAM) (Tusher et al., Proc Natl Acad Sci USA 98, 5116-5121, (2001)), Proc Natl Acad Sci USA 102, 15545-15550 (2005)) was used to search for enrichment across the Molecular Signatures Database (MSigDB) (Liberzon, A. et al. Bioinformatics 27, 1739-1740, (2011)). Among the highest ranked concepts genes positively or negatively correlated with BRM, an enzymatic subunit of the SWI/SNF chromatin remodeling complex (Roberts et al., Nat Rev Cancer 4, 133-142 (2004)) were observed (FIG. 42a, left). This gene set was generated through an analysis of the SWI/SNF complex in human prostate cancer samples (Shen, H. et al. Cancer Res 68, 10154-10162, (2008)), making it an attractive biological insight due to the tissue-specific functions of this complex. This analysis was mirrored by generating gene signatures positive and negatively correlated to BRM in the RNA-Seq dataset and the enrichment for SChLAP-1-regulated genes was confirmed (FIG. 42a, right). SChLAP-1-regulated genes were inversely correlated with both BRM datasets (FIG. 42a). These results demonstrate that SChLAP-1 and SWI/SNF regulate gene transcription in opposing manners, leading to an antagonism of SWI/SNF activity by SChLAP-1.

The SWI/SNF complex operates as a large, multi-protein system that utilizes ATPase enzymatic activity to physically move nucleosomes and, in doing so, regulates gene transcription (Roberts, C. W. & Orkin, S. H. Nat Rev Cancer 4, 133-142, (2004)). Several SWI/SNF complex members are the target of recurrent, inactivating mutations in cancer, including ARID1A (Wiegand, K. C. et al. N Engl J Med 363, 1532-1543, (2010); Jones, S. et al. Science 330, 228-231 (2010)), PBRM1 (Varela, I. et al. Nature 469, 539-542 (2011)), and SNF5 (Versteege, I. et al. Nature 394, 203-206, (1998)), and numerous studies demonstrate that loss of SWI/SNF functionality promotes cancer Progression (Robers et al., supra; Reisman, D., Glaros, S. & Thompson, E. A. Oncogene 28, 1653-1668, (2009)). While SWI/SNF mutations are not commonly observed in prostate cancer, several reports indicate that down-regulation of SWI/SNF complex members, particularly BRM, characterizes some subsets of prostate cancer (Sun, A. et al. Prostate 67, 203-213, (2007); Shen, H. et al. Cancer Res 68, 10154-10162, (2008)), and mice with a prostate-specific BRM deletion exhibit prostatic hyperplasia and castration-resistant cellular proliferation (Shen et al., supra). Thus, antagonism of SWI/SNF activity by SChLAP-1 is consistent with the oncogenic behavior of SChLAP-1 and the tumor suppressive behavior of the SWI-SNF complex.

To test whether SChLAP-1 antagonizes SWI/SNF-mediated gene expression regulation, siRNA knockdown of three key components of the SWI-SNF complex: BRM (also known as SMARCA2), BRG1 (also known as SMARCA4), and SNF5 (also known as SMARCB1) was performed. Like BRM, BRG1 serves as an enzymatic subunit of SWI/SNF complex activity, and SNF5 is an essential subunit thought to bind histone proteins (Dechassa, M. L. et al. Mol Cell Biol 28, 6010-6021, (2008)). Knockdown of BRM, BRG1, and SNF5 in two prostate cell lines, 22Rv1 and LNCaP, followed by expression microarray profiling generated highly overlapping sets of up- and down-regulated genes, demonstrating that these factors have broad commonalities in their function in prostate cells. Knockdown of BRM, BRG1 and SNF5 also increased the invasiveness and proliferation rate of 22Rv1 cells, consistent with the role of SWI/SNF in tumor suppression. Comparison of genes commonly regulated by knockdown of all SWI/SNF proteins (BRM, BRG1, and SNF5) to genes regulated by SChLAP1 demonstrated an antagonistic relationship where SChLAP1 knockdown affected the same genes as SWI/SNF but in the opposing direction (FIG. 42b). These microarray data were used to generate gene signatures for up- and down-regulated genes upon knockdown of each SWI/SNF protein (BRM, BRG1, and SNF5) and SChLAP-1. The significance of the overlap was quantitated using GSEA. Performing this analysis across two cell lines (22Rv1 and LNCaP) showed that SWI/SNF and SChLAP-1 affect gene expression in a highly significant and opposing manner in 23 of 24 total GSEA comparisons (FDR<0.05) (FIG. 42c). Together, these data demonstrate that SChLAP-1 functions to modulate SWI/SNF complex activity in prostate cancer.

To examine the mechanism of SChLAP-1 regulation of the SWI/SNF complex, it was examined whether SChLAP-1 regulated SWI/SNF complex genes themselves. Using Western blots, no change in BRM, BRG1, or SNF5 protein abundance following SChLAP-1 knockdown or overexpression was detected, demonstrating that SChLAP-1 regulates SWI/SNF activity post-translationally. Motivated by reports of lncRNAs coordinating the function of epigenetic complexes through direct RNA-protein binding, RNA immunoprecipitation assays (RIP) were performed for SNF5, a core subunit essential for both BRG1 and BRM function, in 22Rv1 and LNCaP cells. It was found that endogenous SChLAP-1, but not other prostate-specific lncRNAs such as PCA3 and PCAT-1, robustly bound SNF5 protein (FIG. 42d). RIP for androgen receptor (AR) and SNRNP70, which specifically binds to the U1 snRNP, served as additional negative controls for these experiments (FIG. 42d).

Figures 42, 42E:
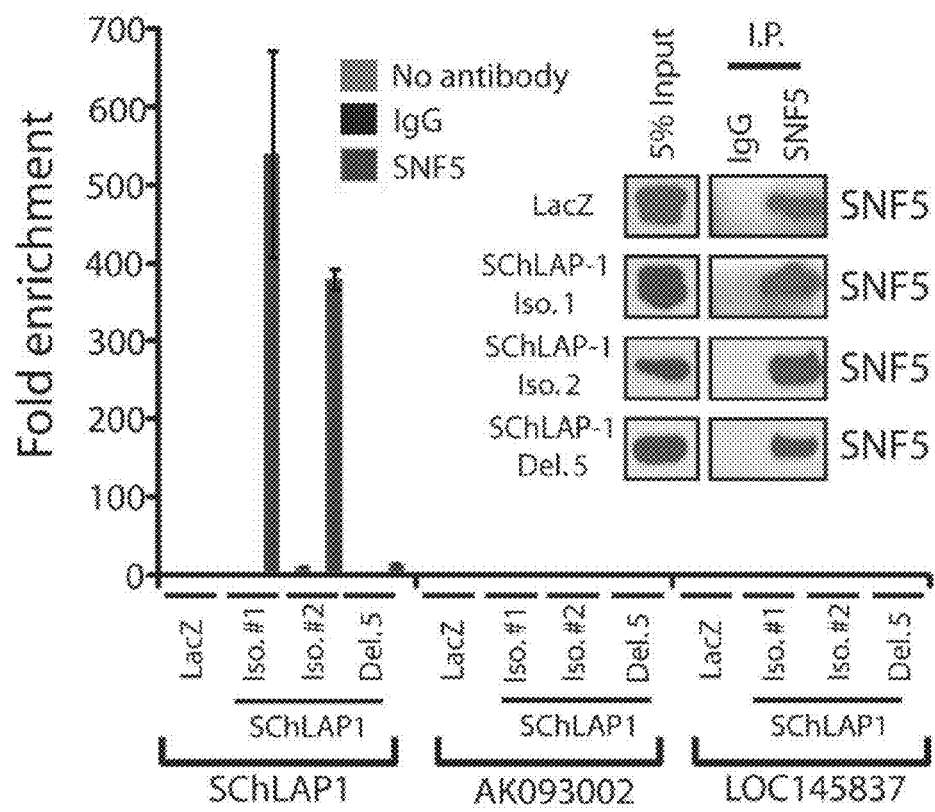
FIG. 42 shows that SChLAP-1 antagonizes SWI/SNF complex function.
(FIG. 42e) RIP analysis of SNF5 in RWPE cells overexpressing LacZ, SChLAP-1 isoform #1, SChLAP-1 isoform #2, or SChLAP-1 deletion construct 5.

The role of SChLAP-1-SWI/SNF interactions in the functional role of SChLAP-1 in inducing cell invasion was tested by evaluating SChLAP-1-SNF5 binding in the RWPE-SChLAP-1 overexpression model, including overexpression of SChLAP-1 deletion construct #5, which failed to induce cell invasion (FIG. 41c). Overexpression of both SChLAP-1 isoform #1 and isoform #2 robustly bound to SNF5, whereas deletion construct 5 (which lacks bps 1001-1250 in SChLAP-1 isoform #1) failed to bind SNF5 (FIG. 42e). As controls, AK093002 and LOC145837, two lncRNAs upregulated in subsets of prostate cancer that are endogenously expressed in RWPE were measured. Control RIP experiments for SNRNP70 demonstrated uniformly strong binding of this protein to U1 in all RWPE cell lines evaluated. Thus, SChLAP-1 regulates SWI/SNF complex activity by directly binding to SWI/SNF proteins through an interaction dependent on base pairs 1001-1250 of the RNA.

To explore a potential link between SChLAP-1 and aggressive prostate cancer associations between SChLAP-1 and gene expression phenotypes curated from published microarray profiling data were explored. Given that SChLAP-1 is currently not measured by microarray platforms, a signature of genes with expression significantly correlated or anti-correlated to SChLAP-1 expression in localized tumors was designed and used as a surrogate for SChLAP-1 expression level. The SChLAP-1 signature was examined using Oncomine concept analysis (Rhodes, D. R. et al. Neoplasia 9, 166-180 (2007)) and network representations of the significantly enriched concepts (p-value<1e-6, odds ratio>3.0) were generated. The networks revealed an association with concepts related to prostate cancer progression (FIG. 43a). Genes positively correlated with SChLAP-1 were over-expressed in metastatic and high-grade localized tumors. Conversely, genes negatively correlated with SChLAP-1 were under-expressed in metastatic and high-grade localized tumors.

The analysis was expanded to include four known cancer genes: EZH2, a known metastasis gene (Kleer, C. G. et al. Proc Natl Acad Sci USA 100; 11606-11611, (2003); Varambally, S. et al. Nature 419, 624-629, (2002)) PCA3, a lncRNA biomarker over-expressed in prostate cancer and used in prostate cancer diagnosis (de Kok, J. B. et al. Cancer Res 62, 2695-2698 (2002); Tomlins, S. A. et al. Sci Transl Med 3, 94ra72, (2011)), AMACR, a tissue biomarker of prostate cancer (Rubin et al., JAMA 287, 1662-1670 (2002)), and BRM, a SWI/SNF enzymatic subunit under-expressed in advanced prostate cancer (Shen et al., supra). Control genes were also analyzed: the nucleoporin genes NUP133 and NUP155, as well as B-actin (ACTB). The expression profiles of each of these seven genes was used to derive correlated and anti-correlated gene sets in the same manner as for SChLAP-1.

Figures 43, 43B:
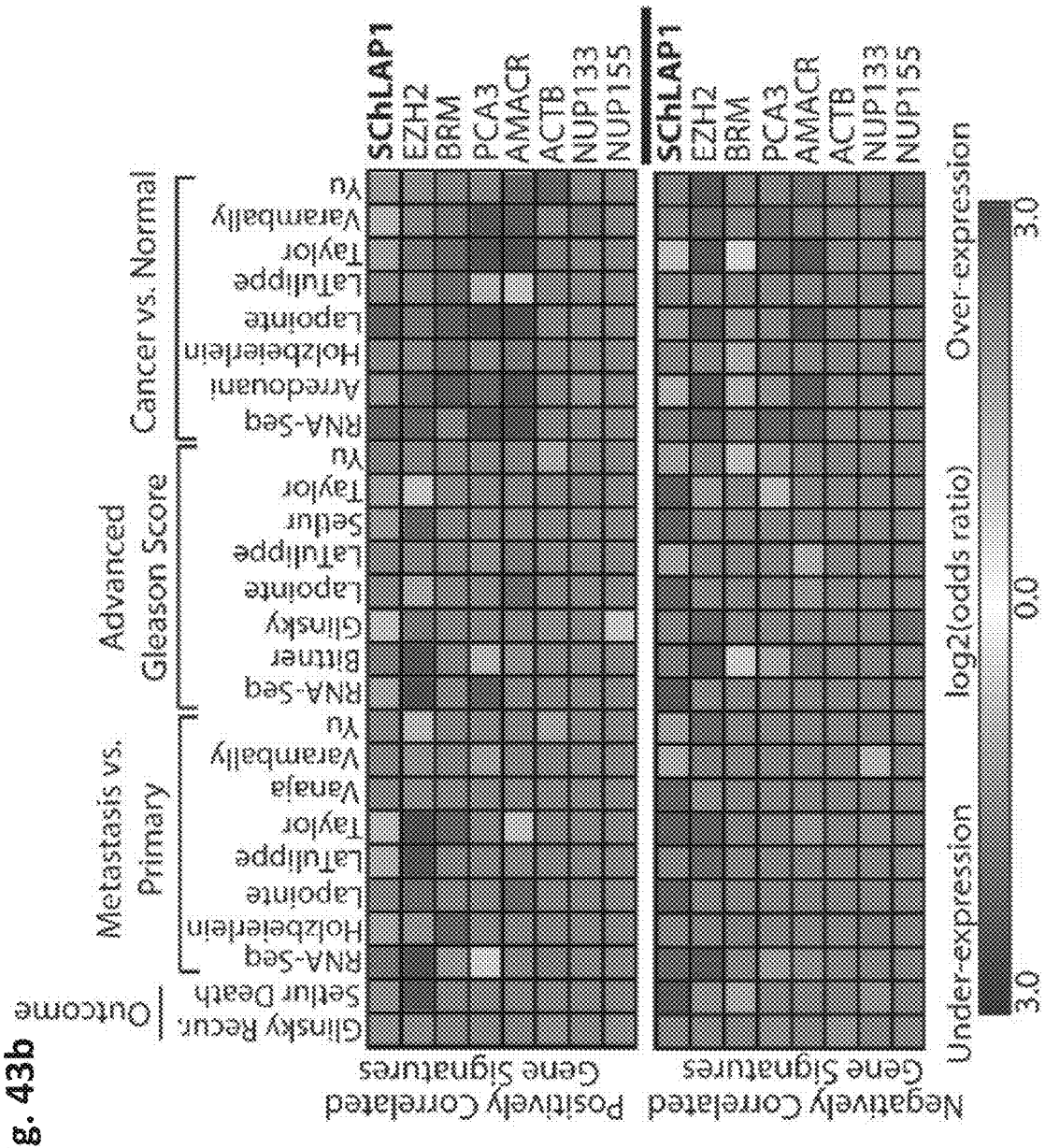
(FIG. 43b) Heatmap representation of comparisons between co-expression gene signatures and molecular concepts.

The statistical association between each dataset in the clinical concept compendium was analyzed with the gene signatures derived from correlation analysis, including signatures from the RNA-Seq cohort delineating localized cancer vs. benign tissues, high grade localized prostate cancer (Gleason≥8 vs. Gleason 6), and metastatic vs. primary tumors. Odds ratios, p-values, and q-values were calculated for each comparison (one-sided Fisher's exact test). A heat-map visualization of statistically significant comparisons (q-value<0.01) confirmed a strong association of SChLAP-1-correlated genes with high-grade and metastatic cancers as well as poor clinical outcomes (FIG. 43b). In this respect, SChLAP-1 was highly similar to EZH2, the positive control, which is widely associated with aggressive, lethal prostate cancer, whereas PCA3 and AMACR, two biomarkers not associated with disease progression, strongly associated with Cancer vs. Normal concepts but not concepts associated with aggressive disease. Kaplan-Meier analysis of publicly-available datasets for biochemical recurrence (Glinsky et al., J Clin Invest 113, 913-923, (2004)) and overall survival (Setlur, S. R. et al. J Natl Cancer Inst 100, 815-825, (2008)) similarly showed significant associations (log rank test, p<0.01) between the SChLAP-1 signature and more rapid disease recurrence and decreased survival probability.

In order to link SChLAP-1 expression with clinical outcomes directly, Affymetrix exon microarrays, which harbor probes mapping to SChLAP-1 exons weas used to profile its expression in a prospectively-designed study of 235 high-risk prostate cancer patients who underwent radical prostatectomy between 2000-2006 at the Mayo Clinic (Buerki, C. et al. ASCO Annual Meeting, Abstract #4565 (2012). Nakagawa, T. et al. PLoS One 3, e2318, (2008)). Unsupervised clustering was used to define patients into low and high SChLAP-1 expression groups and the prognostic utility of SChLAP-1 was evaluated with three clinical endpoints: biochemical recurrence (BCR), clinical progression to systemic disease (CP), and prostate cancer-specific mortality (PCSM). At the time of this analysis, patients had a median follow-up of 8.1 years.

Kaplan-Meier analyses show SChLAP-1 as a powerful single-gene predictor of aggressive prostate cancer (FIG. 43c-e). SChLAP-1 expression was highly significant when distinguishing CP and PCSM (p=0.00005 and p=0.002, respectively); patients with high SChLAP-1 expression had 5-year CP- and PCSM-free survival of only 65% and 85%, respectively, compared to 85% and 95% for patients with low SChLAP-1 expression (FIGS. 43d and 43e). For the BCR endpoint, high SChLAP-1 expression in patient primary tumor specimens was associated with a rapid median time-to-progression (1.9 vs 5.5 years for SChLAP-1 high and low patients, respectively) (FIG. 43c). These data demonstrate that SChLAP-1 expression retains its prognostic utility for defining a subgroup of patients more likely to experience BCR, CP, and PCSM even in high-risk patients, where most individuals experienced disease recurrence within ten years post-prostatectomy (FIG. 43c). To independently validate these findings, the prognostic value of SChLAP-1 for BCR was assessed using qPCR on a University of Michigan cohort and confirmed that SChLAP-1 positive patients are at markedly higher risk for BCR.

Multivariable and univariable regression analyses of the Mayo Clinic data demonstrated that SChLAP-1 expression is an independent predictor of prostate cancer aggressiveness with highly significant hazard ratios for predicting BCR, CP, and PCSM (HR or 3.045, 0.563, and 4.339, respectively, p<0.01) which were comparable to other clinical factors such as Gleason score and advanced clinical stage. Finally, receiver-operator curves (ROC) demonstrated the discriminative ability of SChLAP-1 expression in the Mayo Clinic dataset with area-under-the-curve (AUC) values of 0.63, 0.65, and 0.74 for the 5-year prediction of BCR, CP, and PCSM, which were either equivalent to, or slightly higher than, the AUC values for Gleason score (0.59, 0.65, and 0.71, respectively).

Thus, these data demonstrate that SChLAP-1 expression either out-performs, or is comparable to, standard clinical parameters such as clinical stage, lymph node invasion, pre-operative serum PSA, surgical margin status (SMS) and Gleason score for the prediction of CP, PCSM, and BCR. The particularly strong prognostic value of SChLAP-1 expression for CP and PCSM is important, as it is known that patients who develop BCR do not necessarily progress further to lethal or clinically significant recurrent disease: that is, many patients who experience BCR nevertheless die with prostate cancer but not from it (Simmons et al., Eur Urol 51, 1175-1184, (2007); Boorjian, S. A. et al. Eur Urol 59, 893-899, (2011)). As such, CP and PCSM represent more stringent criteria to define aggressive prostate cancer. Taken together, the findings indicate that measurement of SChLAP-1 expression in the early development of prostate cancer serves as a valuable biomarker to stratify patient outcomes.

To explore this, SChLAP-1 expression was measured in urine sediment RNA from 111 biopsy-confirmed prostate cancer patients with Gleason score. These RNA samples were collected at the time of PSA screening as described previously (Tomlins, S. A. et al. Sci Transl Med 3, 94ra72, (2011)). It was found that SChLAP-1 was significantly higher in Gleason 7 patients vs. Gleason 6 patients (Welch's Two Sample t-test, p=0.01498). These data support the utility of SChLAP-1 as a prognostic screening biomarker for aggressive prostate cancer (Prensner et al., Sci Transl Med 4, 127rv123, (2012)).

In conclusion, this example describes a lineage-specific lncRNA that is highly expressed in 15-30% of prostate cancers but not other tissue or cancer types. In the tissue sets, the sensitivity ranges from 20-35% and the specificity ranges from 94-100%. SChLAP-1 is highly expressed in a subset of cancers and is thus a highly specific marker for those cancers. SChLAP-1 directly binds a core subunit in the SWI/SNF complex, leading to reversion of SWI/SNFmediated gene expression (FIG. 44f). In model systems, SChLAP-1 coordinates prostate cancer cell invasion in vitro and metastatic spread in vivo, and in patient tissue samples SChLAP-1 expression characterizes a metastatic-like gene expression profile associated with high-grade localized prostate cancers and poor clinical outcomes. It was further demonstrated that patients with high SChLAP-1 expression are at markedly increased risk for developing metastatic and lethal prostate cancer.

Table 9 shows genes correlated with SChLAP-1.

TABLE 9

| locus | nearest_ref_id | r | p | qval | pglobal | qglobal | prank | padj |
|---|---|---|---|---|---|---|---|---|
| chr12: 57180908-57181574 | HSD17B6 | -0.546164551 | 0.001483863 | 0.063564631 | 2.21E-06 | 0.002893994 | 0.000660684 | 0.001483863 |
| chr10: 100995269-100995619 | HPSE2 | -0.529744166 | 0 | 0 | 4.25E-06 | 0.003261046 | 0.000935969 | 0.000935969 |
| chr9: 4585311-4587469 | SLC1A1 | -0.528631581 | 0 | 0 | 4.60E-06 | 0.003261046 | 0.001046083 | 0.001046083 |
| chr12: 104234726-104234975 | NT5DC3 | -0.52574655 | 0 | 0 | 4.88E-06 | 0.003261046 | 0.001266311 | 0.001266311 |
| chr1: 85358698-85358896 | LPAR3 | -0.519067947 | 0 | 0 | 5.53E-06 | 0.003261046 | 0.001541596 | 0.001541596 |
| chr7: 12692212-12693228 | SCIN | -0.513485431 | 0 | 0 | 6.48E-06 | 0.003676617 | 0.00165171 | 0.00165171 |
| chr1: 204328821-204329044 | PLEKHA6 | -0.512422441 | 0 | 0 | 6.68E-06 | 0.003676889 | 0.001706767 | 0.001706767 |
| chr22: 31674282-31676066 | LIMK2 | -0.50924733 | 0 | 0 | 8.12E-06 | 0.004015199 | 0.001871937 | 0.001871937 |
| chr16: 85121881-85127826 | KIAA0513 | -0.506320229 | 0 | 0 | 8.39E-06 | 0.004015199 | 0.001926994 | 0.001926994 |
| chr11: 126310080-126310239 | ST3GAL4 | -0.506170919 | 0 | 0 | 8.40E-06 | 0.004015199 | 0.001982051 | 0.001982051 |
| chr2: 102855651-102856462 | IL1RL2 | -0.499389029 | 0 | 0 | 9.02E-06 | 0.004201028 | 0.002037108 | 0.002037108 |
| chr2: 100759172-100759201 | AFF3 | -0.498848742 | 0 | 0 | 9.27E-06 | 0.004210011 | 0.002092165 | 0.002092165 |
| chr3: 87039767-87040269 | VGLL3 | -0.4955607 | 0.001996514 | 0.07433842 | 1.09E-05 | 0.004810345 | 0.002257336 | 0.002257336 |
| chr10: 106058885-106059616 | GSTO2 | -0.481459111 | 0 | 0 | 1.52E-05 | 0.0064619 | 0.002202279 | 0.002202279 |
| chr6: 78005429-78005429 | PARD6G | -0.480259815 | 0.001816685 | 0.07142087 | 1.56E-05 | 0.006424942 | 0.00236745 | 0.00236745 |
| chr5: 14692962-14699820 | FAM105B | -0.478056706 | 0.001989958 | 0.07433842 | 1.76E-05 | 0.007084909 | 0.002422507 | 0.002422507 |
| chr21: 35987058-35987441 | SLC37A2 | -0.477004111 | 0 | 0 | 1.97E-05 | 0.007236461 | 0.002312393 | 0.002312393 |
| chr11: 124955849-124959131 | ACAD8 | -0.474921728 | 0 | 0 | 2.40E-05 | 0.008231158 | 0.002587678 | 0.002587678 |
| chr11: 134134801-134135749 | STAB2 | -0.474825465 | 0 | 0 | 2.45E-05 | 0.008235358 | 0.002642735 | 0.002642735 |
| chr12: 104159806-104160505 | MIPEP | -0.47377468 | 0 | 0 | 2.88E-05 | 0.009222872 | 0.002807906 | 0.002807906 |
| chr1: 153603987-153604513 | ABHD7 | -0.473687887 | 0.000330132 | 0.017740189 | 2.89E-05 | 0.009222872 | 0.003028134 | 0.003028134 |
| chr15: 89784457-89745591 | EEF2K | -0.471488569 | 0.001901732 | 0.07290082 | 3.24E-05 | 0.009557199 | 0.002862963 | 0.002862963 |
| chr16: 2229520-22297954 | SYTL3 | -0.470902458 | 0 | 0 | 3.32E-05 | 0.009557199 | 0.002973077 | 0.002973077 |
| chr6: 159185526-159185908 | RAPH1 | -0.469048813 | 0 | 0 | 4.11E-05 | 0.01071857 | 0.003248362 | 0.003248362 |
| chr2: 204399833-204400133 | RCAN1 | -0.468923289 | 0 | 0 | 4.13E-05 | 0.01071857 | 0.003303419 | 0.003303419 |
| chr21: 35987058-35987441 | PASK | -0.468525633 | 0 | 0 | 4.23E-05 | 0.01082872 | 0.003358476 | 0.003358476 |
| chr2: 242089022-242089679 | S100A1 | -0.467663305 | 0 | 0 | 4.69E-05 | 0.011520023 | 0.00346859 | 0.00346859 |
| chr1: 153603987-153604513 | TRPM6 | -0.466199058 | 0 | 0 | 5.03E-05 | 0.012121545 | 0.003523647 | 0.003523647 |
| chr9: 77502739-77503010 | IL31RA | -0.463269779 | 0 | 0 | 5.40E-05 | 0.012121545 | 0.003578704 | 0.003578704 |
| chr5: 55218223-55218678 | MAST4 | -0.464836512 | 0 | 0 | 5.40E-05 | 0.012121545 | 0.00363761 | 0.00363761 |
| chr5: 66458974-66465423 | ALDH2 | -0.464258794 | 0 | 0 | 5.50E-05 | 0.012121545 | 0.003688818 | 0.003688818 |
| chr12: 112247346-112247782 | GGT7 | -0.464248542 | 0 | 0 | 5.50E-05 | 0.012121545 | 0.004404559 | 0.004404559 |
| chr20: 33460449-33460663 | KLHL36 | -0.462458945 | 0.001623427 | 0.067166971 | 6.03E-05 | 0.012724535 | 0.004074217 | 0.004074217 |
| chr16: 84695183-84701292 | MTMR8 | -0.462171273 | 0 | 0 | 6.09E-05 | 0.012724535 | 0.00401916 | 0.00401916 |
| chr5: 55218223-55218678 | KIAA1609 | -0.461782241 | 0 | 0 | 6.18E-05 | 0.012761283 | 0.004129274 | 0.004129274 |
| chr16: 84538206-84538296 | CDKL5 | -0.461589982 | 0 | 0 | 6.44E-05 | 0.013127093 | 0.004184331 | 0.004184331 |
| chrX: 18671551-18671749 | CPEB3 | -0.461125435 | 0 | 0 | 6.50E-05 | 0.013127093 | 0.004239388 | 0.004239388 |
| chr10: 94050682-94050844 | MPPE1 | -0.460707259 | 0 | 0 | 6.65E-05 | 0.0132686 | 0.004294445 | 0.004294445 |
| chr18: 11908199-11908779 | LEPREL1 | -0.459922767 | 0.002264726 | 0.074896868 | 6.74E-05 | 0.013313983 | 0.0051203 | 0.0051203 |
| chr3: 189839991-189840226 | ATP8B2 | -0.459778607 | 0 | 0 | 7.07E-05 | 0.013784792 | 0.004349502 | 0.004349502 |
| chr11: 154321315-154323783 | ADH5 | -0.459096821 | 0 | 0 | 7.13E-05 | 0.013784792 | 0.004404559 | 0.004404559 |
| chr4: 100009839-100009952 | CFLAR | -0.454603271 | 0 | 0 | 7.21E-05 | 0.013789835 | 0.004514673 | 0.004514673 |
| chr2: 202028557-202029033 | RP11-121M22.1 | -0.453760945 | 0.001896636 | 0.07290082 | 9.16E-05 | 0.016804159 | 0.00456973 | 0.00456973 |
| chr11: 130272233-130273133 | NPNT | -0.453089747 | 0 | 0 | 9.42E-05 | 0.01693939 | 0.005395584 | 0.005395584 |
| chr4: 106924870-106925184 | TMEM100 | -0.452269788 | 0 | 0 | 9.56E-05 | 0.017026472 | 0.004624787 | 0.004624787 |
| chr17: 53809031-53809482 | GREB1L | -0.45014015 | 0 | 0 | 9.71E-05 | 0.017086351 | 0.004734901 | 0.004734901 |
| chr18: 19102618-19102791 | CCDC136 | -0.449966828 | 0 | 0 | 0.000104560 | 0.017905164 | 0.004789958 | 0.004789958 |
| chr7: 128461852-128462186 | TIFA | -0.44794294 | 0 | 0 | 0.000110766 | 0.01821426 | 0.00490072 | 0.00490072 |
| chr4: 113206795-113207059 | ARHGEF7 | -0.447155527 | 0 | 0 | 0.000113277 | 0.018370082 | 0.005010186 | 0.005010186 |
| chr13: 119553537-111958084 | | | | | | | | |

TABLE 9-continued

| locus | nearest_ref_id | r | p | qval | pglobal | qglobal | prank | padj |
|---|---|---|---|---|---|---|---|---|
| chr7: 103086544-103086624 | SLC26A5 | −0.446130747 | 0.001571059 | 0.065901041 | 0.000118707 | 0.018912891 | 0.005615812 | 0.005615812 |
| chr2: 199436579-199437305 | PLCL1 | −0.445732252 | 0 | 0 | 0.000122153 | 0.019126366 | 0.0051203 | 0.0051203 |
| chr7: 99526462-99527243 | GJC3 | −0.44536614 | 0 | 0 | 0.000124666 | 0.019242801 | 0.005175356 | 0.005175356 |
| chr17: 1613360-1613651 | TLCD2 | −0.444818675 | 0.001340945 | 0.059925314 | 0.000126503 | 0.019242801 | 0.005670869 | 0.005670869 |
| chr11: 44640598-44641913 | CD82 | −0.444058521 | 0 | 0 | 0.00013486 | 0.020077586 | 0.005340527 | 0.005340527 |
| chr11: 134094990-134095348 | NCAPD3 | −0.443736551 | 0 | 0 | 0.000136153 | 0.020105287 | 0.005395584 | 0.005395584 |
| chr1: 152297664-152297679 | FLG | −0.442245082 | 0 | 0 | 0.000144867 | 0.020358172 | 0.005560755 | 0.005560755 |
| chr18: 8406106-8406859 | PTPRM | −0.442183213 | 0 | 0 | 0.000145 | 0.020358172 | 0.005615812 | 0.005615812 |
| chr11: 74178676-74178774 | KCNE3 | −0.44185294 | 0 | 0 | 0.000154712 | 0.020358172 | 0.005725926 | 0.005725926 |
| chr17: 7951703-7952452 | ALOX15B | −0.440459014 | 0 | 0 | 0.000150385 | 0.020596714 | 0.005780983 | 0.005780983 |
| chr3: 49213037-49213918 | KLHDC8B | −0.440313623 | 0 | 0 | 0.000150553 | 0.020596714 | 0.00583604 | 0.00583604 |
| chr2: 219696460-219696809 | PRKAG3 | −0.440081326 | 0 | 0 | 0.000150821 | 0.020596714 | 0.005891097 | 0.005891097 |
| chr14: 23778024-23780968 | BCL2L2 | −0.438071628 | 0 | 0 | 0.000162326 | 0.021533748 | 0.005946154 | 0.005946154 |
| chr8: 111182824-11182938 | AF131216.6 | −0.437271292 | 0.00048729 | 0.025803614 | 0.000166756 | 0.021533748 | 0.006331553 | 0.006331553 |
| chr14: 77843278-77843396 | TMED8 | −0.436273666 | 0.002421059 | 0.07683164 | 0.000174114 | 0.021961395 | 0.007763035 | 0.007763035 |
| chr8: 22926263-22926692 | TNFRSF10B | −0.433462746 | 0.002038631 | 0 | 0.000198143 | 0.02464764 | 0.006221439 | 0.006221439 |
| chr11: 118550247-118550399 | TREH | −0.432052092 | 0 | 0 | 0.000206789 | 0.025550394 | 0.006276496 | 0.006276496 |
| chr8: 22471420-22474170 | RP11-582I16.5 | −0.431261913 | 0 | 0 | 0.000215369 | 0.025749707 | 0.006331553 | 0.006331553 |
| chr14: 76668033-76669134 | C14orf118 | −0.431248632 | 0 | 0 | 0.000215491 | 0.025749707 | 0.00638661 | 0.00638661 |
| chr7: 83277743-83278479 | SEMA3E | −0.430438439 | 0 | 0 | 0.00021898 | 0.025995608 | 0.006441667 | 0.006441667 |
| chr11: 109095151-109095913 | RSPO2 | −0.428973643 | 0 | 0 | 0.000231367 | 0.027287785 | 0.006496724 | 0.006496724 |
| chr6: 42931272-42931618 | GNMT | −0.427598114 | 0.000130606 | 0.007299047 | 0.000243869 | 0.027410832 | 0.006661895 | 0.006661895 |
| chr1: 24795475-24799466 | NIPAL3 | −0.426835742 | 0 | 0 | 0.000244945 | 0.027410832 | 0.006661895 | 0.006661895 |
| chrX: 148713225-148713568 | TMEM185A | −0.426606945 | 0 | 0 | 0.000251178 | 0.027410832 | 0.006772009 | 0.006772009 |
| chr6: 52860046-52860176 | GSTA4 | −0.426481126 | 0.002511383 | 0.077005838 | 0.000251189 | 0.027410832 | 0.008974288 | 0.008974288 |
| chr1: 4903048-4904113 | OR51T1 | −0.4264643 | 0.002258333 | 0.074896868 | 0.000252001 | 0.027410832 | 0.008809117 | 0.008809117 |
| chr20: 45362394-45364965 | SLC2A10 | −0.426321136 | 0.002038631 | 0.074404864 | 0.000253538 | 0.027452953 | 0.008809117 | 0.008809117 |
| chr21: 21167513-21168761 | RNASE4 | −0.425769874 | 0.00199731 | 0.07433842 | 0.000255544 | 0.028436048 | 0.006992237 | 0.006992237 |
| chrX: 23786663-23784592 | ACO9 | −0.424946982 | 0 | 0 | 0.000269284 | 0.02846048 | 0.008258548 | 0.008258548 |
| chrX: 22346307-22346307 | CMAS | −0.424346307 | 0.001493347 | 0.063820363 | 0.00028048 | 0.029277918 | 0.008258548 | 0.008258548 |
| chr12: 222180544-222218608 | TMCO3 | −0.423927242 | 0.001408993 | 0.0615812 | 0.0002876 | 0.029849598 | 0.008148434 | 0.008148434 |
| chr13: 114203739-114204542 | GCC1 | −0.423122614 | 0 | 0 | 0.000296624 | 0.030160322 | 0.007212465 | 0.007212465 |
| chr7: 127235551-127233665 | SFT2D2 | −0.422864243 | 0.00101202 | 0.048756847 | 0.000297236 | 0.030160322 | 0.007873149 | 0.007873149 |
| chr16: 168211738-168212378 | SEMA3C | −0.421618187 | 0.000762726 | 0.03891404 | 0.000309825 | 0.030983765 | 0.007818092 | 0.007818092 |
| chr7: 80551580-80551675 | ARHGEF37 | −0.421113016 | 0.00166369 | 0.068211282 | 0.000312739 | 0.030524412 | 0.008974288 | 0.008974288 |
| chr5: 149014531-149014531 | TPD52L1 | −0.420855828 | 0 | 0 | 0.000314397 | 0.030524412 | 0.007377636 | 0.007377636 |
| chr6: 125583979-125585553 | SUN2 | −0.420660125 | 0.000979486 | 0.047441064 | 0.000381186 | 0.030524412 | 0.007542807 | 0.007542807 |
| chr22: 39190072-39190148 | FCF1 | −0.420391618 | 0 | 0 | 0.000321289 | 0.030617528 | 0.007597864 | 0.007597864 |
| chr14: 75201584-75203421 | RNF150 | −0.420201646 | 0.002267743 | 0.074896868 | 0.00032197 | 0.030617528 | 0.010185542 | 0.010185542 |
| chr4: 142133947-142134031 | RSPH3 | −0.419873459 | 0 | 0 | 0.000327348 | 0.030966787 | 0.007652921 | 0.007652921 |
| chr6: 159420466-159421219 | C7orf34 | −0.419724438 | 0.001112591 | 0.052900521 | 0.000329233 | 0.030983765 | 0.008423719 | 0.008423719 |
| chr7: 142637438-142637955 | SNIP1 | −0.417392665 | 0 | 0 | 0.000356182 | 0.03317611 | 0.007763035 | 0.007763035 |
| chr1: 380196066-38019905 | TRAFD1 | −0.416676004 | 0.001376789 | 0.060695692 | 0.000369367 | 0.0338033 | 0.009084402 | 0.009084402 |
| chr12: 112590538-112591407 | NEIL2 | −0.415555366 | 0.000979486 | 0.047441064 | 0.000381186 | 0.0338033 | 0.008699003 | 0.008699003 |
| chr8: 11643471-11644855 | SYTL4 | −0.4151136 | 0 | 0 | 0.000384771 | 0.0338033 | 0.008093377 | 0.008093377 |
| chrX: 99986990-99987110 | MTHFR | −0.414935432 | 0 | 0 | 0.000384771 | 0.0338033 | 0.008203491 | 0.008203491 |
| chr1: 11865403-11866977 | ALDH3A2 | −0.414755637 | 0 | 0 | 0.000386887 | 0.0338033 | 0.008258548 | 0.008258548 |
| chr17: 19578870-19580909 | MTOR | −0.414459145 | 0 | 0 | 0.000388904 | 0.0338033 | 0.008313605 | 0.008313605 |
| chr1: 11322501-11322608 | ZNRF3 | −0.414121517 | 0 | 0 | 0.000393128 | 0.033840648 | 0.008368662 | 0.008368662 |
| chr22: 29449566-29453475 | TUBB2A | −0.413596935 | 0 | 0 | 0.000399369 | 0.033903107 | 0.008423719 | 0.008423719 |
| chr6: 3157640-3157809 | ARHGAP44 | −0.413315388 | 0 | 0 | 0.000403186 | 0.033903107 | 0.00858889 | 0.00858889 |
| chr17: 12893348-12894960 | | | | | | | | |

TABLE 9-continued

| locus | nearest_ref_id | r | p | qval | pglobal | qglobal | prank | padj |
|---|---|---|---|---|---|---|---|---|
| chr1: 110888929-110889299 | RBM15 | −0.413119683 | 0 | 0 | 0.000406617 | 0.033963425 | 0.008643946 | 0.008643946 |
| chr7: 227553-229557 | AC145676.2 | −0.412677313 | 0 | 0 | 0.000407643 | 0.033963425 | 0.008699003 | 0.008699003 |
| chr21: 39288186-39288749 | KCNJ6 | −0.412229747 | 0.00154936 | 0.065292417 | 0.000413797 | 0.034004231 | 0.01040577 | 0.01040577 |
| chr13: 21635484-21635718 | LATS2 | −0.412031798 | 0 | 0 | 0.000415622 | 0.034004231 | 0.008809117 | 0.008809117 |
| chr3: 68981390-68981761 | FAM19A4 | −0.411387043 | 0.002212811 | 0.074896868 | 0.000421217 | 0.034068108 | 0.011561967 | 0.011561967 |
| chr17: 56032285-56032684 | CUEDC1 | −0.411227218 | 0.000689134 | 0.035558916 | 0.000423903 | 0.034068108 | 0.00930463 | 0.00930463 |
| chr11: 94861540-94865809 | ENDOD1 | −0.411164472 | 0 | 0 | 0.000425781 | 0.034068108 | 0.008919231 | 0.008919231 |
| chr9: 5339535-5339873 | RLN1 | −0.410338259 | 0.001605749 | 0.066739616 | 0.000435667 | 0.034246655 | 0.010846226 | 0.010846226 |
| chr8: 22291403-22291642 | SLC39A14 | −0.409172508 | 0.002273186 | 0.074896868 | 0.00045167 | 0.035043161 | 0.01222265 | 0.01222265 |
| chrX: 2790092-2800859 | GYG2 | −0.409121519 | 0 | 0 | 0.000454498 | 0.035043161 | 0.008974288 | 0.008974288 |
| chr5: 10649377-10650308 | ANKRD33B | −0.408925428 | 0 | 0 | 0.000458355 | 0.035043161 | 0.009029345 | 0.009029345 |
| chr3: 33138210-33138293 | TMPPE | −0.408755569 | 0.002067948 | 0.074404864 | 0.000460544 | 0.035043161 | 0.012057479 | 0.012057479 |
| chr17: 74639589-74639894 | ST6GALNAC1 | −0.408601974 | 0 | 0 | 0.000462776 | 0.035043161 | 0.009139459 | 0.009139459 |
| chr4: 108871400-108874613 | CYP2U1 | −0.408590838 | 0 | 0 | 0.000462962 | 0.035043161 | 0.009194516 | 0.009194516 |
| chr13: 24476755-24476794 | C1QTNF9B | −0.4085811 | 0 | 0 | 0.000463125 | 0.035043161 | 0.009249573 | 0.009249573 |
| chr2: 222438569-222438922 | EPHA4 | −0.408496252 | 0.002565861 | 0.077672883 | 0.000463739 | 0.035043161 | 0.012883334 | 0.012883334 |
| chr7: 99573567-99573780 | AZGP1 | −0.408221377 | 0.001762692 | 0.070831349 | 0.000464978 | 0.035043161 | 0.011617024 | 0.011617024 |
| chr11: 134188770-134189458 | GLB1L3 | −0.407453053 | 0 | 0 | 0.00047331 | 0.035377477 | 0.00930463 | 0.00930463 |
| chr15: 90286522-90286868 | WDR93 | −0.407011464 | 0 | 0 | 0.000481285 | 0.035534876 | 0.009359687 | 0.009359687 |
| chr3: 132086547-132087142 | ACPP | −0.40512191 | 0 | 0 | 0.000517458 | 0.037444565 | 0.009579915 | 0.009579915 |
| chr1: 154437609-154441926 | IL6R | −0.404694713 | 0 | 0 | 0.00052751 | 0.037486096 | 0.009634972 | 0.009634972 |
| chr16: 13328886-13329566 | SHISA9 | −0.404456273 | 0.00120856 | 0.054952728 | 0.000529298 | 0.037486096 | 0.010901283 | 0.010901283 |
| chr3: 184999697-184999778 | EHHADH | −0.404337224 | 0 | 0 | 0.000530546 | 0.037486096 | 0.009745086 | 0.009745086 |
| chr7: 30168881-30170096 | PLEKHA8 | −0.404069681 | 0.001124581 | 0.053024689 | 0.000535569 | 0.037486096 | 0.01095634 | 0.01095634 |
| chr21: 43742722-43743963 | ITM2C | −0.404000609 | 0.001502313 | 0.064052833 | 0.000536517 | 0.037486096 | 0.011947366 | 0.011947366 |
| chr15: 43212635-43213007 | TTBK2 | −0.403995065 | 0 | 0 | 0.000536607 | 0.037486096 | 0.0098552 | 0.0098552 |
| chr5: 78531633-78531861 | DMGDH | −0.403410254 | 0.001386979 | 0.060862399 | 0.000556206 | 0.038412018 | 0.011727138 | 0.011727138 |
| chr6: 160199690-160200144 | DPYS | −0.403219685 | 0.006490479 | 0.118025771 | 0.000559086 | 0.038464661 | 0.014535044 | 0.014535044 |
| chr20: 49307662-49308065 | FAM65C | −0.40278536 | 0.001873108 | 0.072385669 | 0.000567068 | 0.038720521 | 0.012883334 | 0.012883334 |
| chr16: 46796951-46797158 | MYLK3 | −0.402096842 | 0.002040434 | 0.074404864 | 0.000586403 | 0.039611265 | 0.013488961 | 0.013488961 |
| chr12: 27167010-27167367 | TM7SF3 | −0.401727922 | 0.003064993 | 0.083839548 | 0.000588837 | 0.039611265 | 0.01459101 | 0.01459101 |
| chr4: 89205557-89205921 | PPM1K | −0.400464856 | 0.001268359 | 0.057164267 | 0.000614304 | 0.040555725 | 0.011617024 | 0.011617024 |
| chr6: 160199690-160200144 | ACAT2 | −0.400341345 | 0.002969949 | 0.083014679 | 0.000617597 | 0.040555725 | 0.014865386 | 0.014865386 |
| chr2: 179914566-179914813 | CCDC141 | −0.400161772 | 0 | 0 | 0.000622444 | 0.040555725 | 0.010075428 | 0.010075428 |
| chr18: 48604625-48611415 | SMAD4 | −0.4000199 | 0.002020762 | 0.074404864 | 0.00062436 | 0.040555725 | 0.013764246 | 0.013764246 |
| chr6: 134373515-134373774 | SLC2A12 | −0.399516711 | 0.001529527 | 0.064908426 | 0.000631345 | 0.040555725 | 0.010130485 | 0.010130485 |
| chr20: 49307662-49308065 | PER2 | −0.398648438 | 0.001873108 | 0.072385669 | 0.000655163 | 0.041198377 | 0.012828277 | 0.012828277 |
| chr3: 195080701-195090060 | TFRC | −0.398416367 | 0.001122515 | 0.053024689 | 0.000653258 | 0.041198377 | 0.01150691 | 0.01150691 |
| chr10: 128994260-128994422 | FAM196A | −0.397675255 | 0 | 0 | 0.000671462 | 0.041773747 | 0.010240599 | 0.010240599 |
| chr19: 18474200-18480763 | PGPEP1 | −0.397511696 | 0.001654324 | 0.067980724 | 0.000672614 | 0.041773747 | 0.013268733 | 0.013268733 |
| chr12: 89913184-89918583 | GALNT4 | −0.3971679 | 0.000720157 | 0.036845671 | 0.000677673 | 0.041773747 | 0.010846226 | 0.010846226 |
| chr8: 27168317-27168836 | TRIM35 | −0.396989147 | 0 | 0 | 0.000679602 | 0.041773747 | 0.01040577 | 0.01040577 |
| chr1: 112459953-112461255 | ERP29 | −0.396890381 | 0 | 0 | 0.000682814 | 0.041773747 | 0.010460827 | 0.010460827 |
| chr6: 160534453-160534539 | IGF2R | −0.396621725 | 0 | 0 | 0.000691279 | 0.041773747 | 0.010681055 | 0.010681055 |
| chr2: 700525887-70053596 | ANXA4 | −0.395776146 | 0 | 0 | 0.000692281 | 0.041773747 | 0.010736112 | 0.010736112 |
| chr14: 25184812-25519503 | STXBP6 | −0.396022636 | 0.00593713 | 0.114006188 | 0.000707484 | 0.042460748 | 0.016572152 | 0.016572152 |
| chr15: 90358003-90358094 | ANPEP | −0.39538808 | 0.001716149 | 0.069576817 | 0.0007237 | 0.042677179 | 0.014259759 | 0.014259759 |
| chr2: 219157188-219157309 | TMBIM1 | −0.394985318 | 0.00305971 | 0.083821279 | 0.000729631 | 0.04274929 | 0.016572152 | 0.016572152 |
| chr10: 34598870-103460352 | TMEM182 | −0.393872182 | 0 | 0 | 0.000751677 | 0.043341943 | 0.011011397 | 0.011011397 |
| chr1: 24861582-24863506 | RCAN3 | −0.392511497 | 0 | 0 | 0.000784044 | 0.043808512 | 0.011231625 | 0.011231625 |
| chrX: 19140559-19140755 | GPR64 | −0.39247745 | 0 | 0 | 0.000784366 | 0.043808512 | 0.011286682 | 0.011286682 |

TABLE 9-continued

| locus | nearest_ref_id | r | p | qval | pglobal | qglobal | prank | padj |
|---|---|---|---|---|---|---|---|---|
| chr2: 130886644-130886795 | POTEF | -0.392414695 | 0.000955249 | 0.046515259 | 0.000786788 | 0.043808512 | 0.012442878 | 0.012442878 |
| chr2: 231911596-231914434 | C2orf72 | -0.391887127 | 0 | 0 | 0.000799811 | 0.043922586 | 0.011451853 | 0.011451853 |
| chr8: 142201372-142205907 | DENND3 | -0.391794001 | 0.001844172 | 0.072262867 | 0.000802553 | 0.043922586 | 0.015471012 | 0.015471012 |
| chr12: 47226109-47226191 | SLC38A4 | -0.391782093 | 0.002190198 | 0.074896868 | 0.000802857 | 0.043922586 | 0.016462038 | 0.016462038 |
| chr4: 8443374-8442450 | ACOX3 | -0.391346718 | 0.005560396 | 0.110932307 | 0.000819972 | 0.044641533 | 0.018223862 | 0.018223862 |
| chr17: 65052160-65052913 | CACNG1 | -0.39017191 | 0.001934814 | 0.073518881 | 0.000852181 | 0.045631286 | 0.015911468 | 0.015911468 |
| chr22: 34318608-34318829 | LARGE | -0.390149896 | 0.002219852 | 0.074896868 | 0.000854631 | 0.045631286 | 0.016737323 | 0.016737323 |
| chr10: 30404295-30404423 | KIAA1462 | -0.390135064 | 0 | 0 | 0.000858999 | 0.045631286 | 0.011617024 | 0.011617024 |
| chrX: 12738647-12742642 | FRMPD4 | -0.390006756 | 0.002157606 | 0.074896868 | 0.000864966 | 0.045631286 | 0.016682266 | 0.016682266 |
| chr4: 75971372-75975325 | PARM1 | -0.38979558 | 0.005925405 | 0.114006188 | 0.000864966 | 0.045708659 | 0.018774432 | 0.018774432 |
| chr21: 47575383-47575481 | FTCD | -0.389547561 | 0 | 0 | 0.000873685 | 0.045863418 | 0.011727138 | 0.011727138 |
| chr4: 6619106-6625089 | MAN2B2 | -0.38950881 | 0.001332285 | 0.059043466 | 0.000877403 | 0.045925836 | 0.014094588 | 0.014094588 |
| chr16: 4969984-4987136 | PPL | -0.389134121 | 0 | 0 | 0.000883987 | 0.046137514 | 0.011782195 | 0.011782195 |
| chr5: 140389211-140391929 | PCDHA4 | -0.389058019 | 0.002205328 | 0.074896868 | 0.000891792 | 0.046411507 | 0.011837252 | 0.011837252 |
| chr1: 150980723-150980854 | FAM63A | -0.388539406 | 0 | 0 | 0.000918534 | 0.047530856 | 0.017177779 | 0.017177779 |
| chr1: 94312625-94312706 | BCAR3 | -0.388149966 | 0.002300474 | 0.074896868 | 0.000930104 | 0.047587285 | 0.011892309 | 0.011892309 |
| chr3: 48340444-48340743 | ZNF589 | -0.388018199 | 0.002464434 | 0.07690982 | 0.00093681 | 0.047661833 | 0.018003634 | 0.018003634 |
| chr11: 62323634-62323719 | AHNAK | -0.387645912 | 0.001560707 | 0.065613351 | 0.000950347 | 0.047947664 | 0.018333976 | 0.018333976 |
| chr12: 13366614-13369708 | EMP1 | -0.387372671 | 0 | 0 | 0.00096088 | 0.048344752 | 0.015360899 | 0.015360899 |
| chr16: 56458984-56459448 | AMFR | -0.387021554 | 0.003775885 | 0.092303358 | 0.000974474 | 0.048758299 | 0.0197104 | 0.0197104 |
| chrX: 17875575-17875784 | TOM1L2 | -0.386445952 | 0.001581429 | 0.066031038 | 0.000989388 | 0.049024274 | 0.015636183 | 0.015636183 |
| chr10: 115489069-115490662 | CASP7 | -0.386338815 | 0.000117675 | 0.006596685 | 0.000993279 | 0.049024274 | 0.012167593 | 0.012167593 |
| chr13: 36871773-36871977 | C13orf38 | -0.386125524 | 0 | 0 | 0.00100519 | 0.049309634 | 0.012112536 | 0.012112536 |
| chr10: 73610938-73611126 | PSAP | -0.386051278 | 0 | 0 | 0.00100738 | 0.049309634 | 0.012167593 | 0.012167593 |
| chr20: 63543646-63544722 | AVPR1A | -0.385980337 | 0 | 0 | 0.001009498 | 0.049309634 | 0.01222265 | 0.01222265 |
| chrX: 70321926-70323385 | FOXO4 | -0.385961192 | 0 | 0 | 0.00100992 | 0.049309634 | 0.012277707 | 0.012277707 |
| chr6: 149394968-149398126 | UST | -0.385088054 | 0.000264232 | 0.014369004 | 0.001040999 | 0.05009999 | 0.01277322 | 0.01277322 |
| chr12: 6346928-6347427 | CD9 | -0.385058406 | 0.002081356 | 0.074416668 | 0.001042658 | 0.05009999 | 0.018003634 | 0.018003634 |
| chr20: 52686971-52687304 | BCAS1 | -0.384835934 | 0.001858984 | 0.072287892 | 0.0010487 | 0.050126946 | 0.017067665 | 0.017067665 |
| chr6: 36891122-36892331 | C6orf89 | -0.384372572 | 0.000705143 | 0.036281919 | 0.001065356 | 0.050387852 | 0.01378847 | 0.01378847 |
| chr18: 55253785-55254004 | FECH | -0.384344223 | 0.002210942 | 0.074896868 | 0.001065873 | 0.050387852 | 0.018554204 | 0.018554204 |
| chr12: 108154733-108155049 | PRDM4 | -0.384286586 | 0 | 0 | 0.001068068 | 0.050387852 | 0.012608049 | 0.012608049 |
| chr4: 87769891-87770416 | SLC10A6 | -0.383888948 | 0 | 0 | 0.001091989 | 0.05125108 | 0.012663106 | 0.012663106 |
| chr4: 166418663-166419472 | CPE | -0.38344051 | 0 | 0 | 0.001102949 | 0.051612302 | 0.012718163 | 0.012718163 |
| chr10: 115423569-115423805 | NRAP | -0.383262593 | 0.001199197 | 0.054952728 | 0.001107713 | 0.051612302 | 0.0149755 | 0.0149755 |
| chr18: 59560027-59560992 | RNF152 | -0.382492767 | 0.002621541 | 0.078272928 | 0.0011386 | 0.052744562 | 0.020150856 | 0.020150856 |
| chr21: 34185901-34186053 | C21orf62 | -0.382395766 | 0 | 0 | 0.001141255 | 0.052744562 | 0.012883334 | 0.012883334 |
| chr1: 114515645-114520426 | HIPK1 | -0.382102457 | 0.003983912 | 0.094835898 | 0.001155036 | 0.053030454 | 0.021417167 | 0.021417167 |
| chr2: 235813848-235814054 | GNG4 | -0.382028045 | 0.006734515 | 0.120383578 | 0.001155036 | 0.053111188 | 0.021747509 | 0.021747509 |
| chr20: 36151068-36152092 | NNAT | -0.381520055 | 0 | 0 | 0.001172766 | 0.053570624 | 0.012938391 | 0.012938391 |
| chr4: 146177069-146177274 | TBC1D9 | -0.381389837 | 0.007537688 | 0.126765765 | 0.001180035 | 0.053586679 | 0.021967737 | 0.021967737 |
| chr15: 90293739-90294541 | MESP1 | -0.381319191 | 0 | 0 | 0.001183079 | 0.053586679 | 0.013048505 | 0.013048505 |
| chr17: 65026581-65029518 | CACNG4 | -0.380258212 | 0.003303945 | 0.085620014 | 0.00122096 | 0.054621439 | 0.021527281 | 0.021527281 |
| chr21: 43735402-43735761 | TFF3 | -0.37982593 | 0 | 0 | 0.001229156 | 0.054707452 | 0.01332279 | 0.01332279 |
| chrX: 71363102-71363424 | NHSL2 | -0.379789027 | 0.003306045 | 0.085620014 | 0.001229655 | 0.054707452 | 0.021637395 | 0.021637395 |
| chr9: 117568082-117568406 | TNFSF15 | -0.379633338 | 0.001517712 | 0.064557866 | 0.001233934 | 0.054707452 | 0.016902494 | 0.016902494 |
| chr4: 111156307-111563279 | PITX2 | -0.379432657 | 0.003164641 | 0.084777841 | 0.001237943 | 0.054707452 | 0.021692452 | 0.021692452 |
| chr7: 7575380-7575484 | COL28A1 | -0.379174401 | 0.003048335 | 0.083821279 | 0.001246135 | 0.054730647 | 0.021417167 | 0.021417167 |
| chr1: 19983358-19984945 | NBL1 | -0.379105575 | 0.005009103 | 0.104695438 | 0.001250341 | 0.054730647 | 0.02193891 | 0.02193891 |
| chr17: 7990613-7991022 | ALOX12B | -0.37885261 | 0.004112088 | 0.09575366 | 0.001260695 | 0.054730647 | 0.022463249 | 0.022463249 |
| chr4: 114899592-114900883 | ARSJ | -0.378760672 | 0.008790649 | 0.13508 | 0.001263618 | 0.054730647 | 0.023013819 | 0.023013819 |

TABLE 9-continued

| locus | nearest_ref_id | r | p | qval | pglobal | qglobal | prank | padj |
|---|---|---|---|---|---|---|---|---|
| chr17: 19237268-19240028 | EPN2 | −0.378663398 | 0 | 0 | 0.001267584 | 0.054730647 | 0.013433904 | 0.013433904 |
| chr1: 162749901-162750237 | DDR2 | −0.378539319 | 0.004597198 | 0.100359255 | 0.001272199 | 0.054730647 | 0.022738534 | 0.022738534 |
| chr10: 117704168-117708503 | ATRNL1 | −0.378216284 | 0 | 0 | 0.001284378 | 0.054730647 | 0.013488961 | 0.013488961 |
| chr15: 39887562-39891119 | THBS1 | −0.378209064 | 0 | 0 | 0.001284498 | 0.054730647 | 0.013544018 | 0.013544018 |
| chr7: 51384289-51384515 | COBL | −0.378105277 | 0 | 0 | 0.001289026 | 0.054730647 | 0.013654132 | 0.013654132 |
| chr7: 6590638-6591067 | GRID2IP | −0.378036482 | 0 | 0 | 0.001292708 | 0.054730647 | 0.013709189 | 0.013709189 |
| chr13: 36047925-36050832 | MAB21L1 | −0.377665681 | 0.002616639 | 0.078272928 | 0.001312128 | 0.055295099 | 0.021417167 | 0.021417167 |
| chr5: 171433461-171433877 | FBXW11 | −0.377240049 | 0.001478969 | 0.063564631 | 0.001336152 | 0.055965232 | 0.01734295 | 0.01734295 |
| chr16: 20911525-20911706 | DCUN1D3 | −0.377176749 | 0.001548826 | 0.065292417 | 0.001337274 | 0.055965232 | 0.017673292 | 0.017673292 |
| chr2: 61148897-61150645 | REL | −0.377068408 | 0 | 0 | 0.001345056 | 0.056118504 | 0.013819303 | 0.013819303 |
| chr2: 175351600-175351822 | GPR155 | −0.376758939 | 0.001703413 | 0.069486359 | 0.001359864 | 0.056348645 | 0.018499147 | 0.018499147 |
| chr4: 110222878-110223813 | COL25A1 | −0.376530527 | 0 | 0 | 0.001371014 | 0.056348645 | 0.013929417 | 0.013929417 |
| chr16: 16317255-16317351 | ABCC6 | −0.376524916 | 0.002250961 | 0.074896868 | 0.00137115 | 0.056348645 | 0.02081154 | 0.02081154 |
| chr14: 55611833-55612147 | LGALS3 | −0.376477741 | 0.001813224 | 0.07142087 | 0.001372424 | 0.056348645 | 0.018994659 | 0.018994659 |
| chr11: 6631692-6632102 | ILK | −0.376273373 | 0 | 0 | 0.001375926 | 0.056348645 | 0.013984474 | 0.013984474 |
| chr20: 8000084-8000476 | TMX4 | −0.37620338 | 0.002797436 | 0.080691396 | 0.001381424 | 0.056348645 | 0.022243022 | 0.022243022 |
| chr2: 23929350-23931481 | KLHL29 | −0.375178691 | 0.003023736 | 0.0837197 | 0.001423641 | 0.057443033 | 0.022903705 | 0.022903705 |
| chr11: 30608288-30608419 | MPPED2 | −0.375114316 | 0.002532313 | 0.077155474 | 0.001425187 | 0.057443033 | 0.021967737 | 0.021967737 |
| chr8: 30585046-30585443 | GSR | −0.375065559 | 0.000240196 | 0.013260404 | 0.001429341 | 0.057443033 | 0.014369873 | 0.014369873 |
| chr9: 91606384-91611055 | C9orf47 | −0.375058726 | 0.001854016 | 0.072262867 | 0.001429513 | 0.057443033 | 0.019380058 | 0.019380058 |
| chr18: 71958981-71959251 | CYB5A | −0.374903816 | 0.002292426 | 0.074896868 | 0.001437928 | 0.057629628 | 0.021527281 | 0.021527281 |
| chr10: 43623559-43625799 | RET | −0.374655986 | 0.00408246 | 0.095677062 | 0.001443629 | 0.057629628 | 0.024335187 | 0.024335187 |
| chr6: 143266235-143266338 | HIVEP2 | −0.374655117 | 0.004838503 | 0.10230714 | 0.001443676 | 0.057629628 | 0.02461047 | 0.02461047 |
| chr11: 74022456-74022702 | P4HA3 | −0.37407796 | 0.003297931 | 0.08562014 | 0.001472566 | 0.058397855 | 0.023839674 | 0.023839674 |
| chr11: 184006228-184006863 | GLT25D2 | −0.373798797 | 0 | 0 | 0.001485133 | 0.058516288 | 0.014204702 | 0.014204702 |
| chr4: 21161705-21162338 | ANG | −0.373610746 | 0.000947353 | 0.046379462 | 0.001492678 | 0.058682923 | 0.01585641 | 0.01585641 |
| chr15: 55581913-55582001 | RAB27A | −0.372372329 | 0.004349301 | 0.09789861 | 0.001551724 | 0.060207441 | 0.025050928 | 0.025050928 |
| chr21: 48084206-48085036 | PRMT7 | −0.372320011 | 0.002611429 | 0.078272928 | 0.001551466 | 0.060207441 | 0.022848648 | 0.022848648 |
| chr11: 130387805-130388211 | TMEM132D | −0.372252514 | 0.002436548 | 0.07683164 | 0.001558254 | 0.060198246 | 0.022353135 | 0.022353135 |
| chr16: 66516774-66519747 | AC132186.2 | −0.372011859 | 0 | 0 | 0.001579208 | 0.060898433 | 0.014259759 | 0.014259759 |
| chr3: 119483898-119485949 | C3orf15 | −0.371762952 | 0.002076929 | 0.074404864 | 0.001586873 | 0.061064346 | 0.020921654 | 0.020921654 |
| chr1: 71707240-71708643 | RNF121 | −0.371621829 | 0 | 0 | 0.001592571 | 0.0611565 | 0.014314816 | 0.014314816 |
| chr18: 71883526-71891231 | ATXN1L | −0.371120686 | 0 | 0 | 0.001619916 | 0.061682467 | 0.01442493 | 0.01442493 |
| chr19: 38886119-38886868 | SPRED3 | −0.370771544 | 0.002710805 | 0.079554175 | 0.001619916 | 0.061976164 | 0.023564389 | 0.023564389 |
| chr15: 78461263-78464291 | IDH3A | −0.370762369 | 0.005599722 | 0.111134243 | 0.00164469 | 0.061976164 | 0.026152067 | 0.026152067 |
| chr17: 42255572-42256451 | ASB16 | −0.370554636 | 0.002239895 | 0.074896868 | 0.001656546 | 0.062263442 | 0.021967737 | 0.021967737 |
| chr19: 57351949-57352097 | ZIM2 | −0.370474327 | 0.000938443 | 0.140270167 | 0.00165917 | 0.062263442 | 0.026592523 | 0.026592523 |
| chr19: 32695347-32695396 | RP13-395E19.1 | −0.370323092 | 0.000183582 | 0.010196928 | 0.001667311 | 0.062439923 | 0.014700215 | 0.014700215 |
| chr1: 214725657-214725792 | PTPN14 | −0.369408066 | 0.005749803 | 0.112400084 | 0.001717473 | 0.064054336 | 0.026372295 | 0.026372295 |
| chr15: 84962535-84966399 | CSPG4P5 | −0.369128441 | 0.002286269 | 0.074896868 | 0.001739999 | 0.064353713 | 0.022518306 | 0.022518306 |
| chr1: 192844464-19284766 | ABHD3 | −0.369063411 | 0.002353978 | 0.075673086 | 0.001741729 | 0.064353713 | 0.022848648 | 0.022848648 |
| chr3: 113005521-113006303 | BOC | −0.36895421 | 0.001134915 | 0.053127463 | 0.001746759 | 0.064353713 | 0.016957551 | 0.016957551 |
| chr2: 30685281-30685616 | GATSL3 | −0.368746426 | 0.001870578 | 0.072385669 | 0.001754562 | 0.064510342 | 0.020371084 | 0.020371084 |
| chr15: 42783294-42783336 | ZFP106 | −0.368565346 | 0.003731514 | 0.091793135 | 0.001766266 | 0.064581327 | 0.025986896 | 0.025986896 |
| chr19: 48700486-48700877 | C19orf68 | −0.36851038 | 0 | 0 | 0.001770365 | 0.064581327 | 0.014535044 | 0.014535044 |
| chrX: 120181461-120183794 | GLUD2 | −0.368504069 | 0.003279187 | 0.08562014 | 0.001770715 | 0.064581327 | 0.025491384 | 0.025491384 |
| chrX: 47064319-47065264 | INE1 | −0.368175848 | 0.001988041 | 0.07433842 | 0.00178612 | 0.065012604 | 0.020866597 | 0.020866597 |
| chr5: 125930698-125931110 | ALDH7A1 | −0.367952163 | 0.002483797 | 0.076926292 | 0.001796019 | 0.065111948 | 0.023674503 | 0.023674503 |
| chr6: 10374385-10375727 | GABARAPL1 | −0.367831123 | 0.005297504 | 0.108851661 | 0.001809339 | 0.065464189 | 0.026977922 | 0.026977922 |
| chr1: 209907648-209908295 | HSD11B1 | −0.367714675 | 0.003052939 | 0.083821279 | 0.001817653 | 0.065634262 | 0.025216099 | 0.025216099 |
| chr22: 40366908-40369725 | GRAP2 | −0.367292326 | 0.003208892 | 0.085084821 | 0.001844113 | 0.066010185 | 0.025821725 | 0.025821725 |

TABLE 9-continued

| locus | nearest_ref_id | r | p | qval | pglobal | qglobal | prank | padj |
|---|---|---|---|---|---|---|---|---|
| chr2: 171572768-171574588 | SP5 | −0.367283441 | 0.002630479 | 0.078272928 | 0.001844519 | 0.066010185 | 0.02445301 | 0.02445301 |
| chr10: 102745374-102745628 | SEMA4G | −0.366880776 | 0 | 0 | 0.001866351 | 0.066079013 | 0.014700215 | 0.014700215 |
| chr11: 33757927-33757991 | CD59 | −0.366726455 | 0.003215396 | 0.085133002 | 0.001876261 | 0.066300655 | 0.0269701 | 0.02609701 |
| chr16: 69152257-69152622 | HAS3 | −0.366420617 | 0.00095903 | 0.046574504 | 0.001898899 | 0.06671121 | 0.016682266 | 0.016682266 |
| chr9: 119158787-119164601 | PAPPA | −0.365815146 | 0.00627853 | 0.116920758 | 0.001925722 | 0.067433539 | 0.028079062 | 0.028079062 |
| chr2: 227659704-227664475 | IRS1 | −0.365509755 | 0.002014141 | 0.074404864 | 0.001946872 | 0.067611907 | 0.021527281 | 0.021527281 |
| chr19: 46148530-46148726 | EML2 | −0.364924449 | 0 | 0 | 0.001983165 | 0.068739822 | 0.014810329 | 0.014810329 |
| chr21: 38639538-38640262 | DSCR3 | −0.364678478 | 0.004475788 | 0.098672627 | 0.001989389 | 0.068739822 | 0.027913891 | 0.027913891 |
| chr7: 79082335-79082890 | MAGI2 | −0.364612272 | 0.005047787 | 0.105261723 | 0.002005363 | 0.068739822 | 0.028244233 | 0.028244233 |
| chr12: 102079359-102079796 | MYBPC1 | −0.364376297 | 0.007651984 | 0.127947875 | 0.002026334 | 0.068739822 | 0.029125145 | 0.029125145 |
| chr12: 57350933-57351418 | RDH16 | −0.364373561 | 0.004448539 | 0.098538814 | 0.002026872 | 0.068739822 | 0.028024005 | 0.028024005 |
| chr22: 36054661-36057404 | APOL6 | −0.364232582 | 0.002353503 | 0.075673086 | 0.002034874 | 0.068625442 | 0.023894731 | 0.023894731 |
| chr14: 81864638-81864927 | VPS39 | −0.364230778 | 0.004382182 | 0.098116492 | 0.002034942 | 0.068739822 | 0.028134119 | 0.028134119 |
| chr7: 91771776-91772266 | STON2 | −0.364210127 | 0 | 0 | 0.002035715 | 0.068739822 | 0.014865386 | 0.014865386 |
| chr3: 159614511-159615149 | CYP51A1 | −0.364186792 | 0.002167089 | 0.074896868 | 0.002036119 | 0.068739822 | 0.022518306 | 0.022518306 |
| chr2: 238820169-238820756 | SCHIP1 | −0.363626284 | 0.000164314 | 0.067674286 | 0.002074537 | 0.069507577 | 0.019875571 | 0.019875571 |
| chr22: 36054661-36057404 | RAMP1 | −0.363509609 | 0.00456657 | 0.099988173 | 0.002085352 | 0.069625442 | 0.028629632 | 0.028629632 |
| chr12: 78604177-78606790 | NAV3 | −0.363115626 | 0.003889133 | 0.094210495 | 0.00210744 | 0.070105185 | 0.027968948 | 0.027968948 |
| chr15: 71407467-71407839 | CT62 | −0.362619907 | 0.000302258 | 0.016339042 | 0.002144543 | 0.070436411 | 0.015636183 | 0.015636183 |
| chr1: 182359631-182361341 | GLUL | −0.36222252 | 0.000311835 | 0.084283617 | 0.002161265 | 0.070749694 | 0.027143093 | 0.027143093 |
| chr6: 144385587-144385735 | PLAGL1 | −0.3622169 | 0.006059476 | 0.11560742 | 0.002161872 | 0.070749694 | 0.029840885 | 0.029840885 |
| chr18: 57364443-57364574 | CCBE1 | −0.361989182 | 0.001160655 | 0.0540538 | 0.002188416 | 0.071361233 | 0.017783406 | 0.017783406 |
| chr9: 108536145-108538893 | TMEM38B | −0.36183798 | 0.003196865 | 0.085052362 | 0.002195984 | 0.071479663 | 0.027528492 | 0.027528492 |
| chr7: 121784214-121784334 | AASS | −0.361635356 | 0.001030161 | 0.049499517 | 0.002205346 | 0.071655996 | 0.017287893 | 0.017287893 |
| chr2: 230135729-230136001 | PID1 | −0.361364734 | 0.007876988 | 0.129133025 | 0.00222318 | 0.07191629 | 0.03066674 | 0.03066674 |
| chr4: 37687821-37687998 | RELL1 | −0.361328155 | 0.004421037 | 0.098285551 | 0.002225236 | 0.07191629 | 0.029235258 | 0.029235258 |
| chr16: 69166386-69166487 | CHTF8 | −0.360655997 | 0.00397391 | 0.094764506 | 0.002272263 | 0.072893957 | 0.028959974 | 0.028959974 |
| chr1: 184943433-184943682 | FAM129A | −0.360529444 | 0.003171679 | 0.084841251 | 0.002281975 | 0.072893957 | 0.02774872 | 0.02774872 |
| chr1: 56112874-56113871 | BLOC1S1 | −0.360323424 | 0.002460351 | 0.07690982 | 0.002289863 | 0.072893957 | 0.025216099 | 0.025216099 |
| chr5: 40691880-40693837 | PTGER4 | −0.360302037 | 0 | 0 | 0.002291607 | 0.072893957 | 0.01514671 | 0.01514671 |
| chr20: 48098450-48099184 | KCNB1 | −0.360156699 | 0.005928121 | 0.114061188 | 0.002302774 | 0.073121129 | 0.030501569 | 0.030501569 |
| chr14: 91282518-91282761 | TTC7B | −0.36000688 | 0.002911014 | 0.08228265 | 0.002317136 | 0.073433881 | 0.026757694 | 0.026757694 |
| chr19: 169721343-169722024 | NOSTRIN | −0.359423859 | 0.002183004 | 0.074896868 | 0.002363841 | 0.074281033 | 0.023399218 | 0.023399218 |
| chr19: 47290656-47291851 | SLC1A5 | −0.358711445 | 0 | 0 | 0.002424278 | 0.075738271 | 0.015250785 | 0.015250785 |
| chr2: 111875192-111875799 | ACOXL | −0.358659464 | 0.00272735 | 0.079641256 | 0.002426894 | 0.075738271 | 0.02664758 | 0.02664758 |
| chr7: 84815993-84816171 | SEMA3D | −0.358554714 | 0.008937979 | 0.1364206 | 0.002433204 | 0.075804938 | 0.031933051 | 0.031933051 |
| chr1: 75528837-75529282 | CHST6 | −0.358161822 | 0.00087259 | 0.134884462 | 0.002458622 | 0.07630902 | 0.015360899 | 0.015360899 |
| chr14: 46216268-46216322 | IPP | −0.358130707 | 0.001959211 | 0.074231845 | 0.002463337 | 0.07630902 | 0.023068876 | 0.023068876 |
| chr15: 30706317-30706463 | AC019322.1 | −0.35739784 | 0.002061859 | 0 | 0.002466189 | 0.077274787 | 0.029015031 | 0.029015031 |
| chr14: 4662297-4665256 | PPAPDC2 | −0.357393072 | 0.003295666 | 0.085620014 | 0.00252278 | 0.077274787 | 0.03231845 | 0.03231845 |
| chr23: 23904828-23904927 | MYH7 | −0.357022956 | 0.008539527 | 0.133479717 | 0.002522928 | 0.077741827 | 0.015801354 | 0.015801354 |
| chr5: 42887392-42887494 | SEPP1 | −0.356433723 | 0.000251827 | 0.013818534 | 0.002549612 | 0.07840198 | 0.031107196 | 0.031107196 |
| chr10: 53455246-53459355 | CSTF2T | −0.356077989 | 0.004618262 | 0.10049394 | 0.002585604 | 0.079043136 | 0.031657766 | 0.031657766 |
| chr1: 82456074-82458107 | LPHN2 | −0.3558649 | 0.005394785 | 0.109381082 | 0.00261112 | 0.079069514 | 0.03297913 | 0.03297913 |
| chr20: 5170747-5178533 | CDS2 | −0.355827803 | 0.00087294 | 0.134884462 | 0.002638622 | 0.079069514 | 0.022463249 | 0.022463249 |
| chr14: 20881563-20881580 | TEP1 | −0.355558706 | 0.00195921 | 0 | 0.002639213 | 0.07907281 | 0.015526069 | 0.015526069 |
| chr17: 62207335-62207502 | ERN1 | −0.355198611 | 0.003341644 | 0.085969228 | 0.002655978 | 0.07955065 | 0.029785828 | 0.029785828 |
| chr22: 24890657-24891042 | C22orf45 | −0.355112593 | 0.00621647 | 0.116920758 | 0.002686132 | 0.07955065 | 0.032758905 | 0.032758905 |
| chrX: 148112508-148118090 | CNTNAP2 | −0.355018684 | 0.003900583 | 0.094210495 | 0.00269465 | 0.07955065 | 0.030611683 | 0.030611683 |
| chrX: 100786630-100788446 | ARMCX4 | −0.354773706 | 0.001780023 | 0.071212674 | 0.002706719 | 0.079648701 | 0.021582338 | 0.021582338 |
| chr9: 100845127-100845357 | NANS | −0.354741743 | 0.00322612 | 0.085267223 | 0.00273199 | 0.079648701 | 0.0295656 | 0.0295656 |

TABLE 9-continued

| locus | nearest_ref_id | r | p | qval | pglobal | qglobal | prank | padj |
|---|---|---|---|---|---|---|---|---|
| chr11: 85338261-85338966 | DLG2 | -0.35458979 | 0.007531741 | 0.126765765 | 0.002743907 | 0.079738981 | 0.033639817 | 0.033639817 |
| chr10: 36810648-36813162 | NAMPTL | -0.354542215 | 0.003272356 | 0.085620014 | 0.002749615 | 0.079738981 | 0.029620657 | 0.029620657 |
| chr3: 51418480-51421629 | DOCK3 | -0.354499487 | 0.009000821 | 0.136900167 | 0.002752827 | 0.079738981 | 0.034190387 | 0.034190387 |
| chr11: 119170204-119177651 | CBL | -0.354474684 | 0 | 0 | 0.002753152 | 0.079738981 | 0.015636183 | 0.015636183 |
| chr7: 92465791-92465908 | CDK6 | -0.354190236 | 0.007309538 | 0.124777387 | 0.002770379 | 0.079997448 | 0.033804988 | 0.033804988 |
| chr11: 110463585-110464173 | PAK3 | -0.353473303 | 0.00372339 | 0.091761103 | 0.002816271 | 0.080681283 | 0.030886968 | 0.030886968 |
| chrX: 213445866-213448116 | RPS6KC1 | -0.353132762 | 0.008090944 | 0.130860029 | 0.002841786 | 0.081115772 | 0.034410615 | 0.034410615 |
| chr1: 203144678-203144941 | MYBPH | -0.353031224 | 0 | 0 | 0.002856557 | 0.08112947 | 0.01569124 | 0.01569124 |
| chr12: 110205816-110208312 | C12orf34 | -0.352927122 | 0.003855714 | 0.093875787 | 0.002863183 | 0.08112947 | 0.031162253 | 0.031162253 |
| chr1: 54483764-54483856 | LDLRAD1 | -0.352368395 | 0.002200147 | 0.074896868 | 0.002907663 | 0.081412629 | 0.024665529 | 0.024665529 |
| chr8: 92052871-92053292 | TMEM55A | -0.352125583 | 0.0024435 | 0.096531516 | 0.00293379 | 0.081412629 | 0.032428564 | 0.032428564 |
| chr5: 90890818-90892669 | GABARAPL3 | -0.352096621 | 0.004075199 | 0.09564239 | 0.002935285 | 0.081412629 | 0.032263393 | 0.032263393 |
| chr5: 126801297-126801429 | MEGF10 | -0.351979071 | 0.005769117 | 0.112671479 | 0.002944893 | 0.081412629 | 0.034245444 | 0.034245444 |
| chr7: 66273872-66276446 | KCTD7 | -0.351787458 | 0.008500777 | 0.133361292 | 0.002966385 | 0.08168847 | 0.035676926 | 0.035676926 |
| chr12: 101521638-101522419 | ANO4 | -0.351661205 | 0.00536422 | 0.109252525 | 0.002977359 | 0.08168847 | 0.033915102 | 0.033915102 |
| chr6: 3231790-3231964 | TUBB2B | -0.350836048 | 0.00415823 | 0.095871025 | 0.00304847 | 0.08306038 | 0.032813962 | 0.032813962 |
| chr14: 76446884-76448092 | TGFB3 | -0.350820631 | 0.007016608 | 0.121921113 | 0.003050227 | 0.08306038 | 0.035456698 | 0.035456698 |
| chr2: 178972980-178973081 | PDE11A | -0.350337632 | 0.005792206 | 0.113000905 | 0.003084538 | 0.083768917 | 0.034630843 | 0.034630843 |
| chr11: 114121047-114121398 | ZBTB16 | -0.349982548 | 0.007051836 | 0.122091644 | 0.00312354 | 0.084675918 | 0.035566812 | 0.035566812 |
| chr3: 97471032-97471304 | EPHA6 | -0.349748772 | 0.004669226 | 0.100696902 | 0.003138997 | 0.084968121 | 0.03358476 | 0.03358476 |
| chr17: 72775105-72777628 | ZNF407 | -0.349595533 | 0.011713078 | 0.154835981 | 0.003165011 | 0.085014912 | 0.03705335 | 0.03705335 |
| chr17: 40540296-40540449 | STAT3 | -0.349348115 | 0 | 0 | 0.003184574 | 0.085285307 | 0.015966525 | 0.015966525 |
| chr16: 9009515-9009309 | C16orf5 | -0.349062505 | 0.002890689 | 0.082124567 | 0.00320901 | 0.085528988 | 0.029070088 | 0.029070088 |
| chr17: 76899215-76899297 | AC100788.1 | -0.349055229 | 0.004954969 | 0.104163323 | 0.003211516 | 0.085528988 | 0.034190387 | 0.034190387 |
| chr2: 11780416-11782914 | GREB1 | -0.348390425 | 0.004885601 | 0.103182756 | 0.003278095 | 0.08669722 | 0.034190387 | 0.034190387 |
| chr3: 169487108-169487683 | AC078802.1 | -0.348375436 | 0.00661627 | 0.119815608 | 0.003280782 | 0.08669722 | 0.035952211 | 0.035952211 |
| chr15: 64126025-64126147 | HERC1 | -0.348284478 | 0.004634897 | 0.10069813 | 0.003288157 | 0.08669722 | 0.033860045 | 0.033860045 |
| chr7: 102301592-102301847 | RP11-577H5.4 | -0.348203645 | 0 | 0 | 0.003300147 | 0.08687039 | 0.016021582 | 0.016021582 |
| chr6: 169764077-169766505 | G6PC2 | -0.347521745 | 0.000531991 | 0.027845969 | 0.003372886 | 0.08827339 | 0.01717779 | 0.01717779 |
| chr10: 127697622-127698161 | FANK1 | -0.346440794 | 0.003260067 | 0.085620014 | 0.003486343 | 0.090400812 | 0.03121731 | 0.03121731 |
| chr1: 68153343-68154021 | GADD45A | -0.346346476 | 0.008456687 | 0.133216661 | 0.003501622 | 0.090469355 | 0.037769091 | 0.037769091 |
| chr14: 93651154-93651260 | MOAP1 | -0.3406439 | 0 | 0 | 0.003532022 | 0.090948774 | 0.016131696 | 0.016131696 |
| chr9: 102625901-102629173 | NR4A3 | -0.346030498 | 0.004972561 | 0.10429172 | 0.003546498 | 0.090948774 | 0.035016242 | 0.035016242 |
| chr20: 42939615-42939809 | FITM2 | -0.345969257 | 0.004756964 | 0.101816018 | 0.003540207 | 0.090948774 | 0.0346859 | 0.0346859 |
| chr2: 239139841-239140318 | AC016757.3 | -0.3458947 | 0.004187488 | 0.096032 | 0.003549594 | 0.090977065 | 0.033915102 | 0.033915102 |
| chr4: 175443509-175444305 | HPGD | -0.345861904 | 0.002242854 | 0.074896868 | 0.003551326 | 0.090977065 | 0.02609701 | 0.02609701 |
| chr17: 24740163-24743424 | C1orf201 | -0.345686354 | 0.005986125 | 0.114759271 | 0.003572886 | 0.091143709 | 0.03650278 | 0.03650278 |
| chr11: 113499460-113499635 | SLC16A1 | -0.345484279 | 0.009716079 | 0.142148692 | 0.003587275 | 0.091208876 | 0.038870231 | 0.038870231 |
| chr10: 14816251-14816896 | FAM107B | -0.345316938 | 0.001800119 | 0.071315614 | 0.00359771 | 0.091264254 | 0.022793591 | 0.022793591 |
| chr12: 85429981-85430055 | TSPAN19 | -0.345103145 | 0.00626591 | 0.116920758 | 0.003625323 | 0.091470629 | 0.037108407 | 0.037108407 |
| chr9: 130869307-130871524 | C16orf85 | -0.345097604 | 0.001129539 | 0.053024689 | 0.003625399 | 0.091470629 | 0.019269944 | 0.019269944 |
| chr16: 88634958-88636548 | ADH1A | -0.344998373 | 0.004254851 | 0.096531516 | 0.003639167 | 0.09167571 | 0.034465672 | 0.034465672 |
| chr4: 100212053-100212185 | CLN8 | -0.344633185 | 0.010423843 | 0.14552518 | 0.003672878 | 0.092268989 | 0.039530914 | 0.039530914 |
| chr8: 1728415-1734738 | POLD4 | -0.344486773 | 0.002625331 | 0.078272928 | 0.003683245 | 0.092274168 | 0.02884986 | 0.02884986 |
| chr6: 6712421-67124443 | TECPR2 | -0.344287946 | 0.00249821 | 0.076926292 | 0.003702508 | 0.092577124 | 0.028189176 | 0.028189176 |
| chr14: 102964439-102968809 | CKM | -0.344265976 | 0.002432096 | 0.07683164 | 0.003705532 | 0.092577124 | 0.027638606 | 0.027638606 |
| chr19: 45826078-45826233 | MBOAT1 | -0.343916793 | 0.005876217 | 0.113663186 | 0.003743468 | 0.092868242 | 0.037108407 | 0.037108407 |
| chr6: 20212366-20212670 | SLC25A25 | -0.343624793 | 0 | 0 | 0.003722717 | 0.093229751 | 0.01624181 | 0.01624181 |
| chr9: 86258343-86259045 | C9orf103 | -0.343444827 | 0.002600596 | 0.078272928 | 0.00380019 | 0.09365204 | 0.028794803 | 0.028794803 |
| chr1: 626020-626078 | CDHR5 | -0.343187787 | 0.008441373 | 0.133216661 | 0.003827747 | 0.093940709 | 0.039475858 | 0.039475858 |
| chr16: 88729418-88729518 | MVD | -0.343137668 | 0.004619966 | 0.10049394 | 0.003827348 | 0.093940709 | 0.035566812 | 0.035566812 |

TABLE 9-continued

| locus | nearest_ref_id | r | p | qval | pglobal | qglobal | prank | padj |
|---|---|---|---|---|---|---|---|---|
| chr12: 52470569-52471278 | C12orf44 | -0.343056136 | 0.000630237 | 0.032893644 | 0.003836004 | 0.094026103 | 0.017453064 | 0.017453064 |
| chr3: 143767509-143767561 | C3orf58 | -0.342338768 | 0.006331044 | 0.117217889 | 0.003897344 | 0.095018782 | 0.038319661 | 0.038319661 |
| chr16: 76592386-76593135 | CNTNAP4 | -0.342102919 | 0.000790908 | 0.040014672 | 0.003922446 | 0.095100371 | 0.018003634 | 0.018003634 |
| chr6: 139113885-139114456 | CCDC28A | -0.341986012 | 0.006517637 | 0.118025771 | 0.003932856 | 0.095100371 | 0.038594946 | 0.038594946 |
| chr17: 33513317-33516364 | UNC45B | -0.341937241 | 0.003818629 | 0.093222797 | 0.003936253 | 0.095100371 | 0.033860045 | 0.033860045 |
| chr10: 135336774-135337062 | RP11-108K14.4 | -0.341903564 | 0.006813291 | 0.120821721 | 0.003993904 | 0.095100371 | 0.038980345 | 0.038980345 |
| chr2: 242162600-242164792 | ANO7 | -0.341869694 | 0.007132564 | 0.123028262 | 0.003942371 | 0.095100371 | 0.039200573 | 0.039200573 |
| chr4: 7940727-7942023 | AC097381.1 | -0.341732589 | 0.008108444 | 0.131026389 | 0.003953134 | 0.095100371 | 0.040026427 | 0.040026427 |
| chr19: 35614344-35615227 | FXYD3 | -0.341197928 | 0.006740632 | 0.120383578 | 0.004021122 | 0.095884062 | 0.039090459 | 0.039090459 |
| chr10: 81373492-81375197 | SFTPA1 | -0.341146486 | 0.001850992 | 0.072262867 | 0.004029421 | 0.095884062 | 0.023344161 | 0.023344161 |
| chr11: 125301061-125303285 | PKNOX2 | -0.341144084 | 0.003301426 | 0.085620014 | 0.004029966 | 0.095884062 | 0.032758905 | 0.032758905 |
| chr8: 27401960-27403081 | EPHX2 | -0.34107733 | 0.004448705 | 0.098538814 | 0.004038502 | 0.095884062 | 0.03578704 | 0.03578704 |
| chr16: 81411019-81413940 | GAN | -0.341026233 | 0.002661769 | 0.078610908 | 0.004051327 | 0.095937748 | 0.029510543 | 0.029510543 |
| chr2: 179695391-179695529 | TTN | -0.340871763 | 0.003439286 | 0.087240779 | 0.004079477 | 0.096315629 | 0.033474646 | 0.033474646 |
| chr3: 49761030-49761384 | GMPPB | -0.340818196 | 0.006392303 | 0.117755656 | 0.004083193 | 0.096315629 | 0.039145516 | 0.039145516 |
| chr11: 125366403-125369424 | AP000708.1 | -0.340419481 | 0.007994613 | 0.12969294 | 0.004125875 | 0.096522303 | 0.040907339 | 0.040907339 |
| chrX: 120836679-120846043 | CHRNA2 | -0.340317829 | 0.01017339 | 0.143603022 | 0.004139783 | 0.096522303 | 0.042393878 | 0.042393878 |
| chr6: 170713850-170716153 | FAM120B | -0.340145296 | 0.006394353 | 0.117755656 | 0.004156806 | 0.096794954 | 0.039475858 | 0.039475858 |
| chr19: 52034835-52035110 | SIGLEC6 | -0.339935646 | 0.00249674 | 0.076926292 | 0.004188755 | 0.097074302 | 0.028519518 | 0.028519518 |
| chr2: 169952053-169952677 | DHRS9 | -0.339663644 | 0 | 0 | 0.004222003 | 0.097438673 | 0.016406981 | 0.016406981 |
| chr15: 2182528-121825513 | SNTB1 | -0.339220559 | 0.013026815 | 0.159180228 | 0.004266128 | 0.098207447 | 0.043329846 | 0.043329846 |
| chr10: 61122866-61122939 | FAM13C | -0.339116788 | 0.012107259 | 0.154294477 | 0.004276251 | 0.098315877 | 0.043219732 | 0.043219732 |
| chr7: 98030113-98030380 | AC093799.1 | -0.339089857 | 0.002803296 | 0.080691396 | 0.004283229 | 0.098315823 | 0.03066674 | 0.03066674 |
| chr5: 131630870-131631008 | P4HA2 | -0.338862866 | 0.004018835 | 0.095037797 | 0.004315256 | 0.098553166 | 0.035566812 | 0.035566812 |
| chr3: 113346492-113348425 | AMOT | -0.338743263 | 0.009557513 | 0.141580566 | 0.004326338 | 0.098553166 | 0.042889391 | 0.042889391 |
| chr1: 118938880-111895635 | SIDT1 | -0.338182328 | 0.016461828 | 0.175467239 | 0.004398853 | 0.098637481 | 0.0445411 | 0.0445411 |
| chr13: 111521577-111522162 | C1orf88 | -0.337856332 | 0.00901587 | 0.136919096 | 0.004436675 | 0.099254224 | 0.043384903 | 0.043384903 |
| chr1: 201860927-201861434 | C13orf29 | -0.3377445 | 0.002559298 | 0.077611339 | 0.004448077 | 0.099254224 | 0.029400429 | 0.029400429 |
| chr11: 134019040-134021896 | SHISA4 | -0.337716435 | 0.002153764 | 0.074896868 | 0.004454992 | 0.099254224 | 0.025766669 | 0.025766669 |
| chr7: 49951629-49952138 | JAM3 | -0.337708293 | 0.002445067 | 0.0769098 | 0.0044553 | 0.099254224 | 0.028519518 | 0.028519518 |
| chr12: 46663762-46663800 | VWC2 | -0.33764517 | 0.005162659 | 0.106835773 | 0.004464114 | 0.099254224 | 0.03887023 | 0.03887023 |
| chr17: 71258247-71258491 | SLC38A1 | -0.33763681 | 0.009933718 | 0.143081782 | 0.004464609 | 0.099254224 | 0.044100644 | 0.044100644 |
| chr1: 156108870-156109880 | CPSF4L | -0.337524821 | 0.006504807 | 0.118025771 | 0.004476868 | 0.099271066 | 0.041182624 | 0.041182624 |
| chr19: 30205813-30206364 | LMNA | -0.337301786 | 0 | 0 | 0.004478365 | 0.099271066 | 0.016517095 | 0.016517095 |
| chr7: 134264258-134264592 | C19orf12 | -0.337294662 | 0.009407927 | 0.140292428 | 0.004509627 | 0.099282857 | 0.044100644 | 0.044100644 |
| chr1: 203765436-203769686 | AKR1B15 | -0.337020674 | 0.005585004 | 0.11106714 | 0.004537761 | 0.099781299 | 0.039696085 | 0.039696085 |
| chr7: 4897363-4901625 | PAPOLB | -0.336643583 | 0.009833222 | 0.142636167 | 0.004590477 | 0.1005752 | 0.044596157 | 0.044596157 |
| chr2: 1317862-11319000 | PQLC3 | -0.33652056 | 0.01347205 | 0.162218034 | 0.004601586 | 0.100593449 | 0.045587183 | 0.045587183 |
| chr14: 39907677-39901704 | FBXO33 | -0.336362403 | 0.004102791 | 0.09575366 | 0.004620935 | 0.100593449 | 0.036667951 | 0.036667951 |
| chr9: 131703723-131704320 | PHYHD1 | -0.336138287 | 0 | 0 | 0.004653093 | 0.100852182 | 0.016572152 | 0.016572152 |
| chr2: 221915322-221915518 | DUSP10 | -0.33590192 | 0.012733827 | 0.158213348 | 0.004690551 | 0.1011811 | 0.045972582 | 0.045972582 |
| chr3: 41301355-41301587 | CTNNB1 | -0.335633668 | 0.006267131 | 0.116920758 | 0.004722562 | 0.101389943 | 0.041457909 | 0.041457909 |
| chr4: 31144094-31144728 | PCDH7 | -0.335237096 | 0.005140064 | 0.106574171 | 0.004771765 | 0.102204685 | 0.039530914 | 0.039530914 |
| chr1: 203765436-203769686 | ZBED6 | -0.335082465 | 0.003469323 | 0.087293121 | 0.004792822 | 0.102293798 | 0.035071299 | 0.035071299 |
| chr3: 3543826-3544028 | C19orf71 | -0.334820013 | 0.004225675 | 0.096464363 | 0.004483625 | 0.102737778 | 0.037548863 | 0.037548863 |
| chr22: 43117170-43117304 | A4GALT | -0.334613222 | 0 | 0 | 0.004885856 | 0.102862951 | 0.016627209 | 0.016627209 |
| chr15: 99791359-99791422 | TTC23 | -0.334607361 | 0.009988191 | 0.143216183 | 0.004859132 | 0.102862951 | 0.046027639 | 0.046027639 |
| chr16: 5064859-5069156 | SEC14L5 | -0.334522135 | 0 | 0 | 0.004874777 | 0.102956744 | 0.016682266 | 0.016682266 |
| chr5: 32786339-32787256 | NPR3 | -0.334311711 | 0.005412112 | 0.10946569 | 0.004899715 | 0.1034075 | 0.04057697 | 0.04057697 |
| chr2: 160918805-160919121 | PLA2R1 | -0.334063845 | 0.005422954 | 0.109562966 | 0.004930911 | 0.103435103 | 0.040632054 | 0.040632054 |
| chr4: 108955394-108956331 | HADH | -0.334047223 | 0.005989748 | 0.114759271 | 0.00493313 | 0.103435103 | 0.041788251 | 0.041788251 |

TABLE 9-continued

| locus | nearest_ref_id | r | p | qval | pglobal | qglobal | prank | padj |
|---|---|---|---|---|---|---|---|---|
| chr3: 14814297-14814541 | C3orf20 | −0.333760773 | 0.004507549 | 0.099237103 | 0.004973307 | 0.103891426 | 0.038539889 | 0.038539889 |
| chr20: 55100838-55100981 | GCNT7 | −0.333749414 | 0.008434475 | 0.133216661 | 0.004976264 | 0.103891426 | 0.045036613 | 0.045036613 |
| chr2: 43762292-43762367 | RASGEF1A | −0.333319387 | 0.001430906 | 0.06194304 | 0.005031975 | 0.10463209 | 0.021857623 | 0.021857623 |
| chr5: 80561957-80562216 | CKMT2 | −0.333284313 | 0.005483096 | 0.109968839 | 0.005040636 | 0.10463209 | 0.04107251 | 0.04107251 |
| chr6: 41031839-41032465 | APOBEC2 | −0.333215576 | 0.004677515 | 0.10098106 | 0.005055389 | 0.104698999 | 0.039310687 | 0.039310687 |
| chr9: 5304369-5304969 | RLN2 | −0.333058195 | 0.005460123 | 0.109968839 | 0.005080302 | 0.104919288 | 0.041127567 | 0.041127567 |
| chr1: 181057637-181059977 | IER5 | −0.332972834 | 0 | 0 | 0.005089809 | 0.104919288 | 0.016847437 | 0.016847437 |
| chr2: 50236168-50236912 | BCDIN3D | −0.332717732 | 0.007849382 | 0.129133025 | 0.005124504 | 0.105409257 | 0.045036613 | 0.045036613 |
| chr14: 95942014-95942173 | C14orf49 | −0.332614322 | 0.008380922 | 0.133216661 | 0.0051347 | 0.105428918 | 0.045752354 | 0.045752354 |
| chr13: 24247510-24250232 | TNFRSF19 | −0.332405917 | 0.0118646 | 0.155153269 | 0.005152212 | 0.105428918 | 0.047954633 | 0.047954633 |
| chr3: 38178355-38178733 | ACAA1 | −0.332380373 | 0.005375471 | 0.109333343 | 0.005154483 | 0.105428918 | 0.041127567 | 0.041127567 |
| chr10: 62761156-62761198 | RHOBTB1 | −0.332293978 | 0.008639609 | 0.134263631 | 0.005169761 | 0.105609324 | 0.044468094 | 0.044468094 |
| chr14: 24114350-24114848 | DHRS2 | −0.332260435 | 0.009216563 | 0.138576518 | 0.005183255 | 0.105609324 | 0.047018664 | 0.047018664 |
| chr19: 53077329-53077383 | ZNF808 | −0.332184126 | 0.004142985 | 0.095871025 | 0.005187576 | 0.105609324 | 0.037989319 | 0.037989319 |
| chrX: 67944146-67945684 | STARD8 | −0.332156945 | 0.005297851 | 0.108851661 | 0.005192553 | 0.105609324 | 0.04107251 | 0.04107251 |
| chr22: 17612504-17612994 | AC006946.15 | −0.332029863 | 0.002076087 | 0.074404864 | 0.00520967 | 0.105609324 | 0.025931839 | 0.025931839 |
| chr15: 100273489-100273766 | LYSMD4 | −0.331196355 | 0.004818502 | 0.102159863 | 0.005217245 | 0.105609324 | 0.040191598 | 0.040191598 |
| chr19: 57802066-57805436 | ZNF460 | −0.331805696 | 0.0062541 | 0.116920758 | 0.005240306 | 0.105872839 | 0.04343996 | 0.04343996 |
| chr1: 110052041-110052360 | AMIGO1 | −0.331748977 | 0.007140297 | 0.12304479 | 0.005247045 | 0.105891205 | 0.044871442 | 0.044871442 |
| chr19: 40931773-40931932 | SERTAD1 | −0.331603747 | 0.004097877 | 0.09575366 | 0.005262839 | 0.10609 2067 | 0.037879205 | 0.037879205 |
| chr22: 23567440-23567781 | B3GALNT2 | −0.331355681 | 0.006921811 | 0.121704609 | 0.005309579 | 0.106561188 | 0.04470 6271 | 0.04470 6271 |
| chr5: 180631588-180632293 | TRIM7 | −0.331070531 | 0.00478817 | 0.102074564 | 0.005350621 | 0.107030103 | 0.040356769 | 0.040356769 |
| chr7: 134849169-134850650 | TMEM140 | −0.330961226 | 0.006462905 | 0.118025771 | 0.005371153 | 0.107215322 | 0.044210758 | 0.044210758 |
| chr1: 203054618-203055164 | MYOG | −0.330806046 | 0 | 0 | 0.005389395 | 0.107215322 | 0.016902494 | 0.016902494 |
| chr22: 24836550-24838328 | ADORA2A | −0.330604462 | 0.009903173 | 0.143081782 | 0.005410806 | 0.107523491 | 0.048780488 | 0.048780488 |
| chr14: 59950207-59951148 | C14orf149 | −0.330342745 | 0.011107988 | 0.150003266 | 0.005452342 | 0.107926139 | 0.049441172 | 0.049441172 |
| chr17: 62833173-62833243 | AC103810.1 | −0.330067269 | 0.004228881 | 0.096464363 | 0.005490444 | 0.108042182 | 0.038925288 | 0.038925288 |
| chr1: 159614511-159615155 | IQCJ-SCHIP1 | −0.329859948 | 0.000512092 | 0.026881861 | 0.005512092 | 0.108469 | 0.018223862 | 0.018223862 |
| chr22: 43411026-43411151 | PACSIN2 | −0.329641143 | 0.00529232 | 0.108851661 | 0.005558398 | 0.108672962 | 0.041953422 | 0.041953422 |
| chr3: 143566989-143567373 | SLC9A9 | −0.329499509 | 0.00957653 | 0.141380566 | 0.005575043 | 0.108881192 | 0.049220944 | 0.049220944 |
| chr6: 147705849-147708707 | STXBP5 | −0.329411447 | 0.005615759 | 0.111134243 | 0.005594365 | 0.109141203 | 0.043109618 | 0.043109618 |
| chr10: 43991463-43991517 | ZNF487P | −0.329209459 | 0.004820294 | 0.102159863 | 0.005620169 | 0.109442547 | 0.041017453 | 0.041017453 |
| chr2: 123384818-123385612 | CLVS2 | −0.328460279 | 0.004405369 | 0.098228128 | 0.005746878 | 0.110636432 | 0.039806199 | 0.039806199 |
| chr2: 168114366-168116263 | XIRP2 | −0.328456174 | 0.001905952 | 0.07290082 | 0.005747901 | 0.110636432 | 0.025050928 | 0.025050928 |
| chr11: 70281131-70282690 | CTTN | −0.328378509 | 0.005485425 | 0.109968839 | 0.005768469 | 0.110636432 | 0.043274789 | 0.043274789 |
| chr3: 39876150-39882154 | KIAA0754 | −0.328304607 | 0.009074575 | 0.137166781 | 0.005784188 | 0.1108209 | 0.049441172 | 0.049441172 |
| chr21: 47648347-47648738 | LSS | −0.328111765 | 0.006302121 | 0.116920758 | 0.005787752 | 0.111151912 | 0.045311898 | 0.045311898 |
| chr8: 75233143-75233563 | JPH1 | −0.327815537 | 0.005395884 | 0.109381098 | 0.005847533 | 0.111316988 | 0.042944448 | 0.042944448 |
| chr17: 46135656-46138906 | NFE2L1 | −0.327788072 | 0.002131117 | 0.074896868 | 0.005851836 | 0.111316988 | 0.026757694 | 0.026757694 |
| chr3: 196065134-196065374 | TM4SF19 | −0.327643438 | 0.004075715 | 0.09564239 | 0.005873115 | 0.111316988 | 0.038650003 | 0.038650003 |
| chr17: 11461070-11462196 | SHISA6 | −0.327641088 | 0.003501168 | 0.08783387 | 0.005873524 | 0.111316988 | 0.03650278 | 0.03650278 |
| chr7: 97841565-97842271 | BHLHA15 | −0.327621915 | 0.007927854 | 0.129538147 | 0.005876584 | 0.111316988 | 0.048174861 | 0.048174861 |
| chr11: 4730834-4731698 | AC103710.1 | −0.327522873 | 0.003710943 | 0.091703214 | 0.005890874 | 0.111454101 | 0.036998293 | 0.036998293 |
| chr10: 75457290-75457639 | AGAP5 | −0.327417008 | 0.00230532 | 0.074904336 | 0.005902846 | 0.111564413 | 0.028959974 | 0.028959974 |
| chr2: 204599506-204602557 | CD28 | −0.327340798 | 0.003182194 | 0.084997327 | 0.005918273 | 0.111739703 | 0.034740957 | 0.034740957 |
| chr21: 200143090-200146552 | NR5A2 | −0.327072728 | 0.000350694 | 0.01878955 | 0.005966581 | 0.112219245 | 0.018058691 | 0.018058691 |
| chr5: 140890513-140892542 | PCDHGC3 | −0.326986718 | 0 | 0 | 0.005977789 | 0.112219245 | 0.017067665 | 0.017067665 |
| chr17: 4926762-4931696 | KIF1C | −0.326823547 | 0.00581312 | 0.11307866 | 0.005999445 | 0.112453997 | 0.044596157 | 0.044596157 |
| chr2: 182794287-182795465 | SSFA2 | −0.326707409 | 0.006909184 | 0.121600292 | 0.006025213 | 0.112704365 | 0.04690855 | 0.04690855 |
| chr6: 159240448-159240444 | EZR | −0.326642824 | 0.006782665 | 0.120633891 | 0.006039277 | 0.112735244 | 0.04690855 | 0.04690855 |
| chr8: 12613432-12613582 | LONRF1 | −0.326542762 | 0.001910521 | 0.07290082 | 0.00605405 | 0.112819565 | 0.02538127 | 0.02538127 |

TABLE 9-continued

| locus | nearest_ref_id | r | p | qval | pglobal | qglobal | prank | padj |
|---|---|---|---|---|---|---|---|---|
| chr1: 111789401-111789574 | AP000907.1 | −0.326455419 | 0.006026463 | 0.115098472 | 0.006606864 | 0.112819565 | 0.045366955 | 0.045366955 |
| chr8: 74235147-74237516 | RDH10 | −0.326283654 | 0 | 0 | 0.006096308 | 0.112957258 | 0.017122722 | 0.017122722 |
| chr9: 36276890-36277053 | GNE | −0.326253035 | 0.007726033 | 0.128531382 | 0.006098553 | 0.112957258 | 0.048615317 | 0.048615317 |
| chr11: 66725792-66725847 | PC | −0.32597854 | 0.002534333 | 0.077155474 | 0.006153849 | 0.11312992 | 0.031052139 | 0.031052139 |
| chr14: 23834216-23834961 | EFS | −0.325910554 | 0.005541994 | 0.110736224 | 0.006160456 | 0.113136859 | 0.044265815 | 0.044265815 |
| chr17: 46198596-46200105 | SNX11 | −0.325404034 | 0.00435117 | 0.09789861 | 0.006240059 | 0.113793372 | 0.04052194 | 0.04052194 |
| chr22: 50450973-50451088 | IL17REL | −0.325024492 | 0.006764548 | 0.120633891 | 0.006301388 | 0.114337768 | 0.047349006 | 0.047349006 |
| chr21: 34265885-34266043 | C21orf49 | −0.324901611 | 0.003697375 | 0.091617209 | 0.006314237 | 0.11445657 | 0.037383692 | 0.037383692 |
| chr5: 135223720-135224326 | SLC25A48 | −0.324491441 | 0.004700972 | 0.101165586 | 0.006379938 | 0.114979041 | 0.041898365 | 0.041898365 |
| chr11: 31451817-31453396 | DNAJC24 | −0.324035319 | 0.007961992 | 0.12969294 | 0.006451988 | 0.11536742 | 0.049881627 | 0.049881627 |
| chr16: 69117387-69119083 | TMCO7 | −0.323930714 | 0.001996814 | 0.07433842 | 0.006474703 | 0.115520654 | 0.025876782 | 0.025876782 |
| chr11: 5256444-5256600 | HBD | −0.323415761 | 0.006496377 | 0.118025771 | 0.00656559 | 0.116542191 | 0.047183835 | 0.047183835 |
| chr6: 60543077-60544205 | MS4A15 | −0.323306954 | 0.005827077 | 0.113914863 | 0.006581838 | 0.116542191 | 0.045477069 | 0.045477069 |
| chr19: 34991033-34992085 | WTIP | −0.323288091 | 0.003628394 | 0.09052543 | 0.00658329 | 0.116542191 | 0.037273578 | 0.037273578 |
| chr21: 33765077-33765335 | URB1 | −0.322605234 | 0.007661761 | 0.127947875 | 0.006703042 | 0.11771242 | 0.0496614 | 0.0496614 |
| chr11: 107590341-107590419 | SLN | −0.32259301 | 0.003198302 | 0.085052362 | 0.006706173 | 0.11771242 | 0.035291527 | 0.035291527 |
| chr1: 16332413-16335302 | C1orf64 | −0.322571114 | 0.003329308 | 0.085908111 | 0.00670942 | 0.11771242 | 0.036282552 | 0.036282552 |
| chr14: 52793938-52795324 | PTGER2 | −0.32254401 | 0.00584014 | 0.113206474 | 0.006714203 | 0.11771242 | 0.045752354 | 0.045752354 |
| chr7: 100734918-100735017 | TRIM56 | −0.32209346 | 0.006276926 | 0.116920758 | 0.006780819 | 0.118195788 | 0.046963607 | 0.046963607 |
| chr4: 6302383-6304992 | WFS1 | −0.321869596 | 0.006860626 | 0.121215509 | 0.006822582 | 0.11880974 | 0.048505203 | 0.048505203 |
| chr5: 65007185-65009955 | HSPA2 | −0.321607655 | 0.004372355 | 0.098043319 | 0.00687538 | 0.119044347 | 0.041127567 | 0.041127567 |
| chr10: 92680757-92681033 | ANKRD1 | −0.32149868 | 0.004154414 | 0.095871025 | 0.006892549 | 0.119114534 | 0.040301712 | 0.040301712 |
| chr2: 169877734-169887832 | ABCB11 | −0.321337647 | 0 | 0 | 0.006926867 | 0.11983107 | 0.017287893 | 0.017287893 |
| chr10: 100937876-100939195 | LONRF2 | −0.321330932 | 0.006819887 | 0.12082172 | 0.006927809 | 0.11983107 | 0.048945659 | 0.048945659 |
| chr3: 9934492-9936033 | JAGN1 | −0.32116212 | 0.00609355 | 0.11601377 | 0.006958825 | 0.11946421 | 0.046853493 | 0.046853493 |
| chr7: 1097127-1098897 | GPR146 | −0.320796122 | 0.00551212 | 0.11031797 | 0.007038213 | 0.11983397 | 0.04525684 | 0.04525684 |
| chr2: 24236884-24237414 | MIF | −0.320238374 | 0.00304999 | 0.08562001 | 0.007147155 | 0.120269498 | 0.036392666 | 0.036392666 |
| chr10: 17171642-17171830 | CUBN | −0.3201406 | 0.006228317 | 0.116920758 | 0.007166704 | 0.120269498 | 0.04762429 | 0.04762429 |
| chr11: 70052238-70053496 | FADD | −0.320086207 | 0.005320566 | 0.10900471 | 0.007176249 | 0.120269498 | 0.04470627 | 0.04470627 |
| chr10: 120355027-120355160 | PRLHR | −0.319837349 | 0.00145870 | 0.06293216 | 0.007235098 | 0.120450124 | 0.02273853 | 0.02273853 |
| chr1: 6674509-6674667 | KLHL21 | −0.319337027 | 0.004808398 | 0.102159863 | 0.007342744 | 0.121897706 | 0.04343996 | 0.04343996 |
| chr1: 167095023-167098402 | DUSP27 | −0.3192654 | 0.003356573 | 0.086049007 | 0.0073544 | 0.121897706 | 0.03694323 | 0.03694323 |
| chr1: 176730009-176730745 | RAB24 | −0.319255928 | 0.003368433 | 0.086049007 | 0.007355607 | 0.121897706 | 0.03710840 | 0.03710840 |
| chr20: 55093142-55093943 | C20orf43 | −0.319047060 | 0.00611259 | 0.11612907 | 0.00739022 | 0.12235981 | 0.04773440 | 0.04773440 |
| chr5: 140389211-140391929 | PCDHA13 | −0.318776843 | 0.005901557 | 0.11395931 | 0.00745036 | 0.122900837 | 0.04718383 | 0.04718383 |
| chr4: 186320723-186321782 | ANKRD37 | −0.318309287 | 0.006407439 | 0.11791181 | 0.007558535 | 0.12362663 | 0.04916588 | 0.04916588 |
| chrX: 138790264-138790386 | MCF2 | −0.31820009 | 0.00390606 | 0.09421756 | 0.00758221 | 0.12379144 | 0.03920057 | 0.03920057 |
| chr12: 124242473-124245549 | ATP6V0A2 | −0.318163539 | 0.005692544 | 0.11209117 | 0.007587454 | 0.12379144 | 0.04679843 | 0.04679843 |
| chr2: 111179634-211179914 | MYL1 | −0.318151264 | 0.00447564 | 0.09867262 | 0.00759623 | 0.12385137 | 0.04239387 | 0.04239387 |
| chr2: 232172439-232177018 | DISC1 | −0.317969164 | 0.00635087 | 0.11746530 | 0.00763877 | 0.12396768 | 0.04927600 | 0.04927600 |
| chr9: 99381500-99382112 | CDC14B | −0.317910194 | 0.00416307 | 0.09587102 | 0.00765129 | 0.12396768 | 0.04112756 | 0.04112756 |
| chr11: 223175726-223179337 | DISP1 | −0.317844696 | 0.00305032 | 0.08382127 | 0.00776596 | 0.12396768 | 0.03457578 | 0.03457578 |
| chr12: 53646601-53648189 | MFSD5 | −0.317723142 | 0 | 0 | 0.00768778 | 0.12398265 | 0.01739800 | 0.01739800 |
| chr22: 50050271-50051190 | C22orf34 | −0.317628122 | 0.00480751 | 0.09653151 | 0.00771255 | 0.12407715 | 0.04189836 | 0.04189836 |
| chr6: 30523907-30525008 | GNL1 | −0.317139954 | 0 | 0 | 0.00783858 | 0.12460580 | 0.01745306 | 0.01745306 |
| chr3: 115962284-11599139 | ATG7 | −0.3169458 | 0.00228137 | 0.07489686 | 0.00783512 | 0.12516208 | 0.02929031 | 0.02929031 |
| chr16: 71264464-71264625 | HYDIN | −0.316806117 | 0.00473105 | 0.10155449 | 0.00786043 | 0.12537498 | 0.04388041 | 0.04388041 |
| chr1: 125136535-125136741 | RP11-687M24.6 | −0.316600832 | 0.00388355 | 0.09421049 | 0.00790514 | 0.12572784 | 0.03936574 | 0.03936574 |
| chr11: 113797134-113797298 | SLC24A6 | −0.315121613 | 0.00410902 | 0.09595366 | 0.00820934 | 0.12737135 | 0.04118262 | 0.04118262 |
| chr11: 66113960-66115163 | B3GNT1 | −0.314657476 | 0.00480075 | 0.10215986 | 0.00829337 | 0.12798847 | 0.04465121 | 0.04465121 |
| chr7: 128498389-128499328 | FLNC | −0.312046294 | 0.00619677 | 0.11692075 | 0.00889331 | 0.13305538 | 0.0496614 | 0.0496614 |

TABLE 9-continued

| locus | nearest_ref_id | r | p | qval | pglobal | qglobal | prank | padj |
|---|---|---|---|---|---|---|---|---|
| chr11: 35441454-35441610 | SLC1A2 | −0.311887865 | 0.004570119 | 0.099888173 | 0.008941084 | 0.133550085 | 0.043715245 | 0.043715245 |
| chr20: 61676650-61676971 | C20orf66 | −0.311455851 | 0.006090275 | 0.116013774 | 0.009052096 | 0.134113878 | 0.049496229 | 0.049496229 |
| chrX: 37312388-37316548 | PRRG1 | −0.311450759 | 0.002311383 | 0.074967239 | 0.009052668 | 0.134113878 | 0.030006056 | 0.030006056 |
| chr6: 3152721-3153812 | BPHL | −0.311242496 | 0.003734797 | 0.091793135 | 0.009105063 | 0.134451428 | 0.03925563 | 0.03925563 |
| chr7: 31697884-31698334 | CCDC129 | −0.311051556 | 0.002109037 | 0.074896868 | 0.009150889 | 0.134908764 | 0.027473435 | 0.027473435 |
| chr2: 26393826-26394927 | TRIM63 | −0.309913705 | 0.005735635 | 0.112400084 | 0.00941526 | 0.137573461 | 0.048395089 | 0.048395089 |
| chr20: 6034475-6034695 | LRRN4 | −0.309273385 | 0.001724002 | 0.069739517 | 0.009551555 | 0.138124918 | 0.024500358 | 0.024500358 |
| chr5: 80689806-80689998 | ACOT12 | −0.308117282 | 0.003117847 | 0.084283617 | 0.009833241 | 0.139750517 | 0.035952211 | 0.035952211 |
| chr8: 33330581-33330940 | FUT10 | −0.307474854 | 0.003443905 | 0.087240779 | 0.010015974 | 0.141095357 | 0.038484832 | 0.038484832 |
| chr1: 182558301-182558391 | RNASEL | −0.307317477 | 0.005481298 | 0.109968839 | 0.010054997 | 0.141331714 | 0.047844519 | 0.047844519 |
| chr7: 107443555-107443670 | SLC26A3 | −0.307261592 | 0.003057062 | 0.083821279 | 0.01010069 | 0.14133171 | 0.035566812 | 0.035566812 |
| chr10: 76868766-76868976 | DUSP13 | −0.306383849 | 0.004406938 | 0.098228128 | 0.010291015 | 0.143011251 | 0.043715245 | 0.043715245 |
| chr19: 54984210-54984411 | CDC42EP5 | −0.305854117 | 0.002287711 | 0.074896868 | 0.010428251 | 0.1441141 | 0.029895942 | 0.029895942 |
| chrX: 118699087-118699397 | CXorf56 | −0.304902726 | 0.002049412 | 0.074404864 | 0.010702524 | 0.146038303 | 0.027088036 | 0.027088036 |
| chr1: 34492914-34493609 | CAT | −0.303602311 | 0.004918322 | 0.103512716 | 0.011093752 | 0.148049083 | 0.046302924 | 0.046302924 |
| chr15: 101454905-101456831 | ALDH1A3 | −0.303374031 | 0.005729864 | 0.112400084 | 0.011162121 | 0.148113807 | 0.049276001 | 0.049276001 |
| chr6: 68855342-68858072 | MYH8 | −0.303265671 | 0.001915237 | 0.072927569 | 0.011183659 | 0.148377506 | 0.026041953 | 0.026041953 |
| chr1: 45792544-45794347 | HPDL | −0.302015312 | 0.005632886 | 0.111327654 | 0.011548044 | 0.151223592 | 0.049220944 | 0.049220944 |
| chr1: 162838442-162838605 | C1orf110 | −0.300571972 | 0 | 0 | 0.011955059 | 0.153135566 | 0.017508121 | 0.017508121 |
| chr6: 39869888-39872648 | DAAM2 | −0.299895021 | 0.00330218 | 0.08562014 | 0.012143277 | 0.154236598 | 0.038044376 | 0.038044376 |
| chr15: 68553342-68858072 | TPCN2 | −0.299814629 | 0.004906377 | 0.10338760 | 0.012168347 | 0.15444702 | 0.046688322 | 0.046688322 |
| chr2: 28634745-28640179 | FOSL2 | −0.299377859 | 0.004661807 | 0.100096902 | 0.012312384 | 0.155291764 | 0.045532126 | 0.045532126 |
| chr22: 20137990-20138399 | AC006547.14 | −0.295216407 | 0.002654087 | 0.078584121 | 0.013677005 | 0.162105645 | 0.03363981 | 0.03363981 |
| chr19: 4867620-4867780 | PLIN3 | −0.292601141 | 0.005346359 | 0.109247654 | 0.014593411 | 0.166406587 | 0.04856026 | 0.04856026 |
| chr7: 152760831-152760978 | HAUS7 | −0.289026884 | 0.00546317 | 0.109968839 | 0.015950755 | 0.171690454 | 0.049386115 | 0.049386115 |
| chrX: 54637701-54638773 | VSTM2A | −0.286077172 | 0.004209951 | 0.096303956 | 0.01714413 | 0.177426489 | 0.043660188 | 0.043660188 |
| chr5: 180000987-180005405 | CNOT6 | 0.280162496 | 0.004272958 | 0.096770254 | 0.019446262 | 0.188776567 | 0.044155701 | 0.044155701 |
| chr1: 226496809-226497570 | TMEM68 | 0.280739417 | 0.004369285 | 0.098043319 | 0.01919878 | 0.18747807 | 0.044486043 | 0.044486043 |
| chr14: 57970057-57970296 | PAPOLA | 0.29310605 | 0.004441351 | 0.098538814 | 0.014374425 | 0.165442335 | 0.044816385 | 0.044816385 |
| chr4: 148593017-148593195 | ARMC1 | 0.29710605 | 0.002912941 | 0.08228265 | 0.014205819 | 0.164448881 | 0.017618235 | 0.017618235 |
| chr8: 66545953-66546442 | EID1 | 0.281783249 | 0.005362125 | 0.109252525 | 0.018777029 | 0.184706905 | 0.048835545 | 0.048835545 |
| chr15: 49170297-49172190 | LIN9 | 0.288853949 | 0.005164445 | 0.106835773 | 0.015911218 | 0.171594243 | 0.048119804 | 0.048119804 |
| chr1: 226496809-226497570 | TUBD1 | 0.291829568 | 0.004543724 | 0.099671077 | 0.014828474 | 0.167285451 | 0.045366955 | 0.045366955 |
| chr15: 38776455-38779911 | TMEM184C | 0.293182401 | 0.004441351 | 0.098538814 | 0.014374425 | 0.165442335 | 0.044816385 | 0.044816385 |
| chr20: 47712344-47713489 | FAM98B | 0.294672563 | 0.002073568 | 0.074404864 | 0.01386087 | 0.16295848 | 0.02774872 | 0.02774872 |
| chr5: 56558420-56560505 | CSE1L | 0.296532783 | 0.002844634 | 0.081237547 | 0.0132032 | 0.159833433 | 0.03485107 | 0.03485107 |
| chr12: 58350469-58351052 | GPBP1 | 0.297506006 | 0 | 0 | 0.012981899 | 0.158781296 | 0.017563178 | 0.017563178 |
| chr19: 44284854-44285409 | XRCC6BP1 | 0.298404618 | 0.005616981 | 0.111134243 | 0.01269914 | 0.157500296 | 0.049716457 | 0.049716457 |
| chr17: 30325676-30328064 | KCNN4 | 0.299794156 | 0.001595016 | 0.066445584 | 0.01221767 | 0.15453101 | 0.023894731 | 0.023894731 |
| chr5: 140698056-140700330 | SUZ12 | 0.300313931 | 0.002768918 | 0.080210303 | 0.012055448 | 0.153550563 | 0.03424544 | 0.03424544 |
| chr17: 185069331-185071740 | TAF7 | 0.30034378 | 0.004413046 | 0.098228128 | 0.0120484 | 0.153550563 | 0.044265815 | 0.044265815 |
| chr17: 58023911-58027925 | RNF2 | 0.301817006 | 0.002256081 | 0.074896868 | 0.011903263 | 0.153135566 | 0.029510543 | 0.029510543 |
| chr1: 151881835-151882284 | RPS6KB1 | 0.301654892 | 0.002463315 | 0.07690982 | 0.011632685 | 0.151675849 | 0.031657766 | 0.031657766 |
| chr19: 196555189-196559518 | THEM4 | 0.303048607 | 0.003891008 | 0.094210495 | 0.011246266 | 0.149099215 | 0.040576997 | 0.040576997 |
| chr3: 56655559-56655846 | PAK2 | 0.304684107 | 0.00565642 | 0.111550003 | 0.010782398 | 0.146149832 | 0.04911083 | 0.04911083 |
| chr9: 130457272-130457460 | CCDC66 | 0.305496446 | 0.004722128 | 0.101500611 | 0.01057924 | 0.14457794 | 0.045311898 | 0.045311898 |
| chr6: 84418064-84419410 | STXBP1 | 0.306449217 | 0.002610067 | 0.078272928 | 0.010347357 | 0.143355492 | 0.032703848 | 0.032703848 |
| chr18: 267965-268059 | SNAP91 | 0.306744409 | 0.00289378 | 0.082124567 | 0.010266638 | 0.142891143 | 0.034465672 | 0.034465672 |
| chr11: 126174102-126174213 | THOC1 | 0.308452954 | 0.002246863 | 0.074896868 | 0.009851067 | 0.139785104 | 0.029235258 | 0.029235258 |
| chr1: 92764481-92764544 | RP11-712L6.5 | 0.308555738 | 0.001968874 | 0.074231845 | 0.009830751 | 0.139750517 | 0.02620124 | 0.02620124 |
| chr1: 92764481-92764544 | GLMN | 0.309420667 | 0.005538193 | 0.113206474 | 0.009611488 | 0.138500189 | 0.04911083 | 0.04911083 |

TABLE 9-continued

| locus | nearest_ref_id | r | p | qval | pglobal | qglobal | prank | padj |
|---|---|---|---|---|---|---|---|---|
| chr5: 68709857-68710628 | RAD17 | 0.309947634 | 0.002036157 | 0.074404864 | 0.009465185 | 0.137886794 | 0.026812751 | 0.026812751 |
| chr12: 51566083-51566926 | TFCP2 | 0.310337811 | 0.002022616 | 0.074404864 | 0.009363899 | 0.136937591 | 0.02664758 | 0.02664758 |
| chr12: 133532828-133532892 | ZNF605 | 0.310370533 | 0.005741782 | 0.112400084 | 0.009352732 | 0.136937591 | 0.048340032 | 0.048340032 |
| chr3: 69129484-69129559 | UBA3 | 0.311955874 | 0.004476434 | 0.098672627 | 0.008962241 | 0.133646293 | 0.043384903 | 0.043384903 |
| chr2: 44222912-44223144 | LRPPRC | 0.311969209 | 0.005806947 | 0.11307866 | 0.008953347 | 0.133626356 | 0.048395089 | 0.048395089 |
| chr12: 106697789-106698057 | CKAP4 | 0.31330448 | 0.005323305 | 0.109004718 | 0.008624532 | 0.130213948 | 0.046468094 | 0.046468094 |
| chr19: 119781120-119780306 | ZNF439 | 0.31399977 | 0.000679969 | 0.03518595 | 0.008487262 | 0.129047959 | 0.01915983 | 0.01915983 |
| chr17: 30714772-30714780 | ZNF207 | 0.314664535 | 0.004663714 | 0.100960902 | 0.008349022 | 0.128620259 | 0.04399053 | 0.04399053 |
| chr3: 178984436-178984790 | KCNMB3 | 0.315313767 | 0.000492826 | 0.026020926 | 0.008225877 | 0.127371355 | 0.018774432 | 0.018774432 |
| chr3: 3192223-3192563 | TRNT1 | 0.315943006 | 0.005904075 | 0.113959318 | 0.008095056 | 0.126641267 | 0.048395089 | 0.048395089 |
| chr2: 37193372-37193615 | STRN | 0.316227369 | 0.004355122 | 0.09789861 | 0.008031757 | 0.126088956 | 0.042614106 | 0.042614106 |
| chr2: 34718269-34720420 | LSM14A | 0.316229966 | 0.005347198 | 0.109247654 | 0.008031588 | 0.126088956 | 0.046137753 | 0.046137753 |
| chr5: 86708251-86708836 | CCNH | 0.31651571 | 0.002285526 | 0.074896868 | 0.007979619 | 0.126029403 | 0.0295656 | 0.0295656 |
| chr12: 12662143-12662327 | ZNF564 | 0.316577163 | 0.001969925 | 0.074231845 | 0.007968372 | 0.1259613 | 0.026041953 | 0.026041953 |
| chr2: 23941548-23941693 | ZNF681 | 0.316870966 | 0.003718019 | 0.091753239 | 0.007903195 | 0.12572784 | 0.038815174 | 0.038815174 |
| chr2: 20103162-20103331 | SUMO1 | 0.317470493 | 0.00313409 | 0.08454882 | 0.007770669 | 0.124580756 | 0.035346584 | 0.035346584 |
| chr11: 85563599-85565986 | AP000974.1 | 0.31748757 | 0.00585555 | 0.11386114 | 0.007768077 | 0.124580756 | 0.047679348 | 0.047679348 |
| chr14: 39649706-39652422 | PNN | 0.317832199 | 0.006385595 | 0.117755656 | 0.007699853 | 0.123982656 | 0.049496229 | 0.049496229 |
| chr8: 142012112-142012315 | PTK2 | 0.318325276 | 0.003146205 | 0.084658552 | 0.007617257 | 0.123967682 | 0.035291527 | 0.035291527 |
| chr20: 57617753-57617964 | SLMO2 | 0.319001046 | 0.005278416 | 0.108821635 | 0.007470271 | 0.122900837 | 0.044981556 | 0.044981556 |
| chr14: 47371239-47371367 | ESD | 0.319016641 | 0.003463992 | 0.087293121 | 0.00746628 | 0.122900837 | 0.037548863 | 0.037548863 |
| chr21: 40721385-40721573 | HMGN1 | 0.319212709 | 0 | 0 | 0.007431424 | 0.122900837 | 0.01734295 | 0.01734295 |
| chr7: 79846618-79848718 | GNAI1 | 0.320340043 | 0.004411903 | 0.098228128 | 0.007217627 | 0.120269498 | 0.041843308 | 0.041843308 |
| chr19: 57764440-57774106 | ZNF805 | 0.320363681 | 0.005385112 | 0.109381082 | 0.007213586 | 0.120269498 | 0.045036613 | 0.045036613 |
| chr19: 3367189-3368574 | ZNF75A | 0.320482104 | 0.002181862 | 0.074896868 | 0.007195218 | 0.120269498 | 0.027583549 | 0.027583549 |
| chr15: 60771201-60771344 | NARG2 | 0.321091259 | 0.004175977 | 0.095889084 | 0.007083234 | 0.120011929 | 0.040742168 | 0.040742168 |
| chr17: 8286474-8286568 | RPL26 | 0.321101419 | 0.003760575 | 0.09205293 | 0.007079283 | 0.120011929 | 0.038319661 | 0.038319661 |
| chr6: 168720067-168720434 | DACT2 | 0.321179692 | 0.002407179 | 0.076804143 | 0.007061216 | 0.119974623 | 0.029895942 | 0.029895942 |
| chr14: 35008760-35008943 | EAPP | 0.321340899 | 0.004534668 | 0.099592725 | 0.007036828 | 0.11983397 | 0.041953422 | 0.041953422 |
| chr2: 99921102-99921205 | LYG1 | 0.321471395 | 0.0062296 | 0.11692075 | 0.007016568 | 0.11983397 | 0.047293949 | 0.047293949 |
| chr13: 41701704-41706882 | KBTBD6 | 0.321594919 | 0.004173426 | 0.095889084 | 0.006991002 | 0.119790156 | 0.040576997 | 0.040576997 |
| chr5: 140602930-140605858 | PCDHB14 | 0.322104178 | 0.006233177 | 0.11692075 | 0.006908505 | 0.119276786 | 0.047128778 | 0.047128778 |
| chr7: 29552179-29553944 | KRR1 | 0.322196506 | 0 | 0 | 0.006889135 | 0.119114534 | 0.017232836 | 0.017232836 |
| chr19: 19843764-19843921 | CHN2 | 0.322296255 | 0.002750261 | 0.080052876 | 0.006871423 | 0.119044347 | 0.032593735 | 0.032593735 |
| chr11: 75851754-75854239 | ZNF14 | 0.322336899 | 0.004015145 | 0.095097797 | 0.00686604 | 0.119044347 | 0.039200573 | 0.039200573 |
| chr19: 75851754-75854239 | UVRAG | 0.322461087 | 0.005592429 | 0.11132704 | 0.006849485 | 0.119044347 | 0.045146727 | 0.045146727 |
| chr3: 93747210-93747454 | STX19 | 0.322908263 | 0.006898306 | 0.121600292 | 0.006746884 | 0.118195788 | 0.048450146 | 0.048450146 |
| chr19: 65739858-65740318 | NOL11 | 0.323113611 | 0.00348465 | 0.087540376 | 0.006746884 | 0.118057478 | 0.037163464 | 0.037163464 |
| chr16: 28331396-28335170 | SBK1 | 0.324007796 | 0.005584472 | 0.111106714 | 0.006597992 | 0.116688728 | 0.044871442 | 0.044871442 |
| chr11: 125825711-125826214 | RP11-680F20.6 | 0.324171654 | 0.007187233 | 0.123441982 | 0.006567812 | 0.11654219 | 0.048780488 | 0.048780488 |
| chrY: 21765682-21768160 | CYorf15B | 0.324250683 | 0 | 0 | 0.006547321 | 0.116473052 | 0.017177779 | 0.017177779 |
| chr15: 59949322-59949740 | GTF2A2 | 0.324886639 | 0.00679345 | 0.120633891 | 0.006441004 | 0.11536742 | 0.047789462 | 0.047789462 |
| chr8: 141524392-141527236 | CHRAC1 | 0.325103238 | 0.006576969 | 0.1185295 | 0.006405193 | 0.115185655 | 0.047293949 | 0.047293949 |
| chr1: 46153654-46153785 | GPBP1L1 | 0.325228449 | 0.00663606 | 0.119219352 | 0.006381042 | 0.11497941 | 0.047349006 | 0.047349006 |
| chr19: 33558797-33559241 | C18orf21 | 0.325286794 | 0.00452516 | 0.099504209 | 0.00626941 | 0.11497941 | 0.041182624 | 0.041182624 |
| chr19: 35174896-35177302 | ZNF302 | 0.325802707 | 0.003260401 | 0.085620014 | 0.006271246 | 0.114247377 | 0.035566812 | 0.035566812 |
| chr4: 170192009-170192256 | SH3RF1 | 0.326613568 | 0.00348468 | 0.087540376 | 0.006138078 | 0.11306887 | 0.0496614 | 0.0496614 |
| chr10: 74927623-74927853 | ECD | 0.326731314 | 0.005005407 | 0.104695438 | 0.00612095 | 0.112957258 | 0.042559049 | 0.042559049 |
| chr5: 170738392-170739138 | TLX3 | 0.326740102 | 0.00772475 | 0.128513382 | 0.00610628 | 0.112957258 | 0.048615317 | 0.048615317 |
| chr2: 217069910-217071026 | XRCC5 | 0.327063734 | 0.004964977 | 0.104253046 | 0.006062514 | 0.112819565 | 0.042338821 | 0.042338821 |
| chr16: 3458320-3459370 | ZNF174 | 0.32719442 | 0.005999522 | 0.114825412 | 0.006031841 | 0.112712273 | 0.045146727 | 0.045146727 |

TABLE 9-continued

| locus | nearest_ref_id | r | p | qval | pglobal | qglobal | prank | padj |
|---|---|---|---|---|---|---|---|---|
| chr8: 82644987-82645138 | ZFAND1 | 0.327291564 | 0.004906685 | 0.103387608 | 0.006017179 | 0.112670125 | 0.04217365 | 0.04217365 |
| chr2: 238166072-238166319 | AC112715.2 | 0.327628695 | 0.006998291 | 0.121921113 | 0.0059458 | 0.112191938 | 0.046743379 | 0.046743379 |
| chr22: 41252434-41253026 | ST13 | 0.327785232 | 0.006664518 | 0.119612287 | 0.0059326 | 0.111893883 | 0.046413037 | 0.046413037 |
| chr19: 21950228-21950330 | ZNF100 | 0.328529297 | 7.16E-05 | 0.00404126 | 0.005819824 | 0.11151912 | 0.017122722 | 0.017122722 |
| chr1: 95007092-95007356 | F3 | 0.328897709 | 0.003923792 | 0.0943921 | 0.005764817 | 0.110636432 | 0.037493806 | 0.037493806 |
| chr12: 72070468-72074419 | THAP2 | 0.328949319 | 0.000936046 | 0.045949726 | 0.005759067 | 0.110636432 | 0.019545229 | 0.019545229 |
| chr13: 37633616-37633850 | FAM48A | 0.329201798 | 0 | 0 | 0.005722694 | 0.11057584 | 0.017012608 | 0.017012608 |
| chr8: 136481506-136482840 | R3HDM1 | 0.329264663 | 0.004476477 | 0.098672627 | 0.005713669 | 0.110519039 | 0.03997137 | 0.03997137 |
| chr9: 66553673-66555928 | RP11-262H14.4 | 0.329390698 | 0.004136364 | 0.095871025 | 0.005693028 | 0.110354813 | 0.038594946 | 0.038594946 |
| chr13: 41345120-41345309 | MRPS31 | 0.329399968 | 0.001803178 | 0.071315614 | 0.005692592 | 0.110354813 | 0.024170016 | 0.024170016 |
| chr17: 4994791-4999668 | ZFP3 | 0.329822496 | 0.00706482 | 0.122091644 | 0.005621863 | 0.109442547 | 0.046027639 | 0.046027639 |
| chr1: 151141461-151142773 | SCNM1 | 0.330275788 | 0.004023788 | 0.095037797 | 0.005557871 | 0.108672962 | 0.037989319 | 0.037989319 |
| chr1: 32623824-32627808 | EIF3M | 0.330560474 | 0.007052809 | 0.122091644 | 0.00551587 | 0.108307841 | 0.045697297 | 0.045697297 |
| chr8: 42029046-42029191 | AP3M2 | 0.330606328 | 0.005212564 | 0.107708532 | 0.005503321 | 0.108178378 | 0.041733194 | 0.041733194 |
| chr11: 64338450-64340347 | SLC22A11 | 0.330712435 | 0.003990159 | 0.094844827 | 0.005487321 | 0.108042182 | 0.037714034 | 0.037714034 |
| chr3: 32814948-32815367 | CNOT10 | 0.330830953 | 0 | 0 | 0.005472663 | 0.107926139 | 0.01695755 | 0.01695755 |
| chrX: 15682840-15683154 | TMEM27 | 0.330854448 | 0.00611417 | 0.11612907 | 0.005472551 | 0.107926139 | 0.04360513 | 0.04360513 |
| chr19: 36909393-36909558 | ZFP82 | 0.330898021 | 0.000308635 | 0.016634253 | 0.00546732 | 0.107926139 | 0.017783406 | 0.017783406 |
| chr14: 23240642-23241007 | OXA1L | 0.33092203 | 0.009077491 | 0.137166781 | 0.005461346 | 0.107926139 | 0.048229918 | 0.048229918 |
| chr7: 64291828-64294054 | ZNF138 | 0.331146193 | 0.004247302 | 0.096531516 | 0.005460375 | 0.107926139 | 0.03887023 | 0.03887023 |
| chr14: 30661071-30661104 | PRKD1 | 0.331146193 | 0.007424771 | 0.125564356 | 0.005422494 | 0.107637992 | 0.04580741 | 0.04580741 |
| chr9: 100777645-100778225 | ANP32B | 0.331404852 | 0.008878 | 0.136076888 | 0.005389395 | 0.107215322 | 0.04773440 | 0.04773440 |
| chr6: 10419650-10419892 | TFAP2A | 0.33145298 | 0.00775069 | 0.128531382 | 0.005385422 | 0.107215322 | 0.046082696 | 0.046082696 |
| chr15: 23334999-23335196 | AC091565.1 | 0.331545817 | 0.002559555 | 0.07761139 | 0.005371808 | 0.107215322 | 0.030336398 | 0.030336398 |
| chr8: 58156056-58156292 | HEATR6 | 0.331671707 | 0.00624891 | 0.11692075 | 0.005348568 | 0.170303 | 0.04360513 | 0.04360513 |
| chr19: 73964536-73965748 | PPME1 | 0.33178239 | 0.011463933 | 0.15344098 | 0.005334853 | 0.169502 | 0.048945659 | 0.048945659 |
| chr19: 56347701-56348128 | NLRP11 | 0.332151069 | 0.003966634 | 0.094764506 | 0.005290822 | 0.106302207 | 0.037218521 | 0.037218521 |
| chr3: 64009480-64009658 | PSMD6 | 0.332227431 | 0.004735818 | 0.101554491 | 0.005282864 | 0.106259871 | 0.040026427 | 0.040026427 |
| chr15: 40331293-40331389 | SRP14 | 0.332257211 | 0.009745137 | 0.142230949 | 0.0052792 | 0.106259871 | 0.048119804 | 0.048119804 |
| chr15: 29409264-29410518 | APBA2 | 0.332585829 | 0.00820806 | 0.13202832 | 0.005221449 | 0.105609324 | 0.046137753 | 0.046137753 |
| chr10: 60588520-60591195 | BICC1 | 0.332588003 | 0.005814869 | 0.11307866 | 0.005221287 | 0.105609324 | 0.042614106 | 0.042614106 |
| chr16: 47174789-47177908 | NETO2 | 0.3326047 | 0.002989626 | 0.083076103 | 0.005219547 | 0.105609324 | 0.032869019 | 0.032869019 |
| chr10: 124713530-124713919 | C10orf88 | 0.332876872 | 0.002993704 | 0.083076103 | 0.005175308 | 0.105428918 | 0.032813962 | 0.032813962 |
| chr12: 127951840-127952218 | PPP6C | 0.332984853 | 0.003994731 | 0.094844827 | 0.005152593 | 0.105428918 | 0.037273578 | 0.037273578 |
| chr1: 151735802-151736040 | MRPL9 | 0.333136616 | 0.004195675 | 0.096098418 | 0.005138632 | 0.105428918 | 0.03815449 | 0.03815449 |
| chr4: 120325655-120326749 | AC110373.1 | 0.333522527 | 0.004232896 | 0.096464363 | 0.005094908 | 0.104919288 | 0.038209547 | 0.038209547 |
| chr1: 152020297-152020383 | S100A11 | 0.333566613 | 0.007855817 | 0.129133025 | 0.005092164 | 0.104919288 | 0.044981556 | 0.044981556 |
| chrX: 24094838-24096088 | EIF2S3 | 0.333582575 | 0.003071993 | 0.083904667 | 0.005091703 | 0.104919288 | 0.033254418 | 0.033254418 |
| chr2: 207582984-207583120 | DYTN | 0.333890074 | 0.014367499 | 0.165520063 | 0.005047289 | 0.104650575 | 0.048119804 | 0.048119804 |
| chr4: 146046877-146050331 | ABCE1 | 0.333923697 | 0.003089387 | 0.084000815 | 0.005039517 | 0.1046329 | 0.033309475 | 0.033309475 |
| chr15: 109492543-109493034 | CCDC138 | 0.333976981 | 0.004349929 | 0.09789861 | 0.005031342 | 0.1046329 | 0.038264604 | 0.038264604 |
| chr2: 231989685-231989832 | HTR2B | 0.334198112 | 0.004153272 | 0.095871025 | 0.00499393 | 0.10438641 | 0.037658977 | 0.037658977 |
| chr1: 59436353-59436471 | PATL1 | 0.334333206 | 0.007983468 | 0.12969294 | 0.004976355 | 0.103891426 | 0.044651214 | 0.044651214 |
| chr12: 58384668-58388515 | ZFP91 | 0.334555856 | 0 | 0 | 0.004937413 | 0.103435103 | 0.01679238 | 0.01679238 |
| chr4: 120315052-120315095 | CIT | 0.334566849 | 0.012110335 | 0.155429477 | 0.00493578 | 0.103435103 | 0.04707372 | 0.04707372 |
| chr9: 97090889-97090926 | FAM22F | 0.334602902 | 0.008513342 | 0.133361292 | 0.004928103 | 0.103435103 | 0.04509167 | 0.04509167 |
| chr8: 103136797-103137135 | NCALD | 0.334783433 | 0 | 0 | 0.004896931 | 0.10324075 | 0.016737323 | 0.016737323 |
| chr2: 99977169-99977521 | MITD1 | 0.33494044 | 0.001482186 | 0.063564631 | 0.004874899 | 0.102956744 | 0.021857623 | 0.021857623 |
| chr5: 140579182-140582618 | PCDHB11 | 0.335046305 | 0.003710523 | 0.091703214 | 0.004858301 | 0.10286295 | 0.035621869 | 0.035621869 |
| chr11: 66610639-66610987 | C11orf80 | 0.335296837 | 0.003954429 | 0.094764506 | 0.004829682 | 0.102718394 | 0.036392666 | 0.036392666 |
| chr12: 93894951-93897545 | MRPL42 | 0.335524039 | 0.00241 0305 | 0.076804143 | 0.004827859 | 0.102718394 | 0.028409404 | 0.028409404 |

TABLE 9-continued

| locus | nearest_ref_id | r | p | qval | pglobal | qglobal | prank | padj |
|---|---|---|---|---|---|---|---|---|
| chr20: 21695108-21696620 | PAX1 | 0.335448884 | 0.007190531 | 0.123441982 | 0.004812345 | 0.102589929 | 0.043054561 | 0.043054561 |
| chr5: 134735438-134735604 | H2AFY | 0.335582907 | 0.007328985 | 0.124979581 | 0.004788569 | 0.102293798 | 0.043164675 | 0.043164675 |
| chr1: 235611984-235612283 | TBCE | 0.335596516 | 0.003395192 | 0.086368012 | 0.004785093 | 0.102293798 | 0.034796014 | 0.034796014 |
| chr19: 51538050-51538486 | KLK12 | 0.335737191 | 0.00967498 | 0.142148692 | 0.004762354 | 0.102123542 | 0.045201784 | 0.045201784 |
| chr18: 12884071-12884337 | PTPN2 | 0.336004992 | 0.002423347 | 0.07683164 | 0.004719445 | 0.101389943 | 0.028464461 | 0.028464461 |
| chr9: 19102521-19103117 | HAUS6 | 0.336050358 | 0.00392889 | 0.0943921 | 0.00471322 | 0.101389943 | 0.036117381 | 0.036117381 |
| chr6: 4322658-4323001 | TFAP4 | 0.336101155 | 0.005641999 | 0.111386545 | 0.004705385 | 0.101380678 | 0.040301712 | 0.040301712 |
| chr6: 32983355-32938493 | HLA-DMA | 0.336336244 | 0.01336062 | 0.16167151 | 0.004682181 | 0.101120629 | 0.046082696 | 0.046082696 |
| chr6: 108508504-108510013 | NR2E1 | 0.336437613 | 0.012157358 | 0.155429477 | 0.004666547 | 0.100902973 | 0.045862468 | 0.045862468 |
| chr12: 6756489-6756626 | ACRBP | 0.336450652 | 0.009063847 | 0.137166781 | 0.004664875 | 0.100902973 | 0.0445411 | 0.0445411 |
| chr11: 3400267-3400448 | ZNF195 | 0.336605687 | 0.002843888 | 0.081237547 | 0.004644004 | 0.100818853 | 0.031437538 | 0.031437538 |
| chr1: 25589934-25558993 | SYF2 | 0.336667727 | 0.004644165 | 0.10077894 | 0.004637665 | 0.100758255 | 0.038099433 | 0.038099433 |
| chr7: 16872879-16873057 | AGR2 | 0.336673057 | 2.81E-05 | 0.001591309 | 0.004624541 | 0.100593449 | 0.016572152 | 0.016572152 |
| chr12: 118405880-118406788 | KSR2 | 0.336775902 | 0.007835265 | 0.129133025 | 0.004620391 | 0.100593449 | 0.042944448 | 0.042944448 |
| chr19: 56988640-56988770 | ZNF667 | 0.336884962 | 0.004098152 | 0.09575366 | 0.004609646 | 0.100593449 | 0.036612894 | 0.036612894 |
| chr15: 83209176-83209208 | RPS17L | 0.336885484 | 0.003539674 | 0.0886737 | 0.004609523 | 0.100593449 | 0.034851071 | 0.034851071 |
| chr10: 5498550-5500426 | NET1 | 0.33716755 | 0.005108136 | 0.10615454 | 0.004561884 | 0.100069441 | 0.039925288 | 0.039925288 |
| chr17: 50237283-50237377 | CA10 | 0.337244385 | 0.008810051 | 0.135263703 | 0.00455085 | 0.099951077 | 0.043825359 | 0.043825359 |
| chr4: 159825617-159829201 | FNIP2 | 0.337761486 | 0.01001205 | 0.143216183 | 0.004503626 | 0.099271066 | 0.044486043 | 0.044486043 |
| chr5: 159855608-159855748 | PTTG1 | 0.337619827 | 0.012232275 | 0.155522345 | 0.004502947 | 0.099271066 | 0.045036613 | 0.045036613 |
| chr14: 36982316-36982990 | SFTA3 | 0.337685044 | 0.009064788 | 0.137166781 | 0.004496721 | 0.099271066 | 0.043935473 | 0.043935473 |
| chr9: 140194082-140196703 | NRARP | 0.337748136 | 0.00700953 | 0.121921113 | 0.004490551 | 0.099271066 | 0.041788251 | 0.041788251 |
| chr9: 104499562-104500862 | GRIN3A | 0.337777935 | 0.003309214 | 0.085620014 | 0.004488935 | 0.099271066 | 0.034080273 | 0.034080273 |
| chr12: 125084818-125085743 | MRRF | 0.338049105 | 0.001250772 | 0.056511886 | 0.004454398 | 0.099254224 | 0.020536255 | 0.020536255 |
| chr3: 167196633-167196792 | SERPINI2 | 0.338488624 | 0.002335643 | 0.075350427 | 0.004396957 | 0.09863748 | 0.027803777 | 0.027803777 |
| chr5: 98134164-98134347 | RGMB | 0.338500085 | 0 | 0 | 0.004395858 | 0.09863748 | 0.016462038 | 0.016462038 |
| chr17: 6920575-6920844 | AC040977.1 | 0.33861797 | 0.005612306 | 0.111134243 | 0.004378814 | 0.098553166 | 0.03925563 | 0.03925563 |
| chr5: 154393314-154397692 | KIF4B | 0.33863313 | 0.006124103 | 0.116167412 | 0.00437565 | 0.098553166 | 0.03997137 | 0.03997137 |
| chr1: 145440852-145442635 | TXNIP | 0.33868063 | 0.009449784 | 0.140634887 | 0.00437237 | 0.098553166 | 0.043274789 | 0.043274789 |
| chr2: 113332423-113334673 | POLR1B | 0.338711651 | 0.005564022 | 0.110932307 | 0.004367673 | 0.098553166 | 0.039145516 | 0.039145516 |
| chr5: 1886975-1887350 | IRX4 | 0.338712821 | 0.002923933 | 0.082464901 | 0.004367596 | 0.098553166 | 0.031272367 | 0.031272367 |
| chr2: 74729793-74732192 | LBX2 | 0.338737246 | 0.01063139 | 0.14358159 | 0.004365639 | 0.098553166 | 0.043495017 | 0.043495017 |
| chr3: 138663065-138665982 | FOXL2 | 0.33877365 | 0.005017129 | 0.104742652 | 0.004361352 | 0.098553166 | 0.038209547 | 0.038209547 |
| chr8: 88897292-88897676 | ISCA1 | 0.339042754 | 0.006559848 | 0.1185295 | 0.004347928 | 0.098553166 | 0.04063054 | 0.04063054 |
| chr10: 98273267-98273675 | TLL2 | 0.339042421 | 0.003673076 | 0.091389151 | 0.00434507 | 0.098553166 | 0.034520729 | 0.034520729 |
| chr2: 30862982-30867091 | LCLAT1 | 0.339179902 | 0.00629765 | 0.116920758 | 0.004338867 | 0.098553166 | 0.04013654 | 0.04013654 |
| chr1: 154440852-... (chr1: 140571941-140575215) | RPL35A | 0.33923522 | 0.00224057 | 0.074896868 | 0.00433140 8 | 0.098553166 | 0.026757694 | 0.026757694 |
| chr5: 114598408-114598569 | PCDHB10 | 0.339319152 | 0.00499115 | 0.104565414 | 0.00433122 1 | 0.098553166 | 0.037989319 | 0.037989319 |
| chr6: 3932908-3984372 | AL138831.1 | 0.339526883 | 0.00263945 8 | 0.07833410 9 | 0.00430389 5 | 0.098553166 | 0.029840885 | 0.029840885 |
| chr2: 171221568-171221602 | C5orf50 | 0.339540771 | 0.0047669 59 | 0.101816018 | 0.0043003 14 | 0.098553166 | 0.037438749 | 0.037438749 |
| chr4: 76911848-76912115 | SDAD1 | 0.339847696 | 0.00416251 6 | 0.09587102 5 | 0.00425413 9 | 0.09805574 7 | 0.03595221 1 | 0.03595221 1 |
| chr1: 92852567-92853730 | RPAP2 | 0.340299513 | 0.0034641 5 | 0.08729312 1 | 0.00421766 9 | 0.09743867 3 | 0.03402521 6 | 0.03402521 6 |
| chr17: 45899031-45899200 | OSBPL7 | 0.34043401 | 0 | 0 | 0.004203259 | 0.097253236 | 0.016351924 | 0.016351924 |
| chr16: 81110740-81110818 | C16orf46 | 0.340560273 | 0.0046150 8 | 0.10049394 | 0.00419018 1 | 0.09707430 2 | 0.03666795 1 | 0.03666795 1 |
| chr19: 55325296-55325972 | KIR2DL4 | 0.340589063 | 0.00257711 4 | 0.077883735 | 0.00418778 | 0.09707430 2 | 0.029125145 | 0.029125145 |
| chr5: 114598408-114598569 | PGGT1B | 0.340742067 | 0.003243526 | 0.085503862 | 0.004169204 | 0.096959354 | 0.032703848 | 0.032703848 |
| chr6: 37225338-37225931 | TMEM217 | 0.34102065 | 0.005320913 | 0.109004718 | 0.00413916 | 0.096522303 | 0.037714034 | 0.037714034 |
| chr9: 131456919-131458679 | SET | 0.34104979 | 0.00334917 | 0.086040971 | 0.004134242 | 0.09652230 3 | 0.03336453 2 | 0.03336453 2 |
| chr7: 130144779-130146133 | MEST | 0.341209576 | 0.002501724 | 0.076926292 | 0.004116829 | 0.096482536 | 0.02868468 9 | 0.02868468 9 |
| chr1: 32798617-32799236 | HDAC1 | 0.341243395 | 0.008437076 | 0.133216661 | 0.004111599 | 0.096482536 | 0.041182624 | 0.041182624 |
| chr7: 117068123-117068177 | ASZ1 | 0.341268169 | 0.018375867 | 0.183687882 | 0.004114502 | 0.096482536 | 0.042559049 | 0.042559049 |

TABLE 9-continued

| locus | nearest_ref_id | r | p | qval | pglobal | qglobal | prank | padj |
|---|---|---|---|---|---|---|---|---|
| chr1: 166818174-166825581 | POGK | 0.341341081 | 0.002180119 | 0.074896868 | 0.004101184 | 0.096482536 | 0.025656555 | 0.025656555 |
| chr3: 169801692-169803191 | GPR160 | 0.341411568 | 0 | 0 | 0.004104013 | 0.096482536 | 0.016296867 | 0.016296867 |
| chr1: 173793699-173793858 | CENPL | 0.341600458 | 0.004386422 | 0.098116492 | 0.004081228 | 0.096315629 | 0.035842097 | 0.035842097 |
| chr9: 37356831-37358146 | ZCCHC7 | 0.341832218 | 0.002878016 | 0.081933244 | 0.004050647 | 0.095937748 | 0.030446512 | 0.030446512 |
| chr6: 153452258-153452384 | RGS17 | 0.341997405 | 0.007479401 | 0.126251813 | 0.004037495 | 0.095884062 | 0.039916313 | 0.039916313 |
| chr19: 2877270-2878501 | ZNF556 | 0.342151748 | 0.009710946 | 0.142148692 | 0.004011074 | 0.095859386 | 0.041237681 | 0.041237681 |
| chr6: 150292504-150294844 | ULBP1 | 0.342179031 | 0.007550635 | 0.126866028 | 0.004000419 | 0.095859386 | 0.039861256 | 0.039861256 |
| chr1: 25824754-25826700 | TMEM57 | 0.342284881 | 0.004046878 | 0.095335211 | 0.003992587 | 0.095669326 | 0.034740957 | 0.034740957 |
| chr3: 26594025-26599989 | ATP5A2 | 0.342473022 | 0.004835519 | 0.10230714 | 0.003972826 | 0.095321592 | 0.036392666 | 0.036392666 |
| chr19: 12551725-12551926 | ZNF443 | 0.342588553 | 0.00297085 | 0.083014679 | 0.003964282 | 0.095242391 | 0.030831911 | 0.030831911 |
| chr1: 146253037-146253110 | Wl2-3658N16.1 | 0.342683663 | 0.012131595 | 0.155429477 | 0.003951763 | 0.095100371 | 0.041402852 | 0.041402852 |
| chr16: 18473011-18473188 | RP11-1212A22.4 | 0.342756738 | 0.007019189 | 0.121921113 | 0.003944395 | 0.095100371 | 0.039090459 | 0.039090459 |
| chr6: 74233169-74233520 | EEF1A1 | 0.342860281 | 0.003454471 | 0.087293121 | 0.003934968 | 0.095100371 | 0.033199361 | 0.033199361 |
| chr2: 102003478-102004057 | CREG2 | 0.342980433 | 0.007909977 | 0.129431455 | 0.003919321 | 0.095100371 | 0.039530914 | 0.039530914 |
| chr5: 113831591-113832321 | KCNN2 | 0.343097059 | 0.004322128 | 0.097640305 | 0.003897428 | 0.095018782 | 0.035126356 | 0.035126356 |
| chr22: 24125597-24126503 | MMP11 | 0.343244705 | 0.006555426 | 0.1185295 | 0.003890015 | 0.095018782 | 0.038429775 | 0.038429775 |
| chr10: 38875800-38879452 | KDELR3 | 0.343585262 | 0.005483917 | 0.109968839 | 0.003855253 | 0.094370558 | 0.036998293 | 0.036998293 |
| chr14: 64108016-64108125 | WDR89 | 0.343869473 | 0.002621089 | 0.078272928 | 0.003816037 | 0.093916923 | 0.029015031 | 0.029015031 |
| chr14: 20825209-20826063 | PARP2 | 0.34415271 | 0.009261923 | 0.139028346 | 0.003783766 | 0.09337573 | 0.039861256 | 0.039861256 |
| chr8: 42229080-42229326 | POLB | 0.344522366 | 0.008229294 | 0.132039458 | 0.003752975 | 0.092868242 | 0.039145516 | 0.039145516 |
| chr12: 110318076-110318293 | GLTP | 0.344549419 | 0.004690493 | 0.101059823 | 0.003751362 | 0.092868242 | 0.035566812 | 0.035566812 |
| chr12: 114320567-114321001 | REXO2 | 0.344608407 | 0.007037485 | 0.122083904 | 0.003745569 | 0.092868242 | 0.038264604 | 0.038264604 |
| chr11: 132204939-132206716 | NTM | 0.344711378 | 0.005128034 | 0.106446266 | 0.003738017 | 0.092868242 | 0.036227495 | 0.036227495 |
| chr19: 58513763-58514717 | ZNF606 | 0.344730774 | 0.003193862 | 0.085052362 | 0.003737347 | 0.092868242 | 0.031657766 | 0.031657766 |
| chr10: 122915799-12292588 | CDC123 | 0.344582993 | 0.005742969 | 0.112400084 | 0.003731737 | 0.092868242 | 0.036723008 | 0.036723008 |
| chr1: 40758116-40759856 | ZMPSTE24 | 0.345388616 | 0.001203172 | 0.054952728 | 0.003545146 | 0.092274168 | 0.029510543 | 0.029510543 |
| chr12: 53873189-53874945 | PCBP2 | 0.345510005 | 0.00245255 | 0.07690982 | 0.003665412 | 0.092208979 | 0.02774872 | 0.02774872 |
| chr11: 4673715-4676718 | OR51E1 | 0.345933376 | 0.003329808 | 0.085908111 | 0.003621687 | 0.091470629 | 0.032098222 | 0.032098222 |
| chr1: 43727512-43727589 | EBNA1BP2 | 0.346047624 | 0.002367912 | 0.075986532 | 0.003607347 | 0.091381097 | 0.027308264 | 0.027308264 |
| chr12: 104359293-104359486 | C12orf73 | 0.346225793 | 0.003975695 | 0.094764506 | 0.003590505 | 0.091208876 | 0.033529703 | 0.033529703 |
| chr3: 52029746-52029958 | RPL29 | 0.346304272 | 0 | 0 | 0.003582254 | 0.091208876 | 0.016186753 | 0.016186753 |
| chr19: 34302695-34306668 | KCTD15 | 0.346487607 | 0.007147226 | 0.123047454 | 0.003572035 | 0.091143709 | 0.037328635 | 0.037328635 |
| chr10: 102224336-102224716 | GNPTAB | 0.346582993 | 0.002656535 | 0.078584121 | 0.003564368 | 0.091143709 | 0.028684689 | 0.028684689 |
| chr18: 28281-186283694 | PRG4 | 0.347040363 | 0.001203172 | 0.054952728 | 0.003515146 | 0.090674291 | 0.019655343 | 0.019655343 |
| chr20: 57485737-57486247 | GNAS | 0.347157354 | 0.011944047 | 0.155429477 | 0.003493992 | 0.090400812 | 0.038539889 | 0.038539889 |
| chr5: 72875701-72877794 | UTP15 | 0.347179955 | 0 | 0 | 0.00349355 | 0.090400812 | 0.016076639 | 0.016076639 |
| chr19: 1652298-1652326 | TCF3 | 0.347341283 | 0.003229855 | 0.085267223 | 0.003469098 | 0.090141966 | 0.031162253 | 0.031162253 |
| chr8: 17104183-17104387 | CNOT7 | 0.347410862 | 0.003680922 | 0.091459073 | 0.003462106 | 0.090089159 | 0.032153279 | 0.032153279 |
| chr4: 88312012-88312538 | HSD17B11 | 0.347520476 | 0.008454701 | 0.133216661 | 0.003453466 | 0.089993264 | 0.037493806 | 0.037493806 |
| chr16: 67418772-67419106 | LRRC36 | 0.347808564 | 0.005934616 | 0.114006188 | 0.003414593 | 0.089108124 | 0.03578704 | 0.03578704 |
| chr16: 70747608-70748773 | CNOT2 | 0.348186738 | 0.001273157 | 0.057173139 | 0.003382668 | 0.088402009 | 0.01993062 | 0.01993062 |
| chr5: 52552383-52556388 | BTF3L4 | 0.348370433 | 0.002680623 | 0.078783422 | 0.003366221 | 0.088226069 | 0.028464461 | 0.028464461 |
| chr17: 36294031-36294915 | TBC1D3F | 0.34873563 | 0.002667289 | 0.078646054 | 0.003331502 | 0.087442296 | 0.028354347 | 0.028354347 |
| chr22: 31363051-31364284 | MORC2 | 0.348951739 | 0.003750785 | 0.092053993 | 0.003316793 | 0.087182226 | 0.032098222 | 0.032098222 |
| chr15: 52356098-52358462 | MAPK6 | 0.34926453 | 0.007410428 | 0.125555604 | 0.003288776 | 0.086696722 | 0.03650278 | 0.03650278 |
| chr10: 50970284-50970425 | OGDHL | 0.349324408 | 0.00510169 | 0.106142027 | 0.003283512 | 0.086696722 | 0.034465672 | 0.034465672 |
| chr6: 7417563-7418270 | RIOK1 | 0.349666416 | 0.007217973 | 0.12367929 | 0.003248587 | 0.08626329 | 0.036117381 | 0.036117381 |
| chr12: 69783926-69784576 | YEATS4 | 0.350000562 | 0.008141607 | 0.131445347 | 0.003216422 | 0.08553422 | 0.036612894 | 0.036612894 |
| chr13: 100622380-100624163 | ZIC5 | 0.35012692 | 0.008295958 | 0.132523738 | 0.003203139 | 0.085528988 | 0.03650278 | 0.03650278 |
| chr9: 95244574-95244788 | ASPN | 0.350256133 | 0.003759281 | 0.092052993 | 0.00318828 | 0.085285307 | 0.031988108 | 0.031988108 |
| chr8: 101965496-101965616 | YWHAZ | 0.350510592 | 0.005746975 | 0.112400084 | 0.00316881 | 0.085014912 | 0.034740957 | 0.034740957 |

TABLE 9-continued

| locus | nearest_ref_id | r | p | qval | pglobal | qglobal | prank | padj |
|---|---|---|---|---|---|---|---|---|
| chr20: 55840760-55841685 | BMP7 | 0.350559373 | 0.002260921 | 0.074896868 | 0.003165373 | 0.085014912 | 0.025821725 | 0.025821725 |
| chr2: 47614696-47614740 | EPCAM | 0.350697329 | 0.005088462 | 0.105988221 | 0.003153567 | 0.084982538 | 0.034080273 | 0.034080273 |
| chr9: 139304779-139305061 | SDCCAG3 | 0.350723691 | 0.003054233 | 0.083821279 | 0.00315322 | 0.084982538 | 0.029730771 | 0.029730771 |
| chr16: 332614-333003 | ARHGDIG | 0.350753346 | 0.010006296 | 0.143216183 | 0.003152829 | 0.084982538 | 0.036723008 | 0.036723008 |
| chr19: 19007369-19007488 | LASS1 | 0.351329035 | 0.010345517 | 0.145135442 | 0.003085471 | 0.083768917 | 0.036667951 | 0.036667951 |
| chr9: 33917015-33920402 | UBE2R2 | 0.351623699 | 0.003205954 | 0.085084821 | 0.003049893 | 0.08306038 | 0.030446512 | 0.030446512 |
| chr1: 33625122-33625190 | NRP1 | 0.351650511 | 0.000150014 | 0.008357973 | 0.003042761 | 0.08306038 | 0.016131696 | 0.016131696 |
| chr4: 70079719-70080449 | UGT2B11 | 0.351862854 | 0.007741352 | 0.128531382 | 0.003023147 | 0.082819628 | 0.035566812 | 0.035566812 |
| chr7: 99679923-99680171 | ZNF3 | 0.352255056 | 0.010014015 | 0.143216183 | 0.002977233 | 0.08168847 | 0.036227495 | 0.036227495 |
| chr17: 40169357-40169715 | DNAJC7 | 0.352324455 | 0.001535738 | 0.065020053 | 0.002970202 | 0.08168847 | 0.020866597 | 0.020866597 |
| chr6: 88376735-88377169 | ORC3 | 0.352508512 | 0 | 0 | 0.002965086 | 0.08168847 | 0.015911468 | 0.015911468 |
| chr1: 2564304-2564481 | MMEL1 | 0.352661402 | 0 | 0 | 0.002944605 | 0.081412629 | 0.01585641 | 0.01585641 |
| chr17: 74944721-74946465 | MGAT5B | 0.352666207 | 0.004035915 | 0.095200415 | 0.002944503 | 0.081412629 | 0.032263393 | 0.032263393 |
| chr19: 52511393-52511483 | ZNF615 | 0.352758492 | 0.000854457 | 0.042519208 | 0.002939828 | 0.081412629 | 0.017673292 | 0.017673292 |
| chr12: 54678041-54680872 | HNRNPA1 | 0.352793166 | 0 | 0 | 0.002935135 | 0.081412629 | 0.015801354 | 0.015801354 |
| chr21: 45079266-45079374 | HSF2BP | 0.352847214 | 0.003836372 | 0.093530226 | 0.002931642 | 0.081412629 | 0.031492595 | 0.031492595 |
| chr6: 76425100-76427997 | SENP6 | 0.352949584 | 0.002051473 | 0.074404864 | 0.002913874 | 0.081412629 | 0.023674503 | 0.023674503 |
| chr8: 86129188-86129387 | E2F5 | 0.352950312 | 0.002863213 | 0.081639789 | 0.002913777 | 0.081412629 | 0.028519518 | 0.028519518 |
| chr16: 19716437-19716880 | C16orf62 | 0.353016377 | 0 | 0 | 0.002908979 | 0.081412629 | 0.015746297 | 0.015746297 |
| chr1: 148025760-148025863 | NBPF14 | 0.353092408 | 0.004067093 | 0.09564239 | 0.002904589 | 0.081412629 | 0.031877994 | 0.031877994 |
| chr7: 155255065-155257526 | EN2 | 0.353146057 | 0.007860271 | 0.129133025 | 0.002900458 | 0.081412629 | 0.0346859 | 0.0346859 |
| chr14: 70826235-70826444 | COX16 | 0.353343863 | 0.002633087 | 0.078272928 | 0.002879251 | 0.08133101 | 0.027638606 | 0.027638606 |
| chr5: 140588268-140591696 | PCDHB12 | 0.353445742 | 0.002137676 | 0.074896868 | 0.002869414 | 0.081179389 | 0.024170016 | 0.024170016 |
| chr6: 97345541-97345757 | NDUFAF4 | 0.353576318 | 0.000829729 | 0.041516184 | 0.002861174 | 0.081129471 | 0.017453064 | 0.017453064 |
| chr19: 21560190-21562104 | ZNF738 | 0.3536571 | 0.005514988 | 0.110317975 | 0.002849301 | 0.081115772 | 0.033089247 | 0.033089247 |
| chr5: 140557370-140560081 | PCDHB8 | 0.353698505 | 0.00831499 | 0.13259453 | 0.002846381 | 0.081115772 | 0.034465672 | 0.034465672 |
| chr4: 55161291-55161439 | FIP1L1 | 0.353817549 | 0.004681278 | 0.10098106 | 0.002837998 | 0.081115772 | 0.032373507 | 0.032373507 |
| chr17: 79771349-79771889 | GCGR | 0.354035638 | 0.005445589 | 0.109898029 | 0.002816245 | 0.080681283 | 0.032924076 | 0.032924076 |
| chr19: 52793318-52795977 | ZNF766 | 0.354146057 | 0.002226165 | 0.074896868 | 0.002813154 | 0.080681283 | 0.0248307 | 0.0248307 |
| chr1: 63788729-63790797 | FOXD3 | 0.354149363 | 0.005405168 | 0.109447113 | 0.002798558 | 0.080555005 | 0.032813962 | 0.032813962 |
| chr1: 147954634-147955419 | PPIAL4A | 0.354222847 | 0.002675456 | 0.078759014 | 0.002795098 | 0.080555005 | 0.027418378 | 0.027418378 |
| chr12: 122496997-122499948 | BCL7A | 0.354825754 | 0.002231741 | 0.074896868 | 0.002757038 | 0.079738981 | 0.024885757 | 0.024885757 |
| chr9: 123605014-123605229 | PSMD5 | 0.355144141 | 0 | 0 | 0.00272948 | 0.079648701 | 0.015581126 | 0.015581126 |
| chr2: 233412778-233415226 | TIGD1 | 0.355197399 | 0.004022874 | 0.095037797 | 0.002724131 | 0.079648701 | 0.031052139 | 0.031052139 |
| chr22: 49246569-49246724 | FAM19A5 | 0.355373328 | 0.00036784 | 0.086049007 | 0.002711088 | 0.079550065 | 0.029950999 | 0.029950999 |
| chr17: 41154888-41154956 | RPL27 | 0.355442918 | 0.002963896 | 0.083014679 | 0.002707158 | 0.079550065 | 0.028079062 | 0.028079062 |
| chr12: 123741359-123742506 | C12orf65 | 0.355530218 | 0.013002282 | 0.159180228 | 0.002698823 | 0.079550065 | 0.033860045 | 0.033860045 |
| chr6: 31937586-31940069 | DOM3Z | 0.355568549 | 0.006009592 | 0.114897067 | 0.002692989 | 0.079550065 | 0.032538678 | 0.032538678 |
| chr17: 5322673-5323000 | NUP88 | 0.355910655 | 0.002129205 | 0.074896868 | 0.002664297 | 0.079071281 | 0.023839674 | 0.023839674 |
| chr8: 26227649-26230196 | PPP2R2A | 0.356005328 | 0.00272447 | 0.079641256 | 0.002663318 | 0.079071281 | 0.02719815 | 0.02719815 |
| chr2: 74734702-74735707 | PCGF1 | 0.356137025 | 0.006485052 | 0.1180257771 | 0.002651333 | 0.079071281 | 0.032648791 | 0.032648791 |
| chr10: 70968355-70968855 | SUPV3L1 | 0.3561651 | 0 | 0 | 0.002650167 | 0.079071281 | 0.015471012 | 0.015471012 |
| chrX: 70519791-70521018 | NONO | 0.356291288 | 0.003965269 | 0.094764506 | 0.002642471 | 0.079069514 | 0.030391455 | 0.030391455 |
| chr2: 44547337-44548633 | SLC3A1 | 0.356342942 | 0.013472925 | 0.162218034 | 0.002636828 | 0.079069514 | 0.033254418 | 0.033254418 |
| chr7: 87536502-87538856 | DBF4 | 0.356363925 | 0.006137741 | 0.116167412 | 0.002636013 | 0.079069514 | 0.032263393 | 0.032263393 |
| chr19: 37019120-37019562 | ZNF260 | 0.356458224 | 0.002725493 | 0.079641256 | 0.002631242 | 0.079069514 | 0.027032979 | 0.027032979 |
| chr1: 149890617-149900236 | SF3B4 | 0.356570693 | 0.002827474 | 0.081130196 | 0.002622595 | 0.079069514 | 0.027418378 | 0.027418378 |
| chr4: 83822235-83822319 | SEC31A | 0.35704326 | 0.00336027 | 0 | 0.002584918 | 0.07840198 | 0.029400429 | 0.029400429 |
| chr19: 19615360-19615540 | CSGALNACT1 | 0.357581398 | 0 | 0 | 0.002555298 | 0.077741827 | 0.015415956 | 0.015415956 |
| chr6: 44221225-44221620 | HSP90AB1 | 0.357638149 | 0.004764199 | 0.101816018 | 0.002555246 | 0.077741827 | 0.030997082 | 0.030997082 |
| chr8: 54934622-54935089 | TCEA1 | 0.357638989 | 0.003470001 | 0.087293121 | 0.002552422 | 0.077741827 | 0.029510543 | 0.029510543 |

TABLE 9-continued

| locus | nearest_ref_id | r | p | qval | pglobal | qglobal | prank | padj |
|---|---|---|---|---|---|---|---|---|
| chr4: 13485699-13485989 | RAB28 | 0.358225721 | 0.00029466 | 0.015975864 | 0.00249312 | 0.07662021 | 0.015966525 | 0.015966525 |
| chr10: 61665879-61666414 | CCDC6 | 0.358410884 | 0.004770436 | 0.101816018 | 0.002484359 | 0.07480369 | 0.030776854 | 0.030776854 |
| chr15: 82939013-82939159 | RP13-98N21.1 | 0.358524403 | 0.003390575 | 0.086368012 | 0.002477524 | 0.07639943 | 0.029235258 | 0.029235258 |
| chr5: 170837530-170838141 | NPM1 | 0.358661212 | 0.003112663 | 0.084283617 | 0.002471593 | 0.07634617 | 0.0282929 | 0.0282929 |
| chr5: 138665033-138667360 | MATR3 | 0.358905176 | 0 | 0 | 0.002449038 | 0.076037393 | 0.015305842 | 0.015305842 |
| chr1: 150443036-150449042 | RPRD2 | 0.358931012 | 0.001044122 | 0.049906291 | 0.00244694 | 0.076037393 | 0.017673292 | 0.017673292 |
| chr19: 39303481-39303740 | LGALS4 | 0.359501829 | 0.002800501 | 0.080691396 | 0.002406051 | 0.075346732 | 0.026812751 | 0.026812751 |
| chr7: 143002032-143004789 | CASP2 | 0.359779958 | 0.0052784 | 0.108821635 | 0.002390425 | 0.074986674 | 0.030501569 | 0.030501569 |
| chr14: 64804615-64805317 | AL161756.1 | 0.360196944 | 0.001852672 | 0.072262867 | 0.002359921 | 0.074281033 | 0.021472224 | 0.021472224 |
| chr17: 44833167-44834830 | NSF | 0.360685738 | 0.004164634 | 0.095871025 | 0.002328796 | 0.073433881 | 0.029620657 | 0.029620657 |
| chr11: 114284677-114284925 | RBM7 | 0.360737625 | 0 | 0 | 0.002325247 | 0.073433881 | 0.015195728 | 0.015195728 |
| chr2: 180725827-180726232 | ZNF385B | 0.360753689 | 0.000458772 | 0.024364569 | 0.002324535 | 0.073433881 | 0.015966525 | 0.015966525 |
| chr15: 51587392-51587502 | KLK14 | 0.361259901 | 0.009570729 | 0.141580566 | 0.002287063 | 0.072893957 | 0.031272367 | 0.031272367 |
| chr19: 52868950-52870375 | ZNF610 | 0.361291389 | 0.001739732 | 0.070219452 | 0.002286182 | 0.072893957 | 0.020701426 | 0.020701426 |
| chr14: 21737456-21737638 | HNRNPC | 0.361477927 | 0.002287559 | 0.074896868 | 0.00227195 | 0.072893957 | 0.0242813 | 0.0242813 |
| chr11: 117155801-117157161 | RNF214 | 0.361847621 | 0.00250308 | 0.076926292 | 0.002256449 | 0.07266646 | 0.025436327 | 0.025436327 |
| chr13: 79979835-79980612 | RBM26 | 0.36206404 | 0.00677961 | 0.120633891 | 0.002239673 | 0.072254321 | 0.030556626 | 0.030556626 |
| chr5: 32601110-32604185 | SUB1 | 0.362303909 | 0 | 0 | 0.002216057 | 0.071875443 | 0.015085614 | 0.015085614 |
| chr6: 53787432-53788919 | LRRC1 | 0.362759243 | 0.001706266 | 0.069486359 | 0.002185744 | 0.071361233 | 0.020371084 | 0.020371084 |
| chr11: 22644078-22647387 | FANCF | 0.363489573 | 0 | 0 | 0.002137025 | 0.070316635 | 0.01503055 | 0.01503055 |
| chr20: 52844491-52844591 | PFDN4 | 0.363560498 | 0 | 0 | 0.002128905 | 0.070176597 | 0.0149755 | 0.0149755 |
| chr6: 30613671-30614600 | ATAT1 | 0.363580156 | 0.003898538 | 0.094210495 | 0.002127962 | 0.070176597 | 0.028134119 | 0.028134119 |
| chr6: 70605575-70608820 | SF3B3 | 0.363659853 | 0.008588833 | 0.134075072 | 0.002122664 | 0.070176597 | 0.030061113 | 0.030061113 |
| chr3: 3355211-3355645 | TIGD7 | 0.363725026 | 0 | 0 | 0.002117779 | 0.070176597 | 0.014920443 | 0.014920443 |
| chr16: 161135146-161135513 | USP21 | 0.363771581 | 0.002323203 | 0.075082439 | 0.002116353 | 0.070176597 | 0.024114959 | 0.024114959 |
| chr8: 101733618-101735037 | PABPC1 | 0.364174471 | 0.002118261 | 0.074896868 | 0.002096667 | 0.069874778 | 0.022463249 | 0.022463249 |
| chr1: 151688094-151689290 | CELF3 | 0.364376964 | 0.002952999 | 0.083014679 | 0.002077995 | 0.069507577 | 0.025986896 | 0.025986896 |
| chr9: 133376362-133376661 | ASS1 | 0.364697462 | 0.00725575 | 0.12409247 | 0.002058452 | 0.069108448 | 0.029510543 | 0.029510543 |
| chr12: 30484476-3050306 | TULP3 | 0.364753258 | 0.006132467 | 0.116167412 | 0.002052882 | 0.069049055 | 0.02918020 | 0.02918020 |
| chr4: 111120255-111120355 | ELOVL6 | 0.364868424 | 0.003051244 | 0.083812279 | 0.002043933 | 0.068857607 | 0.026317238 | 0.026317238 |
| chr9: 19378705-19380252 | RPS6 | 0.365038972 | 0.002300966 | 0.074896868 | 0.002029563 | 0.068739822 | 0.023784617 | 0.023784617 |
| chr10: 121302101-121302220 | RGS10 | 0.365192 | 0.002278591 | 0.074896868 | 0.002017084 | 0.068739822 | 0.023454275 | 0.023454275 |
| chr16: 277240-279462 | LUC7L | 0.365306003 | 0.003898555 | 0.094210495 | 0.002007769 | 0.068739822 | 0.027473435 | 0.027473435 |
| chr19: 2430955-2431643 | ZNF254 | 0.365391007 | 0.0024742 | 0.076926292 | 0.000200416 | 0.068739822 | 0.024335187 | 0.024335187 |
| chrX: 152241317-152243401 | AC152006.1 | 0.365477178 | 0.002089412 | 0.074557938 | 0.001995419 | 0.068739822 | 0.022298079 | 0.022298079 |
| chr1: 116609639-116612675 | SLC22A15 | 0.365617395 | 0.005365482 | 0.109252525 | 0.00198767 | 0.068739822 | 0.028134119 | 0.028134119 |
| chr19: 69113036-69113236 | ANP32A | 0.365537633 | 0.002497996 | 0.076926292 | 0.001939615 | 0.067488924 | 0.024225073 | 0.024225073 |
| chr1: 6463716-6463847 | HPX | 0.36658236 | 0.003082241 | 0.084000815 | 0.00193868 | 0.067488924 | 0.025931839 | 0.025931839 |
| chr17: 4269565-4269969 | UBE2G1 | 0.366624907 | 0 | 0 | 0.001936683 | 0.067488924 | 0.014755272 | 0.014755272 |
| chr17: 30228554-30228731 | UTP6 | 0.366824192 | 0.003624029 | 0.09052543 | 0.001926885 | 0.067433539 | 0.026812751 | 0.026812751 |
| chr5: 178157556-178157703 | ZNF354A | 0.367356176 | 0.002058499 | 0.074404864 | 0.001895907 | 0.06671121 | 0.021747509 | 0.021747509 |
| chr14: 21464685-21465189 | METTL17 | 0.367400305 | 0.002197521 | 0.074896868 | 0.001894065 | 0.06671121 | 0.022298079 | 0.022298079 |
| chr1: 144828540-144830302 | NBPF9 | 0.3679992 | 0.000828298 | 0.041516184 | 0.001866021 | 0.066079013 | 0.016131696 | 0.016131696 |
| chr16: 3284635-3285456 | ZNF200 | 0.368145566 | 0.004814693 | 0.102159863 | 0.001860749 | 0.066079013 | 0.027253207 | 0.027253207 |
| chr19: 33078158-33078322 | PDCD5 | 0.368297261 | 0.004138572 | 0.095871025 | 0.001853504 | 0.06660185 | 0.026977922 | 0.026977922 |
| chr1: 17766040-17766220 | RCC2 | 0.36830465 | 0.006298625 | 0.116920758 | 0.001846595 | 0.06660185 | 0.027693663 | 0.027693663 |
| chr22: 31740317-31742218 | PATZ1 | 0.368414717 | 0 | 0 | 0.001834474 | 0.06601085 | 0.014645158 | 0.014645158 |
| chr4: 96075698-96079599 | BMPR1B | 0.368570648 | 0.001803079 | 0.071315614 | 0.001834136 | 0.065979296 | 0.01459010 | 0.01459010 |
| chr2: 190339938-190340291 | WDR75 | 0.368575508 | 0.001991434 | 0.07433842 | 0.001791727 | 0.065086286 | 0.020040742 | 0.020040742 |
| chr15: 52970768-52970820 | KIAA1370 | 0.369520608 | 0 | 0 | 0.001765165 | 0.065086286 | 0.020976711 | 0.020976711 |
| chr3: 62359972-62359999 | FEZF2 | 0.370011496 | 0.006297319 | 0.116920758 | 0.001765165 | 0.064581327 | 0.026922865 | 0.026922865 |

TABLE 9-continued

| locus | nearest_ref_id | r | p | qval | pglobal | qglobal | prank | padj |
|---|---|---|---|---|---|---|---|---|
| chr14: 36789665-36789882 | MBIP | 0.370390986 | 0.002395341 | 0.076596085 | 0.001743916 | 0.064353713 | 0.022958762 | 0.022958762 |
| chr9: 131303380-131304567 | GLE1 | 0.370432615 | 0.001207478 | 0.054952728 | 0.001740684 | 0.064353713 | 0.01734295 | 0.01734295 |
| chr19: 36726560-36729673 | ZNF146 | 0.37076253 | 0.001797055 | 0.071315614 | 0.001722816 | 0.064121923 | 0.019820514 | 0.019820514 |
| chr11: 76731317-76737841 | ACER3 | 0.371547935 | 0.002473745 | 0.076926292 | 0.001680831 | 0.062816721 | 0.023068876 | 0.023068876 |
| chr5: 44816544-44820530 | MRPS30 | 0.372171618 | 0.001169204 | 0.054060041 | 0.001641165 | 0.061976164 | 0.017012608 | 0.017012608 |
| chr20: 50418817-50419014 | SALL4 | 0.372219721 | 0.002515478 | 0.077005838 | 0.001637383 | 0.061976164 | 0.023013819 | 0.023013819 |
| chr2: 175113179-175113426 | OLA1 | 0.372322556 | 0 | 0 | 0.001629985 | 0.061936008 | 0.01447987 | 0.01447987 |
| chr11: 43876693-43878167 | HSD17B12 | 0.372729256 | 0.002281533 | 0.074896868 | 0.001615677 | 0.061650304 | 0.022132908 | 0.022132908 |
| chr6: 111214678-111216916 | AMD1 | 0.372775014 | 0 | 0 | 0.001613961 | 0.061650304 | 0.014369873 | 0.014369873 |
| chr2: 44999174-44999731 | CAMKMT | 0.372782137 | 0.002908212 | 0.08228265 | 0.001613847 | 0.061650304 | 0.023564389 | 0.023564389 |
| chr17: 30380284-30380517 | LRRC37B | 0.374033979 | 0.002518387 | 0.077005838 | 0.001553193 | 0.060207441 | 0.022573363 | 0.022573363 |
| chr14: 91883974-91884152 | CCDC88C | 0.374642963 | 0.000670737 | 0.034807417 | 0.001530468 | 0.059652123 | 0.015085614 | 0.015085614 |
| chr11: 85514078-85514182 | MCOLN3 | 0.374684625 | 0.003969808 | 0.094764506 | 0.001525996 | 0.059605736 | 0.024720586 | 0.024720586 |
| chr11: 26744853-26744974 | SLC5A12 | 0.375189064 | 0.010525668 | 0.146272153 | 0.001508748 | 0.059059014 | 0.025546441 | 0.025546441 |
| chr3: 52089865-52090566 | DUSP7 | 0.375203447 | 0.002453789 | 0.07690982 | 0.001508582 | 0.059059014 | 0.022298079 | 0.022298079 |
| chr11: 102340904-102341115 | TMEM123 | 0.375721711 | 0.00219416 | 0.074896868 | 0.001485218 | 0.058516288 | 0.021031768 | 0.021031768 |
| chr6: 27368071-27371683 | ZNF391 | 0.375903341 | 0 | 0 | 0.001476676 | 0.058433244 | 0.014149645 | 0.014149645 |
| chr7: 19156293-19157295 | TWIST1 | 0.376075851 | 0.000868692 | 0.043055081 | 0.001471295 | 0.058397855 | 0.015526069 | 0.015526069 |
| chrX: 129063311-129063737 | UTP14A | 0.376243265 | 0.002051346 | 0.074404864 | 0.001461047 | 0.058195149 | 0.020371084 | 0.020371084 |
| chr21: 18965469-18965897 | CXADR | 0.377652362 | 0 | 0 | 0.001396915 | 0.056634289 | 0.014094588 | 0.014094588 |
| chr5: 68665483-68665840 | TAF9 | 0.377769513 | 0.0022028 | 0.074896868 | 0.001392548 | 0.056583554 | 0.020646369 | 0.020646369 |
| chr7: 149470196-149470568 | ZNF467 | 0.377842565 | 0.002987109 | 0.083076103 | 0.001383664 | 0.056348645 | 0.022683477 | 0.022683477 |
| chr14: 89088661-89088615 | ZC3H14 | 0.377843839 | 0 | 0 | 0.001383605 | 0.056348645 | 0.01403953 | 0.01403953 |
| chr6: 137112847-137113656 | MAP3K5 | 0.378372715 | 0.003924303 | 0.0943921 | 0.001365598 | 0.056348645 | 0.023454275 | 0.023454275 |
| chr15: 57079747-155708803 | DAP3 | 0.378584615 | 0 | 0 | 0.001353654 | 0.056261816 | 0.01387436 | 0.01387436 |
| chr12: 118500157-118500235 | WSB2 | 0.378701761 | 0.003285179 | 0.085620014 | 0.001347116 | 0.056118504 | 0.022793591 | 0.022793591 |
| chr12: 122985186-122985518 | ZCCHC8 | 0.37906625 | 0 | 0 | 0.001329462 | 0.055895875 | 0.013764246 | 0.013764246 |
| chr13: 79797763-13799067 | C20orf7 | 0.379646265 | 0.002733521 | 0.079693317 | 0.001301059 | 0.054956129 | 0.021472224 | 0.021472224 |
| chr20: 20693017-20693266 | RALGAPA2 | 0.379953096 | 0.000392922 | 0.02099011 | 0.001289806 | 0.054730647 | 0.01420470 | 0.01420470 |
| chr17: 27940371-27941779 | ANKRD13B | 0.379965834 | 0 | 0 | 0.001287374 | 0.054730647 | 0.013599075 | 0.013599075 |
| chr2: 24991089-24993571 | NCOA1 | 0.380049681 | 0.003108189 | 0.084283617 | 0.001282497 | 0.054730647 | 0.021857623 | 0.021857623 |
| chr1: 2706067-2706280 | TTC34 | 0.380131608 | 0.00112532 | 0.053024689 | 0.001276855 | 0.054730647 | 0.01547112 | 0.01547112 |
| chr6: 61136068-61136683 | TMEM138 | 0.380382477 | 0.002431464 | 0.07683164 | 0.001269747 | 0.054730647 | 0.02059312 | 0.02059312 |
| chr5: 72801016-72801460 | BTF3 | 0.380632257 | 0.004553657 | 0.099768482 | 0.001289835 | 0.054730647 | 0.022518306 | 0.022518306 |
| chr12: 26277650-26278060 | BHLHE41 | 0.380649557 | 0.000869967 | 0.043055081 | 0.001259656 | 0.054730647 | 0.01470215 | 0.01470215 |
| chr7: 77348634-77348850 | CLNS1A | 0.381389378 | 0 | 0 | 0.001244205 | 0.054730647 | 0.01337847 | 0.01337847 |
| chr11: 64940653-64940715 | SPDYC | 0.381489194 | 0.001862618 | 0.072287892 | 0.00123731 | 0.054707452 | 0.018223862 | 0.018223862 |
| chr1: 169555466-169555826 | F5 | 0.382149137 | 0 | 0 | 0.00121279 | 0.054389707 | 0.013268733 | 0.013268733 |
| chr1: 113212613-113214241 | CAPZA1 | 0.382444099 | 0 | 0 | 0.00120243 | 0.054058764 | 0.013213676 | 0.013213676 |
| chr1: 118880070-118889401 | RPS25 | 0.38247485 | 0 | 0 | 0.001202139 | 0.054058764 | 0.013158619 | 0.013158619 |
| chr6: 119228566-119230332 | ASF1A | 0.382887636 | 0 | 0 | 0.001187702 | 0.05362274 | 0.013103562 | 0.013103562 |
| chr9: 96082648-96082854 | WNK2 | 0.383606155 | 0 | 0 | 0.001181597 | 0.053586679 | 0.018884546 | 0.018884546 |
| chr16: 48419114-48419361 | SIAH1 | 0.38346374 | 0.002147218 | 0.074896868 | 0.001173876 | 0.053570624 | 0.012993448 | 0.012993448 |
| chr6: 117252493-117253326 | RFX6 | 0.383666724 | 0.003137472 | 0.08454882 | 0.001165397 | 0.0534523 | 0.020921654 | 0.020921654 |
| chr5: 140890513-140892546 | PCDHGA1 | 0.384828032 | 0 | 0 | 0.001108231 | 0.051908714 | 0.012828277 | 0.012828277 |
| chr1: 203812268-203823252 | ZC3H11A | 0.385182686 | 0 | 0 | 0.001108231 | 0.051612302 | 0.01277322 | 0.01277322 |
| chr12: 57125273-57125412 | NACA | 0.386358061 | 0.002030959 | 0.074404864 | 0.001072585 | 0.05046987 | 0.018058691 | 0.018058691 |
| chr19: 11849631-11849824 | ZNF823 | 0.386599542 | 0 | 0 | 0.001062858 | 0.050387852 | 0.012552992 | 0.012552992 |
| chr22: 41255552-41258130 | DNAJB7 | 0.386599867 | 0 | 0 | 0.001062854 | 0.050387852 | 0.012497935 | 0.012497935 |
| chr9: 86659417-86659569 | HNRNPK | 0.38694272 | 0 | 0 | 0.001048739 | 0.050126946 | 0.012442878 | 0.012442878 |
| chr12: 21391912-21392180 | SLCO1B1 | 0.38730007 | 0 | 0 | 0.00104238 | 0.05009999 | 0.012387821 | 0.012387821 |

TABLE 9-continued

| locus | nearest_ref_id | r | p | qval | pglobal | qglobal | prank | padj |
|---|---|---|---|---|---|---|---|---|
| chr4: 165878099-165880274 | C4orf39 | 0.387654409 | 0 | 0 | 0.001026914 | 0.049738242 | 0.012332764 | 0.012332764 |
| chr13: 53216540-53217919 | HNRNPA1L2 | 0.387659039 | 0.003340795 | 0.085969228 | 0.001026838 | 0.049738242 | 0.019985685 | 0.019985685 |
| chr7: 16921567-16921611 | AGR3 | 0.387702629 | 0.003578066 | 0.089515727 | 0.001026105 | 0.049738242 | 0.020095799 | 0.020095799 |
| chr10: 27035261-27035727 | PDSS1 | 0.388612797 | 0.002981744 | 0.083076103 | 0.000990592 | 0.049024274 | 0.019325001 | 0.019325001 |
| chr12: 15114470-15114662 | ARHGDIB | 0.389098607 | 0 | 0 | 0.000989776 | 0.049024274 | 0.012057479 | 0.012057479 |
| chr9: 74525549-74525847 | FAM108B1 | 0.389315949 | 0 | 0 | 0.000977152 | 0.048858299 | 0.012002423 | 0.012002423 |
| chr4: 77996624-77997158 | CCNI | 0.389761154 | 0.00049489 | 0.026054161 | 0.000969463 | 0.048641844 | 0.011947366 | 0.011947366 |
| chr22: 29137756-29138410 | CHEK2 | 0.390049265 | 0.00315215 | 0.08468855 | 0.000946731 | 0.047898273 | 0.012442878 | 0.012442878 |
| chr4: 69696317-69696914 | UGT2B10 | 0.390286785 | 0.001037899 | 0.049739741 | 0.0009412 | 0.047751429 | 0.0191595983 | 0.0191595983 |
| chr4: 44700560-44702943 | GUF1 | 0.390480296 | 0.002223282 | 0.074896868 | 0.000934167 | 0.047660883 | 0.013378847 | 0.013378847 |
| chr6: 169931098-169931426 | CBR4 | 0.390570946 | 0.000653249 | 0.033997013 | 0.000927605 | 0.047587285 | 0.01745064 | 0.01745064 |
| chr1: 46158875-46160115 | TMEM69 | 0.390666769 | 0.001169718 | 0.054060041 | 0.000926916 | 0.047587285 | 0.012387821 | 0.012387821 |
| chr19: 11494768-11495018 | EPOR | 0.39120734 | 0.002536025 | 0.077155474 | 0.000922982 | 0.047587285 | 0.013654132 | 0.013654132 |
| chr6: 32151657-32152101 | AGER | 0.392382255 | 0 | 0 | 0.000903309 | 0.046876568 | 0.018003634 | 0.018003634 |
| chrX: 51238802-51239448 | NUDT11 | 0.392392838 | 0.001425388 | 0.061936163 | 0.00086822 | 0.045708659 | 0.011672081 | 0.011672081 |
| chr11: 1481729-1483919 | BRSK2 | 0.392659985 | 0.002373224 | 0.07602269 | 0.000867469 | 0.045708659 | 0.01442493 | 0.01442493 |
| chr5: 35927176-35930362 | FZD8 | 0.392764346 | 0.000257339 | 0.014078459 | 0.000859214 | 0.045631286 | 0.017398007 | 0.017398007 |
| chr5: 34924951-34926101 | BRIX1 | 0.393686876 | 0 | 0 | 0.000856629 | 0.045631286 | 0.011892309 | 0.011892309 |
| chr11: 108810972-108811657 | DDX10 | 0.393780109 | 0 | 0 | 0.000832793 | 0.045017925 | 0.011561967 | 0.011561967 |
| chr6: 151422661-151423023 | MTHFD1L | 0.39413346 | 0.002300383 | 0.074896868 | 0.000829888 | 0.044994788 | 0.01150691 | 0.01150691 |
| chr5: 179498455-179499118 | RNF130 | 0.395080106 | 0.002995917 | 0.083076103 | 0.000820915 | 0.044641533 | 0.016902494 | 0.016902494 |
| chr2: 207655342-207657233 | FASTKD2 | 0.395222571 | 0 | 0 | 0.000797601 | 0.043922586 | 0.017508121 | 0.017508121 |
| chr1: 32801547-32801980 | MARCKSL1 | 0.395317713 | 0 | 0 | 0.000791124 | 0.043808512 | 0.011396796 | 0.011396796 |
| chr5: 58073773-58074960 | GRINL1A | 0.395392528 | 0.00249879 | 0.076926292 | 0.000790373 | 0.043808512 | 0.011341739 | 0.011341739 |
| chr1: 150800493-150800669 | RBM22 | 0.395428297 | 0.003088638 | 0.084000815 | 0.000787766 | 0.043808512 | 0.01679238 | 0.01679238 |
| chr1: 58345458-58345693 | LPXN | 0.395807291 | 0 | 0 | 0.000786872 | 0.043808512 | 0.01745064 | 0.01745064 |
| chr1: 167757056-167761156 | MPZL1 | 0.395931922 | 0 | 0 | 0.000777688 | 0.043808512 | 0.011176568 | 0.011176568 |
| chr1: 154531383-154531504 | UBE2Q1 | 0.395993559 | 0 | 0 | 0.000777153 | 0.043808512 | 0.011121511 | 0.011121511 |
| chr2: 27107163-27107984 | ATP5J | 0.395996233 | 0.001203617 | 0.054952728 | 0.000776889 | 0.043808512 | 0.012828277 | 0.012828277 |
| chr1: 84963111-84963473 | RPF1 | 0.396095665 | 0 | 0 | 0.00077556 | 0.043808512 | 0.011066454 | 0.011066454 |
| chr14: 20925149-20925933 | APEX1 | 0.396178148 | 0.001190996 | 0.05490369 | 0.000711737 | 0.043808512 | 0.012718163 | 0.012718163 |
| chr1: 116914142-116918838 | RWDD1 | 0.396503437 | 0.002228124 | 0.074896868 | 0.000766759 | 0.043808512 | 0.015856411 | 0.015856411 |
| chr9: 37798853-33799230 | PRSS3 | 0.397409769 | 0 | 0 | 0.000744555 | 0.043068013 | 0.01095634 | 0.01095634 |
| chr7: 74597572-74600970 | C9orf85 | 0.39749581 | 0 | 0 | 0.000742855 | 0.043068013 | 0.010901283 | 0.010901283 |
| chr11: 62507447-62507756 | TTC9C | 0.397920759 | 0 | 0 | 0.000734445 | 0.042755513 | 0.010846226 | 0.010846226 |
| chr6: 47009926-47010099 | GPR110 | 0.397964341 | 0.002809976 | 0.080755689 | 0.000734128 | 0.042755513 | 0.016351924 | 0.016351924 |
| chr2: 236385090-236385165 | GPR137B | 0.398121433 | 0.002838645 | 0.081237547 | 0.000728916 | 0.04274929 | 0.016351924 | 0.016351924 |
| chr6: 107979410-107981357 | SOBP | 0.39849222 | 0 | 0 | 0.000728577 | 0.042513049 | 0.010791169 | 0.010791169 |
| chr11: 151220338-151222012 | PIP5K1A | 0.398670482 | 0.001578429 | 0.066031038 | 0.000717051 | 0.042513049 | 0.013709189 | 0.013709189 |
| chr12: 21242841-21243179 | RP11-545I16.1 | 0.398687934 | 0.002064621 | 0.074404864 | 0.000716921 | 0.042513049 | 0.015195728 | 0.015195728 |
| chr1: 154243356-154243986 | UBAP2L | 0.398763956 | 0.001640837 | 0.067674286 | 0.000713525 | 0.042513049 | 0.01387436 | 0.01387436 |
| chr2: 9613044-9613230 | CPSF3 | 0.398839677 | 0.000818676 | 0.04119004 | 0.000708342 | 0.042460748 | 0.011617024 | 0.011617024 |
| chr6: 28097207-28097860 | ZSCAN16 | 0.399313964 | 0 | 0 | 0.000690497 | 0.041773747 | 0.010625998 | 0.010625998 |
| chr5: 68849396-68853931 | OCLN | 0.399353915 | 0 | 0 | 0.000689997 | 0.041773747 | 0.010570941 | 0.010570941 |
| chr1: 183567145-183567381 | SMG7 | 0.399418476 | 0 | 0 | 0.000687128 | 0.041773747 | 0.010515884 | 0.010515884 |
| chr12: 50492729-50494495 | SMARCD1 | 0.399272615 | 0 | 0 | 0.000677636 | 0.041773747 | 0.010350713 | 0.010350713 |
| chr10: 33171620-33171802 | C10orf68 | 0.39996233 | 0 | 0 | 0.000677312 | 0.041773747 | 0.010295656 | 0.010295656 |
| chr7: 23571407-23571660 | TRA2A | 0.400385902 | 0.001909912 | 0.07290082 | 0.000656983 | 0.041289887 | 0.013929417 | 0.013929417 |
| chr1: 2520848-2522908 | C1orf93 | 0.401674406 | 0.000832687 | 0.041549723 | 0.000641426 | 0.040735055 | 0.011011397 | 0.011011397 |
| chr21: 33103975-33104431 | SCAF4 | 0.401930251 | 0.00367158 | 0.091389151 | 0.00063637 | 0.040555725 | 0.015526069 | 0.015526069 |
| chr6: 30530165-30531500 | PRR3 | 0.402082178 | 0.003156645 | 0.08468855 | 0.000634398 | 0.040555725 | 0.015360899 | 0.015360899 |

TABLE 9-continued

| locus | nearest_ref_id | r | p | qval | pglobal | qglobal | prank | padj |
|---|---|---|---|---|---|---|---|---|
| chr2: 223520734-223521056 | FARSB | 0.402157653 | 0.001309609 | 0.058443307 | 0.000632879 | 0.040555725 | 0.012002423 | 0.012002423 |
| chr12: 96437066-96437298 | LITA4H | 0.402185173 | 0 | 0 | 0.000632631 | 0.040555725 | 0.010185542 | 0.010185542 |
| chr5: 140041763-140042064 | IK | 0.402703343 | 0.001774987 | 0.071167982 | 0.000626233 | 0.040555725 | 0.013158619 | 0.013158619 |
| chr1: 155248165-155248282 | CLK2 | 0.40304566 | 0.002943221 | 0.082880196 | 0.000619771 | 0.040555725 | 0.014810329 | 0.014810329 |
| chr10: 71871273-71872032 | H2AFY2 | 0.403191879 | 0 | 0 | 0.000616327 | 0.040555725 | 0.010020371 | 0.010020371 |
| chr13: 103491900-103493885 | BIVM | 0.40403719 | 0.000414281 | 0.022066226 | 0.000597551 | 0.039755743 | 0.010350713 | 0.010350713 |
| chr2: 228353174-228353213 | C1orf148 | 0.404051637 | 0.000953353 | 0.046515259 | 0.00059719 | 0.039755743 | 0.010846226 | 0.010846226 |
| chr1: 42719976-42721237 | KCNG3 | 0.404235536 | 0.0011298 | 0.053024689 | 0.000592999 | 0.039744051 | 0.011176568 | 0.011176568 |
| chr2: 54879028-54879152 | SSBP3 | 0.404739966 | 0.001387273 | 0.060862399 | 0.000588247 | 0.039611265 | 0.011837252 | 0.011837252 |
| chr3: 195310748-195311076 | APOD | 0.405410563 | 0 | 0 | 0.000575152 | 0.039125424 | 0.009965314 | 0.009965314 |
| chr9: 129458572-129463311 | LMX1B | 0.406246618 | 0.002026027 | 0.074404864 | 0.000561861 | 0.038509773 | 0.013268733 | 0.013268733 |
| chr11: 93583577-93583697 | C11orf90 | 0.406962716 | 0.002608771 | 0.078272928 | 0.00054174 | 0.037555812 | 0.014039531 | 0.014039531 |
| chr12: 56693943-56694176 | CS | 0.407050318 | 0 | 0 | 0.000535947 | 0.037505344 | 0.009910257 | 0.009910257 |
| chr22: 44258093-44258398 | SULT4A1 | 0.407538876 | 0 | 0 | 0.000530737 | 0.037486096 | 0.009800143 | 0.009800143 |
| chr19: 14201749-14201848 | SAMD1 | 0.407614144 | 0 | 0 | 0.000530518 | 0.037486096 | 0.009690029 | 0.009690029 |
| chr7: 44632896-44633016 | LRRC37A2 | 0.40823187 | 0.00010737 | 0.051188688 | 0.000525864 | 0.037486096 | 0.010625998 | 0.010625998 |
| chr7: 33148832-33149013 | RP9 | 0.408861449 | 0 | 0 | 0.000500039 | 0.036982719 | 0.009524858 | 0.009524858 |
| chr19: 20046830-20046860 | ZNF93 | 0.409274151 | 0 | 0 | 0.000499745 | 0.036453301 | 0.009469801 | 0.009469801 |
| chr15: 77241410-77242601 | RCN2 | 0.409441008 | 0.001415528 | 0.061655257 | 0.000497827 | 0.036453301 | 0.011176568 | 0.011176568 |
| chr1: 26233278-26233482 | STMN1 | 0.409501544 | 0 | 0 | 0.000496568 | 0.036453301 | 0.009414744 | 0.009414744 |
| chr2: 222886085-222886552 | AIDA | 0.410481766 | 0.002794499 | 0.080691396 | 0.000478764 | 0.035493035 | 0.013213676 | 0.013213676 |
| chr13: 100637576-100639018 | ZIC2 | 0.410515198 | 0.001274851 | 0.057173139 | 0.00047822 | 0.035493035 | 0.010625998 | 0.010625998 |
| chr2: 181940922-181941312 | UBE2E3 | 0.410818774 | 0.002071907 | 0.074404864 | 0.000472014 | 0.035337477 | 0.012332764 | 0.012332764 |
| chr8: 97273728-97273838 | MTERFD1 | 0.411514119 | 0 | 0 | 0.000459439 | 0.035043161 | 0.009084402 | 0.009084402 |
| chr6: 80751835-80752244 | TTK | 0.412567895 | 0.000782933 | 0.039721802 | 0.000437005 | 0.034360736 | 0.009579915 | 0.009579915 |
| chr1: 49298433-49230222 | FOLH1 | 0.412967343 | 0.000915002 | 0.045038408 | 0.00043239 | 0.034246655 | 0.009690029 | 0.009690029 |
| chr11: 18127453-18127638 | SAAL1 | 0.413386439 | 0.001716101 | 0.069576817 | 0.00043097 | 0.034246655 | 0.011011397 | 0.011011397 |
| chr2: 747186607-74722013 | TTC31 | 0.413626042 | 0.002320775 | 0.075082439 | 0.000425021 | 0.034068108 | 0.011947366 | 0.011947366 |
| chr1: 1729527303-172954405 | DLX1 | 0.414113678 | 0 | 0 | 0.000421691 | 0.034068108 | 0.008864174 | 0.008864174 |
| chr1: 156051335-156051789 | MEX3A | 0.414360157 | 0.003386848 | 0.086368012 | 0.000415016 | 0.034004231 | 0.00875406 | 0.00875406 |
| chr20: 459854400-45985567 | ZMYND8 | 0.414889711 | 0 | 0 | 0.000413714 | 0.034004231 | 0.011892309 | 0.011892309 |
| chr6: 20490398-20493945 | E2F3 | 0.415096245 | 0 | 0 | 0.000402697 | 0.033903107 | 0.008533833 | 0.008533833 |
| chr9: 17502548-17503921 | CNTLN | 0.415241654 | 0.003399941 | 0.086368012 | 0.000399995 | 0.033903107 | 0.008478776 | 0.008478776 |
| chr11: 125931320-125933230 | CDON | 0.415614971 | 0.000805294 | 0.04062931 | 0.000398772 | 0.033903107 | 0.011561967 | 0.011561967 |
| chr16: 1374730-1377019 | UBE2I | 0.415770608 | 0.002969533 | 0.083014679 | 0.000390959 | 0.033814213 | 0.008919231 | 0.008919231 |
| chr4: 85418711-85419603 | NKX6-1 | 0.415818061 | 0.00226998 | 0.074896868 | 0.000388972 | 0.0338033 | 0.011396796 | 0.011396796 |
| chr1: 2345035-2345236 | PEX10 | 0.41616237 | 0 | 0 | 0.000387542 | 0.0338033 | 0.011066454 | 0.011066454 |
| chr13: 37583320-37583750 | EXOSC8 | 0.41634724 | 0 | 0 | 0.000383013 | 0.0338033 | 0.008148434 | 0.008148434 |
| chr6: 114332294-114332472 | HDAC2 | 0.416396892 | 0 | 0 | 0.00038083 | 0.0338033 | 0.00803832 | 0.00803832 |
| chr1: 94730187-94732682 | KDM4D | 0.416500311 | 0 | 0 | 0.000380412 | 0.0338033 | 0.007983263 | 0.007983263 |
| chr7: 96639107-96640351 | DLX6 | 0.417052551 | 0 | 0 | 0.000379524 | 0.0338033 | 0.007928206 | 0.007928206 |
| chr1: 43316593-43318148 | ZNF691 | 0.417479864 | 0 | 0 | 0.000398822 | 0.0338033 | 0.007873149 | 0.007873149 |
| chr6: 30620387-30620987 | C6orf136 | 0.419671206 | 0 | 0 | 0.000368399 | 0.0338033 | 0.007818092 | 0.007818092 |
| chr1: 38455541-38456593 | SF3A3 | 0.421275822 | 0 | 0 | 0.000337962 | 0.031641224 | 0.007707978 | 0.007707978 |
| chr16: 3450944-3451030 | ZNF434 | 0.421783368 | 0 | 0 | 0.000317223 | 0.030524412 | 0.00748775 | 0.00748775 |
| chr2: 27886195-27886676 | SUPT7L | 0.422059014 | 0.004302763 | 0.097323884 | 0.000315018 | 0.030524412 | 0.007432693 | 0.007432693 |
| chr3: 131221573-131221827 | MRPL3 | 0.42218501 | 0 | 0 | 0.000312506 | 0.030524412 | 0.010130485 | 0.010130485 |
| chr6: 117890782-117891021 | DCBLD1 | 0.422672614 | 0 | 0 | 0.000309822 | 0.030524412 | 0.007322579 | 0.007322579 |
| chr19: 37298819-37300746 | TBC1D22B | 0.422808785 | 0.001307515 | 0.058443307 | 0.0003041 | 0.030437889 | 0.007267522 | 0.007267522 |
| chr12: 52531494-52531680 | ZNF614 | 0.423706864 | 0 | 0 | 0.000301647 | 0.030437889 | 0.008148434 | 0.008148434 |
| chr12: 76478346-76478813 | NAP1L1 | 0.423706864 | 0 | 0 | 0.000294718 | 0.030160322 | 0.007157408 | 0.007157408 |

TABLE 9-continued

| locus | nearest_ref_id | r | p | qval | pglobal | qglobal | prank | padj |
|---|---|---|---|---|---|---|---|---|
| chr6: 110797724-110797844 | SLC22A16 | 0.424337101 | 0 | 0 | 0.000290236 | 0.029952049 | 0.007102351 | 0.007102351 |
| chr17: 38290531-38293040 | MSL1 | 0.425415614 | 0 | 0 | 0.000275367 | 0.028910303 | 0.007047294 | 0.007047294 |
| chr2: 71192087-71192555 | ATP6V1B1 | 0.425997989 | 0 | 0 | 0.00026727 | 0.028388448 | 0.00693718 | 0.00693718 |
| chr1: 236645566-236648026 | EDARADD | 0.426385524 | 0 | 0 | 0.000264197 | 0.028227163 | 0.006882123 | 0.006882123 |
| chr1: 90398625-90402170 | LRRC8D | 0.4277395 | 0 | 0 | 0.000252946 | 0.027410832 | 0.006827066 | 0.006827066 |
| chr15: 34880591-34880704 | GOLGA8A | 0.428326543 | 0.001214634 | 0.055015953 | 0.000250304 | 0.027410832 | 0.006827066 | 0.007542807 |
| chr17: 27277912-27278789 | PHF12 | 0.428894454 | 0.001210213 | 0.054952728 | 0.000250154 | 0.027410832 | 0.007542807 | 0.00748775 |
| chr7: 50632981-50633154 | DDC | 0.428397647 | 0 | 0 | 0.000249544 | 0.027410832 | 0.00748775 | 0.006716952 |
| chr10: 122348814-122349367 | PPAPDC1A | 0.428573634 | 0.002188707 | 0.074896868 | 0.000246644 | 0.027410832 | 0.006716952 | 0.008533833 |
| chr12: 54428061-54429145 | HOXC5 | 0.429414056 | 0.001786691 | 0.071315614 | 0.000246543 | 0.027410832 | 0.008533833 | 0.007983263 |
| chr3: 63849179-63849579 | THOC7 | 0.429484227 | 0 | 0 | 0.000236747 | 0.027410832 | 0.007983263 | 0.006606838 |
| chr17: 57351011-57353322 | GDPD1 | 0.430283967 | 0 | 0 | 0.000212432 | 0.02572268 | 0.006606838 | 0.006551781 |
| chr1: 152992-11530018 | RGL3 | 0.432861793 | 7.75E-05 | 0.004357466 | 0.00021234 | 0.02572268 | 0.006551781 | 0.006331553 |
| chr12: 54423414-54424607 | HOXC6 | 0.432933362 | 0.001968332 | 0.074231845 | 0.000211601 | 0.02572268 | 0.006331553 | 0.007818092 |
| chr6: 107372260-107372546 | C6orf203 | 0.433507583 | 0.000780773 | 0.039721802 | 0.000193726 | 0.024266551 | 0.007818092 | 0.006661895 |
| chr17: 27169675-27169841 | C17orf63 | 0.433700 | 0 | 0 | 0.000191395 | 0.021961395 | 0.006661895 | 0.006166382 |
| chr12: 2113366-2113701 | DCP1B | 0.438106424 | 0.002757557 | 0.080136814 | 0.000168353 | 0.021533748 | 0.006166382 | 0.007818092 |
| chr20: 62168437-62168723 | PTK6 | 0.438444953 | 0.002433076 | 0.07683164 | 0.000167895 | 0.021533748 | 0.007818092 | 0.007763035 |
| chr20: 524315-524482 | CSNK2A1 | 0.438596671 | 0 | 0 | 0.000165764 | 0.021533748 | 0.007763035 | 0.006111325 |
| chr2: 40006253-40006407 | THUMPD2 | 0.438989821 | 0 | 0 | 0.000165526 | 0.021533748 | 0.006111325 | 0.006056268 |
| chr19: 38061359-38061540 | GNL2 | 0.439023194 | 0 | 0 | 0.000163423 | 0.021533748 | 0.006056268 | 0.006001211 |
| chr7: 40899914-40900362 | C7orf10 | 0.439295183 | 0.001314219 | 0.058505314 | 0.000153417 | 0.020640881 | 0.006001211 | 0.006496724 |
| chr12: 54448633-54449814 | HOXC4 | 0.440488904 | 0.00162294 | 0.067166971 | 0.000152321 | 0.020640881 | 0.006496724 | 0.006772009 |
| chr2: 86422460-86422893 | IMMT | 0.440753615 | 0.000251254 | 0.013818534 | 0.000145311 | 0.020358172 | 0.006772009 | 0.006001211 |
| chr4: 147442769-147443123 | SLC10A7 | 0.441806672 | 0.001164603 | 0.054060041 | 0.000145073 | 0.020358172 | 0.006001211 | 0.006111325 |
| chr1: 145368440-145370303 | NBPF10 | 0.441846603 | 0 | 0 | 0.00014216 | 0.020358172 | 0.006111325 | 0.005670869 |
| chr6: 46669594-46672056 | TDRD6 | 0.442466815 | 0 | 0 | 0.000168325 | 0.020261212 | 0.005670869 | 0.005505698 |
| chr5: 74072428-74072737 | SPOCK1 | 0.443225182 | 0 | 0 | 0.000133517 | 0.020041937 | 0.005505698 | 0.005450641 |
| chr4: 39529418-39529931 | UGDH | 0.444185722 | 0 | 0 | 0.000127134 | 0.020042801 | 0.005450641 | 0.00528547 |
| chr8: 145979576-145981802 | ZNF251 | 0.445163073 | 0.001145009 | 0.05346221 | 0.000126188 | 0.019242801 | 0.00528547 | 0.005615812 |
| chr11: 381668-382116 | B4GALNT4 | 0.445270209 | 0 | 0 | 0.000121712 | 0.019242801 | 0.005615812 | 0.005230413 |
| chr5: 68737358-68740157 | MARVELD2 | 0.446183422 | 0.001432367 | 0.06194304 | 0.00011576 | 0.019126366 | 0.005230413 | 0.005560755 |
| chr5: 150325308-150325671 | PRPF3 | 0.447239122 | 0 | 0 | 0.000111313 | 0.018606562 | 0.005560755 | 0.005065243 |
| chr3: 53845139-53846490 | CACNA1D | 0.448853672 | 0 | 0 | 0.000110375 | 0.018214263 | 0.005065243 | 0.004955129 |
| chr9: 126030714-126030855 | STRBP | 0.449208753 | 0 | 0 | 0.000107624 | 0.018214263 | 0.004955129 | 0.004845015 |
| chrX: 109683117-109683461 | AMMECR1 | 0.449831614 | 0.003696425 | 0.091617209 | 0.000105481 | 0.018099813 | 0.004845015 | 0.005946154 |
| chr5: 74072428-74072737 | NSA2 | 0.450170336 | 0.000888381 | 0.043846937 | 9.78E-05 | 0.017905164 | 0.005946154 | 0.005065243 |
| chr19: 19654489-19657468 | CILP2 | 0.451206343 | 0 | 0 | 9.30E-05 | 0.017086351 | 0.005065243 | 0.004679844 |
| chr22: 19770836-19771116 | TBX1 | 0.45229799 | 0.00133281 | 0.059043466 | 8.79E-05 | 0.016887835 | 0.004679844 | 0.004845015 |
| chr16: 11945264-11945442 | RSL1D1 | 0.453363354 | 0.001682554 | 0.068829349 | 8.68E-05 | 0.016293883 | 0.004845015 | 0.004459616 |
| chr11: 56509926-56509935 | PA2G4 | 0.453629094 | 0.001759224 | 0.070831349 | 8.50E-05 | 0.016256711 | 0.004459616 | 0.004900072 |
| chr11: 18063910-18063973 | TPH1 | 0.454146123 | 0 | 0 | 5.67E-05 | 0.016078925 | 0.004900072 | 0.003964103 |
| chr6: 11137010-111137161 | CDK19 | 0.461218971 | 0.000995607 | 0.048093643 | 5.64E-05 | 0.012121545 | 0.003964103 | 0.003909046 |
| chr5: 11903928-11904155 | CTNND2 | 0.46164781 | 0 | 0 | 5.63E-05 | 0.012121545 | 0.003909046 | 0.004404559 |
| chr9: 23825803-23826335 | ELAVL2 | 0.461847559 | 0.00178907 | 0.072455602 | 5.62E-05 | 0.012121545 | 0.004404559 | 0.003853989 |
| chr19: 137910926-137911133 | HSPA9 | 0.46177989 | 0 | 0 | 5.55E-05 | 0.012121545 | 0.003853989 | 0.003798932 |
| chr16: 15224943-15225458 | PKD1P6 | 0.463922149 | 0 | 0 | 5.54E-05 | 0.012121545 | 0.003798932 | 0.003743875 |
| chr10: 115991244-115992063 | TDRD1 | 0.464073889 | 0.000995607 | 0 | 5.36E-05 | 0.012121545 | 0.003743875 | 0.003798932 |
| chr1: 49059029-49059579 | AC084851.1 | 0.464703457 | 0 | 0 | 4.64E-05 | 0.01152023 | 0.003798932 | 0.003413533 |
| chrX: 135962755-135962939 | RBMX | 0.467663273 | 0 | 0 | 4.35E-05 | 0.010985753 | 0.003413533 | 0.003633761 |
| chr15: 74005274-74006859 | CD276 | 0.469036908 | 0.001399893 | 0.061268074 | | | | |

TABLE 9-continued

| locus | nearest_ref_id | r | p | qval | pglobal | qglobal | prank | padj |
|---|---|---|---|---|---|---|---|---|
| chr6: 76624529-76629254 | MYO6 | 0.472241272 | 0 | 0 | 3.98E-05 | 0.010632462 | 0.003193305 | 0.003193305 |
| chr6: 105627707-105627870 | POPDC3 | 0.474183404 | 0 | 0 | 3.80E-05 | 0.010304253 | 0.003138248 | 0.003138248 |
| chr1: 224517772-224518089 | NVL | 0.474352541 | 0.000217576 | 0.012048295 | 3.80E-05 | 0.010304253 | 0.003138248 | 0.003138248 |
| chr9: 93405033-93405386 | DIRAS2 | 0.476231667 | 0 | 0 | 3.72E-05 | 0.01030425 | 0.003083191 | 0.003083191 |
| chr20: 1373477-1373806 | FKBP1A | 0.477529689 | 0 | 0 | 3.37E-05 | 0.009557199 | 0.003028134 | 0.003028134 |
| chr9: 131262245-131263239 | ODF2 | 0.479887989 | 0 | 0 | 3.28E-05 | 0.009557199 | 0.00291802 | 0.00291802 |
| chr10: 124923335-124924886 | BUB3 | 0.481360778 | 0.000709825 | 0.03641962 | 3.21E-05 | 0.009557199 | 0.002973077 | 0.002973077 |
| chr5: 133304136-133304478 | C5orf15 | 0.481540922 | 0 | 0 | 3.20E-05 | 0.009557199 | 0.002807906 | 0.002807906 |
| chr1: 84855461-84855640 | SAMD13 | 0.483553428 | 0 | 0 | 2.97E-05 | 0.009293059 | 0.002752849 | 0.002752849 |
| chr5: 79865972-79866307 | ANKRD34B | 0.48535555 | 0 | 0 | 2.72E-05 | 0.00897817 | 0.002697792 | 0.002697792 |
| chr3: 132004083-132004254 | CPNE4 | 0.487204732 | 0 | 0 | 2.23E-05 | 0.007783374 | 0.002532621 | 0.002532621 |
| chr1: 40783259-40783488 | COL9A2 | 0.488099327 | 0 | 0 | 2.03E-05 | 0.007236461 | 0.002477564 | 0.002477564 |
| chr6: 111346605-111347303 | RPF2 | 0.488404844 | 0 | 0 | 2.02E-05 | 0.007236461 | 0.002422507 | 0.002422507 |
| chr12: 82152992-82153332 | PPFIA2 | 0.488405043 | 0 | 0 | 2.02E-05 | 0.007236461 | 0.00236745 | 0.00236745 |
| chr1: 76076724-76076801 | SLC44A5 | 0.48908972 | 0.00026347 | 0.014369004 | 2.00E-05 | 0.007236461 | 0.00236745 | 0.00236745 |
| chr11: 94965320-94965705 | SESN3 | 0.490557941 | 0 | 0 | 1.94E-05 | 0.007236461 | 0.002257336 | 0.002257336 |
| chr5: 102611597-102614361 | C5orf30 | 0.50386609 | 0 | 0 | 1.15E-05 | 0.00499128 | 0.002147222 | 0.002147222 |
| chr1: 166845396-166845564 | TADA1 | 0.508490879 | 0 | 0 | 7.77E-06 | 0.004015199 | 0.00181688 | 0.00181688 |
| chr6: 28200339-28201260 | ZNF193 | 0.511690319 | 0 | 0 | 7.13E-06 | 0.003810198 | 0.001761823 | 0.001761823 |
| chr4: 122617735-122618268 | ANXA5 | 0.516661902 | 0 | 0 | 5.57E-06 | 0.003261046 | 0.001596653 | 0.001596653 |
| chr2: 203630168-203634480 | FAM117B | 0.517778257 | 0 | 0 | 5.50E-06 | 0.003261046 | 0.001486539 | 0.001486539 |
| chr15: 82554954-82555104 | EFTUD1 | 0.51899271 | 0 | 0 | 5.43E-06 | 0.003261046 | 0.001431482 | 0.001431482 |
| chr6: 46703286-46703430 | PLA2G7 | 0.519577791 | 0 | 0 | 5.40E-06 | 0.003261046 | 0.001376425 | 0.001376425 |
| chr6: 24785865-24786327 | GMNN | 0.522285573 | 0 | 0 | 5.24E-06 | 0.003261046 | 0.001321368 | 0.001321368 |
| chr3: 175520792-175523428 | NAALADL2 | 0.531051532 | 0 | 0 | 4.73E-06 | 0.003261046 | 0.001211254 | 0.001211254 |
| chr1: 70587462-70589164 | LRRC7 | 0.531438025 | 0 | 0 | 4.71E-06 | 0.003261046 | 0.001156197 | 0.001156197 |
| chr6: 38997880-38998301 | DNAH8 | 0.533275843 | 0 | 0 | 4.60E-06 | 0.003261046 | 0.00110114 | 0.00110114 |
| chr1: 31769457-31769662 | SNRNP40 | 0.553891931 | 0.001806154 | 0.071315614 | 4.57E-06 | 0.003261046 | 0.000991026 | 0.000991026 |
| chr3: 3886047-3889387 | LRRN1 | 0.539082031 | 0 | 0 | 3.97E-06 | 0.003261046 | 0.000880912 | 0.000880912 |
| chr17: 4545517-4545589 | ALOX15 | 0.542179201 | 0 | 0 | 3.58E-06 | 0.003261046 | 0.000825855 | 0.000825855 |
| chr18: 55143668-55158530 | ONECUT2 | 0.543914583 | 0 | 0 | 3.36E-06 | 0.003261046 | 0.000770798 | 0.000770798 |
| chr18: 63547636-63552376 | CDH7 | 0.547130694 | 0 | 0 | 2.83E-06 | 0.003261046 | 0.000715741 | 0.000715741 |
| chr11: 129728468-129729898 | TMEM45B | 0.551304803 | 0 | 0 | 2.23E-06 | 0.002893994 | 0.000660684 | 0.000660684 |
| chr17: 38821255-38821393 | SMARCE1 | 0.554810297 | 0 | 0 | 2.07E-06 | 0.002893994 | 0.000605627 | 0.000605627 |
| chr6: 107436293-107436473 | BEND3 | 0.555214105 | 0 | 0 | 2.06E-06 | 0.002893994 | 0.00055057 | 0.00055057 |
| chr1: 180991774-180992047 | STX6 | 0.555781993 | 0 | 0 | 2.03E-06 | 0.002893994 | 0.00055057 | 0.001806154 |
| chr9: 114361882-114362135 | PTGR1 | 0.556369465 | 0 | 0 | 2.00E-06 | 0.002893994 | 0.000495513 | 0.000495513 |
| chr3: 193855471-193856521 | HES1 | 0.556447721 | 0 | 0 | 2.00E-06 | 0.002893994 | 0.000440456 | 0.000440456 |
| chr6: 38670746-38670917 | GLO1 | 0.559523889 | 0 | 0 | 1.86E-06 | 0.002893994 | 0.000385399 | 0.000385399 |
| chr2: 71159896-71160576 | VAX2 | 0.561327888 | 0 | 0 | 1.78E-06 | 0.002893994 | 0.000330342 | 0.000330342 |
| chr8: 136668468-136668965 | KHDRBS3 | 0.563811465 | 0 | 0 | 1.67E-06 | 0.002893994 | 0.000275285 | 0.000275285 |
| chr9: 79634570-79635869 | FOXB2 | 0.583153396 | 0 | 0 | 5.60E-07 | 0.002542246 | 0.000220228 | 0.000220228 |
| chr1: 317123401-317712401 | NKAIN1 | 0.590810474 | 0 | 0 | 0 | 0 | 0.000165171 | 0.000165171 |
| chr6: 107780193-107780768 | PDSS2 | 0.595945426 | 0 | 0 | 0 | 0 | 0.000165171 | 0.000165171 |
| chr2: 181780999-181782519 | SCHLAP1 | 1 | 0 | 0 | 0 | 0 | 0.000165171 | 0.000165171 |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method for treating prostate cancer in a subject, said method comprising:
   (a) processing a sample from the subject to isolate from the sample or to enrich the sample in non-coding RNA (ncRNA)
   (b) detecting an increased level of expression of PCAT-14 ncRNA in said sample compared to a pre-established threshold level, wherein the detecting comprises sequencing, nucleic acid hybridization or nucleic acid amplification, and wherein the PCAT-14 ncRNA has the sequence of any one of SEQ ID NOs: 3-9;
   (c) prognosing the subject as likely having prostate cancer; and
   (d) administering an effective amount of an anti-prostate cancer therapeutic, a chemotherapy, a radiation therapy, an immunotherapy/biological therapy, or a photodynamic therapy to the subject prognosed as likely having prostate cancer.

2. The method of claim 1, wherein the anti-cancer therapeutic is olaparib or ABT-888.

3. The method of claim 1, wherein the sample is selected from the group consisting of tissue, blood, plasma, serum, urine, urine supernatant, urine cell pellet, semen, prostatic secretions and prostate cells.

4. The method of claim 1, wherein the method further comprises detecting a level of expression of KLK3 (PSA) in the sample.

5. The method of claim 1, wherein the prostate cancer is advanced localized prostate cancer.

6. The method of any one of claims 1-2, 3-4, and 5, wherein the sample is a urine sample, and wherein the urine sample is obtained following a digital rectal examination (DRE) of the subject.

7. The method of claim 6, wherein the method further comprises performing a prostate biopsy of the subject if the subject is prognosed as likely having prostate cancer.

* * * * *

```
                              SEQUENCE LISTING

<160> NUMBER OF SEQ ID NOS: 28

<210> SEQ ID NO 1
<211> LENGTH: 621
<212> TYPE: DNA
<213> ORGANISM: Homo sapiens

<400> SEQUENCE: 1
acacatggat attggatatc tgcataggca gcttgctcca cgccagtgcc tacctgtgca      60
gatgggaagg aaaggaaagt ggcaaggagg cagagaaagc atctgtaccc ttacaatttg    120
gtgagacaag aatgtatgaa ttcccacagg tcaaattata atgaagaaag gaacctctct    180
tgagtacaaa gagctaccta tggtggtctg gagccggagg accacagcat caaaggatat    240
aagatgcata gccaactgag gaacctgagc aattaaagag atccacagtt aagtcacact    300
taactggcac ttgtggaagc cccgcaaggc ctgaaggaga gctgacatag gcaccccgga    360
gagccagaat ctggatccca tcttaataag gccatgaaca ccagtggaga agaggcagaa    420
acaccaatgg ataaggaaca ttcacatctt tcttcccatg tgcctctaag tgccagtgca    480
ggccccacag gccaagctac agggagaaag gagatgacgc aaaggaacct aactggactt    540
taatcactag aagtgagaag agaaatctat tggaacctcc caagataatg ccaagggtca    600
aagggtgcgc agatacataa g                                              621

<210> SEQ ID NO 2
<211> LENGTH: 1371
<212> TYPE: DNA
<213> ORGANISM: Homo sapiens

<400> SEQUENCE: 2
accatggaaa taatatcaga caaaaagcag attagagcaa ttttcttttt cgagttcaaa     60
atgggttata aagcagcgga gacaaaccgc aacatcacca acgcctttgg cccaggaact    120
gctaatgaag gtacagtgca gtcactgttc aggaagtttt gcaaaggaga ctagagcctt    180
gaagatgagg agcatagtga ccagccattg gaagtcgaca agaccaatt gagaggaatc     240 attgaagctg atcatcttac aactacacga gaagttgtca agaacgcaa tgttgaccat     300 tgtgtggtct tttcgcattt gaagcaaatt ggaaaggtga aaaacttgat aagtgggtgc    360
cttgtgagct cagcaaaaat ccaaaaaaat aatcattttt aagtgttgtc ttctcttatt    420
ctacgcaaca caataacca ttttgcaatc ggattgtgat gtgcaatgaa aagtggatt      480 ggggccgggc gcggtggctc acgcctgtaa tctcagcact ttggaaggcc aaggcgggca    540
gatcacgagg tcaggagatc aagaccgtcc tggctaacac ggtgaaaccc cgtctctact    600
gaaaatacaa aaaattagcc gggtgtggtg gctggcgcct gtagtcccag ctacaggctg    660
aggcaggaga atggcatgaa cctgggaggc ggagcttgca gtgagccgag accgtgccac    720
tgcactccga cctgggcgac agagcgatac tccgtcaaaa aaaaaaaaa aaaaaaaaa      780 agacaagtgg attttatata tggcaaccag caatgaccag ctcagtggct ggactgagaa    840
gaagctccaa agcactcccc aaagccaaac ttgcaccaaa aaaaggtca gggtcactgt    900 ttggtggtct gctgctggtc tgatccaccg ctgctctctg aatcctggca aaaccattac    960
```

| | | |
|---|---|---|
| atctgagaag tatgctcaac aaatcaatga gctacgccaa aaactgcagc atctgcagct | 1020 | |
| ggcattggtc aacataacgg gtccaattct tctccacgac aacgctcaac tgcaccttgc | 1080 | |
| gcaagcagcg cttcaaaagt tgaacaaatt gggctacata gttttcctc atccgccata | 1140 | |
| ttcacctgac gtcttgccaa ctaactacca cttcttcaag tatctcaaca acttttgca | 1200 | |
| gggaaaacac ttccacaacc agcaggatgc agaacacgct ttccaagagt tgtcgaatc | 1260 | |
| ctgacgcaca gatttttatg ctacaggaat aaactaactt attctcatt ggcaaaaatg | 1320 | |
| tgttgattgt aatggttcct attttgatga ataaatgtgt gtttgagcct a | 1371 | |

<210> SEQ ID NO 3
<211> LENGTH: 238
<212> TYPE: DNA
<213> ORGANISM: Homo sapiens

<400> SEQUENCE: 3

| | | |
|---|---|---|
| atgctgagcg ccggtcccct gggcccactt ttctttctct atactttgtc tctgttgtct | 60 | |
| ttcttttctc aagtctctcg ttccacctga ggagaaatgc ccacagctgt ggaggcgcag | 120 | |
| gccactccat ctggtgccca acgtggatgc ttttctctag ggtgaaggga ctctcgagtg | 180 | |
| tggtcattga ggacaagtca acgagagatt cccgagtacg tctacagtga gccttgtg | 238 | |

<210> SEQ ID NO 4
<211> LENGTH: 79
<212> TYPE: DNA
<213> ORGANISM: Homo sapiens

<400> SEQUENCE: 4

| | | |
|---|---|---|
| ggtgaaggta ctctacagtg tggtcattga ggacaagttg acgagagagt cccaagtacg | 60 | |
| tccacggtca gccttgcgg | 79 | |

<210> SEQ ID NO 5
<211> LENGTH: 79
<212> TYPE: DNA
<213> ORGANISM: Homo sapiens

<400> SEQUENCE: 5

| | | |
|---|---|---|
| acatttaaag ttctacaatg aactcactgg agatgcaaag aaaagtgtgg agatggagac | 60 | |
| accccaatcg actcgccag | 79 | |

<210> SEQ ID NO 6
<211> LENGTH: 682
<212> TYPE: DNA
<213> ORGANISM: Homo sapiens

<400> SEQUENCE: 6

| | | |
|---|---|---|
| tctacaggtg tatccagcag ctccaaagag acagcaacca gcaagaatgg gccatagtga | 60 | |
| cgatggtggt tttgtcaaaa agaaaagggg gggatatgta aggaaaagag agatcagact | 120 | |
| ttcactgtgt ctatgtagaa aaggaagaca taagaaactc cattttgatc tgtactaaga | 180 | |
| aaaattgttt tgccttgaga tgctgttaat ctgtaacttt agccccaacc ctgtgctcac | 240 | |
| ggaaacatgt gctgtaaggt ttaagggatc tagggctgtg caggatgtac cttgttaaca | 300 | |
| atatgtttgc aggcagtatg tttggtaaaa gtcatcgcca ttctccattc tcgattaacc | 360 | |
| aggggctcaa tgcactgtgg aaagccacag gaacctctgc ccaagaaagc ctggctgttg | 420 | |
| tgggaagtca gggaccccga atggagggac cagctggtgc tgcatcagga aacataaatt | 480 | |
| gtgaagattt cttggacatt tatcagtttc caaaattaat acttttataa tttcttacac | 540 | |

```
ctgtcttact ttaatctctt aatcctgtta tctttgtaag ctgaggatat acgtcacctc      600
aggaccacta ttgtacaaat tgattgtaaa acatgttcac atgtgtttga acaatatgaa      660
atcagtgcac cttgaaaatg aa                                               682
```

<210> SEQ ID NO 7
<211> LENGTH: 238
<212> TYPE: DNA
<213> ORGANISM: Homo sapiens

<400> SEQUENCE: 7

```
atgctgagcg ccggtcccct gggcccactt ttctttctct atactttgtc tctgttgtct       60
ttcttttctc aagtctctcg ttccacctga ggagaaatgc ccacagctgt ggaggcgcag      120
gccactccat ctggtgccca acgtggatgc ttttctctag ggtgaaggga ctctcgagtg      180
tggtcattga ggacaagtca acgagagatt cccgagtacg tctacagtga gccttgtg       238
```

<210> SEQ ID NO 8
<211> LENGTH: 5553
<212> TYPE: DNA
<213> ORGANISM: Homo sapiens

<400> SEQUENCE: 8

```
tctctcatcc ctcctgacga gaaatacccca caggtgtgga ggggctggcc cccttcatct      60
gatgcccaat gtgggtgcct ttctctaggg tgaaggtact ctacagtgtg gtcattgagg     120
acaagttgac gagagagtcc caagtacgtc acggtcagc cttgcggtaa gcttgtgtgc     180
ttagaggaac ccagggtaac gatggggcaa actgaaagta aatatgcctc ttatctcagc     240
tttattaaaa ttcttttaag aagagggggga gttagagctt ctacagaaaa tctaattacg     300
ctatttcaaa caatagaaca attctgccca tggtttccag aacagggaac tttagatcta     360
aaagattggg aaaaaattgg caaagaatta aaacaagcaa atagggaagg taaaatcatc     420
ccacttacag tatggaatga ttgggccatt attaaagcaa ctttagaacc atttcaaaca     480
ggagaagata ttgtttcagt ttctgatgcc cctaaaagct gtgtaacaga ttgtgaagaa     540
gaggcaggga cagaatccca gcaaggaacg gaaagttcac attgtaaata tgtagcagag     600
tctgtaatgg ctcagtcaac gcaaaatgtt gactacagtc aattacagga gataatatac     660
cctgaatcat caaaattggg ggaaggaggt ccagaatcat gggggccatc agagcctaaa     720
ccacgatcgc catcaactcc tcctcccgtg gttcagatgc ctgtaacatt acaacctcaa     780
acgcaggtta gacaagcaca aaccccaaga gaaaatcaag tagaaaggga cagagtctct     840
atcccggcaa tgccaactca gatacagtat ccacaatatc agccggtaga aaataagacc     900
caaccgctgg tagtttatca ataccggctg ccaaccgagc ttcagtatcg gcctccttca     960
gaggttcaat acagacctca gcggtgtgt cctgtgccaa atagcacggc accataccag    1020
caacccacag cgatggcgtc taattcacca gcaacacagg acgcggcgct gtatcctcag    1080
ccgcccactg tgagacttaa tcctacagca tcacgtagtg gacagggtgg tgcactgcat    1140
gcagtcattg atgaagccag aaaacagggc gatcttgagg catggcggtt cctggtaatt    1200
ttacaactgg tacaggccgg ggaagagact caagtaggag cgcctgcccg agctgagact    1260
agatgtgaac ctttcaccat gaaaatgtta aagatataaa aggaaggagt taaacaatat    1320
ggatccaact cccccttatat aagaacatta ttagattcca ttgctcatgg aaatagactt    1380
actccttatg actgggaaat tttggccaaa tcttcccttt catcctctca gtatctacag    1440
```

```
tttaaaacct ggtggattga tggagtacaa gaacaggtac gaaaaaatca ggctactaag    1500
cccactgtta atatagacgc agaccaattg ttaggaacag gtccaaattg gagcaccatt    1560
aaccaacaat cagtgatgca gaatgaggct attgaacaag taagggctat ttgcctcagg    1620
gcctggggaa aaattcagga cccaggaaca gctttcccta ttaattcaat tagacaaggc    1680
tctaaagagc catatcctga ctttgtggca agattacaag atgctgctca aaagtctatt    1740
acagatgaca atgcccgaaa agttattgta gaattaatgg cctatgaaaa tgcaaatcca    1800
gaatgtcagt cggccataaa gccattaaaa ggaaaagttc cagcaggagt tgatgtaatt    1860
acagaatatg tgaaggcttg tgatgggatt ggaggagcta tgcataaggc aatgctaatg    1920
gctcaagcaa tgagggggct cactctagga ggacaagtta gaacatttgg gaaaaaatgt    1980
tataattgtg gtcaaatcgg tcatctgaaa aggagttgcc caggcttaaa taaacagaat    2040
ataataaatc aagctattaa cagcaaaaaa taaaaagcca tctggcctgt gtccaaaatg    2100
tggaaaagca aaacattggg ccaatcaatg tcattctaaa tttgataaag atgggcaacc    2160
attgtctgga aacaggaaga ggggccagcc tcaggccccc caacaaactg ggcattccc     2220
agttaaactg tttgttcctc agggttttca aggacaacaa ccctacaga aaataccacc     2280
acttcaggga gtcagccaat tacaacaatc aacagctgt cccgcgccac agcaggcagc     2340
accgcagtag atttatgttc cacccaaatg gtcttttac tccctggaaa gcccccacaa     2400
aagattccta gaggggtata tggcccgctg ccagaaggga gggtaggcct ttgagggaga    2460
tcgtctaaat ttgaagggag tccaaattca tactggggta atttattcag attataaagg    2520
gggaattcag ttagtgatca gctccactgt tccccggagt gccaatccag gtgatagaat    2580
tgctcaatta ctgcttttgc cttatgttaa aattggggaa acaaaaagg aaagaacagg     2640
agggtttgga agtaccaacc ctgcaggaaa agctgcttat tgggctaatc aggtctcaga    2700
ggatagaccc gtgtgtacag tcactattca gggaagagt ttgaaggatt agtggatacc     2760
caggctgatg tttctgtcat cggcataggt actgcctcag aagtgtatca aagtgccatg    2820
attttacatt gtccaggatc tgataatcaa gaaagtacgg ttcagcctgt gatcacttca    2880
ttccaatcaa tttatggggc cgagacttgt tacaacaatg gcatgcagag attactatcc    2940
cagcctccct atacagcccc aggaataaaa aaatcatgac taaaatggga tagctcccta    3000
aaaagggact aggaaagaag tcccaattga ggctgaaaaa aatcaaaaaa gaaaaggaat    3060
agggcatcct ttttaggagc ggtcactgta gagcctccaa aacccattcc attaacttgg    3120
gggaaaaaaa aacaactgta tggtaaatca gcagcgcttc caaaacaaaa actggaggct    3180
ttacatttat tagcaaagaa acaattagaa aaaggacatt gagccttcat tttcgccttg    3240
gaattctgtt tgtaattcag aaaaaatccg gcagatggcg tataatgccg taattcaacc    3300
catgggggct ctcccacccc ggttgccctc tccagccatg gtccccttta attataattg    3360
atctgaagga ttgcttttt accattcctc tggcaaaaca ggattttgaa aaatttgctt    3420
ttaccacacc agcctaaata ataaagaacc agccaccagg tttcagtgga aagtattgcc    3480
tcagggaatg cttaatagtt caactatttg tcagctcaag ctctgcaacc agttagagac    3540
aagttttcag actgttacat cgttcactat gttgatattt tgtgtgctgc agaaacgaga    3600
gacaaattaa ttgaccgtta cacatttctg cagacagagg ttgccaacgc gggactgaca    3660
ataacatctg ataagattca aacctctact ccttttccgtt acttgggaat gcaggtagag    3720
gaaaggaaaa ttaaaccaca aaaaatgaa ataagaaaag acacattaaa agcattaaat     3780
gagtttcaaa agttgctagg agatactaat tggatttgga gatattaatt ggatttggcc    3840
```

```
aactctaggc attcctactt atgccatgtc aaatttgttc tctttcttaa gagggactc     3900 ggaattaaat agtgaaagaa cgttaactcc agaggcaact aaagaaatta aattaattga     3960
agaaaaaatt cggtcagcac aagtaaatag aatagatcac ttggccccac tccaaatttt     4020
gatttttgct actgcacatt ccctaacagg catcattgtt caaaatacag atcttgtgga     4080
gtggtccttc cttcctcaca gtacaattaa gacttttaca ttgtacttgg atcaaatggc     4140
tacattaatt ggtcagggaa gattatgaat aataacattg tgtggaaatg acccagataa     4200
aatcactgtt cctttcaaca agcaacaggt tagacaagcc tttatcaatt ctggtgcatg     4260
gcagattggt cttgccgatt tgtgggaat tattgacaat cgttacccca aaacaaaaat     4320
cttccagttt ttaaaattga ctacttggat tttacctaaa gttaccaaac ataagccttt     4380
aaaaaatgct ctggcagtgt ttactgatgg ttccagcaat ggaaaagtgg cttacaccgg     4440
gccaaaagaa tgagtcatca aaactcagta tcacttgact caaagagcag agttggttgc     4500
cgtcattaca gtgttaacaa gattttaatc agtctattaa cattgtatca gattctgcat     4560
atgtagtaca ggctacaaag gatattgaga gagccctaat caaatacatt atggatgatc     4620
agttaaaccc gctgtttaat ttgttacaac aaaatgtaag aaaaagaaat ttcccatttt     4680
atattactca tattcgagca cacactaatt taccagggcc tttaactaaa gcaaatgaac     4740
aagctgactt gctagtatca tctgcattca tggaagcaca agaacttcat gccttgactc     4800
atgtaaatgc aataggatta aaaataaat ttgatatcac atggaaacag acaaaaaata     4860
ttgtacaaca ttgcacccag tgtcagattc tacacctggc cactcaggag gcaagagtta     4920
atcccagagg tctatgtcct aatgtgttat ggcaaatgga tgtcatgcac gtaccttcat     4980
ttggaaaatt gtcatttgtc catgtgacag ttgatactta ttcacatttc atatgggcaa     5040
cctgccagac aggagaaagt acttcccatg ttaaaagaca tttattatct tgttttcctg     5100
tcatgggagt tccagaaaaa gttaaaacag acaatgggcc aggttactgt agtaaagcag     5160
ttcaaaaatt cttaaatcag tggaaaatta cacatacaat aggaattctc tataattccc     5220
aaggacaggc cataattgaa agaactaata gaacactcaa agctcaattg gttaaacaaa     5280
aaaaaggaaa agacaggagt ataacactcc ccagatgcaa cttaatctag cactctatac     5340
tttaaatgtt ttaaacattt atagaaatca gaccactacc tctgcagaac aacatcttac     5400
tggtaaaagg aacagcccac atgaaggaaa actgatttgg tggaaagata taaaaataa     5460 aacatgggaa atggggaagg tgataacgtg ggggagaggt tttgcttgtg tttccaccagg     5520 agaaaatcag cttcctgttt ggatacccac tag                                 5553

<210> SEQ ID NO 9
<211> LENGTH: 2179
<212> TYPE: DNA
<213> ORGANISM: Homo sapiens

<400> SEQUENCE: 9
gtaaacaaaa tggtgatatc agaagaacag aaaaagttgc cttccatcaa ggaagcagag      60
ttgccaatat aggcacaatt aaagaagctg acacagttag ctaaaaaaaa aagcctagag     120
aatacaaagg tgacaccaac tccagagaat atgctgcttg cagctctgat gattgtatca     180
acggtggtaa gtcttcccaa gtctgcagga gcagctgcag ctaattatac ttactgggcc     240 tatgtgccctt tccacccctt aattcgggca gttacataga tggataatcc tattgaagta     300
gatgttaata atagtgcatg ggtgcctggc cccacagatg actgttgccc tgcccaacct     360
```

```
gaagaaggaa tgatgatgaa tatttccatt gggtatcctt atcctcctgt ttgcctaggg      420
aaggcaccag gatgcttaat gcctacaacc caaaattggt tggtagaagt acctacagtc      480
agtgctacca gtagatttac ttatcacatg gtaagtggaa tgtcacagat aaataattta      540
caggacccct cttatcaaag atcattacaa tgtaggccta aggggaaggc ttgccccaag      600
gaaattccca agaatcaaa aagcccagaa gtcttagtct gcggagaatg tgtggctgat       660
actgcagtgt agtacaaaac aatgaatttt gaactatgat agactgggtc ccttgaggcc      720
aattatatca taactgtaca ggccagactc attcatgttc acaggcccca tccatctggc      780
ccattaatcc agcctatgac ggtgatgtaa ctgaaaggct ggaccaggtt tatagaaggt      840
tagaatcact ctgtccaagg aaatggggtg aaaagggaat ttcatcacct tgaccaaagt      900
tagtcctgtt actggtcctg aacatccaga attaggaagc ttactgtggc ctcacaccac      960
attagaattt gttctggaaa tcaagctata ggaacaagag atcgtaagtc atattatact     1020
atcaacctaa attccagtct gacaattcct ttgcaaaatt gtgtaaaact cccttatatt     1080
gctagttgta ggaaaaacat agttattaaa cctgattccc aaaccataat ctgtgaaaat     1140
tgtggaatgt ttacttgcat tgatttgact tttaattggc agcaccgtat tctactagga     1200
agagcaagag agggtgtgtg gatccttgtg tccatggacc gaccatggga ggcttcgcta     1260
tccatccata ttttaacgga agtattaaaa ggaattctaa ctagatccaa aagattcatt     1320
tttactttga tggcagtgat tatgggcctc attgcagtca cagctactgc tgcggctgct     1380
ggaattgctt tacactcctc tgttcaaact gcagaatacg taaatgattg gcaaaagaat     1440
tcctcaaaat tgtggaattc tcagatccaa atagatcaaa aattggcaaa ccaaattaat     1500
gatcttagac aaactgtcat ttggatggga gaggctcatg agcttggaat atcttttca      1560 gttacgatgt gactggaata catcagattt ttgtgttaca ccacaagcct ataatgagtc     1620
tgagcatcac tgggacatgg ttagatgcca tctgcaagga ggagaagata atcttacttt     1680
agacatttca aaattaaaag aattttttttt ttctttgaga cagagtctcg ctctgtcgcc     1740
caggctggag tgcagtggcg tgatctcagc tcactgcaag ttccgcctcc tgggtttaca     1800
ccattctcct gcctcagcct cccaagtagt tgggactaca ggagcccacc accatgcctg     1860
gctaattttt tttgggtttt taatagagat ggagtttcac cgtgttagcc aggatggtct     1920
cgatctcctg accttgtgat ctgcccacct tggcctccca aagtgctggg attacagtcg     1980
tgagccaccg tgcccagcca agaaaaaatt tttgaggcat caaaagccca tttaaatttg     2040
gtgccaggaa cggagacaat cgtgaaagct gctgatagcc tcacaaatct taagccagtc     2100
acttgggtta aaagcatcag aagtttcact attgtaaatt tcatattaat ccttgtatgc     2160
ctgttctgtc tgttgttag                                                 2179
```

<210> SEQ ID NO 10
<211> LENGTH: 16
<212> TYPE: DNA
<213> ORGANISM: Artificial Sequence
<220> FEATURE:
<223> OTHER INFORMATION: Synthetic

<400> SEQUENCE: 10
ccgaaccaca catgga                                                       16

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagatacata aggtaagc                                                    18

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
tttattttag accatggaaa ta                                               22

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
gatgaataaa tgtgtgtttg agcctagtta tg                                    32

<210> SEQ ID NO 14
<211> LENGTH: 261
<212> TYPE: DNA
<213> ORGANISM: Artificial Sequence
<220> FEATURE:
<223> OTHER INFORMATION: Synthetic

<400> SEQUENCE: 14
cgggtcctcc atatgctgag cgccggtccc ctgggcccac ttttcttcct ctatactttg      60
tctctgttgt ctttctttc tcaagtctct cgttccacct gaggagaaat gcccacagct      120
gtggaggcgc aggccactcc atctggtgcc caacgtggat gcttttctct agggtgaagg     180
gactctcgag tgtggtcatt gaggacaagt caacgagaga ttcccgagta cgtctacagt     240
gagccttgtg gtaagcttgg g                                               261

<210> SEQ ID NO 15
<211> LENGTH: 101
<212> TYPE: DNA
<213> ORGANISM: Artificial Sequence
<220> FEATURE:
<223> OTHER INFORMATION: Synthetic

<400> SEQUENCE: 15
tctttcctca gggtgaaggt actctacagt gtggtcattg aggacaagtt gacgagagag      60
tcccaagtac gtccacggtc agccttgcgg gtgaaggtac t                         101

<210> SEQ ID NO 16
<211> LENGTH: 101
<212> TYPE: DNA
<213> ORGANISM: Artificial Sequence
<220> FEATURE:
<223> OTHER INFORMATION: Synthetic

<400> SEQUENCE: 16
atacccacta gacatttaaa gttctacaat gaactcactg gagatgcaaa gaaaagtgtg      60
gagatggaga caccccaatc gactcgccag gtaaacaaaa t                         101

<210> SEQ ID NO 17
<211> LENGTH: 701
<212> TYPE: DNA
<213> ORGANISM: Artificial Sequence
<220> FEATURE:
<223> OTHER INFORMATION: Synthetic

<400> SEQUENCE: 17

```
tgttgttagt ctacaggtgt atccagcagc tccaaagaga cagcaaccag caagaatggg     60
ccatagtgac gatggtggtt ttgtcaaaaa gaaaaggggg ggatatgtaa ggaaaagaga    120
gatcagactt tcactgtgtc tatgtagaaa aggaagacat aagaaactcc attttgatct    180
gtactaagaa aaattgtttt gccttgagat gctgttaatc tgtaacttta gccccaaccc    240
tgtgctcacg gaaacatgtg ctgtaaggtt taagggatct agggctgtgc aggatgtacc    300
ttgttaacaa tatgtttgca ggcagtatgt ttggtaaaag tcatcgccat tctccattct    360
cgattaacca ggggctcaat gcactgtgga aagccacagg aacctctgcc caagaaagcc    420
tggctgttgt gggaagtcag ggaccccgaa tggagggacc agctggtgct gcatcaggaa    480
acataaattg tgaagatttc ttggacattt atcagtttcc aaaattaata cttttataat    540
ttcttacacc tgtcttactt taatctctta atcctgttat ctttgtaagc tgaggatata    600
cgtcacctca ggaccactat tgtacaaatt gattgtaaaa catgttcaca tgtgtttgaa    660
caatatgaaa tcagtgcacc ttgaaaatga acagaataac a                        701
```

<210> SEQ ID NO 18
<211> LENGTH: 644
<212> TYPE: DNA
<213> ORGANISM: Artificial Sequence
<220> FEATURE:
<223> OTHER INFORMATION: Synthetic

<400> SEQUENCE: 18

```
ggctccgaac acacatggat attggatatc tgcataggca gcttgctcca cgccagtgcc     60
tacctgtgca gatgggaagg aaaggaaagt ggcaaggagg cagagaaagc atctgtaccc    120
ttacaatttg gtgagacaag aatgtatgaa ttcccacagg tcaaattata atgaagaaag    180
gaacctctct tgagtacaaa gagctaccta tggtggtctg gagccggagg accacagcat    240
caaaggatat aagatgcata gccaactgag gaacctgagc aattaaagag atccacagtt    300
aagtcacact taactggcac ttgtggaagc cccgcaaggc ctgaaggaga gctgacatag    360
gcaccccgga gagccagaat ctggatccca tcttaataag gccatgaaca ccagtggaga    420
agaggcagaa acaccaatgg ataaggaaca ttcacatctt tcttcccatg tgcctctaag    480
tgccagtgca ggccccacag gccaagctac agggagaaag gagatgacgc aaaggaacct    540
aactggactt taatcactag aagtgagaag agaaatctat tggaacctcc caagataatg    600
ccaagggtca aagggtgcgc agatacataa ggtaagccct tcgg                     644
```

<210> SEQ ID NO 19
<211> LENGTH: 1376
<212> TYPE: DNA
<213> ORGANISM: Artificial Sequence
<220> FEATURE:
<223> OTHER INFORMATION: Synthetic

<400> SEQUENCE: 19

```
tttagaccat ggaaataata tcagacaaaa agcagattag agcaattttc ttttttcgagt    60 tcaaaatggg ttataaagca gcggagacaa accgcaacat caccaacgcc tttggcccag    120
```

```
gaactgctaa tgaaggtaca gtgcagtcac tgttcaggaa gttttgcaaa ggagactaga      180
gccttgaaga tgaggagcat agtgaccagc cattggaagt cgacaaagac caattgagag      240
gaatcattga agctgatcat cttacaacta cacgagaagt tgtcaaagaa cgcaatgttg      300
accattgtgt ggtctttttcg catttgaagc aaattggaaa ggtgaaaaac ttgataagtg      360
ggtgccttgt gagctcagca aaaatccaaa aaaataatca tttttaagtg ttgtcttctc      420
ttattctacg caacaacaat aaccattttg caatcggatt gtgatgtgca atgaaaagtg      480
gatttggggc cgggcgcggt ggctcacgcc tgtaatctca gcactttgga aggccaaggc      540
gggcagatca cgaggtcagg agatcaagac cgtcctggct aacacggtga acccccgtct      600
ctactgaaaa tacaaaaaat tagccgggtg tggtggctgg cgcctgtagt cccagctaca      660
ggctgaggca ggagaatggc atgaacctgg gaggcggagc ttgcagtgag ccgagaccgt      720
gccactgcac tccagcctgg gcgacagagc gatactccgt caaaaaaaaa aaaaaaaaaa      780
aaaaaagaca agtggatttt atatatggca accagcaatg accagctcag tggctggact      840
gagaagaagc tccaaagcac ttcccaaagc caaacttgca ccaaaaaaaa ggtcagggtc      900
actgtttggt ggtctgctgc tggtctgatc caccgctgct ctctgaatcc tggcaaaacc      960
attacatctg agaagtatgc tcaacaaatc aatgagctac gccaaaaact gcagcatctg     1020
cagctggcat tggtcaacat aacgggtcca attcttctcc acgacaacgc tcaactgcac     1080
cttgcgcaag cagcgcttca aaagttgaac aaattgggct acatagtttt tcctcatccg     1140
ccatattcac ctgacgtctt gccaactaac taccacttct tcaagtatct caacaacttt     1200
ttgcagggaa aacacttcca caaccagcag gatgcagaac acgctttcca agagtttgtc     1260
gaatcctgac gcacagattt ttatgctaca ggaataaact aacttatttc tcattggcaa     1320
aaatgtgttg attgtaatgg ttcctatttt gatgaataaa tgtgtgtttg agccta         1376

<210> SEQ ID NO 20
<211> LENGTH: 813
<212> TYPE: DNA
<213> ORGANISM: Homo sapiens

<400> SEQUENCE: 20
tttctcaggt ctggatgtag ggttagatgc cagttagata taagtgaaat agccggttta       60
cttaccaata gacaggaaag tagtcttttg tgattcccct ctccactaaa tacaaatcag      120
tgctactcag gggctcttta agaaggagt tggccaggtg tggtgactca cgcctgtaat       180
cttagcactt tgggaggttg aggcgggtgg atcacctgag gtcaggagtt cgagaccatt      240
cctgaccaac atggagaaac cctgtctcta aaaatacaaa atcagctggg cgtggtggcg      300
catgcctgta atcccagcta cttgggaggc tgaggcagga gaatcgcttg aacccgggag      360
gcggaggttg tagtgagccg agattgtgcc attgcactcc agcctgggca acaagagcga      420
aactccgact acatgtaccc taaaacttaa agtataataa taataaaatt aaaaaaaaaa      480
aaaaagaaca gcagcagtaa aaaataaata aagaaataaa taaataaata aatgaagaag      540
tcaatcggta ccataagaaa ggacaaaaac caaaacaaac ccaaagcaaa accaaaaact      600
ccccacaaac cagcctcccc taacccttttt aactcaaagc ttcgtaatgt ctctgaattt      660
ataattacga ttttaaagag cactgtttct catgccccat cccccaaccc atttcgggag      720
taaacctttt ctgtcagggt gaggagaaag tgggtaaagg acttcagcat ttacagttga      780
gttagtattt gttgttctcc aaatgtgcag gaa                                   813
```

<210> SEQ ID NO 21
<211> LENGTH: 404
<212> TYPE: DNA
<213> ORGANISM: Homo sapiens

<400> SEQUENCE: 21

| | | | | | | |
|---|---|---|---|---|---|---|
| tccttggtgg | cttagggtac | agttattaat | gctggctgtg | atgaagtttt | gctggggacc | 60 |
| aggataacag | atggtccagt | catggggcct | cagtggtggc | agtgattagc | tgatcatgcc | 120 |
| tgtcctttgg | ccccaggttg | gcttatgctg | gcacttgtgt | tgttaggccc | aagcagtctg | 180 |
| atttggggc | ctccacatgg | tttgctggga | tgttggtagt | ttctgcttcc | tggcctgatg | 240 |
| tggtacatct | gggtgagtgc | cagctctggt | ggtattagca | tgttatgtca | gcctgtcctt | 300 |
| agaccctggg | agaagtgttc | atgtgccaat | ggtggtagac | tgtgctgagt | gatttccagg | 360 |
| cccctggaca | gcatactgaa | ttactgagag | gatgggactg | agca | | 404 |

<210> SEQ ID NO 22
<211> LENGTH: 362
<212> TYPE: DNA
<213> ORGANISM: Artificial Sequence
<220> FEATURE:
<223> OTHER INFORMATION: Synthetic

<400> SEQUENCE: 22

| | | | | | | |
|---|---|---|---|---|---|---|
| tgggtccaca | ctgcttttat | gagctgtaac | actcaccgcg | aaggtccgca | gcttcactcc | 60 |
| tgaagccagc | gagaccacga | gcctactggg | aggaacgaac | aactcccgac | gcgccgcctt | 120 |
| aagagctgta | acactcaccg | cgaaggtctg | cagcttcact | cctgagccag | cgagaccacg | 180 |
| aacccaccag | aaggaaaaaa | ctccgaacac | atctgaacat | cagaagcaac | aaactccgga | 240 |
| cacgccgcct | ttaagaactg | taacactcac | tgcgagggtc | cgcggcttca | ttcttgaagt | 300 |
| gagtgagacc | aagaacccac | cagttctgga | cacaatttca | agtcctcagg | gtgagttttc | 360 |
| cc | | | | | | 362 |

<210> SEQ ID NO 23
<211> LENGTH: 124
<212> TYPE: DNA
<213> ORGANISM: Artificial Sequence
<220> FEATURE:
<223> OTHER INFORMATION: Synthetic

<400> SEQUENCE: 23

| | | | | | | |
|---|---|---|---|---|---|---|
| ctgtgttttc | ttttcagtgc | catcaatatt | ctgaaaatgg | cagtgatttt | tattcaacct | 60 |
| gtataaggca | ctttcaccat | gtacctggaa | gcaacatcta | catcttttc | aggtaatagt | 120 |
| ttcc | | | | | | 124 |

<210> SEQ ID NO 24
<211> LENGTH: 129
<212> TYPE: DNA
<213> ORGANISM: Artificial Sequence
<220> FEATURE:
<223> OTHER INFORMATION: Synthetic

<400> SEQUENCE: 24

| | | | | | | |
|---|---|---|---|---|---|---|
| tcaaccacat | tcctagtttt | cctctgtcca | ctatgaagga | ctttgtgacc | acattctgac | 60 |
| tctgatgaga | tcctgcccag | aattgacctg | aaccccaata | attcacctt | ctctcaggta | 120 |
| atgttttca | | | | | | 129 |

<210> SEQ ID NO 25
<211> LENGTH: 170
<212> TYPE: DNA
<213> ORGANISM: Artificial Sequence
<220> FEATURE:
<223> OTHER INFORMATION: Synthetic

<400> SEQUENCE: 25

| | | |
|---|---|---|
| gtttcttctt ctttcagttt cttctacgcc aggtgtgtgc ttagctccat gacaaaaggt | 60 |
| gacagcttat tctgcagcac acacacatca tcaaagtggg aggtggtgag actggcacac | 120 |
| tgacagtctg tcctagcaga tttcagctca cactggtgag ttccagcatg | 170 |

<210> SEQ ID NO 26
<211> LENGTH: 294
<212> TYPE: DNA
<213> ORGANISM: Artificial Sequence
<220> FEATURE:
<223> OTHER INFORMATION: Synthetic

<400> SEQUENCE: 26

| | | |
|---|---|---|
| ccctacaatg taacagcaat ctagatgctg gggacacaag gtccaccttc caggaatatg | 60 |
| gccatgacac cagaaatcac aaacatgatg agaatggaat gactgggggaa gaagtgccag | 120 |
| atgcttcact tgtaaatgaa gacccagcct ctggggatgc agataccacc tccctgaaga | 180 |
| agctgaatat ctgcagataa gtggagttca ccaatgatga ggagcgggat ggagaaagga | 240 |
| ggtagggaga gtcatccaag gaacatgagc aacatgttaa aaggtaagaa gtga | 294 |

<210> SEQ ID NO 27
<211> LENGTH: 100
<212> TYPE: DNA
<213> ORGANISM: Artificial Sequence
<220> FEATURE:
<223> OTHER INFORMATION: Synthetic

<400> SEQUENCE: 27

| | | |
|---|---|---|
| tctctactct actctagcca agtggtttaa tttctggaga tggtgaaccc aagaggctct | 60 |
| gctgggagac aacaaaaata atgaaggtaa tggatgaaar | 100 |

<210> SEQ ID NO 28
<211> LENGTH: 697
<212> TYPE: DNA
<213> ORGANISM: Artificial Sequence
<220> FEATURE:
<223> OTHER INFORMATION: Synthetic

<400> SEQUENCE: 28

| | | |
|---|---|---|
| acaattgcct tcctagaatt gaaccagagt ccggtgaata tcagcactgg gaccagttag | 60 |
| cagaggaaaa ggaaagaata aaagcgaaaa gaatgaagag tcatatgatt accaactttt | 120 |
| ccttttttcat ataaattgag tgtatatggg tctggaacaa cctgaatttc catcaagtcc | 180 |
| tggctaacct cattatgtcc tatgaatatt tttgactaat cccactttac attaatctgt | 240 |
| attgtgaatg tggatattga attatatttc tttgtaatcc cattatccaa aatccagttc | 300 |
| agagactatt agttaccaat gttcactgtg aaggaaaaaa aaaaaaaaaa agctcagagg | 360 |
| ataaacatgt gatatggttt ggctgtgtcc ccacccaaat atcatcttga attgtagctc | 420 |
| ccataattcc cacgtgttgt gggagggacc cggtgggaga taattgtatc atgggggtgg | 480 |
| ttcccccata ctattctcat agtagtgaat aagtctcaca aaatctgatg gttttatgag | 540 |
| ggaaaacccc tttcacctgg ttctcattct cttctctggt ctgtcgtcat gtaagacatg | 600 |

```
cctttcacct tctccaccat gactgtgagg cctccccagc cacgtggaac tgtgagccca    660
ttaaacctct ttcacttata aattacccag tctctgg                             697
```